US011230542B2

(12) United States Patent
Bernales et al.

(10) Patent No.: US 11,230,542 B2
(45) Date of Patent: Jan. 25, 2022

(54) INHIBITORS OF INTEGRATED STRESS RESPONSE PATHWAY

(71) Applicant: Praxis Biotech LLC, San Francisco, CA (US)

(72) Inventors: Sebastian Bernales, Piedmont, CA (US); Luz Marina Delgado Oyarzo, Santiago (CL); Gonzalo Esteban Núñez Vasquez, Santiago (CL); Gonzalo Andrés Ureta Díaz, Santiago (CL); Brahmam Pujala, Greater Noida (IN); Dayanand Panpatil, Noida (IN); Bhawana Bhatt, Noida (IN); Sarvajit Chakravarty, Edmond, OK (US)

(73) Assignee: PRAXIS BIOTECH LLC, San Francisco, CA (US)

( * ) Notice: Subject to any disclaimer, the term of this patent is extended or adjusted under 35 U.S.C. 154(b) by 0 days.

(21) Appl. No.: 16/219,805

(22) Filed: Dec. 13, 2018

(65) Prior Publication Data
US 2019/0177310 A1    Jun. 13, 2019

Related U.S. Application Data

(60) Provisional application No. 62/598,377, filed on Dec. 13, 2017, provisional application No. 62/690,857, filed on Jun. 27, 2018.

(51) Int. Cl.
*A61K 31/44* (2006.01)
*C07D 413/12* (2006.01)
*C07D 263/24* (2006.01)
*C07D 307/85* (2006.01)
*C07D 401/12* (2006.01)
*C07D 405/12* (2006.01)
*C07D 215/18* (2006.01)
*C07D 211/58* (2006.01)
*C07D 491/048* (2006.01)
*C07D 277/68* (2006.01)
*C12N 5/00* (2006.01)
*C07D 265/36* (2006.01)
*A61P 35/00* (2006.01)
*A61P 21/00* (2006.01)
*A61P 25/28* (2006.01)

(52) U.S. Cl.
CPC .......... *C07D 413/12* (2013.01); *C07D 211/58* (2013.01); *C07D 215/18* (2013.01); *C07D 263/24* (2013.01); *C07D 265/36* (2013.01); *C07D 277/68* (2013.01); *C07D 307/85* (2013.01); *C07D 401/12* (2013.01); *C07D 405/12* (2013.01); *C07D 491/048* (2013.01); *C12N 5/0018* (2013.01); *A61P 21/00* (2018.01); *A61P 25/28* (2018.01); *A61P 35/00* (2018.01); *C12N 2500/32* (2013.01)

(58) Field of Classification Search
None
See application file for complete search history.

(56) References Cited

U.S. PATENT DOCUMENTS

| 5,096,901 | A  | 3/1992  | Ward            |
|-----------|----|---------|-----------------|
| 2004/0138286 | A1 | 7/2004 | Imazaki         |
| 2005/0197350 | A1 | 9/2005 | Sekiguchi et al.|
| 2010/0035898 | A1 | 2/2010 | Beattie         |
| 2011/0039860 | A1 | 2/2011 | Yang            |
| 2011/0300575 | A1 | 12/2011| Imataka et al.  |
| 2015/0314018 | A1 | 11/2015| Sahin et al.    |
| 2016/0318931 | A1 | 11/2016| Hadida-ruah     |
| 2017/0342020 | A1 | 11/2017| Walter et al.   |
| 2019/0177310 | A1 | 6/2019 | Bernales et al. |
| 2020/0101047 | A1 | 4/2020 | Oyarzo et al.   |
| 2020/0270232 | A1 | 8/2020 | Bernales        |

FOREIGN PATENT DOCUMENTS

| WO |       9906387 A2 | 2/1999  |
|----|-----------------|---------|
| WO |    2010068881 A1 | 6/2010  |
| WO |    2011095450 A1 | 8/2011  |
| WO | WO-2014/144952 A2 | 9/2014  |
| WO | WO-2014/144952 A3 | 9/2014  |
| WO | WO-2017/193030 A1 | 11/2017 |
| WO | WO-2017/193034 A1 | 11/2017 |
| WO | WO-2017/193041 A1 | 11/2017 |
| WO | WO-2017/193063 A1 | 11/2017 |
| WO | WO-2017/212423 A1 | 12/2017 |
| WO | WO-2017/212425 A1 | 12/2017 |
| WO |    2018225093 A1 | 12/2018 |
| WO |    2019008506 A1 | 1/2019  |
| WO |    2019008507 A1 | 1/2019  |
| WO | WO-2019/032743 A1 | 2/2019  |
| WO | WO-2019/046779 A1 | 3/2019  |
| WO |    2019090069 A1 | 5/2019  |
| WO |    2019090074 A1 | 5/2019  |
| WO |    2019090076 A1 | 5/2019  |
| WO |    2019090078 A1 | 5/2019  |
| WO |    2019090081 A1 | 5/2019  |

(Continued)

OTHER PUBLICATIONS

Adomavicius, T. et al. (e-pub. Dec. 20, 2018). "The Structural Basis of Translational Control by eIF2 Phosphorylation", Article, 46 pages (including Supplementary Material begins at p. 30 of 46).
Al-Chalabi, A. et al. (2012). "The Genetics and Neuropathology of Amyotrophic Lateral Sclerosis," Acta Neuropathol 124(3):339-352.
Anastassiadis, T. et al. (2011). "Comprehensive Assay of Kinase Catalytic Activity Reveals Features of Kinase Inhibitor Selectivity," Nat Biotechnol. 29(11):1039-1045.
Ardiles et al. (Oct. 15, 2014). "Pannexin 1 Regulates Bidirectional Hippocampal Synaptic Plasticity in Adult Mice," Front Cell Neurosci. 8(326):1-11.
ATCC Product Sheet (2018). "CT26.WT (ATCC CRL-2638)", located at www.atc.org, last visited on Jun. 27, 2019, 3 pages.

(Continued)

*Primary Examiner* — Samantha L Shterengarts
(74) *Attorney, Agent, or Firm* — Morrison & Foerster LLP

(57) ABSTRACT

The present disclosure relates generally to therapeutic agents that may be useful as inhibitors of Integrated Stress Response (ISR) pathway.

58 Claims, 28 Drawing Sheets

(56) References Cited

FOREIGN PATENT DOCUMENTS

| | | | |
|---|---|---|---|
| WO | 2019090082 A1 | 5/2019 | |
| WO | 2019090085 A1 | 5/2019 | |
| WO | 2019090088 A1 | 5/2019 | |
| WO | 2019090090 A1 | 5/2019 | |
| WO | WO-2019/118785 A2 | 6/2019 | |
| WO | WO-2019/183589 A1 | 9/2019 | |
| WO | 2019193540 A1 | 10/2019 | |
| WO | 2019193541 A1 | 10/2019 | |
| WO | 2020012339 A1 | 1/2020 | |
| WO | 2020031107 A1 | 2/2020 | |
| WO | 2020077217 A1 | 4/2020 | |
| WO | 2020167994 A1 | 8/2020 | |
| WO | 2020168011 A1 | 8/2020 | |
| WO | 2020176428 A1 | 9/2020 | |
| WO | 2020181247 A1 | 9/2020 | |
| WO | 2020216764 A1 | 10/2020 | |
| WO | 2020216766 A1 | 10/2020 | |
| WO | 2020223536 A1 | 11/2020 | |
| WO | 2020223538 A1 | 11/2020 | |
| WO | 2020252205 A1 | 12/2020 | |
| WO | 2020252207 A1 | 12/2020 | |

OTHER PUBLICATIONS

Axten, J.M. et al. (2012). "Discovery of 7-methyl-5-(1-{[3-(trifluoromethyl)phenyl]acetyl}-2,3-dihydro-1 H-indol-5-yl)-7H-pyrrolo[2,3-d]pyrimidin-4-amine (GSK2606414), a potent and selective first-in-class inhibitor of protein kinase R (PKR)-like endoplasmic reticulum kinase (PERK)," J Med Chem. 55(16):7193-7207.

Bain, J. et al. (2003). "The Specificities of Protein Kinase Inhibitors: An Update," Biochem J. 371(Pt 1):199-204.

Baird, T.D. et al. (2012). "Eukaryotic Initiation Factor 2 Phosphorylation and Translational Control in Metabolism," Adv Nutr. 3(3):307-321.

Bartsch, D. et al. (1995). "Aplysia CREB2 Represses Long-Term Facilitation: Relief of Repression Converts Transient Facilitation Into Long-Term Functional and Structural Change," Cell 83(6):979-992.

Beck, D. et al. (2013). "Vemurafenib Potently Induces Endoplasmic Reticulum Stress-Mediated Apoptosis in BRAFV600E Melanoma Cells," Sci Signal. 6(260):ra7, 12 pages.

Bi, M. et al. (2005). "ER Stress-Regulated Translation Increases Tolerance to Extreme Hypoxia and Promotes Tumor Growth," EMBO J. 24(19):3470-3481.

BioCare Medical, MM620L "Mouse-on-Mouse HRP-Polymer: Mouse Antibodies on Mouse Tissues Polymer Detection Component, Control No. 902-MM620-090617", Biocare Medical, located at <https://biocare.net/wp-content/uploads/MM620.pdf>, lasted visited Feb. 28, 2019, 2 pages.

Bogorad, A.M. et al. (Feb. 9, 2018). "eIF2B Mechanisms of Action and Regulation: A Thermodynamic View", Biochemistry 57:1426-1435.

Borck, G. et al. (2012). "Eif2gamma Mutation That Disrupts Eif2 Complex Integrity Links Intellectual Disability to Impaired Translation Initiation," Mol Cell 48(4):641-646.

Brazeau, J.F. (2014). "Triazolo[4,5-d]pyrimidine Derivatives as Inhibitors of GCN2m," ACS Med Chem Lett. 5(4):282-283.

Cell Signaling Technology, catalog No. 11815 (Nov. 26, 2018). "ATF-4 (D4B8) Rabbit mAb", located at www.cellsignal.com, last visited on Jun. 27, 2019, 2 pages.

Chang, R.C. et al. (2002). "Involvement of Double-Stranded RNA-Dependent Protein Kinase and Phosphorylation of Eukaryotic Initiation Factor-2alpha in Neuronal Degeneration," J Neurochem 83(5):1215-1225.

Chen, A. et al. (2003). "Inducible Enhancement of Memory Storage and Synaptic Plasticity in Transgenic Mice Expressing an Inhibitor of ATF4 (CREB-2) and C/EBP Proteins," Neuron 39(4):655-669.

Chen, H.M. et al. (2008). "A Chemical Compound Commonly Used to Inhibit PKR, {8-(imidazol-4-ylmethylene)-6H-azolidino[5,4-g]benzothiazol-7-one}, Protects Neurons by Inhibiting Cyclin-Dependent Kinase," Eur J Neurosci. 28(10):2003-2016.

Chou, A. et al. (e-pub. Jul. 10, 2017). "Inhibition of the Integrated Stress Response Reverses Cognitive Deficits After Traumatic Brain Injury", Proc Natl Acad Sci USA 114(31):E6420-E6426.

Clavarino, G. et al. (2016). "Unfolded Protein Response Gene GADD34 is Overexpressed in Rheumatoid Arthritis and Related to the Presence of Circulating Anti-Citrullinated Protein Antibodies," Autoimmunity 49(3):172-178.

Cnop, M. et al. (2007). "Selective Inhibition of Eukaryotic Translation Initiation Factor 2 Alpha Dephosphorylation Potentiates Fatty Acid-Induced Endoplasmic Reticulum Stress and Causes Pancreatic Beta-Cell Dysfunction and Apoptosis," J Biol Chem. 282(6): 3989-3997.

Costa-Mattioli, M. et al. (2007). "eIF2alpha Phosphorylation Bidirectionally Regulates the Switch From Short- to Long-Term Synaptic Plasticity and Memory," Cell 129(1):195-206.

Costa-Mattioli, M. et al. (2005). "Translational control of hippocampal synaptic plasticity and memory by the eIF2alpha kinase GCN2," Nature 436(7054):1166-1173.

Costa-Mattioli, M. et al. (2009). "Translational Control of Long-Lasting Synaptic Plasticity and Memory," Neuron 61(1):10-26.

Costa-Mattioli, M. et al. (2009). "Translational Regulatory Mechanisms in Synaptic Plasticity and Memory Storage," Prog Mol Biol Transl Sci 90:293-311.

Couturier, J. et al. (2010). "Interaction of double-stranded RNA-dependent protein kinase (PKR) with the death receptor signaling pathway in amyloid beta (Abeta)-treated cells and in APPSLPS1 knock-in mice," J Biol Chem. 285(2):1272-1282.

Couturier, J. et al. (2012). "Pharmacological Inhibition of PKR in Appsweps1de9 Mice Transiently Prevents Inflammation at 12 Months of Age But Increases Abeta42 Levels in the Late Stages of the Alzheimer's Disease," Curr Alzheimer Res. 9(3):344-360.

De Benedetti, A. (2004). "EIF-4E Expression and Its Role in Malignancies and Metastases," Oncogene 23(18):3189-99.

Deng, J. et al. (2004). "Translational Repression Mediates Activation of Nuclear Factor Kappa B by Phosphorylated Translation Initiation Factor 2," Mol Cell Biol. 24(23):10161-10168.

Dey, S. et al. (2015). "ATF4-Dependent Induction of Heme Oxygenase 1 Prevents Anoikis and Promotes Metastasis," J Clin Invest. 125(7):2592-608.

Di Prisco, G.V. et al. (Aug. 2014). "Translational Control of MGluR-Dependent Long-Term Depression and Object-Place Learning by eIF2α," Nat Neurosci. 17(8):1073-1082, 29 pages.

Farook, J.M. et al. (2013). "GADD34 Induces Cell Death Through Inactivation of Akt Following Traumatic Brain Injury," Cell Death Dis 4:e754, 9 pages.

Fels, D.R. et al. (2006). The PERK/eIF2alpha/ATF4 module of the UPR in hypoxia resistance and tumor growth. Cancer Biol Ther, 2006. 5(7): p. 723-8.

Fuster, J.J. et al. (Mar. 19, 2019). "Integrated Stress Response Inhibition in Atherosclerosis", JACC 73(10):1170-1172.

Gelman, M.S. et al. (202). "A Principal Role for the Proteasome in Endoplasmic Reticulum-Associated Degradation of Misfolded Intracellular Cystic Fibrosis Transmembrane Conductance Regulator," J Biol Chem. 277(14):11709-11714.

Gordiyenko, Y. et al. (e-pub. Dec. 21, 2018). "Structural Basis for the Inhibition of Translation Through eIF2α Phosphorylation", Article, 37 pages.

Grolleau, A. et al. (2000). "Impaired Translational Response and Increased Protein Kinase PKR Expression in T Cells From Lupus Patients," J. Clin. Invest. 106(12):1561-1568.

Guppy, M. et al. (2005). "Metabolic Depression: A Response of Cancer Cells to Hypoxia?," Comp. Biochem. Physiol. B Biochem. Mol. Biol. 140(2): 233-239.

Halliday, M. et al. (2015, e-pub. Mar. 5, 2015). "Partial Restoration of Protein Synthesis Rates by the Small Molecule ISRIB Prevents Neurodegeneration without Pancreatic Toxicity", Cell Death Dis 6:e1672, 9 pages.

Halliday, M. et al. (2017). "Repurposed Drugs Targeting eIF2a-P-Mediated Translational Repression Prevent Neurodegeneration in Mice", Brain 17 pages.

(56) References Cited

OTHER PUBLICATIONS

Han, S. et al. (2006). "Macrophage Insulin Receptor Deficiency Increases ER Stress-Induced Apoptosis and Necrotic Core Formation in Advanced Atherosclerotic Lesions," Cell Metab. 3(4):257-266.

Harding, H.P. et al. (2003). "An Integrated Stress Response Regulates Amino Acid Metabolism and Resistance to Oxidative Stress," Mol. Cell 11(3):619-633.

Harding, H.P. et al. (2000). "Perk Is Essential for Translational Regulation and Cell Survival During the Unfolded Protein Response," Mol. Cell 5(5):897-904.

Harding, H.P. et al. (2000). "Regulated Translation Initiation Controls Stress-Induced Gene Expression in Mammalian Cells," Mol. Cell 6(5): 1099-1108.

Hearn, B.R. et al. (2016). "Structure-Activity Studies of Bis-O-Arylglycolamides: Inhibitors of the Integrated A Stress Response," Chem. Med. Chem 11:870-880.

Hinnebusch, A.G. (2005). "Translational Regulation of GCN4 and the General Amino Acid Control of Yeast", Annu Rev Microbiol 59:407-450.

Hinnebusch, A.G. et al. (May 5, 2015). "Blocking Stress Response for Better Memory?," Science 348(6238):967-968.

Hodgson, R.E. (Apr. 1, 2019, e-pub. Feb. 6, 2019). "Cellular eIF2B Subunit Localization: Implications for the Integrated Stress Response and its Control by Small Molecule Drugs", Mol. Biol. Cell 30:942-958.

Hosoi, T. et al. (2016, e-pub. Aug. 12, 2016). "Unique Pharmacological Property of ISRIB in Inhibition of Ab-Induced Neuronal Cell Death", J. Pharm. Sci. 131 :292-295.

International Search Report and Written Opinion of the International Searching Authority dated Apr. 19, 2019, for Patent Application No. PCT/US18/65555, filed Dec. 13, 2018, 16 pages.

Invitation to Pay Additional Fees, dated Feb. 14, 2019, for PCT Application No. PCT/US2018/65555, filed Dec. 13, 2018, 3 pages.

Jackson, R J et al. (2010). "The Mechanism of Eukaryotic Translation Initiation and Principles of Its Regulation," Nat. Rev. Mol. Cell Biol. 11(2):113-127.

Jammi, N.V. et al. (2003). Small Molecule Inhibitors of the RNA-Dependent Protein Kinase, Biochem. Biophys. Res. Commun. 308(1):50-57.

Jiang, H.Y. et al. (2005). "GCN2 Phosphorylation of eIF2alpha Activates NF-kappaB in Response to UV Irradiation," Biochem. J. 385(Pt 2):371-380.

Kaidanovich-Belin, O. et al. (2011). "Assessment of Social Interaction Behaviors," J. Vis. Exp. 48:e2473, 6 pages.

Kammer, G.M., et al. (2002). "Abnormal T Cell Signal Transduction in Systemic Lupus Erythematosus," Arthritis Rheum. 46(5):1139-1154.

Kashiwagi, K et al. (2016). "Crystal Structure of Eukaryotic Translation Initiation Factor 2B", Nature 000(00):1-17.

Kashiwagi, K et al. (May 3, 2019). "Structural Basis for eIF2B Inhibition in Integrated Stress Response", Science 364(6439):495-499.

Kim, H.J., et al. (2014). "Therapeutic Modulation of Eif2alpha Phosphorylation Rescues TDP-43 Toxicity in Amyotrophic Lateral Sclerosis Disease Models," Nat Genet. 46(2):152-160.

Kim, S.H. et al. (2000). "Human Breast Cancer Cells Contain Elevated Levels and Activity of the Protein Kinase, PKR," Oncogene 19(27):3086-3094.

Kim, S.H., et al. (2002). "Neoplastic Progression in Melanoma and Colon Cancer Is Associated With Increased Expression and Activity of the Interferon-Inducible Protein Kinase, PKR," Oncogene 21(57):8741-8748.

Krishnamoorthy, T. et al. (2001). "Tight Binding of the Phosphorylated Alpha Subunit of Initiation Factor 2 (eIF2alpha) to the Regulatory Subunits of Guanine Nucleotide Exchange Factor eIF2B Is Required for Inhibition of Translation Initiation," Mol. Cell Biol. 21(15):5018-5030.

Kusio-Kobialka, M. et al. (2012). "The PERK-eIF2alpha Phosphorylation Arm Is a Pro-Survival Pathway of BCR-ABL Signaling and Confers Resistance to Imatinib Treatment in Chronic Myeloid Leukemia Cells," Cell Cycle 11(21):4069-4078.

Lawrence De Koning, A.B., et al. (2003). "Hyperhomocysteinemia and Its Role in the Development of Atherosclerosis," Clin. Biochem. 36(6):431-441.

Lehman, S.L. et al. (Jun. 30, 2015). "Signaling Through Alternative Integrated Stress Response Pathways Compensates for GCN2 Loss in a Mouse Model of Soft Tissue Sarcoma", Sci Rep 5(11781):1-13.

Li, J. et al. (2018). "Deletion of Tmtc4 Activates the Unfolded Protein Response and Causes Postnatal", J Clin Invest 128(11):5150-5162.

Li, K. et al. (2016). "Liver-Specific Gene Inactivation of the Transcription Factor ATF4 Alleviates Alcoholic Liver Steatosis in Mice," J. Biol Chem. 291(35):18536-18546.

Lin, Y. et al. (Sep. 3, 2014). "Impaired Eukaryotic Translation Initiation Factor 2B Activity Specifically in Oligodendrocytes Reproduces the Pathology of Vanishing White Matter Disease in Mice", J Neurosci 34(36):12182-12191.

Lobo, M.V. et al. (2000). "Levels, Phosphorylation Status and Cellular Localization of Translational Factor eIF2 in Gastrointestinal Carcinomas," Histochem. J. 32(3):139-150.

Lopez, J. et al. (2015). "Memory Retrieval Requires Ongoing Protein Synthesis and NMDA Receptor Activity-Mediated AMPA Receptor Trafficking," J. Neurosci. 35(6):2465-2475.

Lu, M., et al. (2014). "Opposing Unfolded-Protein-Response Signals Converge on Death Receptor 5 to Control Apoptosis," Science 345(6192):98-101.

Lu, P.D. et al. (2004). "Translation Reinitiation At Alternative Open Reading Frames Regulates Gene Expression in an Integrated Stress Response," J. Cell Biol. 167(1):27-33.

Ma, T., et al. (2013). "Suppression of eIF2alpha Kinases Alleviates Alzheimer's Disease-Related Plasticity and Memory Deficits," Nat. Neurosci. 16(9):1299-1305.

Ma, X.H., et al. (2014). "Targeting ER Stress-Induced Autophagy Overcomes BRAF Inhibitor Resistance in Melanoma," J. Clin. Invest. 124(3):1406-1417.

Marco, S.D. et al. (2012, e-pub. Jun. 12, 2012) "The Translation Inhibitor Pateamine A Prevents Cachexia-Induced Muscle Wasting in Mice," Nat. Commun. 12(3):896, 12 pages.

Mihailovich, M., et al. (2007). "Complex Translational Regulation of BACE1 Involves Upstream Augs and Stimulatory Elements Within the 5' Untranslated Region," Nucleic Acids Res. 35(9):2975-2985.

Moller, J.T. et al. (1998). "Long-Term Postoperative Cognitive Dysfunction in the Elderly ISPOCD1 Study. ISPOCD investigators. International Study of Post-Operative Cognitive Dysfunction," Lancet 351(9106):857-861.

Moreno, J.A. et al. (2013). "Oral Treatment Targeting the Unfolded Protein Response Prevents Neurodegeneration and Clinical Disease in Prion-Infected Mice," Sci. Transl. Med. 5(206):06ra138, 11 pages.

Moreno, J.A. et al. (2012). "Sustained Translational Repression by eIF2alpha-P Mediates Prion Neurodegeneration," Nature 485(7399):507-511.

Munn, D.H., et al. (2005). "GCN2 kinase in T Cells Mediates Proliferative Arrest and Anergy Induction in Response to Indoleamine 2,3-Dioxygenase," Immunity 22(5):633-642.

Nagaraju, K. et al. (2005). "Activation of the Endoplasmic Reticulum Stress Response in Autoimmune Myositis: Potential Role in Muscle Fiber Damage and Dysfunction," Arthritis Rheum. 52(6):1824-1835.

Nagasawa, I. et al. (2017). "BRAF-Mutated Cells Activate GCN2-Mediated Integrated Stress Response As a Cytoprotective Mechanism in Response to Vemurafenib," Biochem. Biophys. Res. Commun. 482(4):1491-1497.

Nakamura, T. et al. (2014). "Small-Molecule Inhibitors of PKR Improve Glucose Homeostasis in Obese Diabetic Mice," Diabetes 63(2):526-534.

Novoa, I. et al. (2003). "Stress-Induced Gene Expression Requires Programmed Recovery From Translational Repression," EMBO J. 22(5):1180-1187.

(56) References Cited

OTHER PUBLICATIONS

O'Connor, T. et al. (2008). "Phosphorylation of the Translation Initiation Factor EIf2alpha Increases BACE1 Levels and Promotes Amyloidogenesis," Neuron 60(6):988-1009.
Ohno, M. (Apr. 2014). "Roles of eIF2alpha Kinases in the Pathogenesis of Alzheimer's Disease", Front Mol Neurosci 7(22):1-8.
Oliveira, M.M. et al. (2019). "The eIF2B Stimulating Drug ISRIB Alleviates Brain Translational Repression and Rescues Long-Term Memory in Alzheimer's Disease Models", Article, 44 pages.
Oyadomari, S. et al. (2008). "Dephosphorylation of Translation Initiation Factor 2alpha Enhances Glucose Tolerance and Attenuates Hepatosteatosis in Mice," Cell Metab. 7(6):520-532.
Page, G. et al., Activated double-stranded RNA-dependent protein kinase and neuronal death in models of Alzheimer's disease. Neuroscience, 2006. 139(4): 1343-54.
Pakos-Zebrucka, K. et al. (2016, e-pub. Sep. 14, 2016). "The integrated Stress Response", EMBO Reports 17(10):1374-1395.
Palam, L.R. et al. (2011). "Phosphorylation of eIF2 Facilitates Ribosomal Bypass of an Inhibitory Upstream ORF to Enhance CHOP Translation", J Biol Chem. 286(13):10939-10949.
Palam, L.R. et al. (2015, e-pub. Oct. 15, 2015). "Integrated Stress Response is Critical for Gemcitabine Resistance in Pancreatic Ductal Adenocarcinoma", Cell Death and Disease 6(e1913):1-13.
Peel, A.L. et al. (2001). "Double-Stranded RNA-Dependent Protein Kinase, PKR, Binds Preferentially to Huntington's Disease (HD) Transcripts and Is Activated in HD Tissue," Hum Mol Genet. 10(15):1531-1518.
Pike, L.R. et al. (2013). "Transcriptional Up-Regulation of ULK1 by ATF4 Contributes to Cancer Cell Survival," Biochem J 449(2):389-400.
PubChem (Jan. 25, 2012). "AKOS007163870 (N-[2-(4-Chlorophenoxy)ethyl]-1-(3-phenoxypropanoyl)piperidine-4-carboxamide) (PubChemCID:55856026)," located at <https://pubchem.ncbi.nlm.nih.gov/compound/55856026>, last visited Jun. 27, 2019, 10 pages.
PubChem (Jul. 9, 2005). "ISRIB (PubChemCID:1011240)," located at: < https://pubchem.ncbi.nlm.nih.gov/compound/1011240>, lasted visited Jun. 27, 2019, 17 pages.
PubChem (Nov. 29, 2013). "ZINC10313554 MCULE-8385854081 (N-[2-[[2-(2,4-Dichlorophenoxy)acetyl]amino]ethyl]quinoline-2-carboxamide) (PubChemCID:71946601)", 4 pages.
Rabouw, H.H. et al. (Feb. 5, 2019). "Small Molecule ISRIB Suppresses the Integrated Stress Response within a Defined Window of Activation", PNAS 116(6):2097-2102.
Radford, H. et al. (2015). "PERK Inhibition Prevents Tau-Mediated Neurodegeneration in a Mouse Model of Frontotemporal Dementia," Acta Neuropathol. 130(5):633-642.
Raught, B. et al. (1996). "Expression of a Translationally Regulated, Dominant-Negative CCAAT/Enhancer-Binding Protein Beta Isoform and Up-Regulation of the Eukaryotic Translation Initiation Factor 2alpha Are Correlated With Neoplastic Transformation of Mammary Epithelial Cells," Cancer Res. 56(19):4382-4386.
Richardson, J.P. et al. (2004). "Mutations Causing Childhood Ataxia With Central Nervous System Hypomyelination Reduce Eukaryotic Initiation Factor 2B Complex Formation and Activity," Mol Cell Biol. 24(6):2352-2363.
Robert, F. et al. (2009). Blocking UV-Induced Eif2alpha Phosphorylation With Small Molecule Inhibitors of GCN2, Chem Biol Drug Des 74(1):57-67.
Rodriguez, P.C. et al. (2010). "L-Arginine Deprivation Regulates Cyclin D3 mRNA Stability in Human T Cells by Controlling Hur Expression," J Immunol. 185(9):5198-5204.
Romero-Ramirez, L. et al. (Apr. 27, 2017). "Integrated Stress Response as a Therapeutic Target for CNS Injuries", HINDAWI 2017(6953156):1-8.
Ron, D. et al. (2007). Signal Integration in the Endoplasmic Reticulum Unfolded Protein Response, Nat Rev Mol Cell Biol. 8(7):519-29.

Rosenwald, I.B. et al. (2001). "Expression of Eukaryotic Translation Initiation Factors 4E and 2alpha Is Increased Frequently in Bronchioloalveolar But Not in Squamous Cell Carcinomas of the Lung," Cancer 92(8):2164-2171.
Ryoo, H.D. et al. (2017). "Two Distinct Nodes of Translational Inhibition in the Integrated Stress Response", BMP Rep. 50(11):539-545.
Scaiewicz, V. et al. (2013). "CCAAT/Enhancer-Binding Protein Homologous (CHOP) Protein Promotes Carcinogenesis in the DEN-Induced Hepatocellular Carcinoma Model," PLoS One 8(12):e81065.
Scheuner, D., et al. (2001). "Translational Control Is Required for the Unfolded Protein Response and In Vivo Glucose Homeostasis," Mol Cell 7(6):1165-1176.
Sekine, Y. et al. (Apr. 9, 2015). "Mutations in a Translation Initiation Factor Identify the Target of a Memory-Enhancing Compound", Science aaa6986:1-6.
Sharma, D.K. et al. (2016). "Role of Eukaryotic Initiation Factors during Cellular Stress and Cancer Progression," J Nucleic Acids 2016:8235121.
Shrestha, N. et al. (2012). "Eukaryotic Initiation Factor 2 (eIF2) Signaling Regulates Proinflammatory Cytokine Expression and Bacterial Invasion," J Biol Chem. 287(34):28738-28744.
Sidrauski, C. et al. (Apr. 15, 2015). "Pharmacological Dimerization and Activation of the Exchange Factor eIF2B Antagonizes the Integrated Stress Response", Elife 4(e07314):1-27.
Sidrauski, C. et al. (Feb. 26, 2015). "The Small Molecule ISRIB Reverses the Effects of eIF2α Phosphorylation on Translation and Stress Granule Assembly", eLIFE 4(e05033):1-16.
Sidrauski, C. et al. (May 28, 2013). "Pharmacological Brake-Release of mRNA Translation Enhances Cognitive Memory", eLIFE 2(e00498):1-22.
Southwood, C.M. et al. (2002). "The Unfolded Protein Response Modulates Disease Severity in Pelizaeus-Merzbacher Disease," Neuron 36(4):585-596.
Stutzbach, L.D. et al. (2013). "The Unfolded Protein Response Is Activated in Disease-Affected Brain Regions in Progressive Supranuclear Palsy and Alzheimer's Disease," Acta Neuropathol Commun. 1(31):1-13.
Tabas, I. et al. (2011). "Integrating the Mechanisms of Apoptosis Induced by Endoplasmic Reticulum Stress," Nat Cell Biol. 13(3):184-190.
Taylor, S.S. et al. (2005). "PKR and eIF2alpha: Integration of Kinase Dimerization, Activation, and Substrate Docking," Cell 122(6):823-825.
Trinh, M.A. et al. (Oct. 2013). "Translational Control by eIF2α Kinases in Long-lasting Synaptic Plasticity and Long-term Memory", Neurobiol Learn Mem. 105:93-99.
Trinh, M.A. et al., Brain-specific disruption of the eIF2alpha kinase PERK decreases ATF4 expression and impairs behavioral flexibility. Cell Rep, 2012. 1(6): 676-688.
Tsai, J.C. et al. (Mar. 30, 2018). "Structure of the Nucleotide Exchange Factor eIF2B Reveals Mechanism of Memory-Enhancing Molecule", Science 359(6383):1-20.
Van Der Knaap, M.S. et al. (2006). "Vanishing White Matter Disease," Lancet Neurol. 5(5):413-23.
Van Der Voorn, J.P. et al. (2005). "The Unfolded Protein Response in Vanishing White Matter Disease," J Neuropathol Exp Neurol. 64(9):770-775.
Vattem, K.M. et al. (2004). "Reinitiation Involving Upstream ORFS Regulates ATF4 Mrna Translation in Mammalian Cells," Proc Natl Acad Sci U S A 101(31):11269-11274.
Vilas-Boas, et al. (2016). "Impairment of Stress Granule Assembly Via Inhibition of the Eif2alpha Phosphorylation Sensitizes Glioma Cells to Chemotherapeutic Agents," J Neurooncol. 127(2): p. 253-60.
Walter, P. et al. (2011). "The Unfolded Protein Response: From Stress Pathway to Homeostatic Regulation," Science 334(6059):1081-1086.
Wang, C. et al. (Jul. 19, 2018). "Inhibiting the Integrated Stress Response Pathway Prevents Aberrant Chondrocyte Differentiation Thereby Alleviating Chondrodysplasia", eLIFE 7(e37673):1-35.

(56) References Cited

OTHER PUBLICATIONS

Wang, S. et al. (2001). "Expression of Eukaryotic Translation Initiation Factors 4E and 2alpha Correlates With the Progression of Thyroid Carcinoma," Thyroid 11(12):1101-1107.

Wang, S. et al. ( ). Expression of the eukaryotic translation initiation factors 4E and 2alpha in non-Hodgkin's lymphomas. Am J Pathol, 1999. 155(1): p. 247-55.

Wang, Y. et al. (2013). "Amino Acid Deprivation Promotes Tumor Angiogenesis Through the GCN2/ATF4 Pathway," Neoplasia 15(8)989-997.

Way, S. et al. (Apr. 2016). "Harnessing the Integrated Stress Response for the Treatment of Multiple Sclerosis", Lancet Neurol. 15(4):434-443.

Wek, R.C. et al. (2006). "Coping with Stress: eIF2 Kinases and Translational Control," Biochem Soc Trans 34(Pt 1):7-11.

Wek, S.A. et al. (1995). "The Histidyl-tRNA Synthetase-Related Sequence in the Eif-2 Alpha Protein Kinase GCN2 Interacts With TRNA and Is Required for Activation in Response to Starvation for Different Amino Acids," Mol Cell Biol. 15(8):4497-506.

Wong, Y. L. (Jan. 9, 2019). "eIF2B Activator Prevents Neurological Defects Caused by a Chronic Integrated Stress Response", eLIFE 8(e42940):1-31.

Wong, Y. L. et al. (Feb. 28, 2018). "The Small Molecule ISRIB Rescues the Stability and Activity of Vanishing White Matter Disease eIF2B Mutant Complexes", eLIFE 7(e32733):1-23.

Wortham, N.C. (2015). "eIF2B: Recent Structural and Functional Insights into a Key Regulator of Translation", Biochemical Society Transactions 43(6):1234-1240.

Yang, L.B. et al. (2003). "Elevated Beta-Secretase Expression and Enzymatic Activity Detected in Sporadic Alzheimer Disease," Nat Med. 9(1):3-4.

Ye, J. et al.(2010). "The GCN2-ATF4 Pathway Is Critical for Tumour Cell Survival and Proliferation in Response to Nutrient Deprivation," EMBO J. 29(12):2082-2096.

Yefidoff-Freedman, R. et al. (e-pub. Jun. 7, 2017). "Development of 1-((1,4-trans)-4-aryloxycyclohexyl)-3-arylurea Activators of the Heme Regulated Inhibitor as Selective Activators of Eucaryotic Translation Initiation Factor 2 Alpha (eIF2#) Phosphorylation Arm of the Integrated Endoplasmic Reticulum Stress Response", J. Med. Chem. 60(13):1-54.

Zhan, K. et al. (2002). "Phosphorylation of Eukaryotic Initiation Factor 2 by Heme-Regulated Inhibitor Kinase-Related Protein Kinases in Schizosaccharomyces Pombe Is Important for Fesistance to Environmental Stresses," Mol Cell Biol. 22(20):7134-7146.

Zhu, P.J. et al. (2011). "Suppression of PKR Promotes Network Excitability and Enhanced Cognition by Interferon-Gamma-Mediated Disinhibition," Cell 147(6):1384-1396.

Zyryanova, A.F. (Mar. 30, 2018). "Binding of ISRIB Reveals a Regulatory Site in the Nucleotide Exchange Factor, eIF2B", Science 359(6383):1533-1536.

International Search Report dated Oct. 10, 2019, for Patent Application No. PCT/US19/35593, filed Jun. 5, 2019, 5 pages.

Written Opinion of the International Searching Authority dated Oct. 10, 2019, for Patent Application No. PCT/US19/35593, filed Jun. 5, 2019, 7 pages.

Dezwaan-Mccabe, D. et al. (2013). "The Stress-Regulated Transcription Factor CHOP Promotes Hepatic Inflammatory Gene Expression, Fibrosis, and Oncogenesis," PLoS Genet. 9(12):e1003937, 12 pages.

PUBCHEM-CID: 125480315 Create Date: Apr. 10, 2017 pp. 1-5; p. 2 structure.

PUBCHEM-CID: 86000498 Create Date: Nov. 3, 2014 pp. 1-5; p. 2 structure.

Adams, C.M. et al. (May 2017). "Role of ATF4 in Skeletal Muscle Atrophy," Curr Opin. Clin. Nutr. Metab. Care 20(3):164-168.

Cao, Y. et al. (2019). "ER Stress-Induced Mediator C/EBP Homologous Protein Thwarts Effector T Cell Activity in Tumors Through T-Bet Repression," Nature Communications 10:1280, 15 pages.

Chen, L. et al. (Aug. 25, 2012). "Tumor suppression by small molecule inhibitors of translation Initiation," Oncotarget 3(8):869-881.

Ebert, S.M. et al. (Apr. 2010, e-pub. Mar. 2, 2010). "The Transcription Factor ATF4 Promotes Skeletal Myofiber Atrophy during Fasting," Mol. Endocrinol. 24(4):790-799.

Ebert, S.M. et al. (Aug. 10, 2012). "Stress-induced Skeletal Muscle Gadd45a Expression Reprograms Myonuclei and Causes Muscle Atrophy," Journal of Biology Chemistry 287(33):27290-27301.

Ebert, S.M. (Oct. 16, 2015, Published, JBC Papers in Press, Sep. 3, 2015). "Identification and Small Molecule Inhibition of an Activating Transcription Factor 4 (ATF4)-dependent Pathway to Agerelated Skeletal Muscle Weakness and Atrophy," 290(42):25497-25511.

Ebert, S.M. et al. (Feb. 28, 2020, e-pub. Jan. 17, 2020). "Activating Transcription Factor 4 (ATF4) Promotes Skeletal Muscle Atrophy by Forming a Heterodimer With the Transcriptional Regulator C/EBPb," JBC (The Journal of Biological Chemistry) 295:2787-2803, 30 pages.

Eley, H.L. (2008, e-pub. Dec. 18, 2007). "Increased Expression of Phosphorylated Forms of RNA-Dependent Protein Kinase and Eukaryotic Initiation Factor 2a May Signal Skeletal Muscle Atrophy in Weight-Losing Cancer Patients," British Journal of Cancer 98:443-449.

Halliday, M. et al. (2015, e-pub. Mar. 5, 2015). "Partial Restoration of Protein Synthesis Rates by the Small Molecule ISRIB Prevents Neurodegeneration Without Pancreatic Toxicity," Cell Death and Disease 6:e1672, 9 pages.

Hernandez, G. et al. (Jan. 8, 2020). "Pancreatitis Is an FGF21-Deficient State That Is Corrected by Replacement Therapy," Sci. Transl. Med. 12:eaay5186, 12 pages.

Igarashi, T. et al. (2007, e-pub. Feb. 12, 2007). "Clock and ATF4 Transcription System Regulates Drug Resistance in Human Cancer Cell Lines," Oncogene 26:4749-4760.

International Preliminary Report on Patentability dated Jun. 16, 2020, for Patent Application No. PCT/US2018/065555, filed Dec. 13, 2018, 7 pages.

International Search Report and Written Opinion of the International Searching Authority dated Jun. 19, 2020, for Patent Application No. PCT/US2020/019552, filed Feb. 24, 2020, 18 pages.

Jiang, Z. et al. (Feb. 17, 2010). "eIF2α Phosphorylation-Dependent Translation in CA1 Pyramidal Cells Impairs Hippocampal Memory Consolidation Without Affecting General Translation," J. Neurosci. 30(7):2582-2594.

Milani, M. et al. (May 15, 2009). "The Role of ATF4 Stabilization and Autophagy in Resistance of Breast Cancer Cells Treated with Bortezomib," Cancer Res. 69(10):4415-4423.

Namba, T. et al. ( ). "Up-Regulation of 150-kDa Oxygen-Regulated Protein by Celecoxib in Human Gastric Carcinoma Cells," Mol. Pharmacol. 71(3):860-870.

Nguyen, H.G. (May 2, 2018). "Development of a Stress Response Therapy Targeting Aggressive Prostate Cancer," Sci. Transl. Med. 10(439):1-24, 24 pages.

Onat, U.I. et al. (Mar. 19, 2019). "Intercepting the Lipid-Induced Integrated Stress Response Reduces Atherosclerosis," JACC 73(10):1149-1169.

Sacheck, J. M. (2007). "Rapid Disuse and Denervation Atrophy Involve Transcriptional Changes Similar to Those of Muscle Wasting During Systemic Diseases," FASEB J. 21:140-155.

Stone, S. et al. (Jul. 29, 2015). "The Unfolded Protein Response in Multiple Sclerosis," 9(264):1-11, 11 pages.

Thevenot, P.T. et al. (Sep. 18, 2014). "The Stress-Response Sensor Chop Regulates the Function and Accumulation of Myeloid-Derived Suppressor Cells in Tumors," 41(3):389-401.

U.S. Appl. No. 16/799,765, filed Feb. 24, 2020, for Sebastian Bernales, et al. (U.S. Patent Application is not submitted herewith pursuant to the waiver of 37 C.F.R. § 1.98(a)(2)(iii) issued by the Office on Sep. 21, 2004.).

U.S. Appl. No. 16/899,520, filed Jun. 11, 2020, for Luz Marina Delgado Oyarzo, et al. (U.S. Patent Application is not submitted herewith pursuant to the waiver of 37 C.F.R. § 1.98(a)(2)(iii) issued by the Office on Sep. 21, 2004.).

(56) References Cited

OTHER PUBLICATIONS

U.S. Appl. No. 16/899,521, filed Jun. 11, 2020, for Sebastian Bernales, et al. (U.S. Patent Application is not submitted herewith pursuant to the waiver of 37 C.F.R. § 1.98(a)(2)(iii) issued by the Office on Sep. 21, 2004.).

Watanabe, S. et al. (pre-print Feb. 27, 2020). "Resetting Proteostasis With ISRIB Prevents Pulmonary Fibrosis," located at: https://www.biorxiv.org/content/10.1101/2020.02.26.965566v1.article-info, last visted on. Jul. 30, 2020, 42 pages.

Youg-Baird, S.K. et al. (Feb. 20, 2020, e-pub. Dec. 10, 2019). "Suppression of MEHMO Syndrome Mutation in eIF2 by Small Molecule ISRIB," Mol. Cell. 77(4):875-886.e7, 66 pages.

Zhu, P. J. et al. (Nov. 15, 2019). "Activation of the ISR Mediates the Behavioral And Neurophysiological Abnormalities in Down Syndrome," Science 366:843-849, 8 pages.

Dermer, G.B. et al. (Mar. 1994). "Another Anniversary for the War on Cancer," Bio/Technology 12:320, 1 page.

Freshney, R.I. et al. (1983). Culture of Animal Cells, A Manual of Basic Technique, Alan R. Liss, Inc., 1983, New York, p. 4 and pp. 129-133, 9 pages.

Golub, T.R. et al. (1999). "Molecular Classification of Cancer: Class Discovery and Class Prediction by Gene Expression Monitoring," Science 236:531-537.

International Preliminary Report on Patentability dated Dec. 17, 2020, for Patent Application No. PCT/US2019/035593, filed Jun. 5, 2019, 9 pages.

International Search Report and Written Opinion of the International Searching Authority dated Oct. 30, 2020, for International Patent Application No. PCT/US20/37309, filed Jun. 11, 2020, 12 pages.

Invitation to Pay Additional Fees, Apr. 13, 2020, for PCT Application No. PCT/US2020/019552, filed Feb. 24, 2020, 3 pages.

Layzer (1996). "Degenerative Diseases of the Nervous System," Cecil Textbook of Medicine, 20th Edition, vol. 2, pp. 2050-2057.

PubChem (Aug. 6, 2016). "N-[[4-[[2-(4-Chlorophenoxy)acetyl]amino]cyclohexyl]methyl]-2-(4-chlorophenyl) acetamide," PubChem-CID: 121258884; 9 pages.

PubChem (Jul. 30, 2007). "N-(1-Benzylpiperidin-4-yl)-1-cyclopropyl-6,7-difluoro-8-methoxy-4-oxoquinoline-3-carboxamide," PubChem CID 16417729, 13 pages.

Remission. (obtained on Jan. 13, 2021) Definition of Remission. Medical Dictionary from Harvard located at: https://www.health.harvard.edu/medical-dictionary-of-health-terms/q-through-z#R-terms, last visited on Jan. 13, 2021, 2 pages.

Remission. (obtained on Jan. 13, 2021) Definition of Remission. NIH: Dictionary of Cancer Terms located at: https://www.cancer.gov/publications/dictionaries/cancer-terms/def/remission, last visited on Jan. 13, 2021, 1 page.

Simone, J.V. et al. (1996). "Oncology," Part XIV in Cecil Textbook of Medicine, 20th edition, Bennet, J.C. et al. eds., W.B. Saunders Company, pp. 1004-1010.

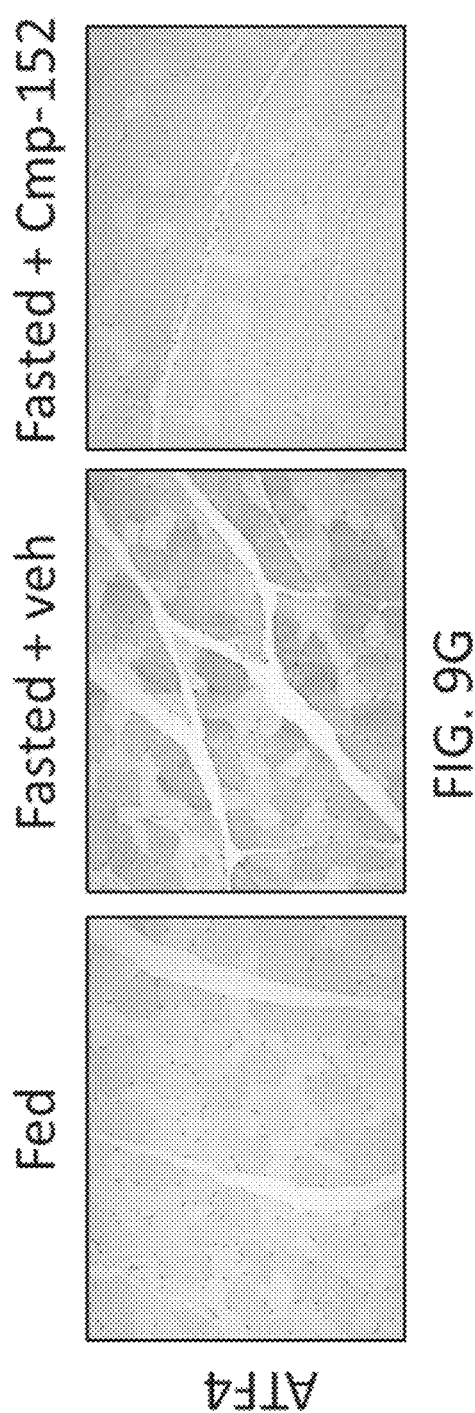

INHIBITORS OF INTEGRATED STRESS RESPONSE PATHWAY

CROSS REFERENCE TO RELATED APPLICATIONS

This application claims the priority benefit of U.S. Provisional Patent Application Nos. 62/598,377, filed Dec. 13, 2017, and 62/690,857, filed Jun. 27, 2018, the disclosures of which are incorporated herein by reference in their entireties.

FIELD

The present disclosure relates generally to therapeutic agents that may be useful as inhibitors of Integrated Stress Response (ISR) pathway.

BACKGROUND

Diverse cellular conditions and stresses activate a widely conserved signaling pathway termed the Integrated Stress Response (ISR) pathway. The ISR pathway is activated in response to intrinsic and extrinsic stresses, such as viral infections, hypoxia, glucose and amino acid deprivation, oncogene activation, UV radiation, and endoplasmic reticulum stress. Upon activation of ISR by one or more of these factors, the eukaryotic initiation factor 2 (eIF2, which is comprised of three subunits, α, β and γ) becomes phosphorylated in its α-subunit and rapidly reduces overall protein translation by binding to the eIF2B complex. This phosphorylation inhibits the eIF2B-mediated exchange of GDP for GTP (i.e., a guanine nucleotide exchange factor (GEF) activity), sequestering eIF2B in a complex with eIF2 and reducing general protein translation of most mRNA in the cell. Paradoxically, eIF2a phosphorylation also increases translation of a subset of mRNAs that contain one or more upstream open reading frames (uORFs) in their 5' untranslated region (UTR). These transcripts include the transcriptional modulator activating transcription factor 4 (ATF4), the transcription factor CHOP, the growth arrest and DNA damage-inducible protein GADD34 and the β-secretase BACE-1.

In animals, the ISR modulates a broad translational and transcriptional program involved in diverse processes such as learning memory, immunity, intermediary metabolism, insulin production and resistance to unfolded protein stress in the endoplasmic reticulum, among others. Activation of the ISR pathway has also been associated with numerous pathological conditions including cancer, neurodegenerative diseases, metabolic diseases (metabolic syndrome), autoimmune diseases, inflammatory diseases, musculoskeletal diseases (such as myopathy), vascular diseases, ocular diseases, and genetic disorders. Aberrant protein synthesis through eIF2a phosphorylation is also characteristic of several other human genetic disorders, cystic fibrosis, amyotrophic lateral sclerosis, Huntington disease and prion disease.

BRIEF SUMMARY

Inhibitors of the Integrated Stress Response (ISR) pathway are described, as are methods of making and using the compounds, or salts thereof.

BRIEF DESCRIPTION OF THE DRAWINGS

9A) or compound 152 (FIG. 9B) administration. FIG. 9G shows visualization of a muscle fiber cross-sectional area (CSA) stained for ATF4 from a fed mouse, a fasting mouse, and a fasting mouse treated with compound 152.

FIG. 14A) or a constitutive promoter (pGAP-PLC; FIG. 14B), cultured in the presence of compound 152 or a control. The arrow in each figure indicates PLC.

FIG. 14C) or a constitutive promoter (pGAP-PLC; FIG. 14D), cultured in the presence of compound 152 or a control, and indicated by fold-change relative to the control.

DETAILED DESCRIPTION

Definitions

Figure 1:
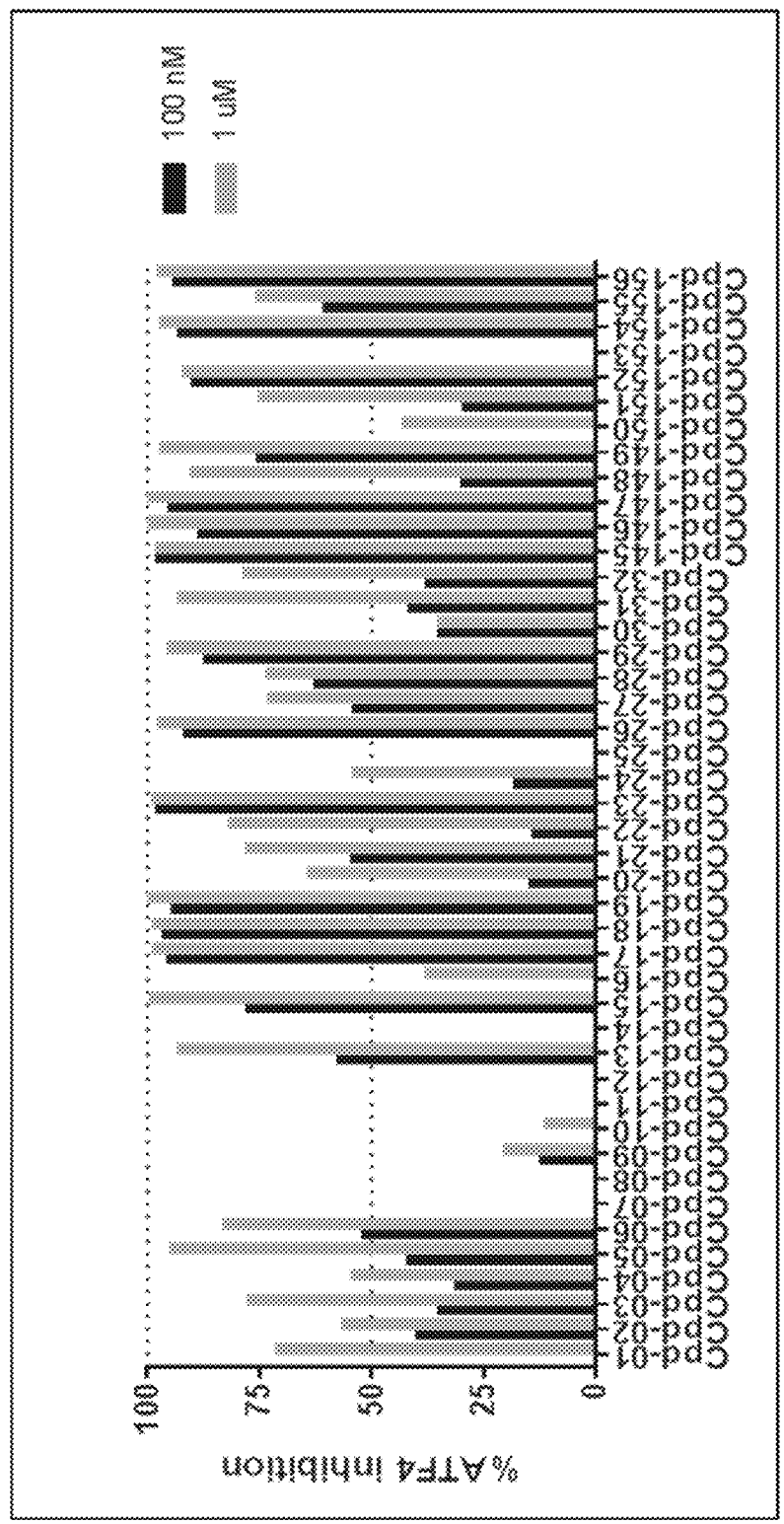
FIG. 1 shows percentage of ATF4 inhibition after induction with thapsigargin (Tg) in the presence of certain test compounds. Percentage of ATF4 inhibition was calculated as the percent reduction normalized to Tg treatment (0% inhibition) and untreated cells (100% inhibition).

For use herein, unless clearly indicated otherwise, use of the terms "a", "an" and the like refers to one or more.

Reference to "about" a value or parameter herein includes (and describes) embodiments that are directed to that value or parameter per se. For example, description referring to "about X" includes description of "X".

"Alkyl" as used herein refers to and includes, unless otherwise stated, a saturated linear (i.e., unbranched) or branched univalent hydrocarbon chain or combination thereof, having the number of carbon atoms designated (i.e., $C_1$-$C_{10}$ means one to ten carbon atoms). Particular alkyl groups are those having 1 to 20 carbon atoms (a "$C_1$-$C_{20}$ alkyl"), having 1 to 10 carbon atoms (a "$C_1$-$C_{10}$ alkyl"), having 6 to 10 carbon atoms (a "$C_6$-$C_{10}$ alkyl"), having 1 to 6 carbon atoms (a "$C_1$-$C_6$ alkyl"), having 2 to 6 carbon atoms (a "$C_2$-$C_6$ alkyl"), or having 1 to 4 carbon atoms (a "$C_1$-$C_4$ alkyl"). Examples of alkyl groups include, but are not limited to, groups such as methyl, ethyl, n-propyl, isopropyl, n-butyl, t-butyl, isobutyl, sec-butyl, n-pentyl, n-hexyl, n-heptyl, n-octyl, n-nonyl, n-decyl, and the like.

"Alkylene" as used herein refers to the same residues as alkyl, but having bivalency. Particular alkylene groups are those having 1 to 20 carbon atoms (a "$C_1$-$C_{20}$ alkylene"), having 1 to 10 carbon atoms (a "$C_1$-$C_{10}$ alkylene"), having 6 to 10 carbon atoms (a "$C_6$-$C_{10}$ alkylene"), having 1 to 6 carbon atoms (a "$C_1$-$C_6$ alkylene"), 1 to 5 carbon atoms (a "$C_1$-$C_5$ alkylene"), 1 to 4 carbon atoms (a "$C_1$-$C_4$ alkylene") or 1 to 3 carbon atoms (a "$C_1$-$C_3$ alkylene"). Examples of alkylene include, but are not limited to, groups such as methylene (—$CH_2$—), ethylene (—$CH_2CH_2$—), propylene (—$CH_2CH_2CH_2$—), isopropylene (—$CH_2CH(CH_3)$—), butylene (—$CH_2(CH_2)_2CH_2$—), isobutylene (—$CH_2CH(CH_3)CH_2$—), pentylene (—$CH_2(CH_2)_3CH_2$—), hexylene (—$CH_2(CH_2)_4CH_2$—), heptylene (—$CH_2(CH_2)_5CH_2$—), octylene (—$CH_2(CH_2)_6CH_2$—), and the like.

"Alkenyl" as used herein refers to and includes, unless otherwise stated, an unsaturated linear (i.e. unbranched) or branched univalent hydrocarbon chain or combination thereof, having at least one site of olefinic unsaturation (i.e., having at least one moiety of the formula C=C) and having the number of carbon atoms designated (i.e., $C_2$-$C_{10}$ means two to ten carbon atoms). An alkenyl group may have "cis" or "trans" configurations, or alternatively have "E" or "Z" configurations. Particular alkenyl groups are those having 2 to 20 carbon atoms (a "$C_2$-$C_{20}$ alkenyl"), having 6 to 10 carbon atoms (a "$C_6$-$C_{10}$ alkenyl"), having 2 to 8 carbon atoms (a "$C_2$-$C_8$ alkenyl"), having 2 to 6 carbon atoms (a "$C_2$-$C_6$ alkenyl"), or having 2 to 4 carbon atoms (a "$C_2$-$C_4$ alkenyl"). Examples of alkenyl group include, but are not limited to, groups such as ethenyl (or vinyl), prop-1-enyl, prop-2-enyl (or allyl), 2-methylprop-1-enyl, but-1-enyl, but-2-enyl, but-3-enyl, buta-1,3-dienyl, 2-methylbuta-1,3-dienyl, pent-1-enyl, pent-2-enyl, hex-1-enyl, hex-2-enyl, hex-3-enyl, and the like.

"Alkenylene" as used herein refers to the same residues as alkenyl, but having bivalency. Particular alkenylene groups are those having 2 to 20 carbon atoms (a "$C_2$-$C_{20}$ alkenylene"), having 2 to 10 carbon atoms (a "$C_2$-$C_{10}$ alkenylene"), having 6 to 10 carbon atoms (a "$C_6$-$C_{10}$ alkenylene"), having 2 to 6 carbon atoms (a "$C_2$-$C_6$ alkenylene"), 2 to 4 carbon atoms (a "$C_2$-$C_4$ alkenylene") or 2 to 3 carbon atoms (a "$C_2$-$C_3$ alkenylene"). Examples of alkenylene include, but are not limited to, groups such as ethenylene (or vinylene) (—CH═CH—), propenylene (—CH═CHCH$_2$—), 1,4-but-1-enylene (—CH═CH—CH$_2$CH$_2$—), 1,4-but-2-enylene (—CH$_2$CH═CHCH$_2$—), 1,6-hex-1-enylene (—CH═CH—(CH$_2$)$_3$CH$_2$—), and the like.

"Alkynyl" as used herein refers to and includes, unless otherwise stated, an unsaturated linear (i.e., unbranched) or branched univalent hydrocarbon chain or combination thereof, having at least one site of acetylenic unsaturation (i.e., having at least one moiety of the formula C≡C) and having the number of carbon atoms designated (i.e., $C_2$-$C_{10}$ means two to ten carbon atoms). Particular alkynyl groups are those having 2 to 20 carbon atoms (a "$C_2$-$C_{20}$ alkynyl"), having 6 to 10 carbon atoms (a "$C_6$-$C_{10}$ alkynyl"), having 2 to 8 carbon atoms (a "$C_2$-$C_8$ alkynyl"), having 2 to 6 carbon atoms (a "$C_2$-$C_6$ alkynyl"), or having 2 to 4 carbon atoms (a "$C_2$-$C_4$ alkynyl"). Examples of alkynyl group include, but are not limited to, groups such as ethynyl (or acetylenyl), prop-1-ynyl, prop-2-ynyl (or propargyl), but-1-ynyl, but-2-ynyl, but-3-ynyl, and the like.

"Alkynylene" as used herein refers to the same residues as alkynyl, but having bivalency. Particular alkynylene groups are those having 2 to 20 carbon atoms (a "$C_2$-$C_{20}$ alkynylene"), having 2 to 10 carbon atoms (a "$C_2$-$C_{10}$ alkynylene"), having 6 to 10 carbon atoms (a "$C_6$-$C_{10}$ alkynylene"), having 2 to 6 carbon atoms (a "$C_2$-$C_6$ alkynylene"), 2 to 4 carbon atoms (a "$C_2$-$C_4$ alkynylene") or 2 to 3 carbon atoms (a "$C_2$-$C_3$ alkynylene"). Examples of alkynylene include, but are not limited to, groups such as ethynylene (or acetylenylene) (—C≡C—), propynylene (—C≡CCH$_2$—), and the like.

"Cycloalkyl" as used herein refers to and includes, unless otherwise stated, saturated cyclic univalent hydrocarbon structures, having the number of carbon atoms designated (i.e., $C_3$-$C_{10}$ means three to ten carbon atoms). Cycloalkyl can consist of one ring, such as cyclohexyl, or multiple rings, such as adamantyl. A cycloalkyl comprising more than one ring may be fused, spiro or bridged, or combinations thereof. Particular cycloalkyl groups are those having from 3 to 12 annular carbon atoms. A preferred cycloalkyl is a cyclic hydrocarbon having from 3 to 8 annular carbon atoms (a "$C_3$-$C_8$ cycloalkyl"), having 3 to 6 carbon atoms (a "$C_3$-$C_6$ cycloalkyl"), or having from 3 to 4 annular carbon atoms (a "$C_3$-$C_4$ cycloalkyl"). Examples of cycloalkyl include, but are not limited to, cyclopropyl, cyclobutyl, cyclopentyl, cyclohexyl, cycloheptyl, norbornyl, and the like.

"Cycloalkylene" as used herein refers to the same residues as cycloalkyl, but having bivalency. Cycloalkylene can consist of one ring or multiple rings which may be fused, spiro or bridged, or combinations thereof. Particular cycloalkylene groups are those having from 3 to 12 annular carbon atoms. A preferred cycloalkylene is a cyclic hydrocarbon having from 3 to 8 annular carbon atoms (a "$C_3$-$C_8$ cycloalkylene"), having 3 to 6 carbon atoms (a "$C_3$-$C_6$ cycloalkylene"), or having from 3 to 4 annular carbon atoms (a "$C_3$-$C_4$ cycloalkylene"). Examples of cycloalkylene include, but are not limited to, cyclopropylene, cyclobutylene, cyclopentylene, cyclohexylene, cycloheptylene, norbornylene, and the like. A cycloalkylene may attach to the remaining structures via the same ring carbon atom or different ring carbon atoms. When a cycloalkylene attaches to the remaining structures via two different ring carbon atoms, the connecting bonds may be cis- or trans- to each other. For example, cyclopropylene may include 1,1-cyclopropylene and 1,2-cyclopropylene (e.g., cis-1,2-cyclopropylene or trans-1,2-cyclopropylene), or a mixture thereof.

"Cycloalkenyl" refers to and includes, unless otherwise stated, an unsaturated cyclic non-aromatic univalent hydrocarbon structure, having at least one site of olefinic unsaturation (i.e., having at least one moiety of the formula C═C) and having the number of carbon atoms designated (i.e., $C_2$-$C_{10}$ means two to ten carbon atoms). Cycloalkenyl can consist of one ring, such as cyclohexenyl, or multiple rings, such as norbornenyl. A preferred cycloalkenyl is an unsaturated cyclic hydrocarbon having from 3 to 8 annular carbon atoms (a "$C_3$-$C_8$ cycloalkenyl"). Examples of cycloalkenyl groups include, but are not limited to, cyclopropenyl, cyclobutenyl, cyclopentenyl, cyclohexenyl, norbornenyl, and the like.

"Cycloalkenylene" as used herein refers to the same residues as cycloalkenyl, but having bivalency.

"Aryl" or "Ar" as used herein refers to an unsaturated aromatic carbocyclic group having a single ring (e.g., phenyl) or multiple condensed rings (e.g., naphthyl or anthryl) which condensed rings may or may not be aromatic. Particular aryl groups are those having from 6 to 14 annular carbon atoms (a "$C_6$-$C_{14}$ aryl"). An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position.

"Arylene" as used herein refers to the same residues as aryl, but having bivalency. Particular arylene groups are those having from 6 to 14 annular carbon atoms (a "$C_6$-$C_{14}$ arylene").

"Heteroaryl" as used herein refers to an unsaturated aromatic cyclic group having from 1 to 14 annular carbon atoms and at least one annular heteroatom, including but not limited to heteroatoms such as nitrogen, oxygen, and sulfur. A heteroaryl group may have a single ring (e.g., pyridyl, furyl) or multiple condensed rings (e.g., indolizinyl, benzothienyl) which condensed rings may or may not be aromatic. Particular heteroaryl groups are 5 to 14-membered rings having 1 to 12 annular carbon atoms and 1 to 6 annular heteroatoms independently selected from nitrogen, oxygen, and sulfur, 5 to 10-membered rings having 1 to 8 annular carbon atoms and 1 to 4 annular heteroatoms independently selected from nitrogen, oxygen, and sulfur, or 5, 6 or 7-membered rings having 1 to 5 annular carbon atoms and 1 to 4 annular heteroatoms independently selected from nitrogen, oxygen, and sulfur. In one variation, particular heteroaryl groups are monocyclic aromatic 5-, 6- or 7-membered rings having from 1 to 6 annular carbon atoms and 1 to 4 annular heteroatoms independently selected from nitrogen, oxygen and sulfur. In another variation, particular heteroaryl groups are polycyclic aromatic rings having from 1 to 12 annular carbon atoms and 1 to 6 annular heteroatoms independently selected from nitrogen, oxygen, and sulfur. A heteroaryl group having more than one ring where at least one ring is non-aromatic may be connected to the parent structure at either an aromatic ring position or at a non-aromatic ring position. In one variation, a heteroaryl group having more than one ring where at least one ring is non-aromatic is connected to the parent structure at an aromatic ring position. A heteroaryl group may be connected to the parent structure at a ring carbon atom or a ring heteroatom.

"Heteroarylene" as used herein refers to the same residues as heteroaryl, but having bivalency.

"Heterocycle", "heterocyclic", or "heterocyclyl" as used herein refers to a saturated or an unsaturated non-aromatic cyclic group having a single ring or multiple condensed rings, and having from 1 to 14 annular carbon atoms and from 1 to 6 annular heteroatoms, such as nitrogen, sulfur or oxygen, and the like. A heterocycle comprising more than one ring may be fused, bridged or spiro, or any combination thereof, but excludes heteroaryl. The heterocyclyl group may be optionally substituted independently with one or more substituents described herein. Particular heterocyclyl groups are 3 to 14-membered rings having 1 to 13 annular carbon atoms and 1 to 6 annular heteroatoms independently selected from nitrogen, oxygen and sulfur, 3 to 12-membered rings having 1 to 11 annular carbon atoms and 1 to 6 annular heteroatoms independently selected from nitrogen, oxygen and sulfur, 3 to 10-membered rings having 1 to 9 annular carbon atoms and 1 to 4 annular heteroatoms independently selected from nitrogen, oxygen and sulfur, 3 to 8-membered rings having 1 to 7 annular carbon atoms and 1 to 4 annular heteroatoms independently selected from nitrogen, oxygen and sulfur, or 3 to 6-membered rings having 1 to 5 annular carbon atoms and 1 to 4 annular heteroatoms independently selected from nitrogen, oxygen and sulfur. In one variation, heterocyclyl includes monocyclic 3-, 4-, 5-, 6- or 7-membered rings having from 1 to 2, 1 to 3, 1 to 4, 1 to 5, or 1 to 6 annular carbon atoms and 1 to 2, 1 to 3, or 1 to 4 annular heteroatoms independently selected from nitrogen, oxygen and sulfur. In another variation, heterocyclyl includes polycyclic non-aromatic rings having from 1 to 12 annular carbon atoms and 1 to 6 annular heteroatoms independently selected from nitrogen, oxygen and sulfur.

"Heterocyclylene" as used herein refers to the same residues as heterocyclyl, but having bivalency.

"Halo" or "halogen" refers to elements of the Group 17 series having atomic number 9 to 85. Preferred halo groups include the radicals of fluorine, chlorine, bromine and iodine. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halogen; thus 4-chloro-3-fluorophenyl is within the scope of dihaloaryl. An alkyl group in which each hydrogen is replaced with a halo group is referred to as a "perhaloalkyl." A preferred perhaloalkyl group is trifluoromethyl ($-CF_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy ($-OCF_3$).

"Carbonyl" refers to the group C=O.

"Thiocarbonyl" refers to the group C=S.

"Oxo" refers to the moiety =O.

"Optionally substituted" unless otherwise specified means that a group may be unsubstituted or substituted by one or more (e.g., 1, 2, 3, 4 or 5) of the substituents listed for that group in which the substituents may be the same of different. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 1 to 3, 1 to 4, 1 to 5, 2 to 3, 2 to 4, or 2 to 5 substituents. In one embodiment, an optionally substituted group is unsubstituted.

Unless clearly indicated otherwise, "an individual" as used herein intends a mammal, including but not limited to a primate, human, bovine, horse, feline, canine, or rodent. In one variation, the individual is a human.

As used herein, "treatment" or "treating" is an approach for obtaining beneficial or desired results including clinical results. For purposes of this disclosure, beneficial or desired results include, but are not limited to, one or more of the following: decreasing one more symptoms resulting from the disease, diminishing the extent of the disease, stabilizing the disease (e.g., preventing or delaying the worsening of the disease), preventing or delaying the spread of the disease, delaying the occurrence or recurrence of the disease, delay or slowing the progression of the disease, ameliorating the disease state, providing a remission (whether partial or total) of the disease, decreasing the dose of one or more other medications required to treat the disease, enhancing effect of another medication, delaying the progression of the disease, increasing the quality of life, and/or prolonging survival. The methods of the present disclosure contemplate any one or more of these aspects of treatment.

As used herein, the term "effective amount" intends such amount of a compound of the invention which should be effective in a given therapeutic form. As is understood in the art, an effective amount may be in one or more doses, i.e., a single dose or multiple doses may be required to achieve the desired treatment endpoint. An effective amount may be considered in the context of administering one or more therapeutic agents (e.g., a compound, or pharmaceutically acceptable salt thereof), and a single agent may be considered to be given in an effective amount if, in conjunction with one or more other agents, a desirable or beneficial result may be or is achieved. Suitable doses of any of the co-administered compounds may optionally be lowered due to the combined action (e.g., additive or synergistic effects) of the compounds.

A "therapeutically effective amount" refers to an amount of a compound or salt thereof sufficient to produce a desired therapeutic outcome.

As used herein, "unit dosage form" refers to physically discrete units, suitable as unit dosages, each unit containing a predetermined quantity of active ingredient calculated to produce the desired therapeutic effect in association with the required pharmaceutical carrier. Unit dosage forms may contain a single or a combination therapy.

As used herein, by "pharmaceutically acceptable" or "pharmacologically acceptable" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

"Pharmaceutically acceptable salts" are those salts which retain at least some of the biological activity of the free (non-salt) compound and which can be administered as drugs or pharmaceuticals to an individual. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Pharmaceutically acceptable salts can be prepared in situ in the manufacturing process, or by separately reacting a purified compound of the present disclosure in its free acid or base form with a suitable organic or inorganic base or acid, respectively, and isolating the salt thus formed during subsequent purification.

The term "excipient" as used herein means an inert or inactive substance that may be used in the production of a drug or pharmaceutical, such as a tablet containing a compound of the present disclosure as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

It is understood that aspects and embodiments described herein as "comprising" include "consisting of" and "consisting essentially of" embodiments.

When a composition is described as "consisting essentially of" the listed components, the composition contains the components expressly listed, and may contain other components which do not substantially affect the disease or condition being treated such as trace impurities. However, the composition either does not contain any other components which do substantially affect the disease or condition being treated other than those components expressly listed; or, if the composition does contain extra components other than those listed which substantially affect the disease or condition being treated, the composition does not contain a sufficient concentration or amount of those extra components to substantially affect the disease or condition being treated. When a method is described as "consisting essentially of" the listed steps, the method contains the steps listed, and may contain other steps that do not substantially affect the disease or condition being treated, but the method does not contain any other steps which substantially affect the disease or condition being treated other than those steps expressly listed.

When a moiety is indicated as substituted by "at least one" substituent, this also encompasses the disclosure of exactly one substituent.

Compounds

In one aspect, provided is a compound of formula (I):

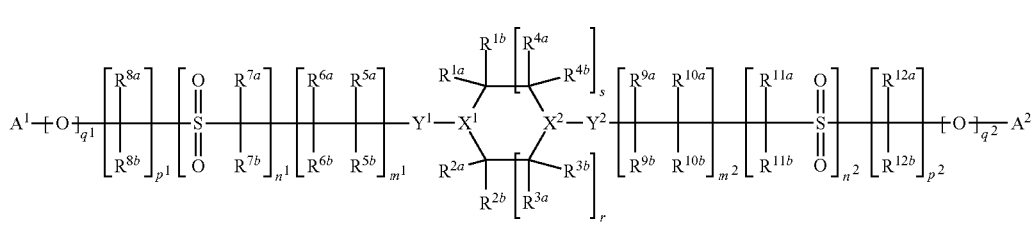

(I)

or a pharmaceutically acceptable salt thereof;
wherein:
$X^1$ and $X^2$, independently of each other, are CH or N;
$Y^1$ is selected from the group consisting of a bond, $NR^{Y1}$, and O; provided that when $X^1$ is N, then $Y^1$ is a bond;
$R^{Y1}$ is hydrogen or $C_1$-$C_6$ alkyl;
$Y^2$ is selected from the group consisting of a bond, $NR^{Y2}$, and O; provided that when $X^2$ is N, then $Y^2$ is a bond;
$R^{Y2}$ is hydrogen or $C_1$-$C_6$ alkyl;
$m^1$, $m^2$, $n^1$, $n^2$, $p^1$, $p^2$, $q^1$, and $q^2$, independently of each other, are 0 or 1;
r and s, independently of each other, are 0, 1, or 2;
$A^1$ is selected from the group consisting of:
a substituent of formula ($A^1$-a)

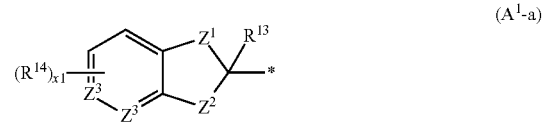

($A^1$-a)

wherein
*represents the attachment point to the remainder of the molecule; $Z^1$ is selected from the group consisting of $CR^{Z1-1}R^{Z1-2}$, $NR^{Z1-2}$, O, S, and $-CR^{Z1-1}=CR^{Z1-1}-$;
wherein $R^{Z1-1}$ is H or $R^{14}$; and $R^{Z1-2}$ is H or $R^{14}$;
$Z^2$ is selected from the group consisting of $CR^{Z2-1}R^{Z2-2}$, $NR^{Z2-2}$; O, S, and $-CR^{Z2-1}=CR^{Z2-1}-$;
wherein $R^{Z2-1}$ is H or $R^{14}$; and $R^{Z2-2}$ is H or $R^{14}$;

$Z^3$, independently at each occurrence, is C or N, provided that at least one $Z^3$ is C;

$R^{13}$ is hydrogen or $R^{14}$, or $R^{13}$ and $R^{Z1-2}$ are taken together to form a double bond between the carbon atom bearing $R^{13}$ and $Z^1$, or $R^{13}$ and $R^{Z2-2}$ are taken together to form a double bond between the carbon atom bearing $R^{13}$ and $Z^2$; and x1 is 0, 1, 2, 3, or 4, provided than when one $Z^3$ is N, then x1 is not 4;

$C_6$-$C_{10}$ aryl optionally substituted with one or more $R^{14}$ substituents; and 5-10 membered heteroaryl optionally substituted with one or more $R^{14}$ substituents;

$R^{14}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —$NH_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —$NR^{14-a}R^{14-b}$, —CN, —C(O)OH, —C(O)O($C_1$-$C_6$ alkyl), —C(O)O($C_1$-$C_6$ haloalkyl), —C(O)$NH_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)$NR^{14-a}R^{14-b}$, —S(O)$_2$OH, —S(O)$_2$O($C_1$-$C_6$ alkyl), —S(O)$_2$O($C_1$-$C_6$ haloalkyl), —S(O)$_2$$NH_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$$NR^{14-a}R^{14-b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);

wherein $R^{14-a}$ and $R^{14-b}$ are taken together with the nitrogen atom which bears them to form a 3-10 membered heterocycle;

$A^2$ is selected from the group consisting of:
a substituent of formula ($A^2$-a)

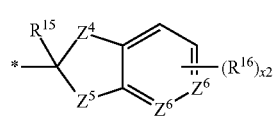

(A²-a)

wherein
* represents the attachment point to the remainder of the molecule; $Z^4$ is selected from the group consisting of $CR^{Z4-1}R^{Z4-2}$, $NR^{Z4-2}$, O, S, and —$CR^{Z4-1}$=$CR^{Z4-1}$—;
wherein $R^{Z4-1}$ is H or $R^{16}$; and $R^{Z4-2}$ is H or $R^{16}$;
$Z^5$ is selected from the group consisting of $CR^{Z5-1}R^{Z5-2}$, $NR^{Z5-2}$, O, S, and —$CR^{Z5-1}$=$CR^{Z5-1}$—;
wherein $R^{Z5-1}$ is H or $R^{16}$; and $R^{Z5-2}$ is H or $R^{16}$;
$Z^6$, independently at each occurrence, is C or N, provided that at least one $Z^6$ is C;

$R^{15}$ is hydrogen or $R^{16}$, or $R^{15}$ and $R^{Z4-2}$ are taken together to form a double bond between the carbon atom bearing $R^{15}$ and $Z^4$, or $R^{15}$ and $R^{Z5-2}$ are taken together to form a double bond between the carbon atom bearing $R^{15}$ and $Z^5$; and x2 is 0, 1, 2, 3, or 4, provided than when one $Z^6$ is N, then x2 is not 4;

$C_6$-$C_{10}$ aryl optionally substituted with one or more $R^{16}$ substituents; and 5-10 membered heteroaryl optionally substituted with one or more $R^{16}$ substituents;

$R^{16}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —$NH_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —$NR^{16-a}R^{16-b}$, —CN, —C(O)OH, —C(O)O($C_1$-$C_6$ alkyl), —C(O)O($C_1$-$C_6$ haloalkyl), —C(O)$NH_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)$NR^{16-a}R^{16-b}$, —S(O)$_2$OH, —S(O)$_2$O($C_1$-$C_6$ alkyl), —S(O)$_2$O($C_1$-$C_6$ haloalkyl), —S(O)$_2$$NH_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$$NR^{16-a}R^{16-b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);

wherein $R^{16-a}$ and $R^{16-b}$ are taken together with the nitrogen atom which bears them to form a 3-10 membered heterocycle;

$R^{1a}$ and $R^{1b}$ are independently selected from the group consisting of hydrogen, $C_1$-$C_6$ alkyl, and halogen;

$R^{2a}$ and $R^{2b}$ are independently selected from the group consisting of hydrogen, $C_1$-$C_6$ alkyl, and halogen;

when present, $R^{3a}$ and $R^{3b}$ are independently at each occurrence selected from the group consisting of hydrogen, $C_1$-$C_6$ alkyl, and halogen;

when present, $R^{4a}$ and $R^{4b}$ are independently at each occurrence selected from the group consisting of hydrogen, $C_1$-$C_6$ alkyl, and halogen;

or alternatively, $R^{1a}$ and $R^{2a}$ are taken together to form a $C_1$-$C_6$ alkylene moiety;

or alternatively, $R^{1a}$ and an $R^{3a}$ moiety, when present, are taken together to form a $C_1$-$C_6$ alkylene moiety, and $R^{1b}$ and the $R^{3b}$ in the geminal position to the $R^{3a}$ taken together with $R^{1a}$, are both hydrogen;

or alternatively, an $R^{3a}$ moiety, when present, and an $R^{4a}$ moiety, when present, are taken together to form a $C_1$-$C_6$ alkylene moiety, and the $R^{3b}$ in the geminal position to the $R^{3a}$ taken together with the $R^{4a}$ moiety and the $R^{4b}$ in the geminal position to the $R^{4a}$ taken together with the $R^{3a}$ moiety, are both hydrogen;

when present, $R^{5a}$ and $R^{5b}$ are taken together to form an oxo (=O) substituent or an imido (=NH) substituent, or alternatively, $R^{5a}$ and $R^{5b}$ are both hydrogen;

when present, $R^{6a}$ is selected from the group consisting of hydrogen, —$OR^{6a-a}$, and —$NR^{6a-b}R^{6a-c}$;

when present, $R^{6b}$ is hydrogen;

or alternatively, $R^{6a}$ and $R^{6b}$ are taken together to form a moiety selected from the group consisting of —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, and —CH$_2$—CH$_2$—CH$_2$—CH$_2$—O—;

when present, $R^{7a}$ and $R^{7b}$ are both hydrogen;

when present, $R^{8a}$ and $R^{8b}$ are taken together to form an oxo (=O) substituent, or alternatively, $R^{8a}$ and $R^{8b}$ are both hydrogen;

when present, $R^{9a}$ and $R^{9b}$ are taken together to form an oxo (=O) substituent or an imido (=NH) substituent, or alternatively, $R^{9a}$ and $R^{9b}$ are both hydrogen;

when present, $R^{10a}$ is selected from the group consisting of hydrogen, —$OR^{10a-a}$, and —$NR^{10a-b}R^{10a-c}$;

when present, $R^{10b}$ is hydrogen;

or alternatively, $R^{10a}$ and $R^{10b}$ are taken together to form a moiety selected from the group consisting of —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, and —CH$_2$—CH$_2$—CH$_2$—CH$_2$—O—;

when present, $R^{11a}$ and $R^{11b}$ are both hydrogen;

when present, $R^{12a}$ and $R^{12b}$ are taken together to form an oxo (=O) substituent, or alternatively, $R^{12a}$ and $R^{12b}$ are both hydrogen;

$R^{6a-a}$ is selected from the group consisting of hydrogen, $C_1$-$C_6$ alkyl, and $C_1$-$C_6$ haloalkyl;

$R^{10a-a}$ is selected from the group consisting of hydrogen, $C_1$-$C_6$ alkyl, and $C_1$-$C_6$ haloalkyl;

or $R^{6a-a}$ and $R^{Y1}$ may be taken together to form a carbonyl (C=O) moiety;

or $R^{10a-a}$ and $R^{Y2}$ may be taken together to form a carbonyl (C=O) moiety;

$R^{6a-b}$ and $R^{6a-c}$, independently of each other, are selected from the group consisting of hydrogen, $C_1$-$C_6$ alkyl, and $C_1$-$C_6$ haloalkyl; and $R^{10a-b}$ and $R^{10a-c}$, independently of each other, are selected from the group consisting of hydrogen, $C_1$-$C_6$ alkyl, and $C_1$-$C_6$ haloalkyl.

In some embodiments, the compound of formula (I) is a compound of formula (1-1):

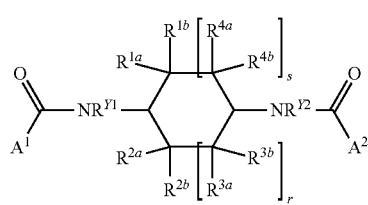

(1-1)

or a pharmaceutically acceptable salt thereof;

wherein:

$A^1$ is a substituent of formula ($A^1$-a)

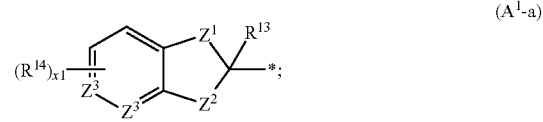

($A^1$-a)

$A^2$ is a substituent of formula ($A^2$-a)

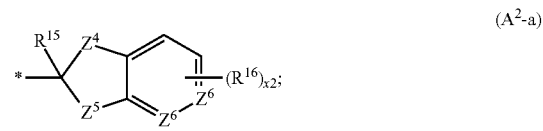

($A^2$-a)

and wherein $R^{Y1}$, $R^{Y2}$, r, s, $Z^1$, $R^{Z1-1}$, $R^{Z1-2}$, $Z^2$, $R^{Z2-1}$, $R^{Z2-2}$, $Z^3$, x1, $Z^4$, $R^{Z4-1}$, $R^{Z4-2}$, $Z^5$, $R^{Z5-1}$, $R^{Z5-2}$, $Z^6$, x2, $R^{1a}$, $R^{1b}$, $R^{2a}$, $R^{2b}$, $R^{3a}$, $R^{3b}$, $R^{4a}$, $R^{4b}$, $R^{13}$, $R^{14}$, $R^{15}$, and $R^{16}$ are as defined in compounds of formula (I).

In some embodiments of the compounds of formula (1-1), ($A^1$-a) is selected from the group consisting of:

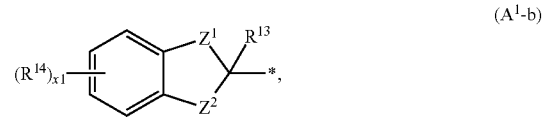

($A^1$-b)

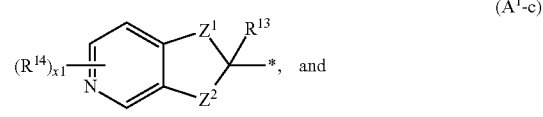

($A^1$-c), and

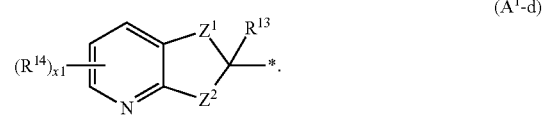

($A^1$-d)

In some embodiments of the compounds of formula (1-1), ($A^1$-a) is ($A^1$-b).

In some embodiments of the compounds of formula (1-1), ($A^1$-a) is ($A^1$-c).

In some embodiments of the compounds of formula (1-1), ($A^1$-a) is ($A^1$-d).

In some embodiments of the compounds of formula (1-1), ($A^1$-a) or ($A^1$-b) is selected from the group consisting of:

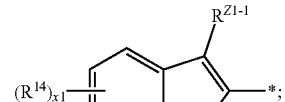

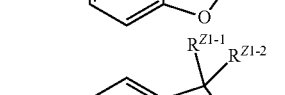

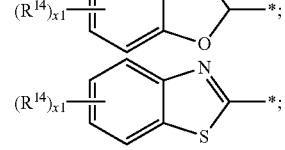

-continued

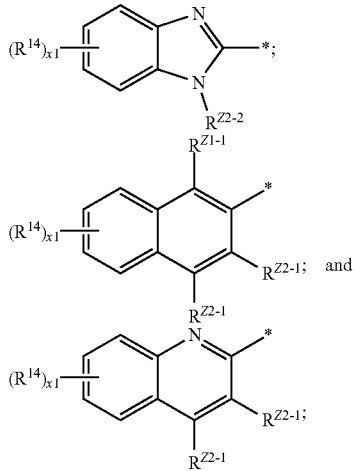

wherein the * represents the attachment point to the remainder of the molecule. In some embodiments, (A¹-a) or (A¹-b) is selected from the group consisting of:

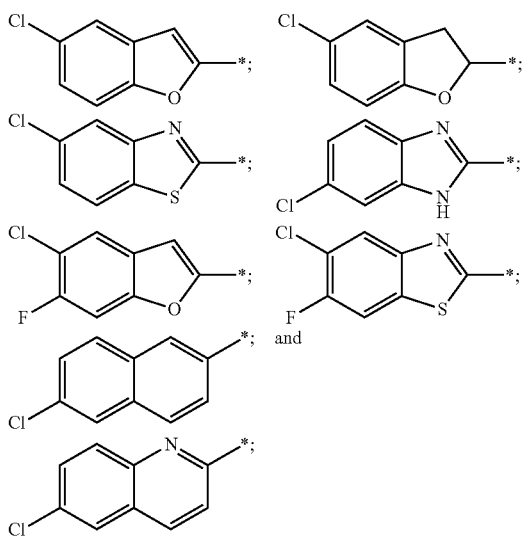

wherein the * represents the attachment point to the remainder of the molecule. In some embodiments, (A¹-a) or (A¹-b) is selected from the group consisting of:

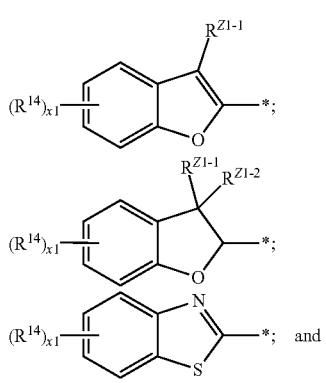

-continued

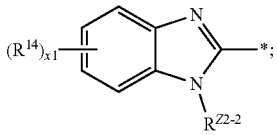

wherein the * represents the attachment point to the remainder of the molecule. In some embodiments, (A¹-a) or (A¹-b) is selected from the group consisting of:

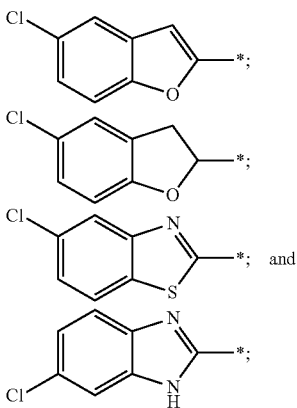

wherein the * represents the attachment point to the remainder of the molecule.

In some embodiments of the compounds of formula (1-1), (A¹-a) or (A¹-c) is selected from the group consisting of:

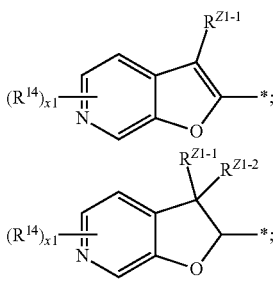

wherein the * represents the attachment point to the remainder of the molecule. In some embodiments, (A¹-a) or (A¹-c) is selected from the group consisting of:

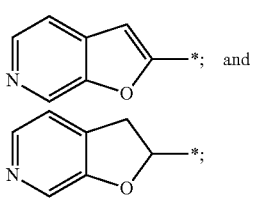

wherein the * represents the attachment point to the remainder of the molecule.

In some embodiments of the compounds of formula (1-1), (A²-a) is selected from the group consisting of:

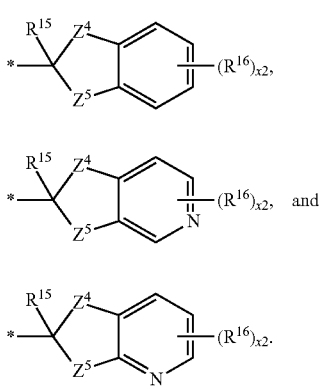

In some embodiments of the compounds of formula (1-1), (A²-a) is (A²-b).

In some embodiments of the compounds of formula (1-1), (A²-a) is (A²-c).

In some embodiments of the compounds of formula (1-1), (A²-a) is (A²-d).

In some embodiments of the compounds of formula (1-1), (A²-a) or (A²-b) is selected from the group consisting of:

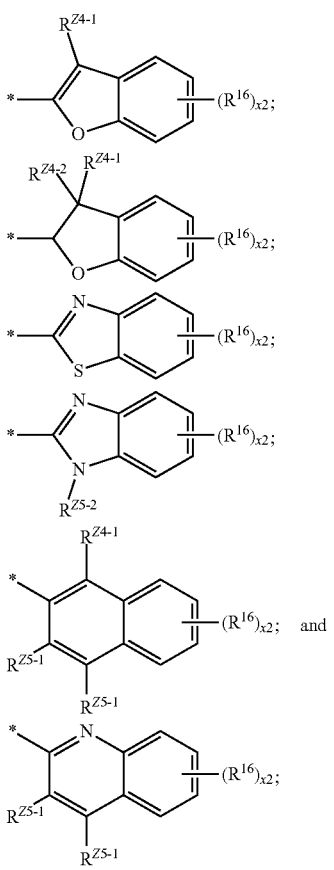

wherein the * represents the attachment point to the remainder of the molecule. In some embodiments, (A²-a) or (A²-b) is selected from the group consisting of:

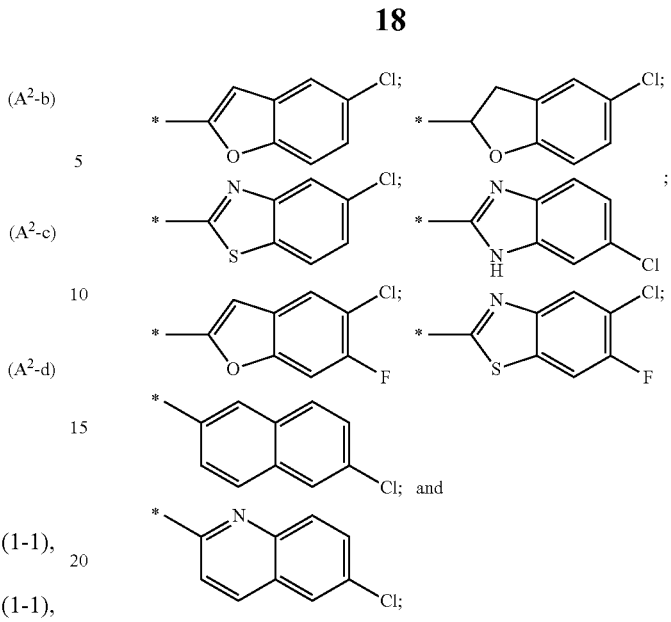

wherein the * represents the attachment point to the remainder of the molecule. In some embodiments, (A²-a) or (A²-b) is selected from the group consisting of:

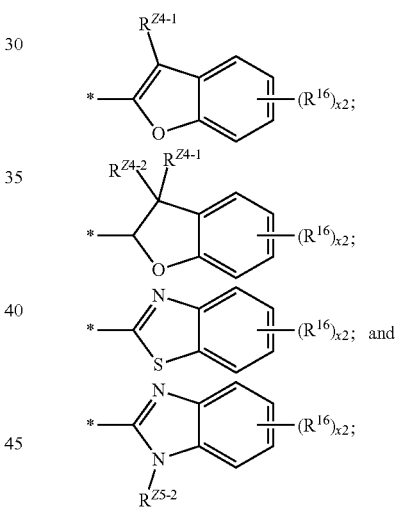

wherein the * represents the attachment point to the remainder of the molecule. In some embodiments, (A²-a) or (A²-b) is selected from the group consisting of:

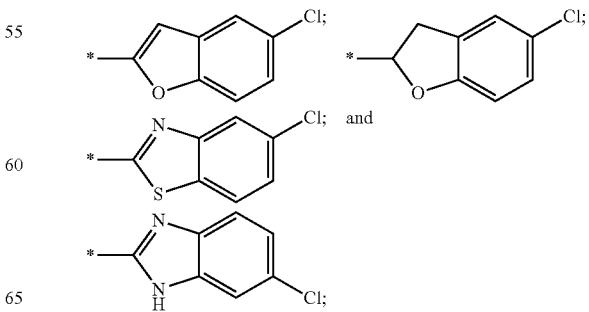

wherein the * represents the attachment point to the remainder of the molecule.

In some embodiments of the compounds of formula (1-1), $(A^2$-a$)$ or $(A^2$-c$)$ is selected from the group consisting of:

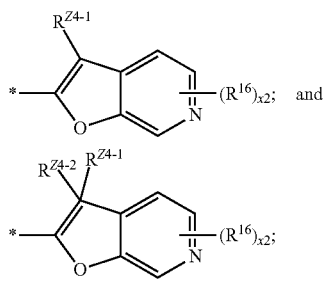

wherein the * represents the attachment point to the remainder of the molecule. In some embodiments, $(A^2$-a$)$ or $(A^2$-c$)$ is selected from the group consisting of:

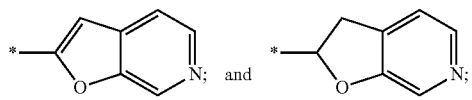 [SMILES: *c1cc2ccncc2o1 ; *C1Cc2ccncc2O1]

wherein the * represents the attachment point to the remainder of the molecule.

In some embodiments, $(A^1$-a$)$ or $(A^1$-b$)$ is selected from the group consisting of:

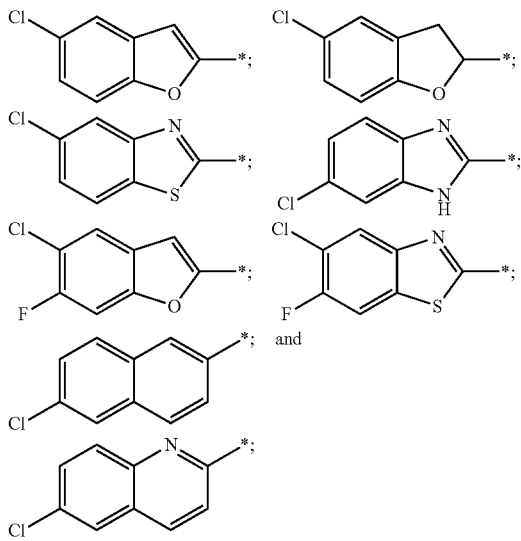

wherein the * represents the attachment point to the remainder of the molecule; and $(A^2$-a$)$ or $(A^2$-b$)$ is selected from the group consisting of:

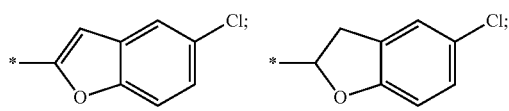

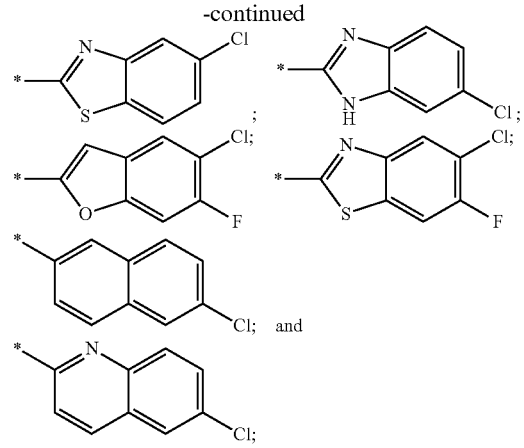

wherein the * represents the attachment point to the remainder of the molecule.

In some embodiments, $(A^1$-a$)$ or $(A^1$-b$)$ is selected from the group consisting of:

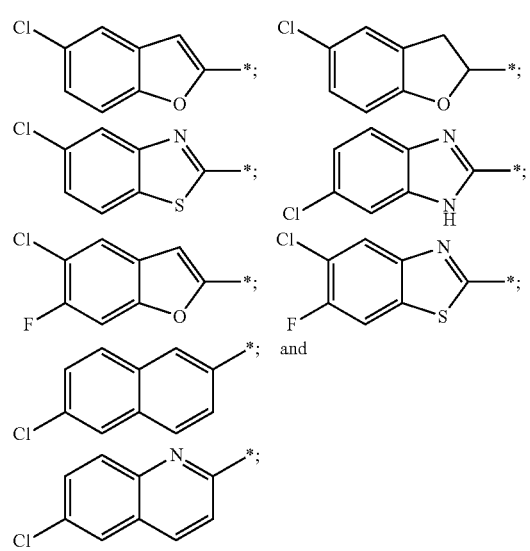

wherein the * represents the attachment point to the remainder of the molecule; and $(A^2$-a$)$ or $(A^2$-b$)$ is selected from the group consisting of:

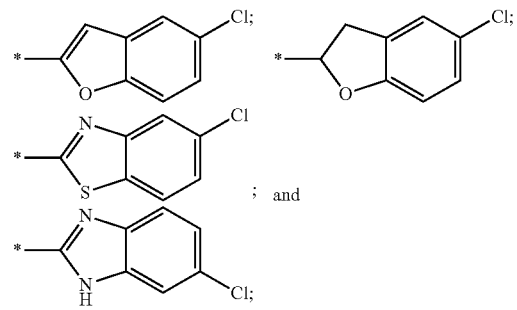

wherein the * represents the attachment point to the remainder of the molecule.

In some embodiments, (A¹-a) or (A¹-b) is selected from the group consisting of:

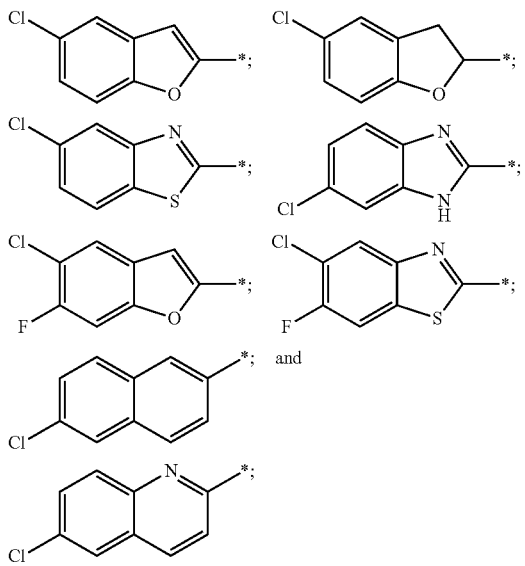

wherein the * represents the attachment point to the remainder of the molecule; and (A²-a) or (A²-c) is selected from the group consisting of:

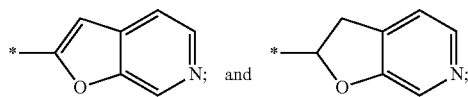 [SMILES: *c1cc2ccncc2o1 ; *C1Cc2ccncc2O1]

wherein the * represents the attachment point to the remainder of the molecule.

In some embodiments, (A¹-a) or (A¹-b) is selected from the group consisting of:

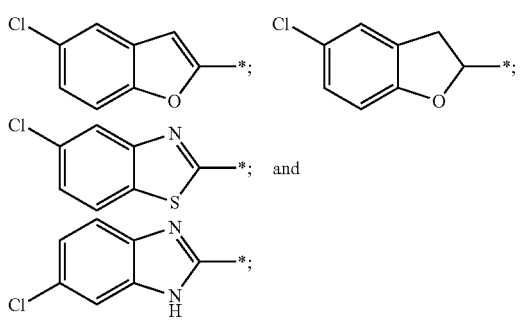

wherein the * represents the attachment point to the remainder of the molecule; and (A²-a) or (A²-b) is selected from the group consisting of:

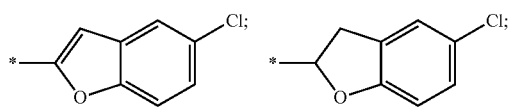

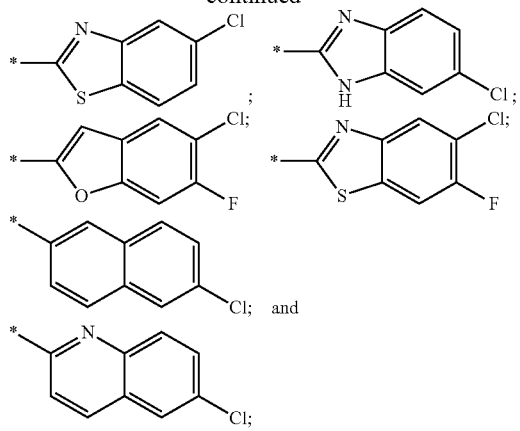

wherein the * represents the attachment point to the remainder of the molecule.

In some embodiments, (A¹-a) or (A¹-b) is selected from the group consisting of:

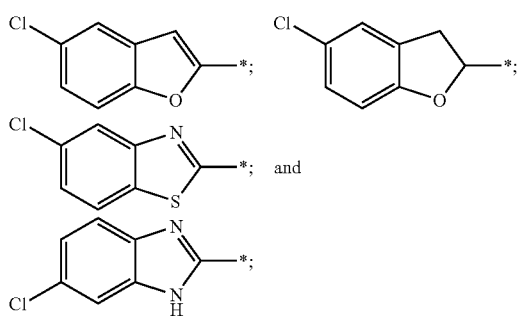

wherein the * represents the attachment point to the remainder of the molecule; and (A²-a) or (A²-b) is selected from the group consisting of:

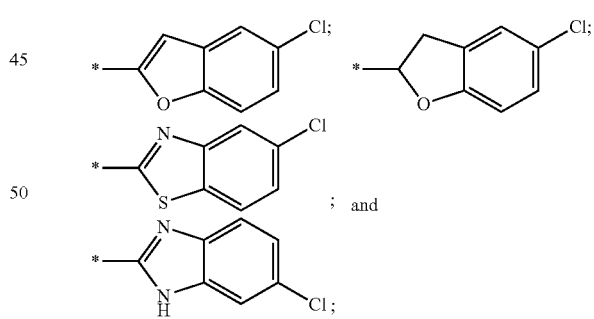

wherein the * represents the attachment point to the remainder of the molecule.

In some embodiments, (A¹-a) or (A¹-b) is selected from the group consisting of:

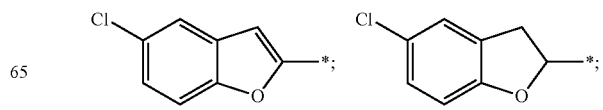

-continued

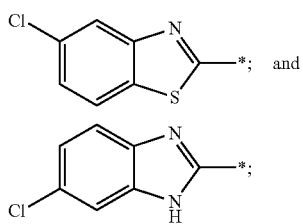

wherein the * represents the attachment point to the remainder of the molecule; and (A²-a) or (A²-c) is selected from the group consisting of:

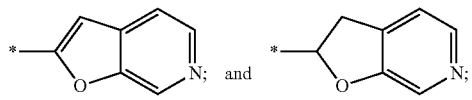 [SMILES: *c1cc2ccncc2o1 ; *C1Cc2ccncc2O1]

wherein the * represents the attachment point to the remainder of the molecule.

In some embodiments, (A¹-a) or (A¹-c) is selected from the group consisting of:

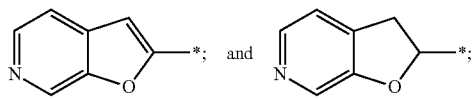

wherein the * represents the attachment point to the remainder of the molecule; and (A²-a) or (A²-b) is selected from the group consisting of:

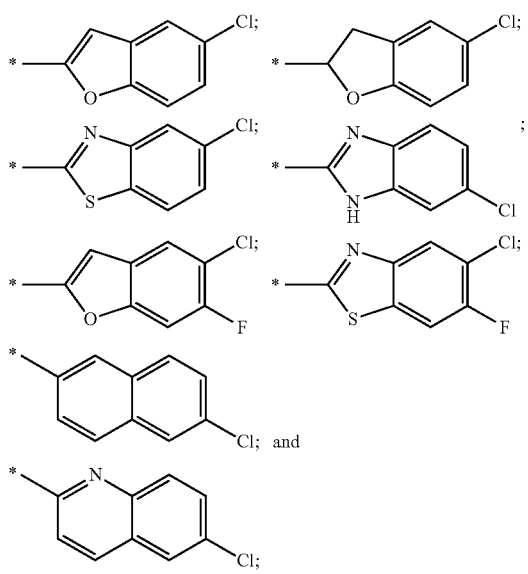

wherein the * represents the attachment point to the remainder of the molecule.

In some embodiments, (A¹-a) or (A¹-c) is selected from the group consisting of:

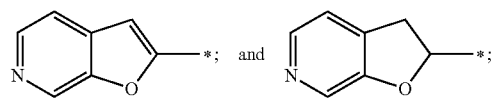

wherein the * represents the attachment point to the remainder of the molecule; and (A²-a) or (A²-b) is selected from the group consisting of:

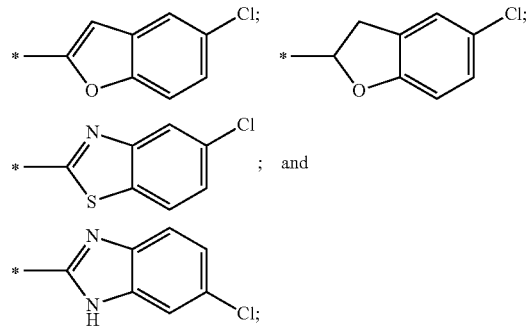

wherein the * represents the attachment point to the remainder of the molecule.

In some embodiments, (A¹-a) or (A¹-c) is selected from the group consisting of:

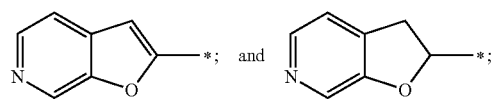

wherein the * represents the attachment point to the remainder of the molecule; and (A²-a) or (A²-c) is selected from the group consisting of:

wherein the * represents the attachment point to the remainder of the molecule.

In some embodiments, the compound of formula (I) is a compound of formula (1-2):

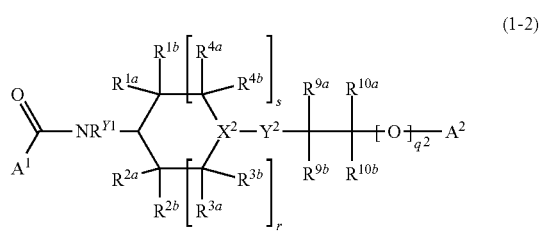

(1-2)

or a pharmaceutically acceptable salt thereof;

wherein:

$A^1$ is a substituent of formula ($A^1$-a)

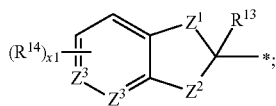
($A^1$-a)

$A^2$ is selected from the group consisting of:
a substituent of formula ($A^2$-a)

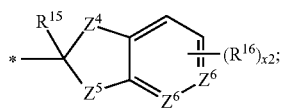
($A^2$-a)

$C_6$-$C_{10}$ aryl optionally substituted with one or more $R^{16}$ substituents; and 5-10 membered heteroaryl optionally substituted with one or more $R^{16}$ substituents;

and wherein $X^2$, $R^{Y1}$, $Y^2$, $R^{Y2}$, $q^2$, r, s, $Z^1$, $R^{Z1-1}$, $R^{Z1-2}$, $Z^2$, $R^{Z2-1}$, $R^{Z2-2}$, $Z^3$, x1, $Z^4$, $R^{Z4-1}$, $R^{Z4-2}$, $Z^5$, $R^{Z5-1}$, $R^{Z5-2}$, $Z^6$, x2, $R^{1a}$, $R^{1b}$, $R^{2a}$, $R^{2b}$, $R^{3a}$, $R^{3b}$, $R^{4a}$, $R^{4b}$, $R^{9a}$, $R^{9b}$, $R^{10a}$, $R^{10a-a}$, $R^{10a-b}$, $R^{10a-c}$, $R^{10b}$, $R^{15}$, and $R^{16}$ are as defined in compounds of formula (I).

In some embodiments of the compounds of formula (1-2), $X^2$ is CH. In some embodiments, r is 1 and s is 1.

In some embodiments of the compounds of formula (1-2), $X^2$ is N and $Y^2$ is a bond. In some embodiments, r is 1 and s is 1. In some embodiments, r is 0 and s is 2.

In some embodiments of the compounds of formula (1-2), ($A^1$-a) is selected from the group consisting of:

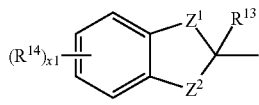
($A^1$-b)

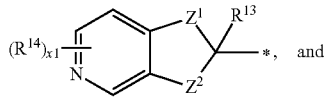
($A^1$-c)

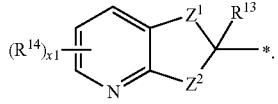
($A^1$-d)

In some embodiments of the compounds of formula (1-2), ($A^1$-a) is ($A^1$-b).

In some embodiments of the compounds of formula (1-2), ($A^1$-a) is ($A^1$-c).

In some embodiments of the compounds of formula (1-2), ($A^1$-a) is ($A^1$-d).

In some embodiments of the compounds of formula (1-2), ($A^1$-a) or ($A^1$-b) is selected from the group consisting of:

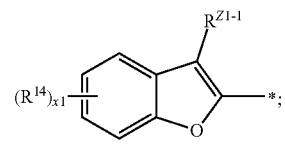

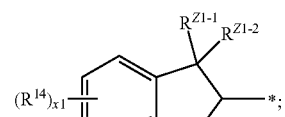

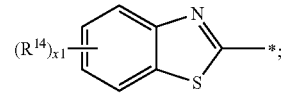

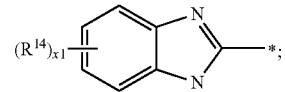

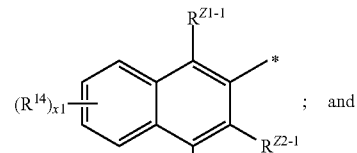
; and

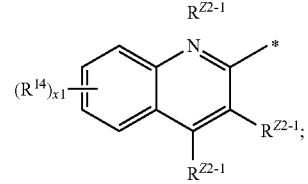

wherein the * represents the attachment point to the remainder of the molecule. In some embodiments, ($A^1$-a) or ($A^1$-b) is selected from the group consisting of:

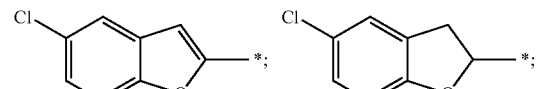

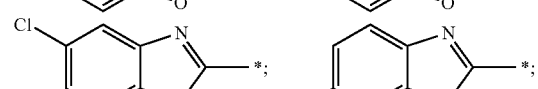

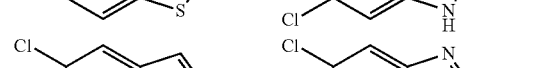

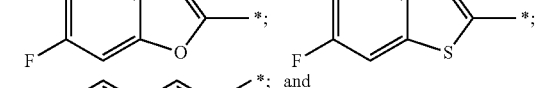

wherein the * represents the attachment point to the remainder of the molecule. In some embodiments, ($A^1$-a) or ($A^1$-b) is selected from the group consisting of:

wherein the * represents the attachment point to the remainder of the molecule. In some embodiments, (A¹-a) or (A¹-b) is selected from the group consisting of:

wherein the * represents the attachment point to the remainder of the molecule.

In some embodiments of the compounds of formula (1-2), (A¹-a) or (A¹-c) is selected from the group consisting of:

wherein the * represents the attachment point to the remainder of the molecule. In some embodiments, (A¹-a) or (A¹-c) is selected from the group consisting of:

wherein the * represents the attachment point to the remainder of the molecule.

In some embodiments of the compounds of formula (1-2):
$q^2$ is 1;
$R^{9a}$ and $R^{9b}$ are taken together to form an oxo (=O) substituent or an imido (=NH) substituent, or alternatively, $R^{9a}$ and $R^{9b}$ are both hydrogen;
$R^{10a}$ is selected from the group consisting of hydrogen, —$OR^{10a-a}$, and —$NR^{10a-b}R^{10a-c}$; $R^{10b}$ is hydrogen;
or alternatively, $R^{10a}$ and $R^{10b}$ are taken together to form a —$CH_2$—O—$CH_2$— moiety; and
$A^2$ is $C_6$-$C_{10}$ aryl optionally substituted with one or more $R^{16}$ substituents, or 5-10 membered heteroaryl optionally substituted with one or more $R^{16}$ substituents.

In some embodiments of the compounds of formula (1-2):
$R^{9a}$ and $R^{9b}$ are taken together to form an oxo (=O) substituent or an imido (=NH) substituent;
$R^{10a}$ is selected from the group consisting of hydrogen, —$OR^{10a-a}$, and —$NR^{10a-b}R^{10a-c}$;
$R^{10b}$ is hydrogen; and
$A^2$ is $C_6$-$C_{10}$ aryl optionally substituted with one or more $R^{16}$ substituents, or 5-10 membered heteroaryl optionally substituted with one or more $R^{16}$ substituents.

In some embodiments of the compounds of formula (1-2), $R^{9a}$ and $R^{9b}$ are taken together to form an oxo (=O) substituent. In some embodiments of the compounds of formula (1-2), $R^{9a}$ and $R^{9b}$ are taken together to form an imido (=NH) substituent. In some embodiments, $R^{10a}$ is hydrogen.

In some embodiments of the compounds of formula (1-2):
$R^{9a}$ and $R^{9b}$ are both hydrogen; and
$R^{10a}$ and $R^{10b}$ are taken together to form a —$CH_2$—O—$CH_2$— moiety.

In some embodiments of the compounds of formula (1-2):
$R^{9a}$ and $R^{9b}$ are both hydrogen; and
$R^{10a}$ and $R^{10b}$ are both hydrogen.

In some embodiments of the compounds of formula (1-2):
$X^2$ is CH;
$R^{Y1}$ is hydrogen or $C_1$-$C_6$ alkyl;
$Y^2$ is selected from the group consisting of $NR^{Y2}$ and O;
$R^{Y2}$ is hydrogen or $C_1$-$C_6$ alkyl;
$q^2$ is 1;
r and s, independently of each other, are 0, 1, or 2;
$A^1$ is a substituent of formula (A¹-a)

(A¹-a)

wherein
represents the attachment point to the remainder of the molecule; $Z^1$ is selected from the group consisting of $CR^{Z1-1}R^{Z1-2}$, $NR^{Z1-2}$, O, S, and —$CR^{Z1-1}$=$CR^{Z1-1}$—;
wherein $R^{Z1-1}$ is H or $R^{14}$; and $R^{Z1-2}$ is H or $R^{14}$;
$Z^2$ is selected from the group consisting of $CR^{Z2-1}R^{Z2-2}$, $NR^{Z2-2}$, O, S, and —$CR^{Z2-1}$=$CR^{Z2-1}$—;
wherein $R^{Z2-1}$ is H or $R^{14}$; and $R^{Z2-2}$ is H or $R^{14}$;
$Z^3$, independently at each occurrence, is C or N, provided that at least one $Z^3$ is C;
$R^{13}$ is hydrogen or $R^{14}$, or $R^{13}$ and $R^{Z1-2}$ are taken together to form a double bond between the carbon atom bearing $R^{13}$ and $Z^1$, or $R^{13}$ and $R^{Z2-2}$ are taken together to form a double bond between the carbon atom bearing $R^{13}$ and $Z^2$; and x1 is 1, 2, 3, or 4, and at least one $R^{14}$ is halogen;

$R^{14}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —NH$_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —NR$^{14\text{-}a}$R$^{14\text{-}b}$, —CN, —C(O)OH, —C(O)O($C_1$-$C_6$ alkyl), —C(O)O($C_1$-$C_6$ haloalkyl), —C(O)NH$_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)NR$^{14\text{-}a}$R$^{14\text{-}b}$, —S(O)$_2$OH, —S(O)$_2$O($C_1$-$C_6$ alkyl), —S(O)$_2$O($C_1$-$C_6$ haloalkyl), —S(O)$_2$NH$_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$NR$^{14\text{-}a}$R$^{14\text{-}b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);

wherein $R^{14\text{-}a}$ and $R^{14\text{-}b}$ are taken together with the nitrogen atom which bears them to form a 3-10 membered heterocycle; $A^2$ is $C_6$-$C_{10}$ aryl substituted by at least one halogen substituent and optionally further substituted with one or more $R^{16}$ substituents, or 5-10 membered heteroaryl substituted by at least one halogen substituent and optionally further substituted with one or more $R^{16}$ substituents;

$R^{16}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —NH$_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —NR$^{16\text{-}a}$R$^{16\text{-}b}$, —CN, —C(O)OH, —C(O)O($C_1$-$C_6$ alkyl), —C(O)O($C_1$-$C_6$ haloalkyl), —C(O)NH$_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)NR$^{16\text{-}a}$R$^{16\text{-}b}$, —S(O)$_2$OH, —S(O)$_2$O($C_1$-$C_6$ alkyl), —S(O)$_2$O($C_1$-$C_6$ haloalkyl), —S(O)$_2$NH$_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$NR$^{16\text{-}a}$R$^{16\text{-}b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);

wherein $R^{16\text{-}a}$ and $R^{16\text{-}b}$ are taken together with the nitrogen atom which bears them to form a 3-10 membered heterocycle;

$R^{1a}$ and $R^{1b}$ are independently selected from the group consisting of hydrogen, $C_1$-$C_6$ alkyl, and halogen;

$R^{2a}$ and $R^{2b}$ are independently selected from the group consisting of hydrogen, $C_1$-$C_6$ alkyl, and halogen;

when present, $R^{3a}$ and $R^{3b}$ are independently at each occurrence selected from the group consisting of hydrogen, $C_1$-$C_6$ alkyl, and halogen;

when present, $R^{4a}$ and $R^{4b}$ are independently at each occurrence selected from the group consisting of hydrogen, $C_1$-$C_6$ alkyl, and halogen;

or alternatively, $R^{1a}$ and $R^{2a}$ are taken together to form a $C_1$-$C_6$ alkylene moiety;

or alternatively, $R^{1a}$ and an $R^{3a}$ moiety, when present, are taken together to form a $C_1$-$C_6$ alkylene moiety, and $R^{1b}$ and the $R^{3b}$ in the geminal position to the $R^{3a}$ taken together with $R^{1a}$, are both hydrogen;

or alternatively, an $R^{3a}$ moiety, when present, and an $R^{4a}$ moiety, when present, are taken together to form a $C_1$-$C_6$ alkylene moiety, and the $R^{3b}$ in the geminal position to the $R^{3a}$ taken together with the $R^{4a}$ moiety and the $R^{4b}$ in the geminal position to the $R^{4a}$ taken together with the $R^{3a}$ moiety, are both hydrogen;

$R^{9a}$ and $R^{9b}$ are taken together to form an oxo (=O) substituent or an imido (=NH) substituent, or alternatively, $R^{9a}$ and $R^{9b}$ are both hydrogen;

$R^{10a}$ is hydrogen; and $R^{10b}$ is hydrogen.

In some embodiments of the compounds of formula (1-2), $R^{Y1}$ is hydrogen. In some embodiments of the compounds of formula (1-2), $R^{Y1}$ is $C_1$-$C_6$ alkyl.

In some embodiments of the compounds of formula (1-2), $Y^2$ is NR$^{Y2}$. In some embodiments of the compounds of formula (1-2), $R^{Y2}$ is hydrogen. In some embodiments of the compounds of formula (1-2), $R^{Y2}$ is $C_1$-$C_6$ alkyl.

In some embodiments of the compounds of formula (1-2), $Y^2$ is O.

In some embodiments of the compounds of formula (1-2), $R^{1a}$ and $R^{1b}$ are independently selected from the group consisting of hydrogen and $C_1$-$C_6$ alkyl. In some embodiments of the compounds of formula (1-2), $R^{1a}$ and $R^{1b}$ are both hydrogen.

In some embodiments of the compounds of formula (1-2), $R^{2a}$ and $R^{2b}$ are independently selected from the group consisting of hydrogen and $C_1$-$C_6$ alkyl. In some embodiments of the compounds of formula (1-2), $R^{2a}$ and $R^{2b}$ are both hydrogen.

In some embodiments of the compounds of formula (1-2), $R^{1a}$ and $R^{2a}$ are taken together to form a $C_1$-$C_6$ alkylene moiety In some embodiments of the compounds of formula (1-2), r is 1 and s is 1. In some embodiments, $R^{3a}$ and $R^{3b}$ are independently selected from the group consisting of hydrogen and $C_1$-$C_6$ alkyl. In some embodiments, $R^{3a}$ and $R^{3b}$ are both hydrogen. In some embodiments, $R^{4a}$ and $R^{4b}$ are independently selected from the group consisting of hydrogen and $C_1$-$C_6$ alkyl. In some embodiments, $R^{4a}$ and $R^{4b}$ are both hydrogen. In some embodiments, $R^{1a}$ and $R^{3a}$ are taken together to form a $C_1$-$C_6$ alkylene moiety, and $R^{1b}$ and $R^{3b}$ are both hydrogen. In some embodiments, $R^{3a}$ and $R^{4a}$ are taken together to form a $C_1$-$C_6$ alkylene moiety, and $R^{3b}$ and $R^{4b}$ are both hydrogen.

In some embodiments of the compounds of formula (1-2), $R^{9a}$ and $R^{9b}$ are taken together to form an oxo (=O)

substituent. In some embodiments of the compounds of formula (1-2), $R^{9a}$ and $R^{9b}$ are taken together to form an imido (=NH) substituent.

In some embodiments of the compounds of formula (1-2), ($A^1$-a) is selected from the group consisting of:

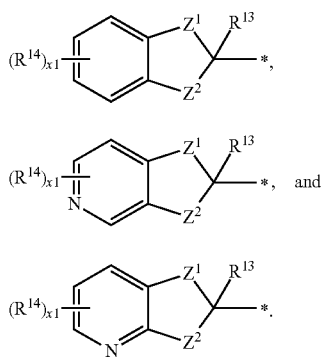

In some embodiments of the compounds of formula (1-2), ($A^1$-a) is ($A^1$-b).

In some embodiments of the compounds of formula (1-2), ($A^1$-a) is ($A^1$-c).

In some embodiments of the compounds of formula (1-2), ($A^1$-a) is ($A^1$-d).

In some embodiments of the compounds of formula (1-2), ($A^1$-a) or ($A^1$-b) is selected from the group consisting of:

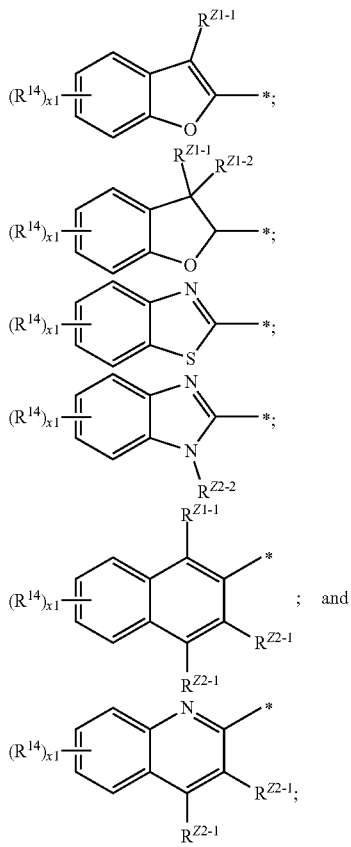

wherein the * represents the attachment point to the remainder of the molecule. In some embodiments x1 is 1, 2, 3, or 4, and at least one $R^{14}$ is halogen. In some embodiments, x1 is 1 and $R^{14}$ is halogen. In some embodiments, x1 is 2 and at least one $R^{14}$ is halogen. In some embodiments, x1 is 3 and at least one $R^{14}$ is halogen. In some embodiments, x1 is 4 and at least one $R^{14}$ is halogen. In some embodiments, ($A^1$-a) or ($A^1$-b) is selected from the group consisting of:

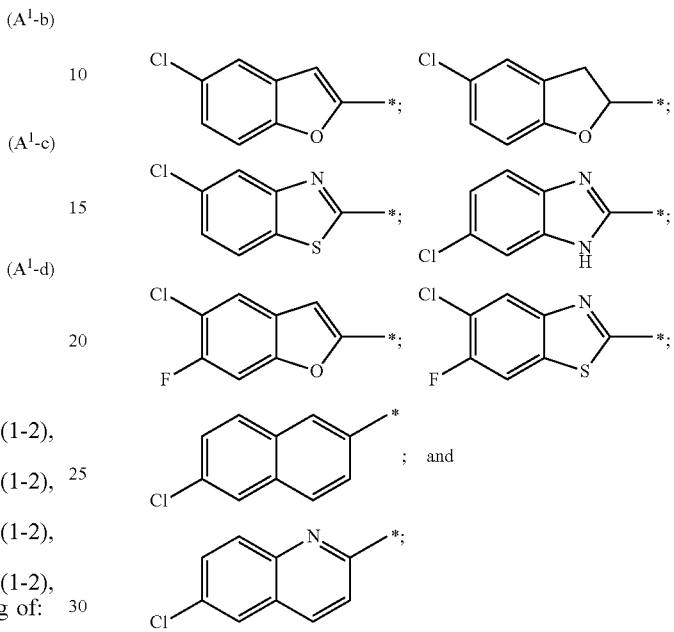

wherein the * represents the attachment point to the remainder of the molecule. In some embodiments, ($A^1$-a) or ($A^1$-b) is selected from the group consisting of:

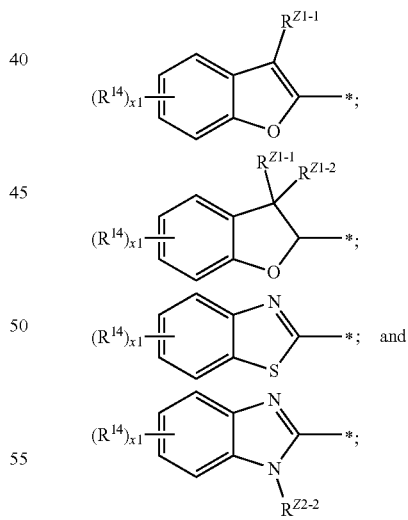

wherein the * represents the attachment point to the remainder of the molecule. In some embodiments x1 is 1, 2, 3, or 4, and at least one $R^{14}$ is halogen. In some embodiments, x1 is 1 and $R^{14}$ is halogen. In some embodiments, x1 is 2 and at least one $R^{14}$ is halogen. In some embodiments, x1 is 3 and at least one $R^{14}$ is halogen. In some embodiments, x1 is 4 and at least one $R^{14}$ is halogen. In some embodiments, ($A^1$-a) or ($A^1$-b) is selected from the group consisting of:

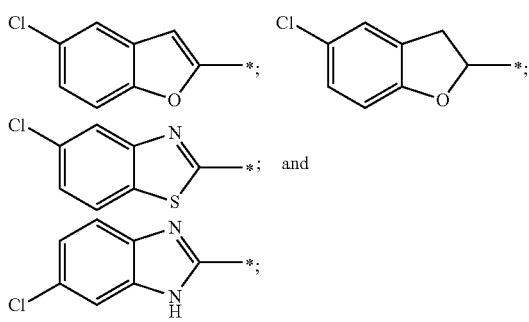

wherein the * represents the attachment point to the remainder of the molecule.

In some embodiments of the compounds of formula (1-2), ($A^1$-a) or ($A^1$-c) is selected from the group consisting of:

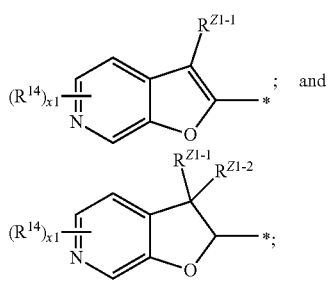

wherein the * represents the attachment point to the remainder of the molecule. In some embodiments, ($A^1$-a) or ($A^1$-c) is selected from the group consisting of:

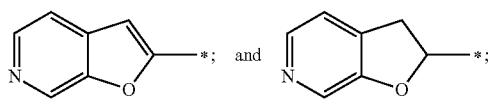

wherein the * represents the attachment point to the remainder of the molecule.

In some embodiments of the compounds of formula (1-2), $A^2$ is $C_6$-$C_{10}$ aryl substituted by at least one halogen substituent and optionally further substituted with one or more $R^{16}$ substituents, or 5-10 membered heteroaryl substituted by at least one halogen substituent and optionally further substituted with one or more $R^{16}$ substituents.

In some embodiments of the compounds of formula (1-2), $A^2$ is $C_6$-$C_{10}$ aryl optionally substituted with one or more $R^{16}$ substituents. In some embodiments, $A^2$ is $C_6$-$C_{10}$ aryl substituted by at least one halogen substituent and optionally further substituted with one or more $R^{16}$ substituents. In some embodiments, $A^2$ is selected from the group consisting of:

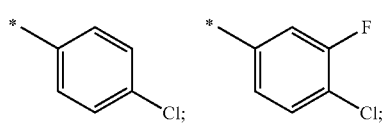

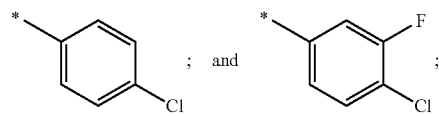

wherein the * represents the attachment point to the remainder of the molecule. In some embodiments, $A^2$ is phenyl optionally substituted with one or more $R^{16}$ substituents. In some embodiments, $A^2$ is phenyl substituted by at least one halogen substituent and optionally further substituted with one or more $R^{16}$ substituents. In some embodiments, $A^2$ is selected from the group consisting of:

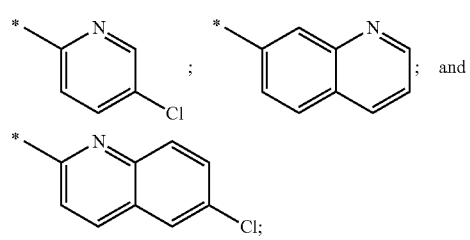

wherein the * represents the attachment point to the remainder of the molecule.

In some embodiments of the compounds of formula (1-2), $A^2$ is 5-10 membered heteroaryl optionally substituted with one or more $R^{16}$ substituents. In some embodiments, $A^2$ is 5-10 membered heteroaryl substituted by at least one halogen substituent and optionally further substituted with one or more $R^{16}$ substituents. In some embodiments, $A^2$ is selected from the group consisting of:

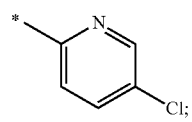

wherein the * represents the attachment point to the remainder of the molecule. In some embodiments, $A^2$ is pyridyl optionally substituted with one or more $R^{16}$ substituents. In some embodiments, $A^2$ is pyridyl substituted by at least one halogen substituent and optionally further substituted with one or more $R^{16}$ substituents. In some embodiments, $A^2$ is wherein the * represents the attachment point to the remainder of the molecule.

In some embodiments of the compounds of formula (1-2):
$q^2$ is 0;
$R^{9a}$ and $R^{9b}$ are both hydrogen;
$R^{10a}$ is —$OR^{10a\text{-}a}$ or —$NR^{10a\text{-}b}R^{10a\text{-}c}$; and
$R^{10b}$ is hydrogen.

In some embodiments of the compounds of formula (1-2):
$R^{10a}$ is —$OR^{10a-a}$ or —$NR^{10a-b}R^{10a-c}$; and
$A^2$ is a substituent of formula ($A^2$-a)

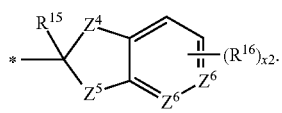
($A^2$-a)

In some embodiments of the compounds of formula (1-2), $R^{10a}$ is —$OR^{10a-a}$.

In some embodiments of the compounds of formula (1-2), ($A^2$-a) is selected from the group consisting of:

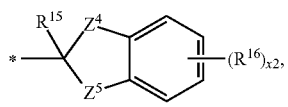
($A^2$-b)

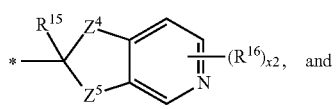
($A^2$-c)

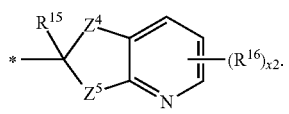
($A^2$-d)

In some embodiments of the compounds of formula (1-2), ($A^2$-a) is ($A^2$-b).

In some embodiments of the compounds of formula (1-2), ($A^2$-a) is ($A^2$-c).

In some embodiments of the compounds of formula (1-2), ($A^2$-a) is ($A^2$-d).

In some embodiments of the compounds of formula (1-2), ($A^2$-a) or ($A^2$-b) is selected from the group consisting of:

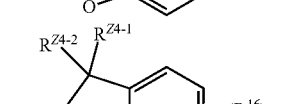


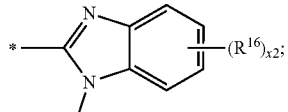

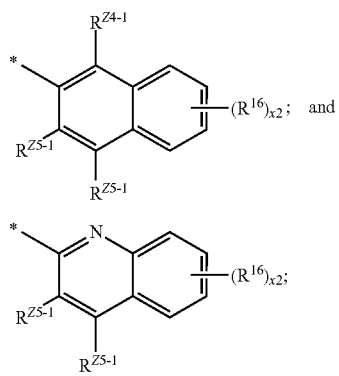

wherein the * represents the attachment point to the remainder of the molecule. In some embodiments, ($A^2$-a) or ($A^2$-b) is selected from the group consisting of:

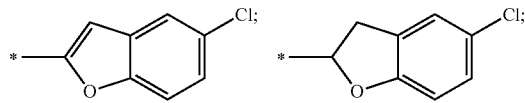

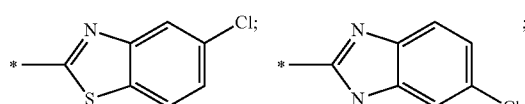

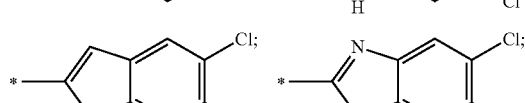

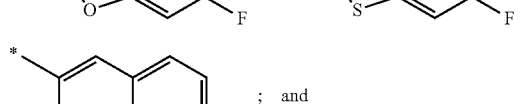

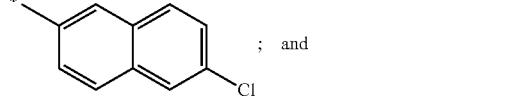

wherein the * represents the attachment point to the remainder of the molecule. In some embodiments, ($A^2$-a) or ($A^2$-b) is selected from the group consisting of:

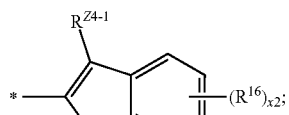


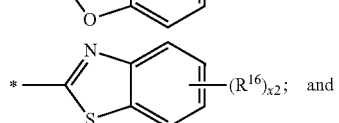

-continued

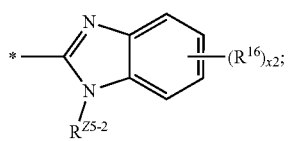

wherein the * represents the attachment point to the remainder of the molecule. In some embodiments, (A²-a) or (A²-b) is selected from the group consisting of:

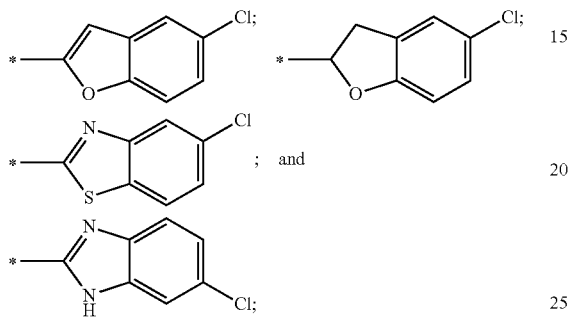

wherein the * represents the attachment point to the remainder of the molecule.

In some embodiments of the compounds of formula (1-2), (A²-a) or (A²-c) is selected from the group consisting of:

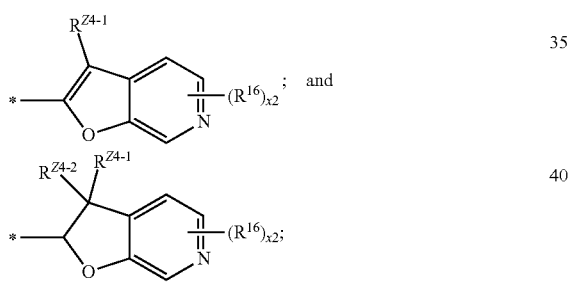

wherein the * represents the attachment point to the remainder of the molecule. In some embodiments, (A²-a) or (A²-c) is selected from the group consisting of:

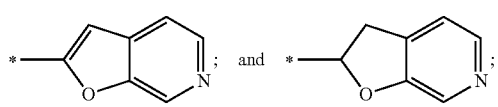

wherein the * represents the attachment point to the remainder of the molecule.

In some embodiments, (A¹-a) or (A¹-b) is selected from the group consisting of:

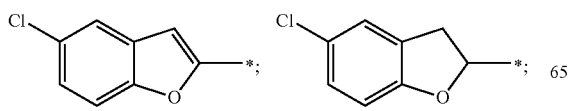

-continued

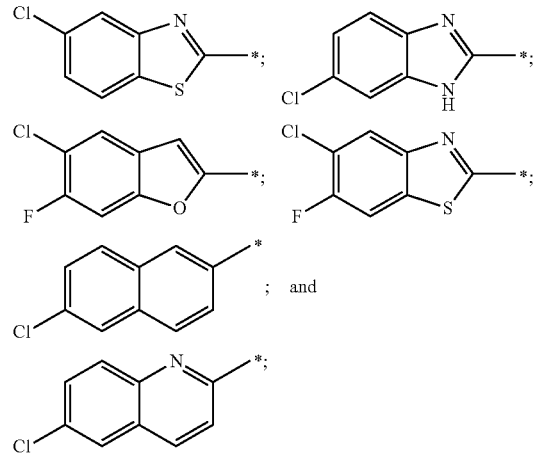

wherein the * represents the attachment point to the remainder of the molecule; and (A²-a) or (A²-b) is selected from the group consisting of:

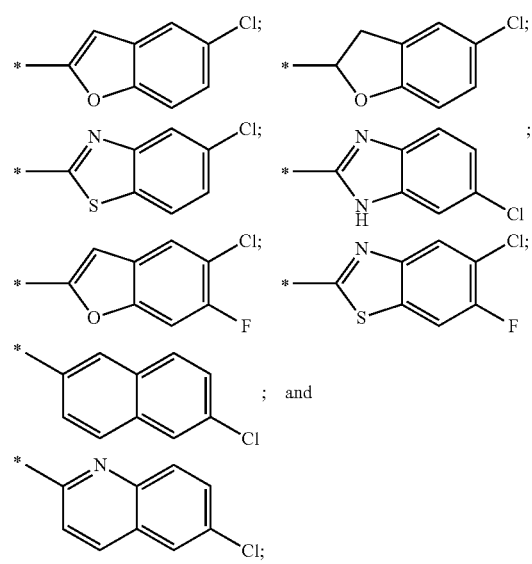

wherein the * represents the attachment point to the remainder of the molecule.

In some embodiments, (A¹-a) or (A¹-b) is selected from the group consisting of:

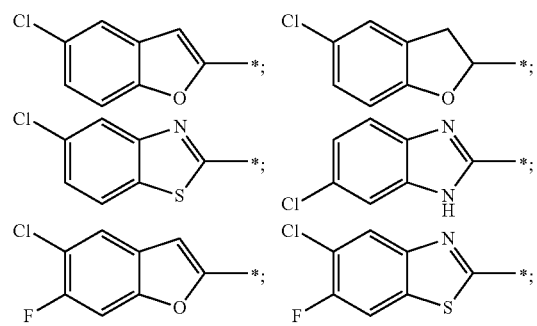

-continued

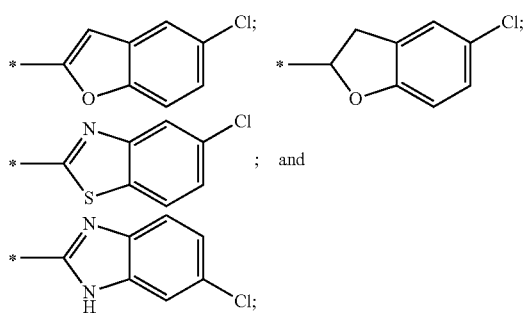

; and wherein the * represents the attachment point to the remainder of the molecule; and (A²-a) or (A²-b) is selected from the group consisting of:

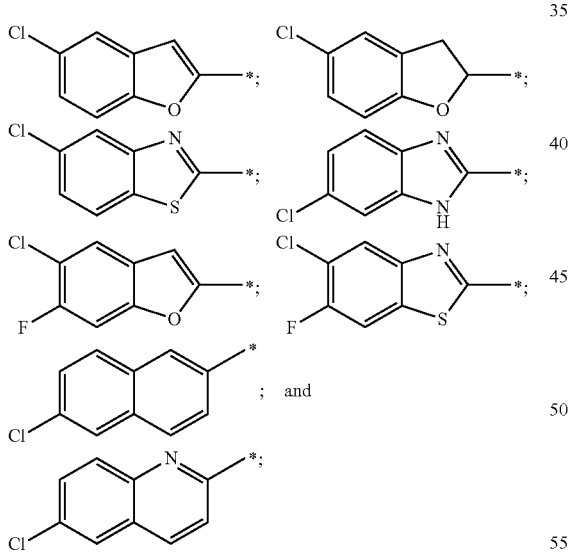

wherein the * represents the attachment point to the remainder of the molecule.

In some embodiments, (A¹-a) or (A¹-b) is selected from the group consisting of:

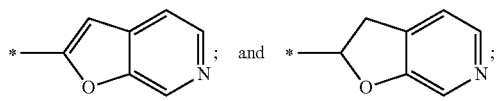

wherein the * represents the attachment point to the remainder of the molecule; and (A²-a) or (A²-c) is selected from the group consisting of:

wherein the * represents the attachment point to the remainder of the molecule.

In some embodiments, (A¹-a) or (A¹-b) is selected from the group consisting of:

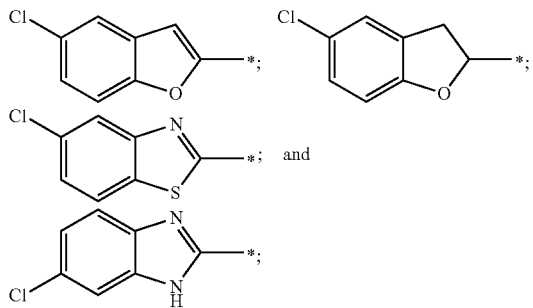

wherein the * represents the attachment point to the remainder of the molecule; and (A²-a) or (A²-b) is selected from the group consisting of:

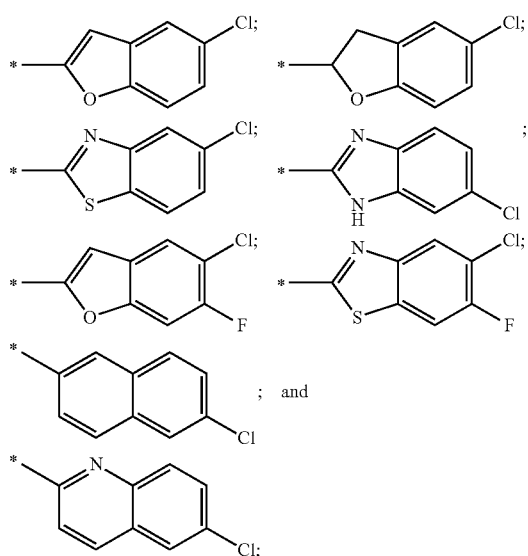

wherein the * represents the attachment point to the remainder of the molecule.

In some embodiments, (A¹-a) or (A¹-b) is selected from the group consisting of:

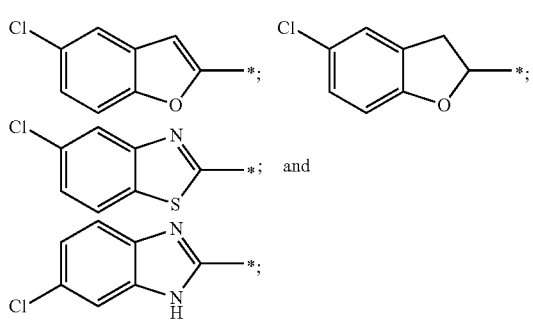

wherein the * represents the attachment point to the remainder of the molecule; and (A²-a) or (A²-b) is selected from the group consisting of:

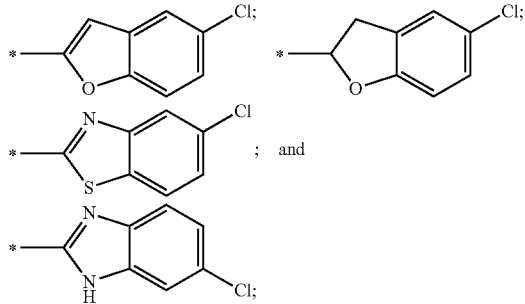

wherein the * represents the attachment point to the remainder of the molecule.

In some embodiments, (A¹-a) or (A¹-b) is selected from the group consisting of:

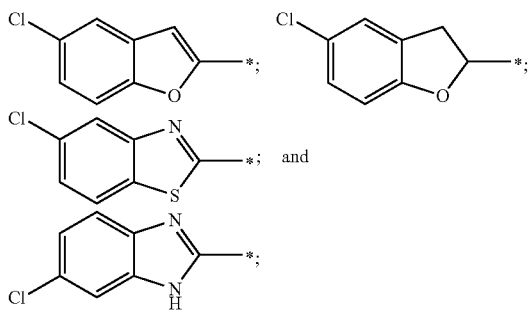

wherein the * represents the attachment point to the remainder of the molecule; and (A²-a) or (A²-c) is selected from the group consisting of:

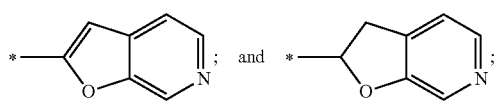

wherein the * represents the attachment point to the remainder of the molecule.

In some embodiments, (A¹-a) or (A¹-c) is selected from the group consisting of:

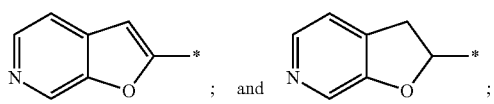 [SMILES: *c1cc2ccncc2o1 ; *C1Cc2ccncc2O1]

wherein the * represents the attachment point to the remainder of the molecule; and (A²-a) or (A²-b) is selected from the group consisting of:

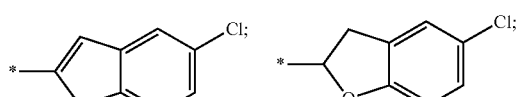

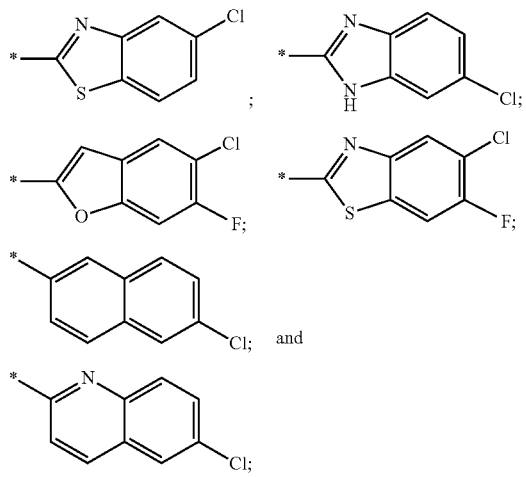

wherein the * represents the attachment point to the remainder of the molecule.

In some embodiments, (A¹-a) or (A¹-c) is selected from the group consisting of:

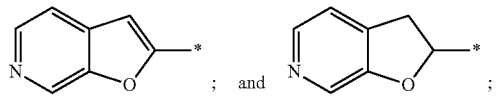 [SMILES: *c1cc2ccncc2o1 ; *C1Cc2ccncc2O1]

wherein the * represents the attachment point to the remainder of the molecule; and (A²-a) or (A²-b) is selected from the group consisting of:

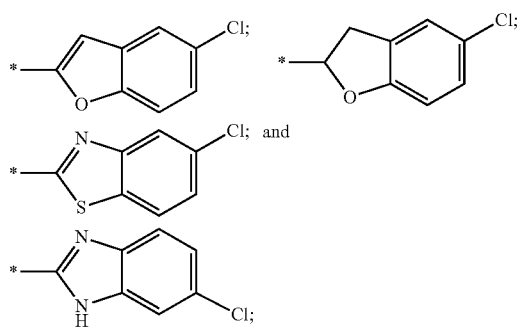

wherein the * represents the attachment point to the remainder of the molecule.

In some embodiments, (A¹-a) or (A¹-c) is selected from the group consisting of:

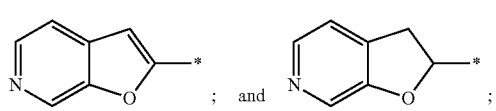 [SMILES: *c1cc2ccncc2o1 ; *C1Cc2ccncc2O1]

wherein the * represents the attachment point to the remainder of the molecule; and (A²-a) or (A²-c) is selected from the group consisting of:

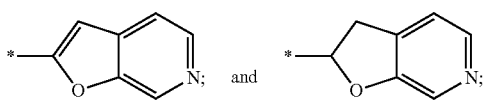 [SMILES: *c1cc2ccncc2o1 ; *C1Cc2ccncc2O1]

wherein the * represents the attachment point to the remainder of the molecule.

In some embodiments, (A¹-a) or (A¹-b) is selected from the group consisting of:

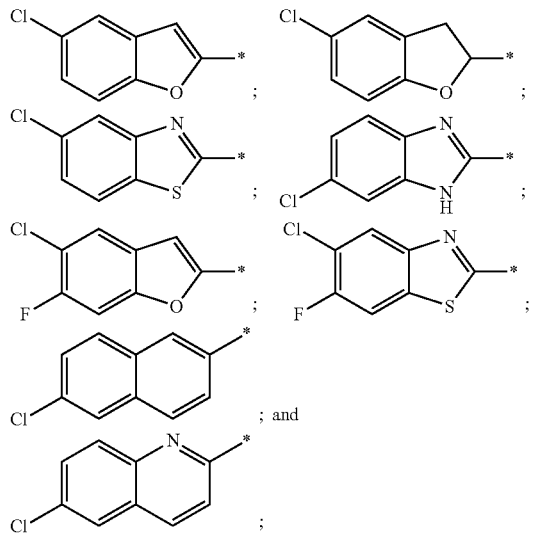

wherein the * represents the attachment point to the remainder of the molecule; and A² is selected from the group consisting of:

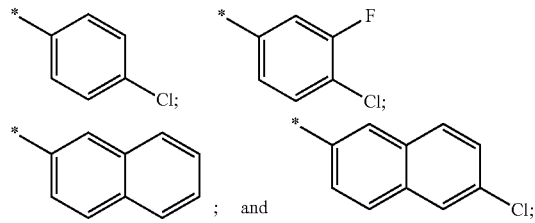

wherein the * represents the attachment point to the remainder of the molecule.

In some embodiments, (A¹-a) or (A¹-b) is selected from the group consisting of:

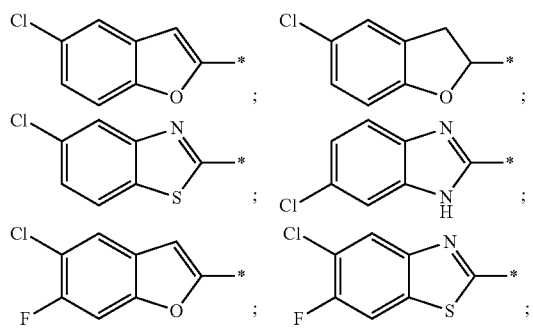

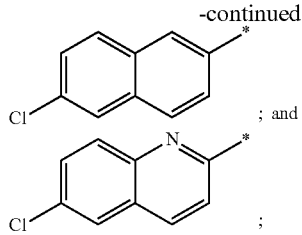

wherein the * represents the attachment point to the remainder of the molecule; and A² is selected from the group consisting of:

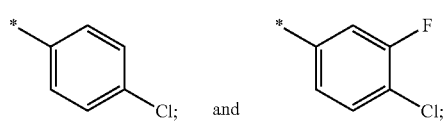 [SMILES: *c1ccc(Cl)cc1 ; *c1ccc(Cl)c(F)c1]

wherein the * represents the attachment point to the remainder of the molecule.

In some embodiments, (A¹-a) or (A¹-b) is selected from the group consisting of:

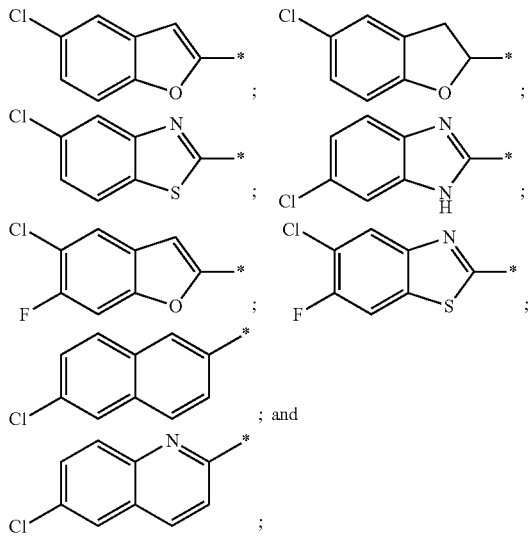

wherein the * represents the attachment point to the remainder of the molecule; and A² is selected from the group consisting of:

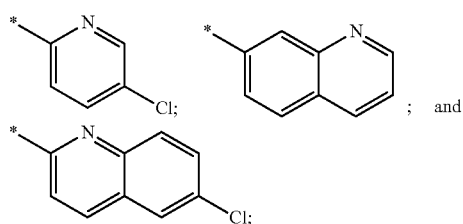

wherein the * represents the attachment point to the remainder of the molecule.

In some embodiments, (A¹-a) or (A¹-b) is selected from the group consisting of:

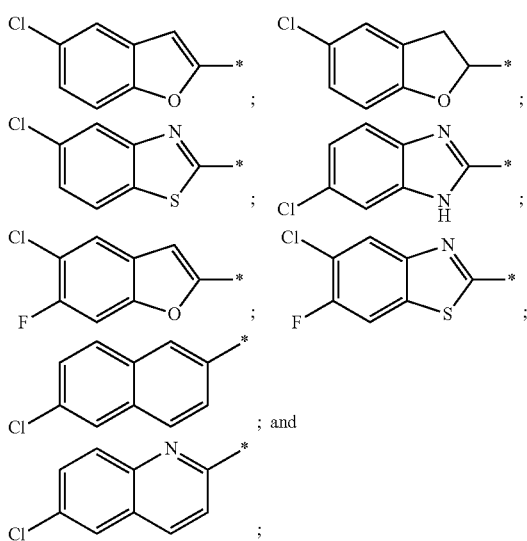

wherein the * represents the attachment point to the remainder of the molecule; and $A^2$ is

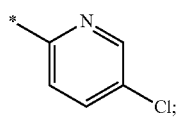 [SMILES: *c1ccc(Cl)cn1]

$C_1$; wherein the * represents the attachment point to the remainder of the molecule.

In some embodiments, $(A^1$-a$)$ or $(A^1$-b$)$ is selected from the group consisting of:

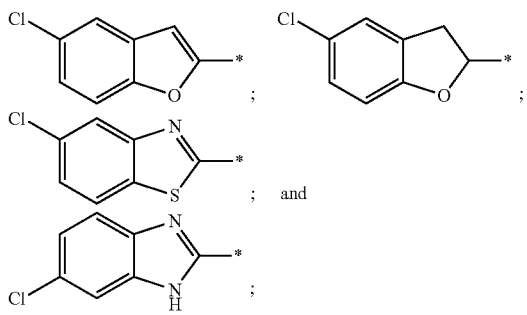

wherein the * represents the attachment point to the remainder of the molecule; and $A^2$ is selected from the group consisting of:

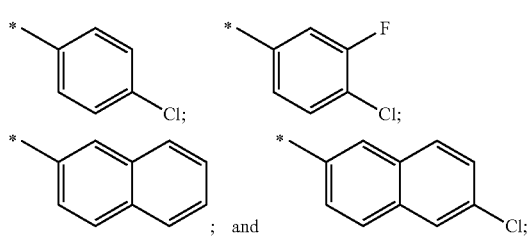

wherein the * represents the attachment point to the remainder of the molecule.

In some embodiments, $(A^1$-a$)$ or $(A^1$-b$)$ is selected from the group consisting of:

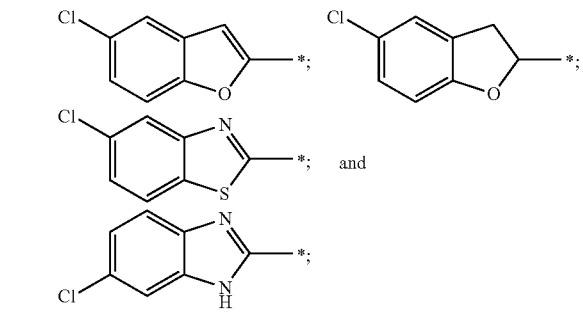

wherein the * represents the attachment point to the remainder of the molecule; and $A^2$ is selected from the group consisting of:

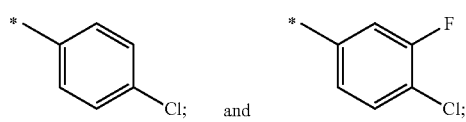

wherein the * represents the attachment point to the remainder of the molecule.

In some embodiments, $(A^1$-a$)$ or $(A^1$-b$)$ is selected from the group consisting of:

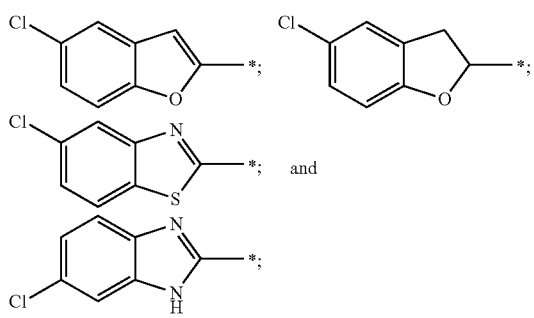

wherein the * represents the attachment point to the remainder of the molecule; and $A^2$ is selected from the group consisting of:

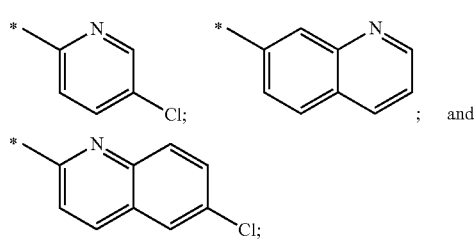

wherein the * represents the attachment point to the remainder of the molecule.

In some embodiments, $(A^1$-a$)$ or $(A^1$-b$)$ is selected from the group consisting of:

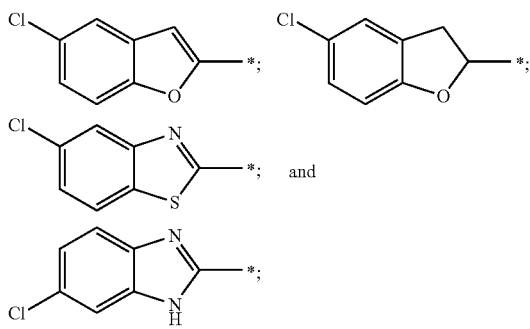

Wherein the * represents the attachment point to the remainder of the molecule; and A² is

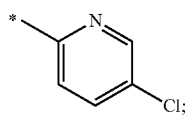

wherein the * represents the attachment point to the remainder of the molecule.

In some embodiments, (A¹-a) or (A¹-c) is selected from the group consisting of:

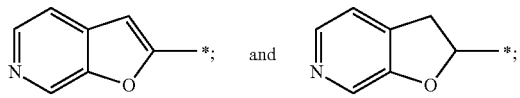

wherein the * represents the attachment point to the remainder of the molecule; and A² is selected from the group consisting of:

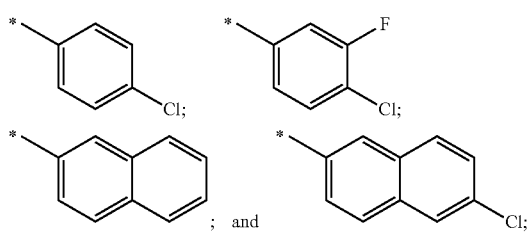

wherein the * represents the attachment point to the remainder of the molecule.

In some embodiments, (A¹-a) or (A¹-c) is selected from the group consisting of:

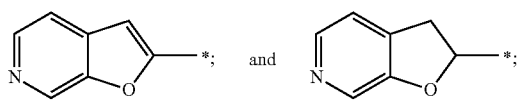

wherein the * represents the attachment point to the remainder of the molecule; and A² is selected from the group consisting of:

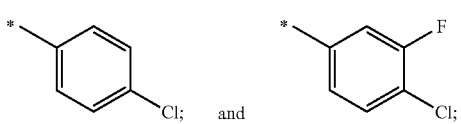

wherein the * represents the attachment point to the remainder of the molecule.

In some embodiments, (A¹-a) or (A¹-c) is selected from the group consisting of:

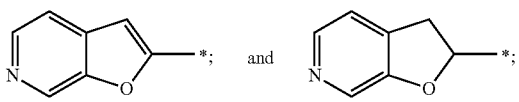

wherein the * represents the attachment point to the remainder of the molecule; and A² is selected from the group consisting of:

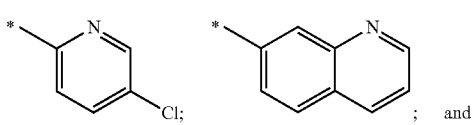

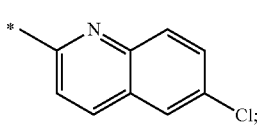

wherein the * represents the attachment point to the remainder of the molecule.

In some embodiments, (A¹-a) or (A¹-c) is selected from the group consisting of:

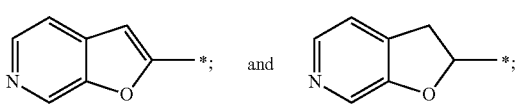

wherein the * represents the attachment point to the remainder of the molecule; and A² is

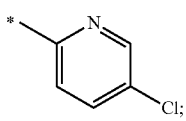

wherein the * represents the attachment point to the remainder of the molecule.

In some embodiments, the compound of formula (I) is a compound of formula d-3):

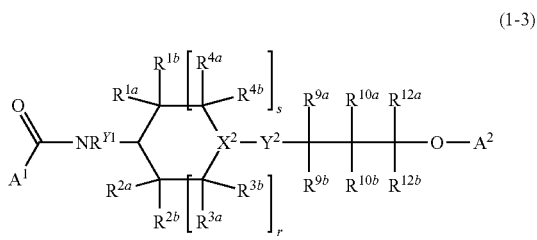

(1-3)

or a pharmaceutically acceptable salt thereof;
wherein:

$A^1$ is a substituent of formula ($A^1$-a)

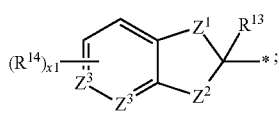

($A^1$-a)

$A^2$ is $C_6$-$C_{10}$ aryl optionally substituted with one or more $R^{16}$ substituents; or 5-10 membered heteroaryl optionally substituted with one or more $R^{16}$ substituents;

and wherein $X^2$, $R^{Y1}$, $Y^2$, $R^{Y2}$, r, s, $Z^1$, $R^{Z1-1}$, $R^{Z1-2}$, $Z^2$, $R^{Z2-1}$, $R^{Z2-2}$, $Z^3$, x1, $R^{1a}$, $R^{1b}$, $R^{2a}$, $R^{2b}$, $R^{3a}$, $R^{3b}$, $R^{4a}$, $R^{4b}$, $R^{9a}$, $R^{9b}$, $R^{10a}$, $R^{10a-a}$, $R^{10a-b}$, $R^{10a-c}$, $R^{10b}$, $R^{12a}$, $R^{12b}$, $R^{13}$, $R^{14}$, and $R^{16}$ are as defined in compounds of formula (I).

In some embodiments of the compounds of formula (1-3), $X^2$ is CH. In some embodiments, r is 1 and s is 1.

In some embodiments of the compounds of formula (1-3), $X^2$ is N and $Y^2$ is a bond. In some embodiments, r is 1 and s is 1. In some embodiments, r is 0 and s is 2.

In some embodiments of the compounds of formula (1-3), ($A^1$-a) is selected from the group consisting of:

($A^1$-b)

($A^1$-c)

($A^1$-d)

In some embodiments of the compounds of formula (1-3), ($A^1$-a) is ($A^1$-b).

In some embodiments of the compounds of formula (1-3), ($A^1$-a) is ($A^1$-c).

In some embodiments of the compounds of formula (1-3), ($A^1$-a) is ($A^1$-d).

In some embodiments of the compounds of formula (1-3), ($A^1$-a) or ($A^1$-b) is selected from the group consisting of:

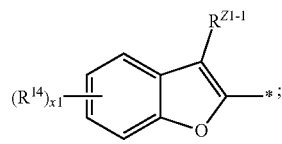

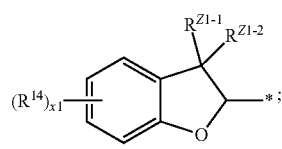


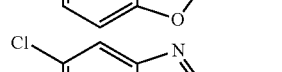

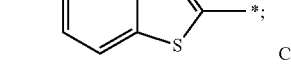

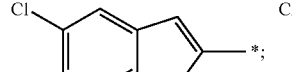

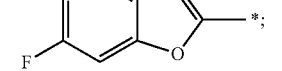

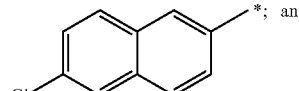

wherein the * represents the attachment point to the remainder of the molecule. In some embodiments, ($A^1$-a) or ($A^1$-b) is selected from the group consisting of:

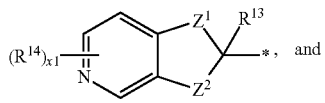

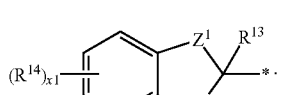

wherein the * represents the attachment point to the remainder of the molecule. In some embodiments, ($A^1$-a) or ($A^1$-b) is selected from the group consisting of:

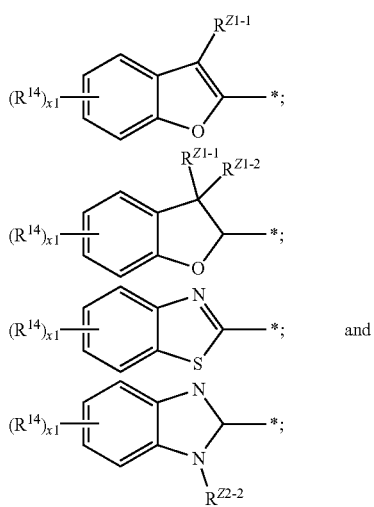

wherein the * represents the attachment point to the remainder of the molecule. In some embodiments, (A¹-a) or (A¹-b) is selected from the group consisting of:

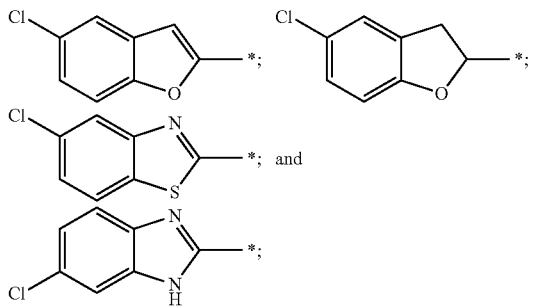

wherein the * represents the attachment point to the remainder of the molecule.

In some embodiments of the compounds of formula (1-3), (A¹-a) or (A¹-c) is selected from the group consisting of:

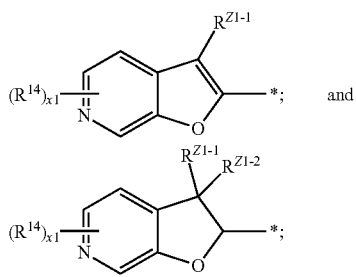

wherein the * represents the attachment point to the remainder of the molecule. In some embodiments, (A¹-a) or (A¹-c) is selected from the group consisting of:

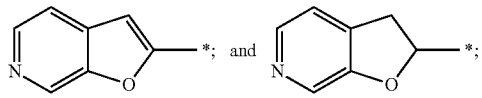

wherein the * represents the attachment point to the remainder of the molecule.

In some embodiments of the compounds of formula (1-3):
$R^{9a}$ and $R^{9b}$ are taken together to form an oxo (=O) substituent or an imido (=NH) substituent, or alternatively, $R^{9a}$ and $R^{9b}$ are both hydrogen;
$R^{10a}$ is selected from the group consisting of hydrogen, —$OR^{10a\text{-}a}$, and —$NR^{10a\text{-}b}R^{10a\text{-}c}$;
$R^{10b}$ is hydrogen; and
$R^{12a}$ and $R^{12b}$ are both hydrogen.

In some embodiments of the compounds of formula (1-3), $R^{9a}$ and $R^{9b}$ are taken together to form an oxo (=O) substituent. In some embodiments, $R^{10a}$ is hydrogen. In some embodiments, $R^{10a}$ is —$OR^{10a\text{-}a}$. In some embodiments, $R^{10a}$ is —$NR^{10a\text{-}b}R^{10a\text{-}c}$.

In some embodiments of the compounds of formula (1-3), $R^{9a}$ and $R^{9b}$ are taken together to form an imido (=NH) substituent. In some embodiments, $R^{10a}$ is hydrogen. In some embodiments, $R^{10a}$ is —$OR^{10a\text{-}a}$. In some embodiments, $R^{10a}$ is —$NR^{10a\text{-}b}R^{10a\text{-}c}$.

In some embodiments of the compounds of formula (1-3), $R^{9a}$ and $R^{9b}$ are both hydrogen. In some embodiments, $R^{10a}$ is hydrogen. In some embodiments, $R^{10a}$ is —$OR^{10a\text{-}a}$. In some embodiments, $R^{10a}$ is —$NR^{10a\text{-}b}R^{10a\text{-}c}$.

In some embodiments of the compounds of formula (1-3):
$X^2$ is CH or N;
$R^{Y1}$ is hydrogen or $C_1$-$C_6$ alkyl;
$Y^2$ is selected from the group consisting of a bond, $NR^{Y2}$, and O; provided that when $X^2$ is N, then $Y^2$ is a bond;
$R^{Y2}$ is hydrogen or $C_1$-$C_6$ alkyl;
r and s, independently of each other, are 0, 1, or 2;
$A^1$ is selected from the group consisting of:
a substituent of formula (A¹-a)

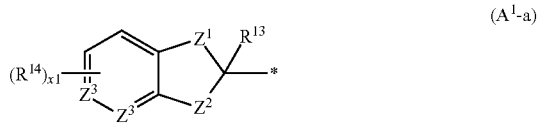

(A¹-a)

wherein
represents the attachment point to the remainder of the molecule; $Z^1$ is selected from the group consisting of $CR^{Z1\text{-}1}R^{Z1\text{-}2}$, $NR^{Z1\text{-}2}$, O, S, and —$CR^{Z1\text{-}1}$=$CR^{Z1\text{-}1}$—;
wherein $R^{Z1}$-1 is H or $R^{14}$; and $R^{Z1\text{-}2}$ is H or $R^{14}$;
$Z^2$ is selected from the group consisting of $CR^{Z2\text{-}1}R^{Z2\text{-}2}$, $NR^{Z2\text{-}2}$, O, S, and —$CR^{Z2\text{-}1}$=$CR^{Z2\text{-}1}$—;
wherein $R^{Z2\text{-}1}$ is H or $R^{14}$; and $R^{Z2\text{-}2}$ is H or $R^{14}$;
$Z^3$, independently at each occurrence, is C or N, provided that at least one $Z^3$ is C;
$R^{13}$ is hydrogen or $R^{14}$, or $R^{13}$ and $R^{Z1\text{-}2}$ are taken together to form a double bond between the carbon atom bearing R and Z, or R and R are taken together to form a double bond between the carbon atom bearing $R^{13}$ and $Z^2$; and
x1 is 1, 2, 3, or 4, and at least one $R^{14}$ is halogen;
$R^{14}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —$NH_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —$NR^{14\text{-}a}$ $R^{14-b}$, —CN, —C(O)OH, —C(O)O($C_1$-$C_6$ alkyl), —C(O)O($C_1$-$C_6$ haloalkyl), —C(O)$NH_2$, —C(O)NH ($C_1$-$C_6$ alkyl), —C(O)NH($C_1$-$C_6$ haloalkyl), —C(O)N ($C_1$-$C_6$ alkyl)$_2$, —C(O)N($C_1$-$C_6$ haloalkyl)$_2$, —C(O) $NR^{14-a}R^{14-b}$, —S(O)$_2$OH, —S(O)$_2$O($C_1$-$C_6$ alkyl), —S(O)$_2$O($C_1$-$C_6$ haloalkyl), —S(O)$_2$$NH_2$, —S(O)$_2$NH ($C_1$-$C_6$ alkyl), —S(O)$_2$NH($C_1$-$C_6$ haloalkyl), —S(O)$_2$N ($C_1$-$C_6$ alkyl)$_2$, —S(O)$_2$N($C_1$-$C_6$ haloalkyl)$_2$, —S(O)$_2$ $NR^{14-a}R^{14-b}$, —OC(O)H, —OC(O)($C_1$-$C_6$ alkyl), —OC(O)($C_1$-$C_6$ haloalkyl), —N(H)C(O)H, —N(H)C (O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C (O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$ ($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);
wherein $R^{14-a}$ and $R^{14-b}$ are taken together with the nitrogen atom which bears them to form a 3-10 membered heterocycle;
$A^2$ is $C_6$-$C_{10}$ aryl substituted by at least one halogen substituent and optionally further substituted with one or more $R^{16}$ substituents, or 5-10 membered heteroaryl substituted by at least one halogen substituent and optionally further substituted with one or more $R^{16}$ substituents;
$R^{16}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —$NH_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —$NR^{16-a}$ $R^{16-b}$, —CN, —C(O)OH, —C(O)O($C_1$-$C_6$ alkyl), —C(O)O($C_1$-$C_6$ haloalkyl), —C(O)$NH_2$, —C(O)NH ($C_1$-$C_6$ alkyl), —C(O)NH($C_1$-$C_6$ haloalkyl), —C(O)N ($C_1$-$C_6$ alkyl)$_2$, —C(O)N($C_1$-$C_6$ haloalkyl)$_2$, —C(O) $NR^{16a}R^{16b}$, —S(O)$_2$OH, —S(O)$_2$O($C_1$-$C_6$ alkyl), —S(O)$_2$O($C_1$-$C_6$ haloalkyl), —S(O)$_2$$NH_2$, —S(O)$_2$NH ($C_1$-$C_6$ alkyl), —S(O)$_2$NH($C_1$-$C_6$ haloalkyl), —S(O)$_2$N ($C_1$-$C_6$ alkyl)$_2$, —S(O)$_2$N($C_1$-$C_6$ haloalkyl)$_2$, —S(O)$_2$ $NR^{16a}R^{16b}$, —OC(O)H, —OC(O)($C_1$-$C_6$ alkyl), —OC (O)($C_1$-$C_6$ haloalkyl), —N(H)C(O)H, —N(H)C(O) ($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);
wherein $R^{16-a}$ and $R^{16-b}$ are taken together with the nitrogen atom which bears them to form a 3-10 membered heterocycle;
$R^{1a}$ and $R^{1b}$ are independently selected from the group consisting of hydrogen, $C_1$-$C_6$ alkyl, and halogen;
$R^{2a}$ and $R^{2b}$ are independently selected from the group consisting of hydrogen, $C_1$-$C_6$ alkyl, and halogen;
when present, $R^{3a}$ and $R^{3b}$ are independently at each occurrence selected from the group consisting of hydrogen, $C_1$-$C_6$ alkyl, and halogen;

when present, $R^{4a}$ and $R^{4b}$ are independently at each occurrence selected from the group consisting of hydrogen, $C_1$-$C_6$ alkyl, and halogen;
or alternatively, $R^{1a}$ and $R^{2a}$ are taken together to form a $C_1$-$C_6$ alkylene moiety;
or alternatively, $R^{1a}$ and an $R^{3a}$ moiety, when present, are taken together to form a $C_1$-$C_6$ alkylene moiety, and $R^{1b}$ and the $R^{3b}$ in the geminal position to the $R^{3a}$ taken together with $R^{1a}$, are both hydrogen;
or alternatively, an $R^{3a}$ moiety, when present, and an $R^{4a}$ moiety, when present, are taken together to form a $C_1$-$C_6$ alkylene moiety, and the $R^{3b}$ in the geminal position to the $R^{3a}$ taken together with the $R^{4a}$ moiety and the $R^{4b}$ in the geminal position to the $R^{4a}$ taken together with the $R^{3a}$ moiety, are both hydrogen;
$R^{9a}$ and $R^{9b}$ are taken together to form an oxo (=O) substituent or an imido (=NH) substituent, or alternatively, $R^{9a}$ and $R^{9b}$ are both hydrogen;
$R^{10a}$ is selected from the group consisting of hydrogen, —$OR^{10a-a}$, and —$NR^{10a-b}R^{10a-c}$;
$R^{10b}$ is hydrogen;
$R^{12a}$ and $R^{12b}$ are taken together to form an oxo (=O) substituent, or alternatively, $R^{12a}$ and $R^{12b}$ are both hydrogen;
$R^{10a-a}$ is selected from the group consisting of hydrogen, $C_1$-$C_6$ alkyl, and $C_1$-$C_6$ haloalkyl;
or $R^{10a-a}$ and $R^{Y2}$ may be taken together to form a carbonyl (C=O) moiety; and
$R^{10a-b}$ and $R^{10a-c}$, independently of each other, are selected from the group consisting of hydrogen, $C_1$-$C_6$ alkyl, and $C_1$-$C_6$ haloalkyl.
In some embodiments of the compounds of formula (1-3), $R^{Y1}$ is hydrogen. In some embodiments of the compounds of formula (1-3), $R^{Y1}$ is $C_1$-$C_6$ alkyl.
In some embodiments of the compounds of formula (1-3), $X^2$ is CH and $Y^2$ is $NR^{Y2}$. In some embodiments of the compounds of formula (1-2), $R^{Y2}$ is hydrogen. In some embodiments of the compounds of formula (1-3), $R^{Y2}$ is $C_1$-$C_6$ alkyl.
In some embodiments of the compounds of formula (1-3), $X^2$ is CH and $Y^2$ is O.
In some embodiments, $X^2$ is N and $Y^2$ is a bond.
In some embodiments of the compounds of formula (1-3), $R^{1a}$ and $R^{1b}$ are independently selected from the group consisting of hydrogen and $C_1$-$C_6$ alkyl. In some embodiments of the compounds of formula (1-3), $R^{1a}$ and $R^{1b}$ are both hydrogen.
In some embodiments of the compounds of formula (1-3), $R^{2a}$ and $R^{2b}$ are independently selected from the group consisting of hydrogen and $C_1$-$C_6$ alkyl. In some embodiments of the compounds of formula (1-3), $R^{2a}$ and $R^{2b}$ are both hydrogen.
In some embodiments of the compounds of formula (1-3), $R^{1a}$ and $R^{2a}$ are taken together to form a $C_1$-$C_6$ alkylene moiety.
In some embodiments of the compounds of formula (1-3), r is 1 and s is 1. In some embodiments, $R^{3a}$ and $R^{3b}$ are independently selected from the group consisting of hydrogen and $C_1$-$C_6$ alkyl. In some embodiments, $R^{3a}$ and $R^{3b}$ are both hydrogen. In some embodiments, $R^{4a}$ and $R^{4b}$ are independently selected from the group consisting of hydrogen and $C_1$-$C_6$ alkyl. In some embodiments, $R^{4a}$ and $R^{4b}$ are both hydrogen. In some embodiments, $R^{1a}$ and $R^{3a}$ are taken together to form a $C_1$-$C_6$ alkylene moiety, and $R^{1b}$ and $R^{3b}$ are both hydrogen. In some embodiments, $R^{3a}$ and $R^{4a}$ are taken together to form a $C_1$-$C_6$ alkylene moiety, and $R^{3b}$ and $R^{4b}$ are both hydrogen.

In some embodiments of the compounds of formula (1-3), $R^{9a}$ and $R^{9b}$ are taken together to form an oxo (=O) substituent. In some embodiments of the compounds of formula (1-3), $R^{9a}$ and $R^{9b}$ are taken together to form an imido (=NH) substituent. In some embodiments of the compounds of formula (1-3), $R^{9a}$ and $R^{9b}$ are both hydrogen.

In some embodiments of the compounds of formula (1-3), $R^{10a}$ is hydrogen and $R^{10b}$ is hydrogen.

In some embodiments of the compounds of formula (1-3), $R^{10a}$ is —$OR^{10a-a}$ and $R^{10b}$ is hydrogen. In some embodiments, $R^{10a-a}$ is selected from the group consisting of hydrogen and $C_1$-$C_6$ alkyl. In some embodiments, $R^{10a-a}$ is hydrogen. In some embodiments, $R^{10a-a}$ is $C_1$-$C_6$ alkyl. In some embodiments, $R^{10a-a}$ and $R^{Y2}$ may be taken together to form a carbonyl (C=O) moiety.

In some embodiments of the compounds of formula (1-3), $R^{10a}$ is —$NR^{10a-b}R^{10a-c}$ and $R^{10b}$ is hydrogen. In some embodiments, $R^{10a-b}$ and $R^{10a-c}$, independently of each other, are selected from the group consisting of hydrogen and $C_1$-$C_6$ alkyl. In some embodiments, $R^{10a-b}$ and $R^{10a-c}$ are hydrogen. In some embodiments, $R^{10a-b}$ and $R^{10a-c}$ are $C_1$-$C_6$ alkyl.

In some embodiments of the compounds of formula (1-3):
$X^2$ is CH;
$R^{Y1}$ is hydrogen;
$Y^2$ is $NR^{Y2}$;
$R^{Y2}$ is hydrogen;
$R^{9a}$ and $R^{9b}$ are both hydrogen;
$R^{10a}$ is —$OR^{10a-a}$;
$R^{10a-a}$ is hydrogen;
$R^{10b}$ is hydrogen; and
$R^{12a}$ and $R^{12b}$ are both hydrogen.

In some embodiments of the compounds of formula (1-3):
$X^2$ is CH;
$Y^2$ is $NR^{Y2}$;
$R^{9a}$ and $R^{9b}$ are both hydrogen;
$R^{10a}$ is —$OR^{10a-a}$;
$R^{12a}$ and $R^{12b}$ are both hydrogen; and
$R^{10a-a}$ and $R^{Y2}$ are taken together to form a carbonyl (C=O) moiety.

In some embodiments of the compounds of formula (1-3):
$X^2$ is CH;
$R^{Y1}$ is hydrogen;
$Y^2$ is $NR^{Y2}$;
$R^{Y2}$ is hydrogen;
$R^{9a}$ and $R^{9b}$ are both hydrogen;
$R^{10a}$ is —$OR^{10a-a}$;
$R^{10b}$ is hydrogen;
$R^{12a}$ and $R^{12b}$ are both hydrogen; and
$R^{10a-a}$ and $R^{Y2}$ are taken together to form a carbonyl (C=O) moiety.

In some embodiments of the compounds of formula (1-3):
$X^2$ is CH;
$R^{Y1}$ is hydrogen;
$Y^2$ is $NR^{Y2}$;
$R^{Y2}$ is hydrogen;
$R^{9a}$ and $R^{9b}$ are both hydrogen;
$R^{10a}$ is hydrogen;
$R^{10b}$ is hydrogen; and
$R^{12a}$ and $R^{12b}$ are both hydrogen.

In some embodiments of the compounds of formula (1-3):
$X^2$ is N;
$R^{Y1}$ is hydrogen;
$Y^2$ is a bond;
$R^{9a}$ and $R^{9b}$ are both hydrogen;
$R^{10a}$ is —$OR^{10a-a}$;
$R^{10a-a}$ is hydrogen;
$R^{10b}$ is hydrogen; and
$R^{12a}$ and $R^{12b}$ are both hydrogen.

In some embodiments of the compounds of formula (1-3):
$X^2$ is N;
$R^{Y1}$ is hydrogen;
$Y^2$ is a bond;
$R^{9a}$ and $R^{9b}$ are both hydrogen;
$R^{10a}$ is hydrogen;
$R^{10b}$ is hydrogen; and
$R^{12a}$ and $R^{12b}$ are both hydrogen.

In some embodiments of the compounds of formula (1-3):
$X^2$ is CH;
$R^{Y1}$ is hydrogen;
$Y^2$ is $NR^{Y2}$;
$R^{Y2}$ is hydrogen;
r and s are both 1;
$R^{9a}$ and $R^{9b}$ are both hydrogen;
$R^{10a}$ is —$OR^{10a-a}$;
$R^{10a-a}$ is hydrogen;
$R^{10b}$ is hydrogen; and
$R^{12a}$ and $R^{12b}$ are both hydrogen.

In some embodiments of the compounds of formula (1-3):
$X^2$ is CH;
$Y^2$ is $NR^{Y2}$;
r and s are both 1;
$R^{9a}$ and $R^{9b}$ are both hydrogen;
$R^{10a}$ is —$OR^{10a-a}$;
$R^{12a}$ and $R^{12b}$ are both hydrogen; and
$R^{10a-a}$ and $R^{Y2}$ are taken together to form a carbonyl (C=O) moiety.

In some embodiments of the compounds of formula (1-3):
$X^2$ is CH;
$R^{Y1}$ is hydrogen;
$Y^2$ is $NR^{Y2}$;
$R^{Y2}$ is hydrogen;
r and s are both 1;
$R^{9a}$ and $R^{9b}$ are both hydrogen;
$R^{10a}$ is —$OR^{10a-a}$;
$R^{10b}$ is hydrogen;
$R^{12a}$ and $R^{12b}$ are both hydrogen; and
$R^{10a-a}$ and $R^{Y2}$ are taken together to form a carbonyl (C=O) moiety.

In some embodiments of the compounds of formula (1-3):
$X^2$ is CH;
$R^{Y1}$ is hydrogen;
$Y^2$ is $NR^{Y2}$;
$R^{Y2}$ is hydrogen;
r and s are both 1;
$R^{9a}$ and $R^{9b}$ are both hydrogen;
$R^{10a}$ is hydrogen;
$R^{10b}$ is hydrogen; and
$R^{12a}$ and $R^{12b}$ are both hydrogen.

In some embodiments of the compounds of formula (1-3):
$X^2$ is N;
$R^{Y1}$ is hydrogen;
$Y^2$ is a bond;
r and s are both 1;
$R^{9a}$ and $R^{9b}$ are both hydrogen;
$R^{10a}$ is —$OR^{10a-a}$;
$R^{10a-a}$ is hydrogen;
$R^{10b}$ is hydrogen; and
$R^{12a}$ and $R^{12b}$ are both hydrogen.

In some embodiments of the compounds of formula (1-3):
$X^2$ is N;
$R^{Y1}$ is hydrogen;
$Y^2$ is a bond;
r and s are both 1;

$R^{9a}$ and $R^{9b}$ are both hydrogen;
$R^{10a}$ is hydrogen;
$R^{10b}$ is hydrogen; and
$R^{12a}$ and $R^{12b}$ are both hydrogen.

$R^{12a}$ and $R^{12b}$ are both hydrogen. In some embodiments of the compounds of formula (1-3), $A^2$ is $C_6$-$C_{10}$ aryl substituted by at least one halogen substituent and optionally further substituted with one or more $R^{16}$ substituents, or 5-10 membered heteroaryl substituted by at least one halogen substituent and optionally further substituted with one or more $R^{16}$ substituents.

In some embodiments of the compounds of formula (1-3), $A^2$ is $C_6$-$C_{10}$ aryl optionally substituted with one or more $R^{16}$ substituents. In some embodiments, $A^2$ is $C_6$-$C_{10}$ aryl substituted by at least one halogen substituent and optionally further substituted with one or more $R^{16}$ substituents. In some embodiments, $A^2$ is selected from the group consisting of:

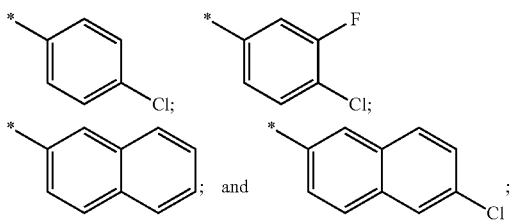

wherein the * represents the attachment point to the remainder of the molecule. In some embodiments, $A^2$ is phenyl optionally substituted with one or more $R^{16}$ substituents. In some embodiments, $A^2$ is phenyl substituted by at least one halogen substituent and optionally further substituted with one or more $R^{16}$ substituents. In some embodiments, $A^2$ is selected from the group consisting of:

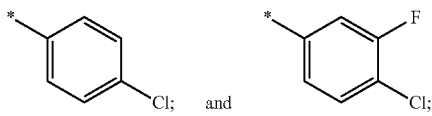

wherein the * represents the attachment point to the remainder of the molecule.

In some embodiments, $A^2$ is 5-10 membered heteroaryl optionally substituted with one or more $R^{16}$ substituents. In some embodiments, $A^2$ is 5-10 membered heteroaryl substituted by at least one halogen substituent and optionally further substituted with one or more $R^{16}$ substituents. In some embodiments, $A^2$ is selected from the group consisting of:

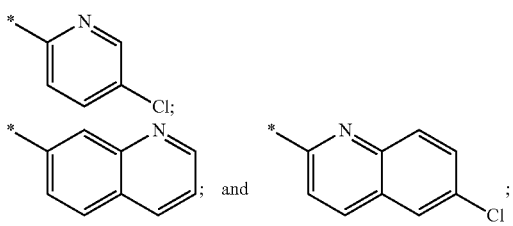

wherein the * represents the attachment point to the remainder of the molecule. In some embodiments, $A^2$ is pyridyl optionally substituted with one or more $R^{16}$ substituents. In some embodiments, $A^2$ is pyridyl substituted by at least one halogen substituent and optionally further substituted with one or more $R^{16}$ substituents. In some embodiments, $A^2$ is

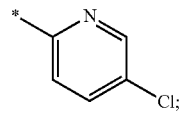

wherein the * represents the attachment point to the remainder of the molecule.

In some embodiments, ($A^1$-a) or ($A^1$-b) is selected from the group consisting of:

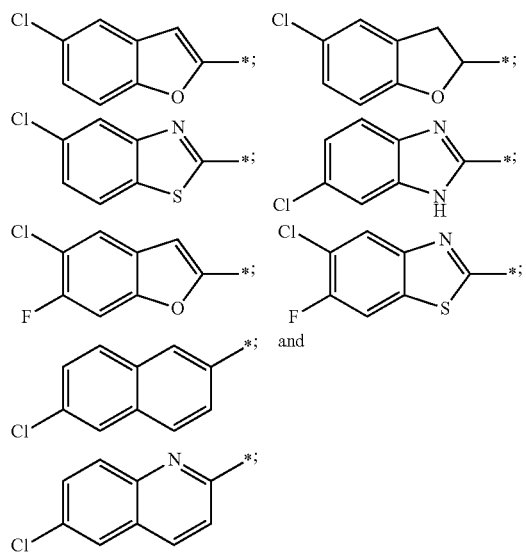

wherein the * represents the attachment point to the remainder of the molecule; and ($A^2$-a) or ($A^2$-b) is selected from the group consisting of:

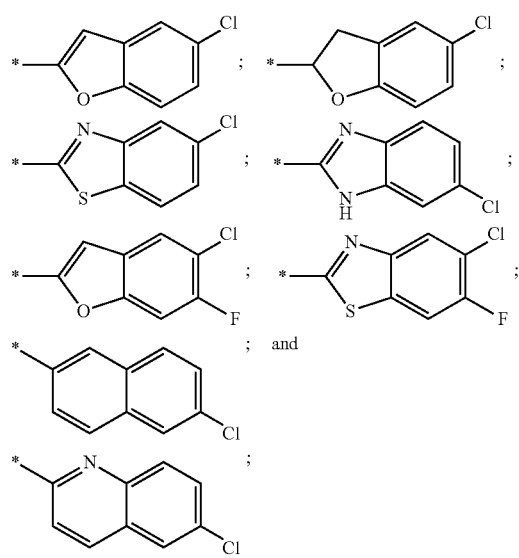

wherein the * represents the attachment point to the remainder of the molecule.

In some embodiments, (A¹-a) or (A¹-b) is selected from the group consisting of:

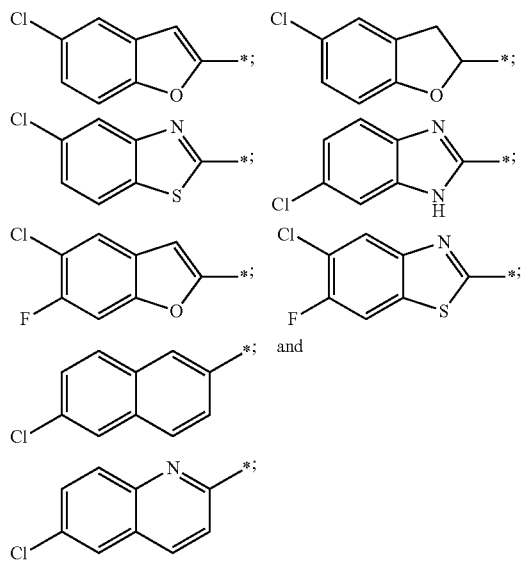

wherein the * represents the attachment point to the remainder of the molecule; and (A²-a) or (A²-b) is selected from the group consisting of:

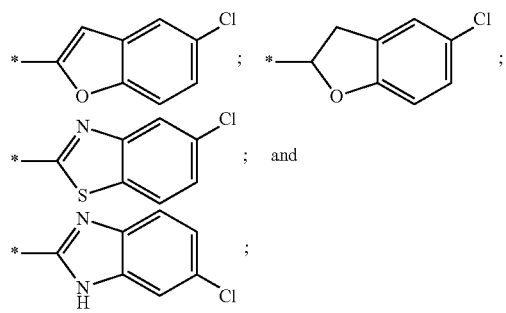

wherein the * represents the attachment point to the remainder of the molecule.

In some embodiments, (A¹-a) or (A¹-b) is selected from the group consisting of:

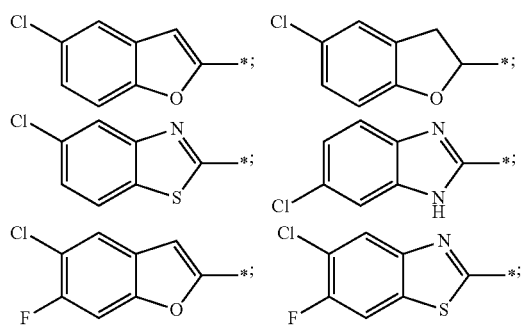

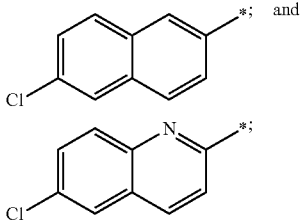

wherein the * represents the attachment point to the remainder of the molecule; and (A²-a) or (A²-c) is selected from the group consisting of:

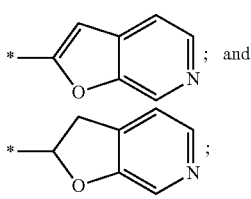

wherein the * represents the attachment point to the remainder of the molecule.

In some embodiments, (A¹-a) or (A¹-b) is selected from the group consisting of:

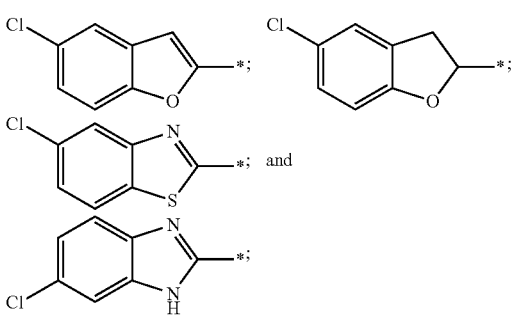

wherein the * represents the attachment point to the remainder of the molecule; and (A²-a) or (A²-b) is selected from the group consisting of:

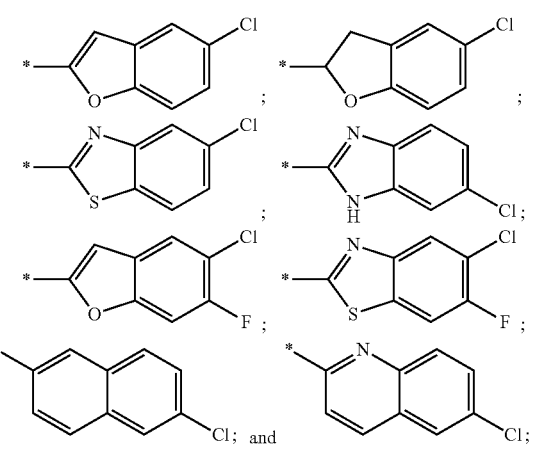

wherein the * represents the attachment point to the remainder of the molecule.

In some embodiments, (A¹-a) or (A¹-b) is selected from the group consisting of:

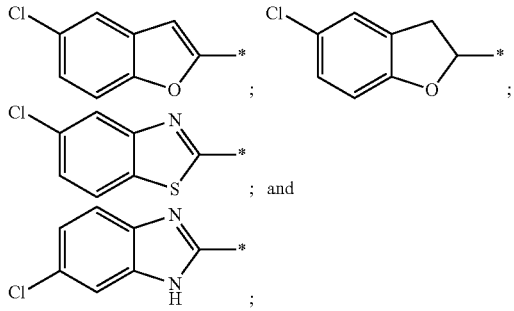

wherein the * represents the attachment point to the remainder of the molecule; and (A²-a) or (A²-b) is selected from the group consisting of:

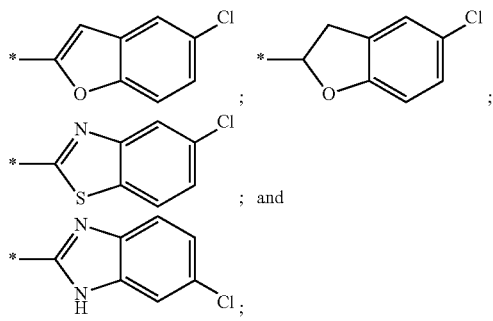

wherein the * represents the attachment point to the remainder of the molecule.

In some embodiments, (A¹-a) or (A¹-b) is selected from the group consisting of:

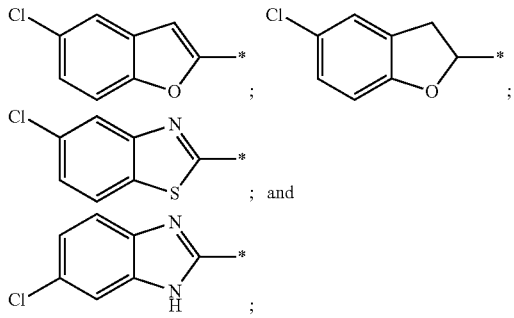

wherein the * represents the attachment point to the remainder of the molecule; and (A²-a) or (A²-c) is selected from the group consisting of:

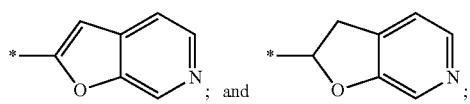 [SMILES: *c1cc2ccncc2o1 ; *C1Cc2ccncc2O1]

wherein the * represents the attachment point to the remainder of the molecule.

In some embodiments, (A¹-a) or (A¹-c) is selected from the group consisting of:

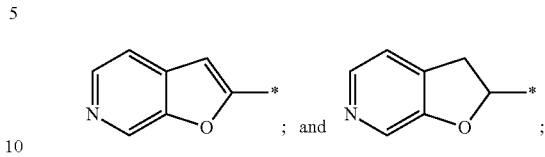

wherein the * represents the attachment point to the remainder of the molecule; and (A²-a) or (A²-b) is selected from the group consisting of:

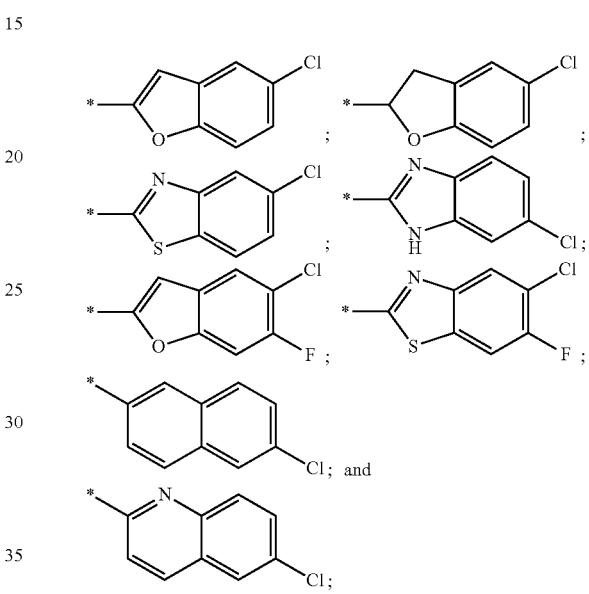

wherein the * represents the attachment point to the remainder of the molecule.

In some embodiments, (A¹-a) or (A¹-c) is selected from the group consisting of:

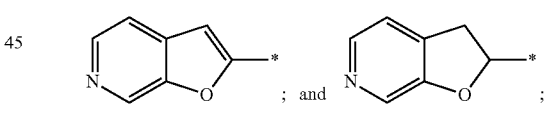

wherein the * represents the attachment point to the remainder of the molecule; and (A²-a) or (A²-b) is selected from the group consisting of:

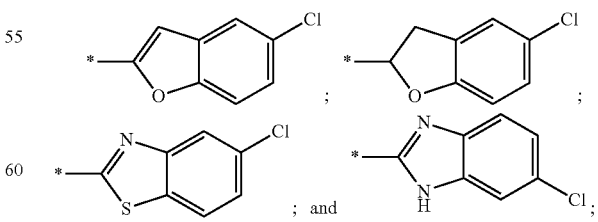

wherein the * represents the attachment point to the remainder of the molecule.

In some embodiments, (A¹-a) or (A¹-c) is selected from the group consisting of:

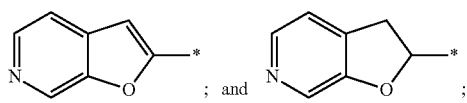 [SMILES: *c1cc2ccncc2o1 ; *C1Cc2ccncc2O1]

wherein the * represents the attachment point to the remainder of the molecule; and (A²-a) or (A²-c) is selected from the group consisting of:

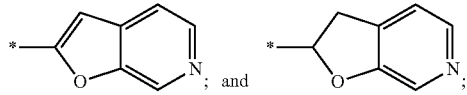 [SMILES: *c1cc2ccncc2o1 ; *C1Cc2ccncc2O1]

wherein the * represents the attachment point to the remainder of the molecule.

In some embodiments, (A¹-a) or (A¹-b) is selected from the group consisting of:

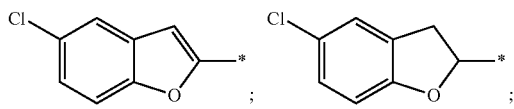


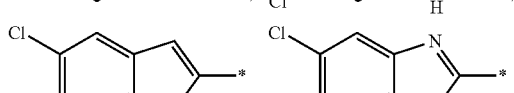

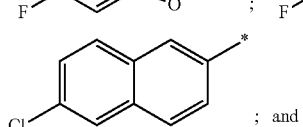

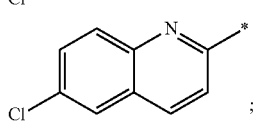

wherein the * represents the attachment point to the remainder of the molecule; and A² is selected from the group consisting of:

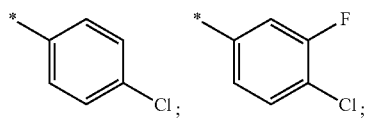

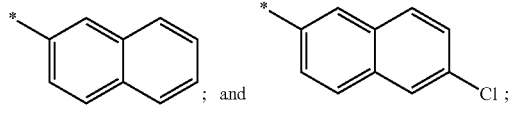

wherein the * represents the attachment point to the remainder of the molecule.

In some embodiments, (A¹-a) or (A¹-b) is selected from the group consisting of:

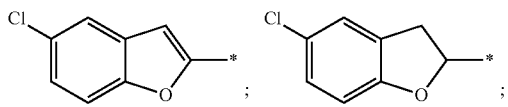

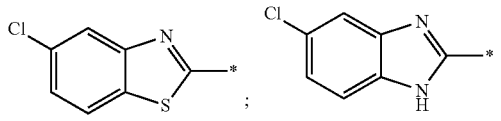

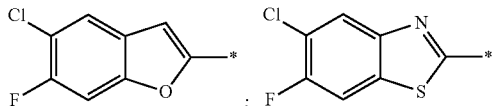

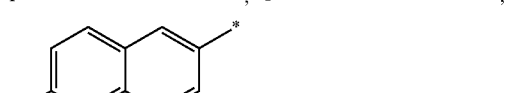

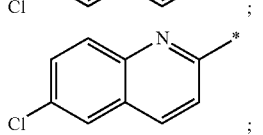

wherein the * represents the attachment point to the remainder of the molecule; and A² is selected from the group consisting of:

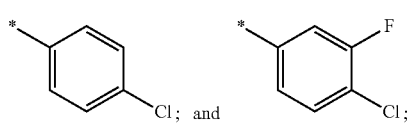 [SMILES: *c1ccc(Cl)cc1 ; *c1ccc(Cl)c(F)c1]

wherein the * represents the attachment point to the remainder of the molecule.

In some embodiments, (A¹-a) or (A¹-b) is selected from the group consisting of:

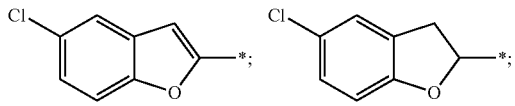

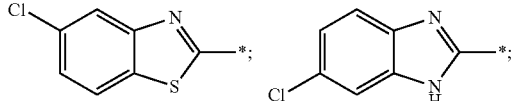

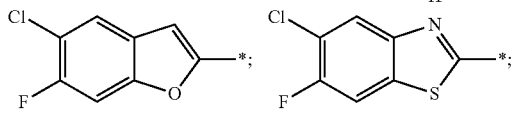

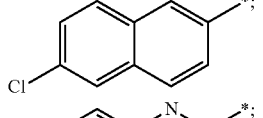

wherein the * represents the attachment point to the remainder of the molecule; and A² is selected from the group consisting of:

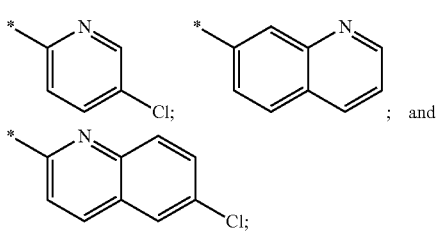

wherein the * represents the attachment point to the remainder of the molecule.

In some embodiments, (A¹-a) or (A¹-b) is selected from the group consisting of:

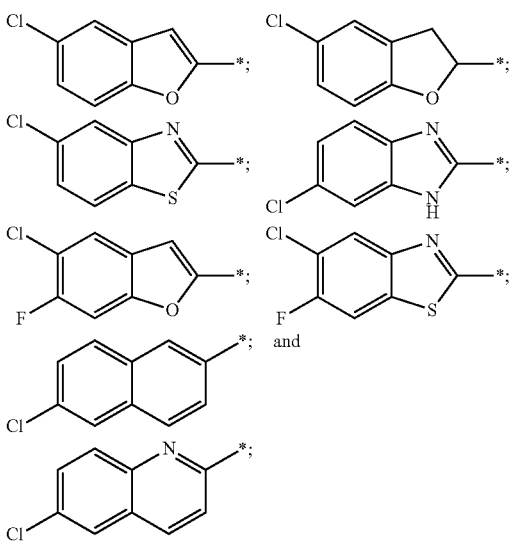

wherein the * represents the attachment point to the remainder of the molecule; and A² is

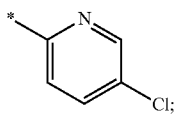

wherein the * represents the attachment point to the remainder of the molecule.

In some embodiments, (A¹-a) or (A¹-b) is selected from the group consisting of:

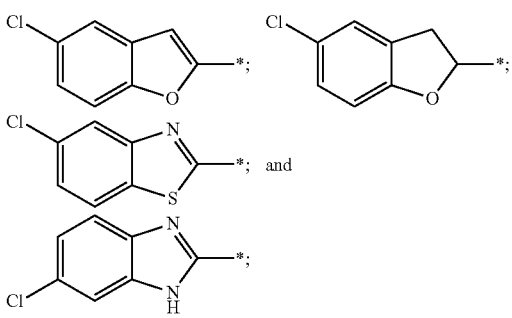

wherein the * represents the attachment point to the remainder of the molecule; and A² is selected from the group consisting of:

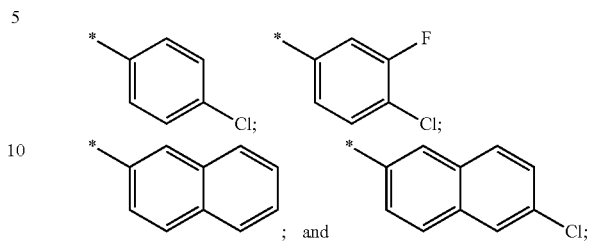

wherein the * represents the attachment point to the remainder of the molecule.

In some embodiments, (A¹-a) or (A¹-b) is selected from the group consisting of:

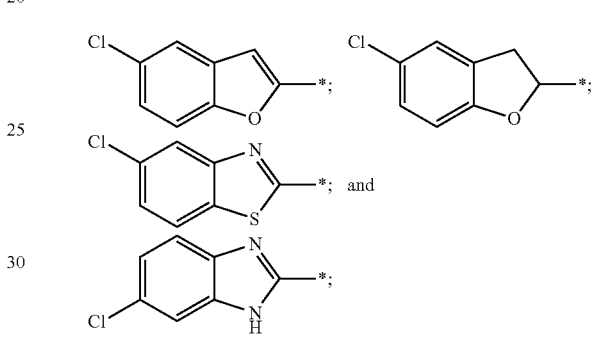

wherein the * represents the attachment point to the remainder of the molecule; and A² is selected from the group consisting of:

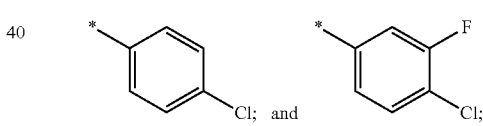

wherein the * represents the attachment point to the remainder of the molecule.

In some embodiments, (A¹-a) or (A¹-b) is selected from the group consisting of:

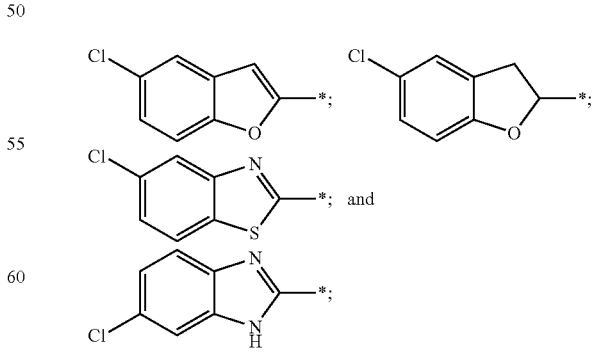

wherein the * represents the attachment point to the remainder of the molecule; and A² is selected from the group consisting of:

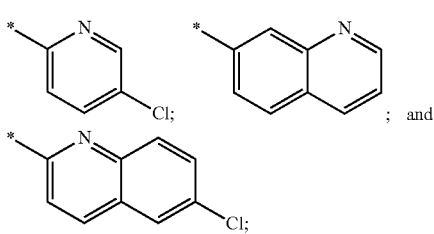

wherein the * represents the attachment point to the remainder of the molecule.

In some embodiments, (A¹-a) or (A¹-b) is selected from the group consisting of:

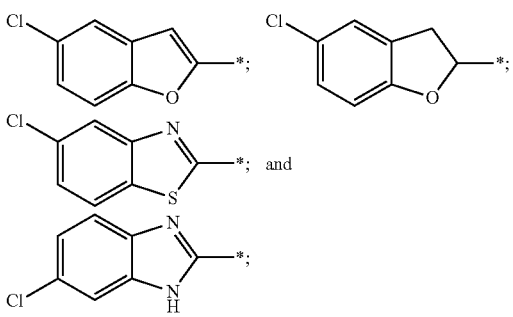

wherein the * represents the attachment point to the remainder of the molecule; and A² is

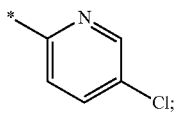 [SMILES: *c1ccc(Cl)cn1]

wherein the * represents the attachment point to the remainder of the molecule.

In some embodiments, (A¹-a) or (A¹-c) is selected from the group consisting of:

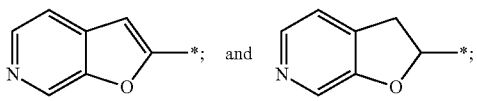

wherein the * represents the attachment point to the remainder of the molecule: and A² is selected from the group consisting of:

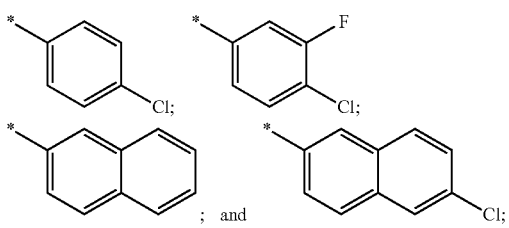

wherein the * represents the attachment point to the remainder of the molecule.

In some embodiments, (A¹-a) or (A¹-c) is selected from the group consisting of:

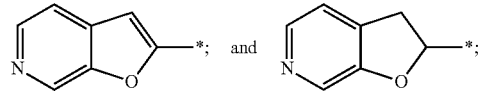

wherein the * represents the attachment point to the remainder of the molecule; and A² is selected from the group consisting of:

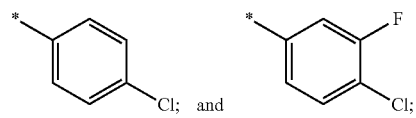

wherein the * represents the attachment point to the remainder of the molecule.

In some embodiments, (A¹-a) or (A¹-c) is selected from the group consisting of:

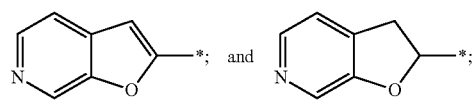

wherein the * represents the attachment point to the remainder of the molecule; and A² is selected from the group consisting of:

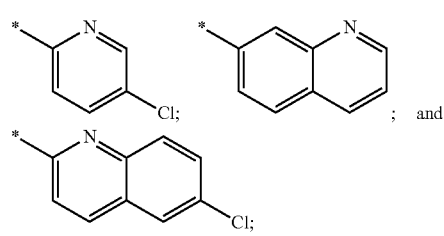

wherein the * represents the attachment point to the remainder of the molecule.

In some embodiments, (A¹-a) or (A¹-c) is selected from the group consisting of:

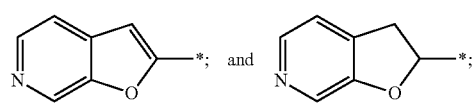

wherein the * represents the attachment point to the remainder of the molecule; and A² is

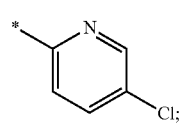 [SMILES: *c1ccc(Cl)cn1]

wherein the * represents the attachment point to the remainder of the molecule.

In some embodiments, the compound of formula (I) is a compound of formula (1-4):

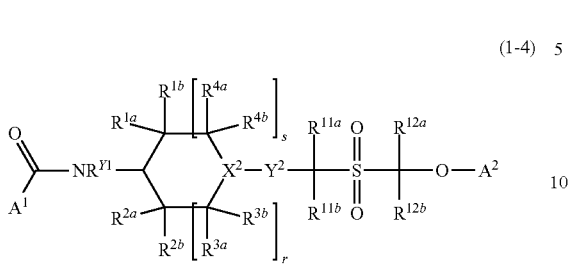 (1-4)

or a pharmaceutically acceptable salt thereof;
wherein:
$A^1$ is a substituent of formula ($A^1$-a)

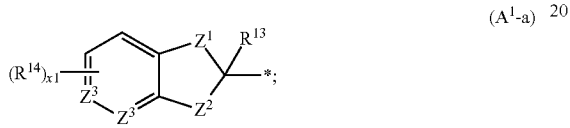 ($A^1$-a)

$A^2$ is $C_6$-$C_{10}$ aryl optionally substituted with one or more $R^{16}$ substituents; or 5-10 membered heteroaryl optionally substituted with one or more $R^{16}$ substituents;
$R^{11a}$ and $R^{11b}$ are both hydrogen;
$R^{12a}$ and $R^{12b}$ are both hydrogen;
and wherein $X^2$, $R^{Y1}$, $Y^2$, $R^{Y2}$, r, s, $A^1$, $Z^1$, $R^{Z1-1}$, $R^{Z1-2}$, $Z^2$, $R^{Z2-1}$, $R^{Z2-2}$, $Z^3$, x1, $R^{1a}$, $R^{1b}$, $R^{2a}$, $R^{2b}$, $R^{3a}$, $R^{3b}$, $R^{4a}$, $R^{4b}$, $R^{13}$, $R^{14}$, and $R^{16}$ are as defined in compounds of formula (I).

In some embodiments of the compounds of formula (1-4), $X^2$ is CH. In some embodiments, r is 1 and s is 1.

In some embodiments of the compounds of formula (1-4), $X^2$ is N and $Y^2$ is a bond. In some embodiments, r is 1 and s is 1. In some embodiments, r is 0 and s is 2.

In some embodiments of the compounds of formula (1-4), ($A^1$-a) is selected from the group consisting of:

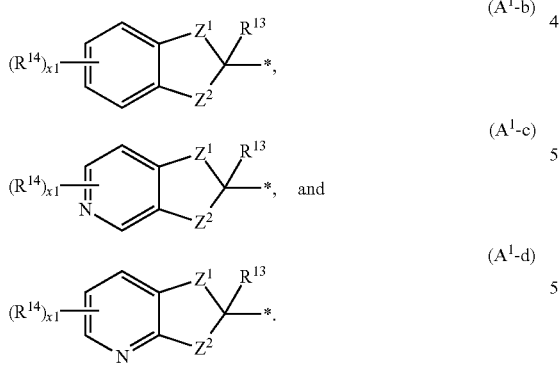

In some embodiments of the compounds of formula (1-4), ($A^1$-a) is ($A^1$-b).
In some embodiments of the compounds of formula (1-4), ($A^1$-a) is ($A^1$-c).
In some embodiments of the compounds of formula (1-4), ($A^1$-a) is ($A^1$-d).
In some embodiments of the compounds of formula (1-4), ($A^1$-a) or ($A^1$-b) is selected from the group consisting of:

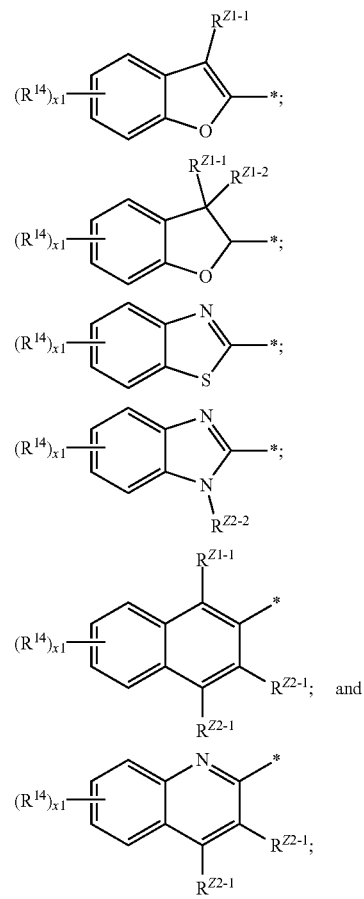

wherein the * represents the attachment point to the remainder of the molecule. In some embodiments, ($A^1$-a) or ($A^1$-b) is selected from the group consisting of:

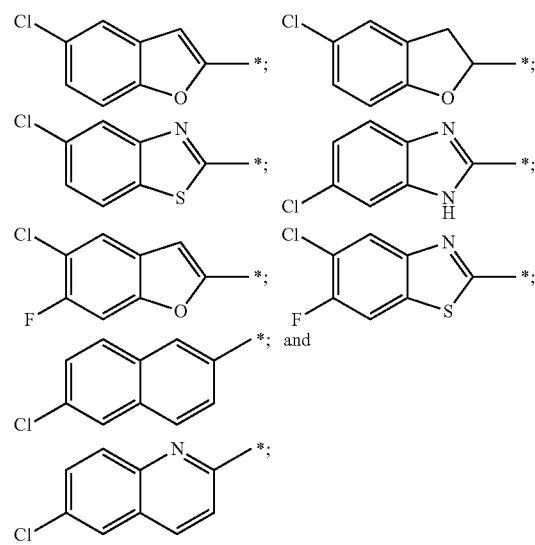

wherein the * represents the attachment point to the remainder of the molecule. In some embodiments, ($A^1$-a) or ($A^1$-b) is selected from the group consisting of:

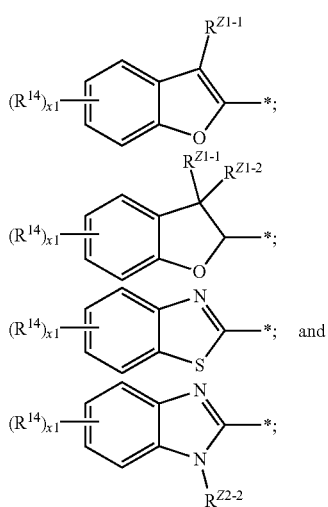

wherein the * represents the attachment point to the remainder of the molecule. In some embodiments, (A$^1$-a) or (A$^1$-b) is selected from the group consisting of:

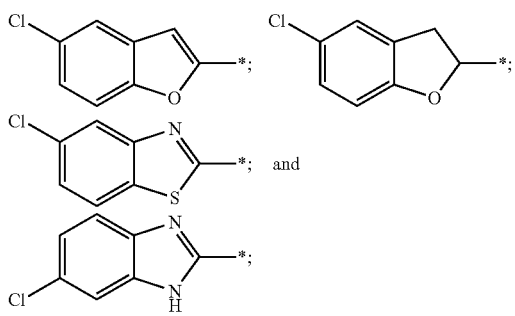

wherein the * represents the attachment point to the remainder of the molecule.

In some embodiments of the compounds of formula (1-4), (A$^1$-a) or (A$^1$-c) is selected from the group consisting of:

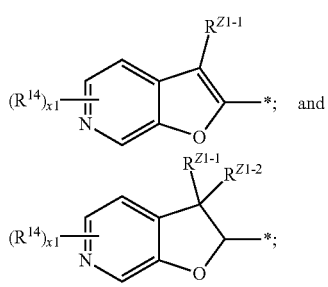

wherein the * represents the attachment point to the remainder of the molecule. In some embodiments, (A$^1$-a) or (A$^1$-c) is selected from the group consisting of:

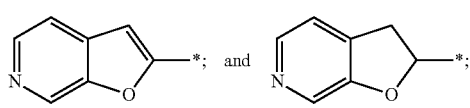

wherein the * represents the attachment point to the remainder of the molecule.

In some embodiments of the compounds of formula (1-4), A$^2$ is C$_6$-C$_{10}$ aryl optionally substituted with one or more R$^{16}$ substituents. In some embodiments, A$^2$ is selected from the group consisting of:

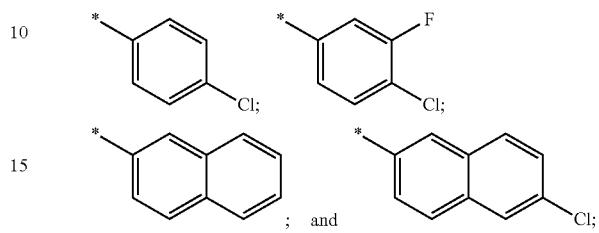

wherein the * represents the attachment point to the remainder of the molecule. In some embodiments, A$^2$ is phenyl optionally substituted with one or more R$^{16}$ substituents. In some embodiments, A$^2$ is selected from the group consisting of:

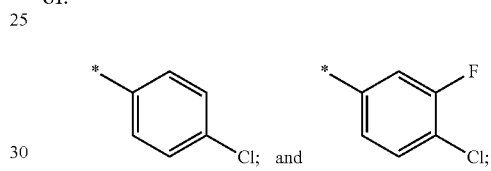

wherein the * represents the attachment point to the remainder of the molecule.

In some embodiments of the compounds of formula (1-4), A$^2$ is 5-10 membered heteroaryl optionally substituted with one or more R$^{16}$ substituents. In some embodiments, A$^2$ is selected from the group consisting of:

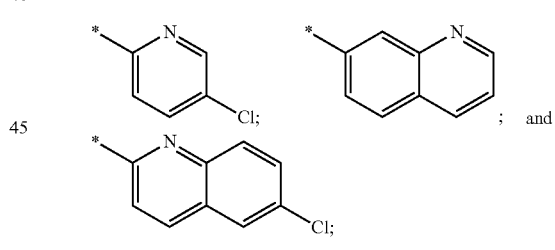

wherein the * represents the attachment point to the remainder of the molecule. In some embodiments, A$^2$ is pyridyl optionally substituted with one or more R$^{16}$ substituents. In some embodiments, A$^2$ is

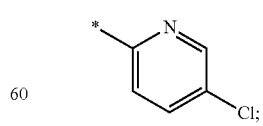

wherein the * represents the attachment point to the remainder of the molecule.

In some embodiments, (A$^1$-a) or (A$^1$-b) is selected from the group consisting of:

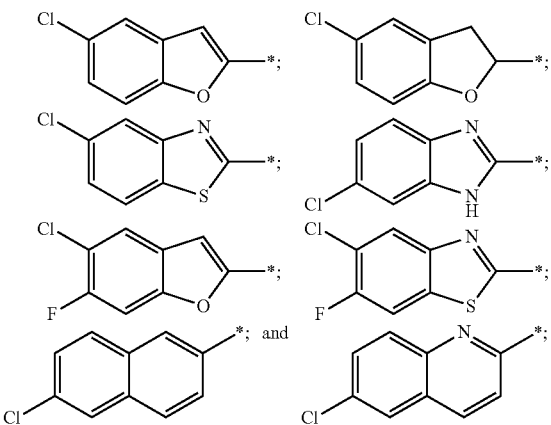

wherein the * represents the attachment point to the remainder of the molecule; and (A²-a) or (A²-b) is selected from the group consisting of:

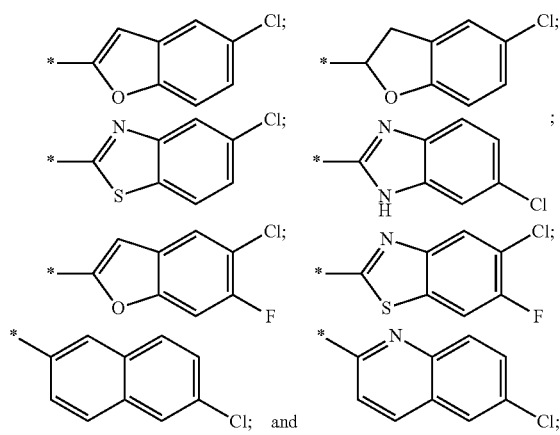

wherein the * represents the attachment point to the remainder of the molecule.

In some embodiments, (A¹-a) or (A¹-b) is selected from the group consisting of:

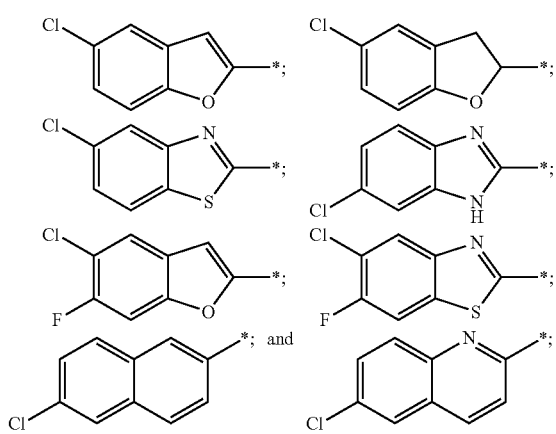

wherein the * represents the attachment point to the remainder of the molecule; and (A²-a) or (A²-b) is selected from the group consisting of:

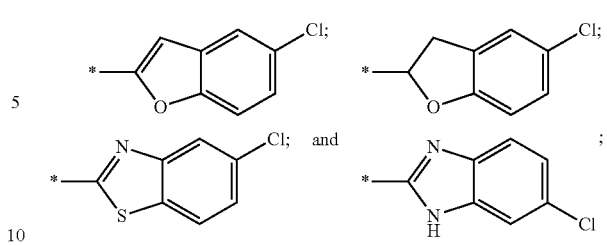

wherein the * represents the attachment point to the remainder of the molecule.

In some embodiments, (A¹-a) or (A¹-b) is selected from the group consisting of:

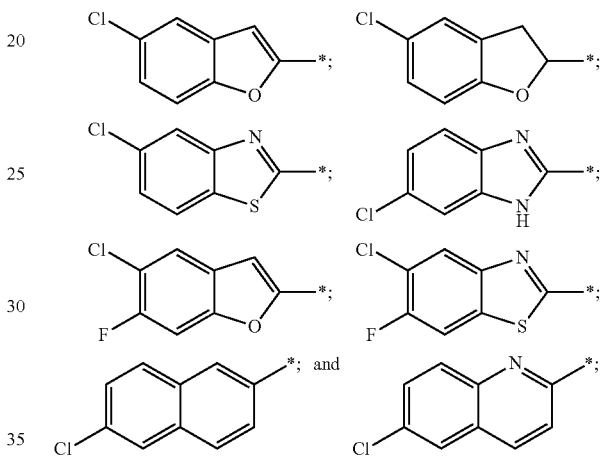

wherein the * represents the attachment point to the remainder of the molecule; and (A²-a) or (A²-c) is selected from the group consisting of:

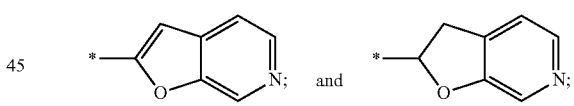

wherein the * represents the attachment point to the remainder of the molecule.

In some embodiments, (A¹-a) or (A¹-b) is selected from the group consisting of:

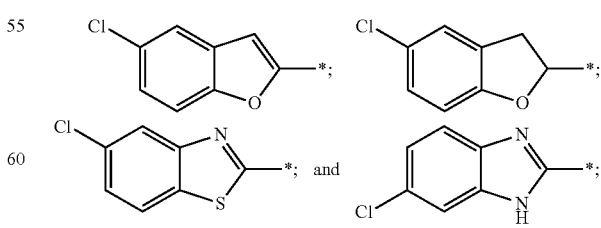

wherein the * represents the attachment point to the remainder of the molecule; and (A²-a) or (A²-b) is selected from the group consisting of:

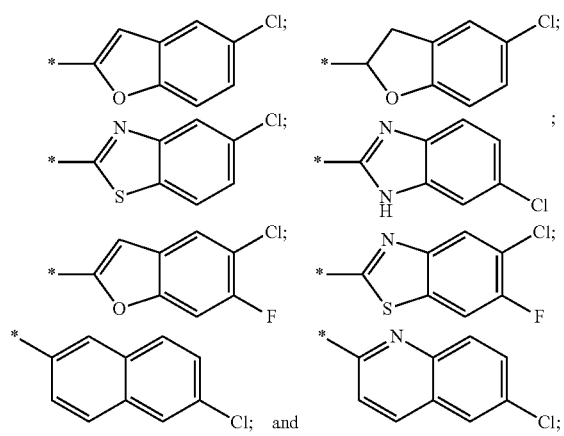

wherein the * represents the attachment point to the remainder of the molecule.

In some embodiments, (A¹-a) or (A¹-b) is selected from the group consisting of:

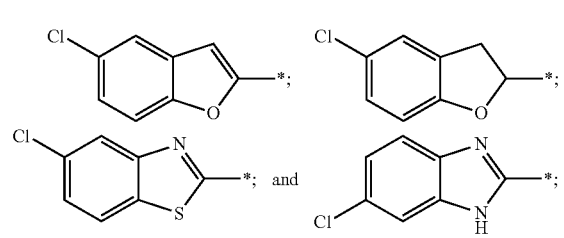

wherein the * represents the attachment point to the remainder of the molecule: and (A²-a) or (A²-b) is selected from the group consisting of:

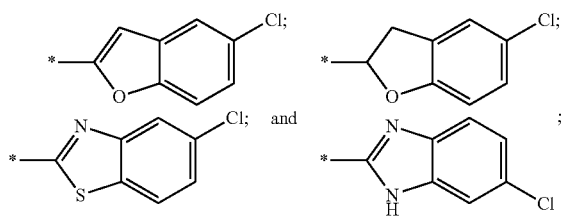

wherein the * represents the attachment point to the remainder of the molecule.

In some embodiments, (A¹-a) or (A¹-b) is selected from the group consisting of:

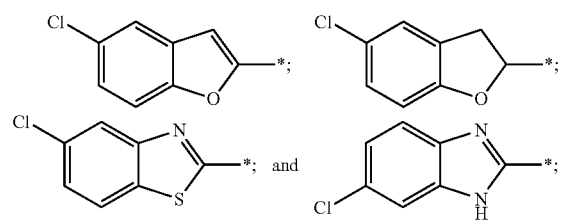

wherein the * represents the attachment point to the remainder of the molecule; and (A²-a) or (A²-c) is selected from the group consisting of:

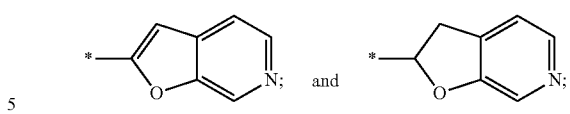

wherein the * represents the attachment point to the remainder of the molecule.

In some embodiments, (A¹-a) or (A¹-c) is selected from the group consisting of:

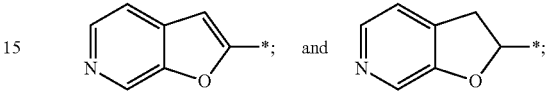

wherein the * represents the attachment point to the remainder of the molecule; and (A²-a) or (A²-b) is selected from the group consisting of:

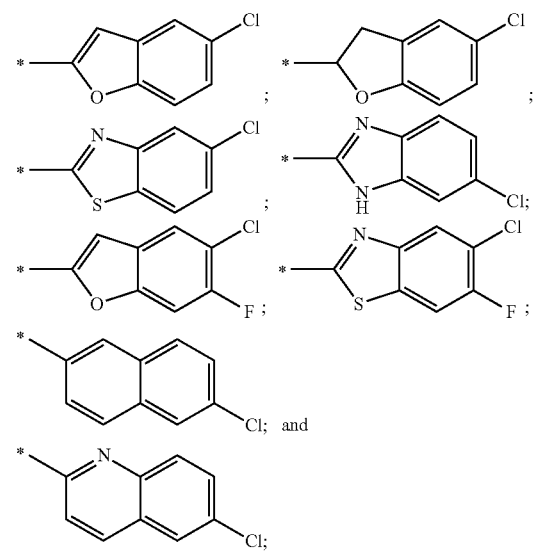

wherein the * represents the attachment point to the remainder of the molecule.

In some embodiments, (A¹-a) or (A¹-c) is selected from the group consisting of:

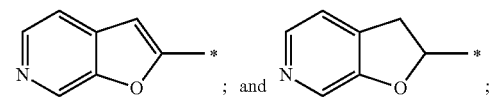

wherein the * represents the attachment point to the remainder of the molecule; and (A²-a) or (A²-b) is selected from the group consisting of:

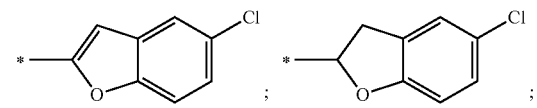

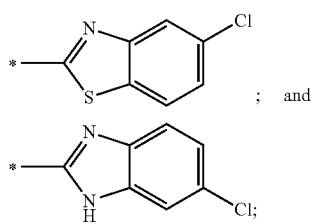
; and

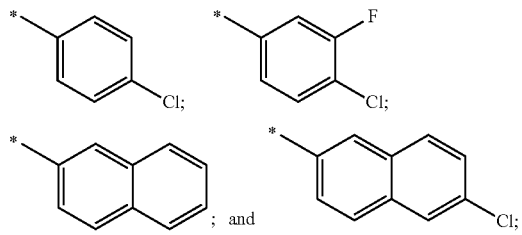
; and wherein the * represents the attachment point to the remainder of the molecule.

In some embodiments, (A¹-a) or (A¹-c) is selected from the group consisting of:

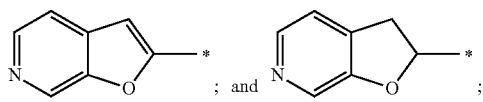

wherein the * represents the attachment point to the remainder of the molecule; and (A²-a) or (A²-c) is selected from the group consisting of:

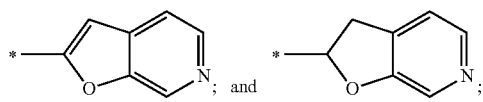

wherein the * represents the attachment point to the remainder of the molecule.

In some embodiments, (A¹-a) or (A¹-b) is selected from the group consisting of:

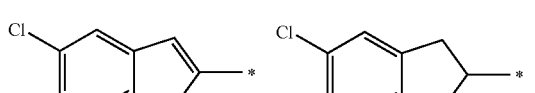

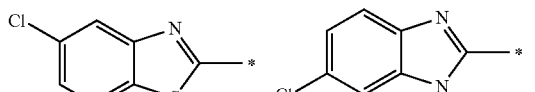

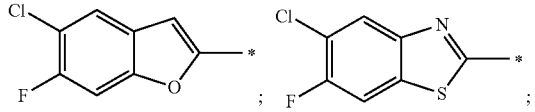

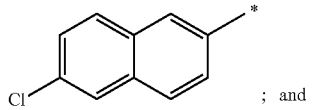

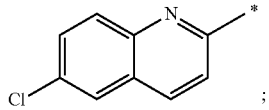

wherein the * represents the attachment point to the remainder of the molecule.

In some embodiments, (A¹-a) or (A¹-b) is selected from the group consisting of:

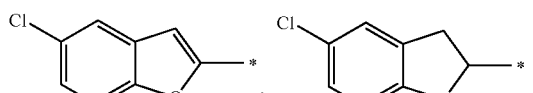

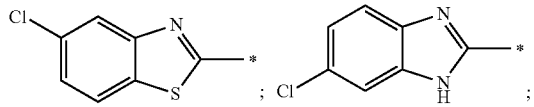

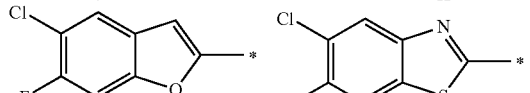

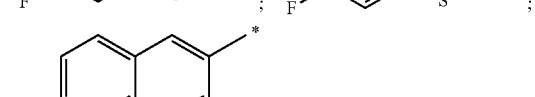

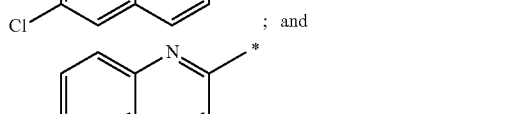

wherein the * represents the attachment point to the remainder of the molecule; and A² is selected from the group consisting of:

wherein the * represents the attachment point to the remainder of the molecule.

In some embodiments, (A¹-a) or (A¹-b) is selected from the group consisting of:

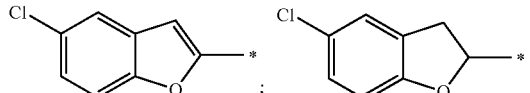

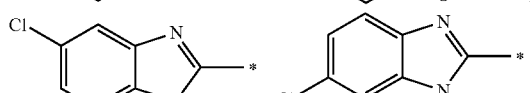

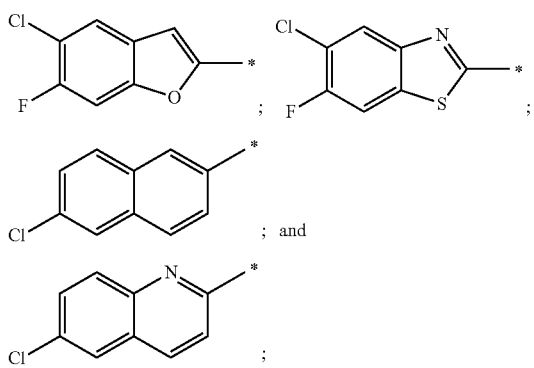

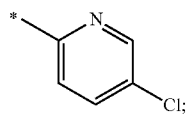

wherein the * represents the attachment point to the remainder of the molecule.

In some embodiments, $(A^1$-a$)$ or $(A^1$-b$)$ is selected from the group consisting of:

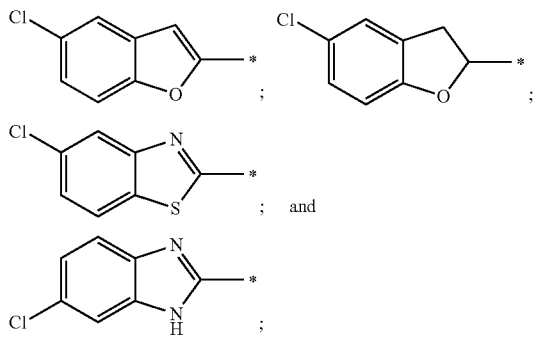

wherein the * represents the attachment point to the remainder of the molecule; and $A^2$ is selected from the group consisting of:

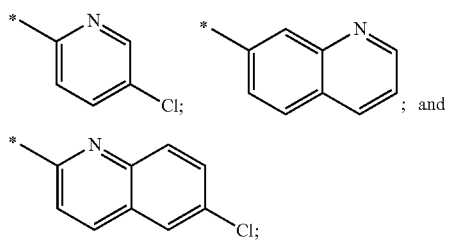

wherein the * represents the attachment point to the remainder of the molecule.

In some embodiments, $(A^1$-a$)$ or $(A^1$-b$)$ is selected from the group consisting of:

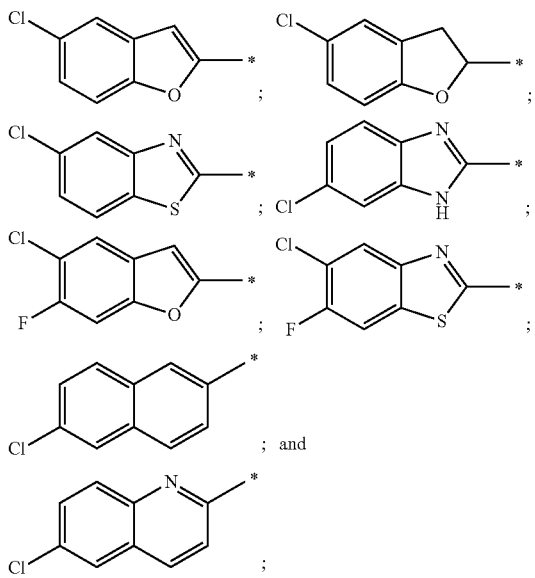

wherein the * represents the attachment point to the remainder of the molecule; and $A^2$ is wherein the * represents the attachment point to the remainder of the molecule.

In some embodiments, $(A^1$-a$)$ or $(A^1$-b$)$ is selected from the group consisting of:

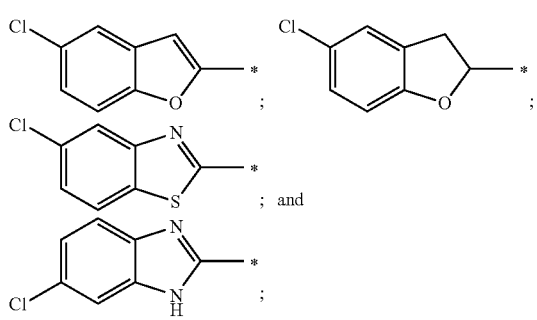

wherein the * represents the attachment point to the remainder of the molecule; and $A^2$ is selected from the group consisting of:

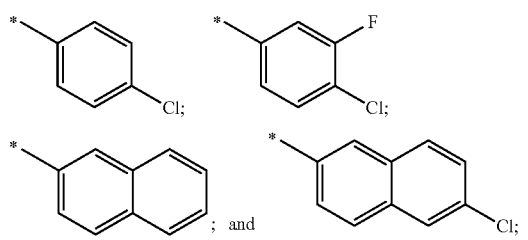

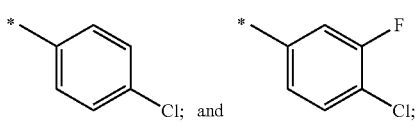

wherein the * represents the attachment point to the remainder of the molecule.

In some embodiments. (A¹-a) or (A¹-b) is selected from the group consisting of:

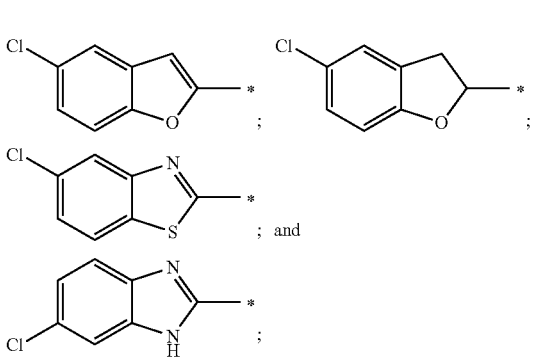

wherein the * represents the attachment point to the remainder of the molecule; and A² is selected from the group consisting of:

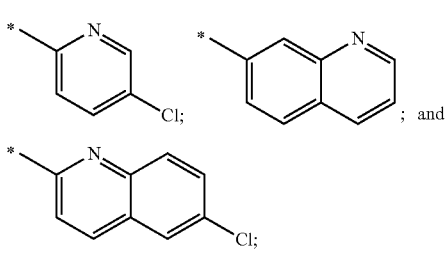

wherein the * represents the attachment point to the remainder of the molecule.

In some embodiments, (A¹-a) or (A¹-b) is selected from the group consisting of:

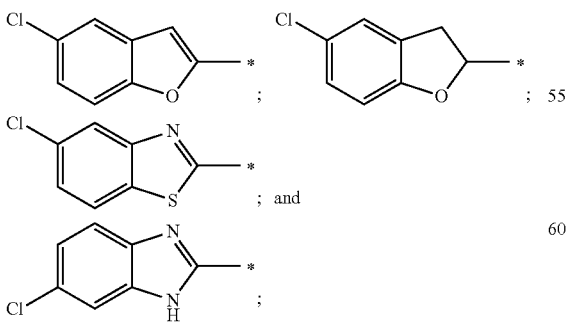

wherein the * represents the attachment point to the remainder of the molecule; and A² is

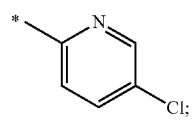

wherein the * represents the attachment point to the remainder of the molecule.

In some embodiments, (A¹-a) or (A¹-c) is selected from the group consisting of:

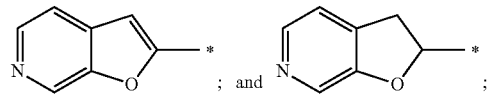

wherein the * represents the attachment point to the remainder of the molecule; and A² is selected from the group consisting of:

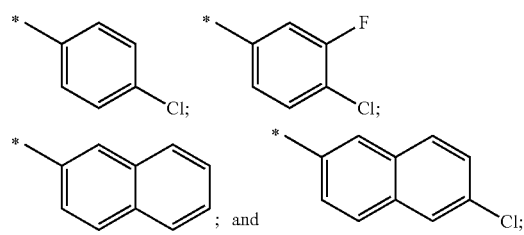

wherein the * represents the attachment point to the remainder of the molecule.

In some embodiments, (A¹-a) or (A¹-c) is selected from the group consisting of:

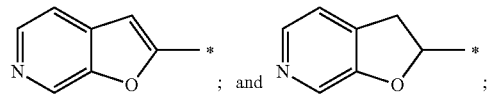

wherein the * represents the attachment point to the remainder of the molecule; and A² is selected from the group consisting of:

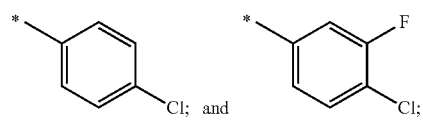

wherein the * represents the attachment point to the remainder of the molecule.

In some embodiments, (A¹-a) or (A¹-c) is selected from the group consisting of:

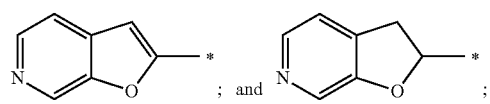

wherein the * represents the attachment point to the remainder of the molecule; and $A^2$ is selected from the group consisting of:

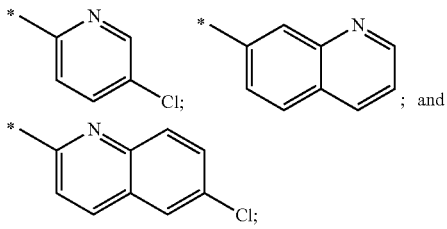

wherein the * represents the attachment point to the remainder of the molecule.

In some embodiments, ($A^1$-a) or ($A^1$-c) is selected from the group consisting of:

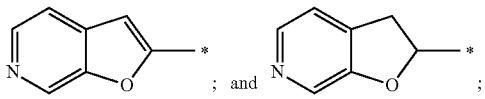

wherein the * represents the attachment point to the remainder of the molecule; and $A^2$ is

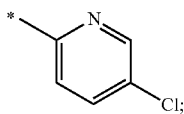

wherein the * represents the attachment point to the remainder of the molecule.

In some embodiments, the compound of formula (I) is a compound of formula (2-2):

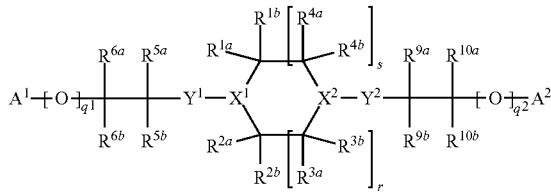

or a pharmaceutically acceptable salt thereof;
wherein:
$A^1$ is selected from the group consisting of:
a substituent of formula ($A^1$-a)

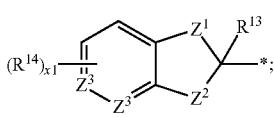

$C_6$-$C_{10}$ aryl optionally substituted with one or more $R^{14}$ substituents; and 5-10 membered heteroaryl optionally substituted with one or more $R^{14}$ substituents;

$A^2$ is selected from the group consisting of:
a substituent of formula ($A^2$-a)

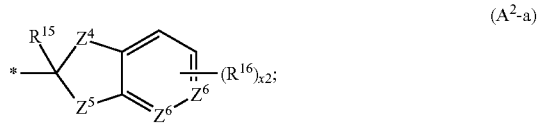

$C_6$-$C_{10}$ aryl optionally substituted with one or more $R^{16}$ substituents; and 5-10 membered heteroaryl optionally substituted with one or more $R^{16}$ substituents;

and wherein $X^2$, $R^{Y1}$, $Y^2$, $R^{Y2}$, $q^2$, r, s, $Z^1$, $R^{Z1-1}$, $R^{Z1-2}$, $Z^2$, $R^{Z2-1}$, $R^{Z2-2}$, $Z^3$, x1, $Z^4$, $R^{Z4-1}$, $R^{Z4-2}$, $Z^5$, $R^{Z5-1}$, $R^{Z5-2}$, $Z^6$, x2, $R^{1a}$, $R^{1b}$, $R^{2a}$, $R^{2b}$, $R^{3a}$, $R^{3b}$, $R^{4a}$, $R^{4b}$, $R^{5a}$, $R^{5b}$, $R^{6a}$, $R^{6a-a}$, $R^{6a-b}$, $R^{6a-c}$, $R^{6b}$, $R^{9a}$, $R^{9b}$, $R^{10a}$, $R^{10a-a}$, $R^{10a-b}$, $R^{10a-c}$, $R^{10b}$, $R^{15}$, and $R^{16}$ are as defined in are as defined in compounds of formula (I).

In some embodiments of the compounds of formula (2-2), $X^1$ is CH and $X^2$ is CH. In some embodiments, r is 1 and s is 1.

In some embodiments of the compounds of formula (2-2), $X^1$ is CH, $X^2$ is N and $Y^2$ is a bond. In some embodiments, r is 1 and s is 1. In some embodiments, r is 0 and s is 2.

In some embodiments of the compounds of formula (2-2), $X^1$ is N, $Y^1$ is a bond, and $X^2$ is CH. In some embodiments, r is 1 and s is 1. In some embodiments, r is 0 and s is 2.

In some embodiments of the compounds of formula (2-2), $X^1$ is N, $Y^1$ is a bond, $X^2$ is N and $Y^2$ is a bond. In some embodiments, r is 1 and s is 1. In some embodiments, r is 0 and s is 2.

In some embodiments of the compounds of formula (2-2):
$q^1$ is 1;
$A^1$ is selected $C_6$-$C_{10}$ aryl optionally substituted with one or more $R^{14}$ substituents; or 5-10 membered heteroaryl optionally substituted with one or more $R^{14}$ substituents;
$A^2$ is selected from the group consisting of:
a substituent of formula ($A^2$-a)

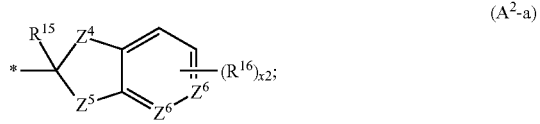

$C_6$-$C_{10}$ aryl optionally substituted with one or more $R^{16}$ substituents; and 5-10 membered heteroaryl optionally substituted with one or more $R^{16}$ substituents;

$R^{5a}$ and $R^{5b}$ are taken together to form an oxo (=O) substituent or an imido (=NH) substituent, or alternatively, $R^{5a}$ and $R^{5b}$ are both hydrogen;

$R^{6a}$ is selected from the group consisting of hydrogen, —$OR^{6a-a}$, and —$NR^{6a-b}R^{6a-c}$; $R^{6b}$ is hydrogen;

or alternatively, $R^{6a}$ and $R^{6b}$ are taken together to form a —$CH_2$—O—$CH_2$— moiety;

$R^{9a}$ and $R^{9b}$ are both hydrogen;

$R^{10a}$ is selected from the group consisting of —$OR^{10a-a}$, and —$NR^{10a-b}R^{10a-c}$; and $R^{10b}$ is hydrogen;

or alternatively, $R^{10a}$ and $R^{10b}$ are taken together to form a —$CH_2$—O—$CH_2$— moiety.

In some embodiments of the compounds of formula (2-2):
$R^{5a}$ and $R^{5b}$ are taken together to form an oxo (=O) substituent;
$R^{6a}$ is hydrogen;
$R^{6b}$ is hydrogen;
$R^{9a}$ and $R^{9b}$ are both hydrogen;
$R^{10a}$ is selected from the group consisting of —$OR^{10a-a}$, and —$NR^{10a-b}R^{10a-c}$; and
$R^{10b}$ is hydrogen;
or alternatively, $R^{10a}$ and $R^{10b}$ are taken together to form a —$CH_2$—O—$CH_2$— moiety.

In some embodiments of the compounds of formula (2-2):
q is 1;
$A^2$ is $C_6$-$C_{10}$ aryl optionally substituted with one or more $R^{16}$ substituents; or 5-10 membered heteroaryl optionally substituted with one or more $R^{16}$ substituents; and
$R^{10a}$ and $R^{10b}$ are taken together to form a —$CH_2$—O—$CH_2$— moiety.

In some embodiments of the compounds of formula (2-2), $A^2$ is $C_6$-$C_{10}$ aryl optionally substituted with one or more $R^{16}$ substituents. In some embodiments, $A^2$ is selected from the group consisting of:

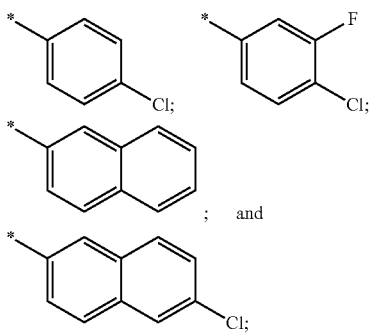

wherein the * represents the attachment point to the remainder of the molecule. In some embodiments, $A^2$ is phenyl optionally substituted with one or more $R^{16}$ substituents. In some embodiments, $A^2$ is selected from the group consisting of:

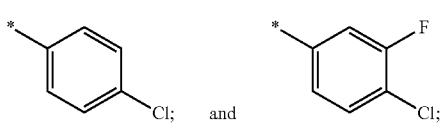 [SMILES: *c1ccc(Cl)cc1 ; "and" ; *c1ccc(Cl)c(F)c1]

wherein the * represents the attachment point to the remainder of the molecule.

In some embodiments of the compounds of formula (2-2), $A^2$ is 5-10 membered heteroaryl optionally substituted with one or more $R^{16}$ substituents. In some embodiments, $A^2$ is selected from the group consisting of:

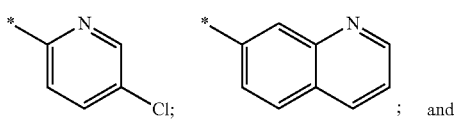

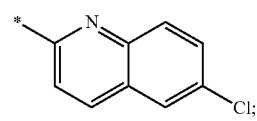

wherein the * represents the attachment point to the remainder of the molecule. In some embodiments, $A^2$ is pyridyl optionally substituted with one or more $R^{16}$ substituents. In some embodiments, $A^2$ is

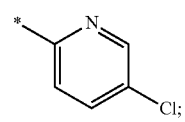 [SMILES: *c1ccc(Cl)cn1]

wherein the * represents the attachment point to the remainder of the molecule.

In some embodiments of the compounds of formula (2-2):
$q^2$ is 0;
$A^2$ is a substituent of formula ($A^2$-a)

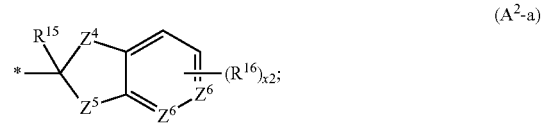

$R^{10a}$ is —$OR^{10a-a}$; and
$R^{10b}$ is hydrogen.

In some embodiments of the compounds of formula (2-2), ($A^2$-a) is selected from the group consisting of:

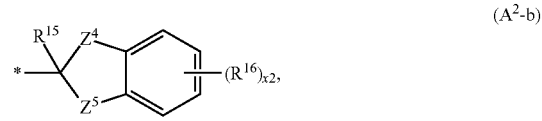

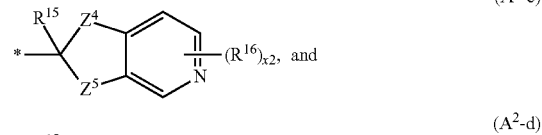

In some embodiments of the compounds of formula (2-2), ($A^2$-a) is ($A^2$-b).

In some embodiments of the compounds of formula (2-2), ($A^2$-a) is ($A^2$-c).

In some embodiments of the compounds of formula (2-2), ($A^2$-a) is ($A^2$-d).

In some embodiments of the compounds of formula (2-2), ($A^2$-a) or ($A^2$-b) is selected from the group consisting of:

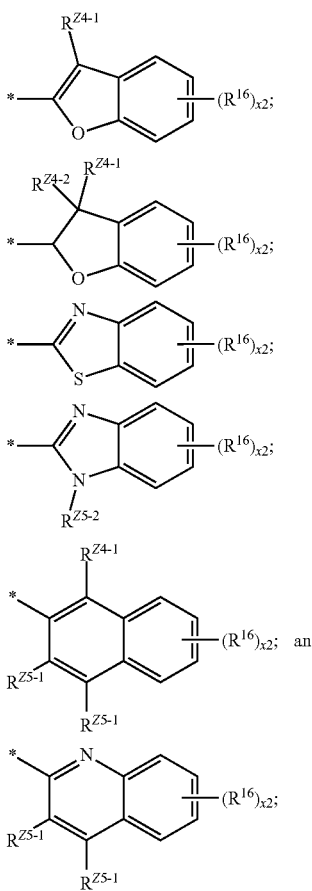

wherein the * represents the attachment point to the remainder of the molecule. In some embodiments, (A²-a) or (A²-b) is selected from the group consisting of:

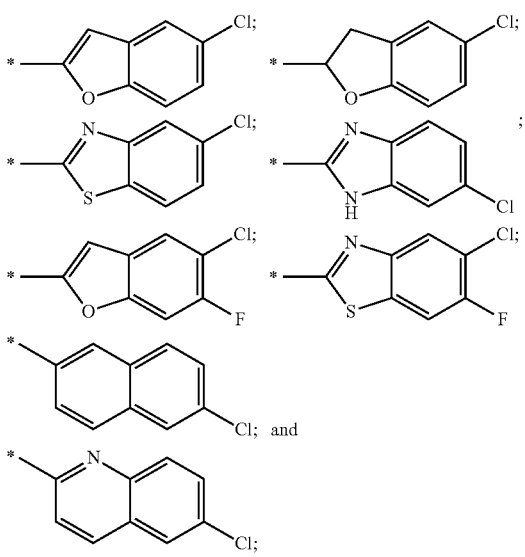

wherein the * represents the attachment point to the remainder of the molecule. In some embodiments, (A²-a) or (A²-b) is selected from the group consisting of:

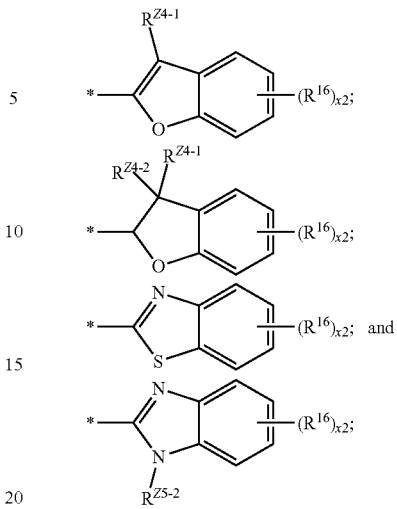

wherein the * represents the attachment point to the remainder of the molecule. In some embodiments, (A²-a) or (A²-b) is selected from the group consisting of:

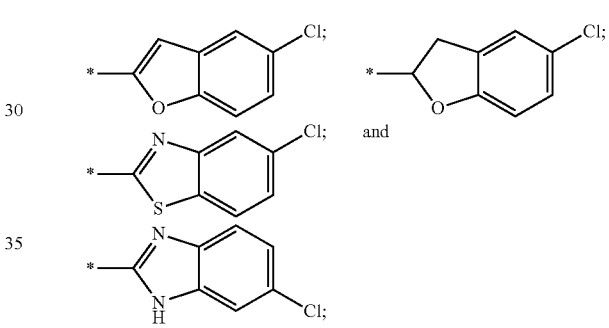

wherein the * represents the attachment point to the remainder of the molecule.

In some embodiments of the compounds of formula (2-2), (A²-a) or (A²-c) is selected from the group consisting of:

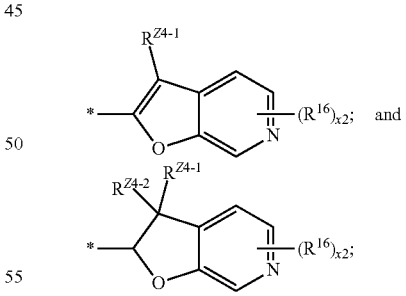

wherein the * represents the attachment point to the remainder of the molecule. In some embodiments, (A²-a) or (A²-c) is selected from the group consisting of:

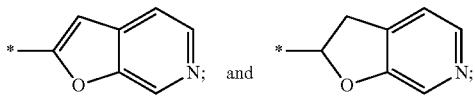 [SMILES: *c1cc2ccncc2o1 ; "and" ; *C1Cc2ccncc2O1]

wherein the * represents the attachment point to the remainder of the molecule.

In some embodiments of the compounds of formula (2-2):
$R^{5a}$ and $R^{5b}$ are both hydrogen;
$R^{6a}$ and $R^{6b}$ are taken together to form a —CH$_2$—O—CH$_2$— moiety;
$R^{10a}$ is selected from the group consisting of —OR$^{10a-a}$, and —NR$^{10a-b}$R$^{10a-c}$; and
$R^{10b}$ is hydrogen;
or alternatively, $R^{10a}$ and $R^{10b}$ are taken together to form a —CH$_2$—O—CH$_2$— moiety.

In some embodiments of the compounds of formula (2-2):
$q^2$ is 1;
$A^2$ is $C_6$-$C_{10}$ aryl optionally substituted with one or more $R^{16}$ substituents; or 5-10 membered heteroaryl optionally substituted with one or more $R^{16}$ substituents; and
$R^{10a}$ and $R^{10b}$ are taken together to form a —CH$_2$—O—CH$_2$— moiety.

In some embodiments of the compounds of formula (2-2), $A^2$ is $C_6$-$C_{10}$ aryl optionally substituted with one or more $R^{16}$ substituents. In some embodiments, $A^2$ is selected from the group consisting of:

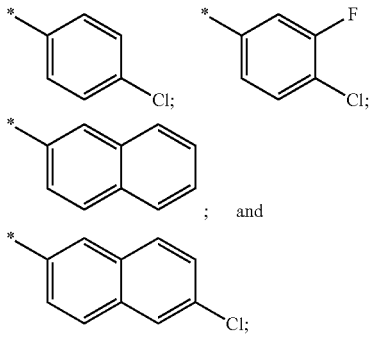

wherein the * represents the attachment point to the remainder of the molecule. In some embodiments, $A^2$ is phenyl optionally substituted with one or more $R^{16}$ substituents. In some embodiments, $A^2$ is selected from the group consisting of:

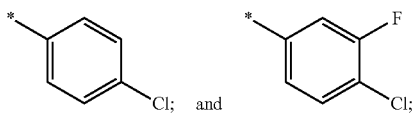

wherein the * represents the attachment point to the remainder of the molecule.

In some embodiments of the compounds of formula (2-2), $A^2$ is 5-10 membered heteroaryl optionally substituted with one or more $R^{16}$ substituents. In some embodiments, $A^2$ is selected from the group consisting of:

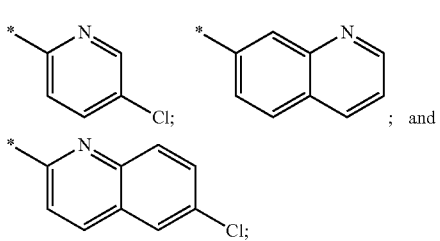

wherein the * represents the attachment point to the remainder of the molecule. In some embodiments, $A^2$ is pyridyl optionally substituted with one or more $R^{16}$ substituents. In some embodiments, $A^2$ is

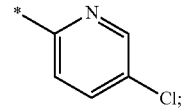

wherein the * represents the attachment point to the remainder of the molecule.

In some embodiments of the compounds of formula (2-2):
$q^2$ is 0;
$A^2$ is a substituent of formula ($A^2$-a)

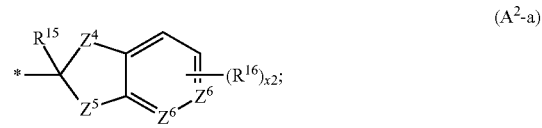

$R^{10a}$ is —OR$^{10a-a}$; and
$R^{10b}$ is hydrogen.

In some embodiments of the compounds of formula (2-2), ($A^2$-a) is selected from the group consisting of:

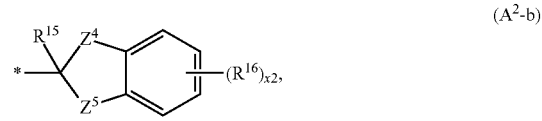

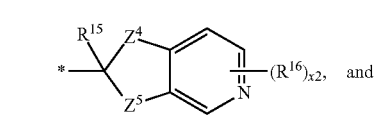

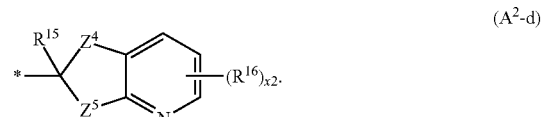

In some embodiments of the compounds of formula (2-2), ($A^2$-a) is ($A^2$-b).

In some embodiments of the compounds of formula (2-2), ($A^2$-a) is ($A^2$-c).

In some embodiments of the compounds of formula (2-2), ($A^2$-a) is ($A^2$-d).

In some embodiments of the compounds of formula (2-2), ($A^2$-a) or ($A^2$-b) is selected from the group consisting of:

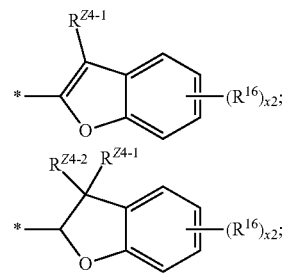

-continued

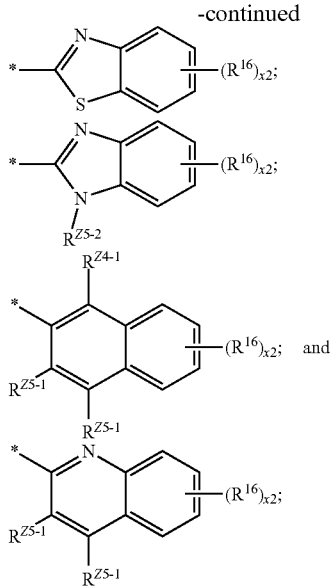

wherein the * represents the attachment point to the remainder of the molecule. In some embodiments, (A²-a) or (A²-b) is selected from the group consisting of:

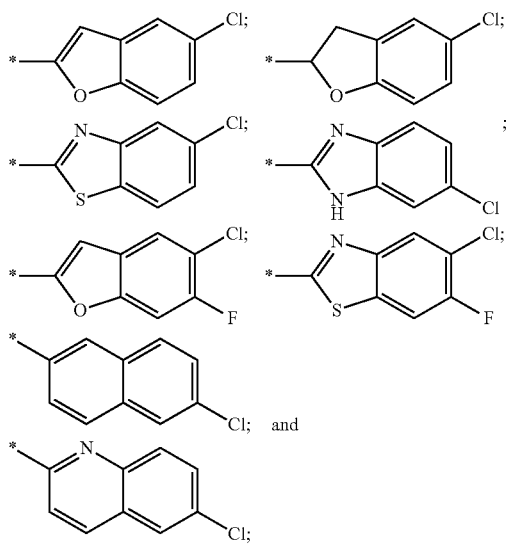

wherein the * represents the attachment point to the remainder of the molecule. In some embodiments, (A²-a) or (A²-b) is selected from the group consisting of:

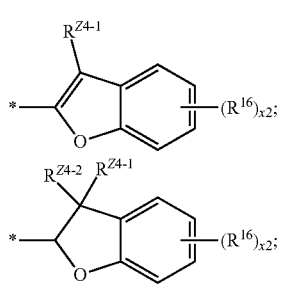

-continued

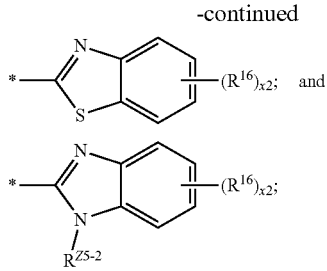

wherein the * represents the attachment point to the remainder of the molecule. In some embodiments, (A²-a) or (A²-b) is selected from the group consisting of:

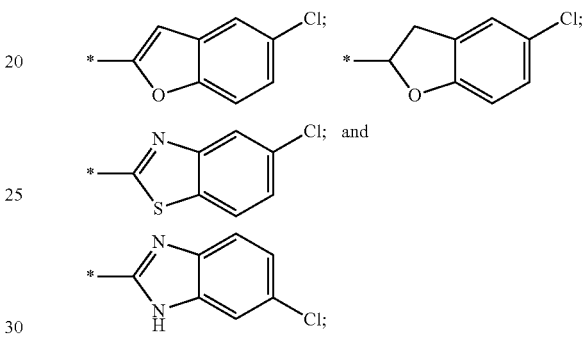

wherein the * represents the attachment point to the remainder of the molecule.

In some embodiments of the compounds of formula (2-2), (A²-a) or (A²-c) is selected from the group consisting of:

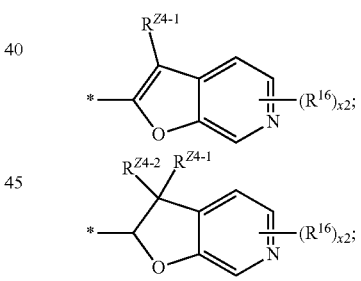

wherein the * represents the attachment point to the remainder of the molecule. In some embodiments, (A²-a) or (A²-c) is selected from the group consisting of:

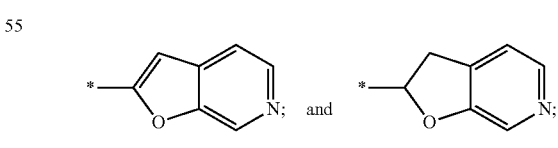

wherein the * represents the attachment point to the remainder of the molecule.

In some embodiments of the compounds of formula (2-2), $A^1$ is $C_6$-$C_{10}$ aryl optionally substituted with one or more $R^{14}$ substituents. In some embodiments, $A^1$ is selected from the group consisting of:

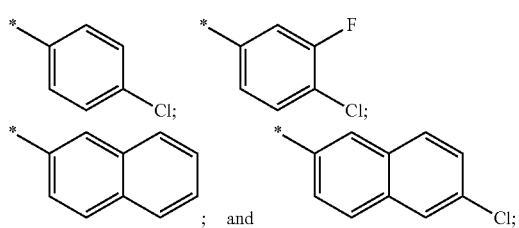

; and wherein the * represents the attachment point to the remainder of the molecule. In some embodiments, $A^1$ is phenyl optionally substituted with one or more $R^{14}$ substituents. In some embodiments, $A^1$ is selected from the group consisting of:

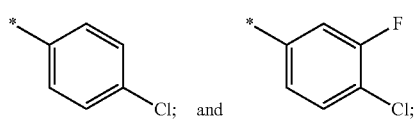

wherein the * represents the attachment point to the remainder of the molecule.

In some embodiments of the compounds of formula (2-2), $A^1$ is 5-10 membered heteroaryl optionally substituted with one or more $R^{14}$ substituents. In some embodiments, $A^1$ is selected from the group consisting of:

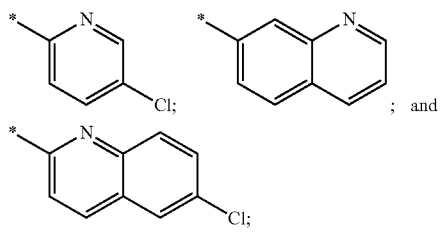

wherein the * represents the attachment point to the remainder of the molecule. In some embodiments, $A^1$ is pyridyl optionally substituted with one or more $R^{14}$ substituents. In some embodiments, $A^1$ is

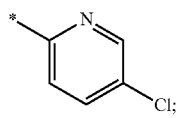 [SMILES: *c1ccc(Cl)cn1]

wherein the * represents the attachment point to the remainder of the molecule.

In some embodiments, ($A^1$-a) or ($A^1$-b) is selected from the group consisting of:

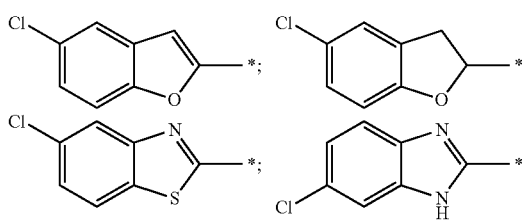

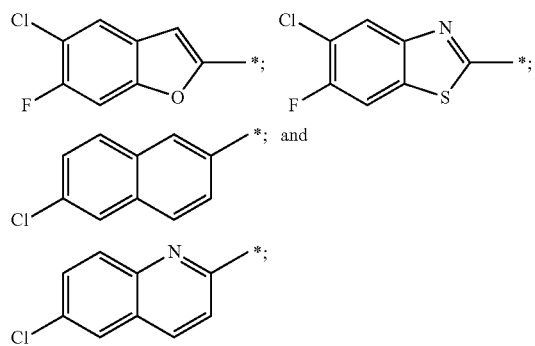

wherein the * represents the attachment point to the remainder of the molecule; and ($A^2$-a) or ($A^2$-b) is selected from the group consisting of:

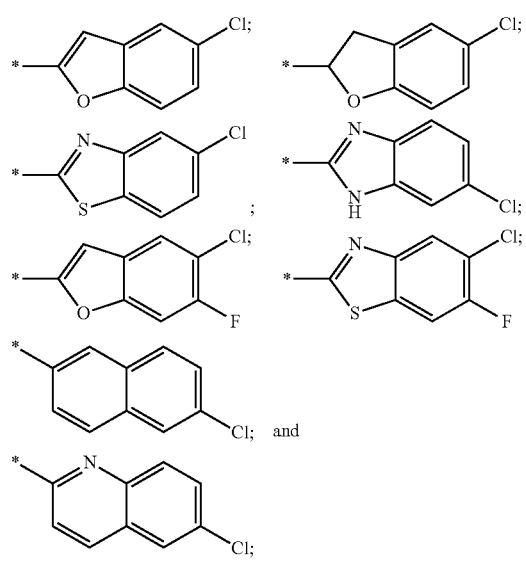

wherein the * represents the attachment point to the remainder of the molecule.

In some embodiments, ($A^1$-a) or ($A^1$-b) is selected from the group consisting of:

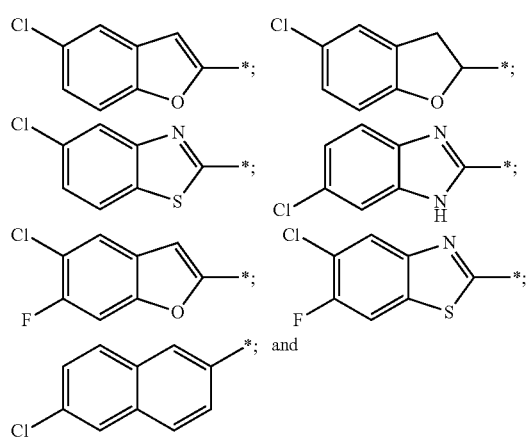

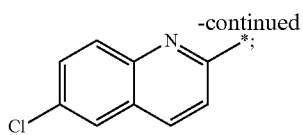

wherein the * represents the attachment point to the remainder of the molecule; and (A²-a) or (A²-b) is selected from the group consisting of:

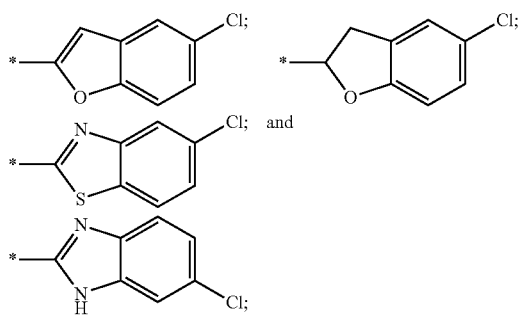

wherein the * represents the attachment point to the remainder of the molecule.

In some embodiments, (A¹-a) or (A¹-b) is selected from the group consisting of:

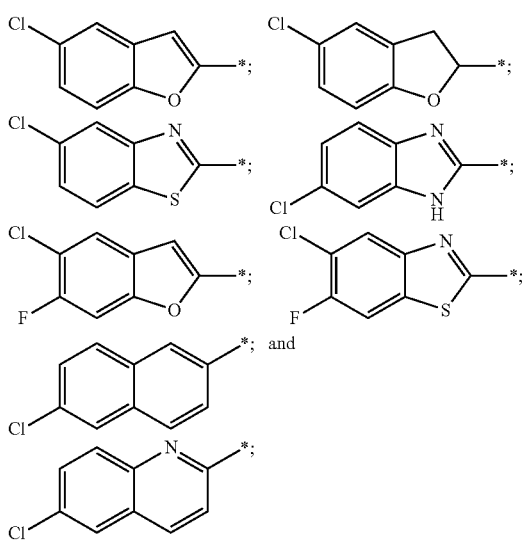

wherein the * represents the attachment point to the remainder of the molecule; and (A²-a) or (A²-c) is selected from the group consisting of:

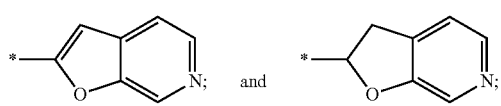 [SMILES: *c1cc2ccncc2o1 ; *C1Cc2ccncc2O1]

wherein the * represents the attachment point to the remainder of the molecule.

In some embodiments, (A¹-a) or (A¹-b) is selected from the group consisting of:

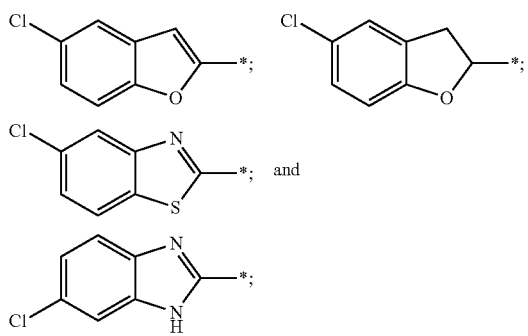

wherein the * represents the attachment point to the remainder of the molecule; and (A²-a) or (A²-b) is selected from the group consisting of:

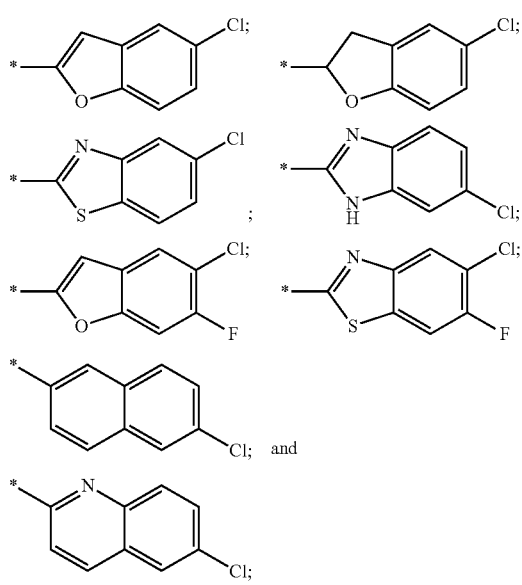

wherein the * represents the attachment point to the remainder of the molecule.

In some embodiments, (A¹-a) or (A¹-b) is selected from the group consisting of:

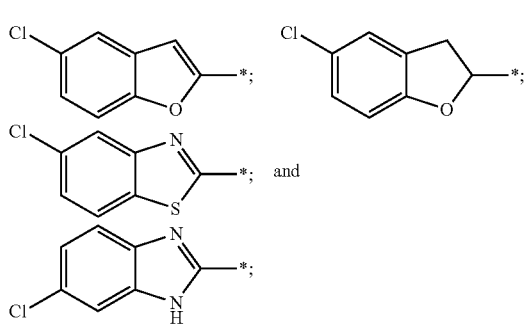

wherein the * represents the attachment point to the remainder of the molecule; and (A²-a) or (A²-b) is selected from the group consisting of:

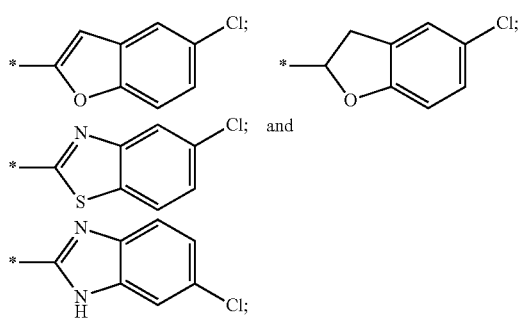

wherein the * represents the attachment point to the remainder of the molecule.

In some embodiments, (A¹-a) or (A¹-b) is selected from the group consisting of:

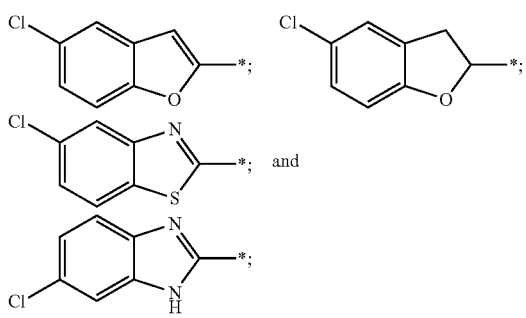

wherein the * represents the attachment point to the remainder of the molecule; and (A²-a) or (A²-c) is selected from the group consisting of:

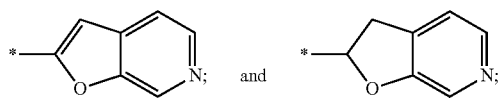 [SMILES: *c1cc2ccncc2o1 ; *C1Cc2ccncc2O1]

wherein the * represents the attachment point to the remainder of the molecule.

In some embodiments, (A¹-a) or (A¹-c) is selected from the group consisting of:

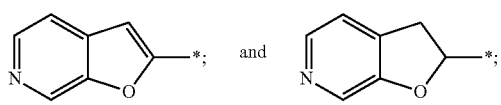

wherein the * represents the attachment point to the remainder of the molecule; and (A²-a) or (A²-b) is selected from the group consisting of:

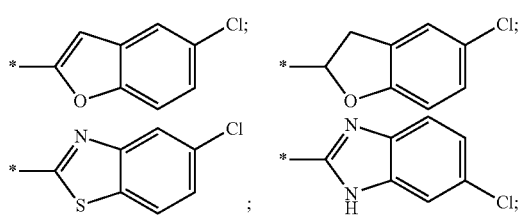

wherein the * represents the attachment point to the remainder of the molecule.

In some embodiments, (A¹-a) or (A¹-c) is selected from the group consisting of:

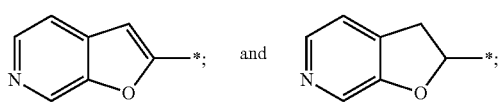

wherein the * represents the attachment point to the remainder of the molecule; and (A²-a) or (A²-b) is selected from the group consisting of:

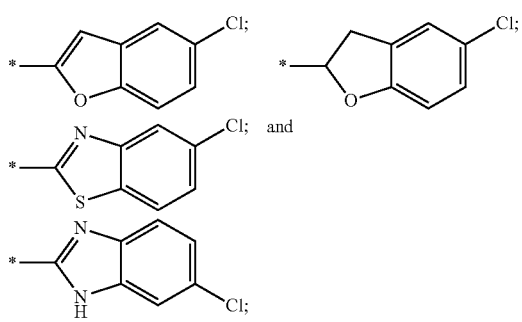

wherein the * represents the attachment point to the remainder of the molecule.

In some embodiments, (A¹-a) or (A¹-c) is selected from the group consisting of:

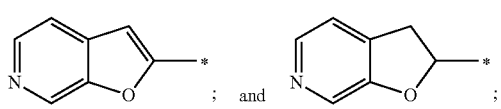

wherein the * represents the attachment point to the remainder of the molecule; and (A²-a) or (A²-c) is selected from the group consisting of:

wherein the * represents the attachment point to the remainder of the molecule.

In some embodiments, (A¹-a) or (A¹-b) is selected from the group consisting of:

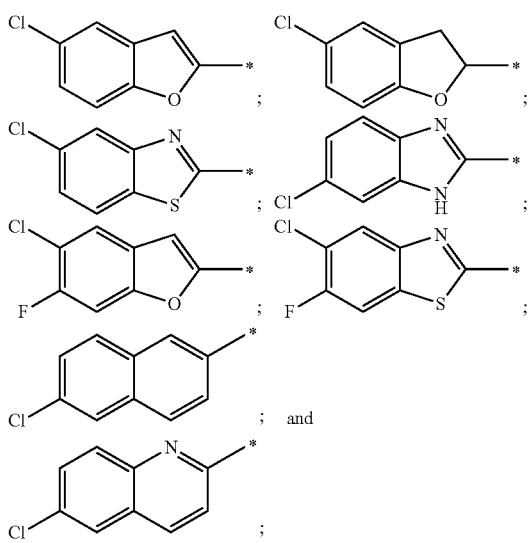

wherein the * represents the attachment point to the remainder of the molecule; and A² is selected from the group consisting of:

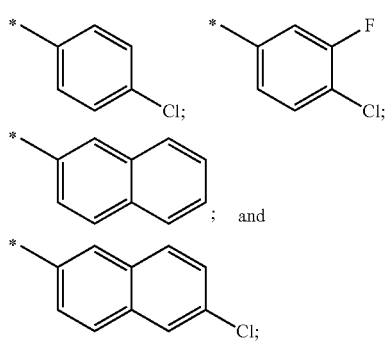

wherein the * represents the attachment point to the remainder of the molecule.

In some embodiments, (A¹-a) or (A¹-b) is selected from the group consisting of:

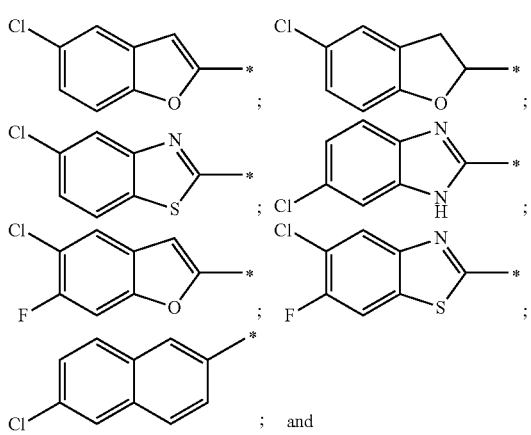

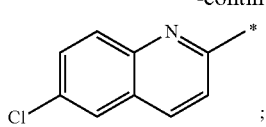

wherein the * represents the attachment point to the remainder of the molecule; and A² is selected from the group consisting of:

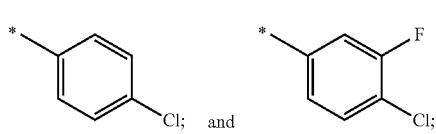

wherein the * represents the attachment point to the remainder of the molecule.

In some embodiments, (A¹-a) or (A¹-b) is selected from the group consisting of:

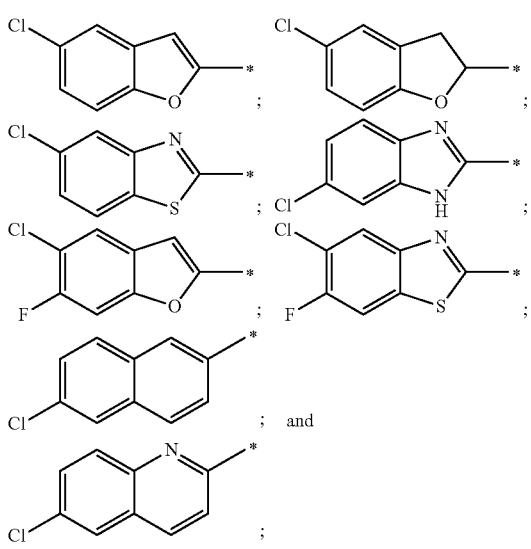

wherein the * represents the attachment point to the remainder of the molecule; and A² is selected from the group consisting of:

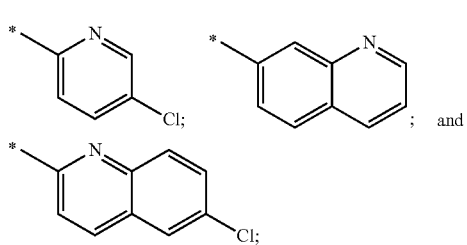

wherein the * represents the attachment point to the remainder of the molecule.

In some embodiments, (A¹-a) or (A¹-b) is selected from the group consisting of:

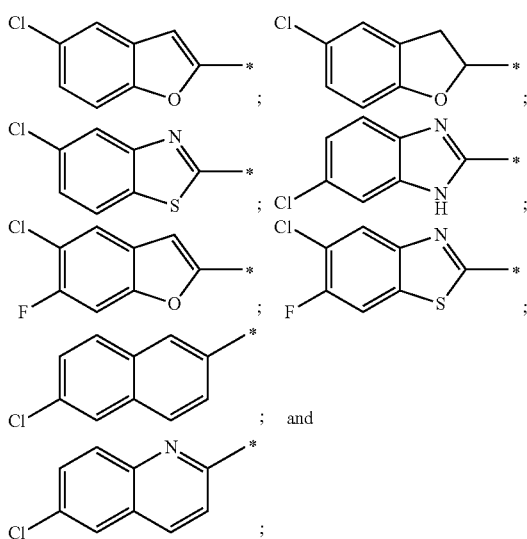

wherein the * represents the attachment point to the remainder of the molecule; and $A^2$ is

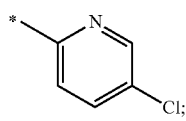

wherein the * represents the attachment point to the remainder of the molecule.

In some embodiments, $(A^1\text{-a})$ or $(A^1\text{-b})$ is selected from the group consisting of:

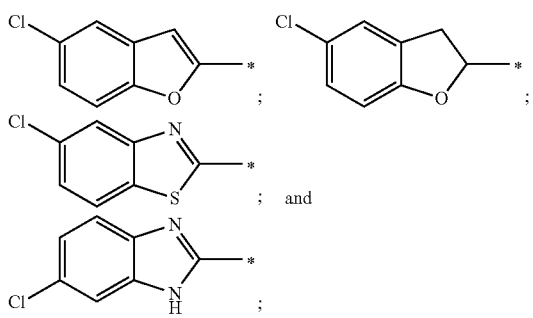

wherein the * represents the attachment point to the remainder of the molecule; and $A^2$ is selected from the group consisting of:

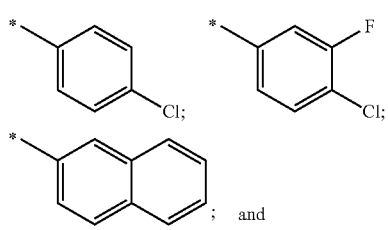

-continued

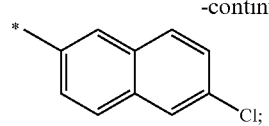

wherein the * represents the attachment point to the remainder of the molecule.

In some embodiments, $(A^1\text{-a})$ or $(A^1\text{-b})$ is selected from the group consisting of:

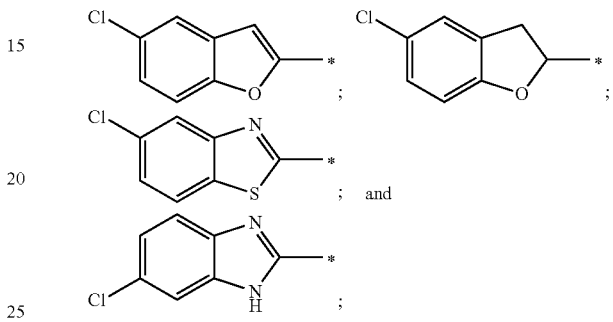

wherein the * represents the attachment point to the remainder of the molecule; and $A^2$ is selected from the group consisting of:

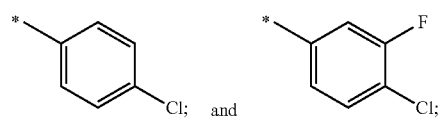

wherein the * represents the attachment point to the remainder of the molecule.

In some embodiments, $(A^1\text{-a})$ or $(A^1\text{-b})$ is selected from the group consisting of:

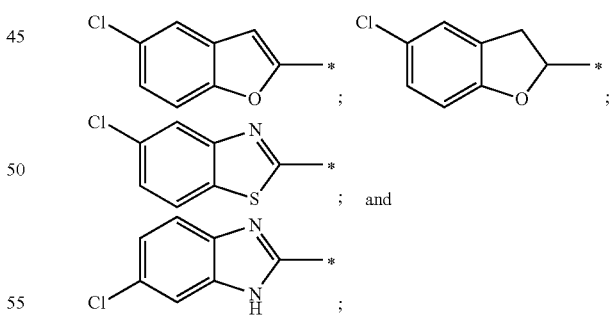

wherein the * represents the attachment point to the remainder of the molecule; and $A^2$ is selected from the group consisting of:

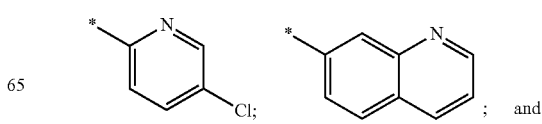

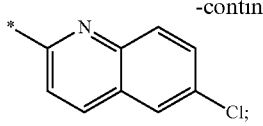

wherein the * represents the attachment point to the remainder of the molecule.

In some embodiments, (A¹-a) or (A¹-b) is selected from the group consisting of:

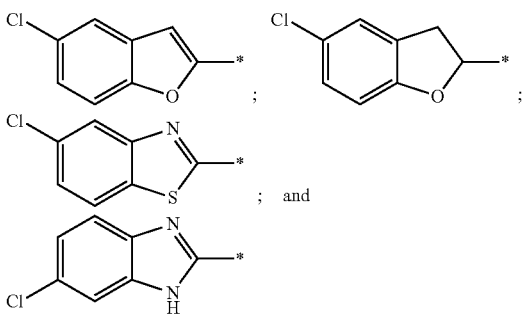

wherein the * represents the attachment point to the remainder of the molecule; and A² is

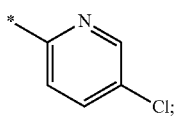 [SMILES: *c1ccc(Cl)cn1]

wherein the * represents the attachment point to the remainder of the molecule.

In some embodiments, (A¹-a) or (A¹-c) is selected from the group consisting of:

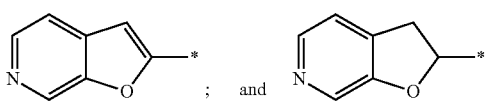 [SMILES: *c1cc2ccncc2o1 ; *C1Cc2ccncc2O1]

wherein the * represents the attachment point to the remainder of the molecule; and A² is selected from the group consisting of:

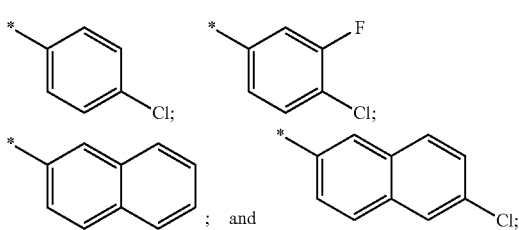

wherein the * represents the attachment point to the remainder of the molecule.

In some embodiments, (A¹-a) or (A¹-c) is selected from the group consisting of:

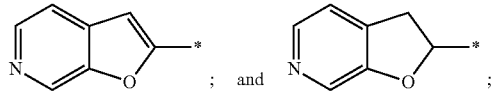 [SMILES: *c1cc2ccncc2o1 ; *C1Cc2ccncc2O1]

wherein the * represents the attachment point to the remainder of the molecule; and A² is selected from the group consisting of:

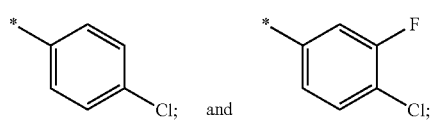

wherein the * represents the attachment point to the remainder of the molecule.

In some embodiments, (A¹-a) or (A¹-c) is selected from the group consisting of:

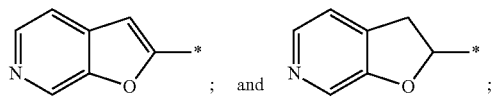 [SMILES: *c1cc2ccncc2o1 ; *C1Cc2ccncc2O1]

wherein the * represents the attachment point to the remainder of the molecule; and A² is selected from the group consisting of:

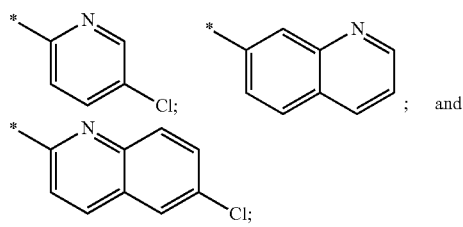

wherein the * represents the attachment point to the remainder of the molecule.

In some embodiments, (A¹-a) or (A¹-c) is selected from the group consisting of:

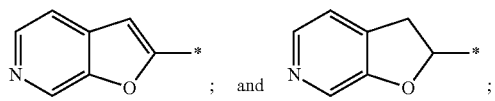 [SMILES: *c1cc2ccncc2o1 ; *C1Cc2ccncc2O1]

wherein the * represents the attachment point to the remainder of the molecule; and A² is

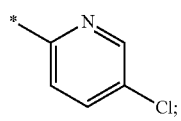

wherein the * represents the attachment point to the remainder of the molecule.

In some embodiments, A¹ is selected from the group consisting of:

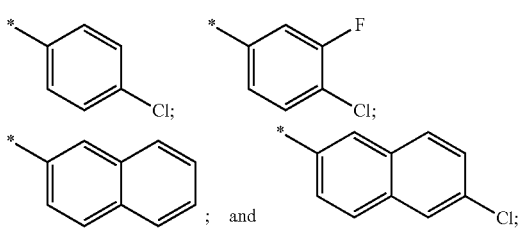

wherein the * represents the attachment point to the remainder of the molecule; and ($A^2$-a) or ($A^2$-b) is selected from the group consisting of:

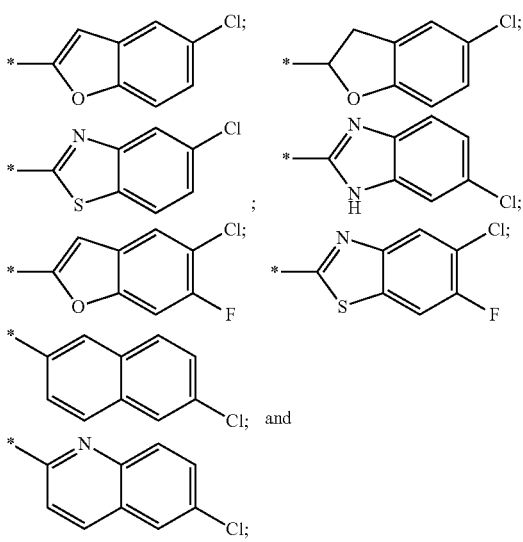

wherein the * represents the attachment point to the remainder of the molecule.

In some embodiments, $A^1$ is selected from the group consisting of:

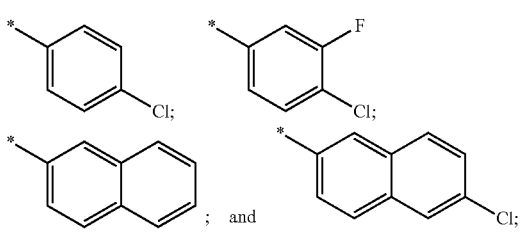

wherein the * represents the attachment point to the remainder of the molecule; and ($A^2$-a) or ($A^2$-b) is selected from the group consisting of:

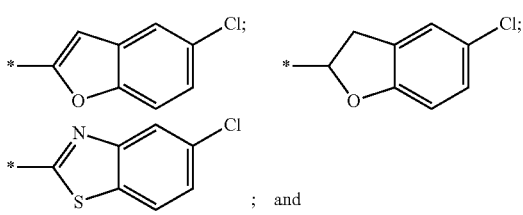

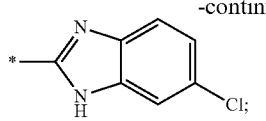

wherein the * represents the attachment point to the remainder of the molecule.

In some embodiments, $A^1$ is selected from the group consisting of:

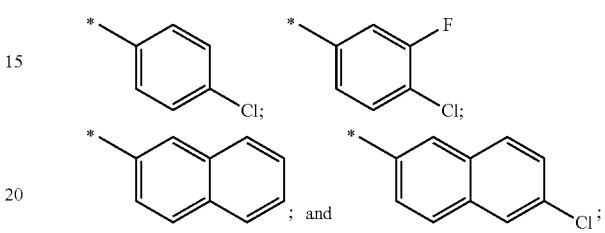

wherein the * represents the attachment point to the remainder of the molecule; and ($A^1$-a) or ($A^2$-c) is selected from the group consisting of:

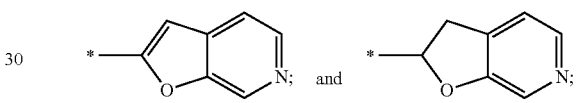

wherein the * represents the attachment point to the remainder of the molecule.

In some embodiments, $A^1$ is selected from the group consisting of:

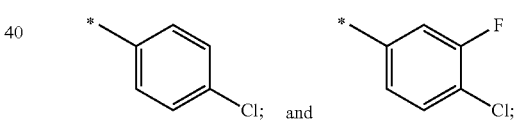

wherein the * represents the attachment point to the remainder of the molecule; and ($A^2$-a) or ($A^2$-b) is selected from the group consisting of:

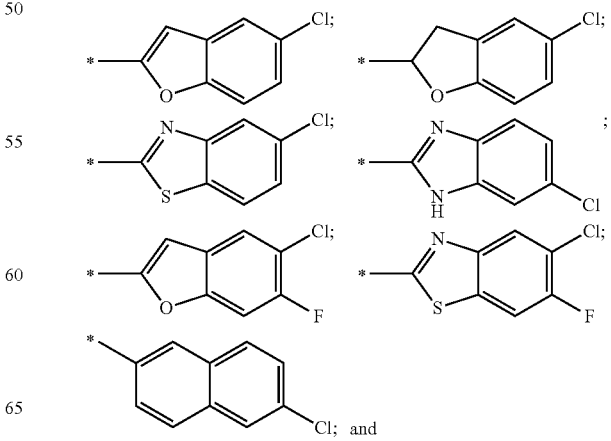

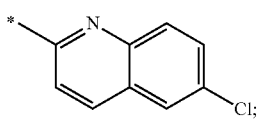

wherein the * represents the attachment point to the remainder of the molecule.

In some embodiments, $A^1$ is selected from the group consisting of:

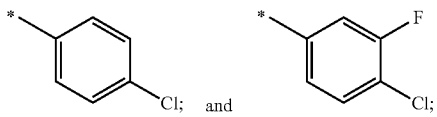

wherein the * represents the attachment point to the remainder of the molecule; and ($A^2$-a) or ($A^2$-b) is selected from the group consisting of:

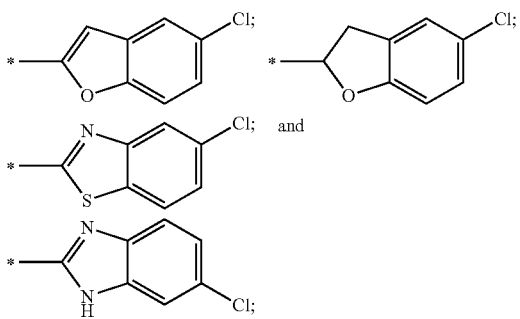

wherein the * represents the attachment point to the remainder of the molecule.

In some embodiments, $A^1$ is selected from the group consisting of:

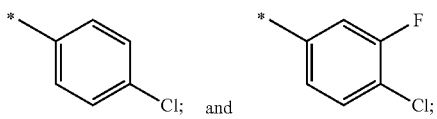

wherein the * represents the attachment point to the remainder of the molecule; and ($A^2$-a) or ($A^2$-c) is selected from the group consisting of:

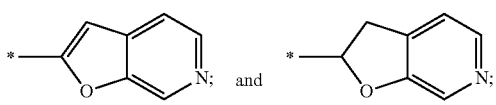

wherein the * represents the attachment point to the remainder of the molecule.

In some embodiments, $A^1$ is selected from the group consisting of:

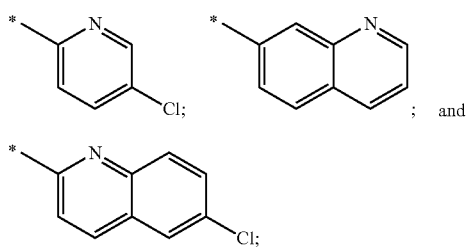

wherein the * represents the attachment point to the remainder of the molecule; and ($A^2$-a) or ($A^2$-b) is selected from the group consisting of:

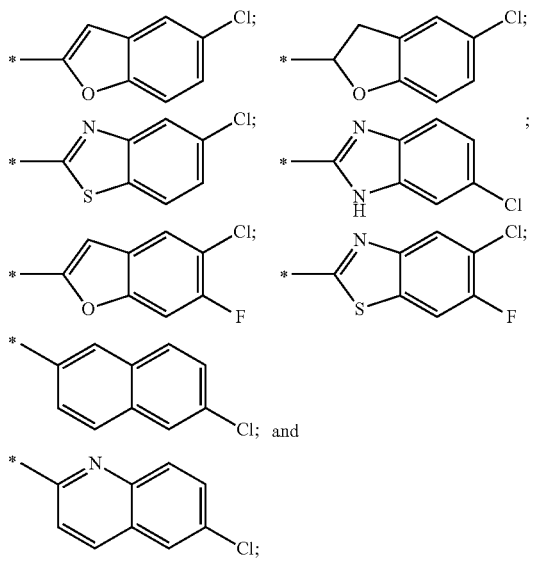

wherein the * represents the attachment point to the remainder of the molecule.

In some embodiments, $A^1$ is selected from the group consisting of:

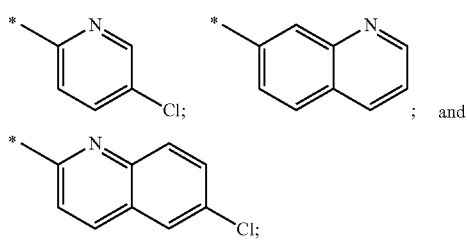

wherein the * represents the attachment point to the remainder of the molecule; and ($A^2$-a) or ($A^2$-b) is selected from the group consisting of:

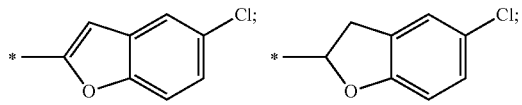

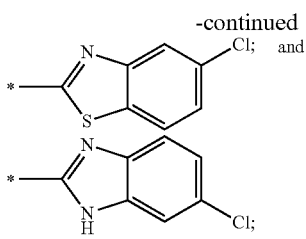

wherein the * represents the attachment point to the remainder of the molecule.

In some embodiments, $A^1$ is selected from the group consisting of:

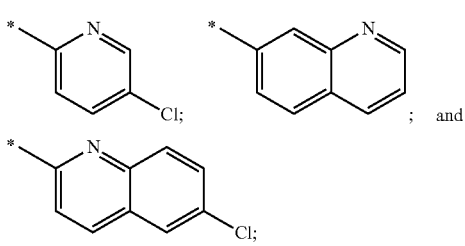

wherein the * represents the attachment point to the remainder of the molecule; and $(A^2$-a) or $(A^2$-c) is selected from the group consisting of:

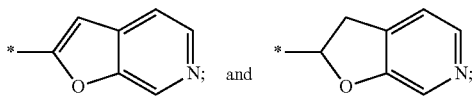 [SMILES: *c1cc2ccncc2o1 ; "and" ; *C1Cc2ccncc2O1]

wherein the * represents the attachment point to the remainder of the molecule.

In some embodiments, $A^1$ is

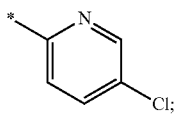 [SMILES: *c1ccc(Cl)cn1]

wherein the * represents the attachment point to the remainder of the molecule; and $(A^2$-a) or $(A^2$-b) is selected from the group consisting of:

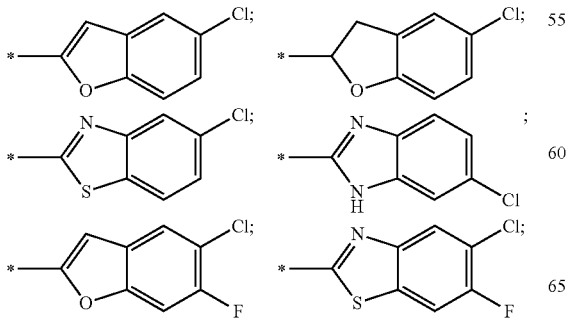

-continued

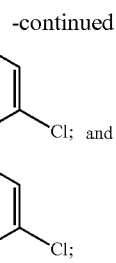

wherein the * represents the attachment point to the remainder of the molecule.

In some embodiments, $A^1$ is wherein the * represents the attachment point to the remainder of the molecule; and $(A^2$-a) or $(A^2$-b) is selected from the group consisting of:

wherein the * represents the attachment point to the remainder of the molecule.

In some embodiments, $A^1$ is selected from the group consisting of:

wherein the * represents the attachment point to the remainder of the molecule; and $A^2$ is selected from the group consisting of:

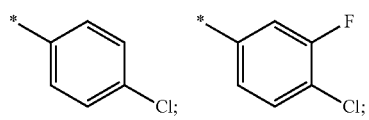

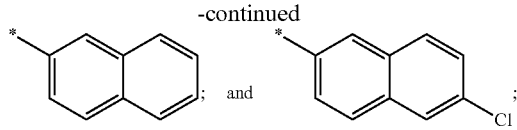

wherein the * represents the attachment point to the remainder of the molecule.

In some embodiments, A¹ is selected from the group consisting of:

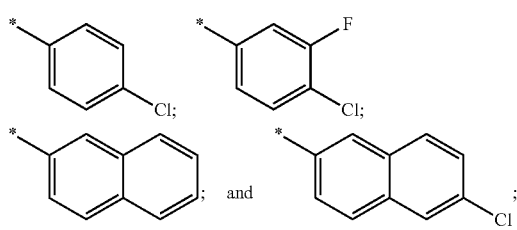

wherein the * represents the attachment point to the remainder of the molecule; and A² is selected from the group consisting of:

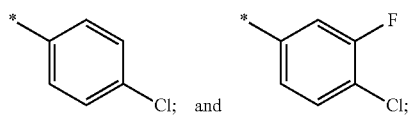 [SMILES: *c1ccc(Cl)cc1 ; "and" ; *c1ccc(Cl)c(F)c1]

wherein the * represents the attachment point to the remainder of the molecule.

In some embodiments, A¹ is selected from the group consisting of:

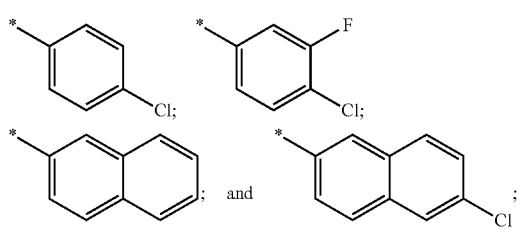

wherein the * represents the attachment point to the remainder of the molecule; and A² is selected from the group consisting of:

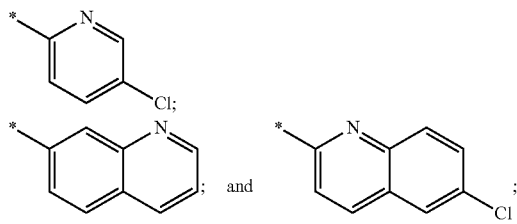

wherein the * represents the attachment point to the remainder of the molecule.

In some embodiments, A¹ is selected from the group consisting of:

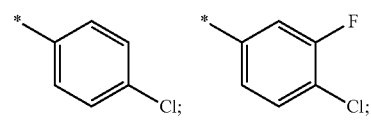

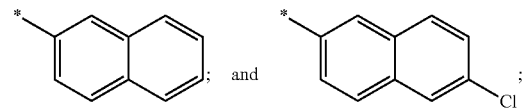

wherein the * represents the attachment point to the remainder of the molecule; and A² is

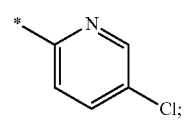

wherein the * represents the attachment point to the remainder of the molecule.

In some embodiments, A¹ is selected from the group consisting of:

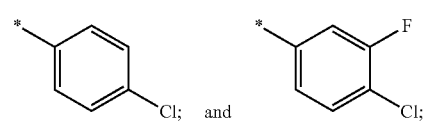

wherein the * represents the attachment point to the remainder of the molecule; and A² is selected from the group consisting of:

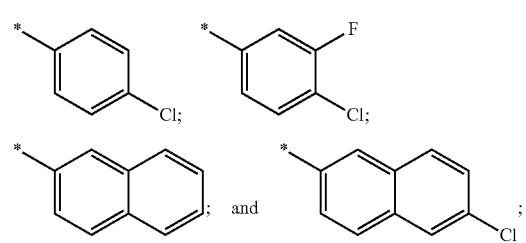

wherein the * represents the attachment point to the remainder of the molecule.

In some embodiments, A¹ is selected from the group consisting of:

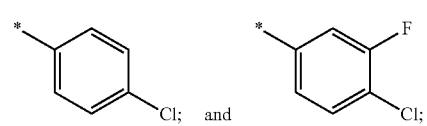

wherein the * represents the attachment point to the remainder of the molecule; and A² is selected from the group consisting of:

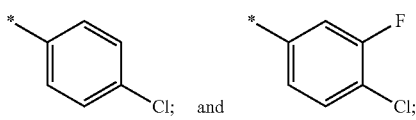 [SMILES: *c1ccc(Cl)cc1 ; "and" ; *c1ccc(Cl)c(F)c1]

wherein the * represents the attachment point to the remainder of the molecule.

In some embodiments, $A^1$ is selected from the group consisting of:

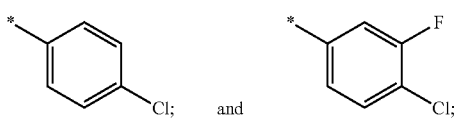 [SMILES: *c1ccc(Cl)cc1 ; "and" ; *c1ccc(Cl)c(F)c1]

wherein the * represents the attachment point to the remainder of the molecule; $A^2$ is selected from the group consisting of:

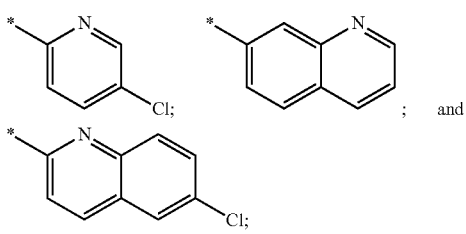

wherein the * represents the attachment point to the remainder of the molecule.

In some embodiments, $A^1$ is selected from the group consisting of:

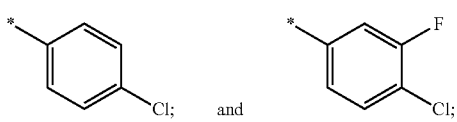 [SMILES: *c1ccc(Cl)cc1 ; "and" ; *c1ccc(Cl)c(F)c1]

wherein the * represents the attachment point to the remainder of the molecule; and $A^2$ is

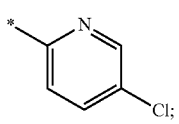

wherein the * represents the attachment point to the remainder of the molecule.

In some embodiments, $A^1$ is selected from the group consisting of:

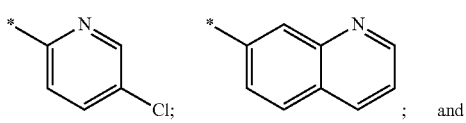

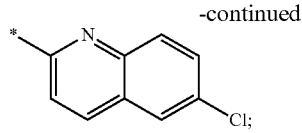

wherein the * represents the attachment point to the remainder of the molecule; and $A^2$ is selected from the group consisting of:

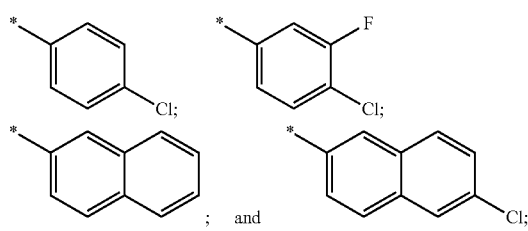

wherein the * represents the attachment point to the remainder of the molecule.

In some embodiments, $A^1$ is selected from the group consisting of:

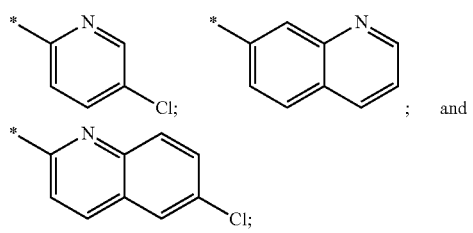

wherein the * represents the attachment point to the remainder of the molecule; and $A^2$ is selected from the group consisting of:

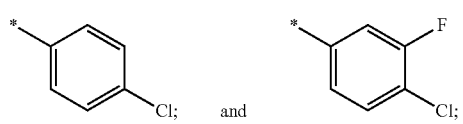 [SMILES: *c1ccc(Cl)cc1 ; "and" ; *c1ccc(Cl)c(F)c1]

wherein the * represents the attachment point to the remainder of the molecule.

In some embodiments, $A^1$ is selected from the group consisting of:

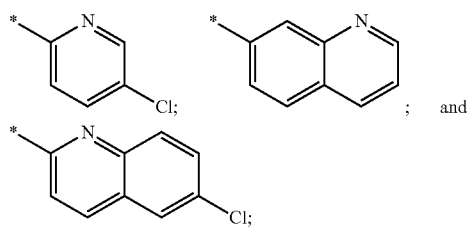

wherein the * represents the attachment point to the remainder of the molecule; $A^2$ is selected from the group consisting of:

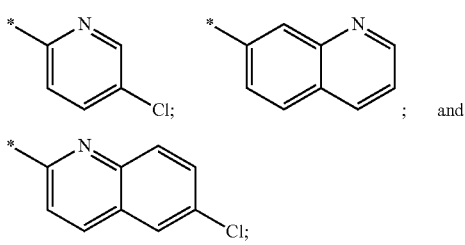

wherein the * represents the attachment point to the remainder of the molecule.

In some embodiments, $A^1$ is selected from the group consisting of:

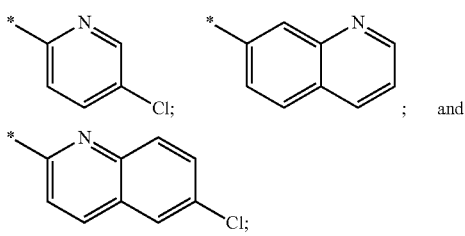

wherein the * represents the attachment point to the remainder of the molecule; and $A^2$ is

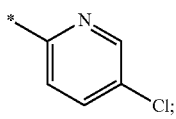 [SMILES: *c1ccc(Cl)cn1]

wherein the * represents the attachment point to the remainder of the molecule.

In some embodiments, $A^1$ is

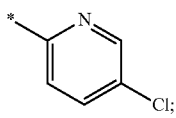 [SMILES: *c1ccc(Cl)cn1]

wherein the * represents the attachment point to the remainder of the molecule; and $A^2$ is selected from the group consisting of:

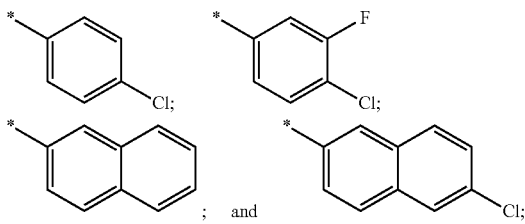

wherein the * represents the attachment point to the remainder of the molecule.

In some embodiments, $A^1$ is

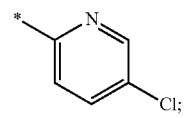

wherein the * represents the attachment point to the remainder of the molecule; and $A^2$ is selected from the group consisting of:

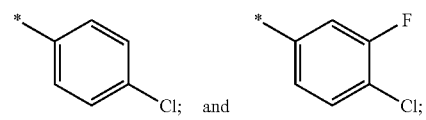

wherein the * represents the attachment point to the remainder of the molecule.

In some embodiments, $A^1$ is

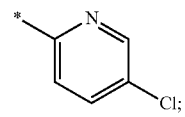

wherein the * represents the attachment point to the remainder of the molecule; and $A^2$ is selected from the group consisting of:

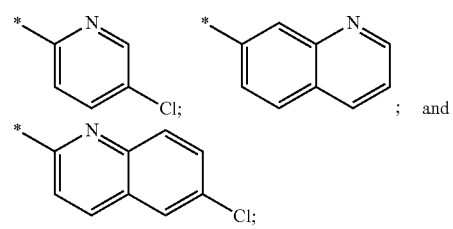

wherein the * represents the attachment point to the remainder of the molecule.

In some embodiments, $A^1$ is

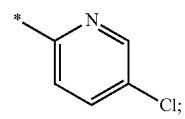

wherein the * represents the attachment point to the remainder of the molecule; and $A^2$ is

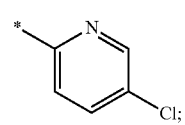 [SMILES: *c1ccc(Cl)cn1]

wherein the * represents the attachment point to the remainder of the molecule.

In some embodiments, the compound of formula (I) is a compound of formula (2-3):

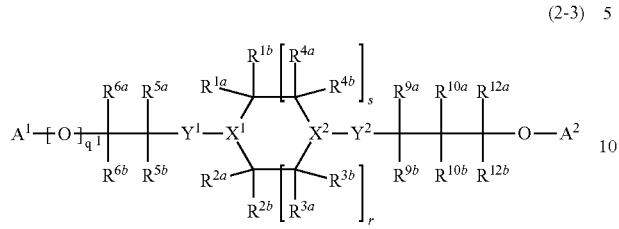

(2-3)

or a pharmaceutically acceptable salt thereof;
wherein:
$A^1$ is selected from the group consisting of:
a substituent of formula ($A^1$-a)

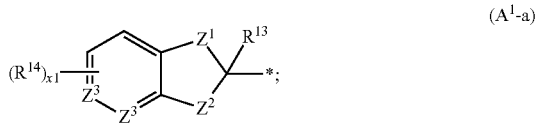

($A^1$-a)

$C_6$-$C_{10}$ aryl optionally substituted with one or more $R^{14}$ substituents; and
5-10 membered heteroaryl optionally substituted with one or more $R^{14}$ substituents;
$A^2$ is $C_6$-$C_{10}$ aryl optionally substituted with one or more $R^{16}$ substituents; or 5-10 membered heteroaryl optionally substituted with one or more $R^{16}$ substituents;
and wherein $X^1$, $X^2$, $Y^1$, $R^{Y1}$, $Y^2$, $R^{Y2}$, $q^1$, r, s, $Z^1$, $R^{Z1-1}$, $R^{Z1-2}$, $Z^2$, $R^{Z2-1}$, $R^{Z2-2}$, $Z^3$, x1, $R^{1a}$, $R^{1b}$, $R^{2a}$, $R^{2b}$, $R^{3a}$, $R^{3b}$, $R^{4a}$, $R^{4b}$, $R^{5a}$, $R^{5b}$, $R^{6a}$, $R^{6a-a}$, $R^{6a-b}$, $R^{6a-c}$, $R^{6b}$, $R^{9a}$, $R^{9b}$, $R^{10a}$, $R^{10a-a}$, $R^{10a-b}$, $R^{10a-c}$, $R^{10b}$, $R^{12a}$, $R^{12b}$, $R^{13}$, $R^{14}$, and $R^{16}$ are as defined in compounds of formula (I).

In some embodiments of the compounds of formula (2-3), $X^1$ is CH and $X^2$ is CH. In some embodiments, r is 1 and s is 1.

In some embodiments of the compounds of formula (2-3), $X^1$ is CH, $X^2$ is N and $Y^2$ is a bond. In some embodiments, r is 1 and s is 1. In some embodiments, r is 0 and s is 2.

In some embodiments of the compounds of formula (2-3), $X^1$ is N, $Y^1$ is a bond, and $X^2$ is CH. In some embodiments, r is 1 and s is 1. In some embodiments, r is 0 and s is 2.

In some embodiments of the compounds of formula (2-3), $X^1$ is N, $Y^1$ is a bond, $X^2$ is N and $Y^2$ is a bond. In some embodiments, r is 1 and s is 1. In some embodiments, r is 0 and s is 2.

In some embodiments of the compounds of formula (2-3):
$q^1$ is 1;
$A^1$ is selected $C_6$-$C_{10}$ aryl optionally substituted with one or more $R^{14}$ substituents; or 5-10 membered heteroaryl optionally substituted with one or more $R^{14}$ substituents;
$A^2$ is $C_6$-$C_{10}$ aryl optionally substituted with one or more $R^{16}$ substituents; or 5-10 membered heteroaryl optionally substituted with one or more $R^{16}$ substituents;
$R^{5a}$ and $R^{5b}$ are taken together to form an oxo (=O) substituent or an imido (=NH) substituent, or alternatively, $R^{5a}$ and $R^{5b}$ are both hydrogen;
$R^{6a}$ is selected from the group consisting of hydrogen, —$OR^{6a-a}$, and —$NR^{6a-b}R^{6a-c}$; and
$R^{6b}$ is hydrogen;
or alternatively, $R^{6a}$ and $R^{6b}$ are taken together to form a —$CH_2$—O—$CH_2$— moiety.

In some embodiments of the compounds of formula (2-3):
$R^{5a}$ and $R^{5b}$ are taken together to form an oxo (=O) substituent;
$R^{6a}$ is hydrogen; and
$R^{6b}$ is hydrogen.

In some embodiments of the compounds of formula (2-3):
$R^{5a}$ and $R^{5b}$ are both hydrogen; and
$R^{6a}$ and $R^{6b}$ are taken together to form a —$CH_2$—O—$CH_2$— moiety.

In some embodiments of the compounds of formula (2-3):
$X^1$ and $X^2$, independently of each other, are CH or N; provided that at least one of $X^1$ and $X^2$ is CH;
$Y^1$ is selected from the group consisting of a bond, $NR^{Y1}$, and O; provided that when $X^1$ is N, then $Y^1$ is a bond;
$R^{Y1}$ is hydrogen or $C_1$-$C_6$ alkyl;
$Y^2$ is selected from the group consisting of a bond, $NR^{Y2}$, and O; provided that when $X^2$ is N, then $Y^2$ is a bond;
$R^{Y2}$ is hydrogen or $C_1$-$C_6$ alkyl;
$q^1$ is 1;
r and s, independently of each other, are 0, 1, or 2;
$A^1$ is $C_6$-$C_{10}$ aryl substituted by at least one halogen substituent and optionally further substituted with one or more $R^{14}$ substituents, or 5-10 membered heteroaryl substituted by at least one halogen substituent and optionally further substituted with one or more $R^{14}$ substituents;
$R^{14}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —$NH_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —$NR^{14-a}R^{14-b}$, —CN, —C(O)OH, —C(O)O($C_1$-$C_6$ alkyl), —C(O)O($C_1$-$C_6$ haloalkyl), —C(O)$NH_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)$NR^{14-a}R^{14-b}$, —S(O)$_2$OH, —S(O)$_2$O($C_1$-$C_6$ alkyl), —S(O)$_2$O($C_1$-$C_6$ haloalkyl), —S(O)$_2NH_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2NR^{14-a}R^{14-b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);
wherein $R^{14-a}$ and $R^{14-b}$ are taken together with the nitrogen atom which bears them to form a 3-10 membered heterocycle;
$A^2$ is $C_6$-$C_{10}$ aryl substituted by at least one halogen substituent and optionally further substituted with one or more $R^{16}$ substituents, or 5-10 membered heteroaryl substituted by at least one halogen substituent and optionally further substituted with one or more $R^{16}$ substituents;
$R^{16}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —$NH_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —$NR^{16-a}R^{16-b}$, —CN, —C(O)OH, —C(O)O($C_1$-$C_6$ alkyl), —C(O)O($C_1$-$C_6$ haloalkyl), —C(O)$NH_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)$NR^{16-a}R^{16-b}$, —S(O)$_2$OH, —S(O)$_2$O($C_1$-$C_6$ alkyl), —S(O)$_2$O($C_1$-$C_6$ haloalkyl), —S(O)$_2$$NH_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$$NR^{16a}R^{16b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);

wherein $R^{16-a}$ and $R^{16-b}$ are taken together with the nitrogen atom which bears them to form a 3-10 membered heterocycle;

$R^{1a}$ and $R^{1b}$ are independently selected from the group consisting of hydrogen, $C_1$-$C_6$ alkyl, and halogen;

$R^{2a}$ and $R^{2b}$ are independently selected from the group consisting of hydrogen, $C_1$-$C_6$ alkyl, and halogen;

when present, $R^{3a}$ and $R^{3b}$ are independently at each occurrence selected from the group consisting of hydrogen, $C_1$-$C_6$ alkyl, and halogen;

when present, $R^{4a}$ and $R^{4b}$ are independently at each occurrence selected from the group consisting of hydrogen, $C_1$-$C_6$ alkyl, and halogen;

or alternatively, $R^{1a}$ and $R^{2a}$ are taken together to form a $C_1$-$C_6$ alkylene moiety;

or alternatively, $R^{1a}$ and an $R^{3a}$ moiety, when present, are taken together to form a $C_1$-$C_6$ alkylene moiety, and $R^{1b}$ and the $R^{3b}$ in the geminal position to the $R^{3a}$ taken together with $R^{1a}$, are both hydrogen;

or alternatively, an $R^{3a}$ moiety, when present, and an $R^{4a}$ moiety, when present, are taken together to form a $C_1$-$C_6$ alkylene moiety, and the $R^{3b}$ in the geminal position to the $R^{3a}$ taken together with the $R^{4a}$ moiety and the $R^{4b}$ in the geminal position to the $R^{4a}$ taken together with the $R^{3a}$ moiety, are both hydrogen;

$R^{5a}$ and $R^{5b}$ are taken together to form an oxo (=O) substituent or an imido (=NH) substituent;

$R^{6a}$ is hydrogen;

$R^{6b}$ is hydrogen;

$R^{9a}$ and $R^{9b}$ are taken together to form an oxo (=O) substituent or an imido (=NH) substituent, or alternatively, $R^{9a}$ and $R^{9b}$ are both hydrogen;

$R^{10a}$ is selected from the group consisting of hydrogen, —$OR^{10a-a}$, and —$NR^{10a-b}R^{10a-c}$;

$R^{10b}$ is hydrogen;

$R^{12a}$ and $R^{12b}$ are taken together to form an oxo (=O) substituent, or alternatively, $R^{12a}$ and $R^{12b}$ are both hydrogen;

$R^{10a-a}$ is selected from the group consisting of hydrogen, $C_1$-$C_6$ alkyl, and $C_1$-$C_6$ haloalkyl;

or $R^{10a-a}$ and $R^{Y2}$ may be taken together to form a carbonyl (C=O) moiety;

$R^{10a-b}$ and $R^{10a-c}$, independently of each other, are selected from the group consisting of hydrogen, $C_1$-$C_6$ alkyl, and $C_1$-$C_6$ haloalkyl; and provided that when $X^2$ is N, then:

$A^1$ is $C_6$-$C_{10}$ aryl substituted by at least two halogen substituents and optionally further substituted with one or more $R^{14}$ substituents, or 5-10 membered heteroaryl substituted by at least two halogen substituents and optionally further substituted with one or more $R^{14}$ substituents; and $A^2$ is $C_6$-$C_{10}$ aryl substituted by at least two halogen substituents and optionally further substituted with one or more $R^{16}$ substituents, or 5-10 membered heteroaryl substituted by at least two halogen substituents and optionally further substituted with one or more $R^{16}$ substituents.

In some embodiments of the compounds of formula (2-3), $R^{1a}$ and $R^{1b}$ are independently selected from the group consisting of hydrogen and $C_1$-$C_6$ alkyl. In some embodiments of the compounds of formula (2-3), $R^{1a}$ and $R^{1b}$ are both hydrogen.

In some embodiments of the compounds of formula (2-3), $R^{2a}$ and $R^{2b}$ are independently selected from the group consisting of hydrogen and $C_1$-$C_6$ alkyl. In some embodiments of the compounds of formula (2-3), $R^{2a}$ and $R^{2b}$ are both hydrogen.

In some embodiments of the compounds of formula (2-3), $R^{1a}$ and $R^{2a}$ are taken together to form a $C_1$-$C_6$ alkylene moiety In some embodiments of the compounds of formula (2-3), r is 1 and s is 1. In some embodiments, $R^{3a}$ and $R^{3b}$ are independently selected from the group consisting of hydrogen and $C_1$-$C_6$ alkyl. In some embodiments, $R^{3a}$ and $R^{3b}$ are both hydrogen. In some embodiments, $R^{4a}$ and $R^{4b}$ are independently selected from the group consisting of hydrogen and $C_1$-$C_6$ alkyl. In some embodiments, $R^{4a}$ and $R^{4b}$ are both hydrogen. In some embodiments, $R^{1a}$ and $R^{3a}$ are taken together to form a $C_1$-$C_6$ alkylene moiety, and $R^{1b}$ and $R^{3b}$ are both hydrogen. In some embodiments, $R^{3a}$ and $R^{4a}$ are taken together to form a $C_1$-$C_6$ alkylene moiety, and $R^{3b}$ and $R^{4b}$ are both hydrogen.

In some embodiments of the compounds of formula (2-3):

$X^1$ is CH;

$X^2$ is CH;

$Y^1$ is selected from the group consisting of $NR^{Y1}$ and O;

$R^{Y1}$ is hydrogen or $C_1$-$C_6$ alkyl;

$Y^2$ is selected from the group consisting of $NR^{Y2}$ and O;

$R^{Y2}$ is hydrogen or $C_1$-$C_6$ alkyl;

$q^1$ and $q^2$ are each 1; and r and s are both 1.

In some embodiments of the compounds of formula (2-3):

$X^1$ is CH;

$X^2$ is CH;

$Y^1$ is $NR^{Y1}$;

$R^{y1}$ is hydrogen;

$Y^2$ is $NR^{Y2}$;

$R^{Y2}$ is hydrogen;

q1 is 1; and r and s are both 1.

In some embodiments of the compounds of formula (2-3), $R^{9a}$ and $R^{9b}$ are taken together to form an oxo (=O) substituent. In some embodiments of the compounds of formula (2-3), $R^{9a}$ and $R^{9b}$ are taken together to form an imido (=NH) substituent. In some embodiments of the compounds of formula (2-3), $R^{9a}$ and $R^{9b}$ are both hydrogen.

In some embodiments of the compounds of formula (2-3), $R^{10a}$ is hydrogen and $R^{10b}$ is hydrogen.

In some embodiments of the compounds of formula (2-3), $R^{10a}$ is —$OR^{10a-a}$ and $R^{10b}$ is hydrogen. In some embodiments, $R^{10a-a}$ is selected from the group consisting of hydrogen and $C_1$-$C_6$ alkyl. In some embodiments, $R^{10a-a}$ is hydrogen. In some embodiments, $R^{10a-a}$ is $C_1$-$C_6$ alkyl. In some embodiments, $R^{10a-a}$ and $R^{Y2}$ may be taken together to form a carbonyl (C=O) moiety.

In some embodiments of the compounds of formula (2-3), $R^{10a}$ is —$NR^{10a-b}R^{10a-c}$ and $R^{10b}$ is hydrogen. In some embodiments, $R^{10a-b}$ and $R^{10a-c}$, independently of each other, are selected from the group consisting of hydrogen and $C_1$-$C_6$ alkyl. In some embodiments, $R^{10a-b}$ and $R^{10a-c}$ are hydrogen. In some embodiments, $R^{10a-b}$ and $R^{10a-c}$ are $C_1$-$C_6$ alkyl.

In some embodiments of the compounds of formula (2-3), $A^1$ is $C_6$-$C_{10}$ aryl substituted by at least one halogen substituent and optionally further substituted with one or more $R^{14}$ substituents, or 5-10 membered heteroaryl substituted by at least one halogen substituent and optionally further substituted with one or more $R^{14}$ substituents.

In some embodiments of the compounds of formula (2-3), $A^1$ is $C_6$-$C_{10}$ aryl optionally substituted with one or more $R^{14}$ substituents. In some embodiments, $A^1$ is $C_6$-$C_{10}$ aryl substituted by at least one halogen substituent and optionally further substituted with one or more $R^{14}$ substituents. In some embodiments, $A^1$ is selected from the group consisting of:

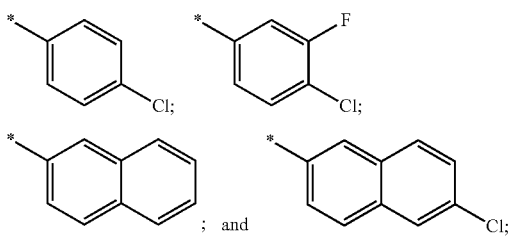

; and wherein the * represents the attachment point to the remainder of the molecule. In some embodiments, $A^1$ is phenyl optionally substituted with one or more $R^{14}$ substituents. In some embodiments, $A^1$ is phenyl substituted by at least one halogen substituent and optionally further substituted with one or more $R^{14}$ substituents. In some embodiments, $A^1$ is selected from the group consisting of:

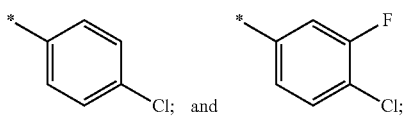 [SMILES: *c1ccc(Cl)cc1 ; "and" ; *c1ccc(Cl)c(F)c1]

Cl; and Cl;

wherein the * represents the attachment point to the remainder of the molecule.

In some embodiments, $A^1$ is 5-10 membered heteroaryl optionally substituted with one or more $R^{14}$ substituents. In some embodiments, $A^1$ is 5-10 membered heteroaryl substituted by at least one halogen substituent and optionally further substituted with one or more $R^{14}$ substituents. In some embodiments, $A^1$ is selected from the group consisting of:

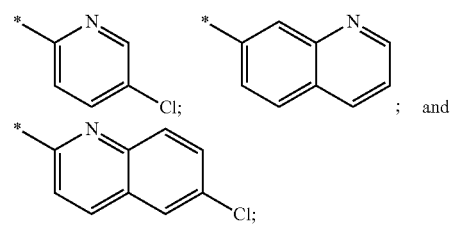

; and wherein the * represents the attachment point to the remainder of the molecule. In some embodiments, $A^1$ is pyridyl optionally substituted with one or more $R^{14}$ substituents. In some embodiments, $A^1$ is pyridyl substituted by at least one halogen substituent and optionally further substituted with one or more $R^{14}$ substituents. In some embodiments, $A^1$ is

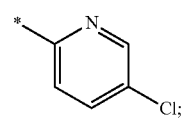

wherein the * represents the attachment point to the remainder of the molecule.

In some embodiments of the compounds of formula (2-3), $A^2$ is $C_6$-$C_{10}$ aryl substituted by at least one halogen substituent and optionally further substituted with one or more $R^{16}$ substituents, or 5-10 membered heteroaryl substituted by at least one halogen substituent and optionally further substituted with one or more $R^{16}$ substituents.

In some embodiments of the compounds of formula (2-3), $A^2$ is $C_6$-$C_{10}$ aryl optionally substituted with one or more $R^{16}$ substituents. In some embodiments, $A^2$ is $C_6$-$C_{10}$ aryl substituted by at least one halogen substituent and optionally further substituted with one or more $R^{16}$ substituents. In some embodiments, $A^2$ is selected from the group consisting of:

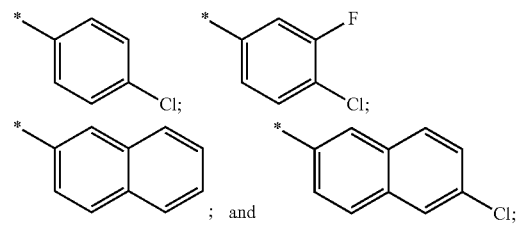

; and wherein the * represents the attachment point to the remainder of the molecule. In some embodiments, $A^2$ is phenyl optionally substituted with one or more $R^{16}$ substituents. In some embodiments, $A^2$ is phenyl substituted by at least one halogen substituent and optionally further substituted with one or more $R^{16}$ substituents. In some embodiments, $A^2$ is selected from the group consisting of:

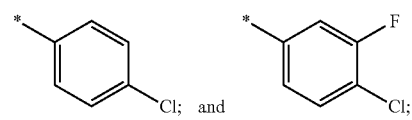

Cl; and Cl;

wherein the * represents the attachment point to the remainder of the molecule.

In some embodiments, $A^2$ is 5-10 membered heteroaryl optionally substituted with one or more $R^{16}$ substituents. In some embodiments, $A^2$ is 5-10 membered heteroaryl substituted by at least one halogen substituent and optionally further substituted with one or more $R^{16}$ substituents. In some embodiments, $A^2$ is selected from the group consisting of:

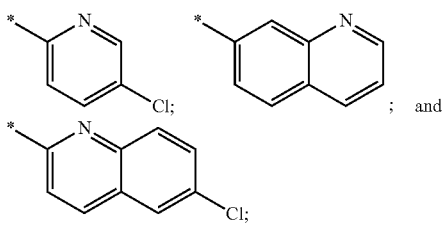
; and wherein the * represents the attachment point to the remainder of the molecule. In some embodiments, $A^2$ is pyridyl optionally substituted with one or more $R^{16}$ substituents. In some embodiments, $A^2$ is pyridyl substituted by at least one halogen substituent and optionally further substituted with one or more $R^{16}$ substituents. In some embodiments, $A^2$ is

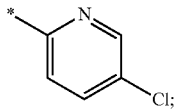

wherein the * represents the attachment point to the remainder of the molecule.

In some embodiments of the compounds of formula (2-3):
$X^1$ is N;
$X^2$ is CH;
$Y^1$ is a bond;
$Y^2$ is selected from the group consisting of $NR^{Y2}$ and O;
$R^{Y2}$ is hydrogen or $C_1$-$C_6$ alkyl;
q1 is 1; and
r and s are both 1.

In some embodiments of the compounds of formula (2-3):
$X^1$ is N;
$X^2$ is CH;
$Y^1$ is a bond;
$Y^2$ is $NR^{Y2}$;
$R^{Y2}$ is hydrogen;
q1 is 1; and
r and s are both 1.

In some embodiments of the compounds of formula (2-3), $R^{9a}$ and $R^{9b}$ are taken together to form an oxo (=O) substituent. In some embodiments of the compounds of formula (2-3), $R^{9a}$ and $R^{9b}$ are taken together to form an imido (=NH) substituent. In some embodiments of the compounds of formula (2-3), $R^{9a}$ and $R^{9b}$ are both hydrogen.

In some embodiments of the compounds of formula (2-3), $R^{10a}$ is hydrogen and $R^{10b}$ is hydrogen.

In some embodiments of the compounds of formula (2-3), $R^{10a}$ is —$OR^{10a-a}$ and $R^{10b}$ is hydrogen. In some embodiments, $R^{10a-a}$ is selected from the group consisting of hydrogen and $C_1$-$C_6$ alkyl. In some embodiments, $R^{10a-a}$ is hydrogen. In some embodiments, $R^{10a-a}$ is $C_1$-$C_6$ alkyl. In some embodiments, $R^{10a-a}$ and $R^{Y2}$ may be taken together to form a carbonyl (C=O) moiety.

In some embodiments of the compounds of formula (2-3), $R^{10a}$ is —$NR^{10a-b}R^{10a-c}$ and $R^{10b}$ is hydrogen. In some embodiments, $R^{10a-b}$ and $R^{10a-c}$, independently of each other, are selected from the group consisting of hydrogen and $C_1$-$C_6$ alkyl. In some embodiments, $R^{10a-b}$ and $R^{10a-c}$ are hydrogen. In some embodiments, $R^{10a-b}$ and $R^{10a-c}$ are $C_1$-$C_6$ alkyl.

In some embodiments of the compounds of formula (2-3), $A^1$ is $C_6$-$C_{10}$ aryl substituted by at least one halogen substituent and optionally further substituted with one or more $R^{14}$ substituents, or 5-10 membered heteroaryl substituted by at least one halogen substituent and optionally further substituted with one or more $R^{14}$ substituents.

In some embodiments of the compounds of formula (2-3), $A^1$ is $C_6$-$C_{10}$ aryl optionally substituted with one or more $R^{14}$ substituents. In some embodiments, $A^1$ is $C_6$-$C_{10}$ aryl substituted by at least one halogen substituent and optionally further substituted with one or more $R^{14}$ substituents. In some embodiments, $A^1$ is selected from the group consisting of:

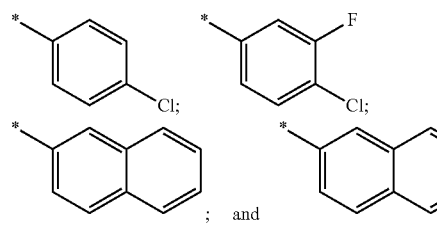
; and wherein the * represents the attachment point to the remainder of the molecule. In some embodiments, $A^1$ is phenyl optionally substituted with one or more $R^{14}$ substituents. In some embodiments, $A^1$ is phenyl substituted by at least one halogen substituent and optionally further substituted with one or more $R^{14}$ substituents. In some embodiments, $A^1$ is selected from the group consisting of:

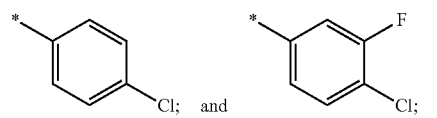

wherein the * represents the attachment point to the remainder of the molecule.

In some embodiments, $A^1$ is 5-10 membered heteroaryl optionally substituted with one or more $R^{14}$ substituents. In some embodiments, $A^1$ is 5-10 membered heteroaryl substituted by at least one halogen substituent and optionally further substituted with one or more $R^{14}$ substituents. In some embodiments, $A^1$ is selected from the group consisting of:

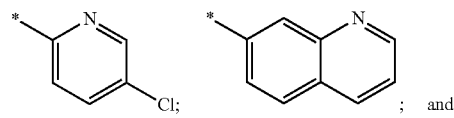
; and

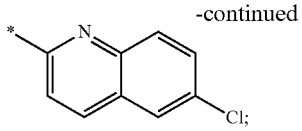

wherein the * represents the attachment point to the remainder of the molecule. In some embodiments, $A^1$ is pyridyl optionally substituted with one or more $R^{14}$ substituents. In some embodiments, $A^1$ is pyridyl substituted by at least one halogen substituent and optionally further substituted with one or more $R^{14}$ substituents. In some embodiments, $A^1$ is

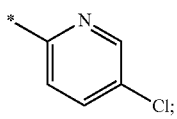 [SMILES: *c1ccc(Cl)cn1]

wherein the * represents the attachment point to the remainder of the molecule.

In some embodiments of the compounds of formula (2-3), $A^2$ is $C_6$-$C_{10}$ aryl substituted by at least one halogen substituent and optionally further substituted with one or more $R^{16}$ substituents, or 5-10 membered heteroaryl substituted by at least one halogen substituent and optionally further substituted with one or more $R^{16}$ substituents.

In some embodiments of the compounds of formula (2-3), $A^2$ is $C_6$-$C_{10}$ aryl optionally substituted with one or more $R^{16}$ substituents. In some embodiments, $A^2$ is $C_6$-$C_{10}$ aryl substituted by at least one halogen substituent and optionally further substituted with one or more $R^{16}$ substituents. In some embodiments, $A^2$ is selected from the group consisting of:

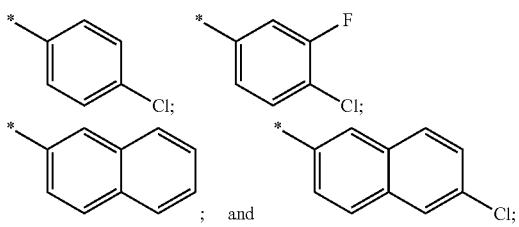

wherein the * represents the attachment point to the remainder of the molecule. In some embodiments, $A^2$ is phenyl optionally substituted with one or more R substituents. In some embodiments, $A^2$ is phenyl substituted by at least one halogen substituent and optionally further substituted with one or more $R^{16}$ substituents. In some embodiments, $A^2$ is selected from the group consisting of:

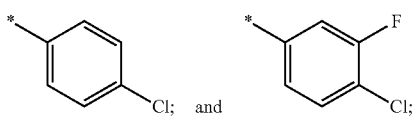

wherein the * represents the attachment point to the remainder of the molecule.
In some embodiments, $A^2$ is 5-10 membered heteroaryl optionally substituted with one or more $R^{16}$ substituents. In some embodiments, $A^2$ is 5-10 membered heteroaryl substituted by at least one halogen substituent and optionally further substituted with one or more $R^{16}$ substituents. In some embodiments, $A^2$ is selected from the group consisting of:

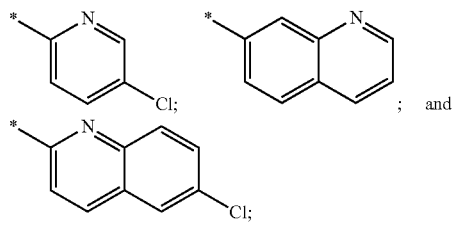

wherein the * represents the attachment point to the remainder of the molecule. In some embodiments, $A^2$ is pyridyl optionally substituted with one or more $R^{16}$ substituents. In some embodiments, $A^2$ is pyridyl substituted by at least one halogen substituent and optionally further substituted with one or more $R^{16}$ substituents. In some embodiments, $A^2$ is

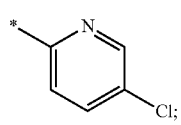

wherein the * represents the attachment point to the remainder of the molecule.

In some embodiments of the compounds of formula (2-3):
$X^1$ is CH;
$X^2$ is N;
$Y^1$ is selected from the group consisting of $NR^{Y1}$ and O;
$R^{Y1}$ is hydrogen or $C_1$-$C_6$ alkyl;
$Y^2$ is a bond;
q1 is 1;
r and s are both 1;
$A^1$ is $C_6$-$C_{10}$ aryl substituted by at least two halogen substituents and optionally further substituted with one or more $R^{14}$ substituents, or 5-10 membered heteroaryl substituted by at least two halogen substituents and optionally further substituted with one or more $R^{14}$ substituents; and
$A^2$ is $C_6$-$C_{10}$ aryl substituted by at least two halogen substituents and optionally further substituted with one or more $R^{16}$ substituents, or 5-10 membered heteroaryl substituted by at least two halogen substituents and optionally further substituted with one or more $R^{16}$ substituents.

In some embodiments of the compounds of formula (2-3):
$X^1$ is CH;
$X^2$ is N;
$Y^1$ is $NR^{Y1}$;
$R^{y1}$ is hydrogen;
$Y^2$ is a bond;
q1 is 1;
r and s are both 1;
$A^1$ is $C_6$-$C_{10}$ aryl substituted by at least two halogen substituents and optionally further substituted with one or more $R^{14}$ substituents, or 5-10 membered heteroaryl substituted by at least two halogen substituents and optionally further substituted with one or more $R^{14}$ substituents; and $A^2$ is $C_6$-$C_{10}$ aryl substituted by at least two halogen substituents and optionally further substituted with one or more $R^{16}$ substituents, or 5-10 membered heteroaryl substituted by at least two halogen substituents and optionally further substituted with one or more $R^{16}$ substituents.

In some embodiments of the compounds of formula (2-3), $R^{9a}$ and $R^{9b}$ are both hydrogen.

In some embodiments of the compounds of formula (2-3), $R^{10a}$ is hydrogen and $R^{10b}$ is hydrogen.

In some embodiments of the compounds of formula (2-3), $R^{10a}$ is —$OR^{10a\text{-}a}$ and $R^{10b}$ is hydrogen. In some embodiments, $R^{10a\text{-}a}$ is selected from the group consisting of hydrogen and $C_1$-$C_6$ alkyl. In some embodiments, $R^{10a\text{-}a}$ is hydrogen. In some embodiments, $R^{10a\text{-}a}$ is $C_1$-$C_6$ alkyl. In some embodiments, $R^{10a\text{-}a}$ and $R^{Y2}$ may be taken together to form a carbonyl (C=O) moiety.

In some embodiments of the compounds of formula (2-3), $R^{10a}$ is —$NR^{10a\text{-}b}R^{10a\text{-}c}$ and $R^{10b}$ is hydrogen. In some embodiments, $R^{10a\text{-}b}$ and $R^{10a\text{-}c}$, independently of each other, are selected from the group consisting of hydrogen and $C_1$-$C_6$ alkyl. In some embodiments, $R^{10a\text{-}b}$ and $R^{10a\text{-}c}$ are hydrogen. In some embodiments, $R^{10a\text{-}b}$ and $R^{10a\text{-}c}$ are $C_1$-$C_6$ alkyl.

In some embodiments of the compounds of formula (2-3), $A^1$ is $C_6$-$C_{10}$ aryl substituted by at least two halogen substituents and optionally further substituted with one or more $R^{14}$ substituents, or 5-10 membered heteroaryl substituted by at least two halogen substituents and optionally further substituted with one or more $R^{14}$ substituents.

In some embodiments of the compounds of formula (2-3), $A^1$ is $C_6$-$C_{10}$ aryl substituted by at least two halogen substituents and optionally further substituted with one or more $R^{14}$ substituents. In some embodiments, $A^1$ is phenyl substituted by at least two halogen substituents and optionally further substituted with one or more $R^{14}$ substituents. In some embodiments, $A^1$ is

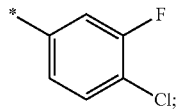 [SMILES: *c1ccc(Cl)c(F)c1]

wherein the * represents the attachment point to the remainder of the molecule. In some embodiments, $A^1$ is 5-10 membered heteroaryl substituted by at least two halogen substituents and optionally further substituted with one or more $R^{14}$ substituents.

In some embodiments of the compounds of formula (2-3), $A^2$ is $C_6$-$C_{10}$ aryl substituted by at least two halogen substituents and optionally further substituted with one or more $R^{16}$ substituents, or 5-10 membered heteroaryl substituted by at least two halogen substituents and optionally further substituted with one or more $R^{16}$ substituents.

In some embodiments of the compounds of formula (2-3), $A^2$ is $C_6$-$C_{10}$ aryl substituted by at least two halogen substituents and optionally further substituted with one or more $R^{16}$ substituents. In some embodiments, $A^2$ is phenyl substituted by at least two halogen substituents and optionally further substituted with one or more $R^{16}$ substituents. In some embodiments, $A^2$ is

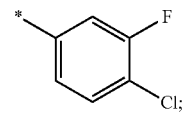

wherein the * represents the attachment point to the remainder of the molecule. In some embodiments, $A^2$ is 5-10 membered heteroaryl substituted by at least two halogen substituent and optionally further substituted with one or more $R^{16}$ substituents.

In some embodiments of the compounds of formula (2-3), $A^1$ is $C_6$-$C_{10}$ aryl optionally substituted with one or more $R^{14}$ substituents. In some embodiments, $A^1$ is selected from the group consisting of:

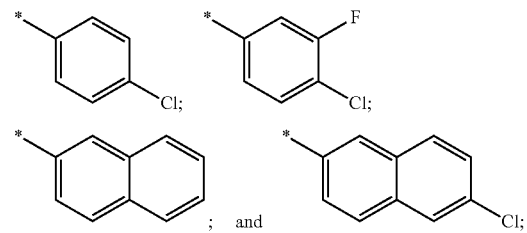

wherein the * represents the attachment point to the remainder of the molecule. In some embodiments, $A^1$ is phenyl optionally substituted with one or more $R^{14}$ substituents. In some embodiments, $A^1$ is selected from the group consisting of:

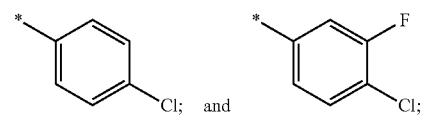

wherein the * represents the attachment point to the remainder of the molecule.

In some embodiments of the compounds of formula (2-3), $A^1$ is 5-10 membered heteroaryl optionally substituted with one or more $R^{14}$ substituents. In some embodiments, $A^1$ is selected from the group consisting of:

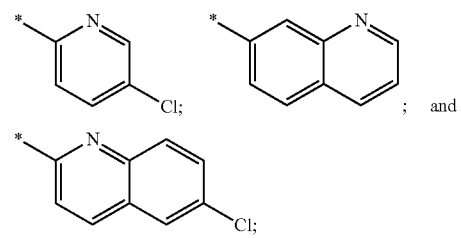

wherein the * represents the attachment point to the remainder of the molecule. In some embodiments, $A^1$ is pyridyl optionally substituted with one or more $R^{14}$ substituents. In some embodiments, $A^1$ is

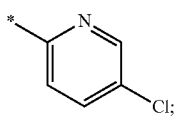

wherein the * represents the attachment point to the remainder of the molecule.

In some embodiments of the compounds of formula (2-3):
$q^1$ is 0;
$A^1$ is a substituent of formula ($A^1$-a)

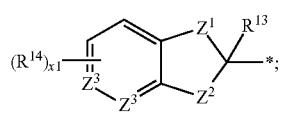

$R^{6a}$ is —$OR^{6a-a}$; and
$R^{6b}$ is hydrogen.

In some embodiments of the compounds of formula (2-3):
$R^{5a}$ and $R^{5b}$ are taken together to form an oxo (=O) substituent;
$R^{6a}$ is hydrogen; and
$R^{6b}$ is hydrogen.

In some embodiments of the compounds of formula (2-3), ($A^1$-a) is selected from the group consisting of:

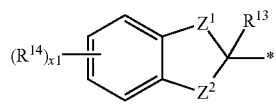

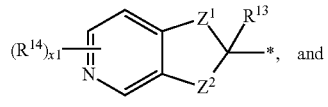

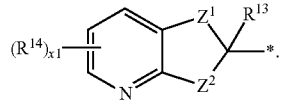

In some embodiments of the compounds of formula (2-3), ($A^1$-a) is ($A^1$-b).

In some embodiments of the compounds of formula (2-3), ($A^1$-a) is ($A^1$-c).

In some embodiments of the compounds of formula (2-3), ($A^1$-a) is ($A^1$-d).

In some embodiments of the compounds of formula (2-3), ($A^1$-a) or ($A^1$-b) is selected from the group consisting of:

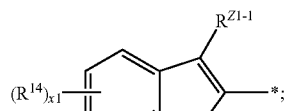

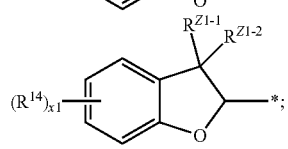

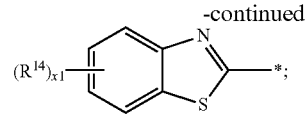

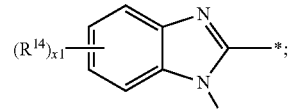

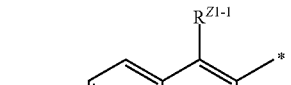

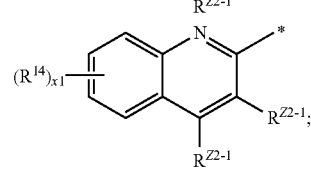

wherein the * represents the attachment point to the remainder of the molecule. In some embodiments. ($A^1$-a) or ($A^1$-b) is selected from the group consisting of:

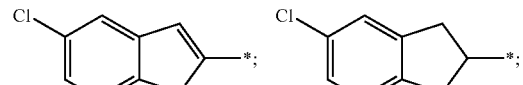

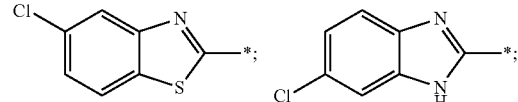

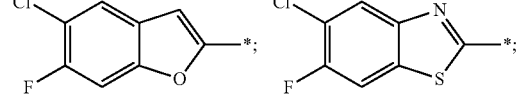

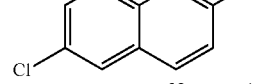

wherein the * represents the attachment point to the remainder of the molecule. In some embodiments, ($A^1$-a) or ($A^1$-b) is selected from the group consisting of:

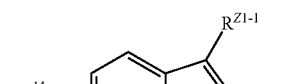

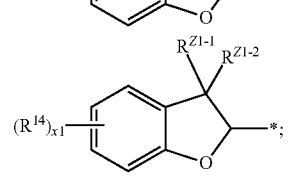

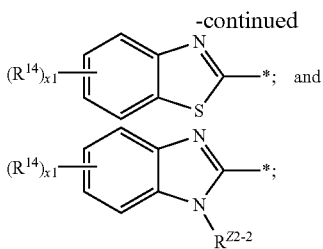

wherein the * represents the attachment point to the remainder of the molecule. In some embodiments, (A¹-a) or (A¹-b) is selected from the group consisting of:

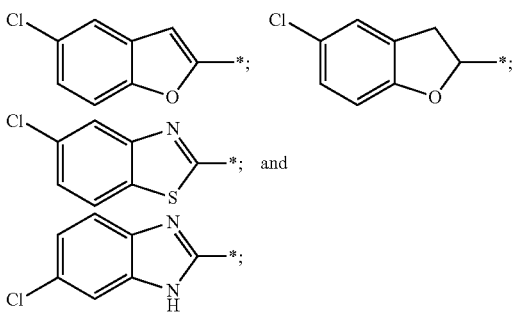

wherein the * represents the attachment point to the remainder of the molecule.

In some embodiments of the compounds of formula (2-3), (A¹-a) or (A¹-c) is selected from the group consisting of:

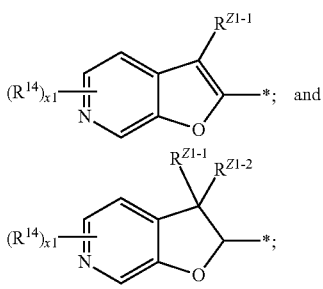

wherein the * represents the attachment point to the remainder of the molecule. In some embodiments, (A¹-a) or (A¹-c) is selected from the group consisting of:

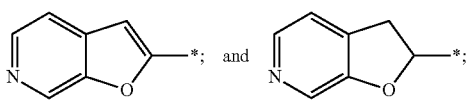

wherein the * represents the attachment point to the remainder of the molecule.

In some embodiments of the compounds of formula (2-3):
R$^{9a}$ and R$^{9b}$ are taken together to form an oxo (=O) substituent or an imido (=NH) substituent, or alternatively, R$^{9a}$ and R$^{9b}$ are both hydrogen;
R$^{10a}$ is selected from the group consisting of hydrogen, —OR$^{10a-a}$, and —NR$^{10a-b}$R$^{10a-c}$;
R$^{10b}$ is hydrogen; and
R$^{12a}$ and R$^{12b}$ are both hydrogen.

In some embodiments of the compounds of formula (2-3), R$^{9a}$ and R$^{9b}$ are taken together to form an oxo (=O) substituent. In some embodiments, R$^{10a}$ is hydrogen. In some embodiments, R$^{10a}$ is —OR$^{10a-a}$. In some embodiments, R$^{10a}$ is —NR$^{10a-b}$R$^{10a-c}$.

In some embodiments of the compounds of formula (2-3), R$^{9a}$ and R$^{9b}$ are taken together to form an imido (=NH) substituent. In some embodiments, R$^{10a}$ is hydrogen. In some embodiments, R$^{10a}$ is —OR$^{10a-a}$. In some embodiments, R$^{10a}$ is —NR$^{10a-b}$R$^{10a-c}$.

In some embodiments of the compounds of formula (2-3), R$^{9a}$ and R$^{9b}$ are both hydrogen. In some embodiments, R$^{10a}$ is hydrogen. In some embodiments, R$^{10a}$ is —OR$^{10a-a}$. In some embodiments, R$^{10a}$ is —NR$^{10a-b}$R$^{10a-c}$.

In some embodiments of the compounds of formula (2-3):
X$^2$ is CH;
Y$^2$ is NR$^{Y2}$;
R$^{9a}$ and R$^{9b}$ are both hydrogen;
R$^{10a}$ is —OR$^{10a-a}$;
R$^{12a}$ and R$^{12b}$ are both hydrogen; and
R$^{10a-a}$ and R$^{Y2}$ are taken together to form a carbonyl (C=O) moiety.

In some embodiments of the compounds of formula (2-3), A$^2$ is C$_6$-C$_{10}$ aryl optionally substituted with one or more R$^{16}$ substituents. In some embodiments, A$^2$ is selected from the group consisting of:

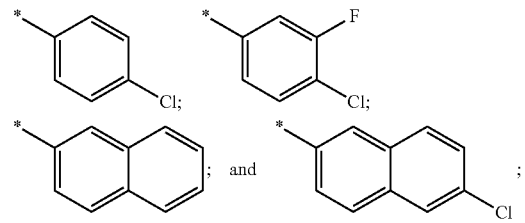

wherein the * represents the attachment point to the remainder of the molecule. In some embodiments, A$^2$ is phenyl optionally substituted with one or more R$^{16}$ substituents. In some embodiments, A$^2$ is selected from the group consisting of:

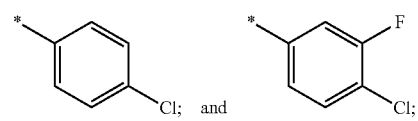 [SMILES: *c1ccc(Cl)cc1 ; *c1ccc(Cl)c(F)c1]

wherein the * represents the attachment point to the remainder of the molecule.

In some embodiments of the compounds of formula (2-3), A$^2$ is 5-10 membered heteroaryl optionally substituted with one or more R$^{16}$ substituents. In some embodiments, A$^2$ is selected from the group consisting of:

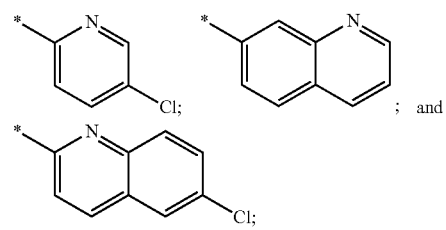

wherein the * represents the attachment point to the remainder of the molecule. In some embodiments, $A^2$ is pyridyl optionally substituted with one or more $R^{16}$ substituents. In some embodiments, $A^2$ is

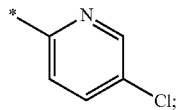 [SMILES: *c1ccc(Cl)cn1]

wherein the * represents the attachment point to the remainder of the molecule.

In some embodiments, ($A^1$-a) or ($A^1$-b) is selected from the group consisting of:

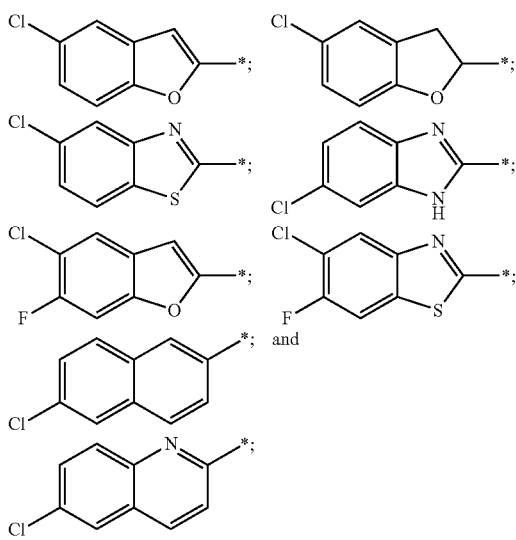

wherein the * represents the attachment point to the remainder of the molecule; and ($A^2$-a) or ($A^2$-b) is selected from the group consisting of:

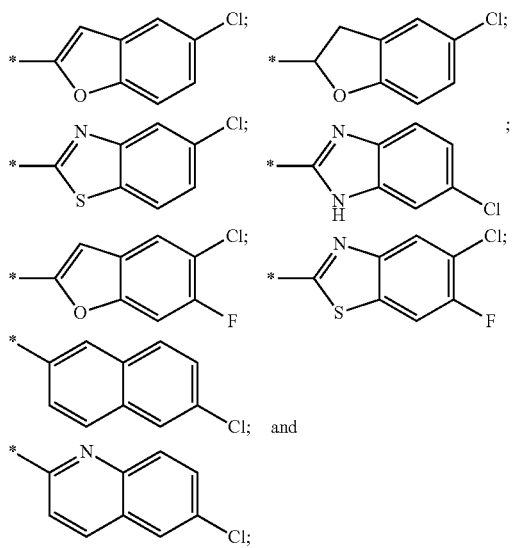

wherein the * represents the attachment point to the remainder of the molecule.

In some embodiments, ($A^1$-a) or ($A^1$-b) is selected from the group consisting of:

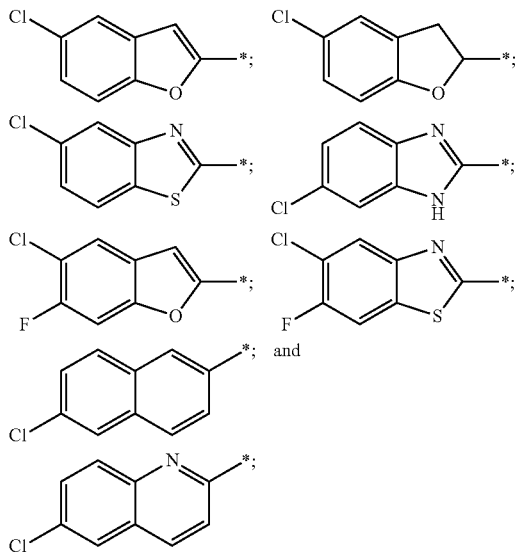

wherein the * represents the attachment point to the remainder of the molecule; and ($A^2$-a) or ($A^2$-b) is selected from the group consisting of:

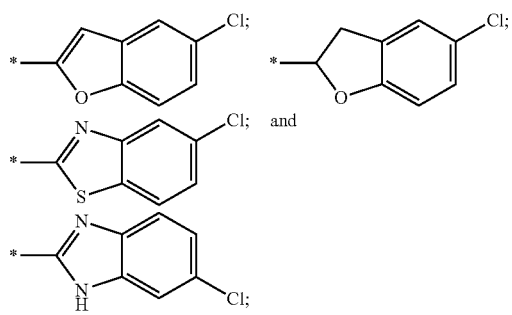

wherein the * represents the attachment point to the remainder of the molecule.

In some embodiments, ($A^1$-a) or ($A^1$-b) is selected from the group consisting of:

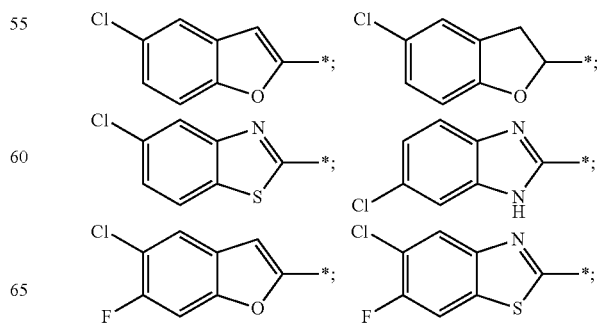

-continued

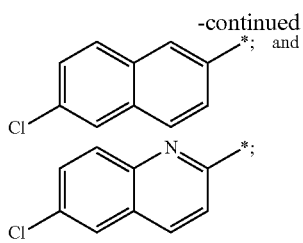
and wherein the * represents the attachment point to the remainder of the molecule; and (A²-a) or (A²-c) is selected from the group consisting of:

and wherein the * represents the attachment point to the remainder of the molecule.

In some embodiments, (A¹-a) or (A¹-b) is selected from the group consisting of:

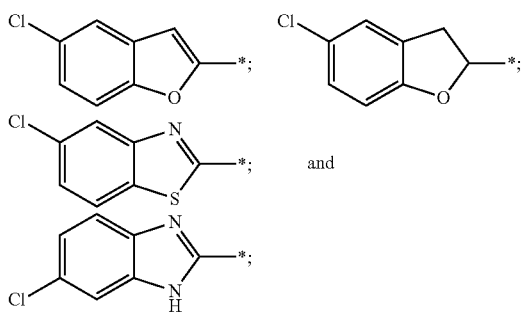
and wherein the * represents the attachment point to the remainder of the molecule; and (A²-a) or (A²-b) is selected from the group consisting of:

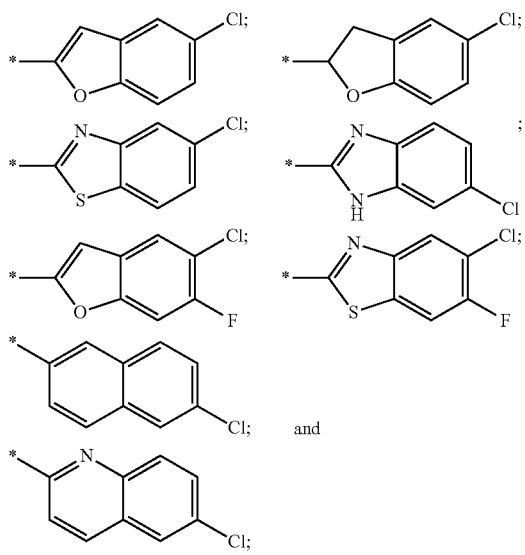
and wherein the * represents the attachment point to the remainder of the molecule.

In some embodiments, (A¹-a) or (A¹-b) is selected from the group consisting of:

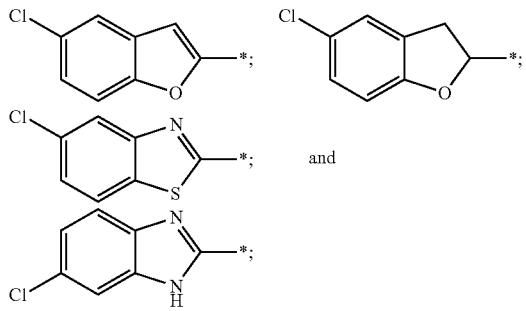
and wherein the * represents the attachment point to the remainder of the molecule; and (A²-a) or (A²-b) is selected from the group consisting of:

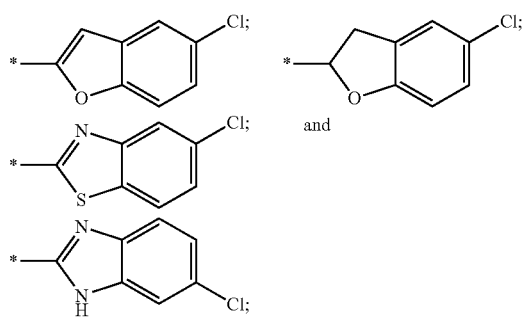
and wherein the * represents the attachment point to the remainder of the molecule.

In some embodiments, (A¹-a) or (A¹-b) is selected from the group consisting of:

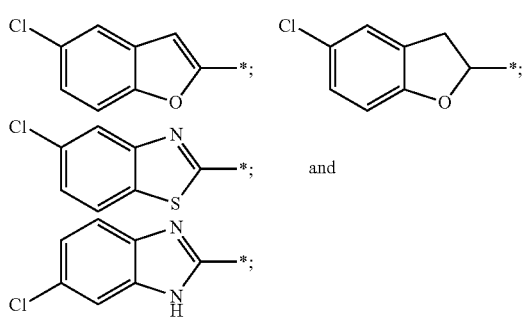
and wherein the * represents the attachment point to the remainder of the molecule; and (A²-a) or (A²-c) is selected from the group consisting of:

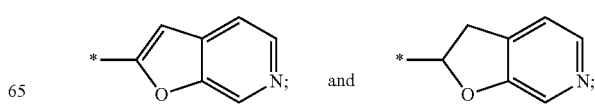
and wherein the * represents the attachment point to the remainder of the molecule.

In some embodiments, (A¹-a) or (A¹-c) is selected from the group consisting of:

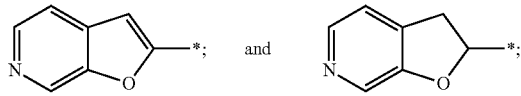 and wherein the * represents the attachment point to the remainder of the molecule; and (A²-a) or (A²-b) is selected from the group consisting of:

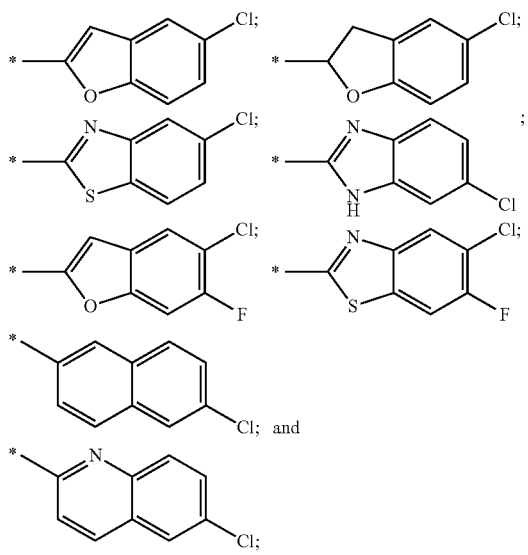

wherein the * represents the attachment point to the remainder of the molecule.

In some embodiments, (A¹-a) or (A¹-c) is selected from the group consisting of:

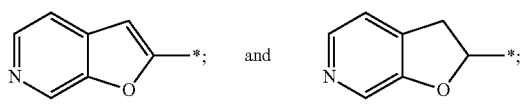 and wherein the * represents the attachment point to the remainder of the molecule; and (A²-a) or (A²-b) is selected from the group consisting of:

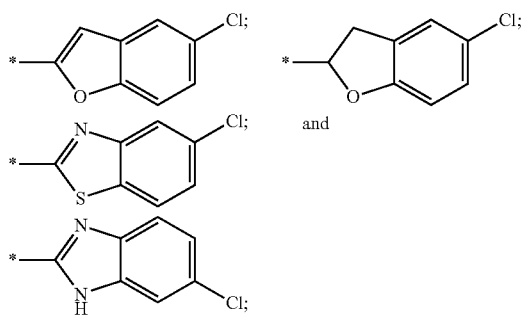

wherein the * represents the attachment point to the remainder of the molecule.

In some embodiments, (A¹-a) or (A¹-c) is selected from the group consisting of:

 and wherein the * represents the attachment point to the remainder of the molecule; and (A²-a) or (A²-c) is selected from the group consisting of:

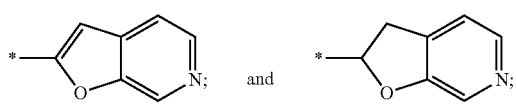 [SMILES: *c1cc2ccncc2o1 ; *C1Cc2ccncc2O1] and wherein the * represents the attachment point to the remainder of the molecule.

In some embodiments, (A¹-a) or (A¹-b) is selected from the group consisting of:

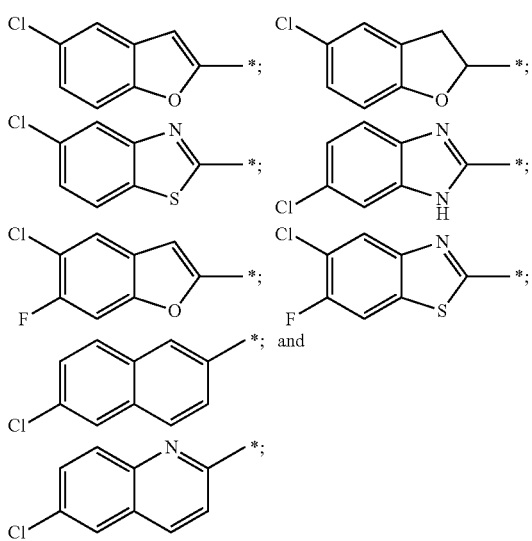

wherein the * represents the attachment point to the remainder of the molecule; and A² is selected from the group consisting of:

wherein the * represents the attachment point to the remainder of the molecule.

In some embodiments, (A¹-a) or (A¹-b) is selected from the group consisting of:

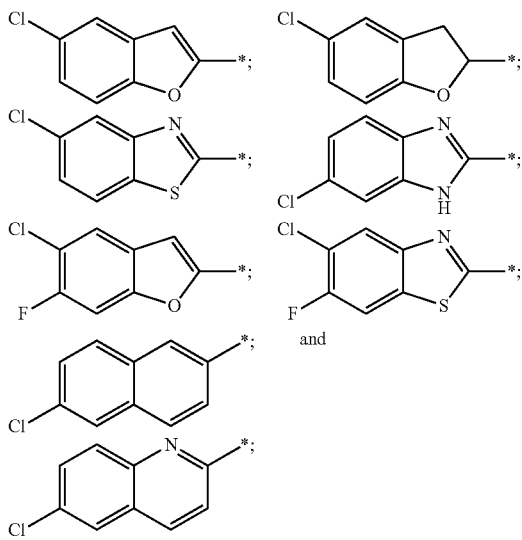

wherein the * represents the attachment point to the remainder of the molecule; and A² is selected from the group consisting of:

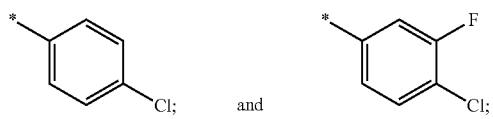 [SMILES: *c1ccc(Cl)cc1 ; *c1ccc(Cl)c(F)c1]

wherein the * represents the attachment point to the remainder of the molecule.

In some embodiments, (A¹-a) or (A¹-b) is selected from the group consisting of:

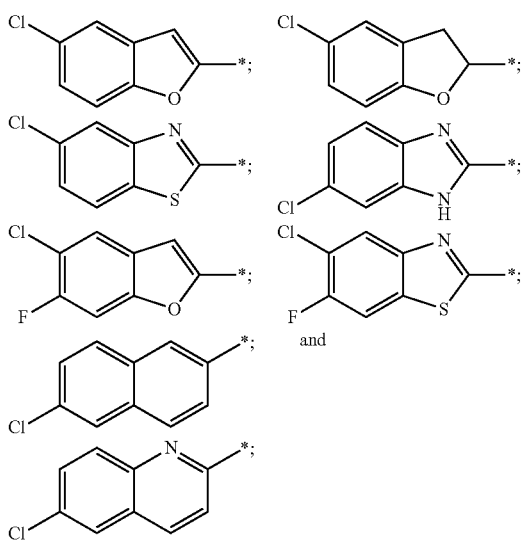

wherein the * represents the attachment point to the remainder of the molecule; and A² is selected from the group consisting of:

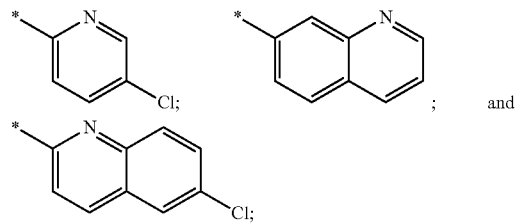

wherein the * represents the attachment point to the remainder of the molecule.

In some embodiments, (A¹-a) or (A¹-b) is selected from the group consisting of:

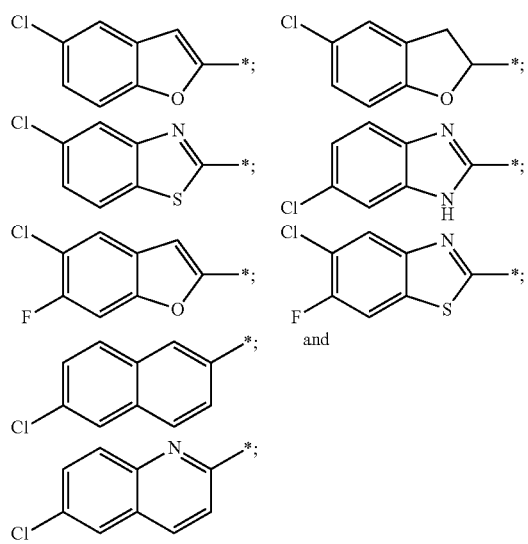

wherein the * represents the attachment point to the remainder of the molecule; and A² is

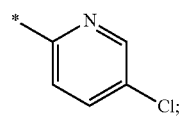

wherein the * represents the attachment point to the remainder of the molecule.

In some embodiments, (A¹-a) or (A¹-b) is selected from the group consisting of:

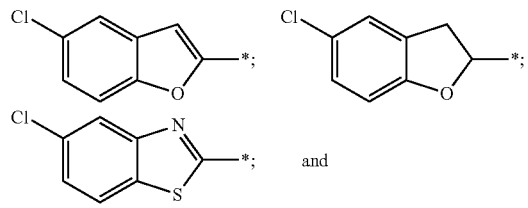

-continued

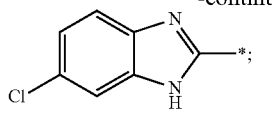

wherein the * represents the attachment point to the remainder of the molecule; and $A^2$ is selected from the group consisting of:

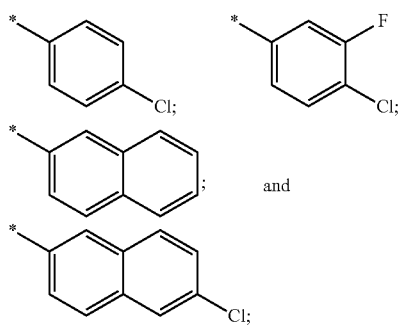

wherein the * represents the attachment point to the remainder of the molecule.

In some embodiments, $(A^1\text{-a})$ or $(A^1\text{-b})$ is selected from the group consisting of:

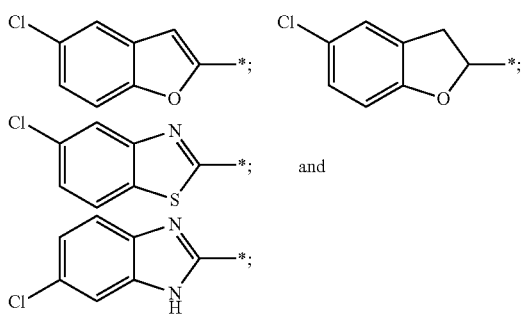

wherein the * represents the attachment point to the remainder of the molecule; and $A^2$ is selected from the group consisting of:

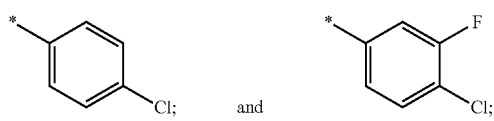 [SMILES: *c1ccc(Cl)cc1 ; *c1ccc(Cl)c(F)c1]

wherein the * represents the attachment point to the remainder of the molecule.

In some embodiments, $(A^1\text{-a})$ or $(A^1\text{-b})$ is selected from the group consisting of:

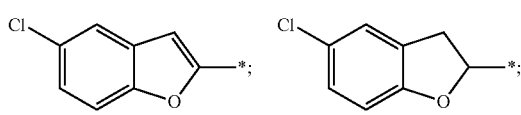

-continued

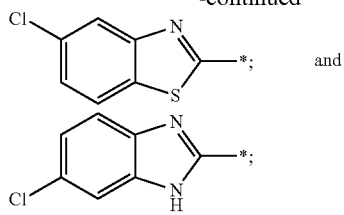

wherein the * represents the attachment point to the remainder of the molecule; and $A^2$ is selected from the group consisting of:

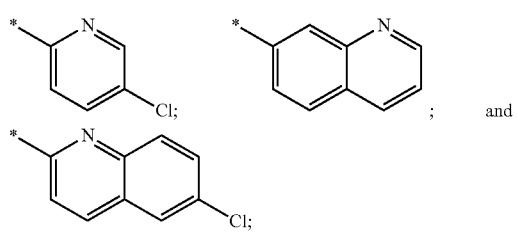

wherein the * represents the attachment point to the remainder of the molecule.

In some embodiments, $(A^1\text{-a})$ or $(A^1\text{-h})$ is selected from the group consisting of:

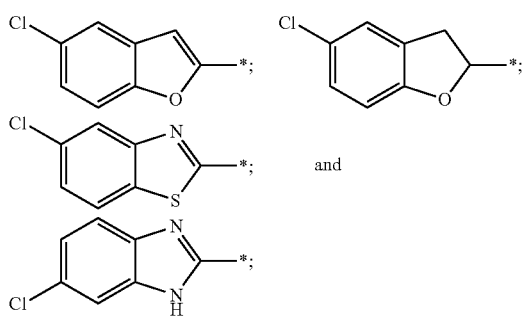

wherein the * represents the attachment point to the remainder of the molecule; and $A^2$ is

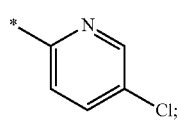

wherein the * represents the attachment point to the remainder of the molecule.

In some embodiments, $(A^1\text{-a})$ or $(A^1\text{-c})$ is selected from the group consisting of:

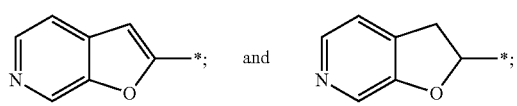

wherein the * represents the attachment point to the remainder of the molecule; and $A^2$ is selected from the group consisting of:

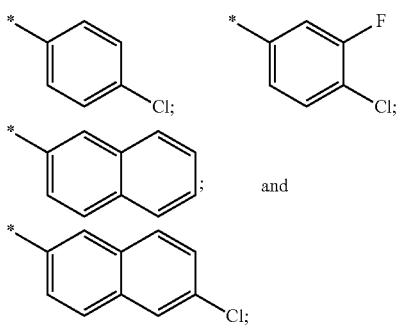

wherein the * represents the attachment point to the remainder of the molecule.

In some embodiments, (A¹-a) or (A¹-c) is selected from the group consisting of:

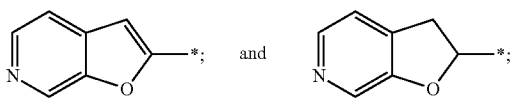

wherein the * represents the attachment point to the remainder of the molecule; and A² is selected from the group consisting of:

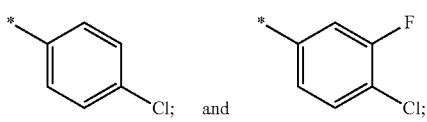 [SMILES: *c1ccc(Cl)cc1 ; "and" ; *c1ccc(Cl)c(F)c1]

wherein the * represents the attachment point to the remainder of the molecule.

In some embodiments, (A¹-a) or (A¹-c) is selected from the group consisting of:

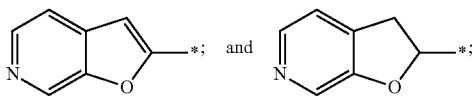 [SMILES: *c1cc2ccncc2o1 ; *C1Cc2ccncc2O1]

wherein the * represents the attachment point to the remainder of the molecule; and A² is selected from the group consisting of:

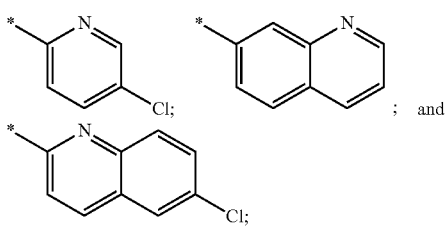

wherein the * represents the attachment point to the remainder of the molecule.

In some embodiments, (A¹-a) or (A¹-c) is selected from the group consisting of:

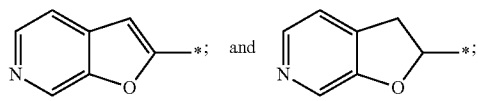 [SMILES: *c1cc2ccncc2o1 ; *C1Cc2ccncc2O1]

wherein the * represents the attachment point to the remainder of the molecule; and A² is

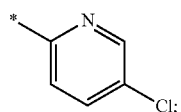

wherein the * represents the attachment point to the remainder of the molecule.

In some embodiments, A¹ is selected from the group consisting of:

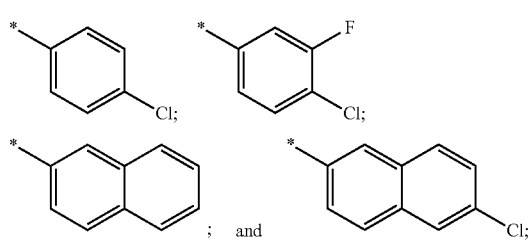

wherein the * represents the attachment point to the remainder of the molecule; and (A²-a) or (A²-b) is selected from the group consisting of:

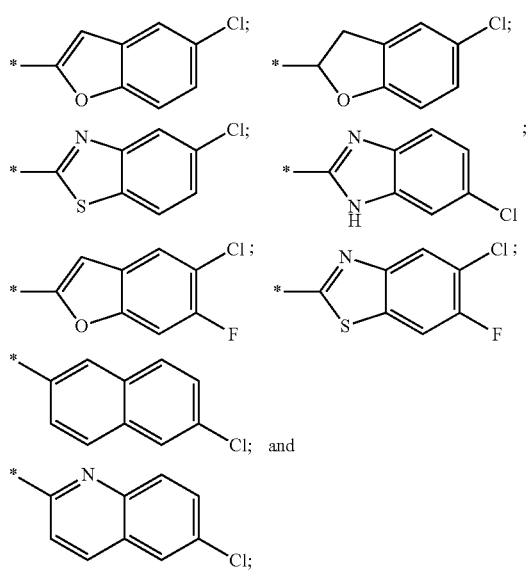

wherein the * represents the attachment point to the remainder of the molecule.

In some embodiments, A¹ is selected from the group consisting of:

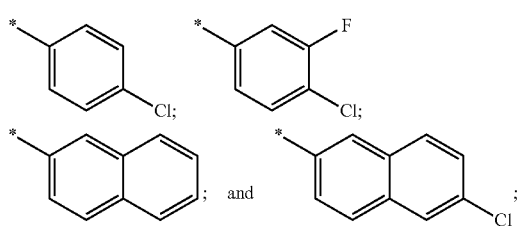

wherein the * represents the attachment point to the remainder of the molecule; and (A¹-a) or (A²-b) is selected from the group consisting of:

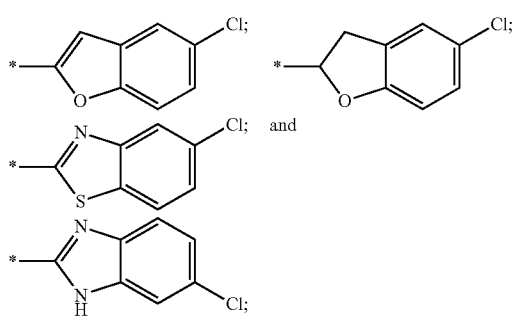

wherein the * represents the attachment point to the remainder of the molecule.

In some embodiments, A¹ is selected from the group consisting of:

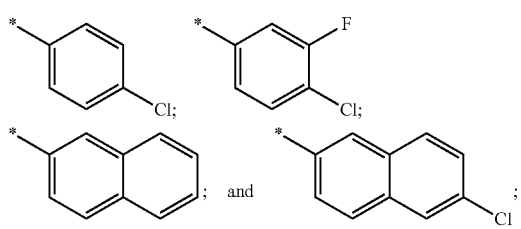

wherein the * represents the attachment point to the remainder of the molecule; and (A²-a) or (A²-c) is selected from the group consisting of:

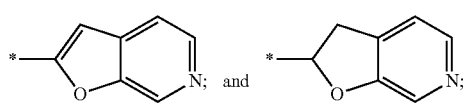 [SMILES: *c1cc2ccncc2o1 ; "and" ; *C1Cc2ccncc2O1]

wherein the * represents the attachment point to the remainder of the molecule.

In some embodiments, A¹ is selected from the group consisting of:

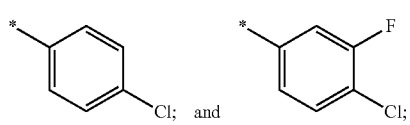 [SMILES: *c1ccc(Cl)cc1 ; "and" ; *c1ccc(Cl)c(F)c1]

wherein the * represents the attachment point to the remainder of the molecule; and (A²-a) or (A²-b) is selected from the group consisting of:

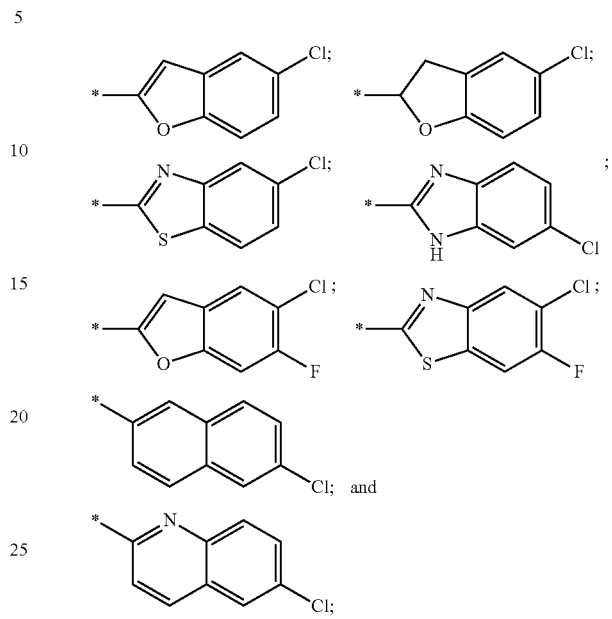

wherein the * represents the attachment point to the remainder of the molecule.

In some embodiments, A¹ is selected from the group consisting of:

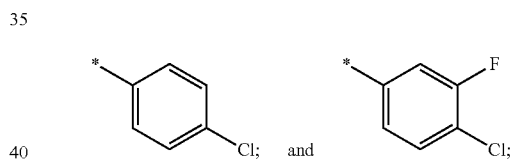

wherein the * represents the attachment point to the remainder of the molecule; and (A²-a) or (A²-b) is selected from the group consisting of:

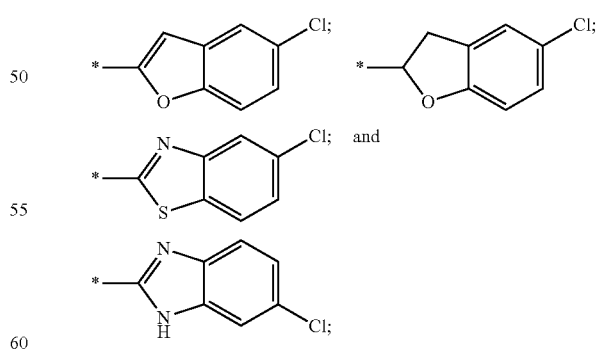

wherein the * represents the attachment point to the remainder of the molecule.

In some embodiments, A¹ is selected from the group consisting of:

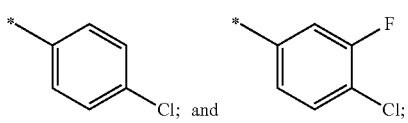

wherein the * represents the attachment point to the remainder of the molecule; and (A²-a) or (A²-c) is selected from the group consisting of:

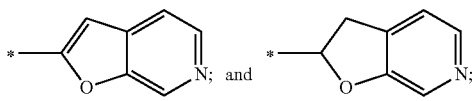

wherein the * represents the attachment point to the remainder of the molecule.

In some embodiments, A¹ is selected from the group consisting of:

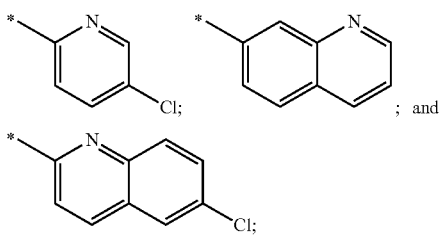

wherein the * represents the attachment point to the remainder of the molecule; and (A²-a) or (A²-b) is selected from the group consisting of:

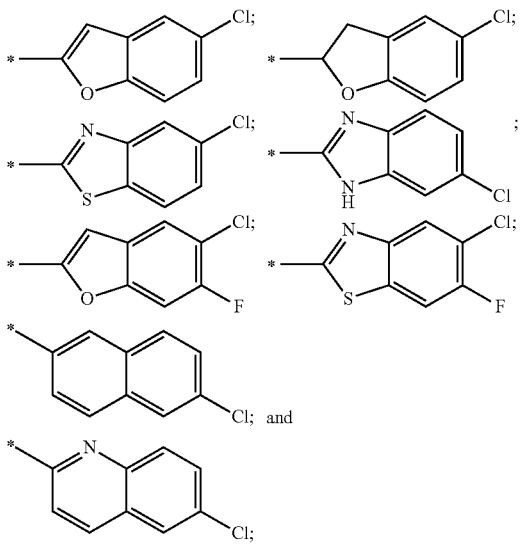

wherein the * represents the attachment point to the remainder of the molecule.

In some embodiments, A¹ is selected from the group consisting of:

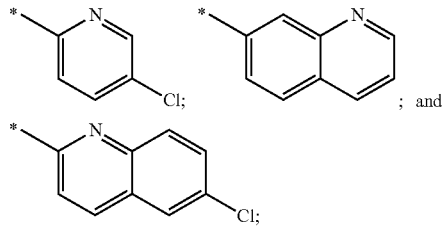

wherein the * represents the attachment point to the remainder of the molecule; and (A²-a) or (A²-b) is selected from the group consisting of:

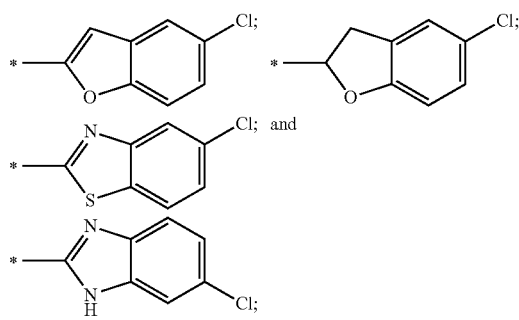

wherein the * represents the attachment point to the remainder of the molecule.

In some embodiments, A¹ is selected from the group consisting of:

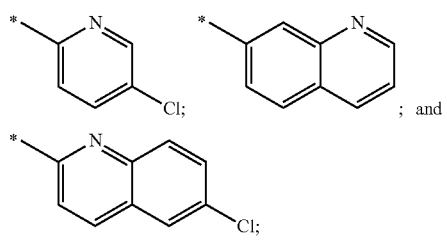

wherein the * represents the attachment point to the remainder of the molecule; and (A²-a) or (A²-c) is selected from the group consisting of:

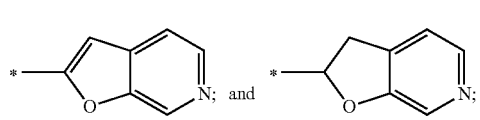

wherein the * represents the attachment point to the remainder of the molecule.

In some embodiments, A¹ is

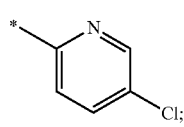

wherein the * represents the attachment point to the remainder of the molecule; and (A²-a) or (A²-b) is selected from the group consisting of:

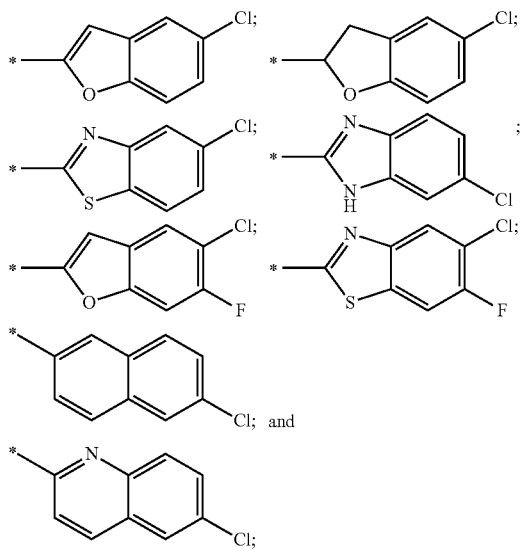

wherein the * represents the attachment point to the remainder of the molecule.

In some embodiments, A¹ is

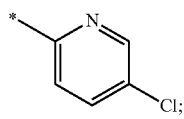

wherein the * represents the attachment point to the remainder of the molecule; and (A²-a) or (A²-b) is selected from the group consisting of:

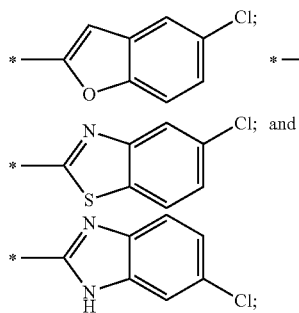

wherein the * represents the attachment point to the remainder of the molecule.

In some embodiments, A¹ is selected from the group consisting of:

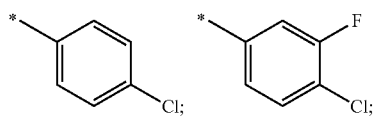

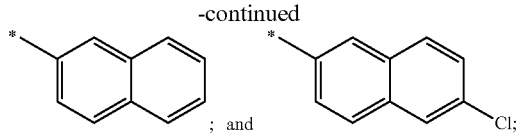

wherein the * represents the attachment point to the remainder of the molecule; and A² is selected from the group consisting of:

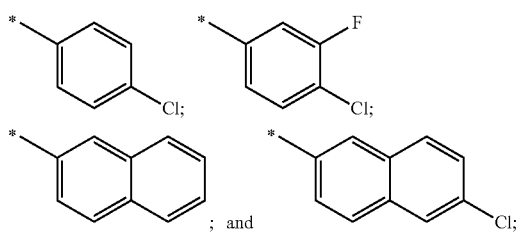

wherein the * represents the attachment point to the remainder of the molecule.

In some embodiments, A¹ is selected from the group consisting of:

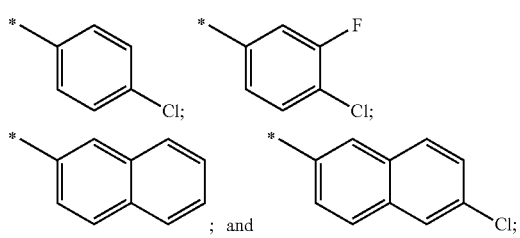

wherein the * represents the attachment point to the remainder of the molecule; and A² is selected from the group consisting of:

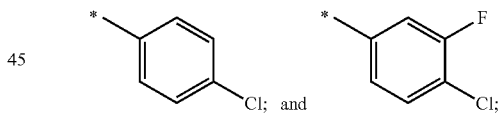

wherein the * represents the attachment point to the remainder of the molecule.

In some embodiments, A¹ is selected from the group consisting of:

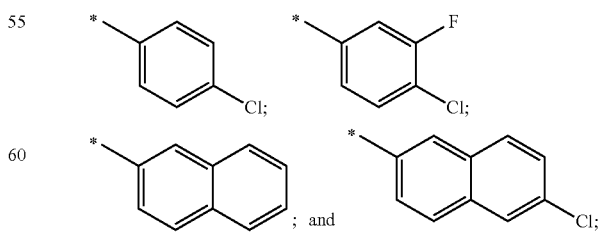

wherein the * represents the attachment point to the remainder of the molecule; and A is selected from the group consisting of:

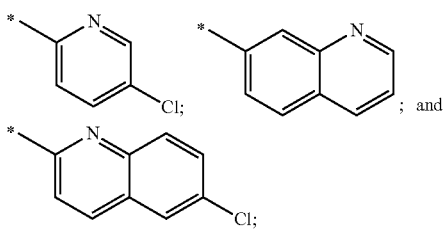

wherein the * represents the attachment point to the remainder of the molecule.

In some embodiments, $A^1$ is selected from the group consisting of:

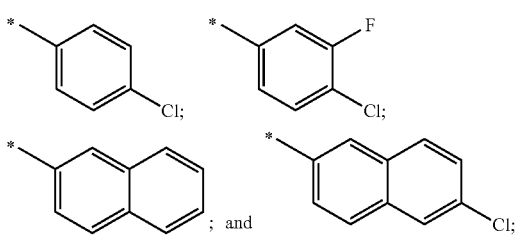

wherein the * represents the attachment point to the remainder of the molecule; and $A^2$ is

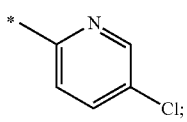

wherein the * represents the attachment point to the remainder of the molecule.

In some embodiments. $A^1$ is selected from the group consisting of:

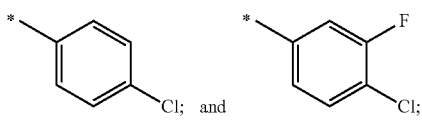

wherein the * represents the attachment point to the remainder of the molecule; and $A^2$ is selected from the group consisting of:

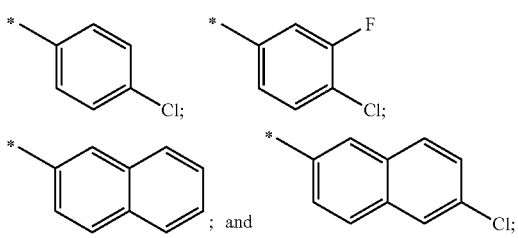

wherein the * represents the attachment point to the remainder of the molecule.

In some embodiments. $A^1$ is selected from the group consisting of:

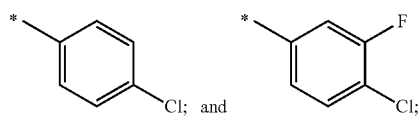

wherein the * represents the attachment point to the remainder of the molecule; and $A^2$ is selected from the group consisting of:

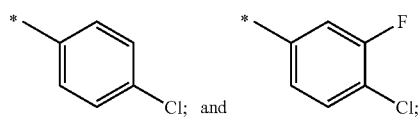

wherein the * represents the attachment point to the remainder of the molecule.

In some embodiments, $A^1$ is selected from the group consisting of:

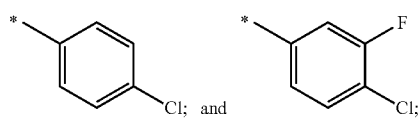

wherein the * represents the attachment point to the remainder of the molecule; $A^2$ is selected from the group consisting of:

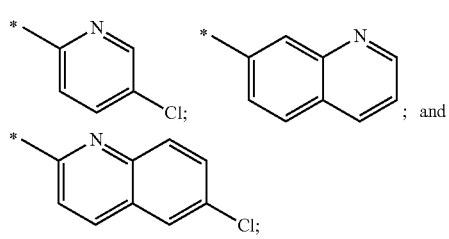

wherein the * represents the attachment point to the remainder of the molecule.

In some embodiments, $A^1$ is selected from the group consisting of:

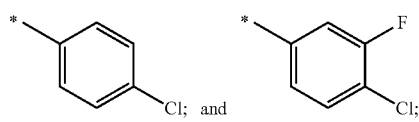

wherein the * represents the attachment point to the remainder of the molecule; and $A^2$ is

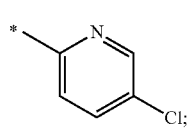

wherein the * represents the attachment point to the remainder of the molecule.

In some embodiments, $A^1$ is selected from the group consisting of:

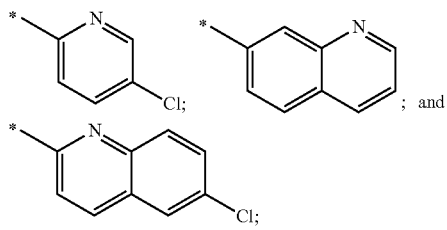

wherein the * represents the attachment point to the remainder of the molecule; and $A^2$ is selected from the group consisting of:

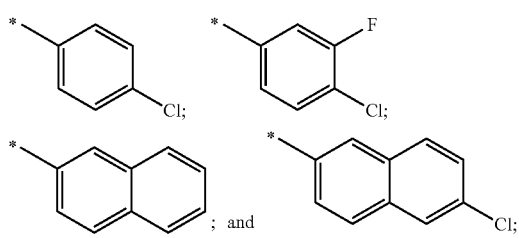

wherein the * represents the attachment point to the remainder of the molecule.

In some embodiments, $A^1$ is selected from the group consisting of:

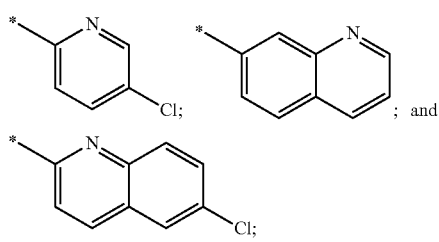

wherein the * represents the attachment point to the remainder of the molecule; and $A^2$ is selected from the group consisting of:

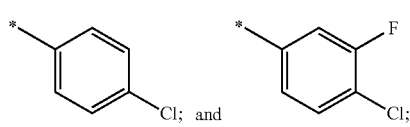

wherein the * represents the attachment point to the remainder of the molecule.

In some embodiments. $A^1$ is selected from the group consisting of:

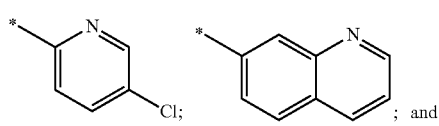

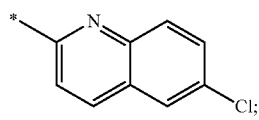

wherein the * represents the attachment point to the remainder of the molecule; $A^2$ is selected from the group consisting of:

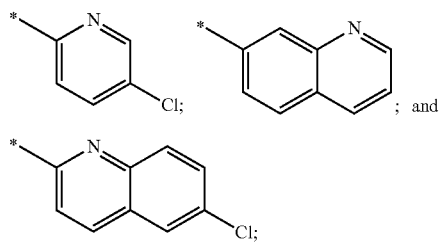

wherein the * represents the attachment point to the remainder of the molecule.

In some embodiments, $A^1$ is selected from the group consisting of:

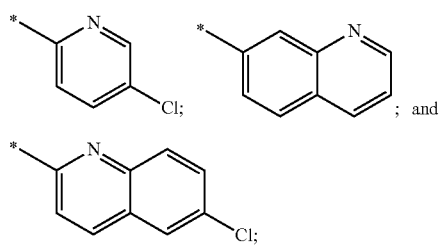

wherein the * represents the attachment point to the remainder of the molecule; and $A^2$ is

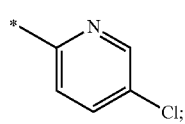

wherein the * represents the attachment point to the remainder of the molecule.

In some embodiments, $A^1$ is

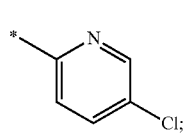

wherein the * represents the attachment point to the remainder of the molecule; and $A^2$ is selected from the group consisting of:

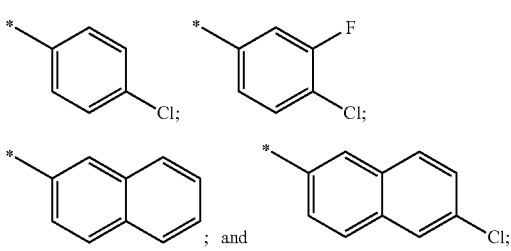
; and wherein the * represents the attachment point to the remainder of the molecule.

In some embodiments, $A^1$ is

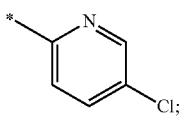

wherein the * represents the attachment point to the remainder of the molecule; and $A^2$ is selected from the group consisting of:

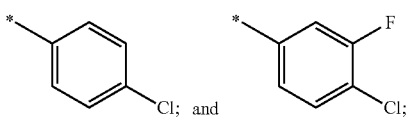

wherein the * represents the attachment point to the remainder of the molecule.

In some embodiments, $A^1$ is

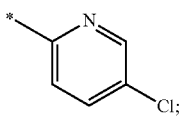

wherein the * represents the attachment point to the remainder of the molecule; and $A^2$ is selected from the group consisting of:

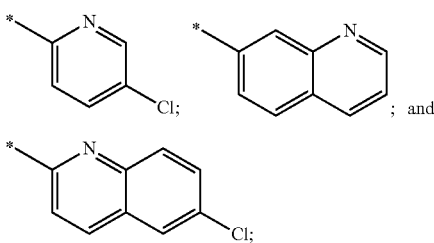

wherein the * represents the attachment point to the remainder of the molecule.

In some embodiments, $A^1$ is

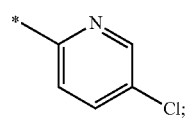

wherein the * represents the attachment point to the remainder of the molecule; and $A^2$ is

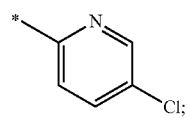

wherein the * represents the attachment point to the remainder of the molecule.

In some embodiments, the compound of formula (I) is a compound of formula (2-4):

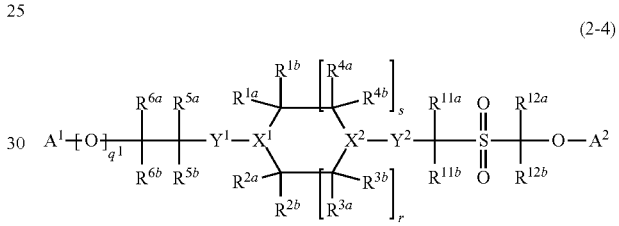

(2-4)

or a pharmaceutically acceptable salt thereof;
wherein:
$A^1$ is selected from the group consisting of:
a substituent of formula ($A^1$-a)

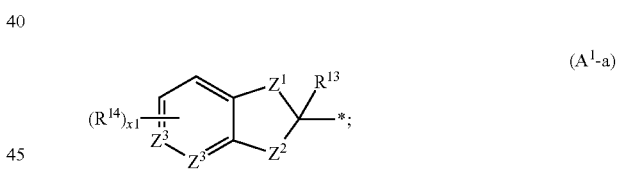

($A^1$-a)

$C_6$-$C_{10}$ aryl optionally substituted with one or more $R^{14}$ substituents; and
5-10 membered heteroaryl optionally substituted with one or more $R^{14}$ substituents;
$A^2$ is $C_6$-$C_{10}$ aryl optionally substituted with one or more $R^{16}$ substituents; or 5-10 membered heteroaryl optionally substituted with one or more $R^{16}$ substituents;
$R^{11a}$ and $R^{11b}$ are both hydrogen;
$R^{12a}$ and $R^{12b}$ are both hydrogen;
and wherein $X^1$, $X^2$, $Y^1$, $R^{Y1}$, $Y^2$, $R^{Y2}$, $q^1$, r, s, $Z^1$, $R^{Z1-1}$, $R^{Z1-2}$, $Z^2$, $R^{Z2-1}$, $R^{Z2-2}$, $Z^3$, x1, $R^{1a}$, $R^{1b}$, $R^{2a}$, $R^{2b}$, $R^{3a}$, $R^{3b}$, $R^{4a}$, $R^{4b}$, $R^{5a}$, $R^{5b}$, $R^{6a}$, $R^{6a-a}$, $R^{6a-b}$, $R^{6a-c}$, $R^{6b}$, $R^{13}$, $R^{14}$, and $R^{16}$ are as defined in compounds of formula (I).

In some embodiments of the compounds of formula (2-4), $X^1$ is CH and $X^2$ is CH. In some embodiments, r is 1 and s is 1.

In some embodiments of the compounds of formula (2-4), $X^1$ is CH, $X^2$ is N and $Y^2$ is a bond. In some embodiments, r is 1 and s is 1. In some embodiments, r is 0 and s is 2.

In some embodiments of the compounds of formula (2-4), $X^1$ is N, $Y^1$ is a bond, and $X^2$ is CH. In some embodiments, r is 1 and s is 1. In some embodiments, r is 0 and s is 2.

In some embodiments of the compounds of formula (2-4), $X^1$ is N, $Y^1$ is a bond, $X^2$ is N and $Y^2$ is a bond. In some embodiments, r is 1 and s is 1. In some embodiments, r is 0 and s is 2.

In some embodiments of the compounds of formula (2-4):
$q^1$ is 1;
$A^1$ is selected $C_6$-$C_{10}$ aryl optionally substituted with one or more $R^{14}$ substituents; or 5-10 membered heteroaryl optionally substituted with one or more $R^{14}$ substituents;
$R^{5a}$ and $R^{5b}$ are taken together to form an oxo (=O) substituent or an imido (=NH) substituent, or alternatively, $R^{5a}$ and $R^{5b}$ are both hydrogen;
$R^{6a}$ is selected from the group consisting of hydrogen, —$OR^{6a-a}$, and —$NR^{6a-b}R^{6a-c}$; and
$R^{6b}$ is hydrogen;
or alternatively, $R^{6a}$ and $R^{6b}$ are taken together to form a —$CH_2$—O—$CH_2$— moiety.

In some embodiments of the compounds of formula (2-4), $R^{5a}$ and $R^{5b}$ are both hydrogen; and $R^{6a}$ and $R^{6b}$ are taken together to form a —$CH_2$—O—$CH_2$— moiety.

In some embodiments of the compounds of formula (2-4), $A^1$ is $C_6$-$C_{10}$ aryl optionally substituted with one or more $R^{14}$ substituents. In some embodiments, $A^1$ is selected from the group consisting of:

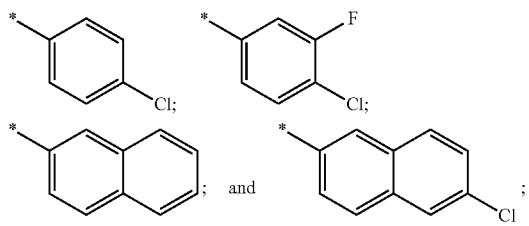

wherein the * represents the attachment point to the remainder of the molecule. In some embodiments, $A^1$ is phenyl optionally substituted with one or more $R^{14}$ substituents. In some embodiments, $A^1$ is selected from the group consisting of:

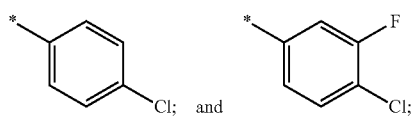

wherein the * represents the attachment point to the remainder of the molecule.

In some embodiments of the compounds of formula (2-4), $A^1$ is 5-10 membered heteroaryl optionally substituted with one or more $R^{14}$ substituents. In some embodiments, $A^1$ is selected from the group consisting of:

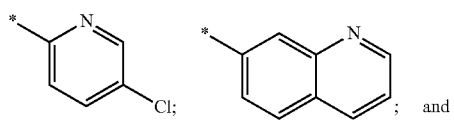

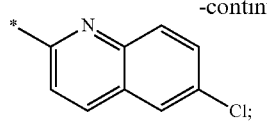

wherein the * represents the attachment point to the remainder of the molecule. In some embodiments, $A^1$ is pyridyl optionally substituted with one or more $R^{14}$ substituents. In some embodiments, $A^1$ is

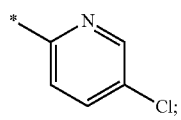

wherein the * represents the attachment point to the remainder of the molecule.

In some embodiments of the compounds of formula (2-4), $A^2$ is $C_6$-$C_{10}$ aryl optionally substituted with one or more $R^{16}$ substituents. In some embodiments, $A^2$ is selected from the group consisting of:

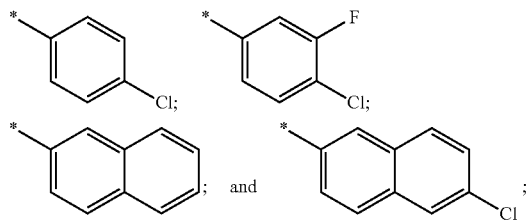

wherein the * represents the attachment point to the remainder of the molecule. In some embodiments, $A^2$ is phenyl optionally substituted with one or more $R^{16}$ substituents. In some embodiments, $A^2$ is selected from the group consisting of:

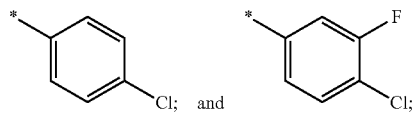

wherein the * represents the attachment point to the remainder of the molecule.

In some embodiments of the compounds of formula (2-4), $A^2$ is 5-10 membered heteroaryl optionally substituted with one or more $R^{16}$ substituents. In some embodiments, $A^2$ is selected from the group consisting of:

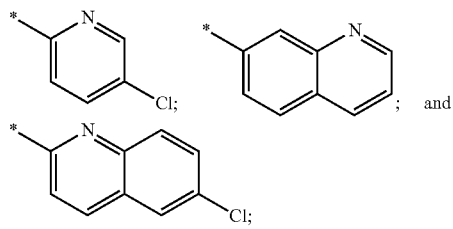

wherein the * represents the attachment point to the remainder of the molecule. In some embodiments, $A^2$ is pyridyl optionally substituted with one or more $R^{16}$ substituents. In some embodiments, $A^2$ is

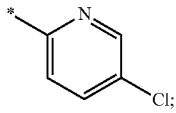

wherein the * represents the attachment point to the remainder of the molecule.

In some embodiments, ($A^1$-a) or ($A^1$-b) is selected from the group consisting of:

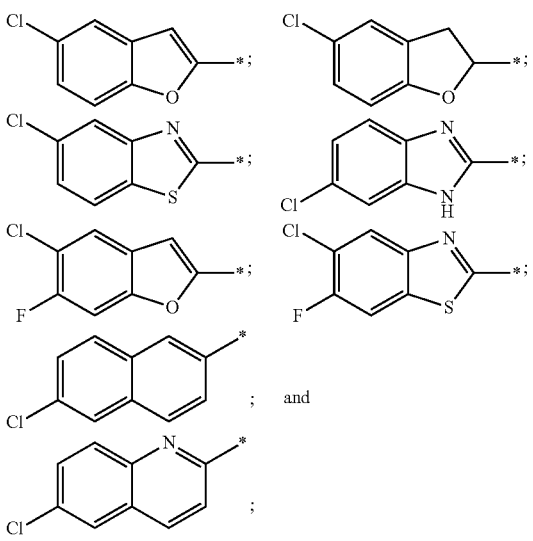

wherein the * represents the attachment point to the remainder of the molecule; and ($A^2$-a) or ($A^2$-b) is selected from the group consisting of:


wherein the * represents the attachment point to the remainder of the molecule.

In some embodiments, ($A^1$-a) or ($A^1$-b) is selected from the group consisting of:

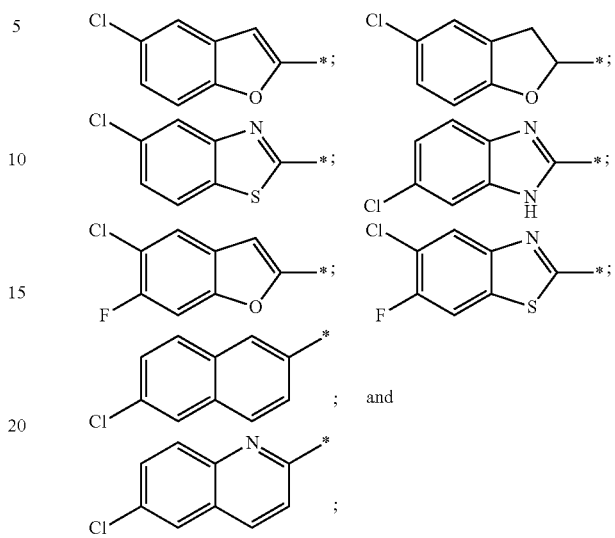

wherein the * represents the attachment point to the remainder of the molecule; and ($A^2$-a) or ($A^2$-b) is selected from the group consisting of:

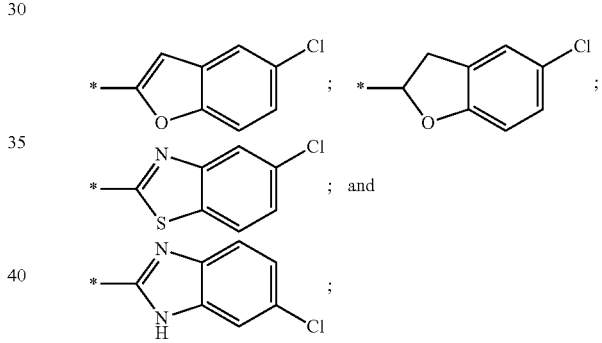

wherein the * represents the attachment point to the remainder of the molecule.

In some embodiments, ($A^1$-a) or ($A^1$-b) is selected from the group consisting of:

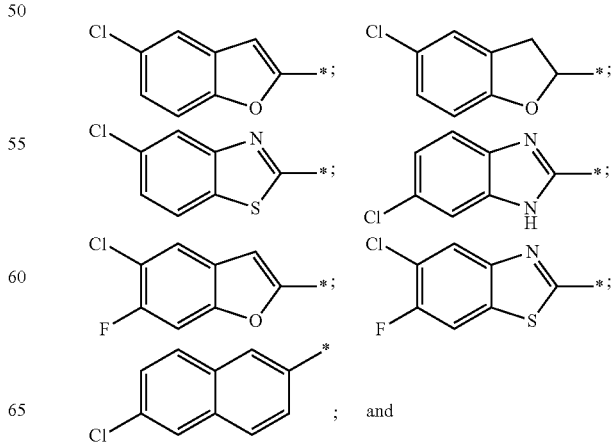

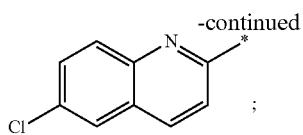

wherein the * represents the attachment point to the remainder of the molecule; and (A²-a) or (A²-c) is selected from the group consisting of:

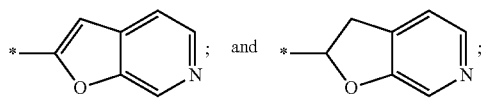 [SMILES: *c1cc2ccncc2o1 ; *C1Cc2ccncc2O1]

wherein the * represents the attachment point to the remainder of the molecule.

In some embodiments, (A¹-a) or (A¹-b) is selected from the group consisting of:

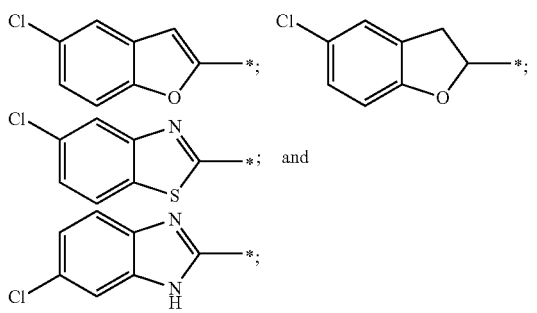

wherein the * represents the attachment point to the remainder of the molecule; and (A¹-a) or (A²-b) is selected from the group consisting of:

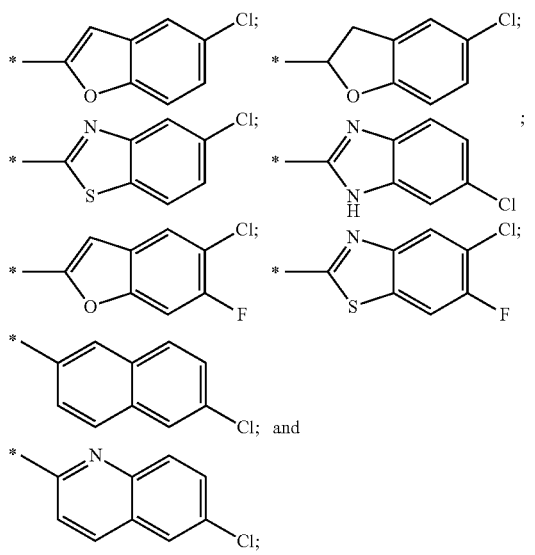

wherein the * represents the attachment point to the remainder of the molecule.

In some embodiments, (A¹-a) or (A¹-b) is selected from the group consisting of:

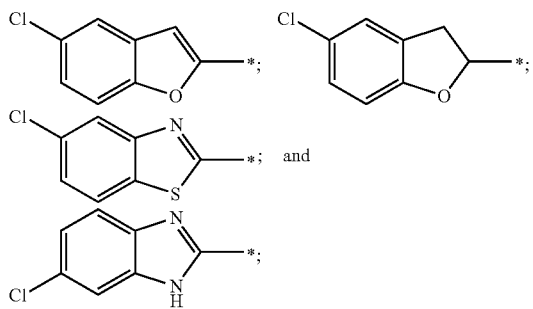

wherein the * represents the attachment point to the remainder of the molecule; and (A²-a) or (A²-b) is selected from the group consisting of:

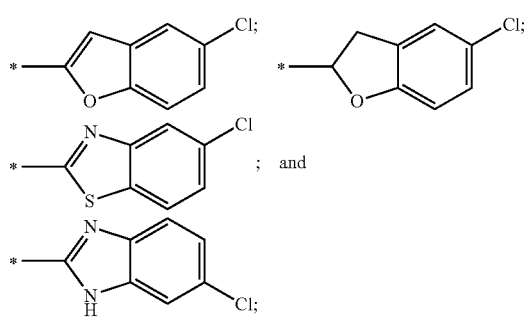

wherein the * represents the attachment point to the remainder of the molecule.

In some embodiments, (A¹-a) or (A¹-b) is selected from the group consisting of:

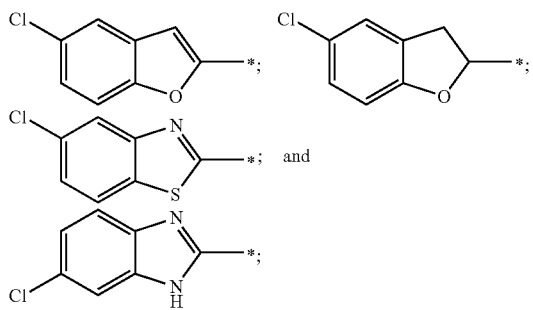

wherein the * represents the attachment point to the remainder of the molecule; and (A²-a) or (A²-c) is selected from the group consisting of:

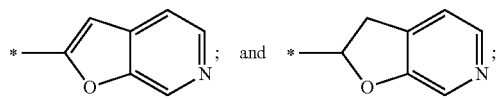

wherein the * represents the attachment point to the remainder of the molecule.

In some embodiments, (A¹-a) or (A¹-c) is selected from the group consisting of:

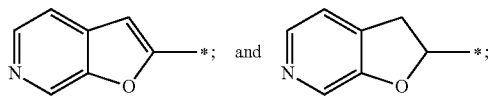

wherein the * represents the attachment point to the remainder of the molecule; and (A²-a) or (A²-b) is selected from the group consisting of:

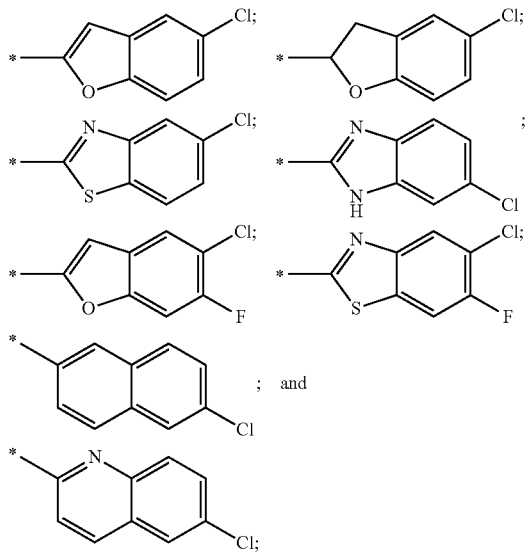

wherein the * represents the attachment point to the remainder of the molecule.

In some embodiments, (A¹-a) or (A¹-c) is selected from the group consisting of:

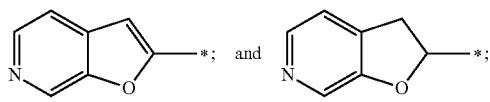

wherein the * represents the attachment point to the remainder of the molecule; and (A²-a) or (A²-b) is selected from the group consisting of:

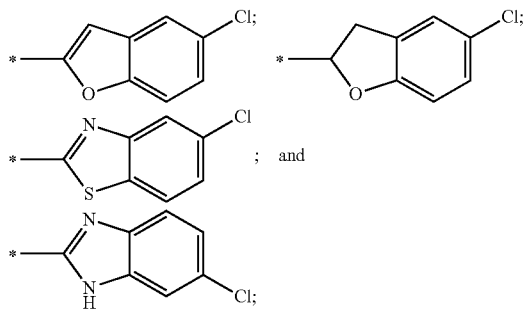

wherein the * represents the attachment point to the remainder of the molecule.

In some embodiments, (A¹-a) or (A¹-c) is selected from the group consisting of:

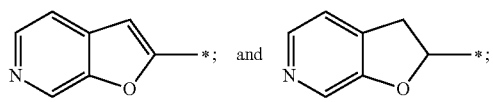

wherein the * represents the attachment point to the remainder of the molecule; and (A²-a) or (A²-c) is selected from the group consisting of:

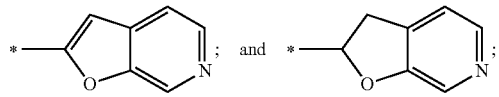

wherein the * represents the attachment point to the remainder of the molecule.

In some embodiments, (A¹-a) or (A¹-b) is selected from the group consisting of:

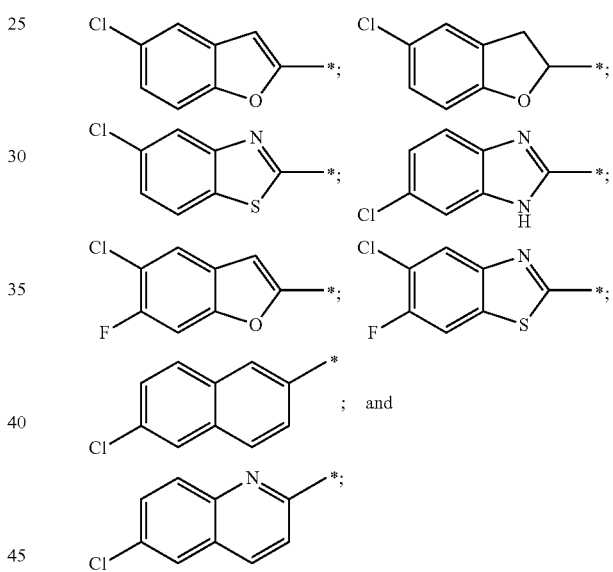

wherein the * represents the attachment point to the remainder of the molecule; and A² is selected from the group consisting of:

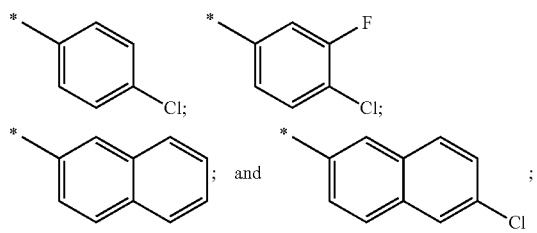

wherein the * represents the attachment point to the remainder of the molecule.

In some embodiments, (A¹-a) or (A¹-b) is selected from the group consisting of:

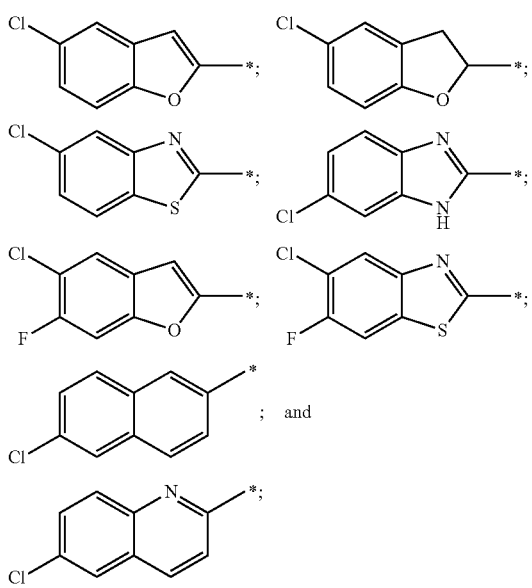

wherein the * represents the attachment point to the remainder of the molecule; and A² is selected from the group consisting of:

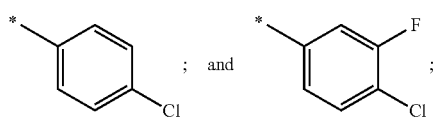

wherein the * represents the attachment point to the remainder of the molecule.

In some embodiments, (A¹-a) or (A¹-b) is selected from the group consisting of:

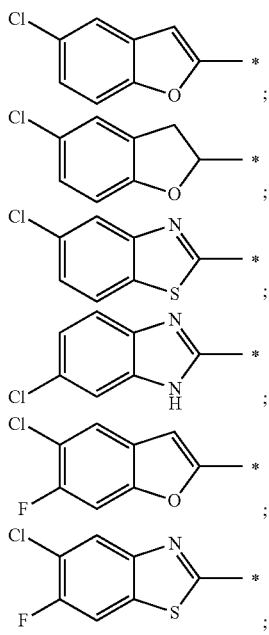

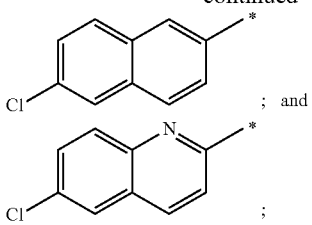

wherein the * represents the attachment point to the remainder of the molecule; and A² is selected from the group consisting of:

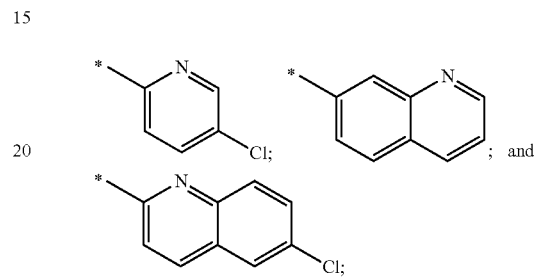

wherein the * represents the attachment point to the remainder of the molecule.

In some embodiments, (A¹-a) or (A¹-b) is selected from the group consisting of:

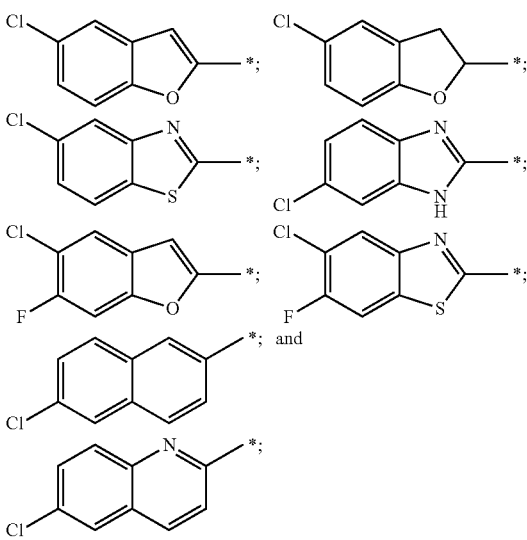

wherein the * represents the attachment point to the remainder of the molecule; and A² is

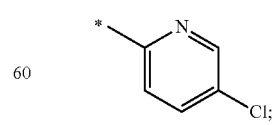

wherein the * represents the attachment point to the remainder of the molecule.

In some embodiments. (A¹-a) or (A¹-b) is selected from the group consisting of:

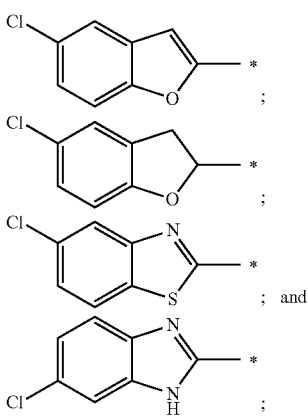

wherein the * represents the attachment point to the remainder of the molecule; and A² is selected from the group consisting of:

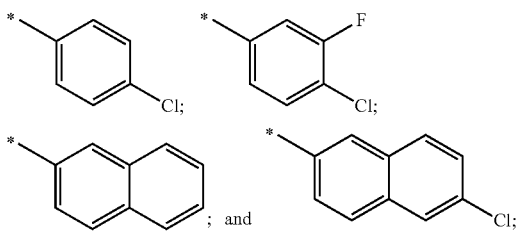

wherein the * represents the attachment point to the remainder of the molecule.

In some embodiments, (A¹-a) or (A¹-b) is selected from the group consisting of:

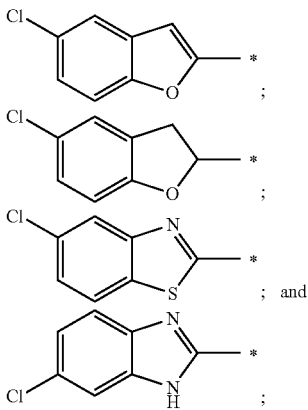

wherein the * represents the attachment point to the remainder of the molecule; and A² is selected from the group consisting of:

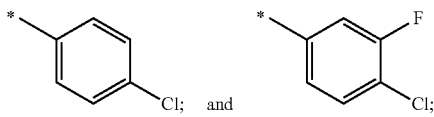

wherein the * represents the attachment point to the remainder of the molecule.

In some embodiments, (A¹-a) or (A¹-b) is selected from the group consisting of:

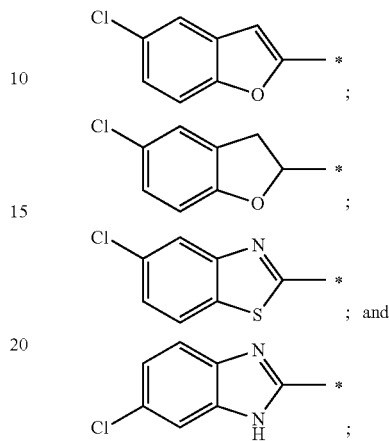

wherein the * represents the attachment point to the remainder of the molecule; and A² is selected from the group consisting of:

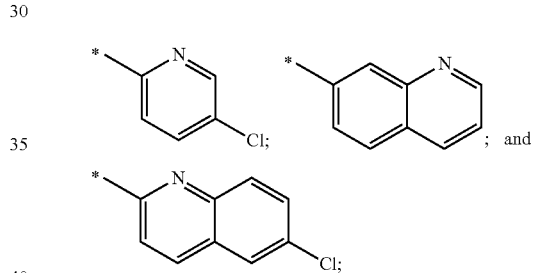

wherein the * represents the attachment point to the remainder of the molecule.

In some embodiments, (A¹-a) or (A¹-b) is selected from the group consisting of:

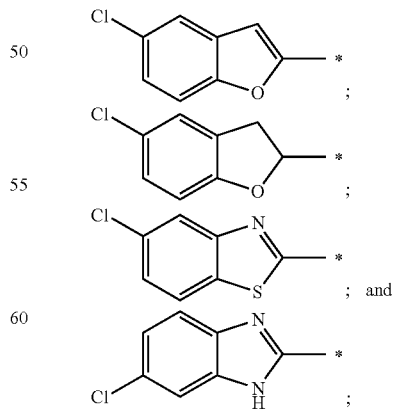

wherein the * represents the attachment point to the remainder of the molecule; and A² is

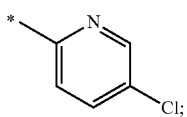

wherein the * represents the attachment point to the remainder of the molecule.

In some embodiments, (A¹-a) or (A¹-c) is selected from the group consisting of:

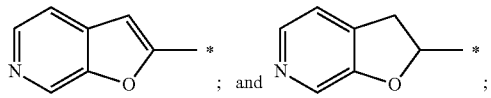

wherein the * represents the attachment point to the remainder of the molecule; and A² is selected from the group consisting of:

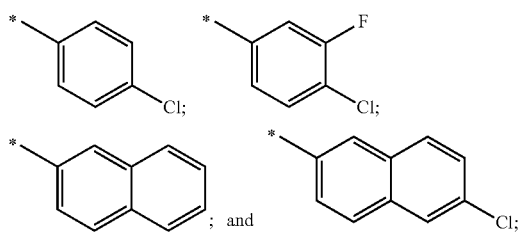

wherein the * represents the attachment point to the remainder of the molecule.

In some embodiments, (A¹-a) or (A¹-c) is selected from the group consisting of:

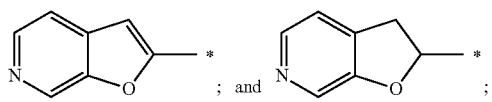

wherein the * represents the attachment point to the remainder of the molecule; and A² is selected from the group consisting of:

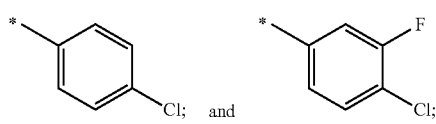

wherein the * represents the attachment point to the remainder of the molecule.

In some embodiments, (A¹-a) or (A¹-c) is selected from the group consisting of:

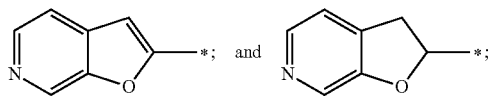

wherein the * represents the attachment point to the remainder of the molecule; and A² is selected from the group consisting of:

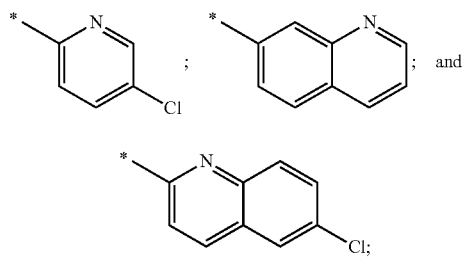

wherein the * represents the attachment point to the remainder of the molecule.

In some embodiments, (A¹-a) or (A¹-c) is selected from the group consisting of:

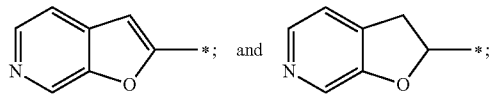

wherein the * represents the attachment point to the remainder of the molecule; and A² is

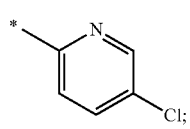

wherein the * represents the attachment point to the remainder of the molecule.

In some embodiments. A¹ is selected from the group consisting of:

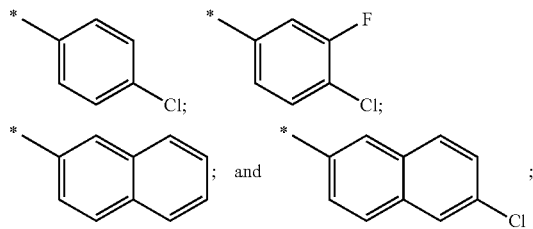

wherein the * represents the attachment point to the remainder of the molecule; and (A²-a) or (A²-b) is selected from the group consisting of:

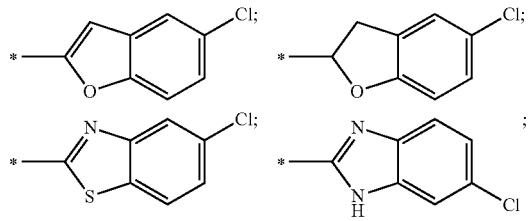

-continued

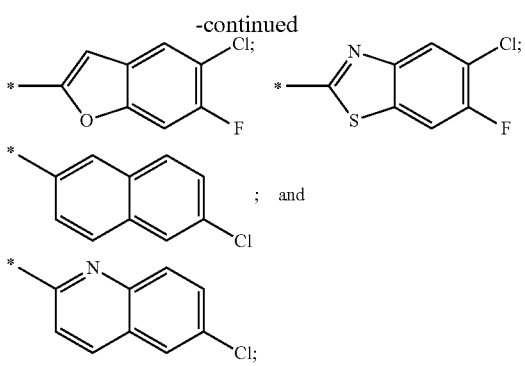

wherein the * represents the attachment point to the remainder of the molecule.

In some embodiments, $A^1$ is selected from the group consisting of:

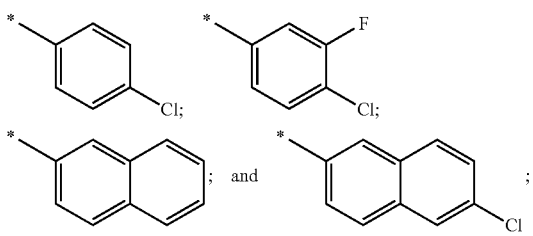

wherein the * represents the attachment point to the remainder of the molecule; and ($A^2$-a) or ($A^2$-b) is selected from the group consisting of:

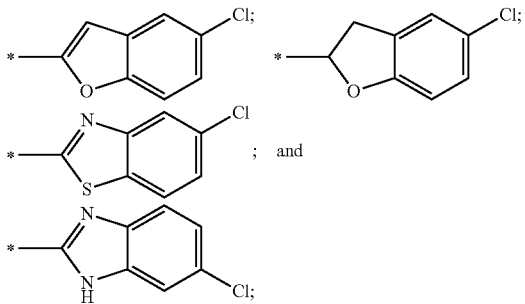

wherein the * represents the attachment point to the remainder of the molecule.

In some embodiments, $A^1$ is selected from the group consisting of:

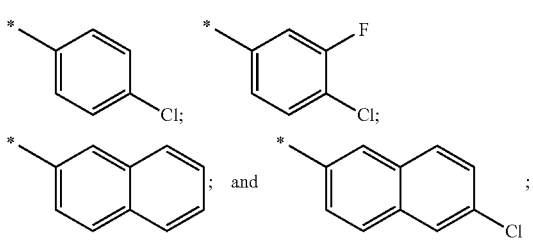

wherein the * represents the attachment point to the remainder of the molecule; and ($A^1$-a) or ($A^2$-c) is selected from the group consisting of:

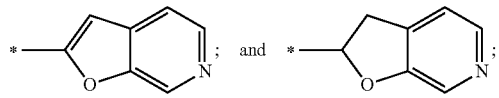

wherein the * represents the attachment point to the remainder of the molecule.

In some embodiments. $A^1$ is selected from the group consisting of:

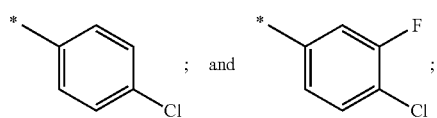

wherein the * represents the attachment point to the remainder of the molecule; and ($A^2$-a) or ($A^2$-b) is selected from the group consisting of:

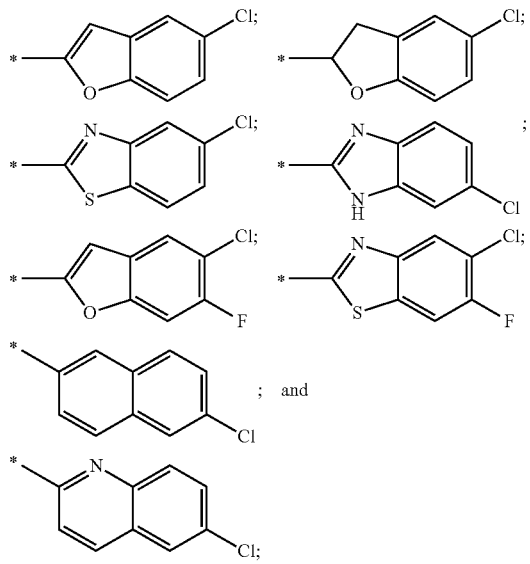

wherein the * represents the attachment point to the remainder of the molecule.

In some embodiments, $A^1$ is selected from the group consisting of:

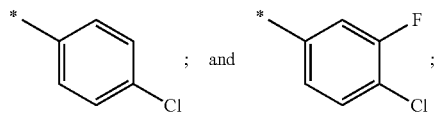

wherein the * represents the attachment point to the remainder of the molecule; and ($A^2$-a) or ($A^2$-b) is selected from the group consisting of:

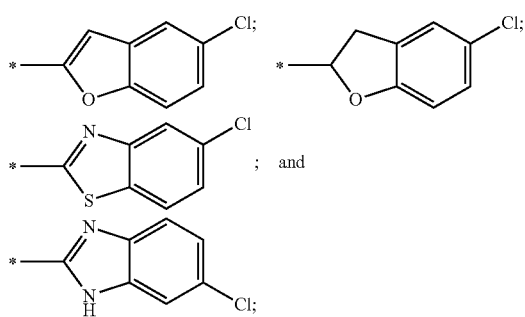

wherein the * represents the attachment point to the remainder of the molecule.

In some embodiments, $A^1$ is selected from the group consisting of:

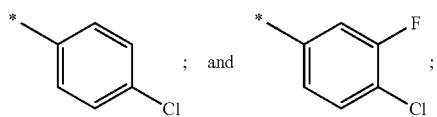

wherein the * represents the attachment point to the remainder of the molecule; and ($A^2$-a) or ($A^2$-c) is selected from the group consisting of:

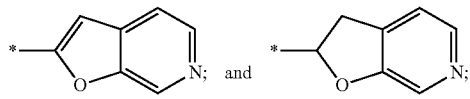 [SMILES: *c1cc2ccncc2o1 ; *C1Cc2ccncc2O1]

wherein the * represents the attachment point to the remainder of the molecule.

In some embodiments, $A^1$ is selected from the group consisting of:

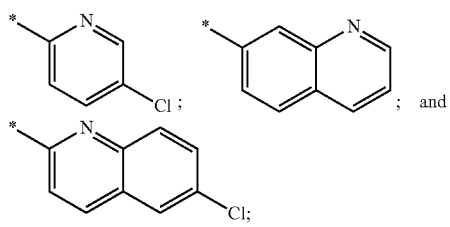

wherein the * represents the attachment point to the remainder of the molecule; and ($A^2$-a) or ($A^2$-b) is selected from the group consisting of:

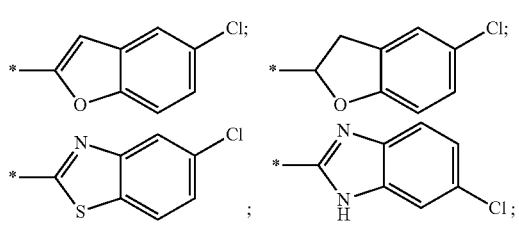

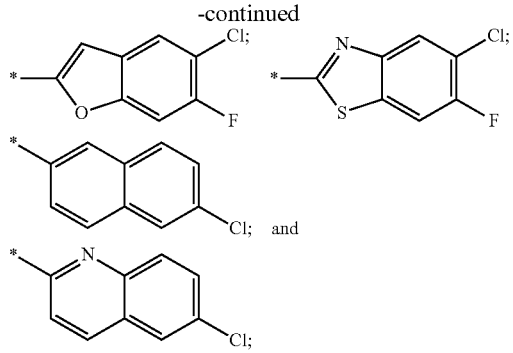

wherein the * represents the attachment point to the remainder of the molecule.

In some embodiments, $A^1$ is selected from the group consisting of:

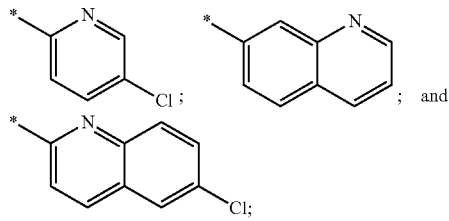

wherein the * represents the attachment point to the remainder of the molecule; and ($A^2$-a) or ($A^2$-b) is selected from the group consisting of:

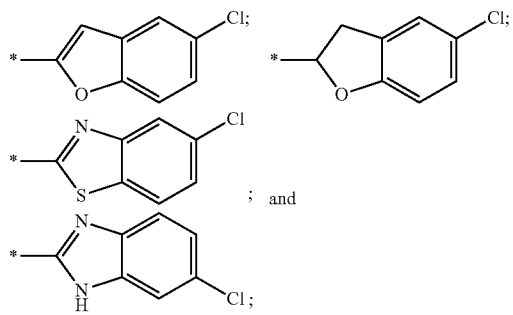

wherein the * represents the attachment point to the remainder of the molecule.

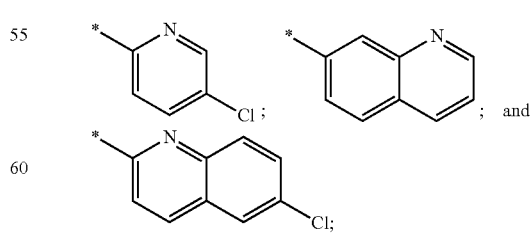

wherein the * represents the attachment point to the remainder of the molecule; and ($A^2$-a) or ($A^2$-c) is selected from the group consisting of:

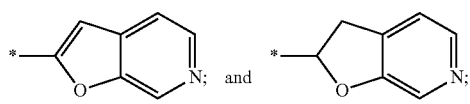 [SMILES: *c1cc2ccncc2o1 ; *C1Cc2ccncc2O1]

wherein the * represents the attachment point to the remainder of the molecule.

In some embodiments, $A^1$ is

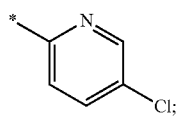

wherein the * represents the attachment point to the remainder of the molecule; and ($A^2$-a) or ($A^2$-b) is selected from the group consisting of:

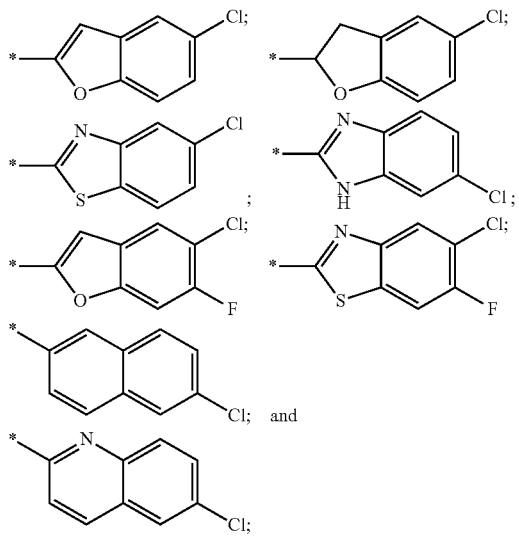

wherein the * represents the attachment point to the remainder of the molecule.

In some embodiments, $A^1$ is

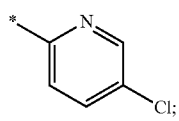

wherein the * represents the attachment point to the remainder of the molecule; and ($A^2$-a) or ($A^2$-b) is selected from the group consisting of:

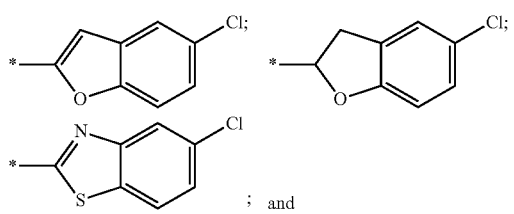

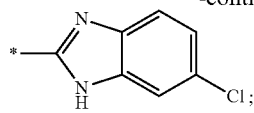

wherein the * represents the attachment point to the remainder of the molecule.

In some embodiments, $A^1$ is selected from the group consisting of:

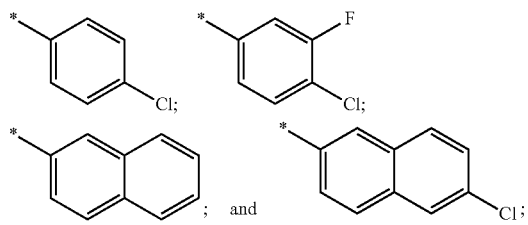

wherein the * represents the attachment point to the remainder of the molecule; and $A^2$ is selected from the group consisting of:

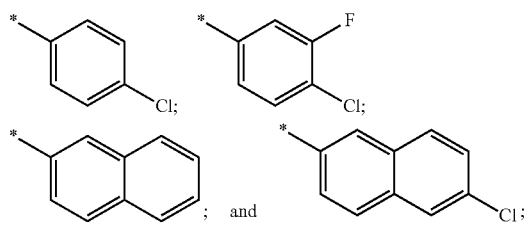

wherein the * represents the attachment point to the remainder of the molecule.

In some embodiments, $A^1$ is selected from the group consisting of:

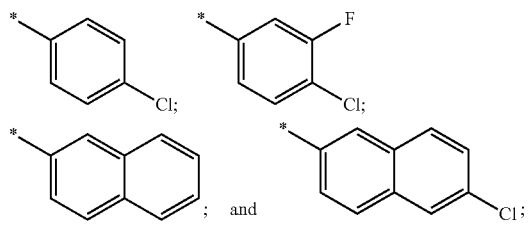

wherein the * represents the attachment point to the remainder of the molecule; and $A^2$ is selected from the group consisting of:

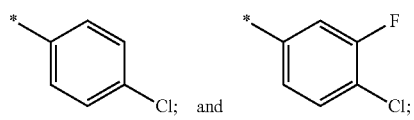

wherein the * represents the attachment point to the remainder of the molecule.

In some embodiments, $A^1$ is selected from the group consisting of:

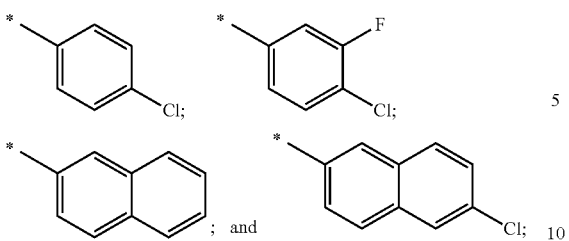

wherein the * represents the attachment point to the remainder of the molecule; and A is selected from the group consisting of:

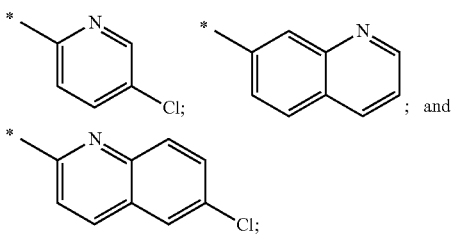

wherein the * represents the attachment point to the remainder of the molecule.

In some embodiments, $A^1$ is selected from the group consisting of:

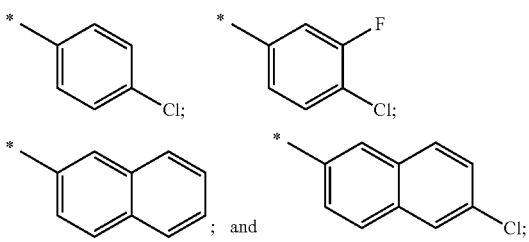

wherein the * represents the attachment point to the remainder of the molecule; and $A^2$ is

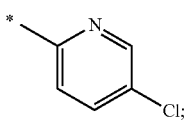

wherein the * represents the attachment point to the remainder of the molecule.

In some embodiments, $A^1$ is selected from the group consisting of:

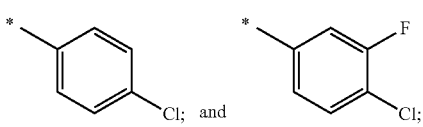

wherein the * represents the attachment point to the remainder of the molecule; and $A^2$ is selected from the group consisting of:

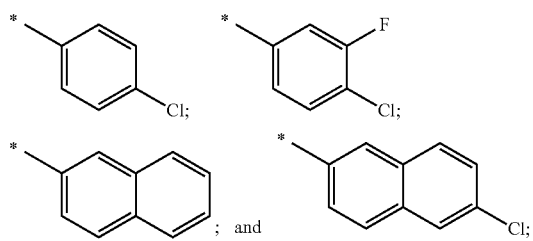

wherein the * represents the attachment point to the remainder of the molecule.

In some embodiments, $A^1$ is selected from the group consisting of:

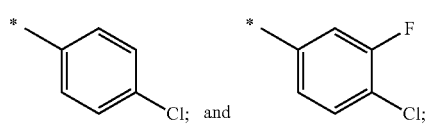

wherein the * represents the attachment point to the remainder of the molecule; and $A^2$ is selected from the group consisting of:

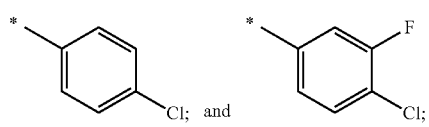

wherein the * represents the attachment point to the remainder of the molecule.

In some embodiments, $A^1$ is selected from the group consisting of:

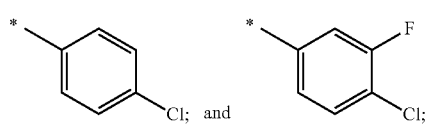

wherein the * represents the attachment point to the remainder of the molecule; $A^2$ is selected from the group consisting of:

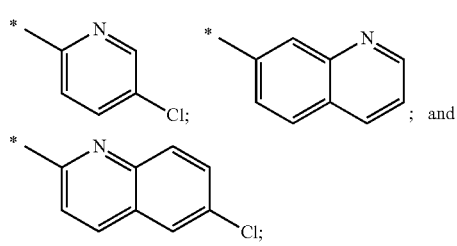

wherein the * represents the attachment point to the remainder of the molecule.

In some embodiments, $A^1$ is selected from the group consisting of:

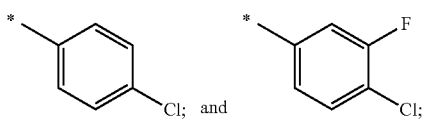

wherein the * represents the attachment point to the remainder of the molecule; and $A^2$ is

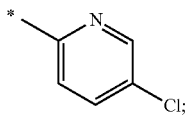

wherein the * represents the attachment point to the remainder of the molecule.

In some embodiments, $A^1$ is selected from the group consisting of:

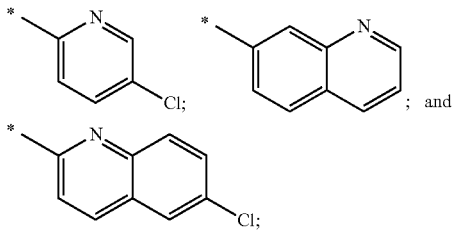

wherein the * represents the attachment point to the remainder of the molecule; and $A^2$ is selected from the group consisting of:

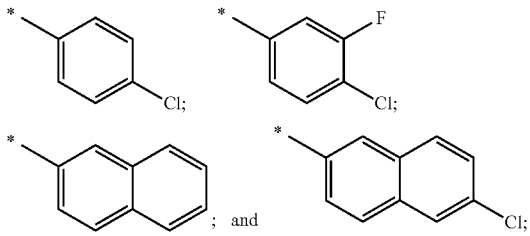

wherein the * represents the attachment point to the remainder of the molecule.

In some embodiments, $A^1$ is selected from the group consisting of:

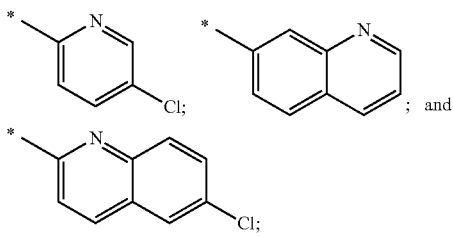

wherein the * represents the attachment point to the remainder of the molecule; and $A^2$ is selected from the group consisting of:

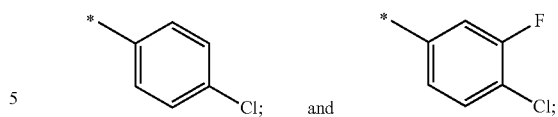

wherein the * represents the attachment point to the remainder of the molecule.

In some embodiments, $A^1$ is selected from the group consisting of:

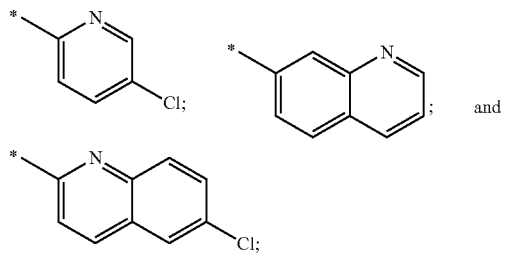

wherein the * represents the attachment point to the remainder of the molecule; $A^2$ is selected from the group consisting of:

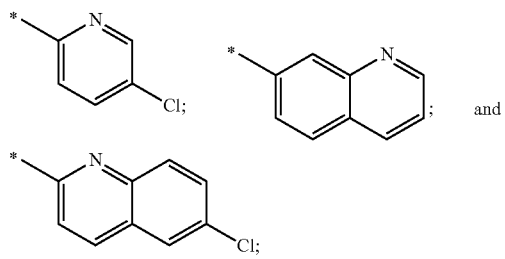

wherein the * represents the attachment point to the remainder of the molecule.

In some embodiments, $A^1$ is selected from the group consisting of:

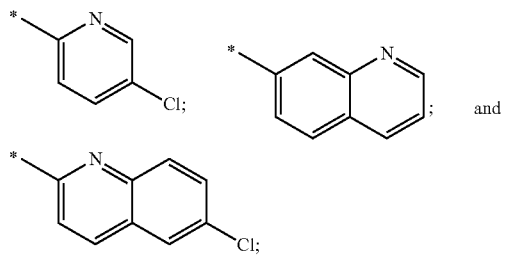

wherein the * represents the attachment point to the remainder of the molecule; and $A^2$ is

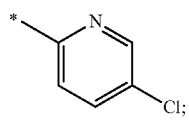

wherein the * represents the attachment point to the remainder of the molecule.

In some embodiments, $A^1$ is

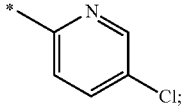

wherein the * represents the attachment point to the remainder of the molecule; and $A^2$ is selected from the group consisting of:

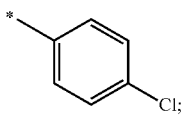 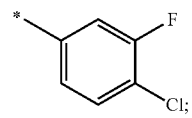

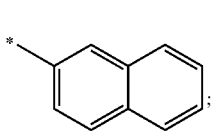 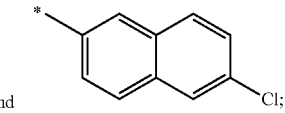

wherein the * represents the attachment point to the remainder of the molecule.

In some embodiments, $A^1$ is

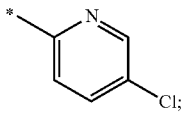

wherein the * represents the attachment point to the remainder of the molecule; and $A^2$ is selected from the group consisting of:

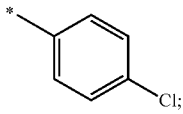 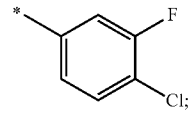

wherein the * represents the attachment point to the remainder of the molecule.

In some embodiments, $A^1$ is

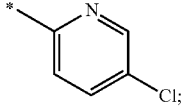

wherein the * represents the attachment point to the remainder of the molecule; and $A^2$ is selected from the group consisting of:

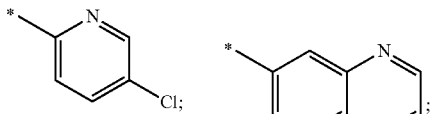

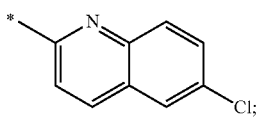

wherein the * represents the attachment point to the remainder of the molecule.

In some embodiments, $A^1$ is

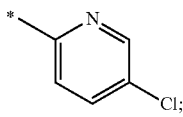

wherein the * represents the attachment point to the remainder of the molecule; and $A^2$ is

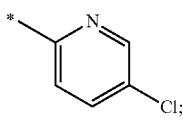

wherein the * represents the attachment point to the remainder of the molecule.

In some embodiments, the compound of formula (I) is a compound of formula (3-3):

(3-3)

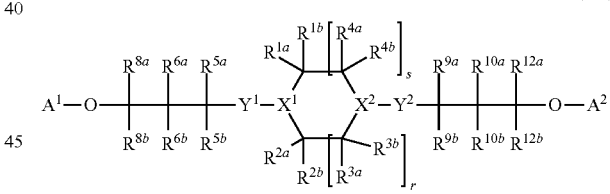

or a pharmaceutically acceptable salt thereof;
wherein:
$A^1$ is $C_6$-$C_{10}$ aryl optionally substituted with one or more $R^{14}$ substituents; or 5-10 membered heteroaryl optionally substituted with one or more $R^{14}$ substituents;
$A^2$ is $C_6$-$C_{10}$ aryl optionally substituted with one or more $R^{16}$ substituents; or 5-10 membered heteroaryl optionally substituted with one or more $R^{16}$ substituents;
and wherein $X^1$, $X^2$, $Y^1$, $R^{Y1}$, $Y^2$, $R^{Y2}$, r, s, $R^{1a}$, $R^{1b}$, $R^{2a}$, $R^{2b}$, $R^{3a}$, $R^{3b}$, $R^{4a}$, $R^{4b}$, $R^{5a}$, $R^{5b}$, $R^{6a}$, $R^{6a\text{-}a}$, $R^{6a\text{-}b}$, $R^{6a\text{-}c}$, $R^{6b}$, $R^{9a}$, $R^{9b}$, $R^{10a}$, $R^{10a\text{-}a}$v $R^{10a\text{-}b}$, $R^{10a\text{-}c}$, $R^{10b}$, $R^{12a}$, $R^{12b}$, $R^{13}$, $R^{14}$, and $R^{16}$ are as defined in compounds of formula (I).

In some embodiments of the compounds of formula (3-3), $X^1$ is CH and $X^2$ is CH. In some embodiments, r is 1 and s is 1.

In some embodiments of the compounds of formula (3-3), $X^1$ is CH, $X^2$ is N and $Y^2$ is a bond. In some embodiments, r is 1 and s is 1. In some embodiments, r is 0 and s is 2.

In some embodiments of the compounds of formula (3-3), $X^1$ is N, $Y^1$ is a bond, and $X^2$ is CH. In some embodiments, r is 1 and s is 1. In some embodiments, r is 0 and s is 2.

In some embodiments of the compounds of formula (3-3), $X^1$ is N, $Y^1$ is a bond, $X^2$ is N and $Y^2$ is a bond. In some embodiments, r is 1 and s is 1. In some embodiments, r is 0 and s is 2.

In some embodiments of the compounds of formula (3-3):
$R^{5a}$ and $R^{5b}$ are taken together to form an oxo (=O) substituent or an imido (=NH) substituent, or alternatively, $R^{5a}$ and $R^{5b}$ are both hydrogen;
$R^{6a}$ is selected from the group consisting of hydrogen, —$OR^{6a-a}$, and —$NR^{6a-b}R^{6a-c}$;
$R^{10b}$ is hydrogen; and
$R^{12a}$ and $R^{12b}$ are both hydrogen.

In some embodiments of the compounds of formula (3-3), $R^{9a}$ and $R^{9b}$ are taken together to form an oxo (=O) substituent. In some embodiments, $R^{10a}$ is hydrogen. In some embodiments, $R^{10a}$ is —$OR^{10a-a}$. In some embodiments, $R^{10a}$ is —$NR^{10a-b}R^{10a-c}$.

In some embodiments of the compounds of formula (3-3), $R^{9a}$ and $R^{9b}$ are taken together to form an imido (=NH) substituent. In some embodiments, $R^{10a}$ is hydrogen. In some embodiments, $R^{10a}$ is —$OR^{10a-a}$. In some embodiments, $R^{10a}$ is —$NR^{10a-b}R^{10a-c}$.

In some embodiments of the compounds of formula (3-3), $R^{9a}$ and $R^{9b}$ are both hydrogen. In some embodiments, $R^{10a}$ is hydrogen. In some embodiments, $R^{10a}$ is —$OR^{10a-a}$. In some embodiments, $R^{10a}$ is —$NR^{10a-b}R^{10a-c}$.

In some embodiments of the compounds of formula (3-3), $A^1$ is $C_6$-$C_{10}$ aryl optionally substituted with one or more $R^{14}$ substituents. In some embodiments, $A^1$ is selected from the group consisting of:

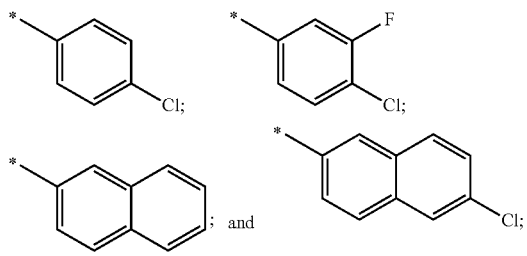

wherein the * represents the attachment point to the remainder of the molecule. In some embodiments, $A^1$ is phenyl optionally substituted with one or more $R^{14}$ substituents. In some embodiments, $A^1$ is selected from the group consisting of:

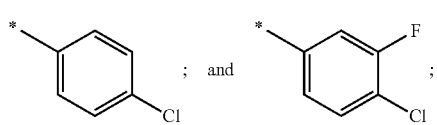

wherein the * represents the attachment point to the remainder of the molecule.

In some embodiments of the compounds of formula (3-3), $A^1$ is 5-10 membered heteroaryl optionally substituted with one or more $R^{14}$ substituents. In some embodiments, $A^1$ is selected from the group consisting of:

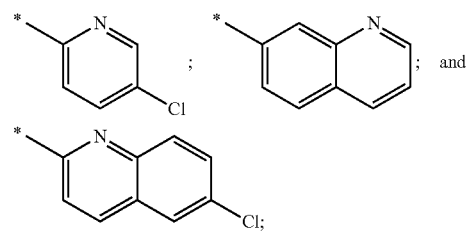

wherein the * represents the attachment point to the remainder of the molecule. In some embodiments, $A^1$ is pyridyl optionally substituted with one or more $R^{14}$ substituents. In some embodiments, $A^1$ is

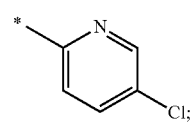

wherein the * represents the attachment point to the remainder of the molecule.

In some embodiments of the compounds of formula (3-3):
$X^2$ is CH;
$Y^2$ is $NR^{y2}$;
$R^{9a}$ and $R^{9b}$ are both hydrogen;
$R^{10a}$ is —$OR^{10a-a}$;
$R^{12a}$ and $R^{12b}$ are both hydrogen; and
$R^{10a-a}$ and $R^{y2}$ are taken together to form a carbonyl (C=O) moiety.

In some embodiments of the compounds of formula (3-3), $A^2$ is $C_6$-$C_{10}$ aryl optionally substituted with one or more $R^{16}$ substituents. In some embodiments, $A^2$ is selected from the group consisting of:

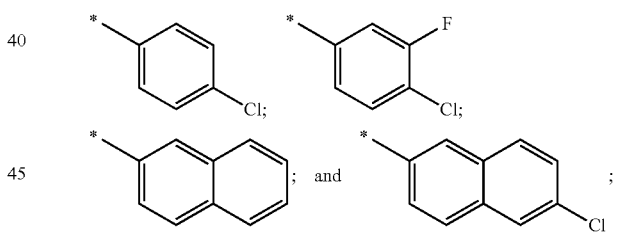

wherein the * represents the attachment point to the remainder of the molecule. In some embodiments, $A^2$ is phenyl optionally substituted with one or more $R^{16}$ substituents. In some embodiments, $A^2$ is selected from the group consisting of:

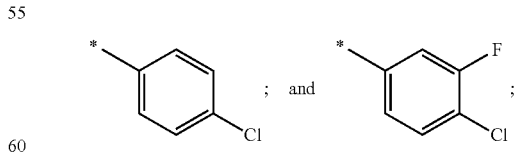

wherein the * represents the attachment point to the remainder of the molecule.

In some embodiments of the compounds of formula (3-3), $A^2$ is 5-10 membered heteroaryl optionally substituted with one or more $R^{16}$ substituents. In some embodiments, $A^2$ is selected from the group consisting of:

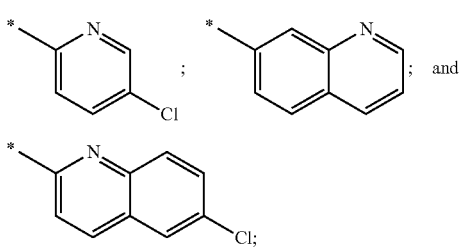

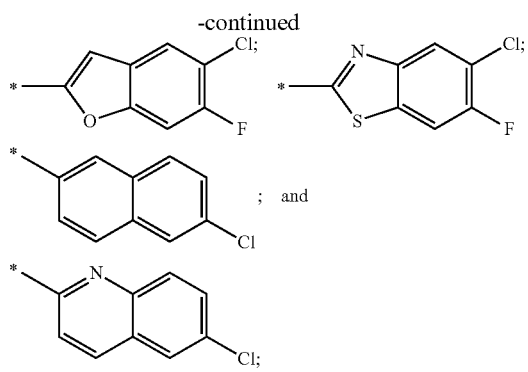

wherein the * represents the attachment point to the remainder of the molecule. In some embodiments, A² is pyridyl optionally substituted with one or more R¹⁶ substituents. In some embodiments, A² is

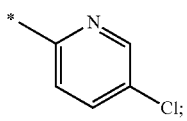

wherein the * represents the attachment point to the remainder of the molecule.

In some embodiments, (A¹-a) or (A¹-b) is selected from the group consisting of:

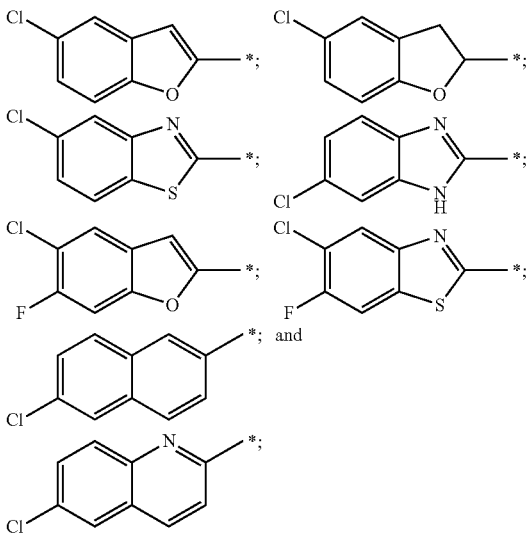

wherein the * represents the attachment point to the remainder of the molecule; and (A²-a) or (A²-b) is selected from the group consisting of:

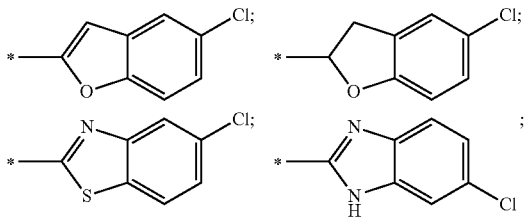

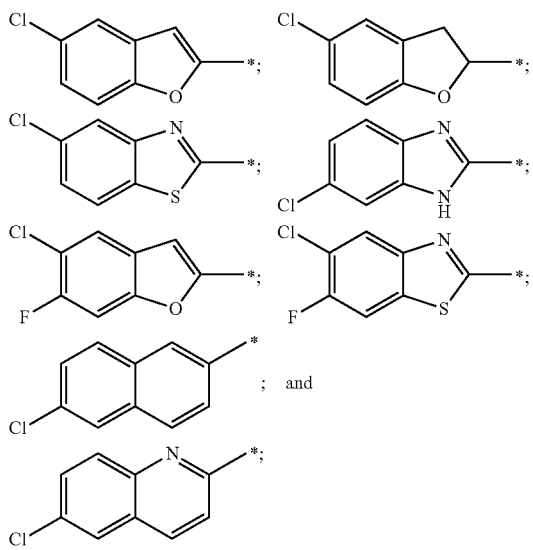

wherein the * represents the attachment point to the remainder of the molecule; and (A²-a) or (A²-b) is selected from the group consisting of:

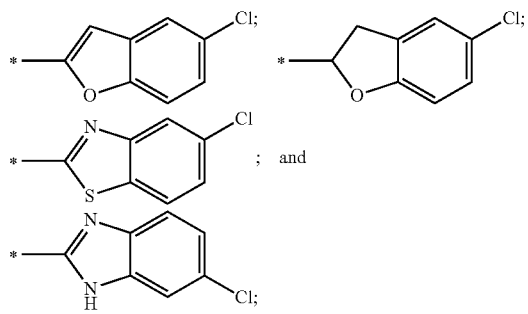

wherein the * represents the attachment point to the remainder of the molecule.

In some embodiments, (A¹-a) or (A¹-b) is selected from the group consisting of:

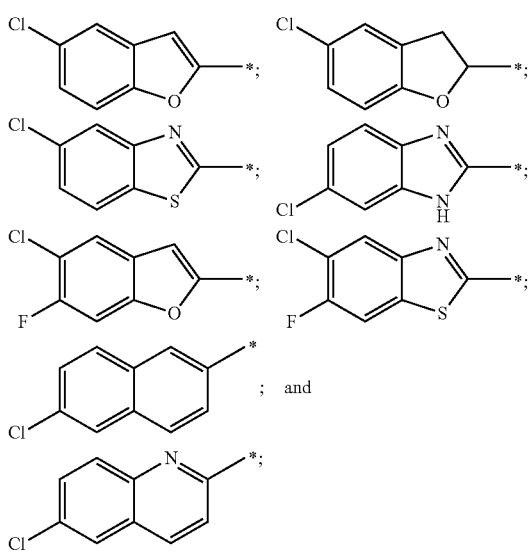

wherein the * represents the attachment point to the remainder of the molecule; and (A²-a) or (A²-c) is selected from the group consisting of:

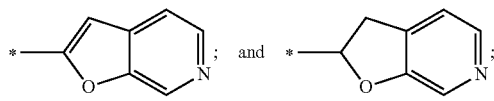

wherein the * represents the attachment point to the remainder of the molecule.

In some embodiments, (A¹-a) or (A¹-b) is selected from the group consisting of:

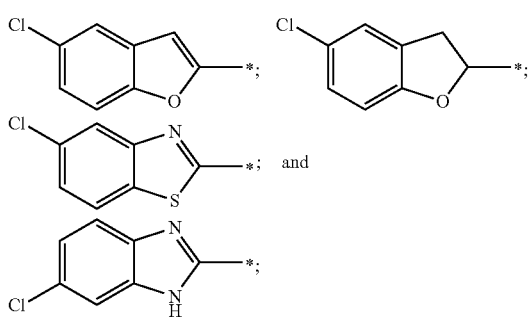

wherein the * represents the attachment point to the remainder of the molecule; and (A²-a) or (A²-b) is selected from the group consisting of:

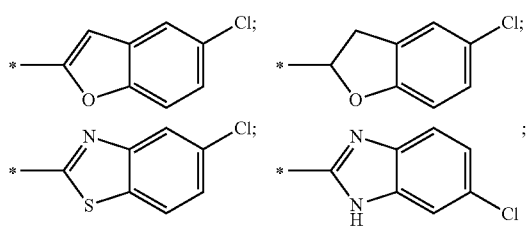

-continued

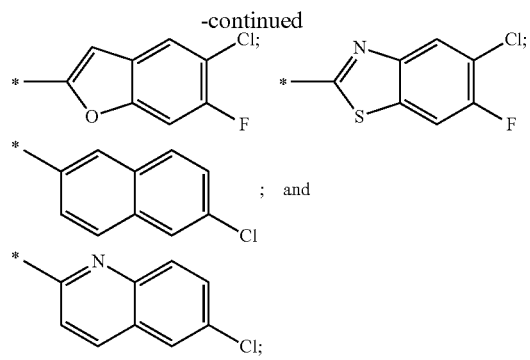

wherein the * represents the attachment point to the remainder of the molecule.

In some embodiments, (A¹-a) or (A¹-b) is selected from the group consisting of:

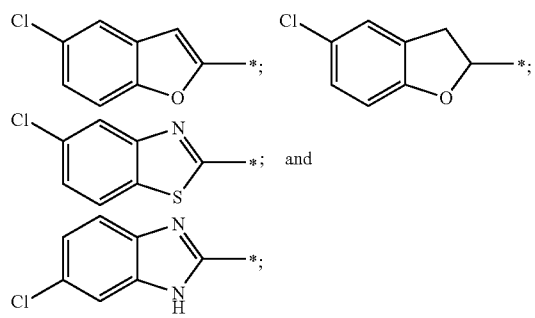

wherein the * represents the attachment point to the remainder of the molecule; and (A¹-a) or (A²-b) is selected from the group consisting of:

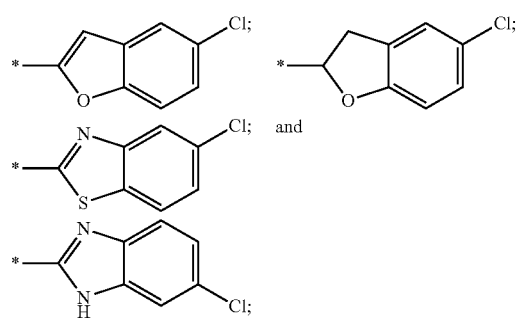

wherein the * represents the attachment point to the remainder of the molecule.

In some embodiments, (A¹-a) or (A¹-b) is selected from the group consisting of:

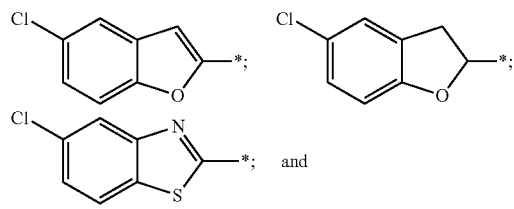

-continued

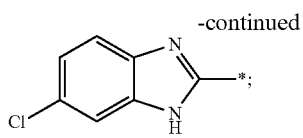

wherein the * represents the attachment point to the remainder of the molecule; and (A²-a) or (A²-c) is selected from the group consisting of:

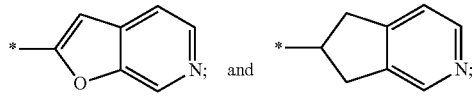 [SMILES: *c1cc2ccncc2o1 ; *C1Cc2ccncc2C1]

wherein the * represents the attachment point to the remainder of the molecule.

In some embodiments, (A¹-a) or (A¹-c) is selected from the group consisting of:

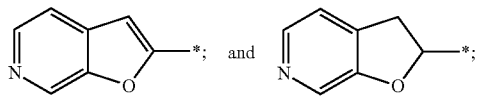

wherein the * represents the attachment point to the remainder of the molecule: and (A²-a) or (A²-b) is selected from the group consisting of:

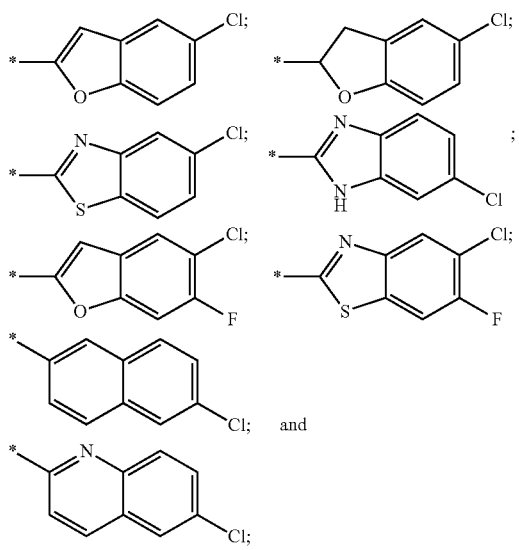

wherein the * represents the attachment point to the remainder of the molecule.

In some embodiments, (A¹-a) or (A¹-c) is selected from the group consisting of:

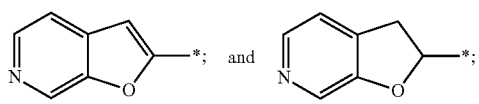

wherein the * represents the attachment point to the remainder of the molecule; and (A²-a) or (A²-b) is selected from the group consisting of:

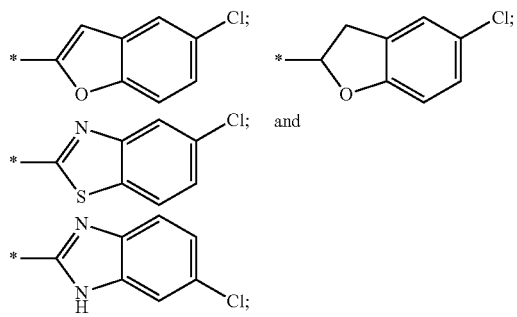

wherein the * represents the attachment point to the remainder of the molecule.

In some embodiments, (A¹-a) or (A¹-c) is selected from the group consisting of:

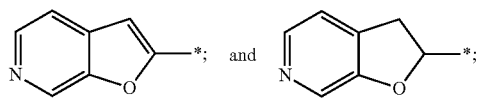

wherein the * represents the attachment point to the remainder of the molecule; and (A²-a) or (A²-c) is selected from the group consisting of:

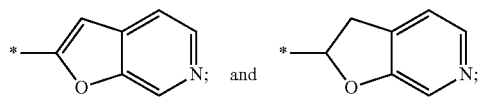 [SMILES: *c1cc2ccncc2o1 ; *C1Cc2ccncc2O1]

wherein the * represents the attachment point to the remainder of the molecule.

In some embodiments, (A¹-a) or (A¹-b) is selected from the group consisting of:

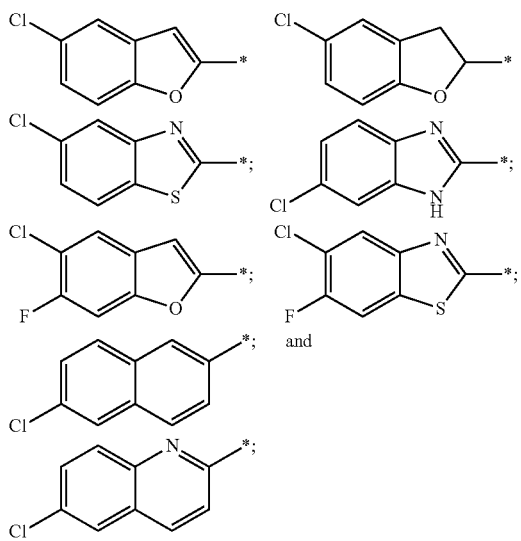

wherein the * represents the attachment point to the remainder of the molecule; and A² is selected from the group consisting of:

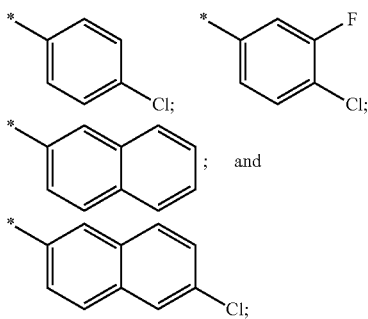

wherein the * represents the attachment point to the remainder of the molecule.

In some embodiments, (A¹-a) or (A¹-b) is selected from the group consisting of:

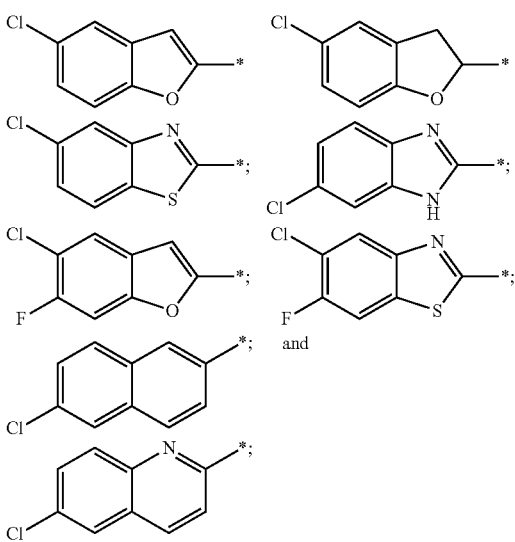

wherein the * represents the attachment point to the remainder of the molecule; and A² is selected from the group consisting of:

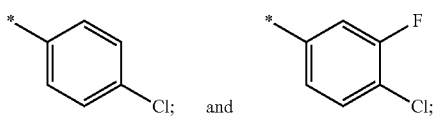 [SMILES: *c1ccc(Cl)cc1 ; *c1ccc(Cl)c(F)c1]

wherein the * represents the attachment point to the remainder of the molecule.

In some embodiments, (A¹-a) or (A¹-b) is selected from the group consisting of:

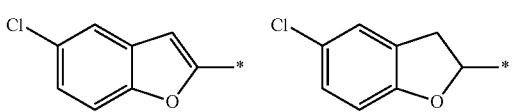

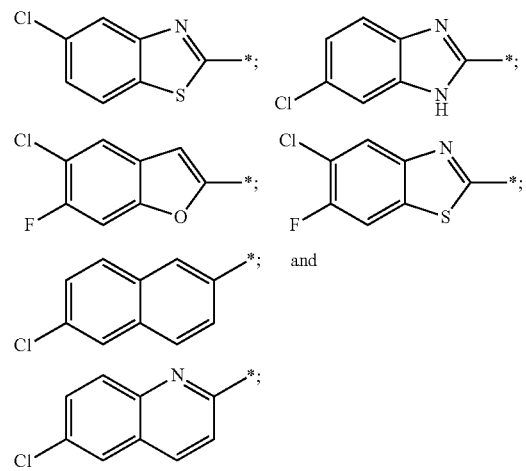

wherein the * represents the attachment point to the remainder of the molecule; and A² is selected from the group consisting of:

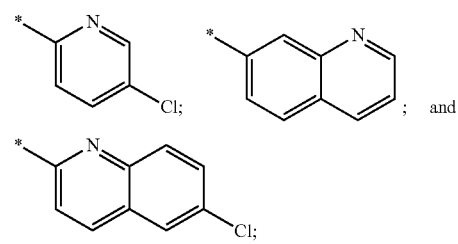

wherein the * represents the attachment point to the remainder of the molecule.

In some embodiments, (A¹-a) or (A¹-b) is selected from the group consisting of:

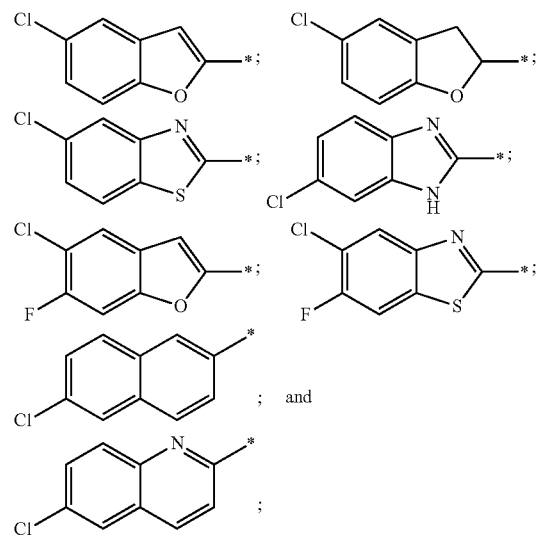

wherein the * represents the attachment point to the remainder of the molecule; and A² is

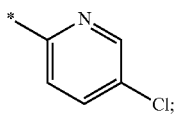

wherein the * represents the attachment point to the remainder of the molecule.

In some embodiments, (A¹-a) or (A¹-b) is selected from the group consisting of:

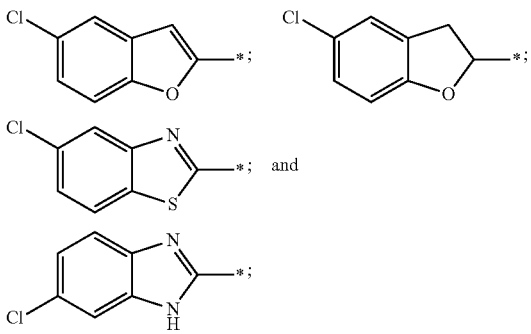

wherein the * represents the attachment point to the remainder of the molecule: and $A^2$ is selected from the group consisting of:

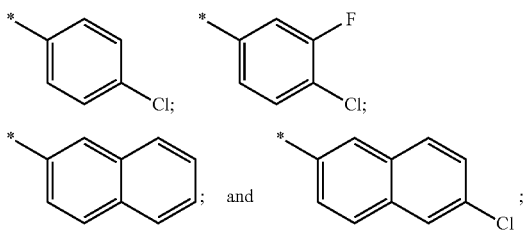

wherein the * represents the attachment point to the remainder of the molecule.

In some embodiments, (A¹-a) or (A¹-b) is selected from the group consisting of:

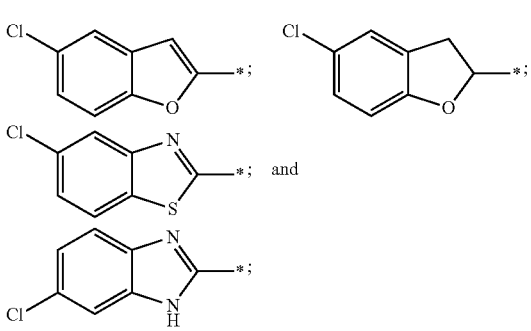

wherein the * represents the attachment point to the remainder of the molecule; and $A^2$ is selected from the group consisting of:

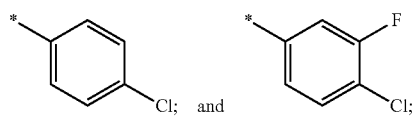

wherein the * represents the attachment point to the remainder of the molecule.

In some embodiments, (A¹-a) or (A¹-b) is selected from the group consisting of:

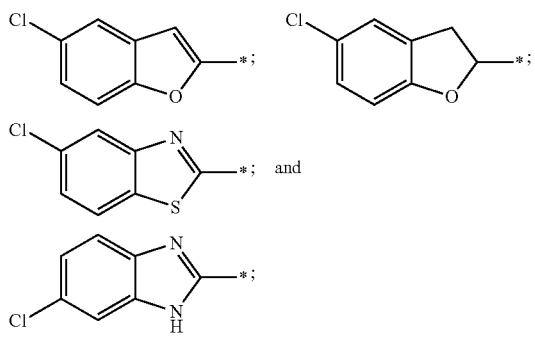

wherein the * represents the attachment point to the remainder of the molecule; and $A^2$ is selected from the group consisting of:

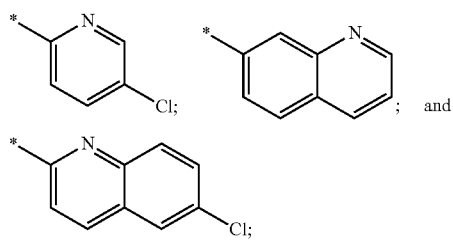

wherein the * represents the attachment point to the remainder of the molecule.

In some embodiments, (A¹-a) or (A¹-b) is selected from the group consisting of:

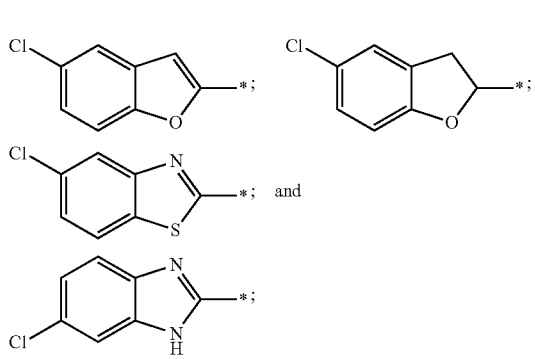

wherein the * represents the attachment point to the remainder of the molecule; and $A^2$ is

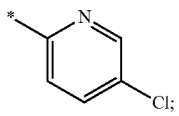 [SMILES: *c1ccc(Cl)cn1]

wherein the * represents the attachment point to the remainder of the molecule.

In some embodiments, (A¹-a) or (A¹-c) is selected from the group consisting of:

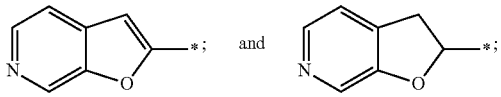 [SMILES: *c1cc2ccncc2o1 ; *C1Cc2ccncc2O1]

wherein the * represents the attachment point to the remainder of the molecule; and A² is selected from the group consisting of:

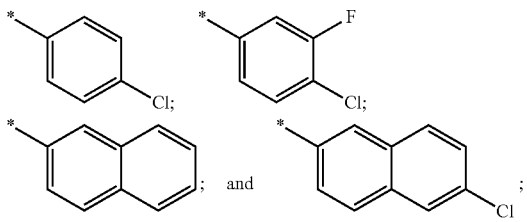

wherein the * represents the attachment point to the remainder of the molecule.

In some embodiments, (A¹-a) or (A¹-c) is selected from the group consisting of:

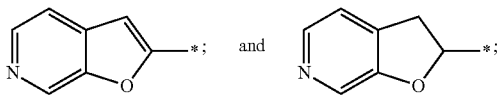 [SMILES: *c1cc2ccncc2o1 ; *C1Cc2ccncc2O1]

wherein the * represents the attachment point to the remainder of the molecule; and A² is selected from the group consisting of:

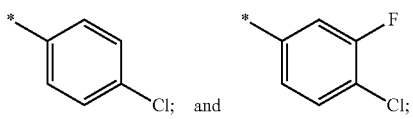

wherein the * represents the attachment point to the remainder of the molecule.

In some embodiments, (A¹-a) or (A¹-c) is selected from the group consisting of:

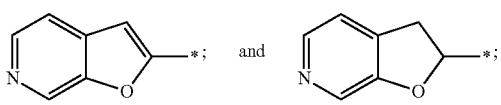 [SMILES: *c1cc2ccncc2o1 ; *C1Cc2ccncc2O1]

wherein the * represents the attachment point to the remainder of the molecule; and A² is selected from the group consisting of:

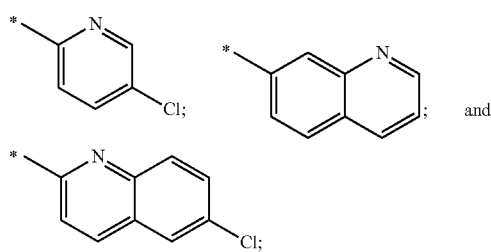

wherein the * represents the attachment point to the remainder of the molecule.

In some embodiments, (A¹-a) or (A¹-c) is selected from the group consisting of:

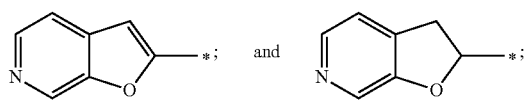

wherein the * represents the attachment point to the remainder of the molecule; and A² is

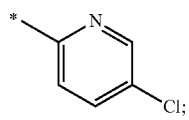

wherein the * represents the attachment point to the remainder of the molecule.

In some embodiments, A¹ is selected from the group consisting of:

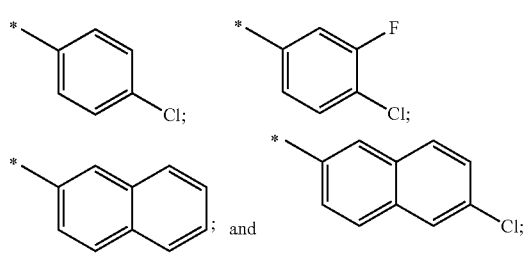

wherein the * represents the attachment point to the remainder of the molecule; and (A²-a) or (A²-b) is selected from the group consisting of:

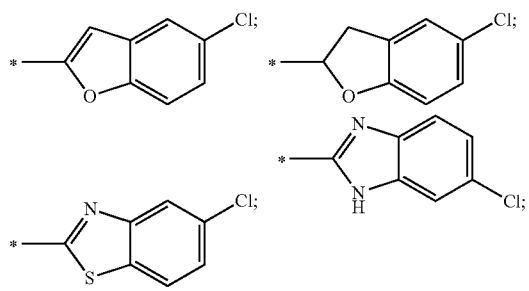

-continued

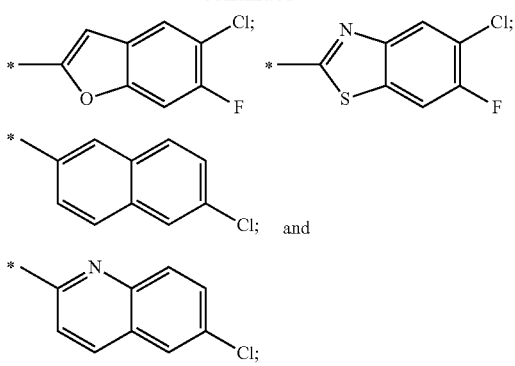

wherein the * represents the attachment point to the remainder of the molecule.

In some embodiments, A¹ is selected from the group consisting of:

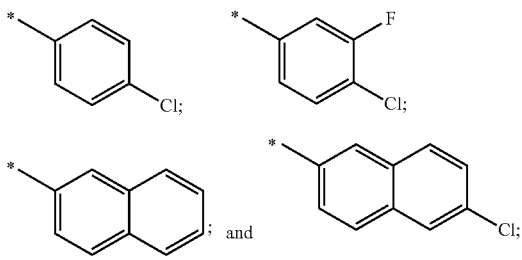

wherein the * represents the attachment point to the remainder of the molecule; and (A²-a) or (A²-b) is selected from the group consisting of:

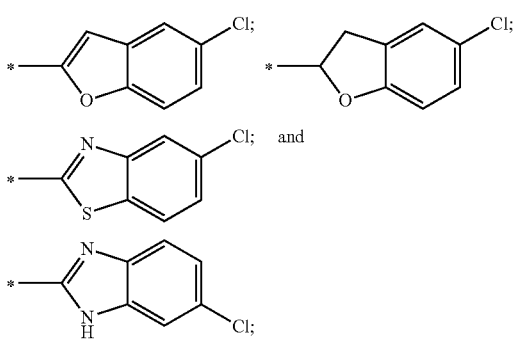

wherein the * represents the attachment point to the remainder of the molecule.

In some embodiments, A¹ is selected from the group consisting of:

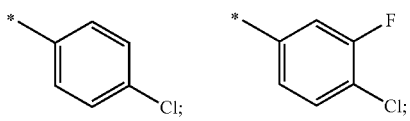

-continued

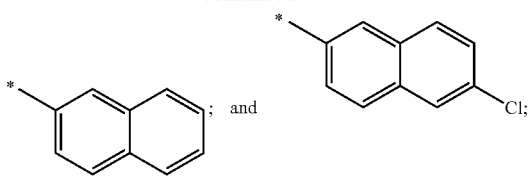

wherein the * represents the attachment point to the remainder of the molecule; and (A²-a) or (A²-c) is selected from the group consisting of:

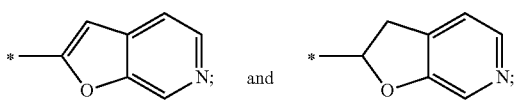

wherein the * represents the attachment point to the remainder of the molecule.

In some embodiments, A¹ is selected from the group consisting of:

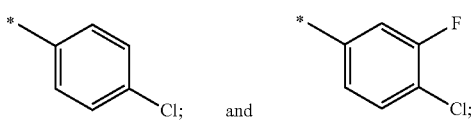

wherein the * represents the attachment point to the remainder of the molecule; and (A²-a) or (A²-b) is selected from the group consisting of:

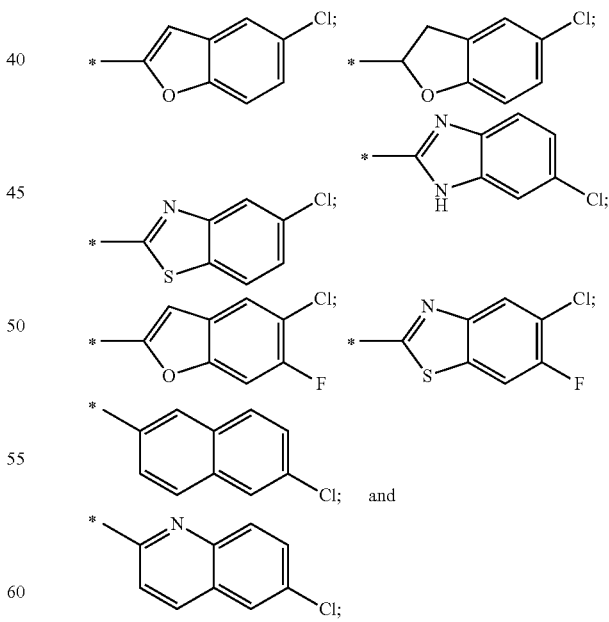

wherein the * represents the attachment point to the remainder of the molecule.

In some embodiments, A¹ is selected from the group consisting of:

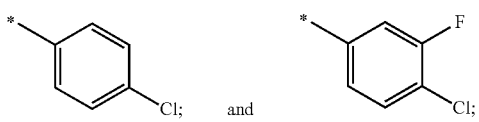

wherein the * represents the attachment point to the remainder of the molecule; and ($A^2$-a) or ($A^2$-b) is selected from the group consisting of:

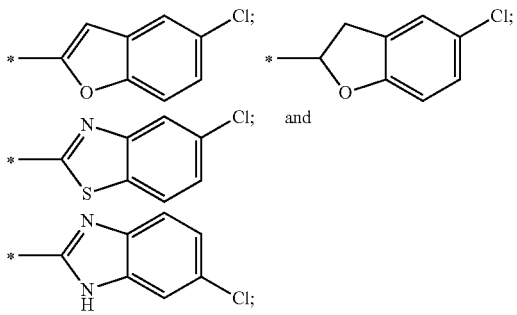

wherein the * represents the attachment point to the remainder of the molecule.

In some embodiments, $A^1$ is selected from the group consisting of:

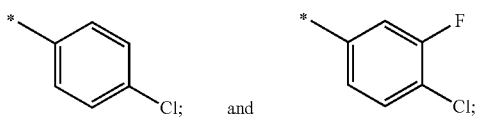

wherein the * represents the attachment point to the remainder of the molecule; and ($A^2$-a) or ($A^2$-c) is selected from the group consisting of:

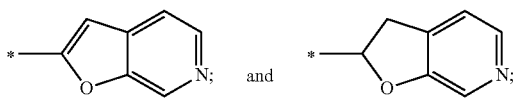

wherein the * represents the attachment point to the remainder of the molecule.

In some embodiments, $A^1$ is selected from the group consisting of:

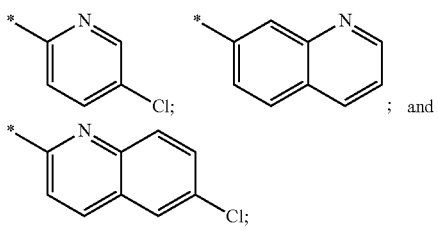

wherein the * represents the attachment point to the remainder of the molecule; and ($A^2$-a) or ($A^2$-b) is selected from the group consisting of:

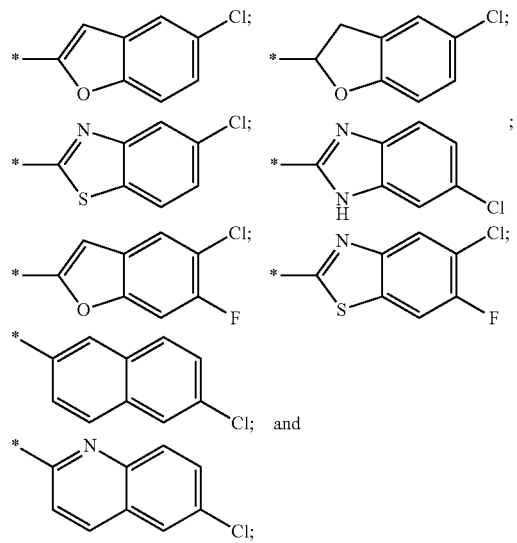

wherein the * represents the attachment point to the remainder of the molecule.

In some embodiments, $A^1$ is selected from the group consisting of:

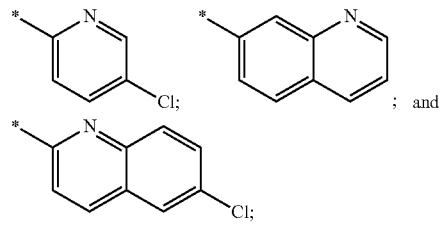

wherein the * represents the attachment point to the remainder of the molecule; and ($A^2$-a) or ($A^2$-b) is selected from the group consisting of:

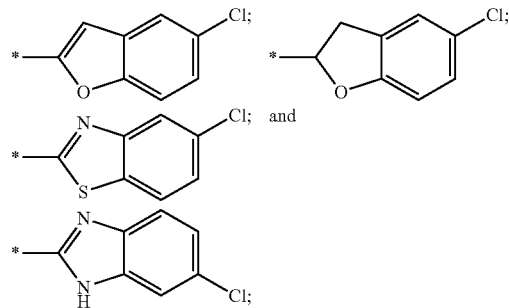

wherein the * represents the attachment point to the remainder of the molecule.

In some embodiments, $A^1$ is selected from the group consisting of:

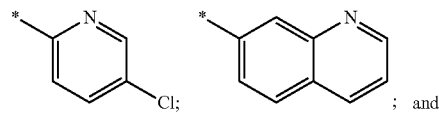

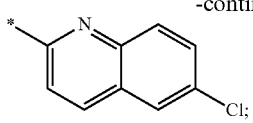

wherein the * represents the attachment point to the remainder of the molecule; and (A²-a) or (A²-c) is selected from the group consisting of:

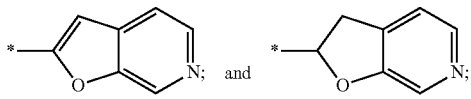 [SMILES: *c1cc2ccncc2o1 ; "and" ; *C1Cc2ccncc2O1]

wherein the * represents the attachment point to the remainder of the molecule.

In some embodiments, A¹ is

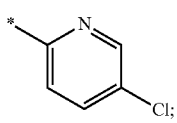

wherein the * represents the attachment point to the remainder of the molecule; and (A²-a) or (A²-b) is selected from the group consisting of:

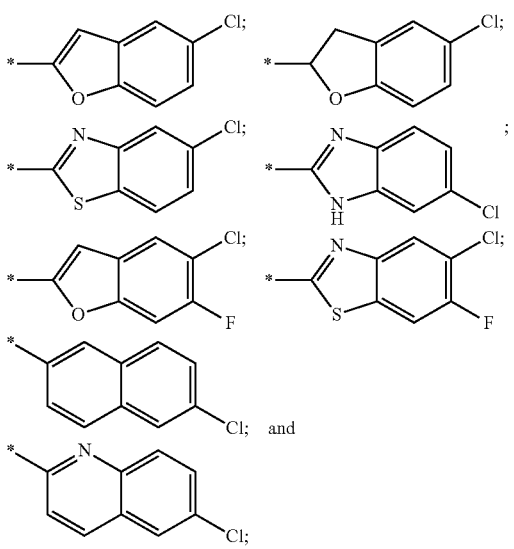

wherein the * represents the attachment point to the remainder of the molecule.

In some embodiments, A¹ is

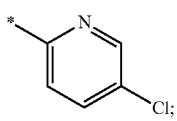 [SMILES: *c1ccc(Cl)cn1]

wherein the * represents the attachment point to the remainder of the molecule; and (A²-a) or (A²-b) is selected from the group consisting of:

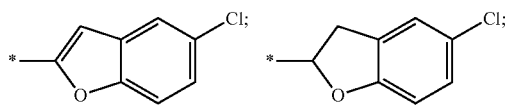

wherein the * represents the attachment point to the remainder of the molecule.

In some embodiments, A¹ is selected from the group consisting of:

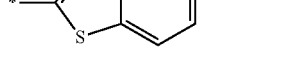
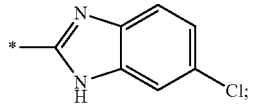

wherein the * represents the attachment point to the remainder of the molecule; and A² is selected from the group consisting of:

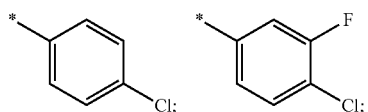
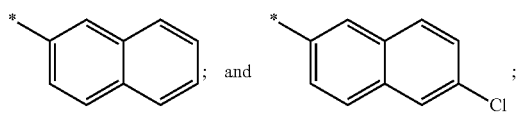

wherein the * represents the attachment point to the remainder of the molecule.

In some embodiments, A¹ is selected from the group consisting of:

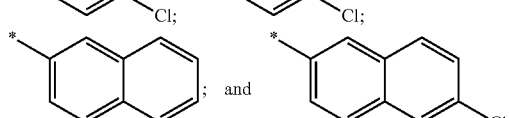

wherein the * represents the attachment point to the remainder of the molecule; and A² is selected from the group consisting of:

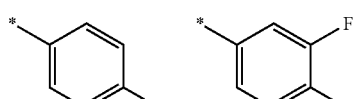
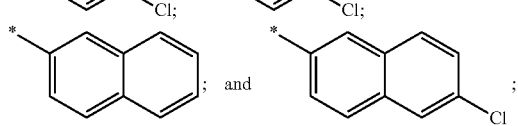

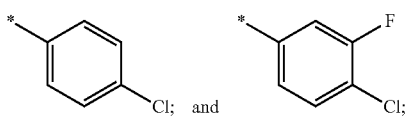

wherein the * represents the attachment point to the remainder of the molecule.

In some embodiments, $A^1$ is selected from the group consisting of:

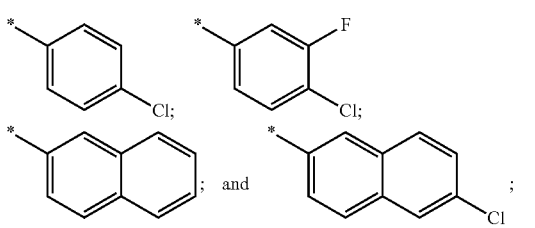

wherein the * represents the attachment point to the remainder of the molecule; and $A^2$ is selected from the group consisting of:

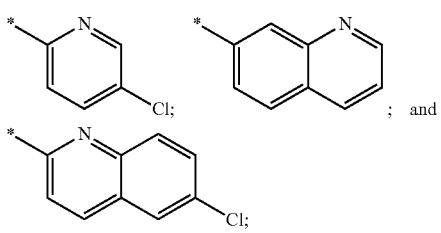

wherein the * represents the attachment point to the remainder of the molecule.

In some embodiments, $A^1$ is selected from the group consisting of:

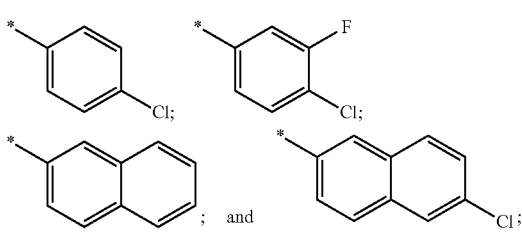

wherein the * represents the attachment point to the remainder of the molecule; and $A^2$ is

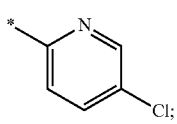 [SMILES: *c1ccc(Cl)cn1]

wherein the * represents the attachment point to the remainder of the molecule.

In some embodiments, $A^1$ is selected from the group consisting of:

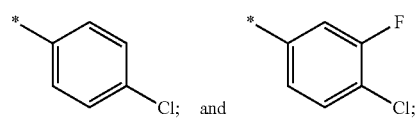 [SMILES: *c1ccc(Cl)cc1 ; *c1ccc(Cl)c(F)c1]

wherein the * represents the attachment point to the remainder of the molecule; and $A^2$ is selected from the group consisting of:

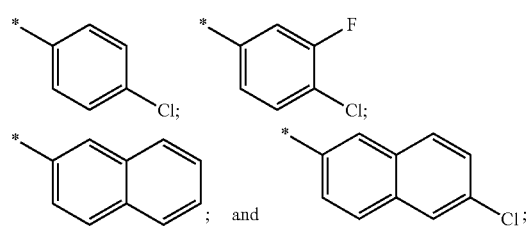

wherein the * represents the attachment point to the remainder of the molecule.

In some embodiments, $A^1$ is selected from the group consisting of:

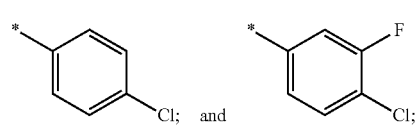 [SMILES: *c1ccc(Cl)cc1 ; *c1ccc(Cl)c(F)c1]

wherein the * represents the attachment point to the remainder of the molecule; and $A^2$ is selected from the group consisting of:

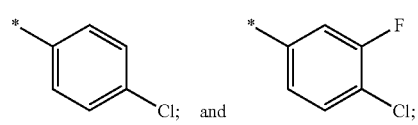

wherein the * represents the attachment point to the remainder of the molecule.

In some embodiments, $A^1$ is selected from the group consisting of:

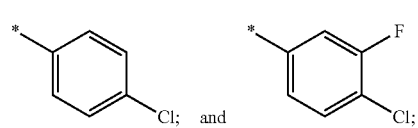 [SMILES: *c1ccc(Cl)cc1 ; *c1ccc(Cl)c(F)c1]

wherein the * represents the attachment point to the remainder of the molecule; $A^2$ is selected from the group consisting of:

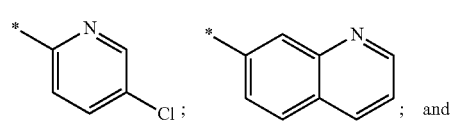

-continued

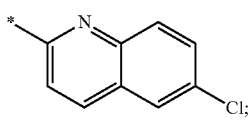

wherein the * represents the attachment point to the remainder of the molecule.

In some embodiments. $A^1$ is selected from the group consisting of:

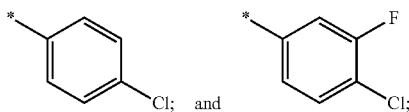 [SMILES: *c1ccc(Cl)cc1 ; *c1ccc(Cl)c(F)c1]

wherein the * represents the attachment point to the remainder of the molecule; and $A^2$ is

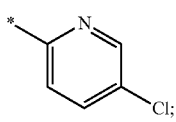

wherein the * represents the attachment point to the remainder of the molecule.

In some embodiments, $A^1$ is selected from the group consisting of:

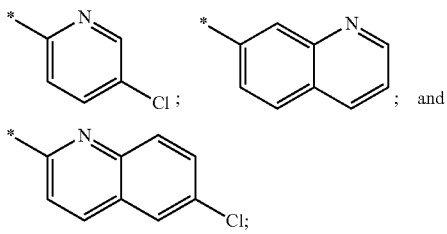

wherein the * represents the attachment point to the remainder of the molecule; and $A^2$ is selected from the group consisting of:

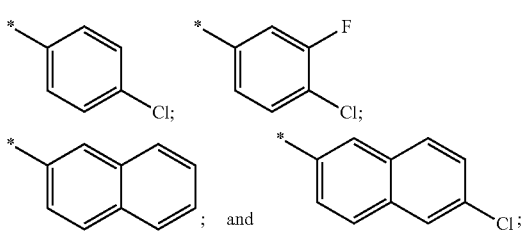

wherein the * represents the attachment point to the remainder of the molecule.

In some embodiments, $A^1$ is selected from the group consisting of:

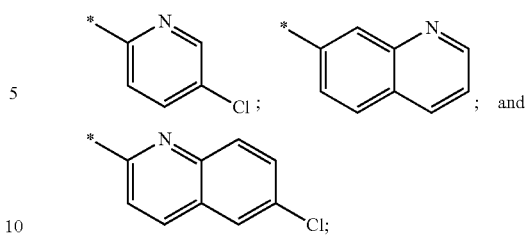

wherein the * represents the attachment point to the remainder of the molecule; and $A^2$ is selected from the group consisting of:

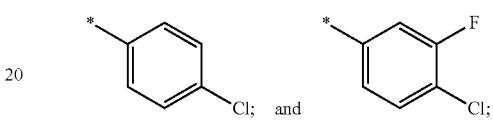

wherein the * represents the attachment point to the remainder of the molecule.

In some embodiments, $A^1$ is selected from the group consisting of:

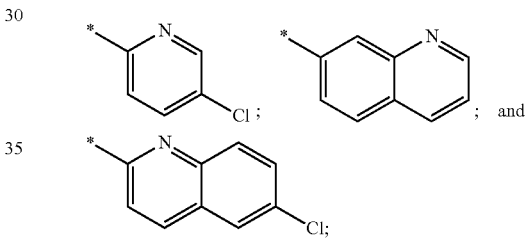

wherein the * represents the attachment point to the remainder of the molecule; $A^2$ is selected from the group consisting of:

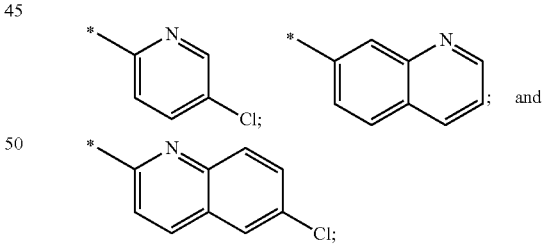

wherein the * represents the attachment point to the remainder of the molecule.

In some embodiments, $A^1$ is selected from the group consisting of:

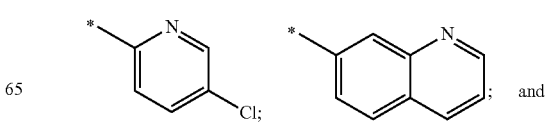

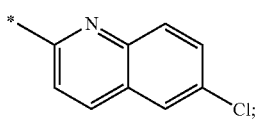

wherein the * represents the attachment point to the remainder of the molecule; and A² is

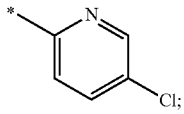

wherein the * represents the attachment point to the remainder of the molecule.

In some embodiments, A¹ is

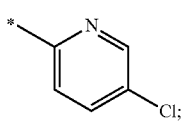

wherein the * represents the attachment point to the remainder of the molecule; and A² is selected from the group consisting of:

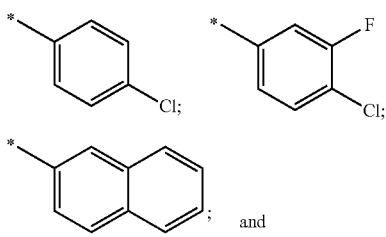

wherein the * represents the attachment point to the remainder of the molecule.

In some embodiments, A¹ is

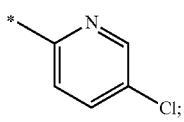

wherein the * represents the attachment point to the remainder of the molecule; and A² is selected from the group consisting of:

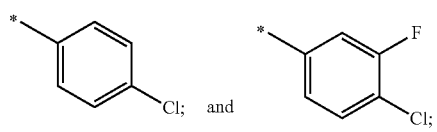

wherein the * represents the attachment point to the remainder of the molecule.

In some embodiments, A¹ is

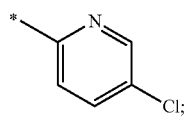

wherein the * represents the attachment point to the remainder of the molecule; and A² is selected from the group consisting of:

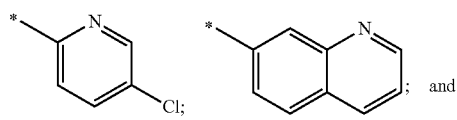

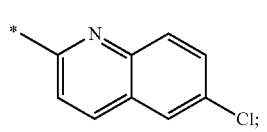

wherein the * represents the attachment point to the remainder of the molecule.

In some embodiments, A¹ is

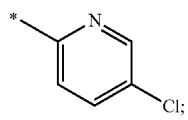

wherein the * represents the attachment point to the remainder of the molecule; and A² is

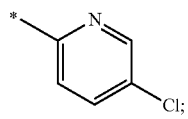

wherein the * represents the attachment point to the remainder of the molecule.

In some embodiments, the compound of formula (I) is a compound of formula (3-4):

(3-4)

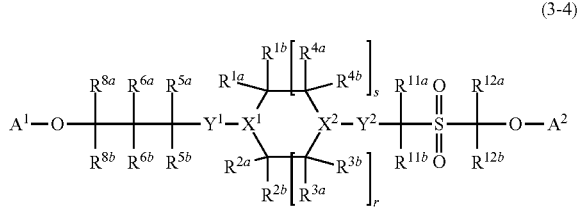

or a pharmaceutically acceptable salt thereof;
wherein:
$A^1$ is $C_6$-$C_{10}$ aryl optionally substituted with one or more $R^{14}$ substituents; or 5-10 membered heteroaryl optionally substituted with one or more $R^{14}$ substituents;
$A^2$ is $C_6$-$C_{10}$ aryl optionally substituted with one or more $R^{16}$ substituents; or 5-10 membered heteroaryl optionally substituted with one or more $R^{16}$ substituents;
$R^{11a}$ and $R^{11b}$ are both hydrogen;
$R^{12a}$ and $R^{12b}$ are both hydrogen;
and wherein $X^1$, $X^2$, $Y^1$, $R^{Y1}$, $Y^2$, $R^{Y2}$, r, s, $R^{1a}$, $R^{1b}$, $R^{2a}$, $R^{2b}$, $R^{3a}$, $R^{3b}$, $R^{4a}$, $R^{4b}$, $R^{5a}$, $R^{5b}$, $R^{6a}$, $R^{6a\text{-}a}$, $R^{6a\text{-}b}$, $R^{6a\text{-}c}$, $R^{6b}$, $R^{8a}$, $R^{8b}$, $R^{14}$, and $R^{16}$ are as defined in compounds of formula (I).

In some embodiments of the compounds of formula (3-4), $X^1$ is CH and $X^2$ is CH. In some embodiments, r is 1 and s is 1.

In some embodiments of the compounds of formula (3-4), $X^1$ is CH, $X^2$ is N and $Y^2$ is a bond. In some embodiments, r is 1 and s is 1. In some embodiments, r is 0 and s is 2.

In some embodiments of the compounds of formula (3-4), $X^1$ is N, $Y^1$ is a bond, and $X^2$ is CH. In some embodiments, r is 1 and s is 1. In some embodiments, r is 0 and s is 2.

In some embodiments of the compounds of formula (3-4), $X^1$ is N, $Y^1$ is a bond, $X^2$ is N and $Y^2$ is a bond. In some embodiments, r is 1 and s is 1. In some embodiments, r is 0 and s is 2.

In some embodiments of the compounds of formula (3-4): $R^{5a}$ and $R^{5b}$ are taken together to form an oxo (=O) substituent or an imido (=NH) substituent, or alternatively, $R^{5a}$ and $R^{5b}$ are both hydrogen;
$R^{6a}$ is selected from the group consisting of hydrogen, —$OR^{6a\text{-}a}$, and $NR^{6a\text{-}b}R^{6a\text{-}c}$;
$R^{10b}$ is hydrogen; and
$R^{12a}$ and $R^{12b}$ are both hydrogen.

In some embodiments of the compounds of formula (3-4), $R^{9a}$ and $R^{9b}$ are taken together to form an oxo (=O) substituent. In some embodiments, $R^{10a}$ is hydrogen. In some embodiments, $R^{10a}$ is —$OR^{10a\text{-}a}$. In some embodiments, $R^{10a}$ is —$NR^{10a\text{-}b}R^{10a\text{-}c}$.

In some embodiments of the compounds of formula (3-4), $R^{9a}$ and $R^{9b}$ are taken together to form an imido (=NH) substituent. In some embodiments, $R^{10a}$ is hydrogen. In some embodiments, $R^{10a}$ is —$OR^{10a\text{-}a}$. In some embodiments, $R^{10a}$ is —$NR^{10a\text{-}b}R^{10a\text{-}c}$.

In some embodiments of the compounds of formula (3-4), $R^{9a}$ and $R^{9b}$ are both hydrogen. In some embodiments, $R^{10a}$ is hydrogen. In some embodiments, $R^{10a}$ is —$OR^{10a\text{-}a}$. In some embodiments, $R^{10a}$ is —$NR^{10a\text{-}b}R^{10a\text{-}c}$.

In some embodiments of the compounds of formula (3-4):
$X^1$ is CH;
$Y^1$ is $NR^{Y1}$;
$R^{5a}$ and $R^{5b}$ are both hydrogen;
$R^{6a}$ is —$OR^{6a\text{-}a}$;
$R^{8a}$ and $R^{8b}$ are both hydrogen; and $R^{6a\text{-}a}$ and $R^{Y1}$ are taken together to form a carbonyl (C=O) moiety.

In some embodiments of the compounds of formula (3-4), $A^1$ is $C_6$-$C_{10}$ aryl optionally substituted with one or more $R^{14}$ substituents. In some embodiments, $A^1$ is selected from the group consisting of:

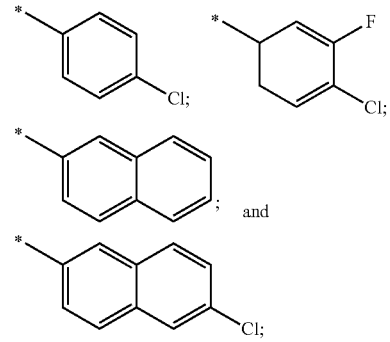

wherein the * represents the attachment point to the remainder of the molecule. In some embodiments, $A^1$ is phenyl optionally substituted with one or more $R^{14}$ substituents. In some embodiments, $A^1$ is selected from the group consisting of:

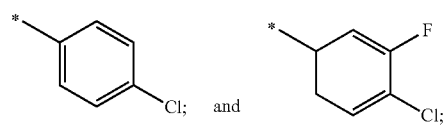

wherein the * represents the attachment point to the remainder of the molecule.

In some embodiments of the compounds of formula (3-4), $A^1$ is 5-10 membered heteroaryl optionally substituted with one or more $R^{14}$ substituents. In some embodiments, $A^1$ is selected from the group consisting of:

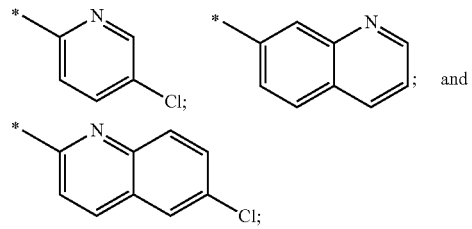

wherein the * represents the attachment point to the remainder of the molecule. In some embodiments, $A^1$ is pyridyl optionally substituted with one or more $R^{14}$ substituents. In some embodiments, $A^1$ is

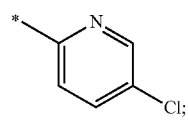

wherein the * represents the attachment point to the remainder of the molecule.

In some embodiments of the compounds of formula (3-4), $A^2$ is $C_6$-$C_{10}$ aryl optionally substituted with one or more $R^{16}$ substituents. In some embodiments, $A^2$ is selected from the group consisting of:

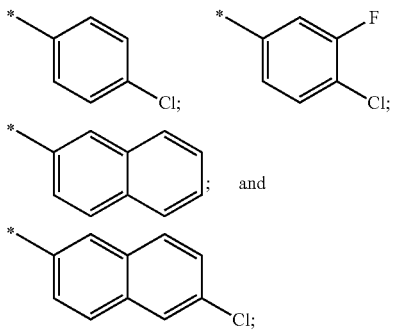

wherein the * represents the attachment point to the remainder of the molecule. In some embodiments, $A^2$ is phenyl optionally substituted with one or more $R^{16}$ substituents. In some embodiments, $A^2$ is selected from the group consisting of:

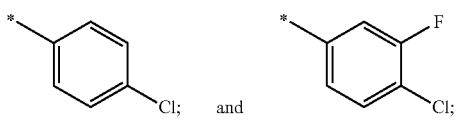

wherein the * represents the attachment point to the remainder of the molecule.

In some embodiments of the compounds of formula (3-4), $A^2$ is 5-10 membered heteroaryl optionally substituted with one or more $R^{16}$ substituents. In some embodiments, $A^2$ is selected from the group consisting of:

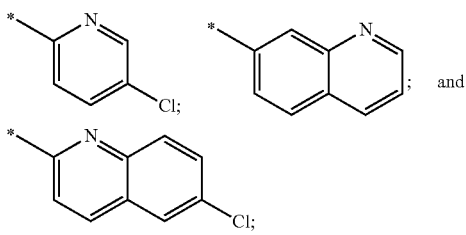

wherein the * represents the attachment point to the remainder of the molecule. In some embodiments, $A^2$ is pyridyl optionally substituted with one or more $R^{16}$ substituents. In some embodiments, $A^2$ is

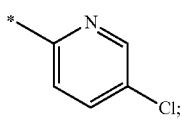

wherein the * represents the attachment point to the remainder of the molecule.

In some embodiments, $(A^1$-a) or $(A^1$-b) is selected from the group consisting of:

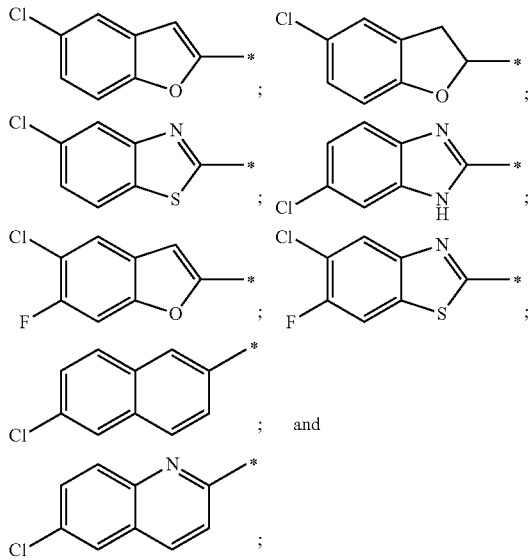

wherein the * represents the attachment point to the remainder of the molecule; and $(A^2$-a) or $(A^2$-b) is selected from the group consisting of:

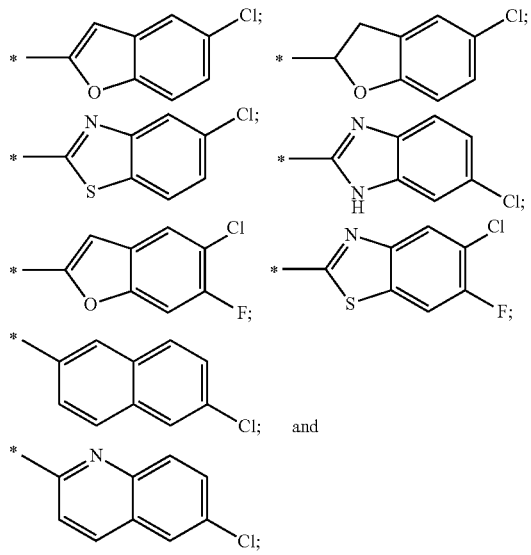

wherein the * represents the attachment point to the remainder of the molecule.

In some embodiments, $(A^1$-a) or $(A^1$-b) is selected from the group consisting of:

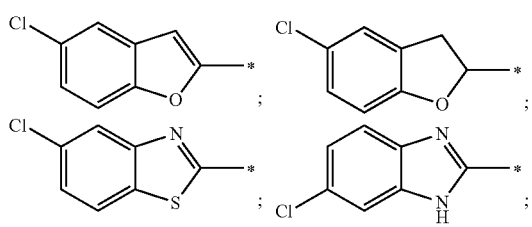

-continued

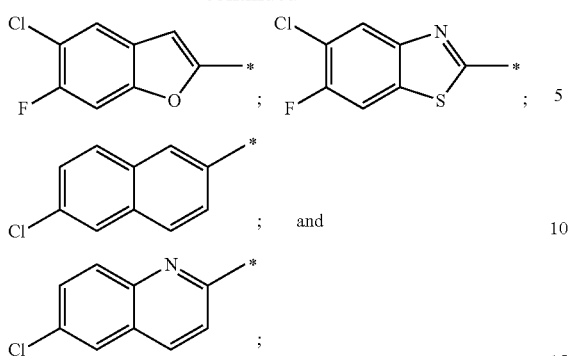

wherein the * represents the attachment point to the remainder of the molecule; and (A²-a) or (A²-b) is selected from the group consisting of:

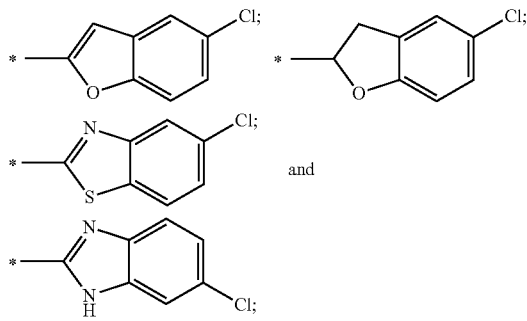

wherein the * represents the attachment point to the remainder of the molecule.

In some embodiments, (A¹-a) or (A¹-b) is selected from the group consisting of:

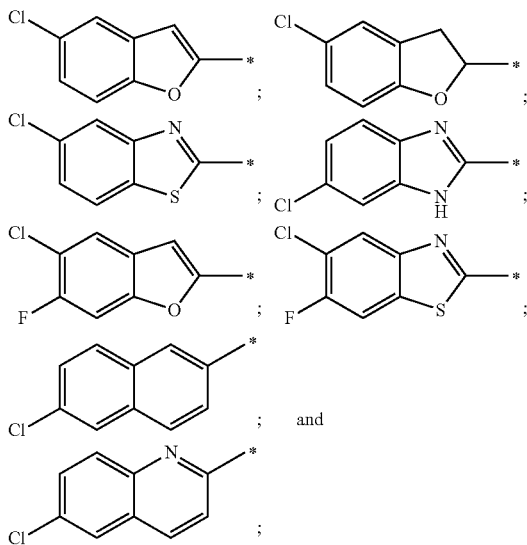

wherein the * represents the attachment point to the remainder of the molecule; and (A²-a) or (A²-c) is selected from the group consisting of:

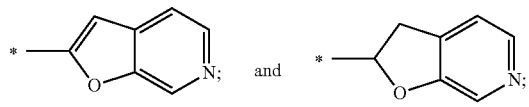

wherein the * represents the attachment point to the remainder of the molecule.

In some embodiments, (A¹-a) or (A¹-b) is selected from the group consisting of:

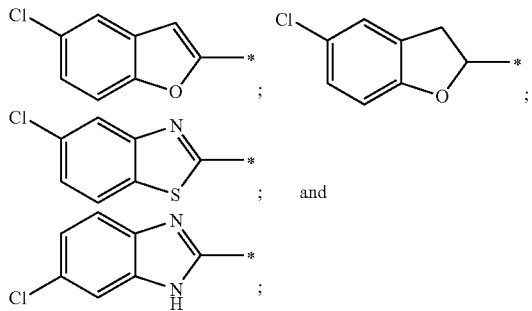

wherein the * represents the attachment point to the remainder of the molecule; and (A²-a) or (A²-b) is selected from the group consisting of:

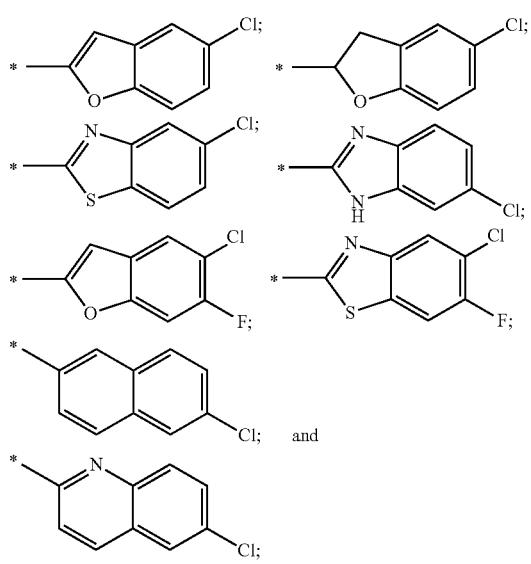

wherein the * represents the attachment point to the remainder of the molecule.

In some embodiments, (A¹-a) or (A¹-b) is selected from the group consisting of:

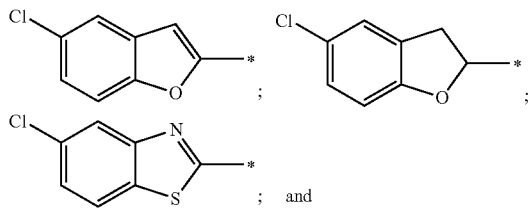

-continued

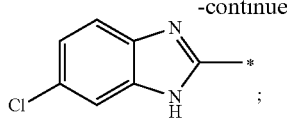

wherein the * represents the attachment point to the remainder of the molecule; and ($A^2$-a) or ($A^2$-b) is selected from the group consisting of:

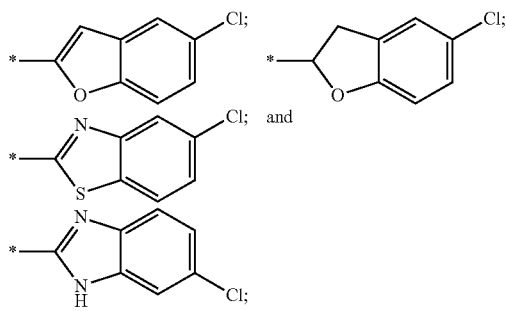

wherein the * represents the attachment point to the remainder of the molecule.

In some embodiments, ($A^1$-a) or ($A^1$-b) is selected from the group consisting of:

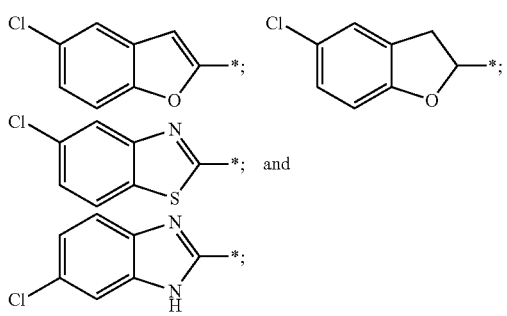

wherein the * represents the attachment point to the remainder of the molecule; and ($A^2$-a) or ($A^2$-c) is selected from the group consisting of:

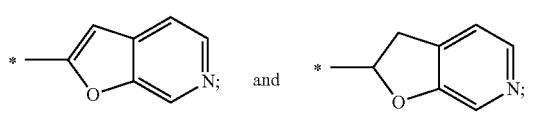

wherein the * represents the attachment point to the remainder of the molecule.

In some embodiments, ($A^1$-a) or ($A^1$-c) is selected from the group consisting of:

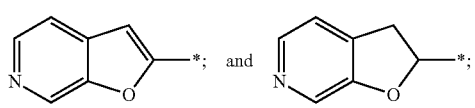

wherein the * represents the attachment point to the remainder of the molecule: and ($A^2$-a) or ($A^2$-b) is selected from the group consisting of:

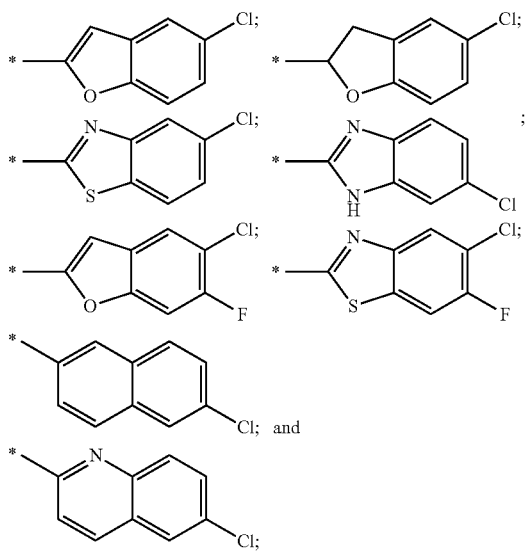

wherein the * represents the attachment point to the remainder of the molecule.

In some embodiments, ($A^1$-a) or ($A^1$-c) is selected from the group consisting of:

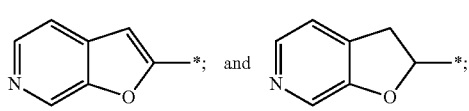

wherein the * represents the attachment point to the remainder of the molecule: and ($A^2$-a) or ($A^2$-b) is selected from the group consisting of:

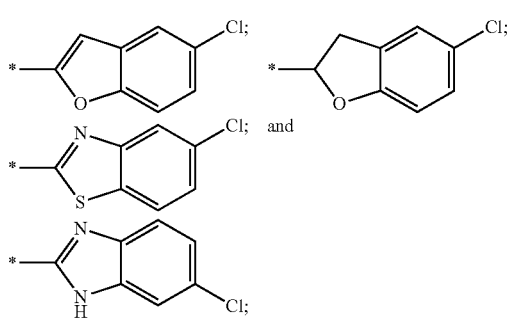

wherein the * represents the attachment point to the remainder of the molecule.

In some embodiments, ($A^1$-a) or ($A^1$-c) is selected from the group consisting of:

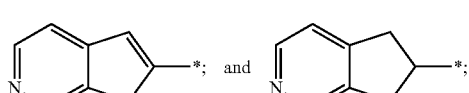

wherein the * represents the attachment point to the remainder of the molecule; and ($A^2$-a) or ($A^2$-c) is selected from the group consisting of:

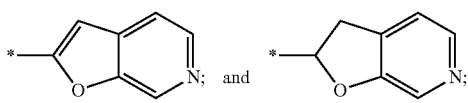

wherein the * represents the attachment point to the remainder of the molecule.

In some embodiments, (A¹-a) or (A¹-b) is selected from the group consisting of:

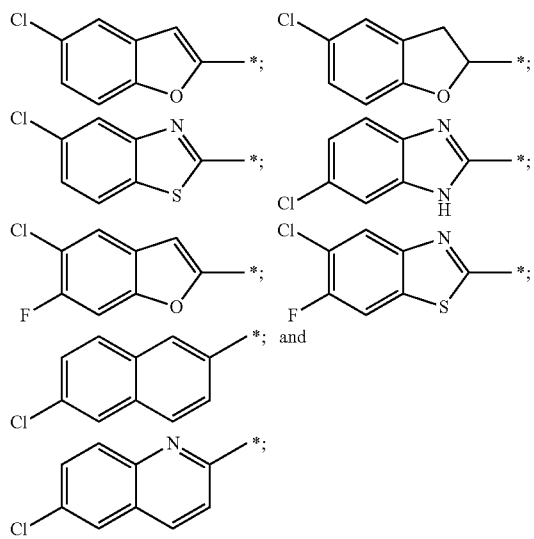

wherein the * represents the attachment point to the remainder of the molecule; and A² is selected from the group consisting of:

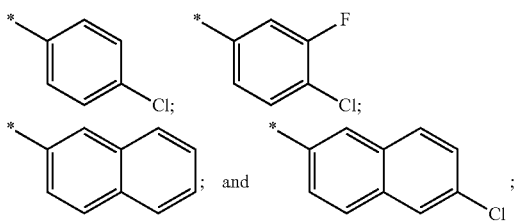

wherein the * represents the attachment point to the remainder of the molecule.

In some embodiments, (A¹-a) or (A¹-b) is selected from the group consisting of:

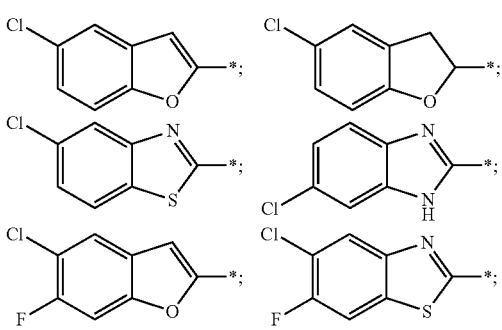

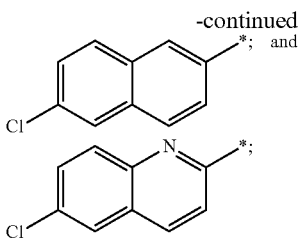

wherein the * represents the attachment point to the remainder of the molecule; and A² is selected from the group consisting of:

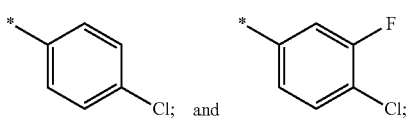

wherein the * represents the attachment point to the remainder of the molecule.

In some embodiments, (A¹-a) or (A¹-b) is selected from the group consisting of:

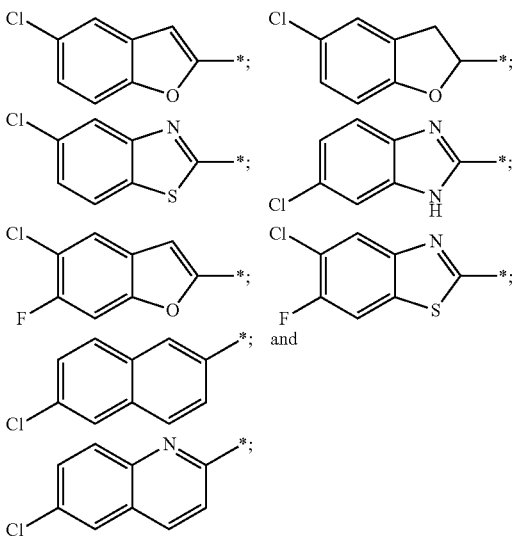

wherein the * represents the attachment point to the remainder of the molecule; and A² is selected from the group consisting of:

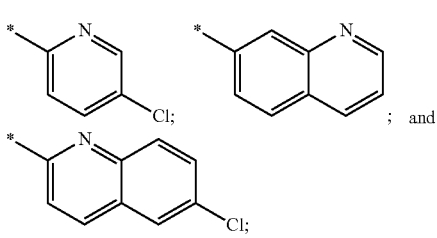

wherein the * represents the attachment point to the remainder of the molecule.

In some embodiments, (A¹-a) or (A¹-b) is selected from the group consisting of:

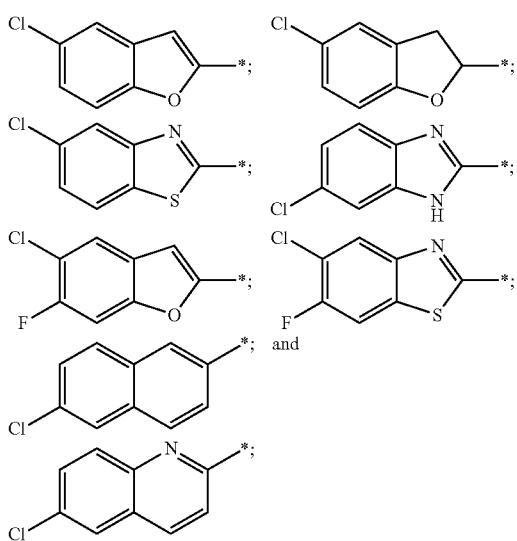

wherein the * represents the attachment point to the remainder of the molecule; and $A^2$ is

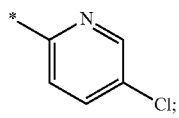

wherein the * represents the attachment point to the remainder of the molecule.

In some embodiments, ($A^1$-a) or ($A^1$-b) is selected from the group consisting of:

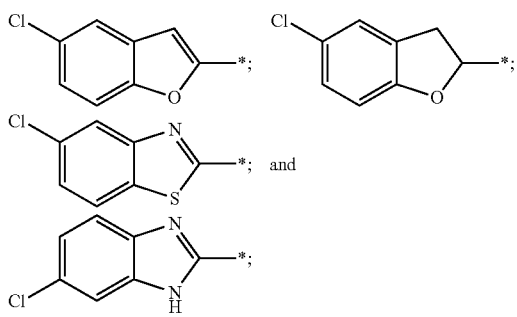

wherein the * represents the attachment point to the remainder of the molecule; and $A^2$ is selected from the group consisting of:

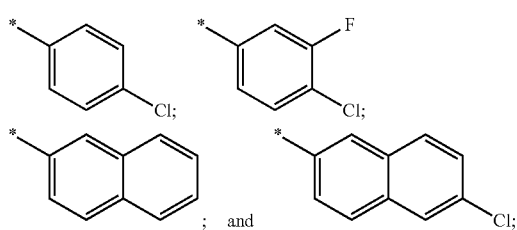

wherein the * represents the attachment point to the remainder of the molecule.

In some embodiments, ($A^1$-a) or ($A^1$-b) is selected from the group consisting of:

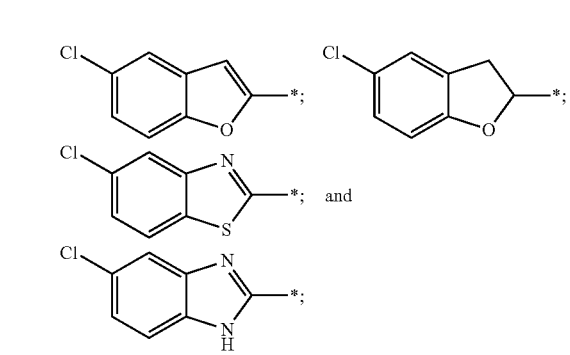

wherein the * represents the attachment point to the remainder of the molecule: and $A^2$ is selected from the group consisting of:

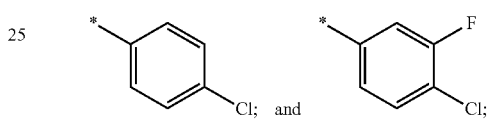

wherein the * represents the attachment point to the remainder of the molecule.

In some embodiments, ($A^1$-a) or ($A^1$-b) is selected from the group consisting of:

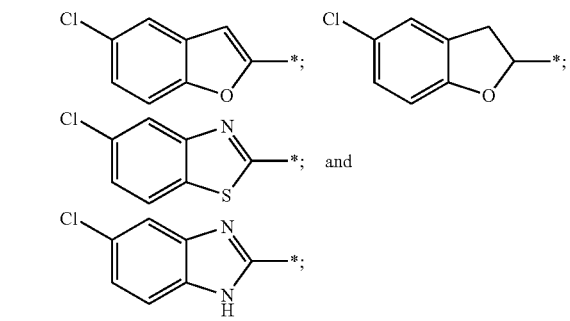

wherein the * represents the attachment point to the remainder of the molecule; and $A^2$ is selected from the group consisting of:

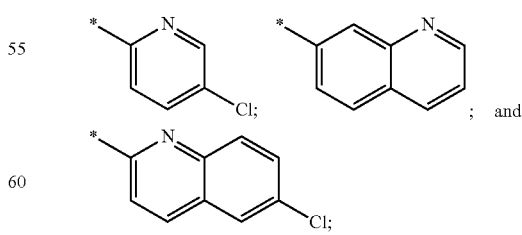

wherein the * represents the attachment point to the remainder of the molecule.

In some embodiments, ($A^1$-a) or ($A^1$-b) is selected from the group consisting of:

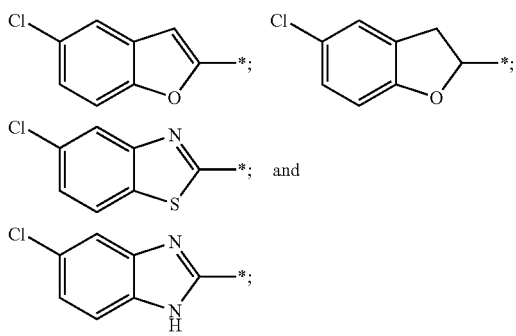

wherein the * represents the attachment point to the remainder of the molecule; and A² is

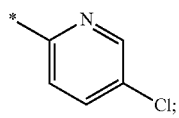 [SMILES: *c1ccc(Cl)cn1]

wherein the * represents the attachment point to the remainder of the molecule.

In some embodiments. (A¹-a) or (A¹-c) is selected from the group consisting of:

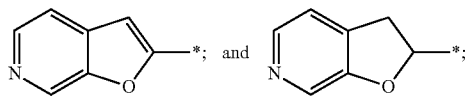

wherein the * represents the attachment point to the remainder of the molecule; and A² is selected from the group consisting of:

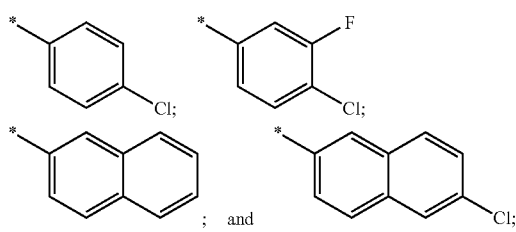

wherein the * represents the attachment point to the remainder of the molecule.

In some embodiments, (A¹-a) or (A¹-c) is selected from the group consisting of:

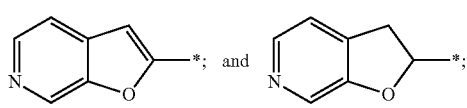

wherein the * represents the attachment point to the remainder of the molecule; and A² is selected from the group consisting of:

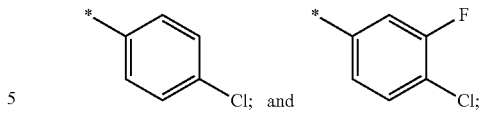

wherein the * represents the attachment point to the remainder of the molecule.

In some embodiments, (A¹-a) or (A¹-c) is selected from the group consisting of:

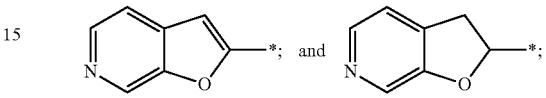

wherein the * represents the attachment point to the remainder of the molecule; and A² is selected from the group consisting of:

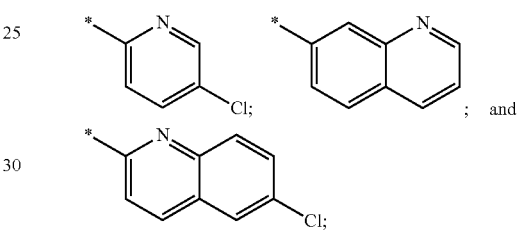

wherein the * represents the attachment point to the remainder of the molecule.

In some embodiments, (A¹-a) or (A¹-c) is selected from the group consisting of:

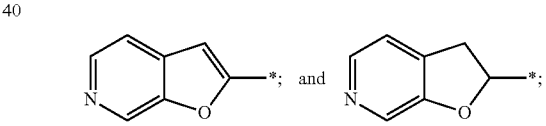

wherein the * represents the attachment point to the remainder of the molecule; and A² is

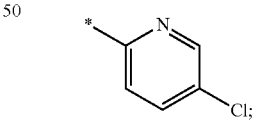

wherein the * represents the attachment point to the remainder of the molecule.

In some embodiments, A¹ is selected from the group consisting of:

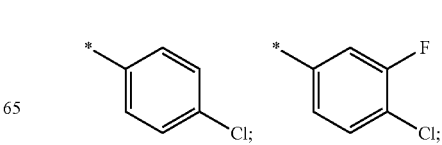

-continued

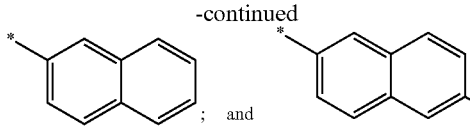

wherein the * represents the attachment point to the remainder of the molecule; and (A²-a) or (A²-b) is selected from the group consisting of:

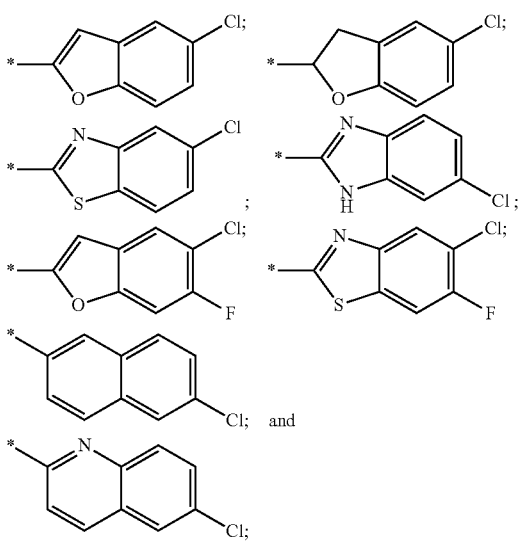

wherein the * represents the attachment point to the remainder of the molecule.

In some embodiments, $A^1$ is selected from the group consisting of:

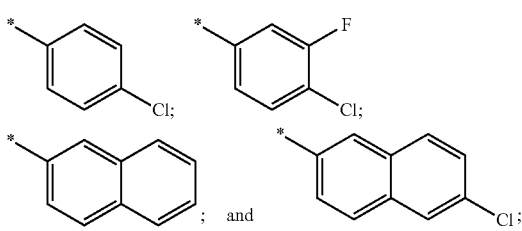

wherein the * represents the attachment point to the remainder of the molecule; and (A²-a) or (A²-b) is selected from the group consisting of:

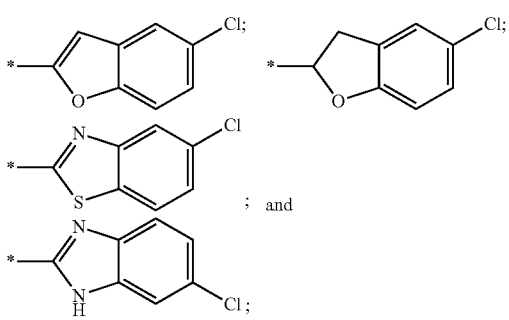

wherein the * represents the attachment point to the remainder of the molecule.

In some embodiments, $A^1$ is selected from the group consisting of:

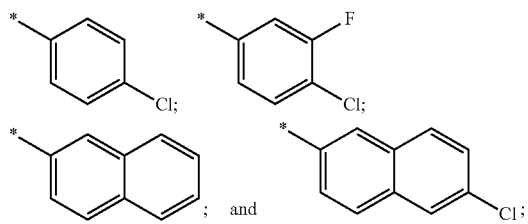

wherein the * represents the attachment point to the remainder of the molecule; and (A¹-a) or (A²-c) is selected from the group consisting of:

wherein the * represents the attachment point to the remainder of the molecule.

In some embodiments, $A^1$ is selected from the group consisting of:

wherein the * represents the attachment point to the remainder of the molecule; and (A²-a) or (A²-b) is selected from the group consisting of:

wherein the * represents the attachment point to the remainder of the molecule.

In some embodiments, $A^1$ is selected from the group consisting of:

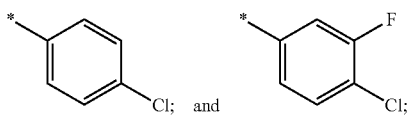

wherein the * represents the attachment point to the remainder of the molecule; and (A²-a) or (A²-b) is selected from the group consisting of:

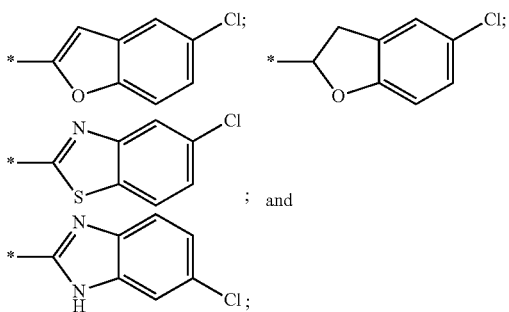

wherein the * represents the attachment point to the remainder of the molecule.

In some embodiments, A¹ is selected from the group consisting of:

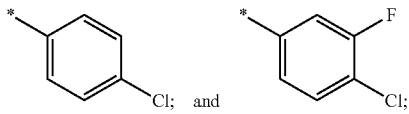

wherein the * represents the attachment point to the remainder of the molecule; and (A²-a) or (A²-c) is selected from the group consisting of:

wherein the * represents the attachment point to the remainder of the molecule.

In some embodiments. A¹ is selected from the group consisting of:

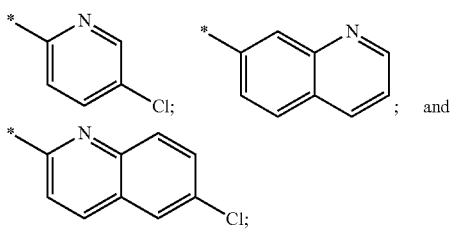

wherein the * represents the attachment point to the remainder of the molecule; and (A²-a) or (A²-b) is selected from the group consisting of:

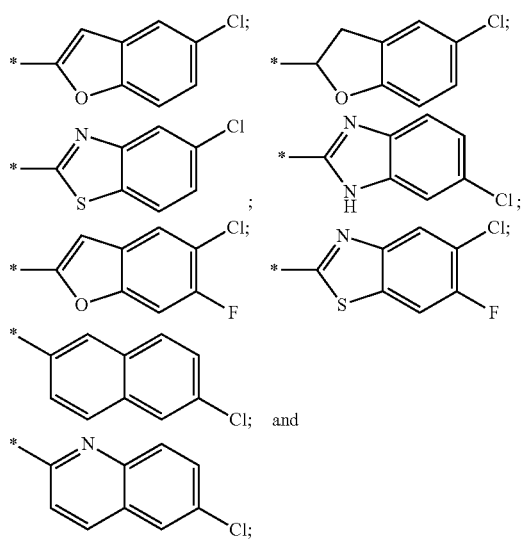

wherein the * represents the attachment point to the remainder of the molecule.

In some embodiments, A¹ is selected from the group consisting of:

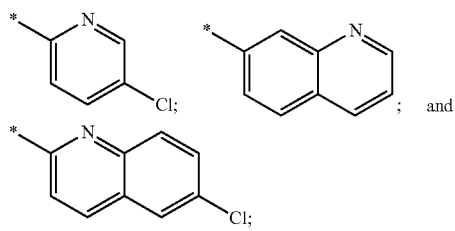

wherein the * represents the attachment point to the remainder of the molecule; and (A²-a) or (A²-b) is selected from the group consisting of:

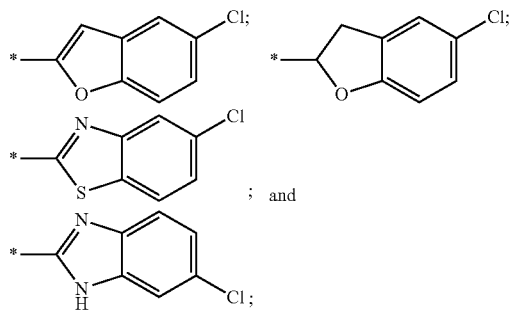

wherein the * represents the attachment point to the remainder of the molecule.

In some embodiments, A¹ is selected from the group consisting of:

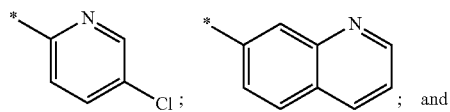

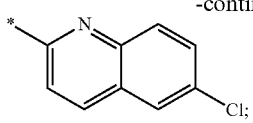

wherein the * represents the attachment point to the remainder of the molecule; and (A²-a) or (A²-c) is selected from the group consisting of:

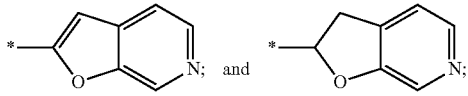 [SMILES: *c1cc2ccncc2o1 ; *C1Cc2ccncc2O1]

wherein the * represents the attachment point to the remainder of the molecule.

In some embodiments, A¹ is

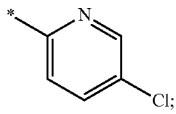

wherein the * represents the attachment point to the remainder of the molecule; and (A²-a) or (A²-b) is selected from the group consisting of:

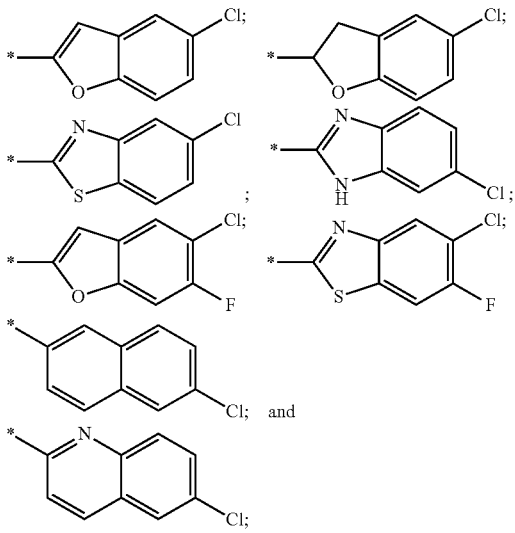

wherein the * represents the attachment point to the remainder of the molecule.

In some embodiments, A¹ is

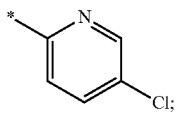 [SMILES: *c1ccc(Cl)cn1]

wherein the * represents the attachment point to the remainder of the molecule; and (A²-a) or (A²-b) is selected from the group consisting of:

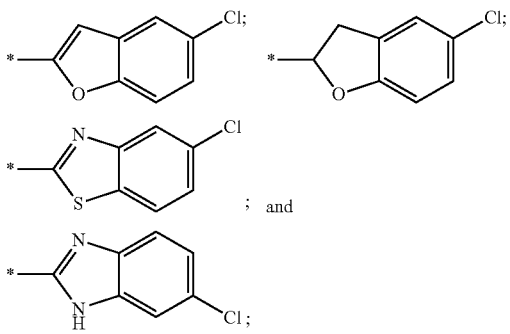

wherein the * represents the attachment point to the remainder of the molecule.

In some embodiments, A¹ is selected from the group consisting of:

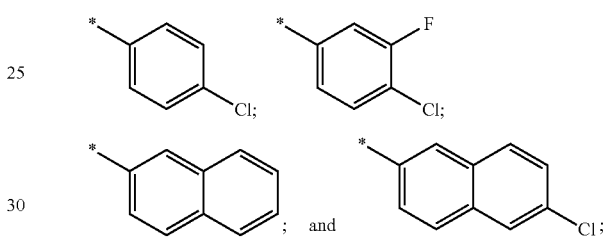

wherein the * represents the attachment point to the remainder of the molecule; and A² is selected from the group consisting of:

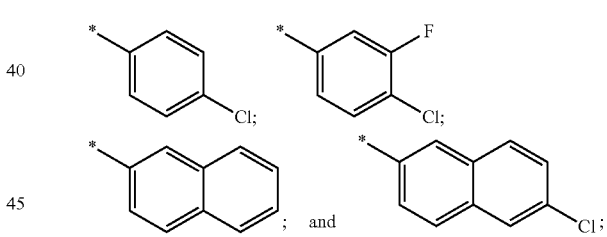

wherein the * represents the attachment point to the remainder of the molecule.

In some embodiments. A¹ is selected from the group consisting of:

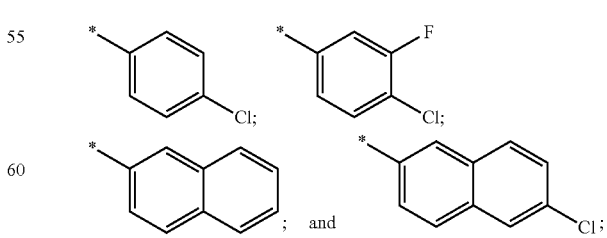

wherein the * represents the attachment point to the remainder of the molecule; and A² is selected from the group consisting of:

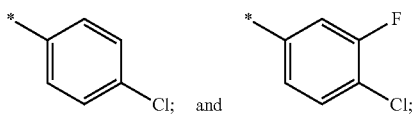

wherein the * represents the attachment point to the remainder of the molecule.

In some embodiments, $A^1$ is selected from the group consisting of:

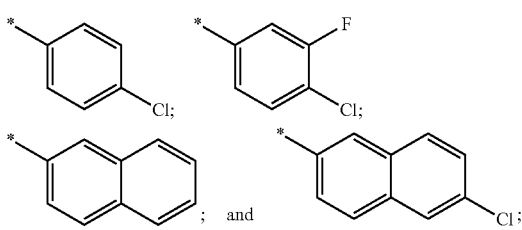

wherein the * represents the attachment point to the remainder of the molecule; and $A^2$ is selected from the group consisting of:

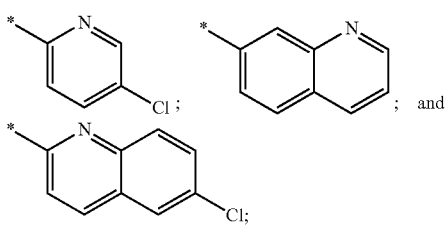

wherein the * represents the attachment point to the remainder of the molecule.

In some embodiments, $A^1$ is selected from the group consisting of:

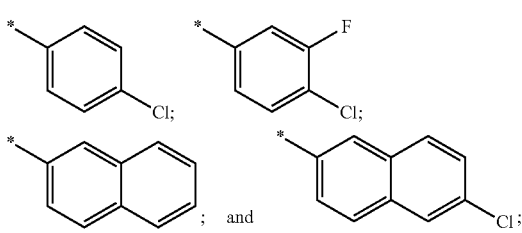

wherein the * represents the attachment point to the remainder of the molecule; and $A^2$ is

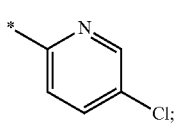

wherein the * represents the attachment point to the remainder of the molecule.

In some embodiments, $A^1$ is selected from the group consisting of:

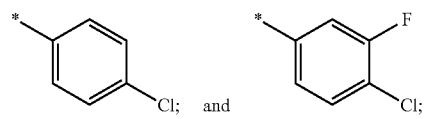

wherein the * represents the attachment point to the remainder of the molecule; and $A^2$ is selected from the group consisting of:

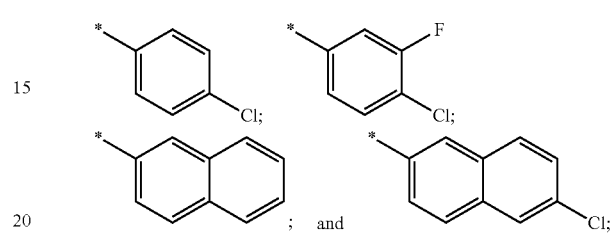

wherein the * represents the attachment point to the remainder of the molecule.

In some embodiments, A is selected from the group consisting of:

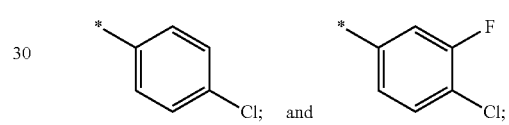

wherein the * represents the attachment point to the remainder of the molecule; and $A^2$ is selected from the group consisting of:

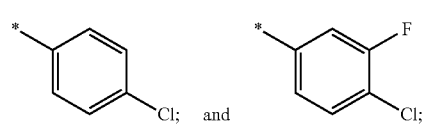 [SMILES: *c1ccc(Cl)cc1 ; "and" ; *c1ccc(Cl)c(F)c1]

wherein the * represents the attachment point to the remainder of the molecule.

In some embodiments, $A^1$ is selected from the group consisting of:

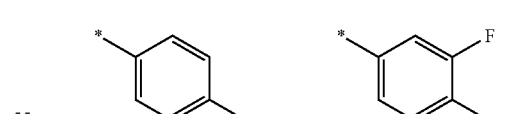

wherein the * represents the attachment point to the remainder of the molecule; $A^2$ is selected from the group consisting of:

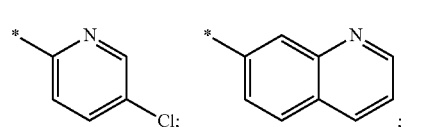

-continued

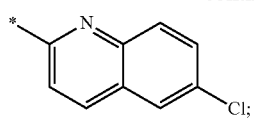

wherein the * represents the attachment point to the remainder of the molecule.

In some embodiments, A¹ is selected from the group consisting of:

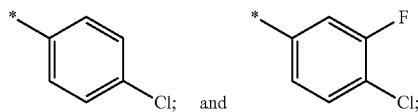 [SMILES: *c1ccc(Cl)cc1 ; "and" ; *c1ccc(Cl)c(F)c1]

wherein the * represents the attachment point to the remainder of the molecule; and A² is

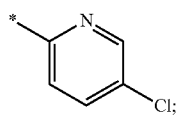

wherein the * represents the attachment point to the remainder of the molecule.

In some embodiments. A¹ is selected from the group consisting of:

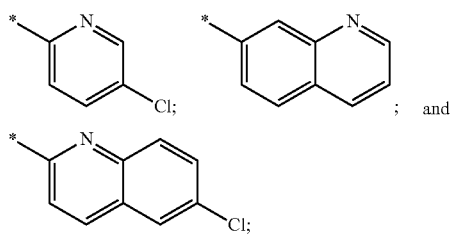

wherein the * represents the attachment point to the remainder of the molecule; and A² is selected from the group consisting of:

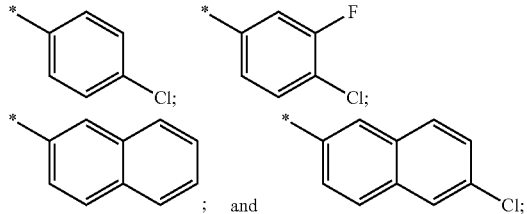

wherein the * represents the attachment point to the remainder of the molecule.

In some embodiments, A¹ is selected from the group consisting of:

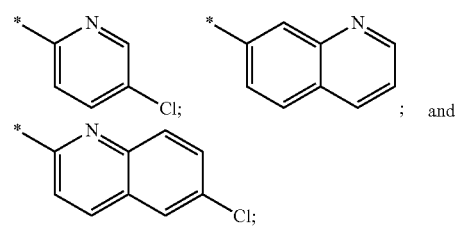

wherein the * represents the attachment point to the remainder of the molecule; and A² is selected from the group consisting of:

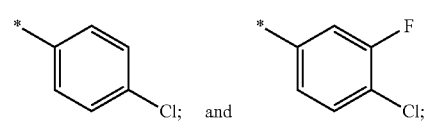 [SMILES: *c1ccc(Cl)cc1 ; "and" ; *c1ccc(Cl)c(F)c1]

wherein the * represents the attachment point to the remainder of the molecule.

In some embodiments, A¹ is selected from the group consisting of:

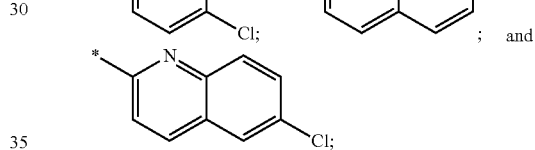

wherein the * represents the attachment point to the remainder of the molecule; A² is selected from the group consisting of:

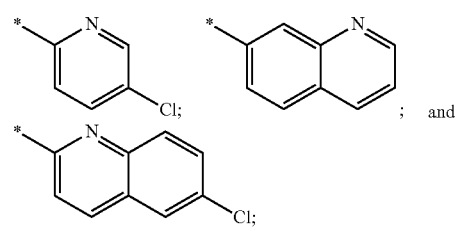

wherein the * represents the attachment point to the remainder of the molecule.

In some embodiments, A¹ is selected from the group consisting of:

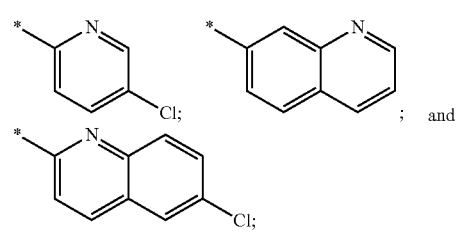

wherein the * represents the attachment point to the remainder of the molecule; and A² is

[structure: pyridine with Cl]

wherein the * represents the attachment point to the remainder of the molecule.

In some embodiments, A is

[structure: pyridine with Cl]

wherein the * represents the attachment point to the remainder of the molecule; and A² is selected from the group consisting of:

[structures: chlorophenyl, fluoro-chlorophenyl, naphthyl, and chloronaphthyl]

wherein the * represents the attachment point to the remainder of the molecule.

In some embodiments, A¹ is

[structure: pyridine with Cl]

wherein the * represents the attachment point to the remainder of the molecule; and A² is selected from the group consisting of:

[structures: chlorophenyl and fluoro-chlorophenyl]

wherein the * represents the attachment point to the remainder of the molecule.

In some embodiments, A¹ is

[structure: pyridine with Cl]

wherein the * represents the attachment point to the remainder of the molecule; and A² is selected from the group consisting of:

[structures: chloropyridine, chloroquinoline; and chloroquinoline]

wherein the * represents the attachment point to the remainder of the molecule.

In some embodiments, A¹ is

[structure: pyridine with Cl]

wherein the * represents the attachment point to the remainder of the molecule; and A² is

[structure: pyridine with Cl]

wherein the * represents the attachment point to the remainder of the molecule.

In some embodiments, the compound of formula (I) is a compound of formula (4-4):

$$A^1-O-\overset{\overset{R^{8a}}{|}\overset{O}{\|}}{\underset{\underset{R^{8b}}{|}\underset{O}{\|}}{S}}-\overset{R^{7a}}{\underset{R^{7b}}{|}}-Y^1-X^1\overset{R^{1a}\left[R^{4a}\right.}{\underset{R^{2a}\left[R^{3a}\right.}{\underset{R^{2b}\left[R^{3b}\right]_r}{|}}}\overset{R^{1b}\left[R^{4b}\right]_s}{\underset{R^{2b}\left[R^{3b}\right]_r}{|}}X^2-Y^2-\overset{R^{11a}}{\underset{R^{11b}}{|}}\overset{O}{\underset{O}{\|}}S-\overset{R^{12a}}{\underset{R^{12b}}{|}}-O-A^2$$ (4-4)

or a pharmaceutically acceptable salt thereof;
wherein:
  $A^1$ is $C_6$-$C_{10}$ aryl optionally substituted with one or more $R^{14}$ substituents; or 5-10 membered heteroaryl optionally substituted with one or more $R^{14}$ substituents;
  $A^2$ is $C_6$-$C_{10}$ aryl optionally substituted with one or more $R^{16}$ substituents; or 5-10 membered heteroaryl optionally substituted with one or more $R^{16}$ substituents;
  $R^{7a}$ and $R^{7b}$ are both hydrogen;
  $R^{8a}$ and $R^{8b}$ are both hydrogen;
  $R^{11a}$ and $R^{11b}$ are both hydrogen;
  $R^{12a}$ and $R^{12b}$ are both hydrogen;
  and wherein $X^1$, $X^2$, $Y^1$, $R^{Y1}$, $Y^2$, $R^{Y2}$, r, s, $R^{1a}$, $R^{1b}$, $R^{2a}$, $R^{2b}$, $R^{3a}$, $R^{3b}$, $R^{4a}$, $R^{4b}$, $R^{14}$, and $R^{16}$ are as defined in compounds of formula (I).

In some embodiments of the compounds of formula (4-4), $X^1$ is CH and $X^2$ is CH. In some embodiments, r is 1 and s is 1.

In some embodiments of the compounds of formula (4-4), $X^1$ is CH, $X^2$ is N and $Y^2$ is a bond. In some embodiments, r is 1 and s is 1. In some embodiments, r is 0 and s is 2.

In some embodiments of the compounds of formula (4-4), $X^1$ is N, $Y^1$ is a bond, and $X^2$ is CH. In some embodiments, r is 1 and s is 1. In some embodiments, r is 0 and s is 2.

In some embodiments of the compounds of formula (4-4), $X^1$ is N, $Y^1$ is a bond, $X^2$ is N and $Y^2$ is a bond. In some embodiments, r is 1 and s is 1. In some embodiments, r is 0 and s is 2.

In some embodiments of the compounds of formula (4-4), $A^1$ is $C_6$-$C_{10}$ aryl optionally substituted with one or more $R^{14}$ substituents. In some embodiments, $A^1$ is selected from the group consisting of:

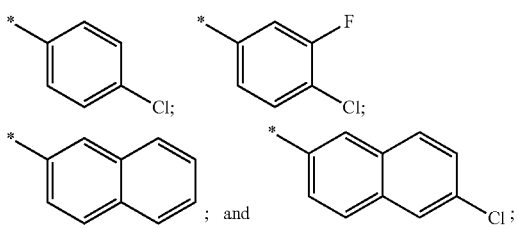

wherein the * represents the attachment point to the remainder of the molecule. In some embodiments, $A^1$ is phenyl optionally substituted with one or more $R^{14}$ substituents. In some embodiments, $A^1$ is selected from the group consisting of:

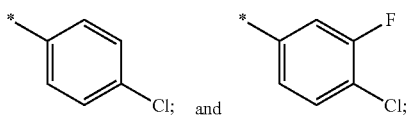

wherein the * represents the attachment point to the remainder of the molecule.

In some embodiments of the compounds of formula (4-4), $A^1$ is 5-10 membered heteroaryl optionally substituted with one or more $R^{14}$ substituents. In some embodiments, $A^1$ is selected from the group consisting of:

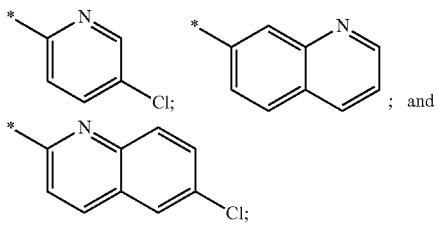

wherein the * represents the attachment point to the remainder of the molecule. In some embodiments, $A^1$ is pyridyl optionally substituted with one or more $R^{14}$ substituents. In some embodiments, $A^1$ is

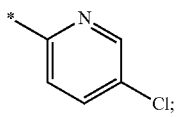 [SMILES: *c1ccc(Cl)cn1]

wherein the * represents the attachment point to the remainder of the molecule.

In some embodiments of the compounds of formula (4-4), $A^2$ is $C_6$-$C_{10}$ aryl optionally substituted with one or more $R^{16}$ substituents. In some embodiments, $A^2$ is selected from the group consisting of:

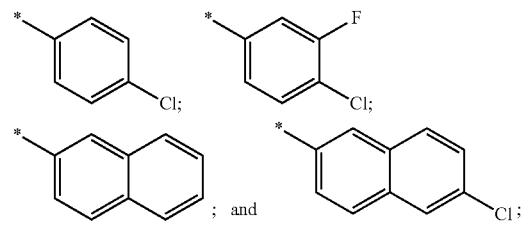

wherein the * represents the attachment point to the remainder of the molecule. In some embodiments, $A^2$ is phenyl optionally substituted with one or more $R^{16}$ substituents. In some embodiments, $A^2$ is selected from the group consisting of:

wherein the * represents the attachment point to the remainder of the molecule.

In some embodiments of the compounds of formula (4-4), $A^2$ is 5-10 membered heteroaryl optionally substituted with one or more $R^{16}$ substituents. In some embodiments, $A^2$ is selected from the group consisting of:

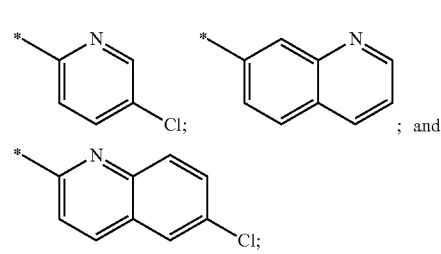

wherein the * represents the attachment point to the remainder of the molecule. In some embodiments, $A^2$ is pyridyl optionally substituted with one or more $R^{16}$ substituents. In some embodiments, $A^2$ is

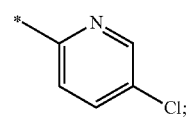

wherein the * represents the attachment point to the remainder of the molecule.

In some embodiments, ($A^1$-a) or ($A^1$-b) is selected from the group consisting of:

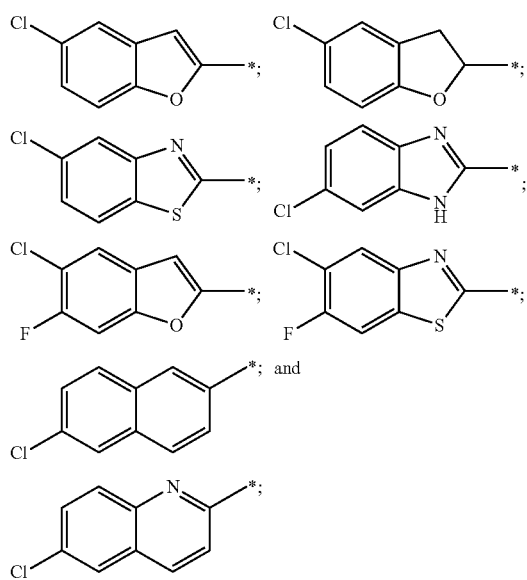

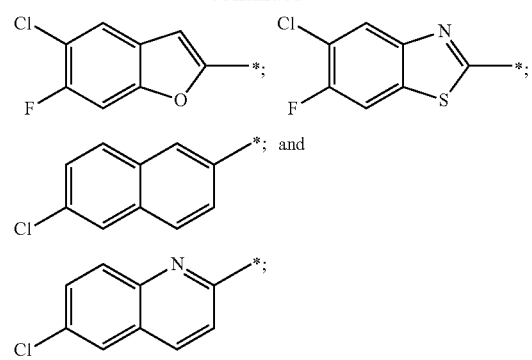

wherein the * represents the attachment point to the remainder of the molecule; and (A²-a) or (A²-b) is selected from the group consisting of:

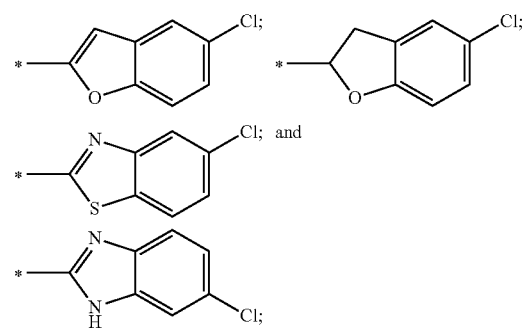

wherein the * represents the attachment point to the remainder of the molecule.

In some embodiments, (A¹-a) or (A¹-b) is selected from the group consisting of:

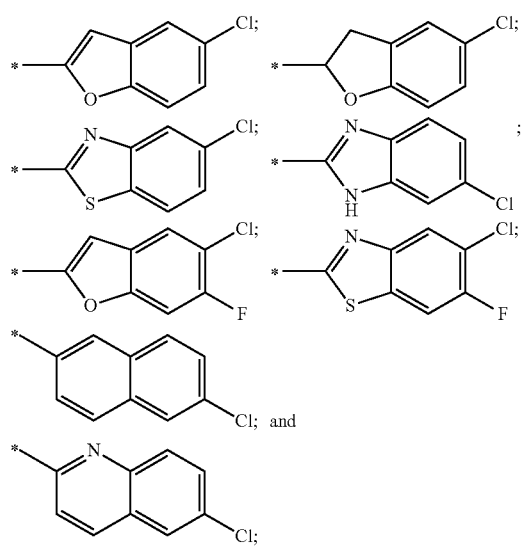

wherein the * represents the attachment point to the remainder of the molecule.

In some embodiments, (A¹-a) or (A¹-b) is selected from the group consisting of:

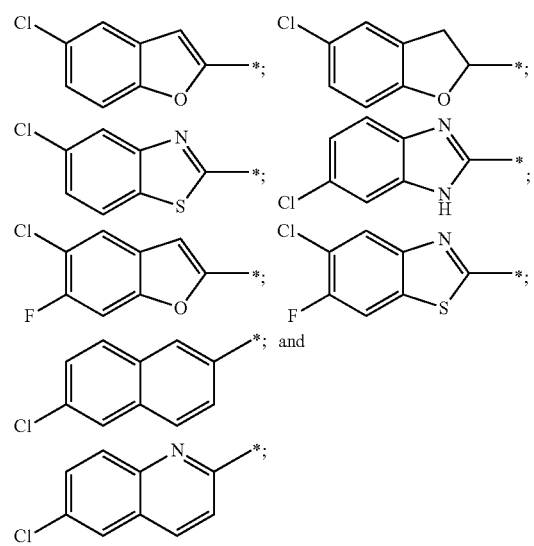

wherein the * represents the attachment point to the remainder of the molecule; and (A²-a) or (A²-c) is selected from the group consisting of:

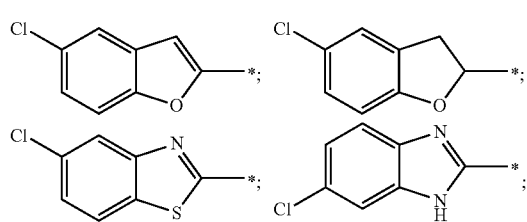

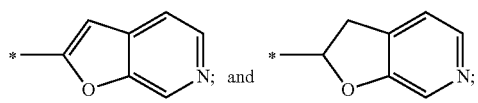

wherein the * represents the attachment point to the remainder of the molecule.

In some embodiments, A-a) or (A¹-b) is selected from the group consisting of:

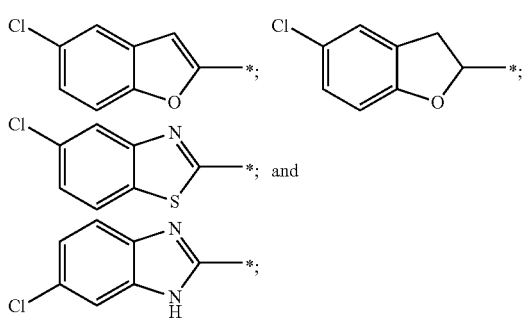

wherein the * represents the attachment point to the remainder of the molecule; and (A²-a) or (A²-b) is selected from the group consisting of:

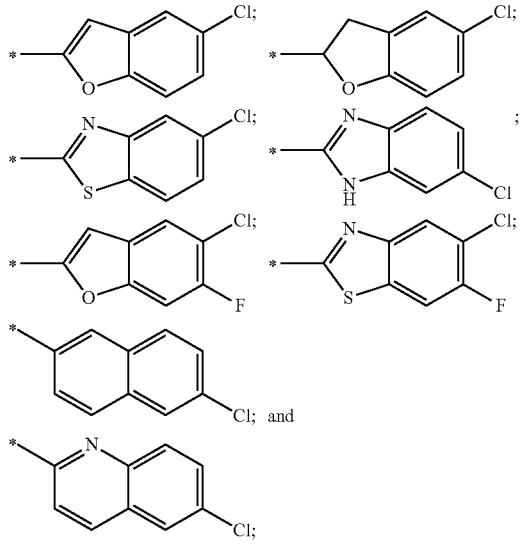

wherein the * represents the attachment point to the remainder of the molecule.

In some embodiments, (A¹-a) or (A¹-b) is selected from the group consisting of:

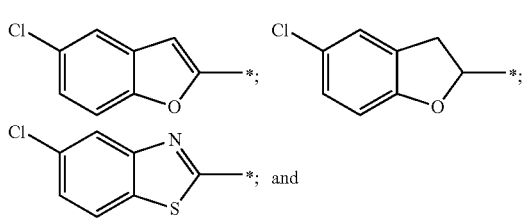

-continued

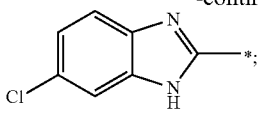

wherein the * represents the attachment point to the remainder of the molecule; and (A²-a) or (A²-b) is selected from the group consisting of:

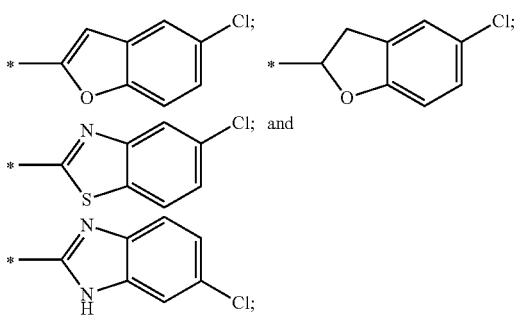

wherein the * represents the attachment point to the remainder of the molecule.

In some embodiments, (A¹-a) or (A¹-b) is selected from the group consisting of:

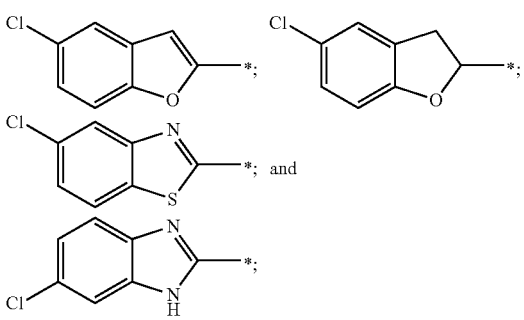

wherein the * represents the attachment point to the remainder of the molecule; and (A²-a) or (A²-c) is selected from the group consisting of:

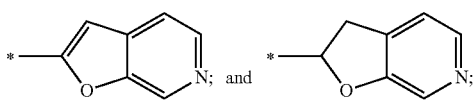

wherein the * represents the attachment point to the remainder of the molecule.

In some embodiments, (A¹-a) or (A¹-c) is selected from the group consisting of:

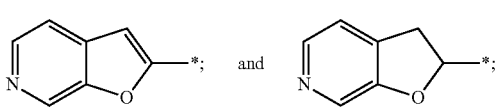

wherein the * represents the attachment point to the remainder of the molecule; and (A²-a) or (A²-b) is selected from the group consisting of:

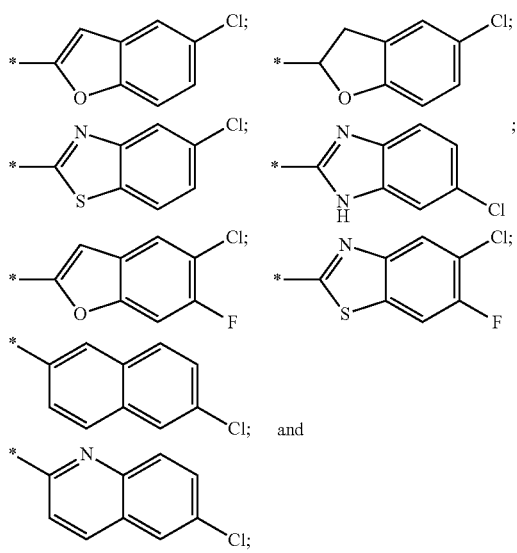

wherein the * represents the attachment point to the remainder of the molecule.

In some embodiments, (A¹-a) or (A¹-c) is selected from the group consisting of:

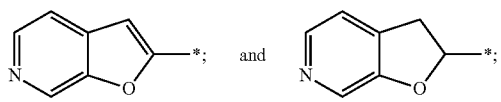

wherein the * represents the attachment point to the remainder of the molecule; and (A¹-a) or (A²-b) is selected from the group consisting of:

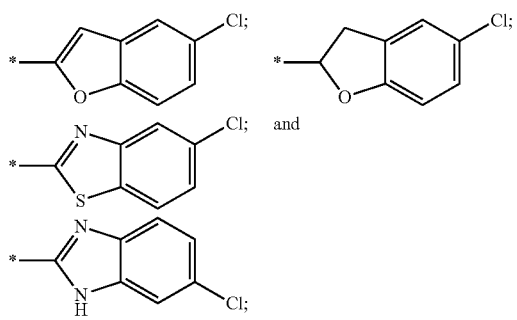

wherein the * represents the attachment point to the remainder of the molecule.

In some embodiments, (A¹-a) or (A¹-c) is selected from the group consisting of:

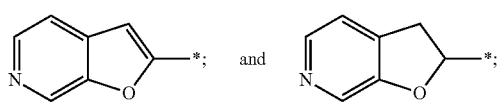

wherein the * represents the attachment point to the remainder of the molecule; and (A²-a) or (A²-c) is selected from the group consisting of:

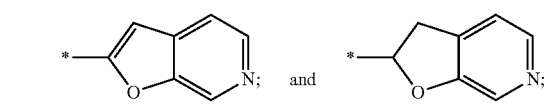 [SMILES: *c1cc2ccncc2o1 ; *C1Cc2ccncc2O1]

wherein the * represents the attachment point to the remainder of the molecule.

In some embodiments, (A¹-a) or (A¹-b) is selected from the group consisting of:

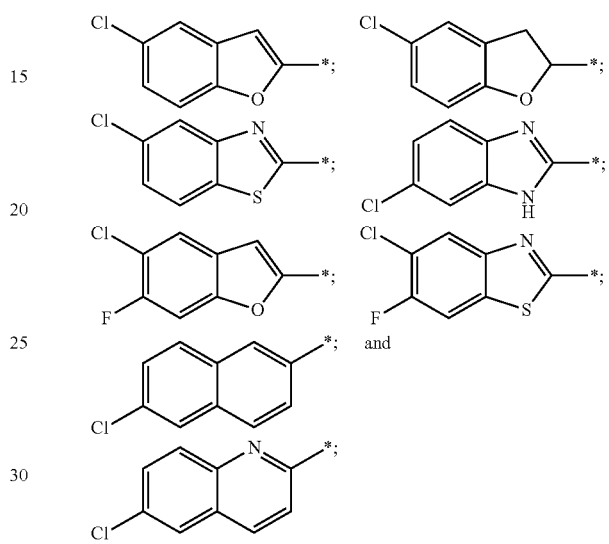

wherein the * represents the attachment point to the remainder of the molecule; and A² is selected from the group consisting of:

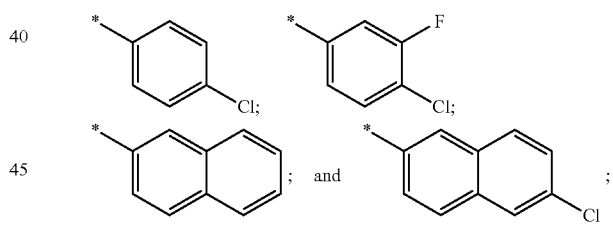

wherein the * represents the attachment point to the remainder of the molecule;

In some embodiments, (A¹-a) or (A¹-b) is selected from the group consisting of:

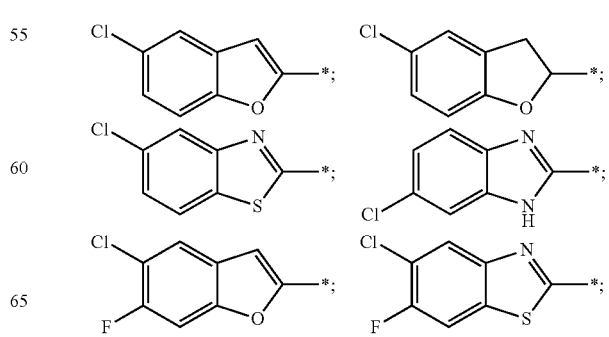

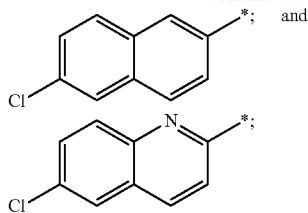

wherein the * represents the attachment point to the remainder of the molecule; and A² is selected from the group consisting of:

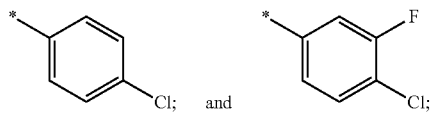

wherein the * represents the attachment point to the remainder of the molecule.

In some embodiments, (A¹-a) or (A¹-b) is selected from the group consisting of:

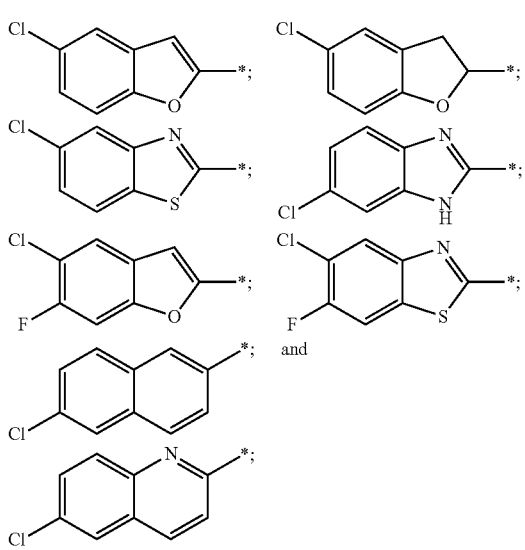

wherein the * represents the attachment point to the remainder of the molecule; and A² is selected from the group consisting of:

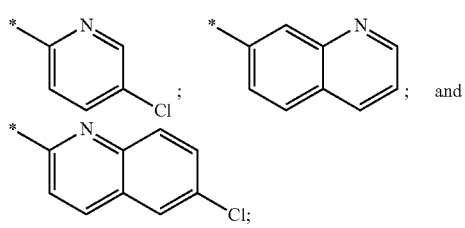

wherein the * represents the attachment point to the remainder of the molecule.

In some embodiments, (A¹-a) or (A¹-b) is selected from the group consisting of:

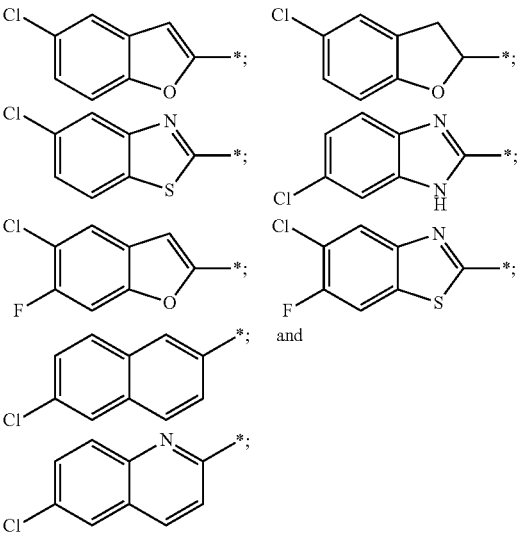

wherein the * represents the attachment point to the remainder of the molecule; and A² is

*—[pyridine]—Cl;

wherein the * represents the attachment point to the remainder of the molecule.

In some embodiments, (A¹-a) or (A¹-b) is selected from the group consisting of:

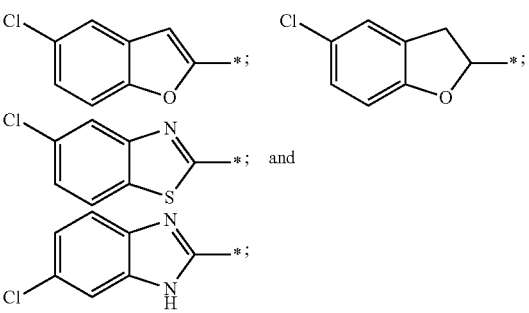

wherein the * represents the attachment point to the remainder of the molecule; and A² is selected from the group consisting of:

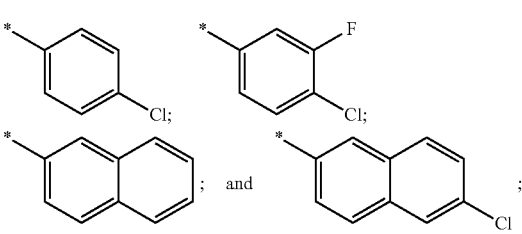

wherein the * represents the attachment point to the remainder of the molecule.

In some embodiments, (A¹-a) or (A¹-b) is selected from the group consisting of:

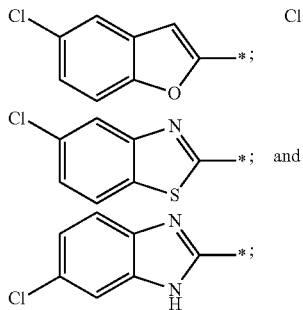

wherein the * represents the attachment point to the remainder of the molecule; and A² is selected from the group consisting of:

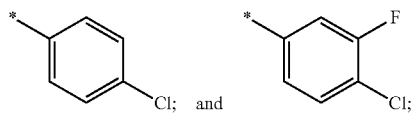

wherein the * represents the attachment point to the remainder of the molecule.

In some embodiments, (A¹-a) or (A¹-b) is selected from the group consisting of:

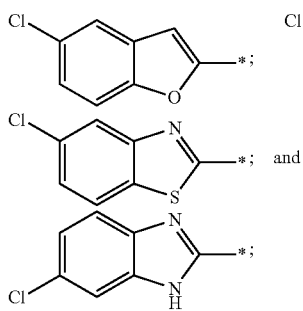

wherein the * represents the attachment point to the remainder of the molecule; and A² is selected from the group consisting of:

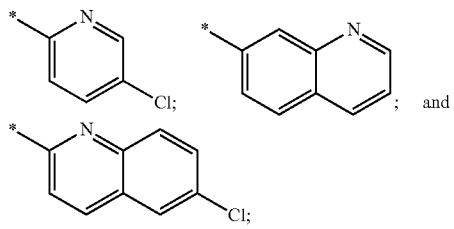

wherein the * represents the attachment point to the remainder of the molecule.

In some embodiments, (A¹-a) or (A¹-b) is selected from the group consisting of:

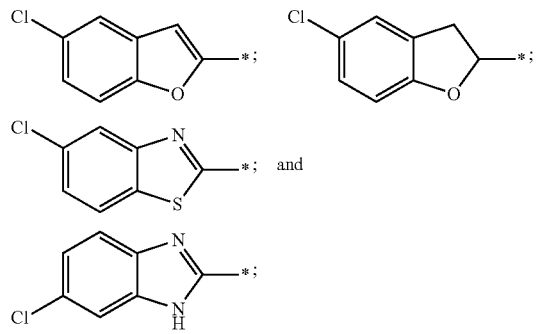

wherein the * represents the attachment point to the remainder of the molecule; and A² is

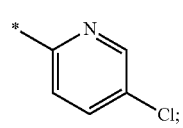

wherein the * represents the attachment point to the remainder of the molecule.

In some embodiments, (A¹-a) or (A¹-c) is selected from the group consisting of:

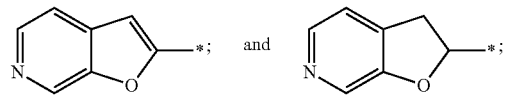 [SMILES: *c1cc2ccncc2o1 ; *C1Cc2ccncc2O1]

wherein the * represents the attachment point to the remainder of the molecule; and A² is selected from the group consisting of:

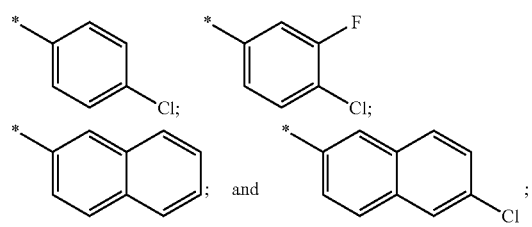

wherein the * represents the attachment point to the remainder of the molecule.

In some embodiments, (A¹-a) or (A¹-c) is selected from the group consisting of:

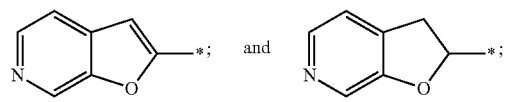 [SMILES: *c1cc2ccncc2o1 ; *C1Cc2ccncc2O1]

wherein the * represents the attachment point to the remainder of the molecule; and A² is selected from the group consisting of:

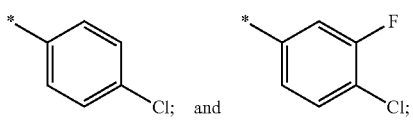

wherein the * represents the attachment point to the remainder of the molecule.

In some embodiments, (A¹-a) or (A¹-c) is selected from the group consisting of:

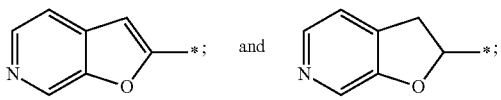 [SMILES: *c1cc2ccncc2o1 ; *C1Cc2ccncc2O1]

wherein the * represents the attachment point to the remainder of the molecule; and A² is selected from the group consisting of:

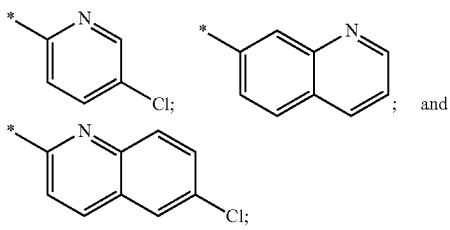

wherein the * represents the attachment point to the remainder of the molecule.

In some embodiments, (A¹-a) or (A¹-c) is selected from the group consisting of:

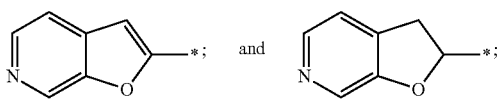 [SMILES: *c1cc2ccncc2o1 ; *C1Cc2ccncc2O1]

wherein the * represents the attachment point to the remainder of the molecule; and A² is

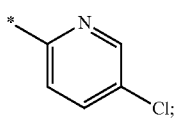

wherein the * represents the attachment point to the remainder of the molecule.

In some embodiments. A¹ is selected from the group consisting of:

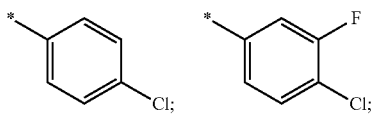

wherein the * represents the attachment point to the remainder of the molecule; and (A¹-a) or (A²-b) is selected from the group consisting of:

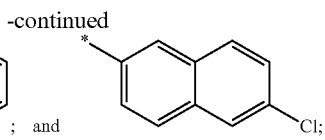

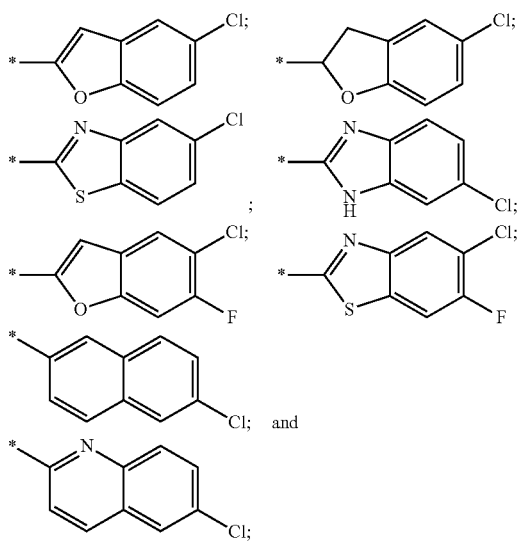

wherein the * represents the attachment point to the remainder of the molecule.

In some embodiments, A¹ is selected from the group consisting of:

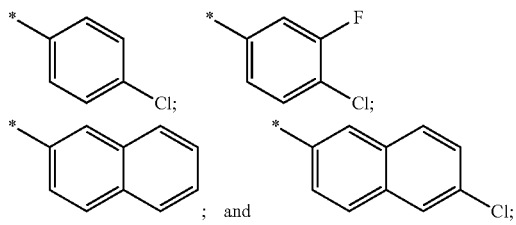

wherein the * represents the attachment point to the remainder of the molecule; and (A²-a) or (A²-b) is selected from the group consisting of:

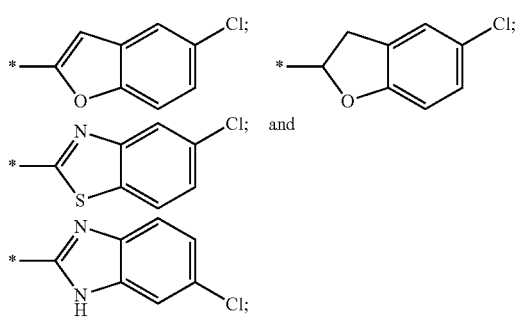

wherein the * represents the attachment point to the remainder of the molecule.

In some embodiments, $A^1$ is selected from the group consisting of:

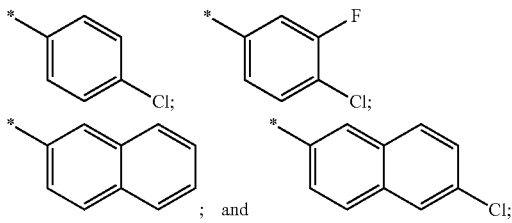

wherein the * represents the attachment point to the remainder of the molecule; and ($A^2$-a) or ($A^2$-c) is selected from the group consisting of:

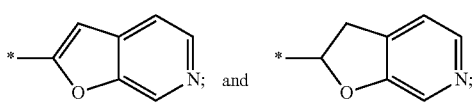

wherein the * represents the attachment point to the remainder of the molecule.

In some embodiments, $A^1$ is selected from the group consisting of:

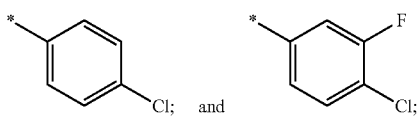

wherein the * represents the attachment point to the remainder of the molecule; and ($A^2$-a) or ($A^2$-b) is selected from the group consisting of:

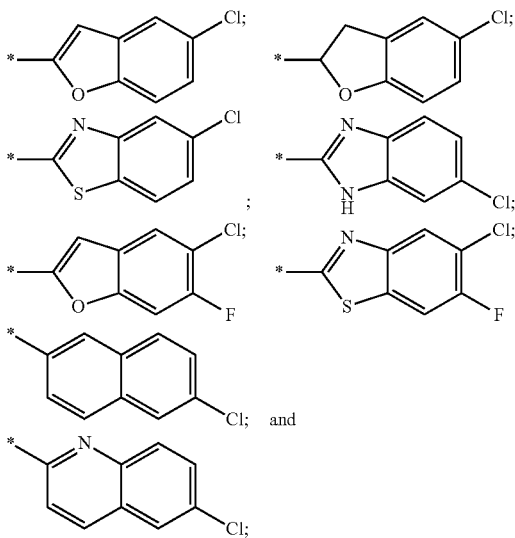

wherein the * represents the attachment point to the remainder of the molecule.

In some embodiments, $A^1$ is selected from the group consisting of:

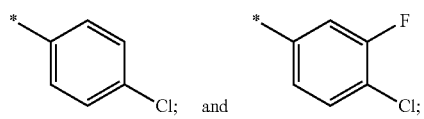

wherein the * represents the attachment point to the remainder of the molecule; and ($A^2$-a) or ($A^2$-b) is selected from the group consisting of:

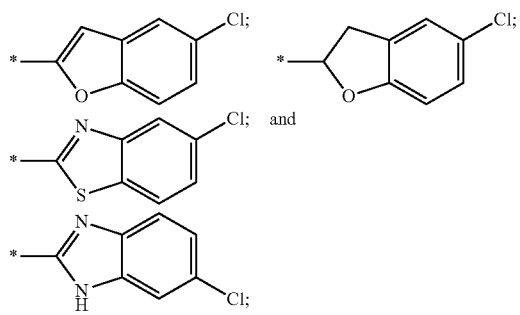

wherein the * represents the attachment point to the remainder of the molecule.

In some embodiments, $A^1$ is selected from the group consisting of:

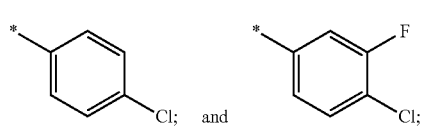

wherein the * represents the attachment point to the remainder of the molecule; and ($A^2$-a) or ($A^2$-c) is selected from the group consisting of:

wherein the * represents the attachment point to the remainder of the molecule.

In some embodiments, $A^1$ is selected from the group consisting of:

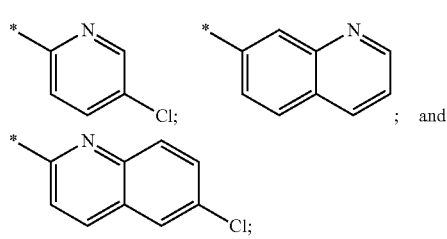

wherein the * represents the attachment point to the remainder of the molecule; and ($A^2$-a) or ($A^2$-b) is selected from the group consisting of:

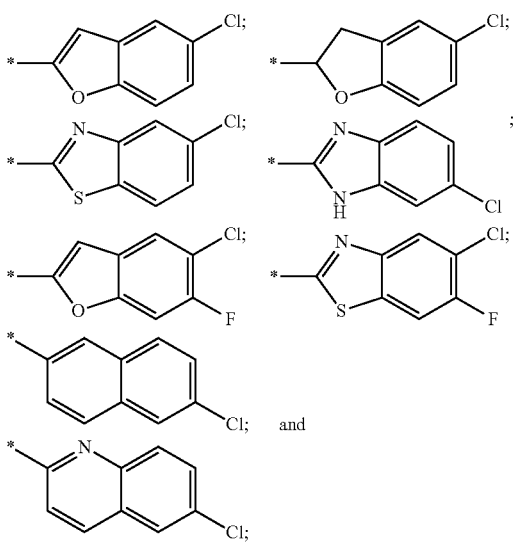

wherein the * represents the attachment point to the remainder of the molecule.

In some embodiments, $A^1$ is selected from the group consisting of:

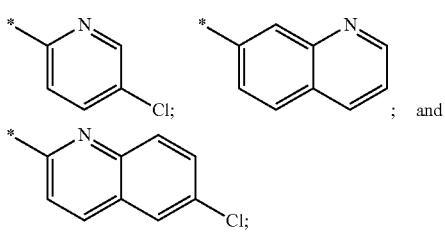

wherein the * represents the attachment point to the remainder of the molecule; and ($A^2$-a) or ($A^2$-b) is selected from the group consisting of:

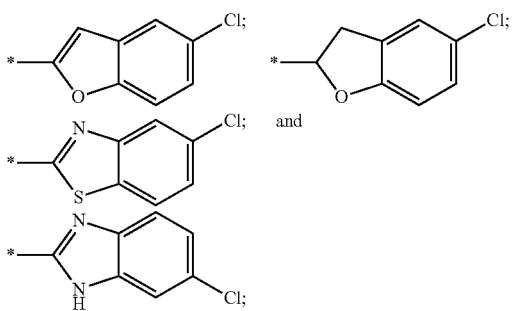

wherein the * represents the attachment point to the remainder of the molecule.

In some embodiments, $A^1$ is selected from the group consisting of:

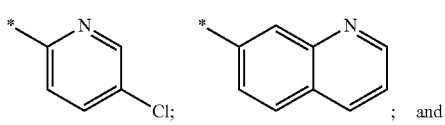

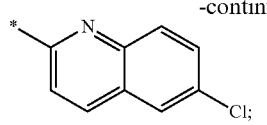

wherein the * represents the attachment point to the remainder of the molecule; and ($A^2$-a) or ($A^2$-c) is selected from the group consisting of:

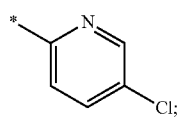

wherein the * represents the attachment point to the remainder of the molecule.

In some embodiments, $A^1$ is

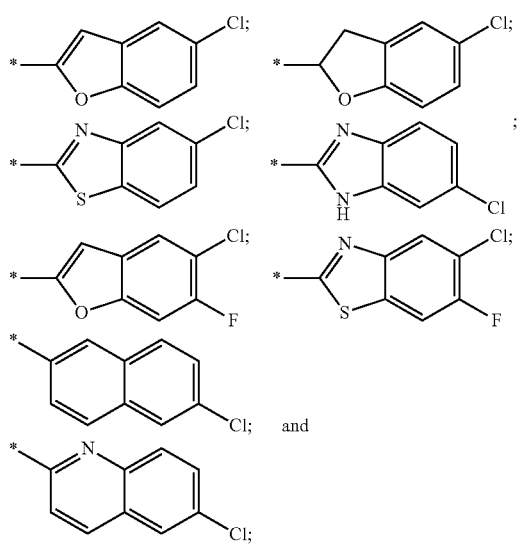

wherein the * represents the attachment point to the remainder of the molecule; and ($A^2$-a) or ($A^2$-b) is selected from the group consisting of:

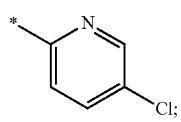

wherein the * represents the attachment point to the remainder of the molecule.

In some embodiments, $A^1$ is wherein the * represents the attachment point to the remainder of the molecule; and ($A^2$-a) or ($A^2$-b) is selected from the group consisting of:

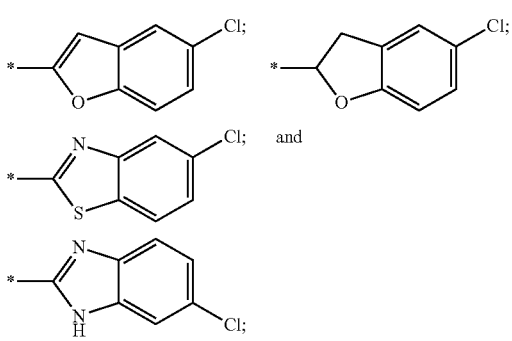

wherein the * represents the attachment point to the remainder of the molecule.

In some embodiments. $A^1$ is selected from the group consisting of:

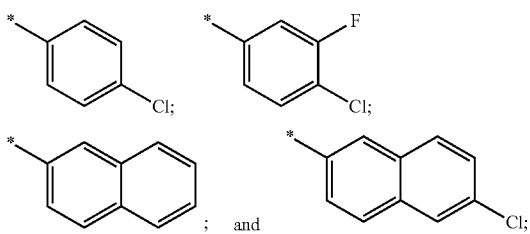

wherein the * represents the attachment point to the remainder of the molecule; and $A^2$ is selected from the group consisting of:

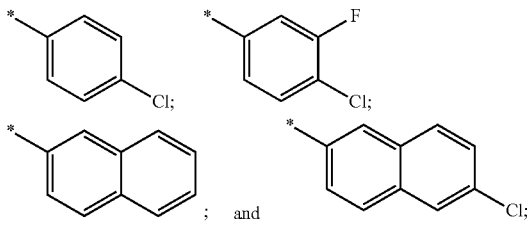

wherein the * represents the attachment point to the remainder of the molecule.

In some embodiments, $A^1$ is selected from the group consisting of:

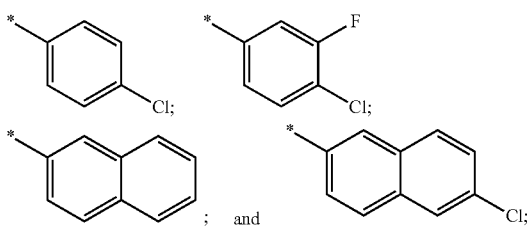

wherein the * represents the attachment point to the remainder of the molecule; and A is selected from the group consisting of:

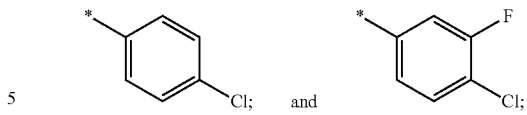

wherein the * represents the attachment point to the remainder of the molecule.

In some embodiments, $A^1$ is selected from the group consisting of:

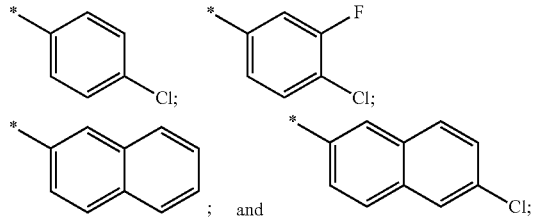

wherein the * represents the attachment point to the remainder of the molecule; and $A^2$ is selected from the group consisting of:

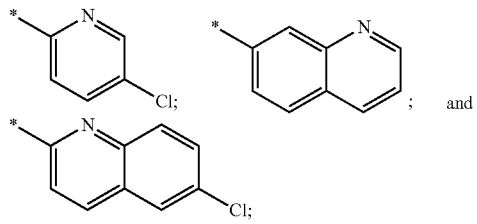

wherein the * represents the attachment point to the remainder of the molecule.

In some embodiments, $A^1$ is selected from the group consisting of:

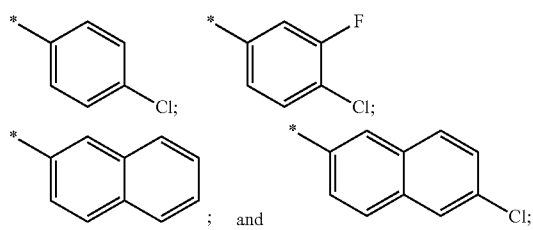

wherein the * represents the attachment point to the remainder of the molecule; and $A^2$ is

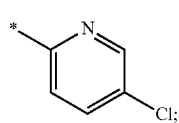

wherein the * represents the attachment point to the remainder of the molecule.

In some embodiments, $A^1$ is selected from the group consisting of:

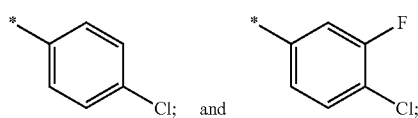

wherein the * represents the attachment point to the remainder of the molecule; and $A^2$ is selected from the group consisting of:

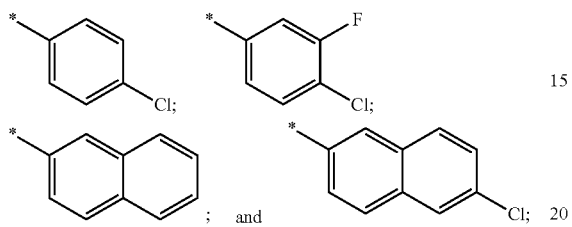

wherein the * represents the attachment point to the remainder of the molecule.

In some embodiments, $A^1$ is selected from the group consisting of:

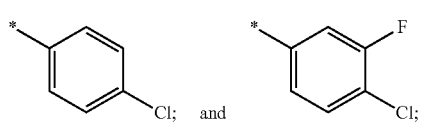

wherein the * represents the attachment point to the remainder of the molecule; and $A^2$ is selected from the group consisting of:

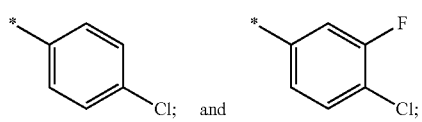 [SMILES: *c1ccc(Cl)cc1 ; "and" ; *c1ccc(Cl)c(F)c1]

wherein the * represents the attachment point to the remainder of the molecule.

In some embodiments, $A^1$ is selected from the group consisting of:

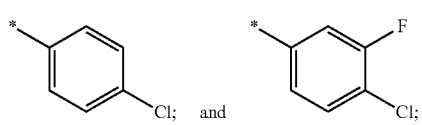 [SMILES: *c1ccc(Cl)cc1 ; "and" ; *c1ccc(Cl)c(F)c1]

wherein the * represents the attachment point to the remainder of the molecule; $A^2$ is selected from the group consisting of:

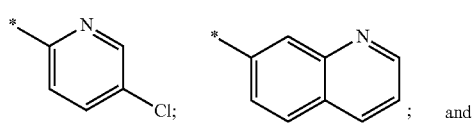

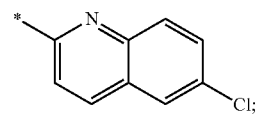

wherein the * represents the attachment point to the remainder of the molecule.

In some embodiments, $A^1$ is selected from the group consisting of:

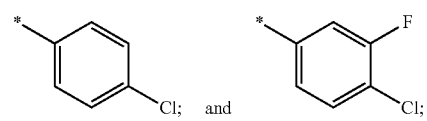

wherein the * represents the attachment point to the remainder of the molecule; and $A^2$ is

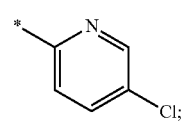

wherein the * represents the attachment point to the remainder of the molecule.

In some embodiments, $A^1$ is selected from the group consisting of:

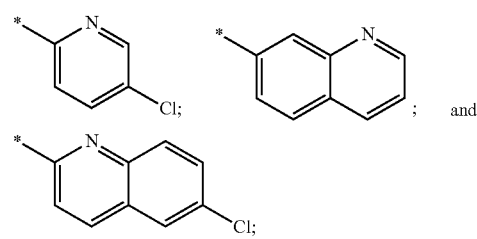

wherein the * represents the attachment point to the remainder of the molecule; and $A^2$ is selected from the group consisting of:

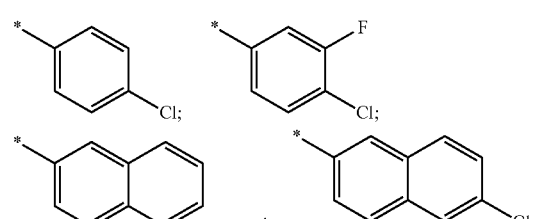

wherein the * represents the attachment point to the remainder of the molecule.

In some embodiments, $A^1$ is selected from the group consisting of:

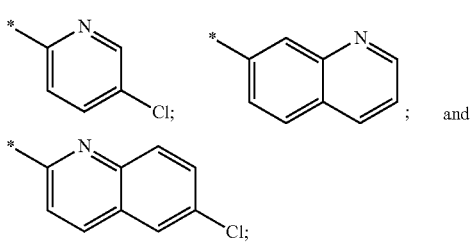

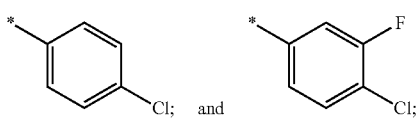

wherein the * represents the attachment point to the remainder of the molecule; and A² is selected from the group consisting of:

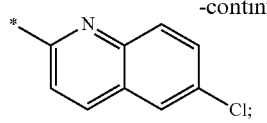

wherein the * represents the attachment point to the remainder of the molecule.

In some embodiments, A¹ is selected from the group consisting of:

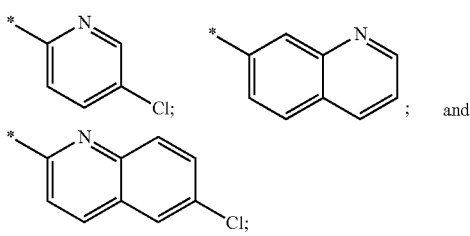

wherein the * represents the attachment point to the remainder of the molecule; A² is selected from the group consisting of:

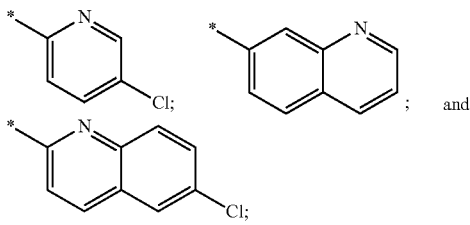

wherein the * represents the attachment point to the remainder of the molecule.

In some embodiments, A¹ is selected from the group consisting of:

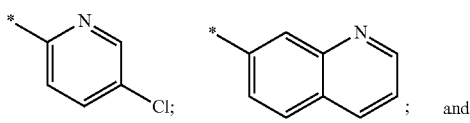

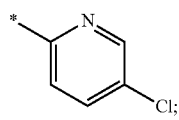 [SMILES: *c1ccc(Cl)cn1]

wherein the * represents the attachment point to the remainder of the molecule; and A² is

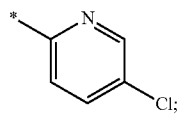 [SMILES: *c1ccc(Cl)cn1]

wherein the * represents the attachment point to the remainder of the molecule.

In some embodiments, A¹ is

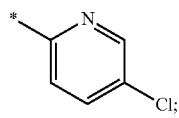

wherein the * represents the attachment point to the remainder of the molecule; and A² is selected from the group consisting of:

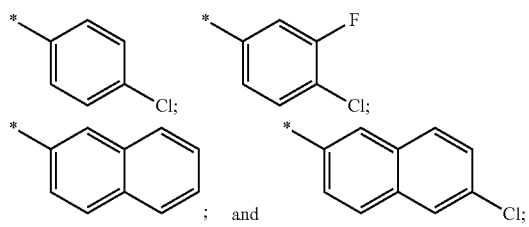

wherein the * represents the attachment point to the remainder of the molecule.

In some embodiments, A¹ is

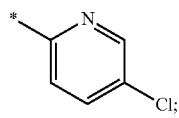

wherein the * represents the attachment point to the remainder of the molecule; and A² is selected from the group consisting of:

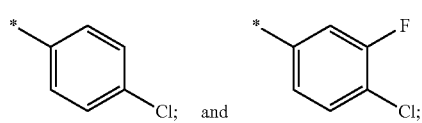

wherein the * represents the attachment point to the remainder of the molecule.

In some embodiments, $A^1$ is

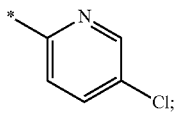 [SMILES: *c1ccc(Cl)cn1]

wherein the * represents the attachment point to the remainder of the molecule; and $A^2$ is selected from the group consisting of:

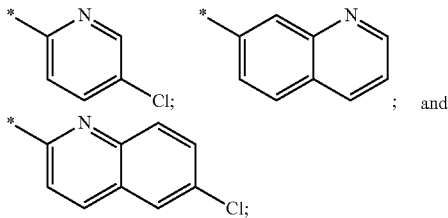

wherein the * represents the attachment point to the remainder of the molecule.

In some embodiments, $A^1$ is

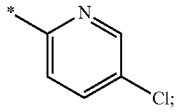

wherein the * represents the attachment point to the remainder of the molecule; and $A^2$ is

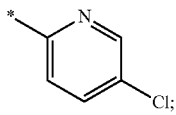 [SMILES: *c1ccc(Cl)cn1]

wherein the * represents the attachment point to the remainder of the molecule.

In one aspect, provided is a compound of formula (II):

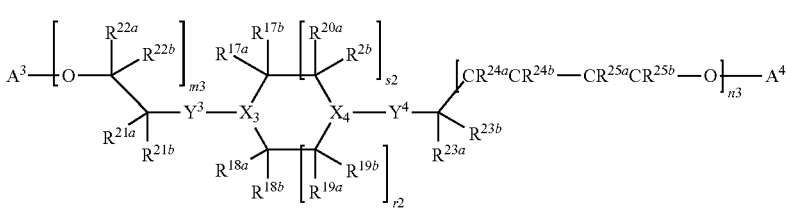

or a pharmaceutically acceptable salt thereof;
wherein:
m3 is 0 or 1;
n3 is 0 or 1;
r2 is 0, 1, or 2;
s2 is 0, 1, or 2;
$X^3$ is CH or N;
$X^4$ is CH or N;
provided that at least one of $X^3$ and $X^4$ is CH;
$Y^3$ is selected from the group consisting of a bond, $NR^{Y3}$, and O;
wherein $R^{Y3}$ is hydrogen or $C_1$-$C_6$ alkyl;
$Y^4$ is selected from the group consisting of a bond, $NR^{Y4}$, and O;
wherein $R^{Y4}$ is hydrogen or $C_1$-$C_6$ alkyl;
provided that:
when $X^3$ is N, then $Y^3$ is a bond and m3 is 1;
when $X^4$ is N, then $Y^4$ is a bond and n3 is 1;
$A^3$ is selected from the group consisting of:
a substituent of the formula ($A^3$-a)

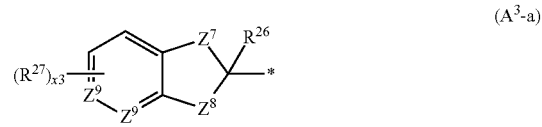

wherein
represents the attachment point to the remainder of the molecule; $Z^7$ is selected from the group consisting of $CR^{Z7-1}R^{Z7-2}$, $NR^{Z7-2}$, O, S, and —$CR^{Z7-1}$=$CR^{Z7-1}$—;
wherein
$R^{Z7-1}$ is H or $R^{27}$; and
$R^{Z7-2}$ is H or $R^{27}$;
$Z^8$ is selected from the group consisting of $CR^{Z8-1}R^{Z8-2}$, $NR^{Z8-2}$; O, S, and —$CR^{Z8-1}$=$CR^{Z8-1}$—;
wherein
$R^{Z8-1}$ is H or $R^{27}$; and
$R^{Z8-2}$ is H or $R^{27}$;
$Z^9$, independently at each occurrence, is C or N, provided that at least one $Z^9$ is C;
$R^{26}$ is hydrogen or $R^{27}$, or $R^{26}$ and $R^{Z7-2}$ are taken together to form a double bond between the carbon atom bearing $R^{26}$ and $Z^7$; and x3 is 0, 1, 2, 3, or 4, provided than when one $Z^9$ is N, then x3 is not 4;
$C_6$-$C_{10}$ aryl optionally substituted with one or more $R^{27}$ substituent; and
5-10 membered heteroaryl optionally substituted with one or more $R^{27}$ substituent; $R^{27}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —$NH_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —$NR^{27-a}R^{27-b}$, —CN, —C(O)OH, —C(O)O($C_1$-$C_6$ alkyl), —C(O)O($C_1$-$C_6$ haloalkyl), —C(O)$NH_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)$NR^{27-a}R^{27-b}$, —S(O)$_2$OH, —S(O)$_2$O(C$_1$-C$_6$ alkyl), —S(O)$_2$O(C$_1$-C$_6$ haloalkyl), —S(O)$_2$NH$_2$, —S(O)$_2$NH(C$_1$-C$_6$ alkyl), —S(O)$_2$NH(C$_1$-C$_6$ haloalkyl), —S(O)$_2$N(C$_1$-C$_6$ alkyl)$_2$, —S(O)$_2$N(C$_1$-C$_6$ haloalkyl)$_2$, —S(O)$_2$NR$^{27-a}$ R$^{27-b}$, —OC(O)H, —OC(O)(C$_1$-C$_6$ alkyl), —OC(O)(C$_1$-C$_6$ haloalkyl), —N(H)C(O)H, —N(H)C(O)(C$_1$-C$_6$ alkyl), —N(H)C(O)(C$_1$-C$_6$ haloalkyl), —N(C$_1$-C$_6$ alkyl)C(O)H, —N(C$_1$-C$_6$ alkyl)C(O)(C$_1$-C$_6$ alkyl), —N(C$_1$-C$_6$ alkyl)C(O)(C$_1$-C$_6$ haloalkyl), —N(C$_1$-C$_6$ haloalkyl)C(O)H, —N(C$_1$-C$_6$ haloalkyl)C(O)(C$_1$-C$_6$ alkyl), —N(C$_1$-C$_6$ haloalkyl)C(O)(C$_1$-C$_6$ haloalkyl), —OS(O)$_2$(C$_1$-C$_6$ alkyl), —OS(O)$_2$(C$_1$-C$_6$ haloalkyl), —N(H)S(O)$_2$(C$_1$-C$_6$ alkyl), —N(H)S(O)$_2$(C$_1$-C$_6$ haloalkyl), —N(C$_1$-C$_6$ alkyl)S(O)$_2$(C$_1$-C$_6$ alkyl), —N(C$_1$-C$_6$ alkyl)S(O)$_2$(C$_1$-C$_6$ haloalkyl), —N(C$_1$-C$_6$ haloalkyl)S(O)$_2$(C$_1$-C$_6$ alkyl), and —N(C$_1$-C$_6$ haloalkyl)S(O)$_2$(C$_1$-C$_6$ haloalkyl);

wherein R$^{27-a}$ and R$^{27-b}$ are taken together with the nitrogen atom which bears them to form a 3-10 membered heterocycle;

A$^4$ is selected from the group consisting of:

a substituent of the formula (A$^4$-a)

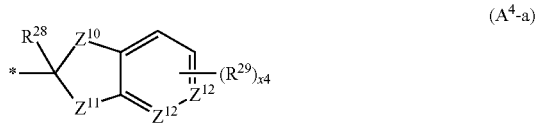

(A$^4$-a)

wherein
represents the attachment point to the remainder of the molecule;
Z$^{10}$ is selected from the group consisting of CR$^{Z10-1}$R$^{Z10-2}$, NR$^{Z10-2}$, O, S, and —CR$^{Z10-1}$=CR$^{Z10-1}$—;
wherein
R$^{Z10-1}$ is H or R$^{29}$; and
R$^{Z10-2}$ is H or R$^{29}$;
Z$^{11}$ is selected from the group consisting of CR$^{Z11-1}$R$^{Z11-2}$, NR$^{Z11-2}$, O, S, and —CR$^{Z11-1}$=CR$^{Z11-1}$—;
wherein
R$^{Z11-1}$ is H or R$^{29}$; and
R$^{Z11-2}$ is H or R$^{29}$;
Z$^{12}$, independently at each occurrence, is C or N, provided that at least one Z$^{12}$ is C;
R$^{28}$ is hydrogen or R$^{29}$, or R$^{28}$ and R$^{Z10-2}$ are taken together to form a double bond between the carbon atom bearing R$^{28}$ and Z$^{10}$; and x4 is 0, 1, 2, 3, or 4, provided than when one Z$^{12}$ is N, then x4 is not 4;
C$_6$-C$_{10}$ aryl optionally substituted with one or more R$^{29}$ substituent; and
5-10 membered heteroaryl optionally substituted with one or more R$^{29}$ substituent; R$^{29}$ is selected, independently at each occurrence, from the group consisting of halogen, C$_1$-C$_6$ alkyl, C$_1$-C$_6$ haloalkyl, —OH, —O(C$_1$-C$_6$ alkyl), —O(C$_1$-C$_6$ haloalkyl), —SH, —S(C$_1$-C$_6$ alkyl), —S(C$_1$-C$_6$ haloalkyl), —NH$_2$, —NH(C$_1$-C$_6$ alkyl), —NH(C$_1$-C$_6$ haloalkyl), —N(C$_1$-C$_6$ alkyl)$_2$, —N(C$_1$-C$_6$ haloalkyl)$_2$, —NR$^{29-a}$R$^{29-b}$, —CN, —C(O)OH, —C(O)O(C$_1$-C$_6$ alkyl), —C(O)O(C$_1$-C$_6$ haloalkyl), —C(O)NH$_2$, —C(O)NH(C$_1$-C$_6$ alkyl), —C(O)NH(C$_1$-C$_6$ haloalkyl), —C(O)N(C$_1$-C$_6$ alkyl)$_2$, —C(O)N(C$_1$-C$_6$ haloalkyl)$_2$, —C(O)NR$^{29-a}$R$^{29-b}$, —S(O)$_2$OH, —S(O)$_2$O(C$_1$-C$_6$ alkyl), —S(O)$_2$O(C$_1$-C$_6$ haloalkyl), —S(O)$_2$NH$_2$, —S(O)$_2$NH(C$_1$-C$_6$ alkyl), —S(O)$_2$NH(C$_1$-C$_6$ haloalkyl), —S(O)$_2$N(C$_1$-C$_6$ alkyl)$_2$, —S(O)$_2$N(C$_1$-C$_6$ haloalkyl)$_2$, —S(O)$_2$NR$^{29-a}$ R$^{29-b}$, —OC(O)H, —OC(O)(C$_1$-C$_6$ alkyl), —OC(O)(C$_1$-C$_6$ haloalkyl), —N(H)C(O)H, —N(H)C(O)(C$_1$-C$_6$ alkyl), —N(H)C(O)(C$_1$-C$_6$ haloalkyl), —N(C$_1$-C$_6$ alkyl)C(O)H, —N(C$_1$-C$_6$ alkyl)C(O)(C$_1$-C$_6$ alkyl), —N(C$_1$-C$_6$ alkyl)C(O)(C$_1$-C$_6$ haloalkyl), —N(C$_1$-C$_6$ haloalkyl)C(O)H, —N(C$_1$-C$_6$ haloalkyl)C(O)(C$_1$-C$_6$ alkyl), —N(C$_1$-C$_6$ haloalkyl)C(O)(C$_1$-C$_6$ haloalkyl), —OS(O)$_2$(C$_1$-C$_6$ alkyl), —OS(O)$_2$(C$_1$-C$_6$ haloalkyl), —N(H)S(O)$_2$(C$_1$-C$_6$ alkyl), —N(H)S(O)$_2$(C$_1$-C$_6$ haloalkyl), —N(C$_1$-C$_6$ alkyl)S(O)$_2$(C$_1$-C$_6$ alkyl), —N(C$_1$-C$_6$ alkyl)S(O)$_2$(C$_1$-C$_6$ haloalkyl), —N(C$_1$-C$_6$ haloalkyl)S(O)$_2$(C$_1$-C$_6$ alkyl), and —N(C$_1$-C$_6$ haloalkyl)S(O)$_2$(C$_1$-C$_6$ haloalkyl);

wherein R$^{29-a}$ and R$^{29-b}$ are taken together with the nitrogen atom which bears them to form a 3-10 membered heterocycle;

R$^{17a}$ and R$^{17b}$ are independently selected from the group consisting of hydrogen, C$_1$-C$_6$ alkyl, and halogen;

R$^{18a}$ and R$^{18b}$ are independently selected from the group consisting of hydrogen, C$_1$-C$_6$ alkyl, and halogen;

when present, R$^{19a}$ and R$^{19b}$ are independently at each occurrence selected from the group consisting of hydrogen, C$_1$-C$_6$ alkyl, and halogen;

when present, R$^{20a}$ and R$^{20b}$ are independently at each occurrence selected from the group consisting of hydrogen, C$_1$-C$_6$ alkyl, and halogen;

or alternatively, R$^{17a}$ and R$^{18a}$ are taken together to form a C$_1$-C$_6$ alkylene moiety;

or alternatively, R$^{17a}$ and an R$^{19a}$ moiety, when present, are taken together to form a C$_1$-C$_6$ alkylene moiety, and R$^{17b}$ and the R$^{19b}$ in the geminal position to the R$^{19a}$ taken together with R$^{17a}$, are both hydrogen;

or alternatively, an R$^{19a}$ moiety, when present, and an R$^{20a}$ moiety, when present, are taken together to form a C$_1$-C$_6$ alkylene moiety, and the R$^{19b}$ in the geminal position to the R$^{19a}$ taken together with the R$^{20a}$ moiety and the R$^{20b}$ in the geminal position to the R$^{20a}$ taken together with the R$^{19a}$ moiety, are both hydrogen;

R$^{21a}$ and R$^{21b}$ are taken together to form an oxo (=O) substituent or an imido (=NH) substituent, or alternatively, R$^{21a}$ and R$^{21b}$ are both hydrogen;

when present, R$^{22a}$ and R$^{22b}$ are both hydrogen;

R$^{23a}$ and R$^{23b}$ are taken together to form an oxo (=O) substituent or an imido (=NH) substituent, or alternatively, R$^{23a}$ and R$^{23b}$ are both hydrogen;

when present, R$^{24a}$ is selected from the group consisting of hydrogen, —OH, and —NH$_2$;

or alternatively, R$^{24a}$ and R$^{Y4}$ are taken together to form a #—C(=O)—O— group, wherein # represent the attachment point to the nitrogen atom bearing R$^{Y4}$;

when present, R$^{24b}$ is hydrogen; and when present, R$^{25a}$ and R$^{25b}$ are both hydrogen;

or alternatively, R$^{25a}$, when present, and one R$^{29}$ of A$^4$ are taken together with the atoms connecting them to form a 5-6 membered heterocycloalkenyl optionally substituted with one or more R$^{29}$ substituent, and R$^{25b}$ is H;

or alternatively, R$^{25a}$, when present, R$^{25b}$, when present, and one R$^{29}$ of A$^4$ are taken together with the atoms connecting them to form a 5-6 membered heteroaryl optionally substituted with one or more R$^{29}$ substituent;

and further provided that one of (i), (ii), (iii) and (iv) applies:

(i) when m3 is 0 and n3 is 0, then:
$X^3$ is CH and $Y^3$ is $NR^{Y3}$;
$X^4$ is CH and $Y^4$ is $NR^{Y4}$;
$R^{21a}$ and $R^{21b}$ are taken together to form an oxo (=O) substituent;
$R^{23a}$ and $R^{23b}$ are taken together to form an oxo (=O) substituent;
$A^3$ is a substituent of the formula ($A^3$-a)

$$(R^{27})_{x3} \overset{Z^7}{\underset{Z^9\ Z^9\ Z^8}{\diagram}} \overset{R^{26}}{*} \quad (A^3\text{-}a)$$

wherein
represents the attachment point to the remainder of the molecule;
$Z^7$ is selected from the group consisting of $CR^{Z7\text{-}1}R^{Z7\text{-}2}$, $NR^{Z7\text{-}2}$, O, S, and —$CR^{Z7\text{-}1}$=$CR^{Z7\text{-}1}$—;
wherein
$R^{Z7\text{-}1}$ is H or $R^{27}$; and
$R^{Z7\text{-}2}$ is H or $R^{27}$;
$Z^8$ is selected from the group consisting of $CR^{Z8\text{-}1}R^{Z8\text{-}2}$, $NR^{Z8\text{-}2}$; O, S, and —$CR^{Z8\text{-}1}$=$CR^{Z8\text{-}1}$—;
wherein
$R^{Z8\text{-}1}$ is H or $R^{27}$; and
$R^{Z8\text{-}2}$ is H or $R^{27}$;
$Z^9$, independently at each occurrence, is C or N, provided that at least one $Z^9$ is C;
$R^{26}$ is hydrogen or $R^{27}$, or $R^{26}$ and $R^{Z7\text{-}2}$ are taken together to form a double bond between the carbon atom bearing $R^{26}$ and $Z^7$;
$R^{27}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —$NH_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —$NR^{27\text{-}a}R^{27\text{-}b}$, —CN, —C(O)OH, —C(O)O($C_1$-$C_6$ alkyl), —C(O)O($C_1$-$C_6$ haloalkyl), —C(O)$NH_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)$NR^{27\text{-}a}R^{27\text{-}b}$, —S(O)$_2$OH, —S(O)$_2$O($C_1$-$C_6$ alkyl), —S(O)$_2$O($C_1$-$C_6$ haloalkyl), —S(O)$_2NH_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2NR^{27\text{-}a}R^{27\text{-}b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);

wherein $R^{27\text{-}a}$ and $R^{27\text{-}b}$ are taken together with the nitrogen atom which bears them to form a 3-10 membered heterocycle;
x3 is 0, 1, 2, 3, or 4, provided than when one $Z^9$ is N, then x3 is not 4;
$A^4$ is a substituent of the formula ($A^4$-a)

$$\overset{R^{28}}{*}\underset{Z^{11}\ Z^{12}}{\overset{Z^{10}}{\diagram}}\overset{}{}(R^{29})_{x4} \quad (A^4\text{-}a)$$

wherein
represents the attachment point to the remainder of the molecule;
$Z^{10}$ is selected from the group consisting of $CR^{Z10\text{-}1}R^{Z10\text{-}2}$, $NR^{Z10\text{-}2}$, O, S, and —$CR^{Z10\text{-}1}$=$CR^{Z10\text{-}1}$—;
wherein
$R^{Z10\text{-}1}$ is H or $R^{29}$; and
$R^{Z10\text{-}2}$ is H or $R^{29}$;
$Z^{11}$ is selected from the group consisting of $CR^{Z11\text{-}1}R^{Z11\text{-}2}$, $NR^{Z11\text{-}2}$; O, S, and —$CR^{Z11\text{-}1}$=$CR^{Z11\text{-}1}$—;
wherein
$R^{Z11\text{-}1}$ is H or $R^{29}$; and
$R^{Z11\text{-}2}$ is H or $R^{29}$;
$Z^{12}$, independently at each occurrence, is C or N, provided that at least one $Z^{12}$ is C;
$R^{28}$ is hydrogen or $R^{29}$, or $R^{28}$ and $R^{Z10\text{-}2}$ are taken together to form a double bond between the carbon atom bearing $R^{28}$ and $Z^{10}$;
$R^{29}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —$NH_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —$NR^{29\text{-}a}R^{29\text{-}b}$, —CN, —C(O)OH, —C(O)O($C_1$-$C_6$ alkyl), —C(O)O($C_1$-$C_6$ haloalkyl), —C(O)$NH_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)$NR^{29\text{-}a}R^{29\text{-}b}$, —S(O)$_2$OH, —S(O)$_2$O($C_1$-$C_6$ alkyl), —S(O)$_2$O($C_1$-$C_6$ haloalkyl), —S(O)$_2NH_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2NR^{29\text{-}a}R^{29\text{-}b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);

wherein $R^{29-a}$ and $R^{29-b}$ are taken together with the nitrogen atom which bears them to form a 3-10 membered heterocycle;

x4 is 0, 1, 2, 3, or 4, provided than when one $Z^{12}$ is N, then x4 is not 4; and provided that $A^3$ and $A^4$ are not both simultaneously a moiety selected from group consisting of:

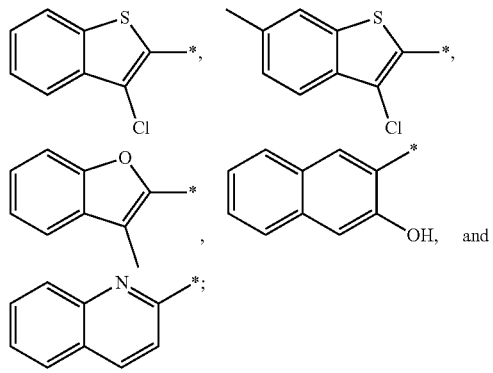

wherein the * represents the attachment point to the remainder of the molecule;

(ii) when m3 is 0 and n3 is 1, then:
r2 is 1 or 2;
s2 is 1 or 2;
$X^3$ is CH and $Y^3$ is $NR^{Y3}$;
$R^{21a}$ and $R^{21b}$ are taken together to form an oxo (=O) substituent;
$R^{24a}$ is selected from the group consisting of hydrogen, —OH, and —NH$_2$;
$A^3$ is a substituent of the formula ($A^3$-a)

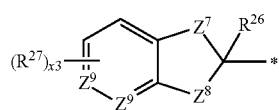

(A$^3$-a)

wherein
represents the attachment point to the remainder of the molecule;
$Z^7$ is selected from the group consisting of $CR^{Z7-1}R^{Z7-2}$, $NR^{Z7-2}$, O, S, and —$CR^{Z7-1}$=$CR^{Z7-1}$—;
wherein
$R^{Z7-1}$ is H or $R^{27}$; and
$R^{Z7-2}$ is H or $R^{27}$;
$Z^8$ is selected from the group consisting of $CR^{Z8-1}R^{Z8-2}$, $NR^{Z8-2}$; O, S, and —$CR^{Z8-1}$=$CR^{Z8-1}$—;
wherein
$R^{Z8-1}$ is H or $R^{27}$; and
$R^{Z8-2}$ is H or $R^{27}$;
$Z^9$, independently at each occurrence, is C or N, provided that at least one $Z^9$ is C;
$R^{26}$ is hydrogen or $R^{27}$, or $R^{26}$ and $R^{Z7-2}$ are taken together to form a double bond between the carbon atom bearing $R^{26}$ and $Z^7$;
$R^{27}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —NH$_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —$NR^{27-a}R^{27-b}$, —CN, —C(O)OH, —C(O)O($C_1$-$C_6$ alkyl), —C(O)O($C_1$-$C_6$ haloalkyl), —C(O)NH$_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)$NR^{27-a}R^{27-b}$, —S(O)$_2$OH, —S(O)$_2$O($C_1$-$C_6$ alkyl), —S(O)$_2$O($C_1$-$C_6$ haloalkyl), —S(O)$_2$NH$_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$$NR^{27-a}R^{27-b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);

wherein $R^{27-a}$ and $R^{27-b}$ are taken together with the nitrogen atom which bears them to form a 3-10 membered heterocycle;

x3 is 0, 1, 2, 3, or 4, provided than when one $Z^9$ is N, then x3 is not 4;

$A^4$ is $C_6$-$C_{10}$ aryl optionally substituted with one or more $R^{29}$ substituent, or 5-10 membered heteroaryl optionally substituted with one or more $R^{29}$ substituent;

$R^{29}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —NH$_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —$NR^{29-a}R^{29-b}$, —CN, —C(O)OH, —C(O)O($C_1$-$C_6$ alkyl), —C(O)O($C_1$-$C_6$ haloalkyl), —C(O)NH$_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)$NR^{29-a}R^{29-b}$, —S(O)$_2$OH, —S(O)$_2$O($C_1$-$C_6$ alkyl), —S(O)$_2$O($C_1$-$C_6$ haloalkyl), —S(O)$_2$NH$_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$$NR^{29-a}R^{29-b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);

wherein $R^{29-a}$ and $R^{29-b}$ are taken together with the nitrogen atom which bears them to form a 3-10 membered heterocycle;

provided that when $R^{23a}$ and $R^{23b}$ are taken together to form an oxo (=O) substituent, then $R^{24a}$ is —OH or —NH$_2$;

(iii) when m3 is 1 and n3 is 0, then:
$X^4$ is CH and $Y^4$ is $NR^{Y4}$;
$R^{21a}$ and $R^{21b}$ are taken together to form an oxo (=O) substituent or an imido (=NH) substituent;
$R^{23a}$ and $R^{23b}$ are taken together to form an oxo (=O) substituent;
$A^3$ is $C_6$-$C_{10}$ aryl optionally substituted with one or more $R^{27}$ substituent, or 5-10 membered heteroaryl optionally substituted with one or more $R^{27}$ substituent;
$R^{27}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —NH$_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —NR$^{27-a}$R$^{27-b}$, —CN, —C(O)OH, —C(O)O($C_1$-$C_6$ alkyl), —C(O)O($C_1$-$C_6$ haloalkyl), —C(O)NH$_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)NR$^{27-a}$R$^{27-b}$, —S(O)$_2$OH, —S(O)$_2$O($C_1$-$C_6$ alkyl), —S(O)$_2$O($C_1$-$C_6$ haloalkyl), —S(O)$_2$NH$_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$NR$^{27-a}$R$^{27-b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);
wherein $R^{27-a}$ and $R^{27-b}$ are taken together with the nitrogen atom which bears them to form a 3-10 membered heterocycle;
$A^4$ is a substituent of the formula ($A^4$-a)

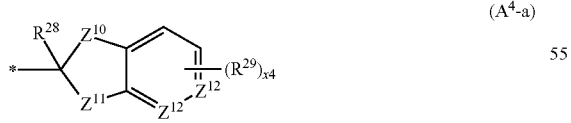

(A$^4$-a)

wherein
represents the attachment point to the remainder of the molecule; $Z^{10}$ is selected from the group consisting of $CR^{Z10-1}R^{Z10-2}$, $NR^{Z10-2}$, O, S, and —CR$^{Z10-1}$=CR$^{Z10-1}$—;
wherein
$R^{Z10-1}$ is H or $R^{29}$; and
$R^{Z10-2}$ is H or $R^{29}$;

$Z^{11}$ is selected from the group consisting of $CR^{Z11-1}R^{Z11-2}$, $NR^{Z11-2}$; O, S, and —CR$^{Z11-1}$=CR$^{Z11-1}$—;
wherein
$R^{Z11-1}$ is H or $R^{29}$; and
$R^{Z11-2}$ is H or $R^{29}$;
$Z^{12}$, independently at each occurrence, is C or N, provided that at least one $Z^{12}$ is C;
$R^{28}$ is hydrogen or $R^{29}$, or $R^{28}$ and $R^{Z10-2}$ are taken together to form a double bond between the carbon atom bearing $R^{28}$ and $Z^{10}$; $R^{29}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —NH$_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —NR$^{29-a}$R$^{29-b}$, —CN, —C(O)OH, —C(O)O($C_1$-$C_6$ alkyl), —C(O)O($C_1$-$C_6$ haloalkyl), —C(O)NH$_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)NR$^{29-a}$R$^{29-b}$, —S(O)$_2$OH, —S(O)$_2$O($C_1$-$C_6$ alkyl), —S(O)$_2$O($C_1$-$C_6$ haloalkyl), —S(O)$_2$NH$_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$NR$^{29-a}$R$^{29-b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);
wherein $R^{29-a}$ and $R^{29-b}$ are taken together with the nitrogen atom which bears them to form a 3-10 membered heterocycle;
x4 is 0, 1, 2, 3, or 4, provided than when one $Z^{12}$ is N, then x4 is not 4;

(iv) when m3 is 1 and n3 is 1, then:
$R^{21a}$ and $R^{21b}$ are taken together to form an oxo (=O) substituent or an imido (=NH) substituent;
$A^3$ is $C_6$-$C_{10}$ aryl optionally substituted with one or more $R^{27}$ substituent, or 5-10 membered heteroaryl optionally substituted with one or more $R^{27}$ substituent;
$R^{27}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —NH$_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —NR$^{27-a}$R$^{27-b}$, —CN, —C(O)OH, —C(O)O($C_1$-$C_6$ alkyl), —C(O)O($C_1$-$C_6$ haloalkyl), —C(O)NH$_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)NR$^{27-a}$R$^{27-b}$, —S(O)$_2$OH, —S(O)$_2$O($C_1$-$C_6$ alkyl), —S(O)$_2$O($C_1$-$C_6$ haloalkyl), —S(O)$_2$NH$_2$, —S(O)$_2$NH($C_1$-$C_6$ alkyl), —S(O)$_2$ NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$NR$^{27-a}$R$^{27-b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);

wherein R$^{27-a}$ and R$^{27-b}$ are taken together with the nitrogen atom which bears them to form a 3-10 membered heterocycle;

$A^4$ is $C_6$-$C_{10}$ aryl optionally substituted with one or more R$^{29}$ substituent, or 5-10 membered heteroaryl optionally substituted with one or more R$^{29}$ substituent;

R$^{29}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —NH$_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —NR$^{29-a}$R$^{29-b}$, —CN, —C(O)OH, —C(O)O($C_1$-$C_6$ alkyl), —C(O)O($C_1$-$C_6$ haloalkyl), —C(O)NH$_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)NR$^{29-a}$R$^{29-b}$, —S(O)$_2$OH, —S(O)$_2$O($C_1$-$C_6$ alkyl), —S(O)$_2$O($C_1$-$C_6$ haloalkyl), —S(O)$_2$NH$_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$NR$^{29-a}$R$^{29-b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);

wherein R$^{29-a}$ and R$^{29-b}$ are taken together with the nitrogen atom which bears them to form a 3-10 membered heterocycle;

provided that:
when one of $X^3$ or $X^4$ is N, then r2 is 1 or 2 and s2 is 1 or 2; and
when R$^{23a}$ and R$^{23b}$ are taken together to form an oxo (=O) substituent,
then R$^{24a}$ is —OH or —NH$_2$.

In some embodiments of compounds of formula (II):
m3 is 0 or 1;
n3 is 0 or 1;
r2 is 0, 1, or 2;
s2 is 0, 1, or 2;

$X^3$ is CH or N;
$X^4$ is CH or N;
provided that at least one of $X^3$ and $X^4$ is CH;
$Y^3$ is selected from the group consisting of a bond, NR$^{Y3}$, and O;
wherein R$^{Y3}$ is hydrogen or $C_1$-$C_6$ alkyl;
$Y^4$ is selected from the group consisting of a bond, NR$^{Y4}$, and O;
wherein R$^{Y4}$ is hydrogen or $C_1$-$C_6$ alkyl;
provided that:
when $X^3$ is N, then $Y^3$ is a bond and m3 is 1;
when $X^4$ is N, then $Y^4$ is a bond and n3 is 1;
$A^3$ is selected from the group consisting of:

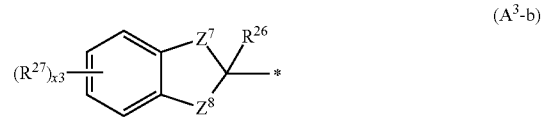

(A$^3$-b)

wherein
represents the attachment point to the remainder of the molecule; $Z^7$ is selected from the group consisting of CR$^{Z7-1}$R$^{Z7-2}$, NR$^{Z7-2}$, O, S, and —CR$^{Z7-1}$=CR$^{Z7-1}$—;
wherein
R$^{Z7-1}$ is H or R$^{27}$; and
R$^{Z7-2}$ is H or R$^{27}$;
$Z^8$ is selected from the group consisting of CR$^{Z8-1}$R$^{Z8-2}$, NR$^{Z8-2}$; O, S, and —CR$^{Z8-1}$=CR$^{Z8-1}$—;
wherein
R$^{Z8-1}$ is H or R$^{27}$; and
R$^{Z8-2}$ is H or R$^{27}$;
R$^{26}$ is hydrogen or R$^{27}$, or R$^{26}$ and R$^{Z7-2}$ are taken together to form a double bond between the carbon atom bearing R$^{26}$ and $Z^7$; and x3 is 0, 1, 2, 3, or 4;

$C_6$-$C_{10}$ aryl optionally substituted with one or more R$^{27}$ substituent; and
5-10 membered heteroaryl optionally substituted with one or more R$^{27}$ substituent; R$^{27}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —NH$_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —NR$^{27-a}$R$^{27-b}$, —CN, —C(O)OH, —C(O)O($C_1$-$C_6$ alkyl), —C(O)O($C_1$-$C_6$ haloalkyl), —C(O)NH$_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)NR$^{27-a}$R$^{27-b}$, —S(O)$_2$OH, —S(O)$_2$O($C_1$-$C_6$ alkyl), —S(O)$_2$O($C_1$-$C_6$ haloalkyl), —S(O)$_2$NH$_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$NR$^{27-a}$ R$^{27-b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ haloalkyl), —OS(O)$_2$($C_1$-$C_6$ haloalkyl), —N(H)S(O)$_2$($C_1$-$C_6$ alkyl), —N(H)S(O)$_2$(C$_1$-C$_6$ haloalkyl), —N(C$_1$-C$_6$ alkyl)S(O)$_2$(C$_1$-C$_6$ alkyl), —N(C$_1$-C$_6$ alkyl)S(O)$_2$(C$_1$-C$_6$ haloalkyl), —N(C$_1$-C$_6$ haloalkyl)S(O)$_2$(C$_1$-C$_6$ alkyl), and —N(C$_1$-C$_6$ haloalkyl)S(O)$_2$(C$_1$-C$_6$ haloalkyl);

wherein $R^{27-a}$ and $R^{27-b}$ are taken together with the nitrogen atom which bears them to form a 3-10 membered heterocycle;

$A^4$ is selected from the group consisting of:

a substituent of the formula ($A^4$-b)

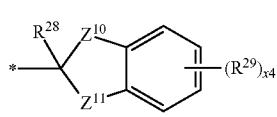

wherein represents the attachment point to the remainder of the molecule; $Z^{10}$ is selected from the group consisting of $CR^{Z10-1}R^{Z10-2}$, $NR^{Z10-2}$, O, S, and —$CR^{Z10-1}$=$CR^{Z10-1}$—;

wherein $R^{Z10-1}$ is H or $R^{29}$; and $R^{Z10-2}$ is H or $R^{29}$;

$Z^{11}$ is selected from the group consisting of $CR^{Z11-1}R^{Z11-2}$, $NR^{Z11-2}$; O, S, and —$CR^{Z11-1}$=$CR^{Z11-1}$—;

wherein $R^{Z11-1}$ is H or $R^{29}$; and $R^{Z11-2}$ is H or $R^{29}$;

$R^{28}$ is hydrogen or $R^{29}$, or $R^{28}$ and $R^{Z10-2}$ are taken together to form a double bond between the carbon atom bearing $R^{28}$ and $Z^{10}$; and x4 is 0, 1, 2, 3, or 4;

$C_6$-$C_{10}$ aryl optionally substituted with one or more $R^{29}$ substituent; and 5-10 membered heteroaryl optionally substituted with one or more $R^{29}$ substituent;

$R^{29}$ is selected, independently at each occurrence, from the group consisting of halogen, C$_1$-C$_6$ alkyl, C$_1$-C$_6$ haloalkyl, —OH, —O(C$_1$-C$_6$ alkyl), —O(C$_1$-C$_6$ haloalkyl), —SH, —S(C$_1$-C$_6$ alkyl), —S(C$_1$-C$_6$ haloalkyl), —NH$_2$, —NH(C$_1$-C$_6$ alkyl), —NH(C$_1$-C$_6$ haloalkyl), —N(C$_1$-C$_6$ alkyl)$_2$, —N(C$_1$-C$_6$ haloalkyl)$_2$, —NR$^{29-a}$R$^{29-b}$, —CN, —C(O)OH, —C(O)O(C$_1$-C$_6$ alkyl), —C(O)O(C$_1$-C$_6$ haloalkyl), —C(O)NH$_2$, —C(O)NH(C$_1$-C$_6$ alkyl), —C(O)NH(C$_1$-C$_6$ haloalkyl), —C(O)N(C$_1$-C$_6$ alkyl)$_2$, —C(O)N(C$_1$-C$_6$ haloalkyl)$_2$, —C(O)NR$^{29-a}$R$^{29-b}$, —S(O)$_2$OH, —S(O)$_2$O(C$_1$-C$_6$ alkyl), —S(O)$_2$O(C$_1$-C$_6$ haloalkyl), —S(O)$_2$NH$_2$, —S(O)$_2$NH(C$_1$-C$_6$ alkyl), —S(O)$_2$NH(C$_1$-C$_6$ haloalkyl), —S(O)$_2$N(C$_1$-C$_6$ alkyl)$_2$, —S(O)$_2$N(C$_1$-C$_6$ haloalkyl)$_2$, —S(O)$_2$NR$^{29-a}$R$^{29-b}$, —OC(O)H, —OC(O)(C$_1$-C$_6$ alkyl), —OC(O)(C$_1$-C$_6$ haloalkyl), —N(H)C(O)H, —N(H)C(O)(C$_1$-C$_6$ alkyl), —N(H)C(O)(C$_1$-C$_6$ haloalkyl), —N(C$_1$-C$_6$ alkyl)C(O)H, —N(C$_1$-C$_6$ alkyl)C(O)(C$_1$-C$_6$ alkyl), —N(C$_1$-C$_6$ alkyl)C(O)(C$_1$-C$_6$ haloalkyl), —N(C$_1$-C$_6$ haloalkyl)C(O)H, —N(C$_1$-C$_6$ haloalkyl)C(O)(C$_1$-C$_6$ alkyl), —N(C$_1$-C$_6$ haloalkyl)C(O)(C$_1$-C$_6$ haloalkyl), —OS(O)$_2$(C$_1$-C$_6$ alkyl), —OS(O)$_2$(C$_1$-C$_6$ haloalkyl), —N(H)S(O)$_2$(C$_1$-C$_6$ alkyl), —N(H)S(O)$_2$(C$_1$-C$_6$ haloalkyl), —N(C$_1$-C$_6$ alkyl)S(O)$_2$(C$_1$-C$_6$ alkyl), —N(C$_1$-C$_6$ alkyl)S(O)$_2$(C$_1$-C$_6$ haloalkyl), —N(C$_1$-C$_6$ haloalkyl)S(O)$_2$(C$_1$-C$_6$ alkyl), and —N(C$_1$-C$_6$ haloalkyl)S(O)$_2$(C$_1$-C$_6$ haloalkyl);

wherein $R^{29-a}$ and $R^{29-b}$ are taken together with the nitrogen atom which bears them to form a 3-10 membered heterocycle;

$R^{17a}$ and $R^{17b}$ are independently selected from the group consisting of hydrogen, C$_1$-C$_6$ alkyl, and halogen;

$R^{18a}$ and $R^{18b}$ are independently selected from the group consisting of hydrogen, C$_1$-C$_6$ alkyl, and halogen;

when present, $R^{19a}$ and $R^{19b}$ are independently at each occurrence selected from the group consisting of hydrogen, C$_1$-C$_6$ alkyl, and halogen;

when present, $R^{20a}$ and $R^{20b}$ are independently at each occurrence selected from the group consisting of hydrogen, C$_1$-C$_6$ alkyl, and halogen;

or alternatively, $R^{17a}$ and $R^{18a}$ are taken together to form a C$_1$-C$_6$ alkylene moiety;

or alternatively, $R^{17a}$ and an $R^{19a}$ moiety, when present, are taken together to form a C$_1$-C$_6$ alkylene moiety, and $R^{17b}$ and the $R^{19b}$ in the geminal position to the $R^{19a}$ taken together with $R^{17a}$, are both hydrogen;

or alternatively, an $R^{19a}$ moiety, when present, and an $R^{20a}$ moiety, when present, are taken together to form a C$_1$-C$_6$ alkylene moiety, and the $R^{19b}$ in the geminal position to the $R^{19a}$ taken together with the $R^{20a}$ moiety and the $R^{20b}$ in the geminal position to the $R^{20a}$ taken together with the $R^{19a}$ moiety, are both hydrogen;

$R^{21a}$ and $R^{21b}$ are taken together to form an oxo (=O) substituent or an imido (=NH) substituent, or alternatively, $R^{21a}$ and $R^{21b}$ are both hydrogen;

when present, $R^{22a}$ and $R^{22b}$ are both hydrogen;

$R^{23a}$ and $R^{23b}$ are taken together to form an oxo (=O) substituent or an imido (=NH) substituent, or alternatively, $R^{23a}$ and $R^{23b}$ are both hydrogen;

when present, $R^{24a}$ is selected from the group consisting of hydrogen, —OH, and —NH$_2$;

or alternatively, $R^{24a}$ and $R^{Y4}$ are taken together to form a #—C(=O)—O— group, wherein # represent the attachment point to the nitrogen atom bearing $R^{Y4}$;

when present, $R^{24b}$ is hydrogen; and when present, $R^{25a}$ and $R^{25b}$ are both hydrogen;

or alternatively, $R^{25a}$, when present, and one $R^{29}$ of $A^4$ are taken together with the atoms connecting them to form a 5-6 membered heterocycloalkenyl optionally substituted with one or more $R^{29}$ substituent, and $R^{25b}$ is H;

or alternatively, $R^{25a}$, when present, $R^{25b}$, when present, and one $R^{29}$ of $A^4$ are taken together with the atoms connecting them to form a 5-6 membered heteroaryl optionally substituted with one or more $R^{29}$ substituent;

and further provided that one of (i), (ii), (iii) and (iv) applies:

(i) when m3 is 0 and n3 is 0, then:

$X^3$ is CH and $Y^3$ is NR$^{Y3}$;

$X^4$ is CH and $Y^4$ is NR$^{Y4}$;

$R^{21a}$ and $R^{21b}$ are taken together to form an oxo (=O) substituent;

$R^{23a}$ and $R^{23b}$ are taken together to form an oxo (=O) substituent;

$A^3$ is a substituent of the formula ($A^3$-b)

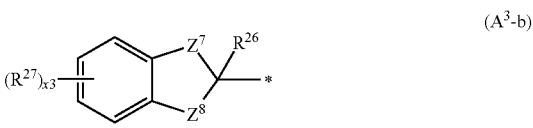

wherein
represents the attachment point to the remainder of the molecule;

$Z^7$ is selected from the group consisting of $CR^{Z7-1}R^{Z7-2}$, $NR^{Z7-2}$, O, S, and $-CR^{Z7-1}=CR^{Z7-1}-$;
wherein
$R^{Z7-1}$ is H or $R^{27}$; and
$R^{Z7-2}$ is H or $R^{27}$;

$Z^8$ is selected from the group consisting of $CR^{Z8-1}R^{Z8-2}$, $NR^{Z8-2}$, O, S, and $-CR^{Z8-1}=CR^{Z8-1}-$;
wherein
$R^{Z8-1}$ is H or $R^{27}$; and
$R^{Z8-2}$ is H or $R^{27}$;

$R^{26}$ is hydrogen or $R^{27}$, or $R^{26}$ and $R^{27-2}$ are taken together to form a double bond between the carbon atom bearing $R^{26}$ and $Z^7$;

$R^{27}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —NH$_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —NR$^{27-a}$R$^{27-b}$, —CN, —C(O)OH, —C(O)O($C_1$-$C_6$ alkyl), —C(O)O($C_1$-$C_6$ haloalkyl), —C(O)NH$_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)NR$^{27-a}$R$^{27-b}$, —S(O)$_2$OH, —S(O)$_2$O($C_1$-$C_6$ alkyl), —S(O)$_2$O($C_1$-$C_6$ haloalkyl), —S(O)$_2$NH$_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$NR$^{27-a}$R$^{27-b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);
wherein $R^{27-a}$ and $R^{27-b}$ are taken together with the nitrogen atom which bears them to form a 3-10 membered heterocycle;

x3 is 0, 1, 2, 3, or 4;

$A^4$ is a substituent of the formula ($A^4$-b)

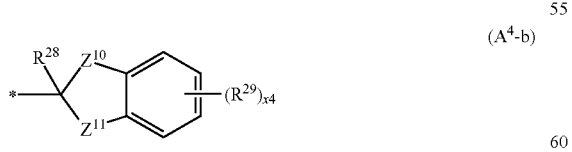

(A$^4$-b)

wherein
represents the attachment point to the remainder of the molecule;

$Z^{10}$ is selected from the group consisting of $CR^{Z10-1}R^{Z10-2}$, $NR^{Z10-2}$, O, S, and $-CR^{Z10-1}=CR^{Z10-1}-$;

wherein
$R^{Z10-1}$ is H or $R^{29}$; and
$R^{Z10-2}$ is H or $R^{29}$;

$Z^{11}$ is selected from the group consisting of $CR^{Z11-1}R^{Z11-2}$, $NR^{Z11-2}$, O, S, and $-CR^{Z11-1}=CR^{Z11-1}-$;
wherein
$R^{Z11-1}$ is H or $R^{29}$; and
$R^{Z11-2}$ is H or $R^{29}$;

$R^{28}$ is hydrogen or $R^{29}$, or $R^{28}$ and $R^{Z10-2}$ are taken together to form a double bond between the carbon atom bearing $R^{28}$ and $Z^{10}$;

$R^{29}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —NH$_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —NR$^{29-a}$R$^{29-b}$, —CN, —C(O)OH, —C(O)O($C_1$-$C_6$ alkyl), —C(O)O($C_1$-$C_6$ haloalkyl), —C(O)NH$_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)NR$^{29-a}$R$^{29-b}$, —S(O)$_2$OH, —S(O)$_2$O($C_1$-$C_6$ alkyl), —S(O)$_2$O($C_1$-$C_6$ haloalkyl), —S(O)$_2$NH$_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$NR$^{29-a}$R$^{29-b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);
wherein $R^{29-a}$ and $R^{29-b}$ are taken together with the nitrogen atom which bears them to form a 3-10 membered heterocycle;

x4 is 0, 1, 2, 3, or 4; and provided that $A^3$ and $A^4$ are not both simultaneously a moiety selected from group consisting of:

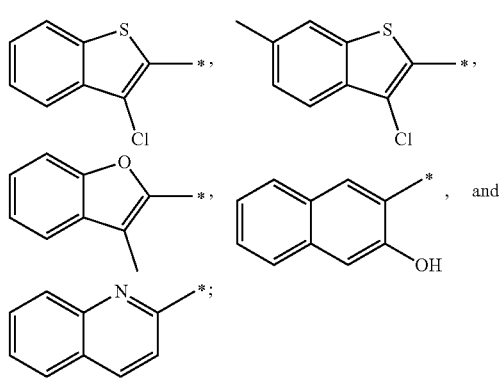

wherein the * represents the attachment point to the remainder of the molecule;

(ii) when m3 is 0 and n3 is 1, then:
  r2 is 1 or 2;
  s2 is 1 or 2;
  $X^3$ is CH and $Y^3$ is $NR^{Y3}$;
  $R^{21a}$ and $R^{21b}$ are taken together to form an oxo (=O) substituent;
  $R^{24a}$ is selected from the group consisting of hydrogen, —OH, and —NH$_2$;
  $A^3$ is a substituent of the formula (A$^3$-b)

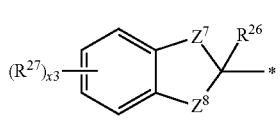
(A$^3$-b)

wherein
  represents the attachment point to the remainder of the molecule;
  $Z^7$ is selected from the group consisting of $CR^{Z7-1}R^{Z7-2}$, $NR^{Z7-2}$, O, S, and —$CR^{Z7-1}$=$CR^{Z7-1}$—;
    wherein
    $R^{Z7-1}$ is H or $R^{27}$; and
    $R^{Z7-2}$ is H or $R^{27}$;
  $Z^8$ is selected from the group consisting of $CR^{Z8-1}R^{Z8-2}$, $NR^{Z8-2}$; O, S, and —$CR^{Z8-1}$=$CR^{Z8-1}$—;
    wherein
    $R^{Z8-1}$ is H or $R^{27}$; and
    $R^{Z8-2}$ is H or $R^{27}$;
  $R^{26}$ is hydrogen or $R^{27}$, or $R^{26}$ and $R^{Z7-2}$ are taken together to form a double bond between the carbon atom bearing $R^{26}$ and $Z^7$;
  $R^{27}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —NH$_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —NR$^{27-a}$R$^{27-b}$, —CN, —C(O)OH, —C(O)O($C_1$-$C_6$ alkyl), —C(O)O($C_1$-$C_6$ haloalkyl), —C(O)NH$_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)NR$^{27-a}$R$^{27-b}$, —S(O)$_2$OH, —S(O)$_2$O($C_1$-$C_6$ alkyl), —S(O)$_2$O($C_1$-$C_6$ haloalkyl), —S(O)$_2$NH$_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$NR$^{27-a}$R$^{27-b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);
    wherein $R^{27-a}$ and $R^{27-b}$ are taken together with the nitrogen atom which bears them to form a 3-10 membered heterocycle;
  x3 is 0, 1, 2, 3, or 4;
  $A^4$ is $C_6$-$C_{10}$ aryl optionally substituted with one or more $R^{29}$ substituent, or 5-10 membered heteroaryl optionally substituted with one or more $R^{29}$ substituent;
  $R^{29}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —NH$_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —NR$^{29-a}$R$^{29-b}$, —CN, —C(O)OH, —C(O)O($C_1$-$C_6$ alkyl), —C(O)O($C_1$-$C_6$ haloalkyl), —C(O)NH$_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)NR$^{29-a}$R$^{29-b}$, —S(O)$_2$OH, —S(O)$_2$O($C_1$-$C_6$ alkyl), —S(O)$_2$O($C_1$-$C_6$ haloalkyl), —S(O)$_2$NH$_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$NR$^{29-a}$R$^{29-b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);
    wherein $R^{29-a}$ and $R^{29-b}$ are taken together with the nitrogen atom which bears them to form a 3-10 membered heterocycle;
  provided that when $R^{23a}$ and $R^{23b}$ are taken together to form an oxo (=O) substituent, then $R^{24a}$ is —OH or —NH$_2$;
(iii) when m3 is 1 and n3 is 0, then:
  $X^4$ is CH and $Y^4$ is $NR^{Y4}$;
  $R^{21a}$ and $R^{21b}$ are taken together to form an oxo (=O) substituent or an imido (=NH) substituent;
  $R^{23a}$ and $R^{23b}$ are taken together to form an oxo (=O) substituent;
  $A^3$ is $C_6$-$C_{10}$ aryl optionally substituted with one or more $R^{27}$ substituent, or 5-10 membered heteroaryl optionally substituted with one or more $R^{27}$ substituent;
  $R^{27}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —NH$_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —NR$^{27-a}$R$^{27-b}$, —CN, —C(O)OH, —C(O)O($C_1$-$C_6$ alkyl), —C(O)O($C_1$-$C_6$ haloalkyl), —C(O)NH$_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)NR$^{27-a}$R$^{27-b}$, —S(O)$_2$OH, —S(O)$_2$O($C_1$-$C_6$ alkyl), —S(O)$_2$O($C_1$-$C_6$ haloalkyl), —S(O)$_2$NH$_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$NR$^{27-a}$R$^{27-b}$, —OC(O)H, —OC(O)($C_1$-$C_6$ alkyl), —OC (O)(C$_1$-C$_6$ haloalkyl), —N(H)C(O)H, —N(H)C(O)(C$_1$-C$_6$ alkyl), —N(H)C(O)(C$_1$-C$_6$ haloalkyl), —N(C$_1$-C$_6$ alkyl)C(O)H, —N(C$_1$-C$_6$ alkyl)C(O)(C$_1$-C$_6$ alkyl), —N(C$_1$-C$_6$ alkyl)C(O)(C$_1$-C$_6$ haloalkyl), —N(C$_1$-C$_6$ haloalkyl)C(O)H, —N(C$_1$-C$_6$ haloalkyl)C(O)(C$_1$-C$_6$ alkyl), —N(C$_1$-C$_6$ haloalkyl)C(O)(C$_1$-C$_6$ haloalkyl), —OS(O)$_2$(C$_1$-C$_6$ alkyl), —OS(O)$_2$(C$_1$-C$_6$ haloalkyl), —N(H)S(O)$_2$(C$_1$-C$_6$ alkyl), —N(H)S(O)$_2$(C$_1$-C$_6$ haloalkyl), —N(C$_1$-C$_6$ alkyl)S(O)$_2$(C$_1$-C$_6$ alkyl), —N(C$_1$-C$_6$ alkyl)S(O)$_2$(C$_1$-C$_6$ haloalkyl), —N(C$_1$-C$_6$ haloalkyl)S(O)$_2$(C$_1$-C$_6$ alkyl), and —N(C$_1$-C$_6$ haloalkyl)S(O)$_2$(C$_1$-C$_6$ haloalkyl);

wherein R$^{27-a}$ and R$^{27-b}$ are taken together with the nitrogen atom which bears them to form a 3-10 membered heterocycle;

A$^4$ is a substituent of the formula (A$^4$-b)

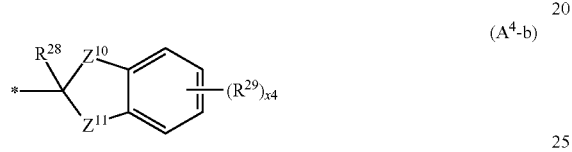

(A$^4$-b)

wherein
* represents the attachment point to the remainder of the molecule;
Z$^{10}$ is selected from the group consisting of CR$^{Z10-1}$R$^{Z10-2}$, NR$^{Z10-2}$, O, S, and —CR$^{Z10-1}$=CR$^{Z10-1}$—;
wherein
R$^{Z10-1}$ is H or R$^{29}$; and
R$^{Z10-2}$ is H or R$^{29}$;
Z$^{11}$ is selected from the group consisting of CR$^{Z11-1}$R$^{Z11-2}$, NR$^{Z11-2}$; O, S, and —CR$^{Z11-1}$=CR$^{Z11-1}$—;
wherein
R$^{Z11-1}$ is H or R$^{29}$; and
R$^{Z11-2}$ is H or R$^{29}$;
R$^{28}$ is hydrogen or R$^{29}$, or R$^{28}$ and R$^{Z10-2}$ are taken together to form a double bond between the carbon atom bearing R$^{28}$ and Z$^{10}$;
R$^{29}$ is selected, independently at each occurrence, from the group consisting of halogen, C$_1$-C$_6$ alkyl, C$_1$-C$_6$ haloalkyl, —OH, —O(C$_1$-C$_6$ alkyl), —O(C$_1$-C$_6$ haloalkyl), —SH, —S(C$_1$-C$_6$ alkyl), —S(C$_1$-C$_6$ haloalkyl), —NH$_2$, —NH(C$_1$-C$_6$ alkyl), —NH(C$_1$-C$_6$ haloalkyl), —N(C$_1$-C$_6$ alkyl)$_2$, —N(C$_1$-C$_6$ haloalkyl)$_2$, —NR$^{29-a}$R$^{29-b}$, —CN, —C(O)OH, —C(O)O(C$_1$-C$_6$ alkyl), —C(O)O(C$_1$-C$_6$ haloalkyl), —C(O)NH$_2$, —C(O)NH(C$_1$-C$_6$ alkyl), —C(O)NH(C$_1$-C$_6$ haloalkyl), —C(O)N(C$_1$-C$_6$ alkyl)$_2$, —C(O)N(C$_1$-C$_6$ haloalkyl)$_2$, —C(O)NR$^{29-a}$R$^{29-b}$, —S(O)$_2$OH, —S(O)$_2$O(C$_1$-C$_6$ alkyl), —S(O)$_2$O(C$_1$-C$_6$ haloalkyl), —S(O)$_2$NH$_2$, —S(O)$_2$NH(C$_1$-C$_6$ alkyl), —S(O)$_2$NH(C$_1$-C$_6$ haloalkyl), —S(O)$_2$N(C$_1$-C$_6$ alkyl)$_2$, —S(O)$_2$N(C$_1$-C$_6$ haloalkyl)$_2$, —S(O)$_2$NR$^{29-a}$R$^{29-b}$, —OC(O)H, —OC(O)(C$_1$-C$_6$ alkyl), —OC(O)(C$_1$-C$_6$ haloalkyl), —N(H)C(O)H, —N(H)C(O)(C$_1$-C$_6$ alkyl), —N(H)C(O)(C$_1$-C$_6$ haloalkyl), —N(C$_1$-C$_6$ alkyl)C(O)H, —N(C$_1$-C$_6$ alkyl)C(O)(C$_1$-C$_6$ alkyl), —N(C$_1$-C$_6$ alkyl)C(O)(C$_1$-C$_6$ haloalkyl), —N(C$_1$-C$_6$ haloalkyl)C(O)H, —N(C$_1$-C$_6$ haloalkyl)C(O)(C$_1$-C$_6$ alkyl), —N(C$_1$-C$_6$ haloalkyl)C(O)(C$_1$-C$_6$ haloalkyl), —OS(O)$_2$(C$_1$-C$_6$ alkyl), —OS(O)$_2$(C$_1$-C$_6$ haloalkyl), —N(H)S(O)$_2$(C$_1$-C$_6$ alkyl), —N(H)S(O)$_2$(C$_1$-C$_6$ haloalkyl), —N(C$_1$-C$_6$ alkyl)S(O)$_2$(C$_1$-C$_6$ alkyl), —N(C$_1$-C$_6$ alkyl)S(O)$_2$(C$_1$-C$_6$ haloalkyl), —N(C$_1$-C$_6$ haloalkyl)S(O)$_2$(C$_1$-C$_6$ alkyl), and —N(C$_1$-C$_6$ haloalkyl)S(O)$_2$(C$_1$-C$_6$ haloalkyl);

wherein R$^{29-a}$ and R$^{29-b}$ are taken together with the nitrogen atom which bears them to form a 3-10 membered heterocycle;

x4 is 0, 1, 2, 3, or 4;

(iv) when m3 is 1 and n3 is 1, then:
R$^{21a}$ and R$^{21b}$ are taken together to form an oxo (=O) substituent or an imido (=NH) substituent;

A$^3$ is C$_6$-C$_{10}$ aryl optionally substituted with one or more R$^{27}$ substituent, or 5-10 membered heteroaryl optionally substituted with one or more R$^{27}$ substituent;

R$^{27}$ is selected, independently at each occurrence, from the group consisting Dihalogen, C$_1$-C$_6$ alkyl, C$_1$-C$_6$ haloalkyl, —OH, —O(C$_1$-C$_6$ alkyl), —O(C$_1$-C$_6$ haloalkyl), —SH, —S(C$_1$-C$_6$ alkyl), —S(C$_1$-C$_6$ haloalkyl), —NH$_2$, —NH(C$_1$-C$_6$ alkyl), —NH(C$_1$-C$_6$ haloalkyl), —N(C$_1$-C$_6$ alkyl)$_2$, —N(C$_1$-C$_6$ haloalkyl)$_2$, —NR$^{27-a}$R$^{27-b}$, —CN, —C(O)OH, —C(O)O(C$_1$-C$_6$ alkyl), —C(O)O(C$_1$-C$_6$ haloalkyl), —C(O)NH$_2$, —C(O)NH(C$_1$-C$_6$ alkyl), —C(O)NH(C$_1$-C$_6$ haloalkyl), —C(O)N(C$_1$-C$_6$ alkyl)$_2$, —C(O)N(C$_1$-C$_6$ haloalkyl)$_2$, —C(O)NR$^{27-a}$R$^{27-b}$, —S(O)$_2$OH, —S(O)$_2$O(C$_1$-C$_6$ alkyl), —S(O)$_2$O(C$_1$-C$_6$ haloalkyl), —S(O)$_2$NH$_2$, —S(O)$_2$NH(C$_1$-C$_6$ alkyl), —S(O)$_2$NH(C$_1$-C$_6$ haloalkyl), —S(O)$_2$N(C$_1$-C$_6$ alkyl)$_2$, —S(O)$_2$N(C$_1$-C$_6$ haloalkyl)$_2$, —S(O)$_2$NR$^{27-a}$R$^{27-b}$, —OC(O)H, —OC(O)(C$_1$-C$_6$ alkyl), —OC(O)(C$_1$-C$_6$ haloalkyl), —N(H)C(O)H, —N(H)C(O)(C$_1$-C$_6$ alkyl), —N(H)C(O)(C$_1$-C$_6$ haloalkyl), —N(C$_1$-C$_6$ alkyl)C(O)H, —N(C$_1$-C$_6$ alkyl)C(O)(C$_1$-C$_6$ alkyl), —N(C$_1$-C$_6$ alkyl)C(O)(C$_1$-C$_6$ haloalkyl), —N(C$_1$-C$_6$ haloalkyl)C(O)H, —N(C$_1$-C$_6$ haloalkyl)C(O)(C$_1$-C$_6$ alkyl), —N(C$_1$-C$_6$ haloalkyl)C(O)(C$_1$-C$_6$ haloalkyl), —OS(O)$_2$(C$_1$-C$_6$ alkyl), —OS(O)$_2$(C$_1$-C$_6$ haloalkyl), —N(H)S(O)$_2$(C$_1$-C$_6$ alkyl), —N(H)S(O)$_2$(C$_1$-C$_6$ haloalkyl), —N(C$_1$-C$_6$ alkyl)S(O)$_2$(C$_1$-C$_6$ alkyl), —N(C$_1$-C$_6$ alkyl)S(O)$_2$(C$_1$-C$_6$ haloalkyl), —N(C$_1$-C$_6$ haloalkyl)S(O)$_2$(C$_1$-C$_6$ alkyl), and —N(C$_1$-C$_6$ haloalkyl)S(O)$_2$(C$_1$-C$_6$ haloalkyl);

wherein R$^{27-a}$ and R$^{27-b}$ are taken together with the nitrogen atom which bears them to form a 3-10 membered heterocycle;

A$^4$ is C$_6$-C$_{10}$ aryl optionally substituted with one or more R$^{29}$ substituent, or 5-10 membered heteroaryl optionally substituted with one or more R$^{29}$ substituent;

R$^{29}$ is selected, independently at each occurrence, from the group consisting of halogen, C$_1$-C$_6$ alkyl, C$_1$-C$_6$ haloalkyl, —OH, —O(C$_1$-C$_6$ alkyl), —O(C$_1$-C$_6$ haloalkyl), —SH, —S(C$_1$-C$_6$ alkyl), —S(C$_1$-C$_6$ haloalkyl), —NH$_2$, —NH(C$_1$-C$_6$ alkyl), —NH(C$_1$-C$_6$ haloalkyl), —N(C$_1$-C$_6$ alkyl)$_2$, —N(C$_1$-C$_6$ haloalkyl)$_2$, —NR$^{29-a}$R$^{29-b}$, —CN, —C(O)OH, —C(O)O(C$_1$-C$_6$ alkyl), —C(O)O(C$_1$-C$_6$ haloalkyl), —C(O)NH$_2$, —C(O)NH(C$_1$-C$_6$ alkyl), —C(O)NH(C$_1$-C$_6$ haloalkyl), —C(O)N(C$_1$-C$_6$ alkyl)$_2$, —C(O)N(C$_1$-C$_6$ haloalkyl)$_2$, —C(O)NR$^{29-a}$R$^{29-b}$, —S(O)$_2$OH, —S(O)$_2$ O($C_1$-$C_6$ alkyl), —S(O)$_2$O($C_1$-$C_6$ haloalkyl), —S(O)$_2$NH$_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$NR$^{29-a}$R$^{29-b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);

wherein R$^{29-a}$ and R$^{29-b}$ are taken together with the nitrogen atom which bears them to form a 3-10 membered heterocycle;

provided that:
when one of X$^3$ or X$^4$ is N, then r2 is 1 or 2 and s2 is 1 or 2; and
when R$^{23a}$ and R$^{23b}$ are taken together to form an oxo (=O) substituent, then R$^{24a}$ is —OH or —NH$_2$.

In some embodiments the compound of formula (II) is a compound of formula (III):

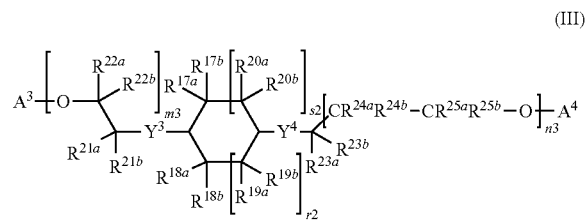

(III)

wherein Y$^3$, R$^{Y3}$, Y$^4$, R$^{Y4}$, m3, n3, r2, s2, A$^3$, Z$^7$, R$^{Z7-1}$, R$^{Z7-2}$, Z$^8$, R$^{Z8-1}$, R$^{Z8-2}$, Z$^9$, x3, A$^4$, Z$^{10}$, R$^{Z10-1}$, R$^{Z10-2}$, Z$^{11}$, R$^{Z11-1}$, R$^{Z11-2}$, Z$^{12}$, x4, R$^{17a}$, R$^{17b}$, R$^{18a}$, R$^{18b}$, R$^{19a}$, R$^{19b}$, R$^{20a}$, R$^{20b}$, R$^{21a}$, R$^{21b}$, R$^{22a}$, R$^{22b}$, R$^{23a}$, R$^{23b}$, R$^{24a}$, R$^{24b}$, R$^{25a}$, R$^{25b}$, R$^{26}$, R$^{27}$, R$^{28}$, and R$^{29}$ are as defined in compounds of formula (II);

or a pharmaceutically acceptable salt thereof.

In some embodiments the compound of formula (II) is a compound of formula (IV):

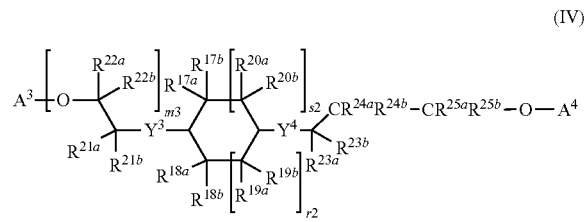

(IV)

wherein Y$^3$, R$^{Y3}$, m3, r2, s2, A$^3$, Z$^7$, R$^{Z7-1}$, R$^{Z7-2}$, Z$^8$, R$^{Z8-1}$, R$^{Z8-2}$, Z$^9$, x3, A$^4$, Z$^{10}$, R$^{Z10-1}$, R$^{Z10-2}$, Z$^{11}$, R$^{Z11-1}$, R$^{Z11-2}$, Z$^{12}$, x4, R$^{17a}$, R$^{17b}$, R$^{18a}$, R$^{18b}$, R$^{19a}$, R$^{19b}$, R$^{20a}$, R$^{20b}$, R$^{21a}$, R$^{21b}$, R$^{22a}$, R$^{22b}$, R$^{23a}$, R$^{23b}$, R$^{24a}$, R$^{24b}$, R$^{25a}$, R$^{25b}$, R$^{26}$, R$^{27}$, R$^{28}$, and R$^{29}$ are as defined in compounds of formula (II);

or a pharmaceutically acceptable salt thereof.

In some embodiments the compound of formula (II) is a compound of formula (V):

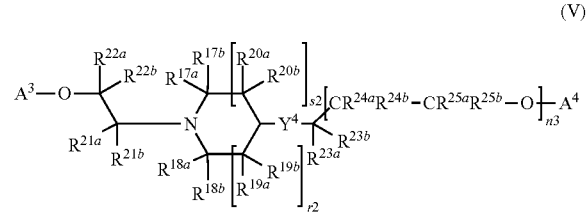

(V)

wherein Y$^3$, R$^{Y4}$, m3, r2, s2, A$^3$, Z$^7$, R$^{Z7-1}$, R$^{Z7-2}$, Z$^8$, R$^{Z8-1}$, R$^{Z8-2}$, Z$^9$, x3, A$^4$, Z$^{10}$, R$^{Z10-1}$, R$^{Z10-2}$, Z$^{11}$, R$^{Z11-1}$, R$^{Z11-2}$, Z$^{12}$, x4, R$^{17a}$, R$^{17b}$, R$^{18a}$, R$^{18b}$, R$^{19a}$, R$^{19b}$, R$^{20a}$, R$^{20b}$, R$^{21a}$, R$^{21b}$, R$^{22a}$, R$^{22b}$, R$^{23a}$, R$^{23b}$, R$^{24a}$, R$^{24b}$, R$^{25a}$, R$^{25b}$, R$^{26}$, R$^{27}$, R$^{28}$, and R$^{29}$ are as defined in compounds of formula (II);

or a pharmaceutically acceptable salt thereof.

In some embodiments of the compounds of formula (II), (III), (IV), or (V), R$^{17a}$ and R$^{17b}$ are independently hydrogen or $C_1$-$C_6$ alkyl. In some embodiments, R$^{17a}$ and R$^{17b}$ are both hydrogen. In some embodiments, R$^{17a}$ and R$^{17b}$ are both $C_1$-$C_6$ alkyl. In some embodiments, R$^{17a}$ and R$^{17b}$ are both methyl. In some embodiments, R$^{17a}$ is hydrogen and R$^{17b}$ is $C_1$-$C_6$ alkyl. In some embodiments, R$^{17a}$ is hydrogen and R$^{17b}$ is methyl.

In some embodiments of the compounds of formula (II), (III), (IV), or (V), R$^{18a}$ and R$^{18b}$ are independently hydrogen or $C_1$-$C_6$ alkyl. In some embodiments, R$^{18a}$ and R$^{18b}$ are both hydrogen. In some embodiments, R$^{18a}$ and R$^{18b}$ are both $C_1$-$C_6$ alkyl. In some embodiments, R$^{18a}$ and R$^{18b}$ are both methyl. In some embodiments, R$^{18a}$ is hydrogen and R$^{18b}$ is $C_1$-$C_6$ alkyl. In some embodiments, R$^{18a}$ is hydrogen and R$^{18b}$ is methyl.

In some embodiments of the compounds of formula (II), (III), (IV), or (V), R$^{17a}$, R$^{17b}$, R$^{18a}$, and R$^{18b}$ are hydrogen.

In some embodiments of the compounds of formula (II), (III), (IV), or (V), R$^{17a}$, R$^{17b}$, R$^{18a}$, and R$^{18b}$ are independently $C_1$-$C_6$ alkyl. In some embodiments, R$^{17a}$, R$^{17b}$, R$^{18a}$, and R$^{18b}$ are methyl.

In some embodiments of the compounds of formula (II), (III), (IV), or (V), R$^{17a}$ and R$^{18a}$ are independently $C_1$-$C_6$ alkyl, and R$^{17b}$ and R$^{18b}$ are both hydrogen. R$^{17a}$ and R$^{18a}$ are both methyl, and R$^{17b}$ and R$^{18b}$ are both hydrogen.

In some embodiments of the compounds of formula (II), (III), (IV), or (V), R$^{17a}$ and R$^{18a}$ are taken together to form a $C_1$-$C_6$ alkylene moiety, and R$^{17b}$ and R$^{18b}$ are both hydrogen. In some embodiments, R$^{17a}$ and R$^{18a}$ are taken together to form an ethylene (—CH$_2$—CH$_2$—) moiety, and R$^{17b}$ and R$^{18b}$ are both hydrogen. In some embodiments, R$^{17a}$ and R$^{18a}$ are taken together to form a propylene (—CH$_2$—CH$_2$—CH$_2$—) moiety, and R$^{17b}$ and R$^{18b}$ are both hydrogen.

In some embodiments of the compounds of formula (II), (III), (IV), or (V), r2 is 1 and s2 is 1. In some embodiments, R$^{17a}$ and R$^{17b}$ are independently hydrogen or $C_1$-$C_6$ alkyl. In some embodiments, R$^{17a}$ and R$^{17b}$ are both hydrogen. In some embodiments, R$^{17a}$ and R$^{17b}$ are both $C_1$-$C_6$ alkyl. In some embodiments, R$^{17a}$ and R$^{17b}$ are both methyl. In some embodiments, R$^{17a}$ is hydrogen and R$^{17b}$ is $C_1$-$C_6$ alkyl. In some embodiments, R$^{17a}$ is hydrogen and R$^{17b}$ is methyl. In some embodiments, R$^{18a}$ and R$^{18b}$ are independently hydrogen or $C_1$-$C_6$ alkyl. In some embodiments, R$^{18a}$ and R$^{18b}$ are both hydrogen. In some embodiments, R$^{18a}$ and R$^{18b}$ are both $C_1$-$C_6$ alkyl. In some embodiments, $R^{18a}$ and $R^{18b}$ are both methyl. In some embodiments, $R^{18a}$ is hydrogen and $R^{18b}$ is $C_1$-$C_6$ alkyl. In some embodiments, $R^{18a}$ is hydrogen and $R^{18b}$ is methyl. In some embodiments, $R^{17a}$, $R^{17b}$, $R^{18a}$, and $R^{18b}$ are hydrogen. In some embodiments, $R^{17a}$, $R^{17b}$, $R^{18a}$, and $R^{18b}$ are independently $C_1$-$C_6$ alkyl. In some embodiments, $R^{17a}$, $R^{17b}$, $R^{18a}$, and $R^{18b}$ are methyl. In some embodiments, $R^{17a}$ and $R^{18a}$ are independently $C_1$-$C_6$ alkyl, and $R^{17b}$ and $R^{18b}$ are both hydrogen. $R^{17a}$ and $R^{18a}$ are both methyl, and $R^{17b}$ and $R^{18b}$ are both hydrogen. In some embodiments, $R^{17a}$ and $R^{18a}$ are taken together to form a $C_1$-$C_6$ alkylene moiety, and $R^{17b}$ and $R^{18b}$ are both hydrogen. In some embodiments, $R^{17a}$ and $R^{18a}$ are taken together to form an ethylene (—$CH_2$—$CH_2$—) moiety, and $R^{17b}$ and $R^{18b}$ are both hydrogen. In some embodiments, $R^{17a}$ and $R^{18a}$ are taken together to form a propylene (—$CH_2$—$CH_2$—$CH_2$—) moiety, and $R^{17b}$ and $R^{18b}$ are both hydrogen. In some embodiments, $R^{19a}$ and $R^{19b}$ are independently hydrogen or $C_1$-$C_6$ alkyl. In some embodiments, $R^{19a}$ and $R^{19b}$ are both hydrogen. In some embodiments, $R^{19a}$ and $R^{19b}$ are both $C_1$-$C_6$ alkyl. In some embodiments, $R^{19a}$ and $R^{19b}$ are both methyl. In some embodiments, $R^{19a}$ is hydrogen and $R^{19b}$ is $C_1$-$C_6$ alkyl. In some embodiments, $R^{19a}$ is hydrogen and $R^{19b}$ is methyl. In some embodiments, $R^{20a}$ and $R^{20b}$ are independently hydrogen or $C_1$-$C_6$ alkyl. In some embodiments, $R^{20a}$ and $R^{20b}$ are both hydrogen. In some embodiments, $R^{20a}$ and $R^{20b}$ are both $C_1$-$C_6$ alkyl. In some embodiments, $R^{20a}$ and $R^{20b}$ are both methyl. In some embodiments, $R^{20a}$ is hydrogen and $R^{20b}$ is $C_1$-$C_6$ alkyl. In some embodiments, $R^{20a}$ is hydrogen and $R^{20b}$ is methyl. In some embodiments, $R^{19a}$, $R^{19b}$, $R^{20a}$, and $R^{20b}$ are hydrogen. In some embodiments, $R^{19a}$, $R^{19b}$, $R^{20a}$, and $R^{20b}$ are independently $C_1$-$C_6$ alkyl. In some embodiments, $R^{19a}$, $R^{19b}$, $R^{20a}$, and $R^{20b}$ are methyl. In some embodiments, $R^{19a}$ and $R^{20a}$ are independently $C_1$-$C_6$ alkyl, and $R^{19b}$ and $R^{20b}$ are both hydrogen. In some embodiments, $R^{19a}$ and $R^{20a}$ are both methyl, and $R^{19b}$ and $R^{20b}$ are both hydrogen. In some embodiments, $R^{19a}$ and $R^{20a}$ are taken together to form a $C_1$-$C_6$ alkylene moiety, and $R^{19b}$ and $R^{20b}$ are both hydrogen. In some embodiments, $R^{19a}$ and $R^{20a}$ are taken together to form an ethylene (—$CH_2$—$CH_2$—) moiety, and $R^{19b}$ and $R^{20b}$ are both hydrogen. In some embodiments, $R^{19a}$ and $R^{20a}$ are taken together to form a propylene (—$CH_2$—$CH_2$—$CH_2$—) moiety, and $R^{19b}$ and $R^{20b}$ are both hydrogen. In some embodiments, $R^{17a}$ and $R^{19a}$ are taken together to form a $C_1$-$C_6$ alkylene moiety, and $R^{17b}$ and $R^{19b}$ are both hydrogen. In some embodiments, $R^{17a}$ and $R^{19a}$ are taken together to form an ethylene (—$CH_2$—$CH_2$—) moiety, and $R^{17b}$ and $R^{19b}$ are both hydrogen. In some embodiments, $R^{17a}$ and $R^{19a}$ are taken together to form a propylene (—$CH_2$—$CH_2$—$CH_2$—) moiety, and $R^{17b}$ and $R^{19b}$ are both hydrogen.

In some embodiments of the compounds of formula (II), (III), (IV), or (V), r2 is 2 and s2 is 0. In some embodiments, $R^{17a}$ and $R^{17b}$ are independently hydrogen or $C_1$-$C_6$ alkyl. In some embodiments, $R^{17a}$ and $R^{17b}$ are both hydrogen. In some embodiments, $R^{17a}$ and $R^{17b}$ are both $C_1$-$C_6$ alkyl. In some embodiments, $R^{17a}$ and $R^{17b}$ are both methyl. In some embodiments, $R^{17a}$ is hydrogen and $R^{17b}$ is $C_1$-$C_6$ alkyl. In some embodiments, $R^{17a}$ is hydrogen and $R^{17b}$ is methyl. In some embodiments, $R^{18a}$ and $R^{18b}$ are independently hydrogen or $C_1$-$C_6$ alkyl. In some embodiments, $R^{18a}$ and $R^{18b}$ are both hydrogen. In some embodiments, $R^{18a}$ and $R^{18b}$ are both $C_1$-$C_6$ alkyl. In some embodiments, $R^{18a}$ and $R^{18b}$ are both methyl. In some embodiments, $R^{18a}$ is hydrogen and $R^{18b}$ is $C_1$-$C_6$ alkyl. In some embodiments, $R^{18a}$ is hydrogen and $R^{18b}$ is methyl. In some embodiments, $R^{17a}$, $R^{17b}$, $R^{18a}$, and $R^{18b}$ are hydrogen. In some embodiments, $R^{17a}$, $R^{17b}$, $R^{18a}$, and $R^{18b}$ are independently $C_1$-$C_6$ alkyl. In some embodiments, $R^{17a}$, $R^{17b}$, $R^{18a}$, and $R^{18b}$ are methyl. In some embodiments, $R^{17a}$ and $R^{18a}$ are independently $C_1$-$C_6$ alkyl, and $R^{17b}$ and $R^{18b}$ are both hydrogen. $R^{17a}$ and $R^{18a}$ are both methyl, and $R^{17b}$ and $R^{18b}$ are both hydrogen. In some embodiments, $R^{17a}$ and $R^{18a}$ are taken together to form a $C_1$-$C_6$ alkylene moiety, and $R^{17b}$ and $R^{18b}$ are both hydrogen. In some embodiments, $R^{17a}$ and $R^{18a}$ are taken together to form an ethylene (—$CH_2$—$CH_2$—) moiety, and $R^{17b}$ and $R^{18b}$ are both hydrogen. In some embodiments, $R^{17a}$ and $R^{18a}$ are taken together to form a propylene (—$CH_2$—$CH_2$—$CH_2$—) moiety, and $R^{17b}$ and $R^{18b}$ are both hydrogen. In some embodiments, $R^{19a}$ and $R^{19b}$ are independently at each occurrence hydrogen or $C_1$-$C_6$ alkyl. In some embodiments, $R^{19a}$ and $R^{19b}$ are independently at each occurrence hydrogen or methyl. In some embodiments, $R^{19a}$ and $R^{19b}$ are both at each occurrence hydrogen. In some embodiments, $R^{19a}$ and $R^{19b}$ are both at each occurrence $C_1$-$C_6$ alkyl. In some embodiments, $R^{19a}$ and $R^{19b}$ are both at each occurrence methyl. In some embodiments, $R^{19a}$ is at each occurrence hydrogen and $R^{19b}$ is at each occurrence $C_1$-$C_6$ alkyl. In some embodiments, $R^{19a}$ is at each occurrence hydrogen and $R^{19b}$ is at each occurrence methyl. In some embodiments, $R^{19a}$ is at each occurrence hydrogen and $R^{19b}$ is at each occurrence methyl. In some embodiments, one $R^{19a}$ is hydrogen and the other $R^{19a}$ is $C_1$-$C_6$ alkyl and $R^{19b}$ is at each occurrence hydrogen. In some embodiments, one $R^{19a}$ is hydrogen and the other $R^{19a}$ is methyl, and $R^{19b}$ is at each occurrence hydrogen. In some embodiments, $R^{19a}$ is at each occurrence hydrogen, one $R^{19b}$ is hydrogen, and the other $R^{19b}$ is $C_1$-$C_6$ alkyl. In some embodiments, $R^{19a}$ is at each occurrence hydrogen, one $R^{19b}$ is hydrogen, and the other $R^{19b}$ is methyl. In some embodiments, $R^{17a}$ and an $R^{19a}$ moiety are taken together to form a $C_1$-$C_6$ alkylene moiety, and $R^{17b}$ and the $R^{19b}$ in the geminal position to the $R^{19a}$ taken together with $R^{17a}$, are both hydrogen. In some embodiments, $R^{17a}$ and an $R^{19a}$ moiety are taken together to form an ethylene (—$CH_2$—$CH_2$—) moiety, and $R^{17b}$ and the $R^{19b}$ in the geminal position to the $R^{19a}$ taken together with $R^{17a}$, are both hydrogen. In some embodiments, $R^{17a}$ and an $R^{19a}$ moiety are taken together to form a propylene (—$CH_2$—$CH_2$—$CH_2$—) moiety, and $R^{17b}$ and the $R^{19b}$ in the geminal position to the $R^{19a}$ taken together with $R^{17a}$, are both hydrogen.

In some embodiments of the compounds of formula (II), (III), (IV), or (V), $R^{27}$, independently at each occurrence, is halogen. In some embodiments, $R^{27}$, independently at each occurrence, is selected from the group consisting of fluoro and chloro.

In some embodiments of the compounds of formula (II), (III), (IV), or (V), $R^{29}$, independently at each occurrence, is halogen. In some embodiments, $R^{29}$, independently at each occurrence, is selected from the group consisting of fluoro and chloro.

In some embodiments of the compounds of formula (II), (III), (IV), or (V):

m3 is 0 and n3 is 0;
$X^3$ is CH and $Y^3$ is $NR^{13}$;
$X^4$ is CH and $Y^4$ is $NR^{14}$;
$R^{21a}$ and $R^{21b}$ are taken together to form an oxo (=O) substituent;
$R^{23a}$ and $R^{23b}$ are taken together to form an oxo (=O) substituent;

$A^3$ is a substituent of the formula ($A^3$-b)

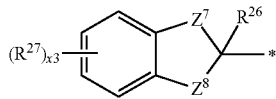

wherein
represents the attachment point to the remainder of the molecule;
$Z^7$ is selected from the group consisting of $CR^{Z7-1}R^{Z7-2}$, $NR^{Z7-2}$, O, S, and —$CR^{Z7-1}$=$CR^{Z7-1}$—;
wherein
$R^{Z7-1}$ is H or $R^{27}$; and
$R^{Z7-2}$ is H or $R^{27}$;
$Z^8$ is selected from the group consisting of $CR^{Z8-1}R^{Z8-2}$, $NR^{Z8-2}$; O, S, and —$CR^{Z8-1}$=$CR^{Z8-1}$—;
wherein
$R^{Z8-1}$ is H or $R^{27}$; and
$R^{Z8-2}$ is H or $R^{27}$;
$R^{26}$ is hydrogen or $R^{27}$, or $R^{26}$ and $R^{Z7-2}$ are taken together to form a double bond between the carbon atom bearing $R^{26}$ and $Z^7$;
$R^{27}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —$NH_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —$NR^{27-a}R^{27-b}$, —CN, —C(O)OH, —C(O)O($C_1$-$C_6$ alkyl), —C(O)O($C_1$-$C_6$ haloalkyl), —C(O)$NH_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)$NR^{27-a}R^{27-b}$, —S(O)$_2$OH, —S(O)$_2$O($C_1$-$C_6$ alkyl), —S(O)$_2$O($C_1$-$C_6$ haloalkyl), —S(O)$_2$$NH_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$$NR^{27-a}R^{27-b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);
wherein $R^{27-a}$ and $R^{27-b}$ are taken together with the nitrogen atom which bears them to form a 3-10 membered heterocycle;
x3 is 0, 1, 2, 3, or 4;
$A^4$ is a substituent of the formula ($A^4$-b)

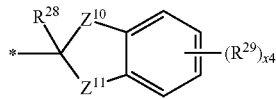

wherein
represents the attachment point to the remainder of the molecule; $Z^{10}$ is selected from the group consisting of $CR^{Z10-1}R^{Z10-2}$, $NR^{Z10-2}$, O, S, and —$CR^{Z10-1}$=$CR^{Z10-1}$—;
wherein
$R^{Z10-1}$ is H or $R^{29}$; and
$R^{Z10-2}$ is H or $R^{29}$;
$Z^{11}$ is selected from the group consisting of $CR^{Z11-1}R^{Z11-2}$, $NR^{Z11-2}$; O, S, and —$CR^{Z11-1}$=$CR^{Z11-1}$—;
wherein
$R^{Z11-1}$ is H or $R^{29}$; and
$R^{Z11-2}$ is H or $R^{29}$;
$R^{28}$ is hydrogen or $R^{29}$, or $R^{28}$ and $R^{Z10-2}$ are taken together to form a double bond between the carbon atom bearing $R^{28}$ and $Z^{10}$;
$R^{29}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —$NH_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —$NR^{29-a}R^{29-b}$, —CN, —C(O)OH, —C(O)O($C_1$-$C_6$ alkyl), —C(O)O($C_1$-$C_6$ haloalkyl), —C(O)$NH_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)$NR^{29-a}R^{29-b}$, —S(O)$_2$OH, —S(O)$_2$O($C_1$-$C_6$ alkyl), —S(O)$_2$O($C_1$-$C_6$ haloalkyl), —S(O)$_2$$NH_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$$NR^{29-a}R^{29-b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);
wherein $R^{29-a}$ and $R^{29-b}$ are taken together with the nitrogen atom which bears them to form a 3-10 membered heterocycle;
x4 is 0, 1, 2, 3, or 4; and
provided that $A^3$ and $A^4$ are not both simultaneously a moiety selected from group consisting of:

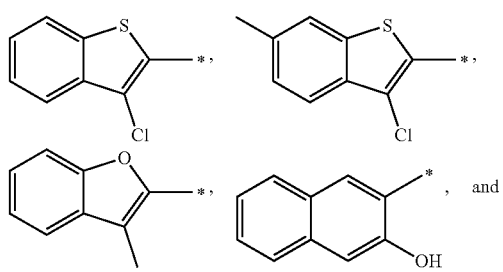

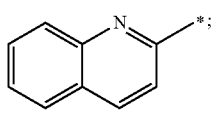

wherein the * represents the attachment point to the remainder of the molecule.

In some embodiments of the compounds of formula (II), (III), (IV), or (V), wherein m3 is 0 and n3 is 0, $X^3$ is CH, $Y^3$ is $NR^{Y3}$, $X^4$ is CH, $Y^4$ is $NR^{Y4}$, $R^{21a}$ and $R^{21b}$ are taken together to form an oxo (=O) substituent, and $R^{23a}$ and $R^{23b}$ are taken together to form an oxo (=O) substituent; ($A^3$-b) is selected from the group consisting of:

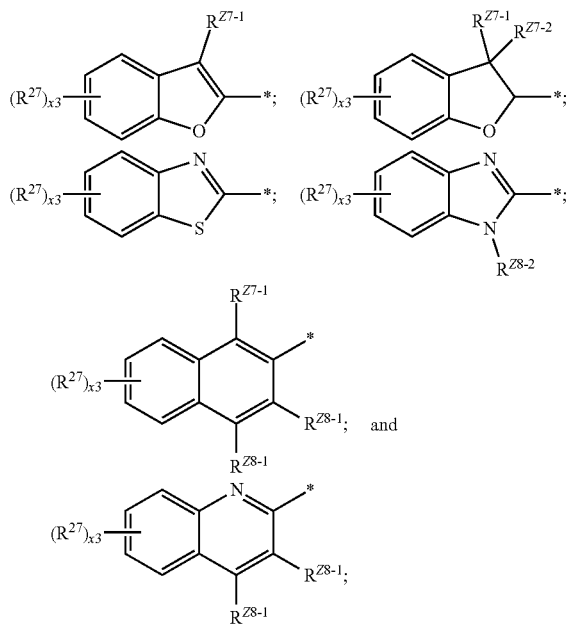

wherein the * represents the attachment point to the remainder of the molecule. In some embodiments, ($A^3$-b) is selected from the group consisting of:

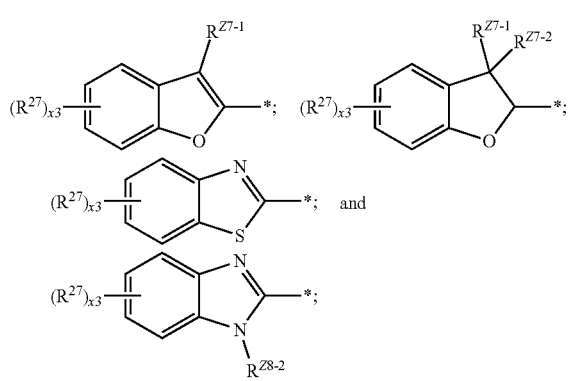

wherein the * represents the attachment point to the remainder of the molecule. In some embodiments, ($A^3$-b) is selected from the group consisting of:

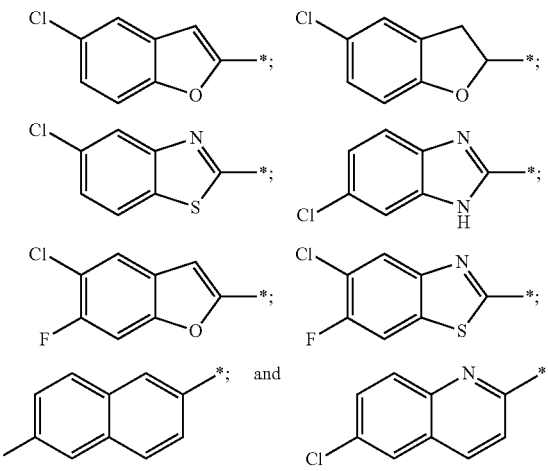

wherein the * represents the attachment point to the remainder of the molecule. In some embodiments, ($A^3$-b) is selected from the group consisting of:

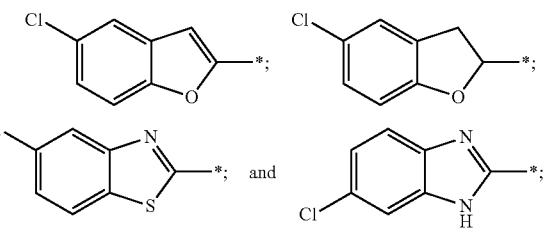

wherein the * represents the attachment point to the remainder of the molecule.

In some embodiments of the compounds of formula (II), (III), (IV), or (V), wherein m3 is 0 and n3 is 0, $X^3$ is CH, $Y^3$ is $NR^{Y3}$, $X^4$ is CH, $Y^4$ is $NR^{Y4}$, $R^{21a}$ and $R^{21b}$ are taken together to form an oxo (=O) substituent, and $R^{23a}$ and $R^{23b}$ are taken together to form an oxo (=O) substituent; ($A^4$-b) is selected from the group consisting of:

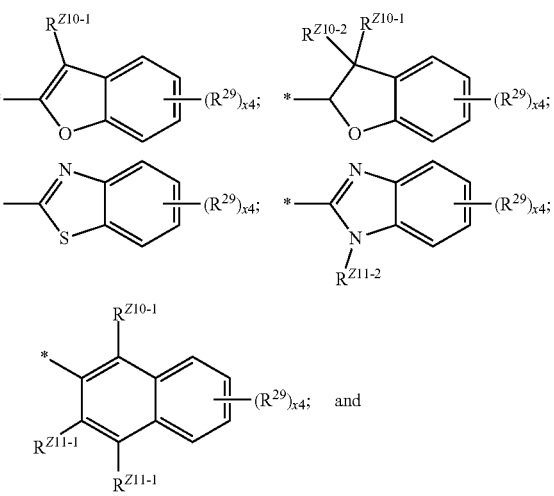

-continued

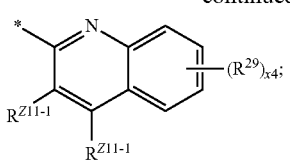

wherein the * represents the attachment point to the remainder of the molecule. In some embodiments, (A⁴-b) is selected from the group consisting of:

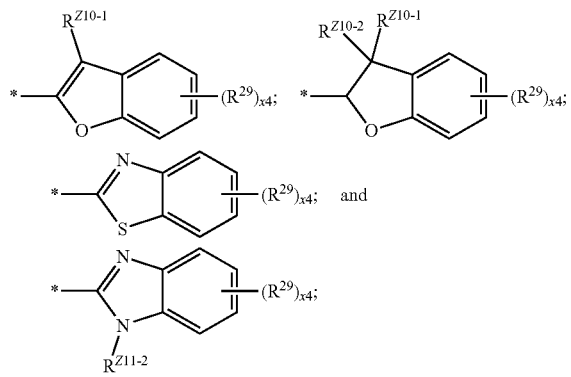

wherein the * represents the attachment point to the remainder of the molecule. In some embodiments, (A⁴-b) is selected from the group consisting of:

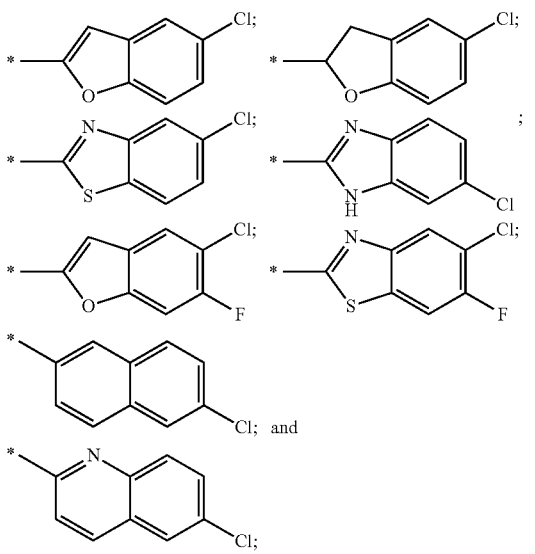

wherein the * represents the attachment point to the remainder of the molecule. In some embodiments, (A⁴-b) is selected from the group consisting of:

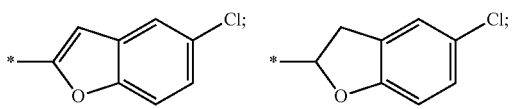

-continued

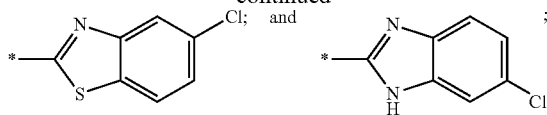

wherein the * represents the attachment point to the remainder of the molecule.

In some embodiments of the compounds of formula (II), (III), (IV), or (V):
m3 is 0 and n3 is 1;
r2 is 1 or 2;
s2 is 1 or 2;
X³ is CH and Y³ is NR^{Y3};
R^{21a} and R^{21b} are taken together to form an oxo (=O) substituent;
R^{24a} is selected from the group consisting of hydrogen, —OH, and —NH₂;
R^{25a} and R^{25b} are both hydrogen;
A³ is a substituent of the formula (A³-b)

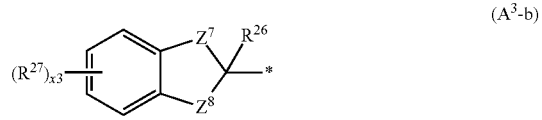

wherein
represents the attachment point to the remainder of the molecule; Z⁷ is selected from the group consisting of CR^{Z7-1}R^{Z7-2}, NR^{Z7-2}, O, S, and —CR^{Z7-1}=CR^{Z7-1}—;
wherein
R^{Z7-1} is H or R^{27}; and
R^{Z7-2} is H or R^{27};
Z⁸ is selected from the group consisting of CR^{Z8-1}R^{Z8-2}, NR^{Z8-2}; O, S, and —CR^{Z8-1}=CR^{Z8-1}—;
wherein
R^{Z8-1} is H or R^{27}; and
R^{Z8-2} is H or R^{27};
R^{26} is hydrogen or R^{27}, or R^{26} and R^{Z7-2} are taken together to form a double bond between the carbon atom bearing R^{26} and Z⁷;
R^{27} is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —NH₂, —NH($C_1$-$C_6$ alkyl), —NH($C_1$-$C_6$ haloalkyl), —N($C_1$-$C_6$ alkyl)₂, —N($C_1$-$C_6$ haloalkyl)₂, —NR^{27-a}R^{27-b}, —CN, —C(O)OH, —C(O)O($C_1$-$C_6$ alkyl), —C(O)O($C_1$-$C_6$ haloalkyl), —C(O)NH₂, —C(O)NH($C_1$-$C_6$ alkyl), —C(O)NH($C_1$-$C_6$ haloalkyl), —C(O)N($C_1$-$C_6$ alkyl)₂, —C(O)N($C_1$-$C_6$ haloalkyl)₂, —C(O)NR^{27-a}R^{27-b}, —S(O)₂OH, —S(O)₂O($C_1$-$C_6$ alkyl), —S(O)₂O($C_1$-$C_6$ haloalkyl), —S(O)₂NH₂, —S(O)₂NH($C_1$-$C_6$ alkyl), —S(O)₂NH($C_1$-$C_6$ haloalkyl), —S(O)₂N($C_1$-$C_6$ alkyl)₂, —S(O)₂N($C_1$-$C_6$ haloalkyl)₂, —S(O)₂NR^{27-a}R^{27-b}, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-

$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);

wherein $R^{27\text{-}a}$ and $R^{27\text{-}b}$ are taken together with the nitrogen atom which bears them to form a 3-10 membered heterocycle;

x3 is 0, 1, 2, 3, or 4; and $A^4$ is $C_6$-$C_{10}$ aryl optionally substituted with one or more $R^{29}$ substituent, or 5-10 membered heteroaryl optionally substituted with one or more $R^{29}$ substituent;

$R^{29}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —NH$_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —NR$^{29\text{-}a}$R$^{29\text{-}b}$, —CN, —C(O)OH, —C(O)O($C_1$-$C_6$ alkyl), —C(O)O($C_1$-$C_6$ haloalkyl), —C(O)NH$_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)NR$^{29\text{-}a}$R$^{29\text{-}b}$, —S(O)$_2$OH, —S(O)$_2$O($C_1$-$C_6$ alkyl), —S(O)$_2$O($C_1$-$C_6$ haloalkyl), —S(O)$_2$NH$_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$NR$^{29\text{-}a}$R$^{29\text{-}b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);

wherein $R^{29\text{-}a}$ and $R^{29\text{-}b}$ are taken together with the nitrogen atom which bears them to form a 3-10 membered heterocycle.

In some embodiments of the compounds of formula (II), (III), (IV), or (V), wherein m3 is 0, n3 is 1, r2 is 1 or 2, s2 is 1 or 2, $X^3$ is CH, $Y^3$ is NR$^{Y3}$, $R^{21a}$ and $R^{21b}$ are taken together to form an oxo (=O) substituent, $R^{24a}$ is selected from the group consisting of hydrogen, —OH, and —NH$_2$, and $R^{25a}$ and $R^{25b}$ are both hydrogen; $X^4$ is CH. In some embodiments, $Y^4$ is a bond. In some embodiments, Y is a NR. In some embodiments, R is hydrogen. In some embodiments, $R^{Y4}$ is $C_1$-$C_6$ alkyl. In some embodiments, $R^{Y4}$ is methyl. In some embodiments, $R^{Y4}$ is ethyl. In some embodiments, $Y^4$ is a O. In some embodiments, $R^{23a}$ and $R^{23b}$ are taken together to form an oxo (=O) substituent and $R^{24a}$ is —OH or —NH$_2$. In some embodiments, $R^{24a}$ is —OH. In some embodiments, $R^{24a}$ is —NH$_2$. In some embodiments, $R^{23a}$ and $R^{23b}$ are taken together to form an imido (=NH) substituent. In some embodiments, $R^{24a}$ is hydrogen. In some embodiments, $R^{24a}$ is —OH. In some embodiments, $R^{24a}$ is —NH$_2$.

In some embodiments of the compounds of formula (II), (III), (IV), or (V), wherein m3 is 0, n3 is 1, r2 is 1 or 2, s2 is 1 or 2, $X^3$ is CH, $Y^3$ is NR$^{Y3}$, $R^{21a}$ and $R^{21b}$ are taken together to form an oxo (=O) substituent, $R^{24a}$ is selected from the group consisting of hydrogen, —OH, and —NH$_2$, and $R^{25a}$ and $R^{25b}$ are both hydrogen; $X^4$ is N. In some embodiments, $R^{23a}$ and $R^{23b}$ are taken together to form an oxo (=O) substituent and $R^{24a}$ is —OH or —NH$_2$. In some embodiments, $R^{24a}$ is —OH. In some embodiments, $R^{24a}$ is —NH$_2$. In some embodiments, $R^{23a}$ and $R^{23b}$ are taken together to form an imido (=NH) substituent. In some embodiments, $R^{24a}$ is hydrogen. In some embodiments, $R^{24a}$ is —OH. In some embodiments, $R^{24a}$ is —NH$_2$. In some embodiments, $R^{23a}$ and $R^{23b}$ are both hydrogen. In some embodiments, $R^{24a}$ is hydrogen. In some embodiments, $R^{24a}$ is —OH. In some embodiments, $R^{24a}$ is —NH$_2$.

In some embodiments of the compounds of formula (II), (III), (IV), or (V), wherein m3 is 0, n3 is 1, r2 is 1 or 2, s2 is 1 or 2, $X^3$ is CH, $Y^3$ is NR$^{Y3}$, $R^{21a}$ and $R^{21b}$ are taken together to form an oxo (=O) substituent, $R^{24a}$ is selected from the group consisting of hydrogen, —OH, and —NH$_2$, and $R^{25a}$ and $R^{25b}$ are both hydrogen; ($A^3$-b) is selected from the group consisting of:

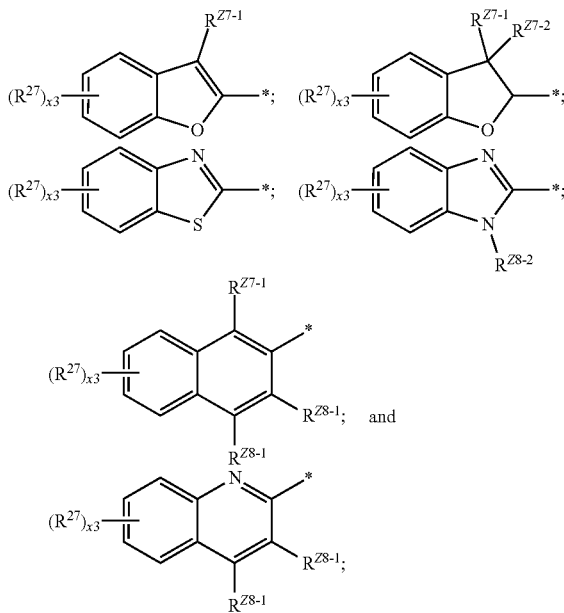

wherein the * represents the attachment point to the remainder of the molecule. In some embodiments, ($A^3$-b) is selected from the group consisting of:

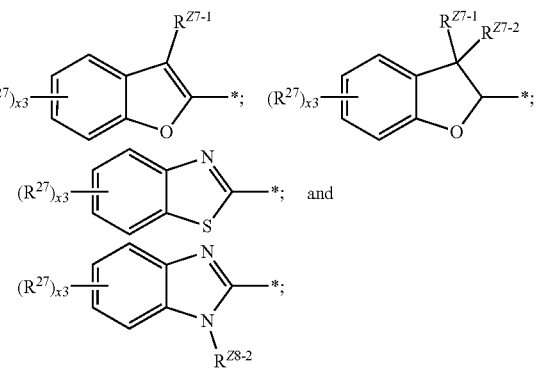

wherein the * represents the attachment point to the remainder of the molecule. In some embodiments, (A³-b) is selected from the group consisting of:

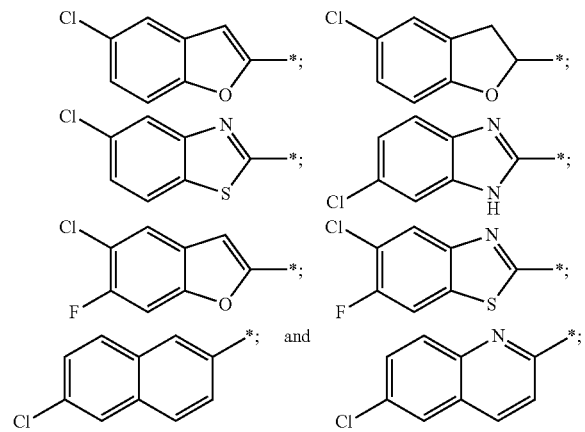

wherein the * represents the attachment point to the remainder of the molecule. In some embodiments, (A³-b) is selected from the group consisting of:

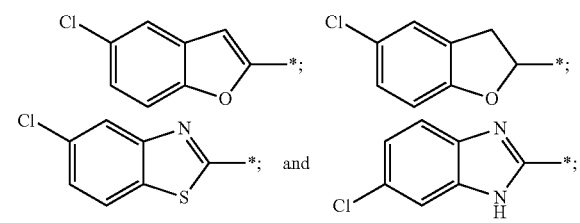

wherein the * represents the attachment point to the remainder of the molecule.

In some embodiments of the compounds of formula (II), (III), (IV), or (V), wherein m3 is 0, n3 is 1, r2 is 1 or 2, s2 is 1 or 2, $X^3$ is CH, $Y^3$ is $NR^{Y3}$, $R^{21a}$ and $R^{21b}$ are taken together to form an oxo (=O) substituent, $R^{24a}$ is selected from the group consisting of hydrogen, —OH, and —NH₂, and $R^{25a}$ and $R^{25b}$ are both hydrogen; $A^4$ is $C_6$-$C_{10}$ aryl optionally substituted with one or more $R^{29}$ substituent. In some embodiments, $A^4$ is selected from the group consisting of:

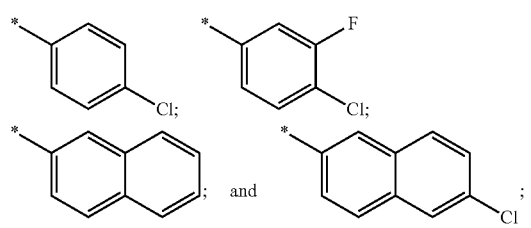

wherein the * represents the attachment point to the remainder of the molecule.

In some embodiments of the compounds of formula (II), (III), (IV), or (V), wherein m3 is 0, n3 is 1, r2 is 1 or 2, s2 is 1 or 2, $X^3$ is CH, $Y^3$ is $NR^{Y3}$, $R^{21a}$ and $R^{21b}$ are taken together to form an oxo (=O) substituent, $R^{24a}$ is selected from the group consisting of hydrogen, —OH, and —NH₂, and $R^{25a}$ and $R^{25b}$ are both hydrogen; $A^4$ is 5-10 membered heteroaryl optionally substituted with one or more $R^{29}$ substituent. In some embodiments, $A^4$ is selected from the group consisting of:

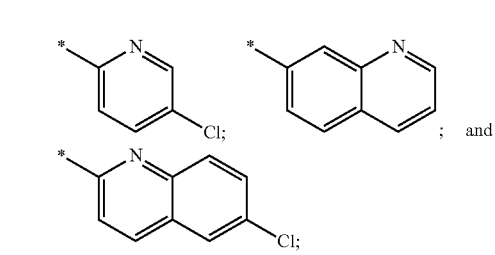

wherein the * represents the attachment point to the remainder of the molecule.

In some embodiments of the compounds of formula (II), (III), (IV), or (V):

m3 is 1 and n3 is 0;

$X^4$ is CH and $Y^4$ is $NR^{Y4}$;

$R^{21a}$ and $R^{21b}$ are taken together to form an oxo (=O) substituent or an imido (=NH) substituent;

$R^{23a}$ and $R^{23b}$ are taken together to form an oxo (=O) substituent;

$A^3$ is $C_6$-$C_{10}$ aryl optionally substituted with one or more $R^{27}$ substituent, or 5-10 membered heteroaryl optionally substituted with one or more $R^{27}$ substituent;

$R^{27}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —NH₂, —NH($C_1$-$C_6$ alkyl), —NH($C_1$-$C_6$ haloalkyl), —N($C_1$-$C_6$ alkyl)₂, —N($C_1$-$C_6$ haloalkyl)₂, —NR$^{27-a}$R$^{27-b}$, —CN, —C(O)OH, —C(O)O($C_1$-$C_6$ alkyl), —C(O)O($C_1$-$C_6$ haloalkyl), —C(O)NH₂, —C(O)NH($C_1$-$C_6$ alkyl), —C(O)NH($C_1$-$C_6$ haloalkyl), —C(O)N($C_1$-$C_6$ alkyl)₂, —C(O)N($C_1$-$C_6$ haloalkyl)₂, —C(O)NR$^{27-a}$R$^{27-b}$, —S(O)₂OH, —S(O)₂O($C_1$-$C_6$ alkyl), —S(O)₂O($C_1$-$C_6$ haloalkyl), —S(O)₂NH₂, —S(O)₂NH($C_1$-$C_6$ alkyl), —S(O)₂NH($C_1$-$C_6$ haloalkyl), —S(O)₂N($C_1$-$C_6$ alkyl)₂, —S(O)₂N($C_1$-$C_6$ haloalkyl)₂, —S(O)₂NR$^{27-a}$ R$^{27-b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)₂($C_1$-$C_6$ alkyl), —OS(O)₂($C_1$-$C_6$ haloalkyl), —N(H)S(O)₂($C_1$-$C_6$ alkyl), —N(H)S(O)₂($C_1$-$C_6$ haloalkyl), —N($C_1$-$C_6$ alkyl)S(O)₂($C_1$-$C_6$ alkyl), —N($C_1$-$C_6$ alkyl)S(O)₂($C_1$-$C_6$ haloalkyl), —N($C_1$-$C_6$ haloalkyl)S(O)₂($C_1$-$C_6$ alkyl), and —N($C_1$-$C_6$ haloalkyl)S(O)₂($C_1$-$C_6$ haloalkyl);

wherein $R^{27-a}$ and $R^{27-b}$ are taken together with the nitrogen atom which bears them to form a 3-10 membered heterocycle;

$A^4$ is a substituent of the formula ($A^4$-b)

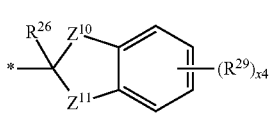

wherein
represents the attachment point to the remainder of the molecule; $Z^{10}$ is selected from the group consisting of $CR^{Z10-1}R^{Z10-2}$, $NR^{Z10-2}$, O, S, and —$CR^{Z10-1}$=$CR^{Z10-1}$—;
wherein
$R^{Z10-1}$ is H or $R^{29}$; and
$R^{Z10-2}$ is H or $R^{29}$;
$Z^{11}$ is selected from the group consisting of $CR^{Z11-1}R^{Z11-2}$, $NR^{Z11-2}$; O, S, and —$CR^{Z11-1}$=$CR^{Z11-1}$—;
wherein
$R^{Z11-1}$ is H or $R^{29}$; and
$R^{Z11-2}$ is H or $R^{29}$;
$R^{28}$ is hydrogen or $R^{29}$, or $R^{28}$ and $R^{Z10-2}$ are taken together to form a double bond between the carbon atom bearing $R^{28}$ and $Z^{10}$; $R^{29}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —$NH_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —$NR^{29-a}R^{29-b}$, —CN, —C(O)OH, —C(O)O($C_1$-$C_6$ alkyl), —C(O)O($C_1$-$C_6$ haloalkyl), —C(O)$NH_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)$NR^{29-a}R^{29-b}$, —S(O)$_2$OH, —S(O)$_2$O($C_1$-$C_6$ alkyl), —S(O)$_2$O($C_1$-$C_6$ haloalkyl), —S(O)$_2NH_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2NR^{29-a}R^{29-b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);
wherein $R^{29-a}$ and $R^{29-b}$ are taken together with the nitrogen atom which bears them to form a 3-10 membered heterocycle;
x4 is 0, 1, 2, 3, or 4.

In some embodiments of the compounds of formula (II), (III), (IV), or (V), wherein m3 is 1, n3 is 0, $X^4$ is CH, $Y^4$ is $NR^{Y4}$, $R^{21a}$ and $R^{21b}$ are taken together to form an oxo (=O) substituent or an imido (=NH) substituent, and $R^{23a}$ and $R^{23b}$ are taken together to form an oxo (=O) substituent; $X^3$ is CH. In some embodiments, $Y^3$ is a bond. In some embodiments, $Y^3$ is a NR. In some embodiments, R is hydrogen. In some embodiments, R is $C_1$-$C_6$ alkyl. In some embodiments, $R^{Y3}$ is methyl. In some embodiments, $R^{Y3}$ is ethyl. In some embodiments, $Y^3$ is a O. In some embodiments, $X^3$ is N. In some embodiments, $R^{21a}$ and $R^{21b}$ are taken together to form an oxo (=O) substituent. In some embodiments, $R^{21a}$ and $R^{21b}$ are taken together to form an imido (=NH) substituent.

In some embodiments of the compounds of formula (II), (III), (IV), or (V), wherein m3 is 1, n3 is 0, $X^4$ is CH, $Y^4$ is $NR^{Y4}$, $R^{21a}$ and $R^{21b}$ are taken together to form an oxo (=O) substituent or an imido (=NH) substituent, and $R^{23a}$ and $R^{23b}$ are taken together to form an oxo (=O) substituent; $A^3$ is $C_6$-$C_{10}$ aryl optionally substituted with one or more $R^{27}$ substituent. In some embodiments, $A^3$ is selected from the group consisting of:

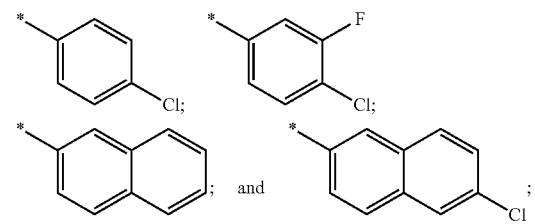

wherein the * represents the attachment point to the remainder of the molecule.

In some embodiments of the compounds of formula (II), (III), (IV), or (V), wherein m3 is 1, n3 is 0, $X^4$ is CH, $Y^4$ is $NR^{Y4}$, $R^{21a}$ and $R^{21b}$ are taken together to form an oxo (=O) substituent or an imido (=NH) substituent, and $R^{23a}$ and $R^{23b}$ are taken together to form an oxo (=O) substituent; $A^3$ is 5-10 membered heteroaryl optionally substituted with one or more $R^{27}$ substituent. In some embodiments, $A^3$ is selected from the group consisting of:

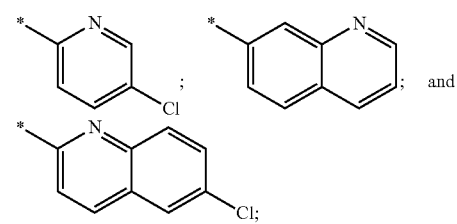

wherein the * represents the attachment point to the remainder of the molecule.

In some embodiments of the compounds of formula (II), (III), (IV), or (V), wherein m3 is 1, n3 is 0, $X^4$ is CH, $Y^4$ is $NR^{Y4}$, $R^{21a}$ and $R^{21b}$ are taken together to form an oxo (=O) substituent or an imido (=NH) substituent, and $R^{23a}$ and $R^{23b}$ are taken together to form an oxo (=O) substituent; ($A^4$-b) is selected from the group consisting of:

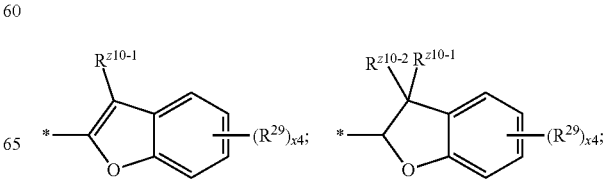

-continued

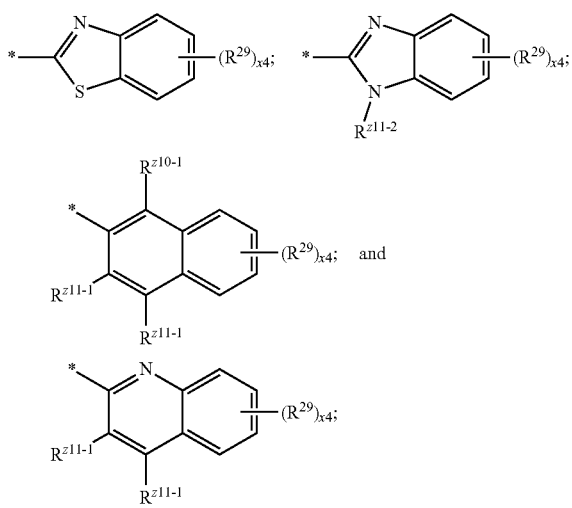

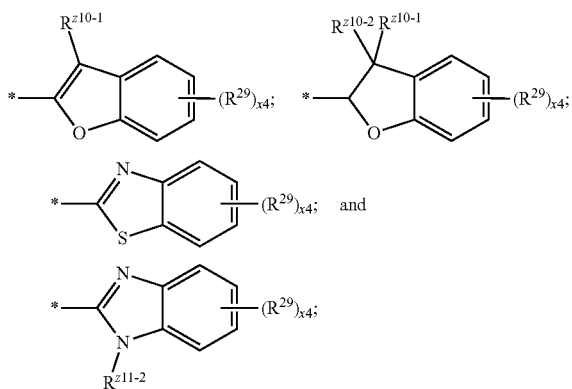

wherein the * represents the attachment point to the remainder of the molecule. In some embodiments, (A⁴-b) is selected from the group consisting of:

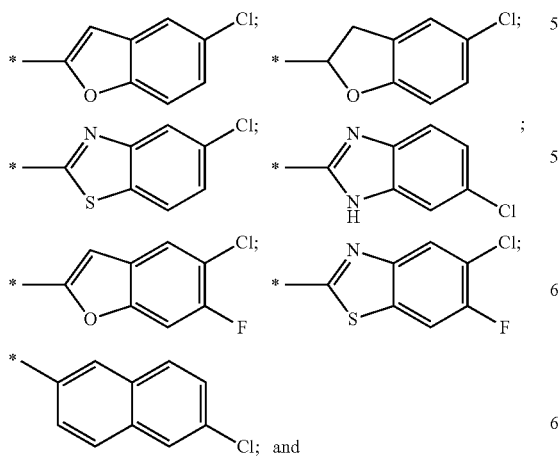

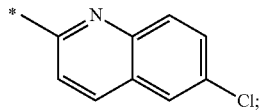

wherein the * represents the attachment point to the remainder of the molecule. In some embodiments, (A⁴-b) is selected from the group consisting of:

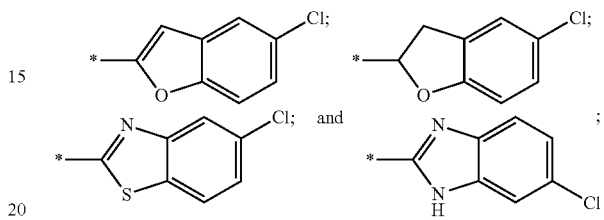

wherein the * represents the attachment point to the remainder of the molecule.

In some embodiments of the compounds of formula (II), (III), (IV), or (V):

m3 is 1 and n3 is 1;

$R^{21a}$ and $R^{21b}$ are taken together to form an oxo (=O) substituent or an imido (=NH) substituent;

$A^3$ is $C_6$-$C_{10}$ aryl optionally substituted with one or more $R^{27}$ substituent, or 5-10 membered heteroaryl optionally substituted with one or more $R^{27}$ substituent;

$R^{27}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —NH$_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —NR$^{27-a}$R$^{27-b}$, —CN, —C(O)OH, —C(O)O($C_1$-$C_6$ alkyl), —C(O)O($C_1$-$C_6$ haloalkyl), —C(O)NH$_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)NR$^{27-a}$R$^{27-b}$, —S(O)$_2$OH, —S(O)$_2$O($C_1$-$C_6$ alkyl), —S(O)$_2$O($C_1$-$C_6$ haloalkyl), —S(O)$_2$NH$_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$NR$^{27-a}$R$^{27-b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);

wherein $R^{27-a}$ and $R^{27-b}$ are taken together with the nitrogen atom which bears them to form a 3-10 membered heterocycle;

$A^4$ is $C_6$-$C_{10}$ aryl optionally substituted with one or more $R^{29}$ substituent, or 5-10 membered heteroaryl optionally substituted with one or more $R^{29}$ substituent;

$R^{29}$ is selected, independently at each occurrence, from the group consisting of halogen, $C_1\text{-}C_6$ alkyl, $C_1\text{-}C_6$ haloalkyl, —OH, —O($C_1\text{-}C_6$ alkyl), —O($C_1\text{-}C_6$ haloalkyl), —SH, —S($C_1\text{-}C_6$ alkyl), —S($C_1\text{-}C_6$ haloalkyl), —NH$_2$, —NH($C_1\text{-}C_6$ alkyl), —NH($C_1$-$C_6$ haloalkyl), —N($C_1\text{-}C_6$ alkyl)$_2$, —N($C_1\text{-}C_6$ haloalkyl)$_2$, —NR$^{29\text{-}a}$R$^{29\text{-}b}$, —CN, —C(O)OH, —C(O)O($C_1\text{-}C_6$ alkyl), —C(O)O($C_1\text{-}C_6$ haloalkyl), —C(O)NH$_2$, —C(O)NH($C_1\text{-}C_6$ alkyl), —C(O)NH($C_1\text{-}C_6$ haloalkyl), —C(O)N($C_1\text{-}C_6$ alkyl)$_2$, —C(O)N($C_1\text{-}C_6$ haloalkyl)$_2$, —C(O)NR$^{29\text{-}a}$R$^{29\text{-}b}$, —S(O)$_2$OH, —S(O)$_2$O($C_1\text{-}C_6$ alkyl), —S(O)$_2$O($C_1\text{-}C_6$ haloalkyl), —S(O)$_2$NH$_2$, —S(O)$_2$NH($C_1\text{-}C_6$ alkyl), —S(O)$_2$NH($C_1\text{-}C_6$ haloalkyl), —S(O)$_2$N($C_1\text{-}C_6$ alkyl)$_2$, —S(O)$_2$N($C_1\text{-}C_6$ haloalkyl)$_2$, —S(O)$_2$NR$^{29\text{-}a}$R$^{29\text{-}b}$, —OC(O)H, —OC(O)($C_1\text{-}C_6$ alkyl), —OC(O)($C_1\text{-}C_6$ haloalkyl), —N(H)C(O)H, —N(H)C(O)($C_1\text{-}C_6$ alkyl), —N(H)C(O)($C_1\text{-}C_6$ haloalkyl), —N($C_1\text{-}C_6$ alkyl)C(O)H, —N($C_1\text{-}C_6$ alkyl)C(O)($C_1\text{-}C_6$ alkyl), —N($C_1\text{-}C_6$ alkyl)C(O)($C_1\text{-}C_6$ haloalkyl), —N($C_1\text{-}C_6$ haloalkyl)C(O)H, —N($C_1\text{-}C_6$ haloalkyl)C(O)($C_1\text{-}C_6$ alkyl), —N($C_1\text{-}C_6$ haloalkyl)C(O)($C_1\text{-}C_6$ haloalkyl), —OS(O)$_2$($C_1\text{-}C_6$ alkyl), —OS(O)$_2$($C_1\text{-}C_6$ haloalkyl), —N(H)S(O)$_2$($C_1\text{-}C_6$ alkyl), —N(H)S(O)$_2$($C_1\text{-}C_6$ haloalkyl), —N($C_1\text{-}C_6$ alkyl)S(O)$_2$($C_1\text{-}C_6$ alkyl), —N($C_1\text{-}C_6$ alkyl)S(O)$_2$($C_1\text{-}C_6$ haloalkyl), —N($C_1\text{-}C_6$ haloalkyl)S(O)$_2$($C_1\text{-}C_6$ alkyl), and —N($C_1\text{-}C_6$ haloalkyl)S(O)$_2$($C_1\text{-}C_6$ haloalkyl);

wherein $R^{29\text{-}a}$ and $R^{29\text{-}b}$ are taken together with the nitrogen atom which bears them to form a 3-10 membered heterocycle;

provided that:

when one of $X^3$ or $X^4$ is N, then r2 is 1 or 2 and s2 is 1 or 2; and when $R^{23a}$ and $R^{23b}$ are taken together to form an oxo (=O) substituent, then $R^{24a}$ is —OH or —NH$_2$.

In some embodiments of the compounds of formula (II), (III), (IV), or (V), wherein m3 is 1, n3 is 1, and $R^{21a}$ and $R^{21b}$ are taken together to form an oxo (=O) substituent or an imido (=NH) substituent; $X^3$ is CH. In some embodiments, $Y^3$ is a bond. In some embodiments, $Y^3$ is a NR$^{Y3}$. In some embodiments, $R^{Y3}$ is hydrogen. In some embodiments, $R^{Y3}$ is $C_1\text{-}C_6$ alkyl. In some embodiments, $R^{Y3}$ is methyl. In some embodiments, $R^{Y3}$ is ethyl. In some embodiments, $Y^3$ is a O.

In some embodiments of the compounds of formula (II), (III), (IV), or (V), wherein m3 is 1, n3 is 1, and $R^{21a}$ and $R^{21b}$ are taken together to form an oxo (=O) substituent or an imido (=NH) substituent; $X^3$ is N. In some embodiments, $R^{21a}$ and $R^{21b}$ are taken together to form an oxo (=O) substituent. In some embodiments, $R^{21a}$ and $R^{21b}$ are taken together to form an imido (=NH) substituent.

In some embodiments of the compounds of formula (II), (III), (IV), or (V), wherein m3 is 1, n3 is 1, and $R^{21a}$ and $R^{21b}$ are taken together to form an oxo (=O) substituent or an imido (=NH) substituent; $X^4$ is CH. In some embodiments, $Y^4$ is a bond. In some embodiments, $Y^4$ is a NR$^{Y4}$. In some embodiments, R is hydrogen. In some embodiments, R is $C_1\text{-}C_6$ alkyl. In some embodiments, $R^{Y4}$ is methyl. In some embodiments, $R^{Y4}$ is ethyl. In some embodiments, $Y^4$ is a O. In some embodiments, $R^{23a}$ and $R^{23b}$ are taken together to form an oxo (=O) substituent and $R^{24a}$ is —OH or —NH$_2$. In some embodiments, $R^{24a}$ is —OH. In some embodiments, $R^{24a}$ is —NH$_2$. In some embodiments, $R^{23a}$ and $R^{23b}$ are taken together to form an imido (=NH) substituent. In some embodiments, $R^{24a}$ is hydrogen. In some embodiments, $R^{24a}$ is —OH. In some embodiments, $R^{24a}$ is —NH$_2$. In some embodiments, $R^{23a}$ and $R^{23b}$ are both hydrogen. In some embodiments, $R^{24a}$ is hydrogen. In some embodiments, $R^{24a}$ is —OH. In some embodiments, $R^{24a}$ is —NH$_2$.

In some embodiments of the compounds of formula (II), (III), (IV), or (V), wherein m3 is 1, n3 is 1, and $R^{21a}$ and $R^{21b}$ are taken together to form an oxo (=O) substituent or an imido (=NH) substituent; $X^4$ is N. In some embodiments, $R^{23a}$ and $R^{23b}$ are taken together to form an oxo (=O) substituent and $R^{24a}$ is —OH or —NH$_2$. In some embodiments, $R^{24a}$ is —OH. In some embodiments, $R^{24a}$ is —NH$_2$. In some embodiments, $R^{23a}$ and $R^{23b}$ are taken together to form an imido (=NH) substituent. In some embodiments, $R^{24a}$ is hydrogen. In some embodiments, $R^{24a}$ is —OH. In some embodiments, $R^{24a}$ is —NH$_2$. In some embodiments, $R^{23a}$ and $R^{23b}$ are both hydrogen. In some embodiments, $R^{24a}$ is hydrogen. In some embodiments, $R^{24a}$ is —OH. In some embodiments, $R^{24a}$ is —NH$_2$.

In some embodiments of the compounds of formula (II), (III), (IV), or (V), wherein m3 is 1, n3 is 1, and $R^{21a}$ and $R^{21b}$ are taken together to form an oxo (=O) substituent or an imido (=NH) substituent; $A^3$ is $C_6\text{-}C_{10}$ aryl optionally substituted with one or more $R^{27}$ substituent. In some embodiments, $A^3$ is selected from the group consisting of:

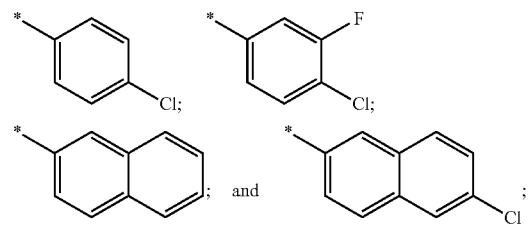

wherein the * represents the attachment point to the remainder of the molecule.

In some embodiments of the compounds of formula (II), (III), (IV), or (V), wherein m3 is 1, n3 is 1, and $R^{21a}$ and $R^{21b}$ are taken together to form an oxo (=O) substituent or an imido (=NH) substituent; $A^3$ is 5-10 membered heteroaryl optionally substituted with one or more $R^{27}$ substituent. In some embodiments, $A^3$ is selected from the group consisting of:

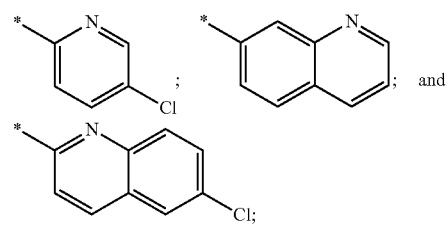

wherein the * represents the attachment point to the remainder of the molecule.

In some embodiments of the compounds of formula (II), (III), (IV), or (V), wherein m3 is 1, n3 is 1, and $R^{21a}$ and $R^{21b}$ are taken together to form an oxo (=O) substituent or an imido (=NH) substituent; $A^4$ is $C_6\text{-}C_{10}$ aryl optionally substituted with one or more $R^{29}$ substituent. In some embodiments, $A^4$ is selected from the group consisting of:

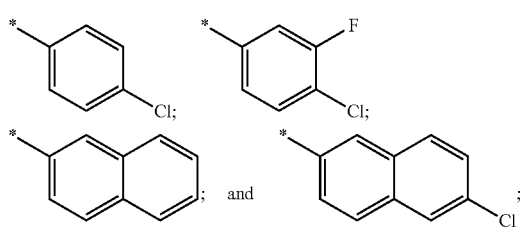

and wherein the * represents the attachment point to the remainder of the molecule.

In some embodiments of the compounds of formula (II), (III), (IV), or (V), wherein m3 is 1, n3 is 1, and $R^{21a}$ and $R^{21b}$ are taken together to form an oxo (=O) substituent or an imido (=NH) substituent; $A^4$ is 5-10 membered heteroaryl optionally substituted with one or more $R^{29}$ substituent. In some embodiments, $A^4$ is selected from the group consisting of:

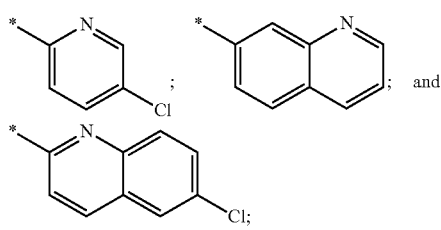

wherein the * represents the attachment point to the remainder of the molecule.

In one aspect, provided is a compound of formula (X-1):

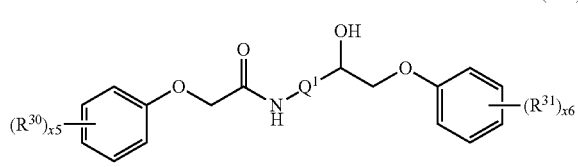

(X-1)

or a pharmaceutically acceptable salt thereof;
wherein:
$R^{30}$ and $R^{31}$ are, independently of each other and independently at each occurrence, halogen;
x5 and x6 are independently of each other 0, 1, 2, 3, 4 or 5;
$Q^1$ is selected from the group consisting of:

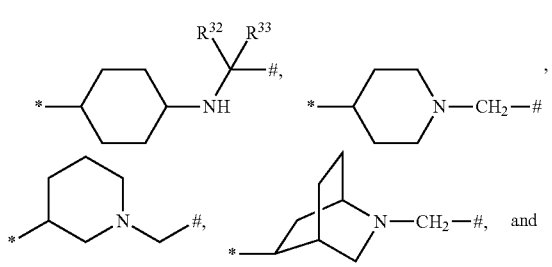

and

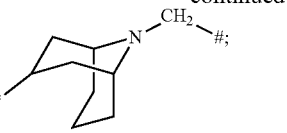

wherein * represents the point of attachment to the

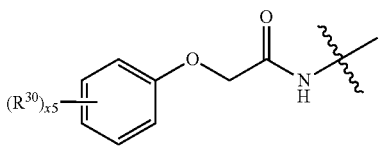

moiety, and # represents the point of attachment to the

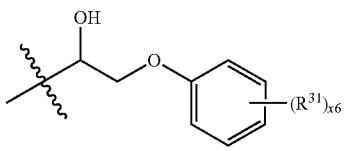

moiety; and
$R^{32}$ and $R^{33}$ are both hydrogen, or $R^{32}$ and $R^{33}$ are taken together to form an oxo (=O) substituent.

In some embodiments of the compounds of formula (X-1), $Q^1$ is

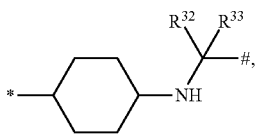

and $R^{32}$ and $R^{33}$ are both hydrogen.

In some embodiments of the compounds of formula (X-1), $Q^1$ is

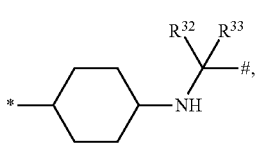

and $R^{32}$ and $R^{33}$ are taken together to form an oxo (=O) substituent.

In some embodiments of the compounds of formula (X-1), $Q^1$ is

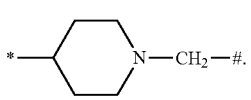

In some embodiments of the compounds of formula (X-1), $Q^1$ is

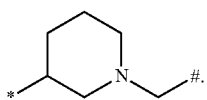

In some embodiments of the compounds of formula (X-1), $Q^1$ is

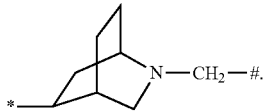

In some embodiments of the compounds of formula (X-1), $Q^1$ is

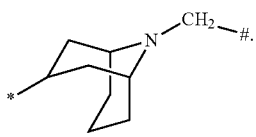

In some embodiments of the compounds of formula (X-1), $R^{30}$ and $R^{31}$ are, independently of each other and independently at each occurrence, selected from fluoro and chloro.

In some embodiments of the compounds of formula (X-1), x5 and x6 are both 1. In some embodiments, x5 is 1 and x6 is 2. In some embodiments, x5 is 2 and x6 is 1. In some embodiments, x5 and x6 are both 2.

In one aspect, provided is a compound of formula (X-2):

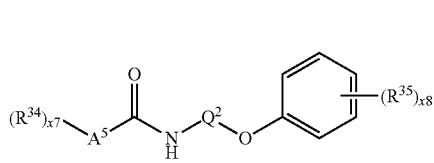
(X-2)

or a pharmaceutically acceptable salt thereof;
wherein:
$R^{34}$ and $R^{35}$ are, independently of each other and independently at each occurrence, halogen;
x7 and x8 are, independently of each other, 0, 1, 2, 3, 4, or 5;
$A^5$ is a 5-12 membered heteroaryl;
$Q^2$ is selected from the group consisting of:

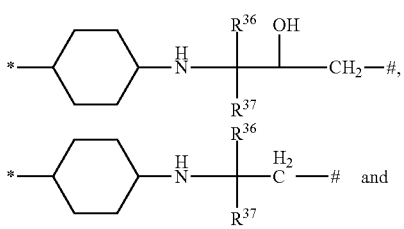

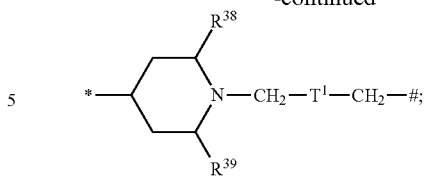

wherein * represents the point of attachment to the

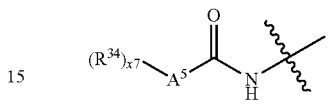

moiety, and # represents the point of attachment to the

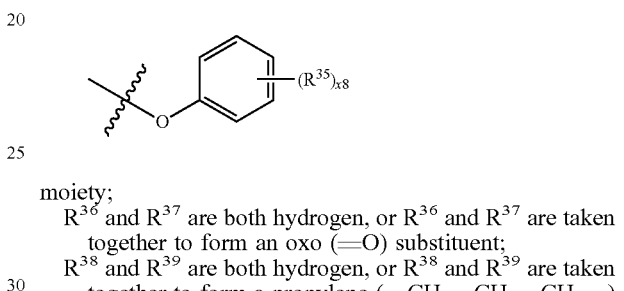

moiety;
$R^{36}$ and $R^{37}$ are both hydrogen, or $R^{36}$ and $R^{37}$ are taken together to form an oxo (=O) substituent;
$R^{38}$ and $R^{39}$ are both hydrogen, or $R^{38}$ and $R^{39}$ are taken together to form a propylene (—$CH_2$—$CH_2$—$CH_2$—) moiety; and
$T^1$ is —$CR^{40}R^{41}$— or $S(=O)_2$—, wherein $R^{40}$ is selected from the group consisting of hydrogen, —OH, and —$NH_2$; and $R^{41}$ is hydrogen.

In some embodiments of the compounds of formula (X-2), $Q^2$ is

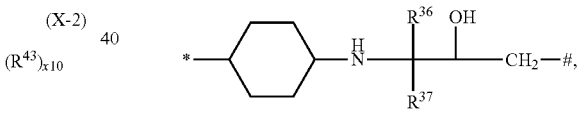

and $R^{36}$ and $R^{37}$ are both hydrogen.

In some embodiments of the compounds of formula (X-2), $Q^2$ is

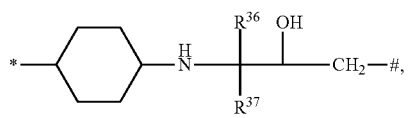

and $R^{36}$ and $R^{37}$ are taken together to form an oxo (=O) substituent.

In some embodiments of the compounds of formula (X-2), $Q^2$ is

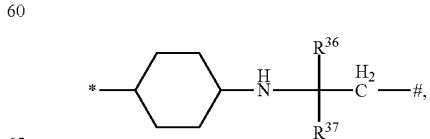

and $R^{36}$ and $R^{37}$ are both hydrogen.

In some embodiments of the compounds of formula (X-2), $Q^2$ is

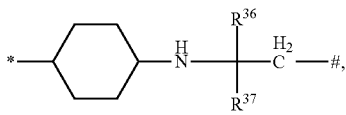

and $R^{36}$ and $R^{37}$ are taken together to form an oxo (=O) substituent.

In some embodiments of the compounds of formula (X-2), $Q^2$ is

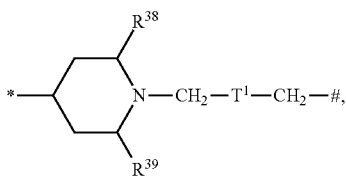

and $R^{38}$ and $R^{39}$ are both hydrogen. In some embodiments, $T^1$ is $-CR^{40}R^{41}-$. In some embodiments, $T^1$ is $-CR^{40}R^{41}-$, and $R^{40}$ is selected from the group consisting of hydrogen, $-OH$, and $-NH_2$; and $R^{41}$ is hydrogen. In some embodiments, $T^1$ is $-CR^{40}R^{41}-$, $R^{40}$ is hydrogen and $R^{41}$ is hydrogen. In some embodiments, $T^1$ is $-CR^{40}R^{41}-$, $R^{40}$ is $-OH$, and $R^{41}$ is hydrogen. In some embodiments, $T^1$ is $-CR^{40}R^{41}-$, $R^{40}$ is $-NH_2$, and $R^{41}$ is hydrogen. In other embodiments, $T^1$ is $S(=O)_2-$.

In some embodiments of the compounds of formula (X-2), $Q^2$ is

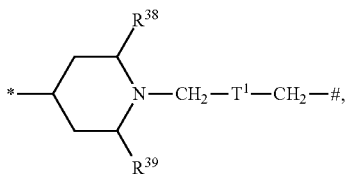

and $R^{38}$ and $R^{39}$ are taken together to form a propylene ($-CH_2-CH_2-CH_2-$) moiety. In some embodiments, $T^1$ is $-CR^{40}R^{41}-$. In some embodiments, $T^1$ is $-CR^{40}R^{41}-$, and $R^{40}$ is selected from the group consisting of hydrogen, $-OH$, and $-NH_2$; and $R^{41}$ is hydrogen. In some embodiments, $T^1$ is $-CR^{40}R^{41}-$, $R^{40}$ is hydrogen and $R^{41}$ is hydrogen. In some embodiments, $T^1$ is $-CR^{40}R^{41}-$, $R^{40}$ is $-OH$, and $R^{41}$ is hydrogen. In some embodiments, $T^1$ is $-CR^{40}R^{41}-$, $R^{40}$ is $-NH_2$, and $R^{41}$ is hydrogen. In other embodiments, $T^1$ is $S(=O)_2-$.

In some embodiments of the compounds of formula (X-2), $R^{34}$ and $R^{35}$ are, independently of each other and independently at each occurrence, selected from fluoro and chloro.

In some embodiments of the compounds of formula (X-1), x7 and x8 are both 1. In some embodiments, x7 is 1 and x8 is 2. In some embodiments, x7 is 2 and x8 is 1. In some embodiments, x7 and x8 are both 2.

In one aspect, provided is a compound of formula (X-3):

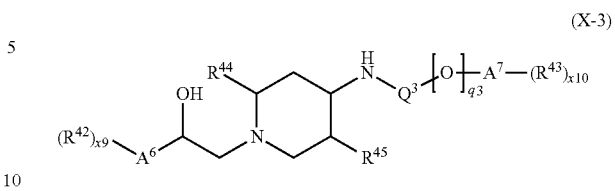

or a pharmaceutically acceptable salt thereof;
wherein:
$R^{42}$ and $R^{43}$ are, independently of each other and independently at each occurrence, halogen;
x9 and x10 are, independently of each other, 0, 1, 2, 3, 4, or 5;
$R^{44}$ and $R^{45}$ are both hydrogen, or $R^{44}$ and $R^{45}$ are taken together to form an ethylene ($-CH_2-CH_2-$) moiety;
$A^6$ is a 5-12 membered heteroaryl;
$A^7$ is $C_6$-$C_{10}$ aryl or 5-12 membered heteroaryl;
$Q^3$ is selected from the group consisting of:

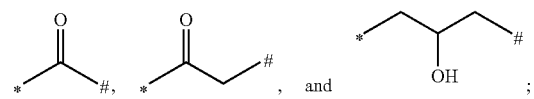

wherein * represents the point of attachment to the

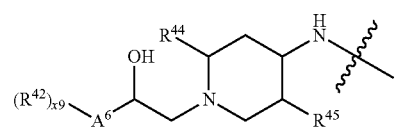

moiety, and # represents the point of attachment to the

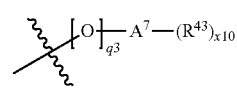

moiety; and
provided that one of (i) or (ii) applies:
(i) q3 is 0, $Q^3$ is

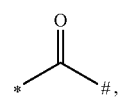

and $A^7$ is 5-12 membered heteroaryl;
(ii) q3 is 1, $Q^3$ is

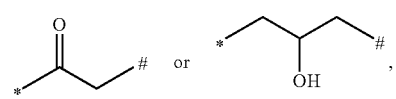

and $A^7$ is $C_6$-$C_{10}$ aryl.

In some embodiments of the compounds of formula (X-3), q3 is 0, $Q^3$ is

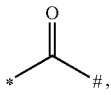

and A⁷ is 5-12 membered heteroaryl.

In some embodiments of the compounds of formula (X-3), q3 is 1, Q³ is

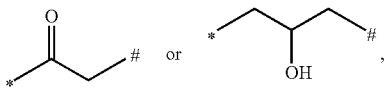

and A⁷ is $C_6$-$C_{10}$ aryl. In some embodiments of the compounds of formula (X-3), q3 is 1, Q³ is

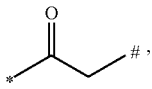

and A⁷ is $C_6$-$C_{10}$ aryl. In some embodiments of the compounds of formula (X-3), q3 is 1, Q³ is

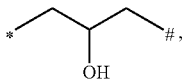

and A⁷ is $C_6$-$C_{10}$ aryl. In some embodiments, A⁷ is phenyl.

In some embodiments of the compounds of formula (X-3), $R^{44}$ and $R^{45}$ are both hydrogen. In some embodiments of the compounds of formula (X-3), $R^{44}$ and $R^{45}$ are taken together to form an ethylene (—CH₂—CH₂—) moiety.

In some embodiments of the compounds of formula (X-3), $R^{42}$ and $R^{43}$ are, independently of each other and independently at each occurrence, selected from fluoro and chloro.

In some embodiments of the compounds of formula (X-3), x9 and x10 are both 1. In some embodiments, x9 is 1 and x10 is 2. In some embodiments, x9 is 2 and x10 is 1. In some embodiments, x9 and x10 are both 2.

In one aspect, provided is a compound of formula (X-4):

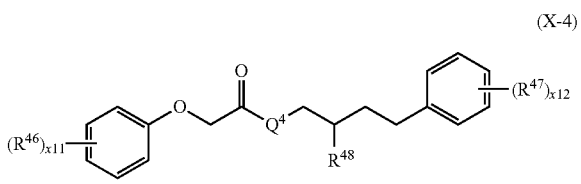

(X-4)

or a pharmaceutically acceptable salt thereof;
wherein:
 $R^{46}$ and $R^{47}$ are, independently of each other and independently at each occurrence, halogen;
 x11 and x12 are, independently of each other, 0, 1, 2, 3, 4, or 5;
 $R^{48}$ is hydrogen or —OH;
 Q⁴ is selected from the group consisting of:

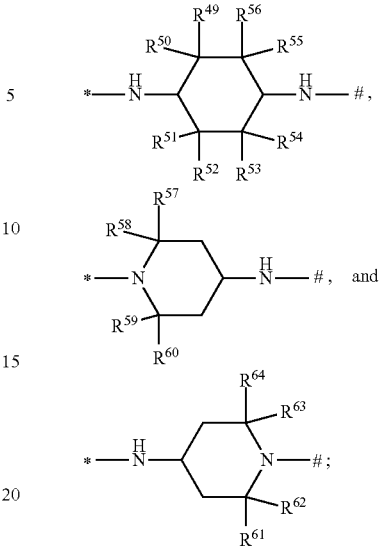

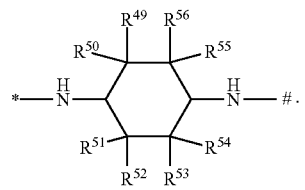

wherein * represents the point of attachment to the

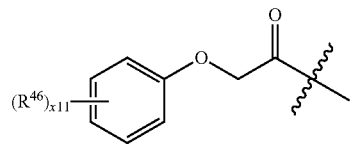

moiety, and # represents the point of attachment to the

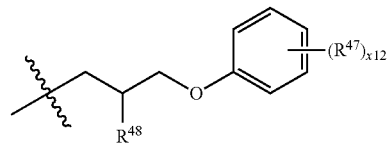

$R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, and $R^{64}$ are, independently of each other, hydrogen or $C_1$-$C_6$ alkyl.

In some embodiments of the compounds of formula (X-4), Q⁴ is

In some embodiments, $R^{49}$ and $R^{51}$ are both $C_1$-$C_6$ alkyl, and $R^{50}$, $R^{52}$, $R^{53}$, $R^{54}$, $R^{55}$, and $R^{56}$ are all hydrogen. In some embodiments, $R^{49}$ and $R^{51}$ are both methyl, and $R^{50}$, $R^{52}$, $R^{53}$, $R^{54}$, $R^{55}$, and $R^{56}$ are all hydrogen. In some embodiments, $R^{53}$ and $R^{55}$ are both $C_1$-$C_6$ alkyl, and $R^{49}$, $R^{50}$, $R^{51}$, $R^{52}$, $R^{54}$, and $R^{56}$ are all hydrogen. In some embodiments, $R^{53}$ and $R^{55}$ are both methyl, and $R^{49}$, $R^{50}$, $R^{51}$, $R^{52}$, $R^{54}$, and $R^{56}$ are all hydrogen. In some embodiments, $R^{49}$, $R^{50}$, $R^{51}$, and $R^{52}$ are all $C_1$-$C_6$ alkyl, $R^{53}$, $R^{54}$, $R^{55}$, and $R^{56}$ are all hydrogen. In some embodiments, $R^{49}$, $R^{50}$, $R^{51}$, and $R^{52}$ are all methyl, $R^{53}$, $R^{54}$, $R^{55}$, and $R^{56}$ are all hydrogen. In some embodiments, $R^{49}$, $R^{50}$, $R^{51}$, and $R^{52}$ are all hydrogen, $R^{53}$, $R^{54}$, $R^{55}$, and $R^{56}$ are all $C_1$-$C_6$ alkyl. In some embodiments, $R^{49}$, $R^{50}$, $R^{51}$, and $R^{52}$ are all hydrogen, $R^{53}$, $R^{54}$, $R^{55}$, and $R^{56}$ are all methyl. In some embodiments, $R^{49}$, $R^{50}$, $R^{51}$, $R^{52}$, $R^{53}$, $R^{54}$, $R^{55}$, and $R^{56}$ are all hydrogen.

In some embodiments of the compounds of formula (X-4), $Q^4$ is

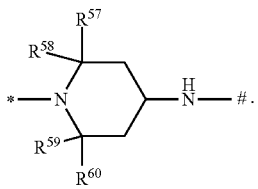

In some embodiments, $R^{57}$, $R^{58}$, $R^{59}$, and $R^{60}$ are all $C_1$-$C_6$ alkyl. In some embodiments, $R^{57}$, $R^{58}$, $R^{59}$, and $R^{60}$ are all methyl. In some embodiments, $R^{57}$ and $R^{59}$ are both $C_1$-$C_6$ alkyl, and $R^{58}$ and $R^{60}$ are both hydrogen. In some embodiments, $R^{57}$ and $R^{59}$ are both methyl, and $R^{58}$ and $R^{60}$ are both hydrogen. In some embodiments, $R^{57}$, $R^{58}$, $R^{59}$, and $R^{60}$ are all hydrogen.

In some embodiments of the compounds of formula (X-4), $Q^4$ is

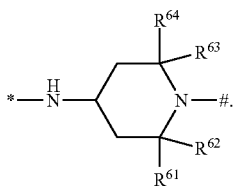

In some embodiments, $R^{61}$, $R^{62}$, $R^{63}$, and $R^{64}$ are all $C_1$-$C_6$ alkyl. In some embodiments, $R^{61}$, $R^{62}$, $R^{63}$, and $R^{64}$ are all methyl. In some embodiments, $R^{61}$ and $R^{63}$ are both $C_1$-$C_6$ alkyl, and $R^{62}$ and $R^{64}$ are both hydrogen. In some embodiments, $R^{61}$ and $R^{63}$ are both methyl, and $R^{62}$ and $R^{64}$ are both hydrogen. In some embodiments, $R^{61}$, $R^{62}$, $R^{63}$, and $R^{64}$ are all hydrogen.

In some embodiments of the compounds of formula (X-4), $R^{48}$ is hydrogen.

In some embodiments of the compounds of formula (X-4), $R^{48}$ is —OH.

In some embodiments of the compounds of formula (X-4), $R^{46}$ and $R^{47}$ are, independently of each other and independently at each occurrence, selected from fluoro and chloro.

In some embodiments of the compounds of formula (X-4), x11 and x12 are both 1. In some embodiments, x11 is 1 and x12 is 2. In some embodiments, x11 is 2 and x12 is 1. In some embodiments, x11 and x12 are both 2.

In one aspect, provided is a compound of formula (X-5):

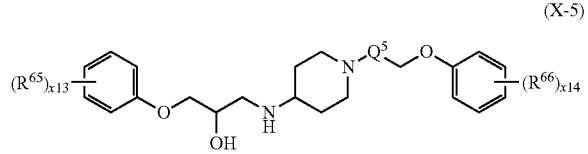

(X-5)

or a pharmaceutically acceptable salt thereof;

wherein:
$R^{65}$ and $R^{66}$ are, independently of each other and independently at each occurrence, halogen;
x13 and x14 are, independently of each other, 0, 1, 2, 3, 4, or 5;
$Q^5$ is selected from the group consisting of:

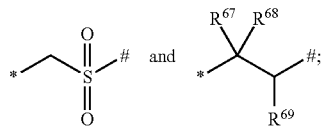

wherein * represents the point of attachment to the

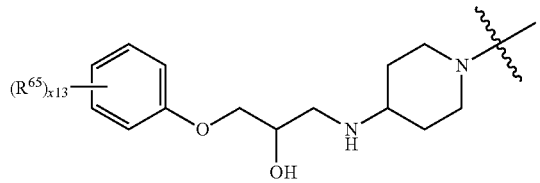

moiety, and # represents the point of attachment to the

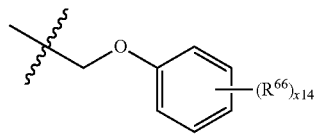

moiety;
$R^{67}$ and $R^{68}$ are both hydrogen, or $R^{67}$ and $R^{68}$ are taken together to form an imino (=NH) substituent; and
$R^{69}$ is hydrogen or —NH$_2$.

In some embodiments of the compounds of formula (X-5), $Q^5$ is

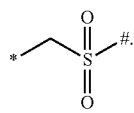

In some embodiments of the compounds of formula (X-5), $Q^5$ is

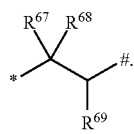

In some embodiments, $R^{67}$ and $R^{68}$ are both hydrogen, and $R^{69}$ is hydrogen or —NH$_2$. In some embodiments, $R^{67}$ and $R^{68}$ are both hydrogen, and $R^{69}$ is hydrogen. In some embodiments, $R^{67}$ and $R^{68}$ are both hydrogen, and $R^{69}$ is —NH$_2$. In some embodiments, $R^{67}$ and $R^{68}$ are taken together to form an imino (=NH) substituent, and $R^{69}$ is hydrogen or —NH$_2$. In some embodiments, $R^{67}$ and $R^{68}$ are taken together to form an imino (=NH) substituent, and $R^{69}$ is hydrogen. In some embodiments, $R^{67}$ and $R^{68}$ are taken together to form an imino (=NH) substituent, and $R^{69}$ is -NH$_2$.

In some embodiments of the compounds of formula (X-5), $R^{65}$ and $R^{66}$ are, independently of each other and independently at each occurrence, selected from fluoro and chloro.

In some embodiments of the compounds of formula (X-5), x13 and x14 are both 1. In some embodiments, x13 is 1 and x14 is 2. In some embodiments, x13 is 2 and x14 is 1. In some embodiments, x13 and x14 are both 2.

In one aspect, provided is a compound of formula (X-6):

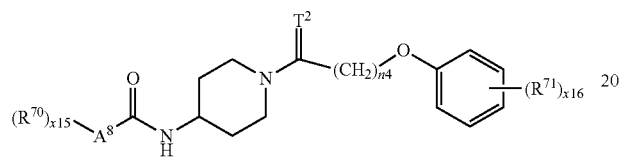

(X-6)

or a pharmaceutically acceptable salt thereof;
wherein:
$R^{70}$ and $R^{71}$ are, independently of each other and independently at each occurrence, halogen;
x15 and x16 are, independently of each other, 0, 1, 2, 3, 4, or 5;
n4 is 1 or 2;
$T^2$ is O or NH; and
$A^8$ is a 5-12 membered heteroaryl.

In some embodiments of the compounds of formula (X-6), n4 is 1.

In some embodiments of the compounds of formula (X-6), n4 is 2.

In some embodiments of the compounds of formula (X-6), $T^2$ is O.

In some embodiments of the compounds of formula (X-6), $T^2$ is NH.

In some embodiments of the compounds of formula (X-5), $R^{70}$ and $R^{71}$ are, independently of each other and independently at each occurrence, selected from fluoro and chloro.

In some embodiments of the compounds of formula (X-5), x15 and x16 are both 1. In some embodiments, x15 is 1 and x16 is 2. In some embodiments, x15 is 2 and x16 is 1. In some embodiments, x15 and x16 are both 2.

In one aspect, provided is a compound of formula (X-7):

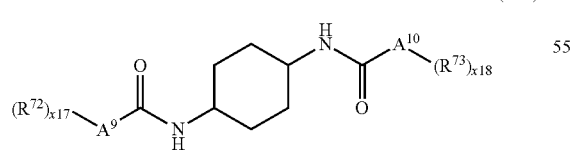

(X-7)

or a pharmaceutically acceptable salt thereof;
wherein:
$R^{72}$ and $R^{73}$ are, independently of each other and independently at each occurrence, halogen;
x17 and x18 are, independently of each other, 0, 1, 2, 3, 4, or 5;
$A^9$ is a 5-12 membered heteroaryl; and $A^{10}$ is a 5-12 membered heteroaryl;
provided that $A^9$ and $A^{10}$ are not both simultaneously a moiety selected from group consisting of:

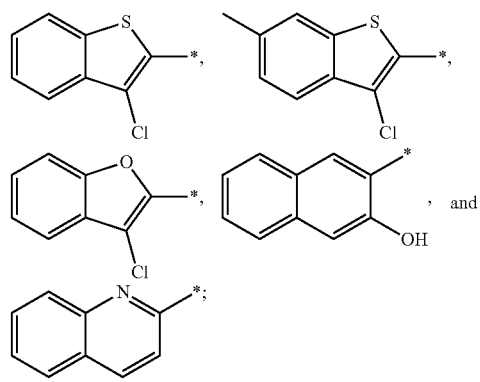

wherein the * represents the attachment point to the remainder of the molecule.

In some embodiments of the compounds of formula (X-7), $R^{72}$ and $R^{73}$ are, independently of each other and independently at each occurrence, selected from fluoro and chloro.

In some embodiments of the compounds of formula (X-7), x17 and x18 are both 1. In some embodiments, x17 is 1 and x18 is 2. In some embodiments, x17 is 2 and x18 is 1. In some embodiments, x17 and x18 are both 2.

In one aspect, provided is a compound of formula (X-8):

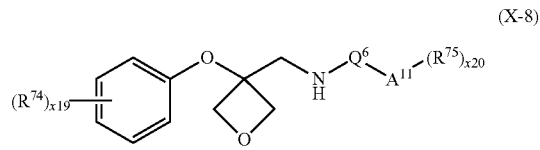

(X-8)

or a pharmaceutically acceptable salt thereof;
wherein:
$R^{74}$ and $R^{75}$ are, independently of each other and independently at each occurrence, halogen;
x19 and x20 are, independently of each other, 0, 1, 2, 3, 4, or 5;
$A^{11}$ is $C_6$-$C_{10}$ aryl or 5-12 membered heteroaryl;
$Q^6$ is selected from the group consisting of:

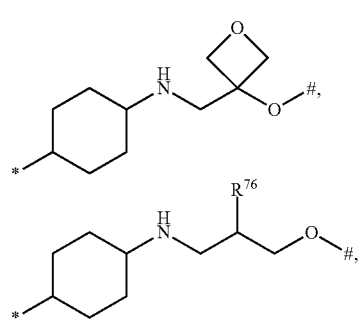

-continued

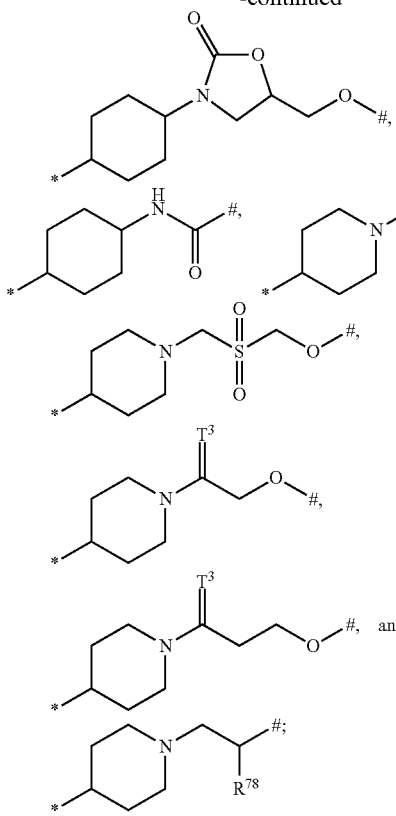

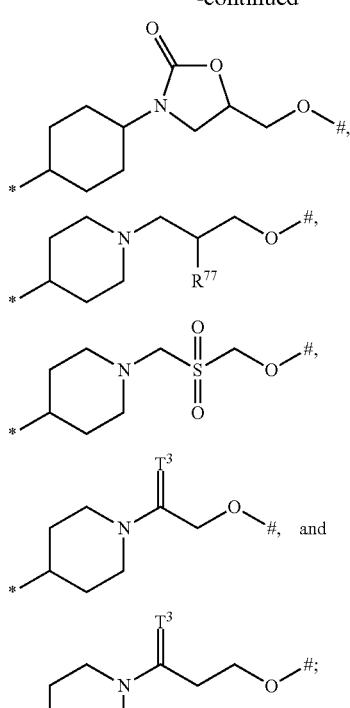

wherein * represents the point of attachment to the

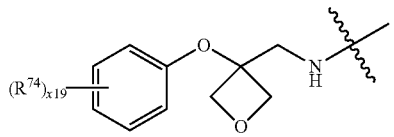

moiety, and # represents the point of attachment to the -A$^{11}$-(R$^{75}$)$_{x20}$ moiety;
T$^3$ is O or NH;
T$^4$ is O or NH;
R$^{76}$ is selected from hydrogen, —OH, and —NH$_2$;
R$^{77}$ is selected from hydrogen, —OH, and —NH$_2$;
R$^{78}$ is hydrogen or —OH; and
provided that one of (i) or (ii) applies:
(i) when A$^{11}$ is C$_6$-C$_{10}$ aryl, Q$^6$ is selected from the group consisting of:

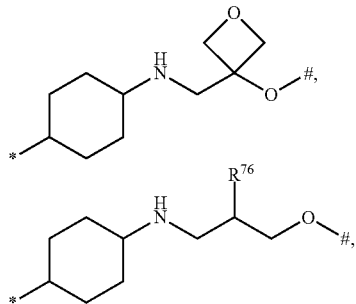

(ii) when A is 5-12 membered heteroaryl, Q is

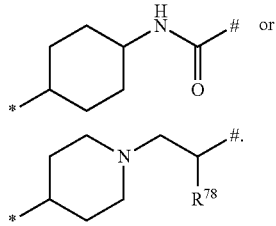

In some embodiments of the compounds of formula (X-8), A$^{11}$ is C$_6$-C$_{10}$ aryl, and Q$^6$ is selected from the group consisting of:

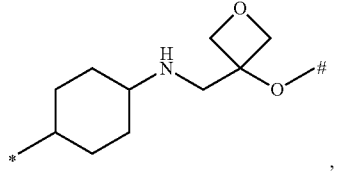

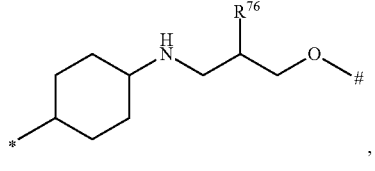

-continued

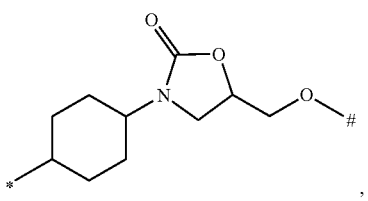
,

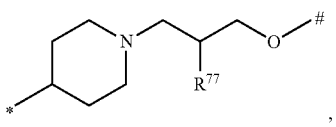
,

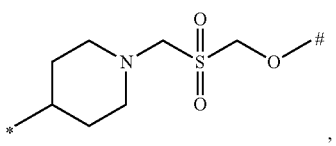
,

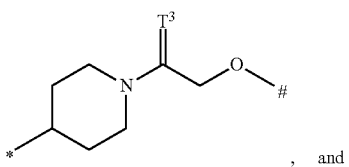
, and

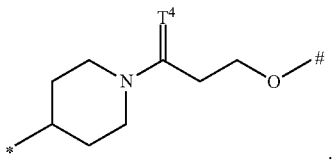
.

In some embodiments of the compounds of formula (X-8), $A^{11}$ is $C_6$-$C_{10}$ aryl, and $Q^6$

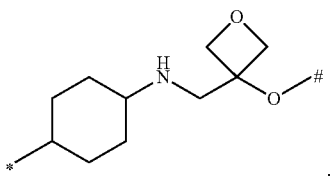

In some embodiments, $A^{11}$ is phenyl.

In some embodiments of the compounds of formula (X-8), $A^{11}$ is $C_6$-$C_{10}$ aryl, and $Q^6$

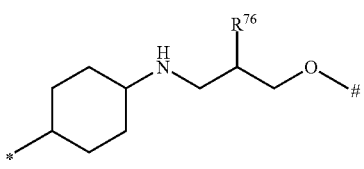

In some embodiments, $R^{76}$ is hydrogen. In some embodiments, $R^{76}$ is —OH. In some embodiments, $R^{76}$ is —NH$_2$. In some embodiments, $A^{11}$ is phenyl.

In some embodiments of the compounds of formula (X-8), $A^{11}$ is $C_6$-$C_{10}$ aryl, and $Q^6$

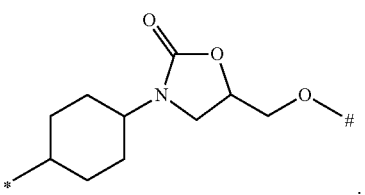

In some embodiments, $A^{11}$ is phenyl.

In some embodiments of the compounds of formula (X-8), $A^{11}$ is $C_6$-$C_{10}$ aryl, and $Q^6$

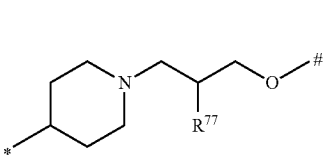

In some embodiments, $R^{77}$ is hydrogen. In some embodiments, $R^{77}$ is —OH. In some embodiments, $R^{77}$ is NH$_2$. In some embodiments, $A^{11}$ is phenyl.

In some embodiments of the compounds of formula (X-8), $A^{11}$ is $C_6$-$C_{10}$ aryl, and $Q^6$

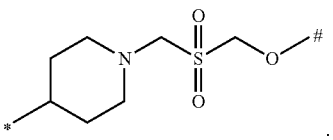

In some embodiments, $A^{11}$ is phenyl.

In some embodiments of the compounds of formula (X-8), $A^{11}$ is $C_6$-$C_{10}$ aryl, and $Q^6$ is

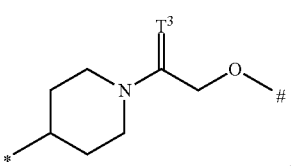

In some embodiments, T is O. In some embodiments, T is NH. In some embodiments, $A^{11}$ is phenyl.

In some embodiments of the compounds of formula (X-8), $A^{11}$ is $C_6$-$C_{10}$ aryl, and $Q^6$

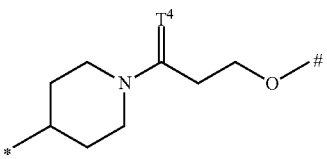

In some embodiments, $T^4$ is O. In some embodiments, $T^4$ is NH. In some embodiments, $A^{11}$ is phenyl.

In some embodiments of the compounds of formula (X-8), $A^{11}$ is 5-12 membered heteroaryl, and $Q^6$ is

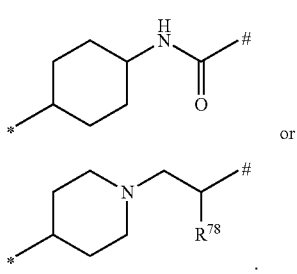

In some embodiments of the compounds of formula (X-8), $A^{11}$ is 5-12 membered heteroaryl, and $Q^6$ is

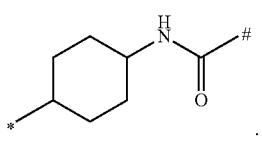

In some embodiments of the compounds of formula (X-8), $A^{11}$ is 5-12 membered heteroaryl, and $Q^6$ is

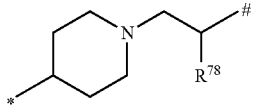

In some embodiments, $R^{78}$ is hydrogen. In some embodiments, $R^{78}$ is -OH.

In some embodiments of the compounds of formula (X-8), $R^{74}$ and $R^{75}$ are, independently of each other and independently at each occurrence, selected from fluoro and chloro.

In some embodiments of the compounds of formula (X-8), x19 and x20 are both 1. In some embodiments, x19 is 1 and x20 is 2. In some embodiments, x19 is 2 and x20 is 1. In some embodiments, x19 and x20 are both 2.

In one aspect, provided is a compound of formula (X-9):

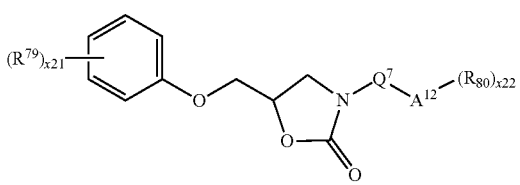

(X-9)

or a pharmaceutically acceptable salt thereof;
wherein:
$R^{79}$ and $R^{80}$ are, independently of each other and independently at each occurrence, halogen;
x21 and x22 are, independently of each other, 0, 1, 2, 3, 4, or 5;
$A^{12}$ is $C_6$-$C_{10}$ aryl or 5-12 membered heteroaryl;

$Q^7$ is selected from the group consisting of:

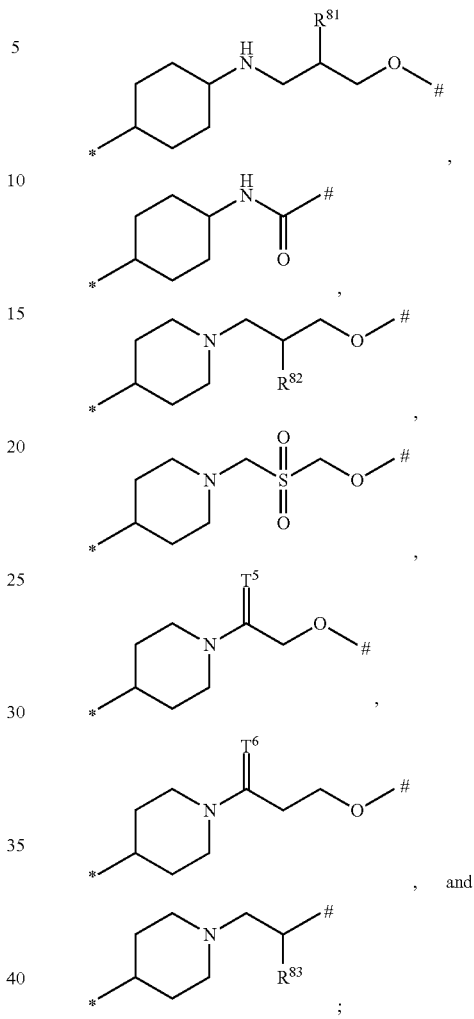

and wherein * represents the point of attachment to the

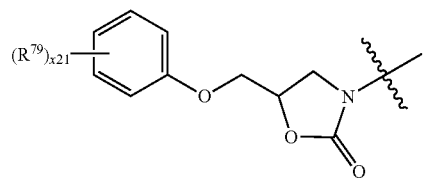

moiety, and # represents the point of attachment to the -$A^{12}$-$(R^{80})_{x22}$ moiety;

$T^5$ is O or NH;
$T^6$ is O or NH;
$R^{81}$ is selected from hydrogen, —OH, and —NH$_2$;
$R^{82}$ is selected from hydrogen, —OH, and —NH$_2$;
$R^{83}$ is hydrogen or —OH; and
provided that one of (i) or (ii) applies:
(i) when $A^{12}$ is $C_6$-$C_{10}$ aryl, $Q^7$ is selected from the group consisting of:

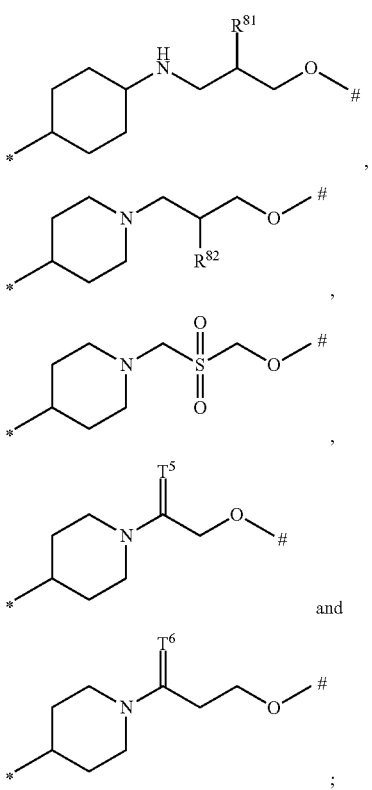

(ii) when $A^{12}$ is 5-12 membered heteroaryl, $Q^7$ is

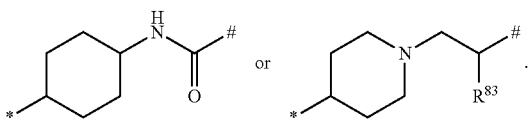

In some embodiments of the compounds of formula (X-9), $A^{12}$ is $C_6$-$C_{10}$ aryl, and $Q^7$ is selected from the group consisting of:

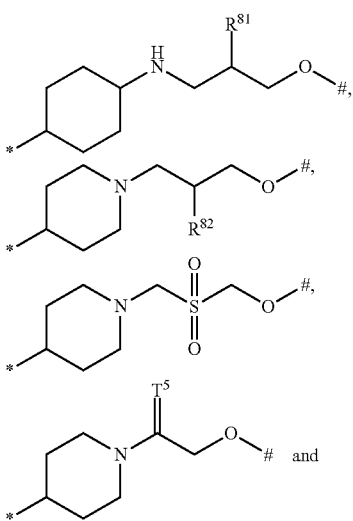

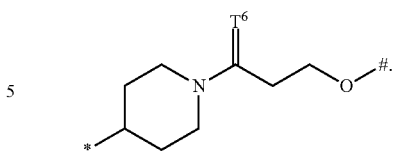

In some embodiments of the compounds of formula (X-9), $A^{12}$ is $C_6$-$C_{10}$ aryl, and $Q^7$

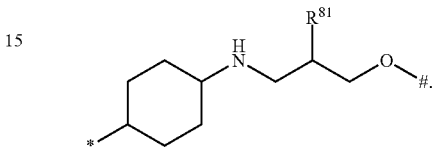

In some embodiments, $R^{81}$ is hydrogen. In some embodiments, $R^{81}$ is selected from —OH. In some embodiments, $R^{81}$ is selected from —NH$_2$. In some embodiments, $A^{12}$ is phenyl.

In some embodiments of the compounds of formula (X-9), $A^{12}$ is $C_6$-$C_{10}$ aryl, and $Q^7$

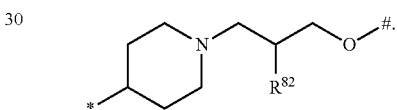

In some embodiments, $R^{82}$ is hydrogen. In some embodiments, $R^{82}$ is selected from —OH. In some embodiments, $R^{82}$ is selected from —NH$_2$. In some embodiments, $A^{12}$ is phenyl.

In some embodiments of the compounds of formula (X-9), $A^{12}$ is $C_6$-$C_{10}$ aryl, and $Q^7$

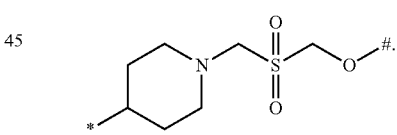

In some embodiments, $A^{12}$ is phenyl.

In some embodiments of the compounds of formula (X-9), $A^{12}$ is $C_6$-$C_{10}$ aryl, and $Q^7$ is

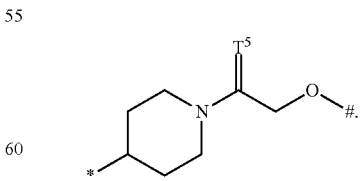

In some embodiments, $T^5$ is O. In some embodiments, $T^5$ is NH. In some embodiments, $A^{12}$ is phenyl.

In some embodiments of the compounds of formula (X-9), $A^{12}$ is $C_6$-$C_{10}$ aryl, and $Q^7$ is In some embodiments, T⁶ is O. In some embodiments, T⁶ is NH. In some embodiments, A¹² is phenyl.

In some embodiments of the compounds of formula (X-9), A¹² is 5-12 membered heteroaryl, and Q⁷ is In some embodiments of the compounds of formula (X-9), A¹² is 5-12 membered heteroaryl, and Q⁷ is In some embodiments of the compounds of formula (X-9), A¹² is 5-12 membered heteroaryl, and Q⁷ is In some embodiments, R⁸³ is hydrogen. In some embodiments, R⁸³ is -OH.

In some embodiments of the compounds of formula (X-9), R⁷⁹ and R⁸⁰ are, independently of each other and independently at each occurrence, selected from fluoro and chloro.

In some embodiments of the compounds of formula (X-9), x21 and x22 are both 1. In some embodiments, x21 is 1 and x22 is 2. In some embodiments, x21 is 2 and x22 is 1. In some embodiments, x21 and x22 are both 2.

In one aspect, provided is a compound of formula (XX):

(XX)

or a pharmaceutically acceptable salt thereof;

wherein:
$X^5$ is CH or N;
$Y^5$ is selected from the group consisting of a bond, $NR^{Y5}$, and O; provided that when $X^5$ is N, then $Y^5$ is a bond;
$R^{Y5}$ is hydrogen or $C_1$-$C_6$ alkyl;
$R^N$ is hydrogen or $C_1$-$C_6$ alkyl;
$m^4$, $n^5$, $p^3$, and $q^4$, independently of each other, are 0 or 1;
r3 and s3, independently of each other, are 0, 1, or 2;
$A^{13}$ is selected from the group consisting of:
  $C_6$-$C_{10}$ aryl optionally substituted with one or more $R^{95}$ substituents; and
  5-10 membered heteroaryl optionally substituted with one or more $R^{95}$ substituents;
$R^{95}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —NH₂, —NH($C_1$-$C_6$ alkyl), —NH($C_1$-$C_6$ haloalkyl), —N($C_1$-$C_6$ alkyl)₂, —N($C_1$-$C_6$ haloalkyl)₂, —NR$^{95-a}$R$^{95-b}$, —CN, —C(O)OH, —C(O)O($C_1$-$C_6$ alkyl), —C(O)O($C_1$-$C_6$ haloalkyl), —C(O)NH₂, —C(O)NH($C_1$-$C_6$ alkyl), —C(O)NH($C_1$-$C_6$ haloalkyl), —C(O)N($C_1$-$C_6$ alkyl)₂, —C(O)N($C_1$-$C_6$ haloalkyl)₂, —C(O)NR$^{95-a}$R$^{95-b}$, —S(O)₂OH, —S(O)₂O($C_1$-$C_6$ alkyl), —S(O)₂O($C_1$-$C_6$ haloalkyl), —S(O)₂NH₂, —S(O)₂NH($C_1$-$C_6$ alkyl), —S(O)₂NH($C_1$-$C_6$ haloalkyl), —S(O)₂N($C_1$-$C_6$ alkyl)₂, —S(O)₂N($C_1$-$C_6$ haloalkyl)₂, —S(O)₂NR$^{95a}$R$^{95b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)₂($C_1$-$C_6$ alkyl), —OS(O)₂($C_1$-$C_6$ haloalkyl), —N(H)S(O)₂($C_1$-$C_6$ alkyl), —N(H)S(O)₂($C_1$-$C_6$ haloalkyl), —N($C_1$-$C_6$ alkyl)S(O)₂($C_1$-$C_6$ alkyl), —N($C_1$-$C_6$ alkyl)S(O)₂($C_1$-$C_6$ haloalkyl), —N($C_1$-$C_6$ haloalkyl)S(O)₂($C_1$-$C_6$ alkyl), and —N($C_1$-$C_6$ haloalkyl)S(O)₂($C_1$-$C_6$ haloalkyl);
  wherein $R^{95-a}$ and $R^{95-b}$ are taken together with the nitrogen atom which bears them to form a 3-10 membered heterocycle;
$R^{84a}$ and $R^{84b}$ are independently selected from the group consisting of hydrogen, $C_1$-$C_6$ alkyl, and halogen;
$R^{85a}$ and $R^{85b}$ are independently selected from the group consisting of hydrogen, $C_1$-$C_6$ alkyl, and halogen;

when present, $R^{86a}$ and $R^{86b}$ are independently at each occurrence selected from the group consisting of hydrogen, $C_1$-$C_6$ alkyl, and halogen;

when present, $R^{87a}$ and $R^{87b}$ are independently at each occurrence selected from the group consisting of hydrogen, $C_1$-$C_6$ alkyl, and halogen;

or, $R^{84a}$ and $R^{85a}$ are taken together to form a $C_1$-$C_6$ alkylene moiety;

or, $R^{84a}$ and an $R^{86a}$ moiety, when present, are taken together to form a $C_1$-$C_6$ alkylene moiety;

or, an $R^{86a}$ moiety, when present, and an $R^{87a}$ moiety, when present, are taken together to form a $C_1$-$C_6$ alkylene moiety;

$R^{88}$ is selected from the group consisting of hydrogen, $C_1$-$C_6$ alkyl, $C_1$-$C_6$ haloalkyl, —C(O)($C_1$-$C_6$ alkyl), —C(O)($C_1$-$C_6$ haloalkyl), —C(O)OH, —C(O)O($C_1$-$C_6$ alkyl), —C(O)O($C_1$-$C_6$ haloalkyl), —C(O)NH$_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)NR$^{88\text{-}a}$R$^{88\text{-}b}$, —S(O)$_2$OH, —S(O)$_2$O($C_1$-$C_6$ alkyl), —S(O)$_2$O($C_1$-$C_6$ haloalkyl), —S(O)$_2$NH$_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, and —S(O)$_2$NR$^{88\text{-}a}$R$^{88\text{-}b}$; wherein $R^{88\text{-}a}$ and $R^{88\text{-}b}$ are taken together with the nitrogen atom which bears them to form a 3-10 membered heterocycle;

$R^{89}$ is selected, independently at each occurrence, from the group consisting of hydrogen, halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —NH$_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —NR$^{89\text{-}a}$R$^{89\text{-}b}$, —CN, —C(O)OH, —C(O)O($C_1$-$C_6$ alkyl), —C(O)O($C_1$-$C_6$ haloalkyl), —C(O)NH$_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)NR$^{89\text{-}a}$R$^{89\text{-}b}$, —S(O)$_2$OH, —S(O)$_2$O($C_1$-$C_6$ alkyl), —S(O)$_2$O($C_1$-$C_6$ haloalkyl), —S(O)$_2$NH$_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$NR$^{89\text{-}a}$R$^{89\text{-}b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O) ($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);

wherein $R^{89\text{-}a}$ and $R^{89\text{-}b}$ are taken together with the nitrogen atom which bears them to form a 3-10 membered heterocycle;

when present, $R^{90a}$ and $R^{90b}$ are taken together to form an oxo (=O) substituent or an imido (=NH) substituent, or alternatively, $R^{90a}$ and $R^{90b}$ are both hydrogen; when present, $R^{91a}$ is selected from the group consisting of hydrogen, —OR$^{91a\text{-}a}$, and —NR$^{91a\text{-}b}$R$^{91a\text{-}c}$;

when present, $R^{91b}$ is hydrogen;

or alternatively, $R^{91a}$ and $R^{91b}$ are taken together to form a moiety selected from the group consisting of —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, and —CH$_2$—CH$_2$—CH$_2$—CH$_2$—O—;

when present, $R^{92a}$ and $R^{92b}$ are both hydrogen;

when present, $R^{93a}$ and $R^{93b}$ are taken together to form an oxo (=O) substituent, or alternatively, $R^{93a}$ and $R^{93b}$ are both hydrogen; $R^{91a\text{-}a}$ is selected from the group consisting of hydrogen, $C_1$-$C_6$ alkyl, and $C_1$-$C_6$ haloalkyl; or $R^{91a\text{-}a}$ and $R^{Y5}$ may be taken together to form a carbonyl (C=O) moiety; and $R^{91a\text{-}b}$ and $R^{91a\text{-}c}$, independently of each other, are selected from the group consisting of hydrogen, $C_1$-$C_6$ alkyl, and $C_1$-$C_6$ haloalkyl;

provided that when m$^4$ is 0, n$^5$ is 0, and q$^4$ is 0, then A$^{13}$ is a substituent of formula (A$^{13}$-a)

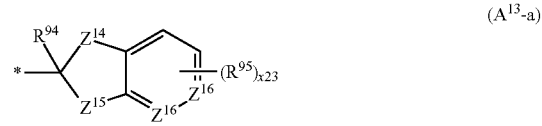

(A$^{13}$-a)

wherein

* represents the attachment point to the remainder of the molecule; $Z^{14}$ is selected from the group consisting of CR$^{Z14\text{-}1}$R$^{Z14\text{-}2}$, NR$^{Z14\text{-}2}$, C(R$^{Z14\text{-}1}$R$^{Z14\text{-}2}$)N(R$^{Z14\text{-}2}$), O, C(R$^{Z14\text{-}1}$R$^{Z14\text{-}2}$)O, S, C(R$^{Z14\text{-}1}$R$^{Z14\text{-}2}$)S, and —CR$^{Z14\text{-}1}$=CR$^{Z14\text{-}1}$—; wherein R$^{Z14\text{-}1}$ is hydrogen or R$^{16}$; and R$^{Z14\text{-}2}$ is hydrogen or R$^{95}$; $Z^{15}$ is selected from the group consisting of CR$^{Z15\text{-}1}$R$^{Z15\text{-}2}$, NR$^{Z15\text{-}2}$, C(R$^{Z15\text{-}1}$R$^{Z15\text{-}2}$)N(R$^{Z15\text{-}2}$), O, C(R$^{Z15\text{-}1}$R$^{Z15\text{-}2}$)O, S, C(R$^{Z15\text{-}1}$R$^{Z15\text{-}2}$)S, and —CR$^{Z15\text{-}1}$=CR$^{Z15\text{-}1}$—; wherein R$^{Z15\text{-}1}$ is hydrogen or R$^{95}$; and R$^{Z15\text{-}2}$ is hydrogen or R$^{95}$;

$Z^{16}$, independently at each occurrence, is CH, CR$^{95}$, or N; $R^{94}$ is hydrogen or R$^{95}$, or R$^{94}$ and R$^{Z14\text{-}2}$ are taken together to form a double bond between the carbon atom bearing R$^{94}$ and Z$^{14}$, or R$^{94}$ and R$^{Z15\text{-}2}$ are taken together to form a double bond between the carbon atom bearing R$^{94}$ and Z$^{15}$; and x23 is 0, 1, 2, 3, or 4.

In some embodiments of the compounds of formula (XX):

X$^5$ is CH or N;

Y$^5$ is selected from the group consisting of a bond, NR$^{Y5}$, and O; provided that when X$^5$ is N, then Y$^5$ is a bond;

R$^{Y5}$ is hydrogen or $C_1$-$C_6$ alkyl;

R$^N$ is hydrogen or $C_1$-$C_6$ alkyl;

m$^4$, n$^5$, p$^3$, and q$^4$, independently of each other, are 0 or 1;

r3 and s3, independently of each other, are 0, 1, or 2;

A$^{13}$ is selected from the group consisting of:

$C_6$-$C_{10}$ aryl optionally substituted with one or more R$^{95}$ substituents; and 5-10 membered heteroaryl optionally substituted with one or more R$^{95}$ substituents;

R$^{95}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —NH$_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —NR$^{95\text{-}a}$R$^{95\text{-}b}$, —CN, —C(O)OH, —C(O)O($C_1$-$C_6$ alkyl), —C(O)O($C_1$-$C_6$ haloalkyl), —C(O)NH$_2$, —C(O)NH ($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)NR$^{95a}$R$^{95b}$, —S(O)$_2$OH, —S(O)$_2$O($C_1$-$C_6$ alkyl), —S(O)$_2$O($C_1$-$C_6$ haloalkyl), —S(O)$_2$NH$_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$NR$^{95a}$R$^{95b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);

wherein R$^{95-a}$ and R$^{95-b}$ are taken together with the nitrogen atom which bears them to form a 3-10 membered heterocycle;

R$^{84a}$ and R$^{84b}$ are independently selected from the group consisting of hydrogen, $C_1$-$C_6$ alkyl, and halogen;

R$^{85a}$ and R$^{85b}$ are independently selected from the group consisting of hydrogen, $C_1$-$C_6$ alkyl, and halogen;

when present, R$^{86a}$ and R$^{86b}$ are independently at each occurrence selected from the group consisting of hydrogen, $C_1$-$C_6$ alkyl, and halogen;

when present, R$^{87a}$ and R$^{87b}$ are independently at each occurrence selected from the group consisting of hydrogen, $C_1$-$C_6$ alkyl, and halogen;

or, R$^{84a}$ and R$^{85a}$ are taken together to form a $C_1$-$C_6$ alkylene moiety;

or, R$^{84a}$ and an R$^{86a}$ moiety, when present, are taken together to form a $C_1$-$C_6$ alkylene moiety;

or, an R$^{86a}$ moiety, when present, and an R$^{87a}$ moiety, when present, are taken together to form a $C_1$-$C_6$ alkylene moiety;

R$^{88}$ is selected from the group consisting of hydrogen, $C_1$-$C_6$ alkyl, $C_1$-$C_6$ haloalkyl, —C(O)($C_1$-$C_6$ alkyl), —C(O)($C_1$-$C_6$ haloalkyl), —C(O)OH, —C(O)O($C_1$-$C_6$ alkyl), —C(O)O($C_1$-$C_6$ haloalkyl), —C(O)NH$_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)NR$^{88-a}$R$^{88-b}$, —S(O)$_2$OH, —S(O)$_2$O($C_1$-$C_6$ alkyl), —S(O)$_2$O($C_1$-$C_6$ haloalkyl), —S(O)$_2$NH$_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, and —S(O)$_2$NR$^{88-a}$R$^{88-b}$;

wherein R$^{88-a}$ and R$^{88-b}$ are taken together with the nitrogen atom which bears them to form a 3-10 membered heterocycle;

R$^{89}$ is selected, independently at each occurrence, from the group consisting of hydrogen, halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —NH$_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —NR$^{89-a}$R$^{89-b}$, —CN, —C(O)OH, —C(O)O($C_1$-$C_6$ alkyl), —C(O)O($C_1$-$C_6$ haloalkyl), —C(O)NH$_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)NR$^{89-a}$R$^{89-b}$, —S(O)$_2$OH, —S(O)$_2$O($C_1$-$C_6$ alkyl), —S(O)$_2$O($C_1$-$C_6$ haloalkyl), —S(O)$_2$NH$_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$NR$^{89-a}$R$^{89-b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl); wherein R$^{89-a}$ and R$^{89-b}$ are taken together with the nitrogen atom which bears them to form a 3-10 membered heterocycle;

when present, R$^{90a}$ and R$^{90b}$ are taken together to form an oxo (=O) substituent or an imido (=NH) substituent, or alternatively, R$^{90a}$ and R$^{90b}$ are both hydrogen;

when present, R$^{91a}$ is selected from the group consisting of hydrogen, —OR$^{91a-a}$, and —NR$^{91a-b}$R$^{91a-c}$;

when present, R$^{91b}$ is hydrogen;

or alternatively, R$^{91a}$ and R$^{91b}$ are taken together to form a moiety selected from the group consisting of —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, and —CH$_2$—CH$_2$—CH$_2$—CH$_2$—O—;

when present, R$^{92a}$ and R$^{92b}$ are both hydrogen;

when present, R$^{93a}$ and R$^{93b}$ are taken together to form an oxo (=O) substituent, or alternatively, R$^{93a}$ and R$^{93b}$ are both hydrogen;

R$^{91a-a}$ is selected from the group consisting of hydrogen, $C_1$-$C_6$ alkyl, and $C_1$-$C_6$ haloalkyl;

or R$^{91a-a}$ and R$^{Y5}$ may be taken together to form a carbonyl (C=O) moiety; and R$^{91a-b}$ and R$^{91a-c}$, independently of each other, are selected from the group consisting of hydrogen, $C_1$-$C_6$ alkyl, and $C_1$-$C_6$ haloalkyl;

provided that when m$^4$ is 0, n$^5$ is 0, and q$^4$ is 0, then p$^3$ is 1 and A$^{13}$ is a substituent of formula (A$^{13}$-a)

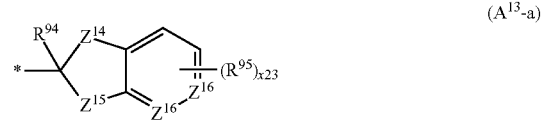

(A$^{13}$-a)

wherein
* represents the attachment point to the remainder of the molecule;

Z$^{14}$ is selected from the group consisting of CR$^{Z14-1}$R$^{Z14-2}$, NR$^{Z14-2}$, C(R$^{Z14-1}$R$^{Z14-2}$)N(R$^{Z14-2}$), O, C(R$^{Z14-1}$R$^{Z14-2}$)O, S, C(R$^{Z14-1}$R$^{Z14-2}$)S, and —CR$^{Z14-1}$=CR$^{z141}$—;

wherein R$^{Z14-1}$ is hydrogen or R$^{16}$; and R$^{Z14-2}$ is hydrogen or R$^{95}$;

Z$^{15}$ is selected from the group consisting of CR$^{Z15-1}$R$^{Z15-2}$, NR$^{Z15-2}$, C(R$^{Z15-1}$R$^{Z15-2}$)N(R$^{Z15-2}$), O, C(R$^{Z15-1}$R$^{Z15-2}$)O, S, C(R$^{Z15-1}$R$^{Z15-2}$)S, and —CR$^{Z15-1}$=CR$^{Z15-1}$—;

wherein $R^{Z15-1}$ is hydrogen or $R^{95}$; and $R^{Z15-2}$ is hydrogen or $R^{95}$;

$Z^{16}$, independently at each occurrence, is CH, $CR^{95}$, or N;

$R^{94}$ is hydrogen or $R^{95}$, or $R^{94}$ and $R^{Z14-2}$ are taken together to form a double bond between the carbon atom bearing $R^{94}$ and $Z^{14}$, or $R^{94}$ and $R^{Z15-2}$ are taken together to form a double bond between the carbon atom bearing $R^{94}$ and $Z^{15}$; and x23 is 0, 1, 2, 3, or 4.

In some embodiments, the compound of formula (XX) is a compound of formula

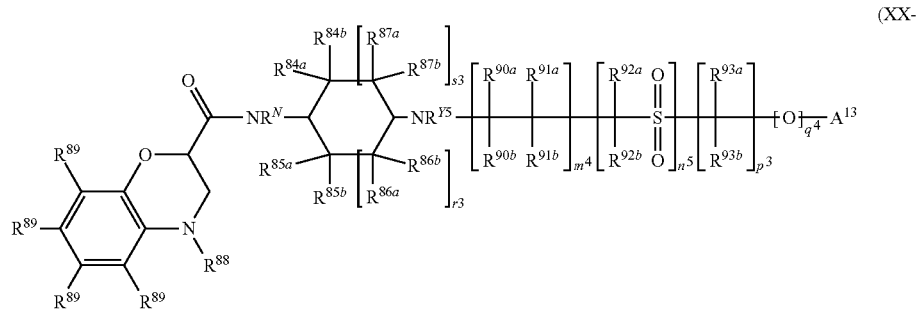

(XX-I)

or a pharmaceutically acceptable salt thereof;
wherein $R^N$, $R^{Y5}$, $m^4$, $n^5$, $p^3$, $q^4$, r3, s3, $A^{13}$, $R^{84a}$, $R^{84b}$, $R^{85a}$, $R^{85b}$, $R^{86a}$, $R^{86b}$, $R^{87a}$, $R^{87b}$, $R^{88}$, $R^{89}$, $R^{90a}$, $R^{90b}$, $R^{91a}$, $R^{91b}$, $R^{92a}$, $R^{92b}$, $R^{93a}$, and $R^{93b}$ are as defined for the compounds of formula (XX).

In some embodiments, the compound of formula (XX) is a compound of formula (XX-II):

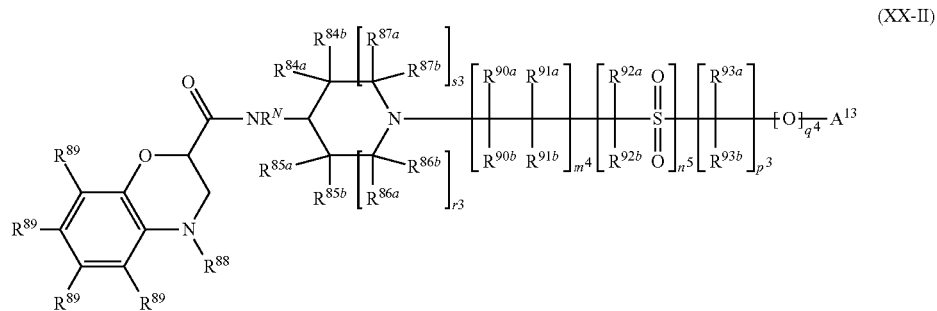

(XX-II)

or a pharmaceutically acceptable salt thereof;
wherein $R^N$, $m^4$, $n^5$, $p^3$, $q^4$, r3, s3, $A^{13}$, $R^{84a}$, $R^{84b}$, $R^{85a}$, $R^{85b}$, $R^{86a}$, $R^{86b}$, $R^{87a}$, $R^{87b}$, $R^{88}$, $R^{89}$, $R^{90a}$, $R^{90b}$, $R^{91a}$, $R^{91b}$, $R^{92a}$, $R^{92b}$, $R^{93a}$, and $R^{93b}$ are as defined for the compounds of formula (XX).

In some embodiments of the compounds of formulae (XX), (XX-I), and (XX-II), the moiety

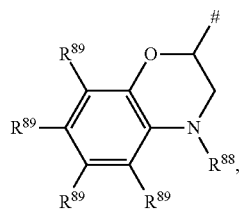

wherein # represents the attachment point to the remainder of the molecule, is

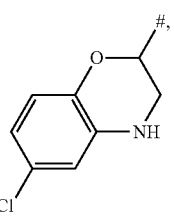

wherein # represents the attachment point to the remainder of the molecule.

In some embodiments, the compound of formula (XX) or the compound of formula (XX-I) is a compound of formula (XX-I-1):

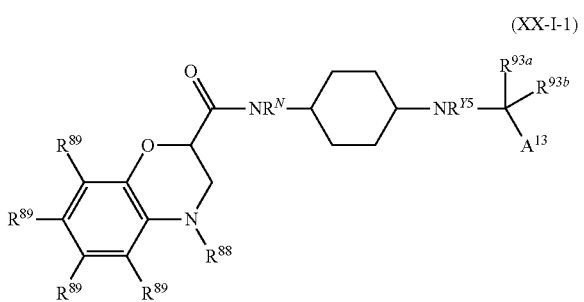

(XX-I-1)

or a pharmaceutically acceptable salt thereof;
wherein $R^N$, $R^{Y5}$, $R^{88}$, $R^{89}$, $R^{93a}$, and $R^{93b}$ are as defined in the compounds of formula (XX), and wherein $A^{13}$ is a substituent of formula ($A^{13}$-a)

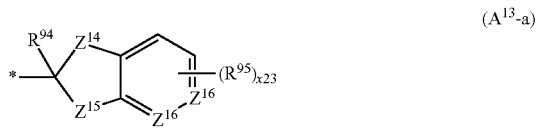

($A^{13}$-a)

wherein
* represents the attachment point to the remainder of the molecule; $Z^{14}$ is selected from the group consisting of $CR^{Z14-1}R^{Z14-2}$, $NR^{Z14-2}$, $C(R^{Z14-1}R^{Z14-2})N(R^{Z14-2})$, O, $C(R^{Z14-1}R^{Z14-2})O$, S, $C(R^{Z14-1}R^{Z14-2})S$, and $-CR^{Z14-1}=CR^{Z14-1}-$; wherein $R^{Z14-1}$ is hydrogen or $R^{16}$; and $R^{Z14-2}$ is hydrogen or $R^{95}$;
$Z^{15}$ is selected from the group consisting of $CR^{Z15-1}R^{Z15-2}$, $NR^{Z15-2}$, $C(R^{Z15-1}R^{Z15-2})N(R^{Z15-2})$, O, $C(R^{Z15-1}R^{Z15-2})O$, S, $C(R^{Z15-1}R^{Z15-2})S$, and $-CR^{Z15-1}=CR^{z151}-$; wherein $R^{Z15-1}$ is hydrogen or $R^{95}$; and $R^{Z15-2}$ is hydrogen or $R^{95}$;
$Z^{16}$, independently at each occurrence, is CH, $CR^{95}$, or N;
$R^{94}$ is hydrogen or $R^{95}$, or $R^{94}$ and $R^{Z14-2}$ are taken together to form a double bond between the carbon atom bearing $R^{94}$ and $Z^{14}$, or $R^{94}$ and $R^{Z15-2}$ are taken together to form a double bond between the carbon atom bearing $R^{94}$ and $Z^{15}$;
x23 is 0, 1, 2, 3, or 4; and
$R^{95}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —NH$_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —NR$^{95-a}$R$^{95-b}$, —CN, —C(O)OH, —C(O)O($C_1$-$C_6$ alkyl), —C(O)O($C_1$-$C_6$ haloalkyl), —C(O)NH$_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)NR$^{95-a}$R$^{95-b}$, —S(O)$_2$OH, —S(O)$_2$O($C_1$-$C_6$ alkyl), —S(O)$_2$O($C_1$-$C_6$ haloalkyl), —S(O)$_2$NH$_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$NR$^{95-a}$R$^{95-b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl).

In some embodiments of the compounds of formula (XX-I-1), $R^N$ is hydrogen or $C_1$-$C_6$ alkyl. In some embodiments of the compounds of formula (XX-I-1), $R^N$ is hydrogen.

In some embodiments of the compounds of formula (XX-I-1), $R^{Y5}$ is hydrogen or $C_1$-$C_6$ alkyl. In some embodiments of the compounds of formula (XX-I-1), $R^{Y5}$ is hydrogen.

In some embodiments of the compounds of formula (XX-I-1), $R^{88}$ is hydrogen, $C_1$-$C_6$ alkyl, or $C_1$-$C_6$ haloalkyl. In some embodiments, $R^{88}$ is hydrogen.

In some embodiments of the compounds of formula (XX-I-1), $R^{89}$ is selected, independently at each occurrence, from the group consisting of hydrogen, halogen, $C_1$-$C_6$ alkyl, and $C_1$-$C_6$ haloalkyl. In some embodiments of the compounds of formula (XX-I-1), $R^{89}$ is, independently at each occurrence, hydrogen or halogen. In some embodiments, $R^{89}$ is, independently at each occurrence, hydrogen, fluoro or chloro. In some embodiments, one $R^{89}$ is chloro and the remaining $R^{89}$ substituents are hydrogen.

In some embodiments of the compounds of formula (XX-I-1), $R^{93a}$ and $R^{93b}$ are taken together to form an oxo (=O) substituent. In some embodiments of the compounds of formula (XX-I-1), $R^{93a}$ and $R^{93b}$ are both hydrogen.

In some embodiments of the compounds of formula (XX-I-1), ($A^{13}$-a) is selected from the group consisting of:

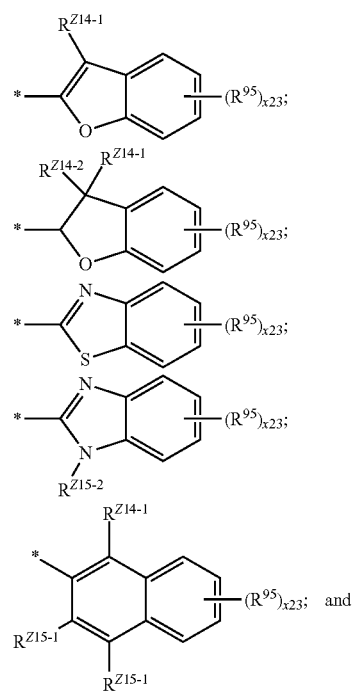

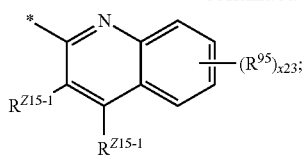

wherein the * represents the attachment point to the remainder of the molecule. In some embodiments, (A$^{13}$-a) is selected from the group consisting of:

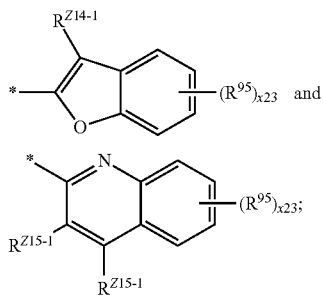

wherein the * represents the attachment point to the remainder of the molecule. In some embodiments, (A$^{13}$-a) is selected from the group consisting of:

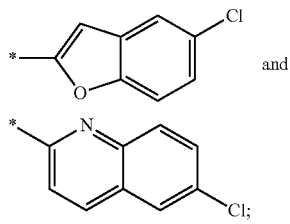

wherein the * represents the attachment point to the remainder of the molecule. In some embodiments, (A$^{13}$-a) is

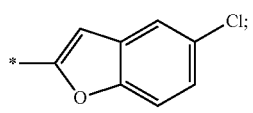 [SMILES: *c1cc2cc(Cl)ccc2o1]

wherein the * represents the attachment point to the remainder of the molecule. In some embodiments, (A$^{13}$-a) is

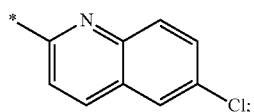

wherein the * represents the attachment point to the remainder of the molecule.

In some embodiments of the compounds of formula (XX-I-1), the moiety

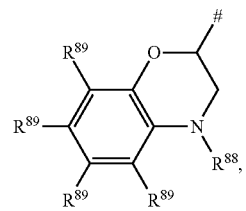

wherein # represents the attachment point to the remainder of the molecule, is

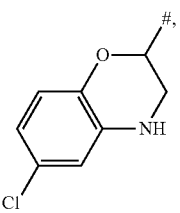

wherein # represents the attachment point to the remainder of the molecule.

In some embodiments, the compound of formula (XX) or the compound of formula (XX-I) is a compound of formula (XX-I-2):

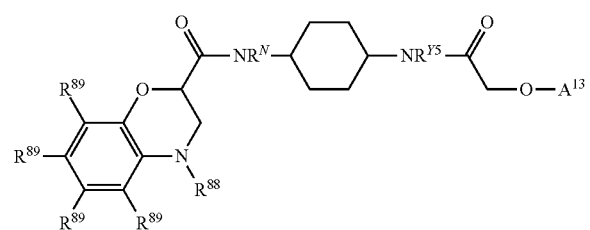

(XX-I-2)

or a pharmaceutically acceptable salt thereof;
wherein R$^N$, R$^{Y5}$, A$^{13}$, R$^{88}$, and R$^{89}$ are as defined in the compounds of formula (XX).

In some embodiments of the compounds of formula (XX-I-2), R$^N$ is hydrogen or C$_1$-C$_6$ alkyl. In some embodiments of the compounds of formula (XX-I-2), R$^N$ is hydrogen.

In some embodiments of the compounds of formula (XX-I-2), R$^{Y5}$ is hydrogen or C$_1$-C$_6$ alkyl. In some embodiments of the compounds of formula (XX-I-2), R$^{Y5}$ is hydrogen.

In some embodiments of the compounds of formula (XX-I-2), R$^{88}$ is hydrogen, C$_1$-C$_6$ alkyl, or C$_1$-C$_6$ haloalkyl. In some embodiments, R$^{88}$ is hydrogen.

In some embodiments of the compounds of formula (XX-I-2), R$^{89}$ is selected, independently at each occurrence, from the group consisting of hydrogen, halogen, C$_1$-C$_6$ alkyl, and C$_1$-C$_6$ haloalkyl. In some embodiments of the compounds of formula (XX-I-2), R$^{89}$ is, independently at each occurrence, hydrogen or halogen. In some embodiments, R$^{89}$ is, independently at each occurrence, hydrogen, fluoro or chloro. In some embodiments, one R$^{89}$ is chloro and the remaining R$^{89}$ substituents are hydrogen.

In some embodiments of the compounds of formula (XX-I-2), A$^{13}$ is selected from the group consisting of $C_6$-$C_{14}$ aryl optionally substituted with one or more $R^{95}$ substituents; and 5-14 membered heteroaryl optionally substituted with one or more $R^{95}$ substituents. In some embodiments, $A^{13}$ is $C_6$-$C_{14}$ aryl optionally substituted with one or more $R^{95}$ substituents. In some embodiments, $A^{13}$ is $C_6$-$C_{10}$ aryl optionally substituted with one or more $R^{95}$ substituents. In some embodiments, $A^{13}$ is selected from the group consisting of

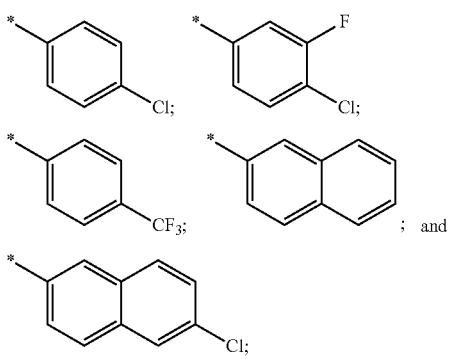

wherein the * represents the attachment point to the remainder of the molecule. In some embodiments, $A^{13}$ is phenyl optionally substituted with one or more $R^{95}$ substituents. In some embodiments, $A^{13}$ is selected from the group consisting of

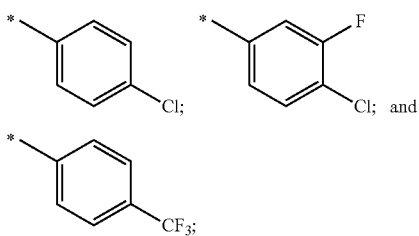

wherein the * represents the attachment point to the remainder of the molecule. In some embodiments, $A^{13}$ is

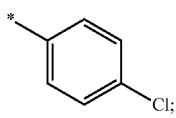

wherein the * represents the attachment point to the remainder of the molecule. In some embodiments, $A^{13}$ is

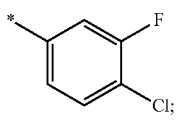

wherein the * represents the attachment point to the remainder of the molecule. In some embodiments, $A^{13}$ is

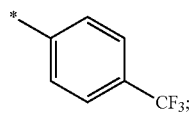

wherein the * represents the attachment point to the remainder of the molecule. In some embodiments, $A^{13}$ is naphthyl optionally substituted with one or more $R^{95}$ substituents. In some embodiments, $A^{13}$ is selected from the group consisting of

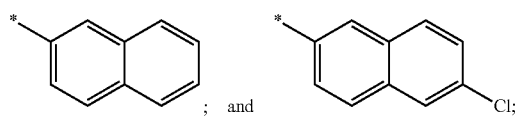 [SMILES: *c1ccc2ccccc2c1 ; "and" ; *c1ccc2cc(Cl)ccc2c1]

wherein the * represents the attachment point to the remainder of the molecule. In some embodiments, $A^{13}$ is

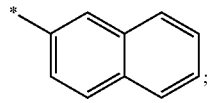 [SMILES: *c1ccc2ccccc2c1]

wherein the * represents the attachment point to the remainder of the molecule. In some embodiments, $A^{13}$ is

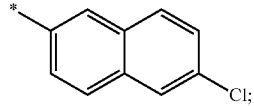 [SMILES: *c1ccc2cc(Cl)ccc2c1]

wherein the * represents the attachment point to the remainder of the molecule.

In some embodiments of the compounds of formula (XX-I-2), $A^{13}$ is 5-14 membered heteroaryl optionally substituted with one or more $R^{95}$ substituents. In some embodiments, $A^{13}$ is 5-10 membered heteroaryl optionally substituted with one or more $R^{95}$ substituents. In some embodiments, $A^{13}$ is selected from the group consisting of

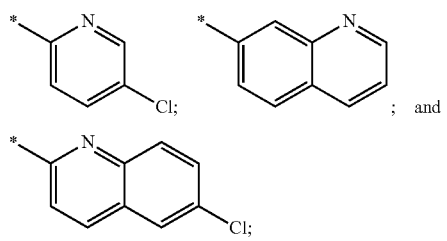

wherein the * represents the attachment point to the remainder of the molecule. In some embodiments, $A^{13}$ is pyridyl optionally substituted with one or more $R^{95}$ substituents. In some embodiments, $A^{13}$ is

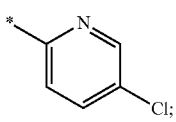

wherein the * represents the attachment point to the remainder of the molecule. In some embodiments, $A^{13}$ is quinolinyl optionally substituted with one or more $A^{13}$ substituents. In some embodiments, A is selected from the group consisting of

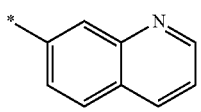 ; and 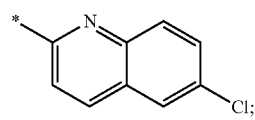

wherein the * represents the attachment point to the remainder of the molecule. In some embodiments, $A^{13}$ is

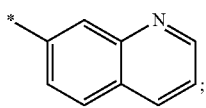 [SMILES: *c1ccc2cccnc2c1] ;

wherein the * represents the attachment point to the remainder of the molecule. In some embodiments, $A^{13}$ is and

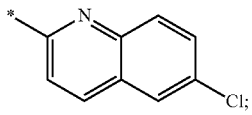

wherein the * represents the attachment point to the remainder of the molecule.

In some embodiments of the compounds of formula (XX-I-2), the moiety

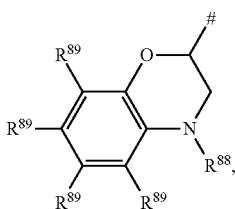

wherein # represents the attachment point to the remainder of the molecule, is

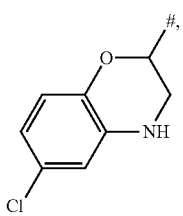

wherein # represents the attachment point to the remainder of the molecule.

In some embodiments, the compound of formula (XX) or the compound of formula (XX-I) is a compound of formula (XX-I-2b):

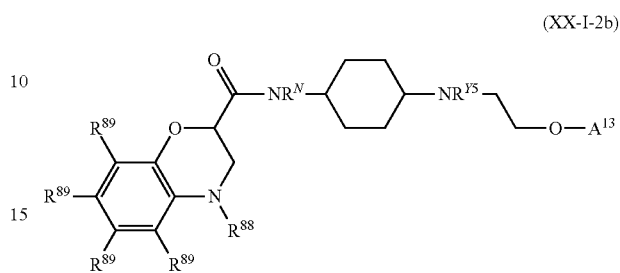

(XX-I-2b)

or a pharmaceutically acceptable salt thereof;
wherein $R^N$, $R^{Y5}$, $A^{13}$, $R^{88}$, and $R^{89}$ are as defined in the compounds of formula (XX).

In some embodiments of the compounds of formula (XX-I-2b), $R^N$ is hydrogen or $C_1$-$C_6$ alkyl. In some embodiments of the compounds of formula (XX-I-2b), $R^N$ is hydrogen.

In some embodiments of the compounds of formula (XX-I-2b), $R^{Y5}$ is hydrogen or $C_1$-$C_6$ alkyl. In some embodiments of the compounds of formula (XX-I-2b), $R^{Y5}$ is hydrogen.

In some embodiments of the compounds of formula (XX-I-2b), $R^{88}$ is hydrogen, $C_1$-$C_6$ alkyl, or $C_1$-$C_6$ haloalkyl. In some embodiments, $R^{88}$ is hydrogen.

In some embodiments of the compounds of formula (XX-I-2b), $R^{89}$ is selected, independently at each occurrence, from the group consisting of hydrogen, halogen, $C_1$-$C_6$ alkyl, and $C_1$-$C_6$ haloalkyl. In some embodiments of the compounds of formula (XX-I-2b), $R^{89}$ is, independently at each occurrence, hydrogen or halogen. In some embodiments, $R^{89}$ is, independently at each occurrence, hydrogen, fluoro or chloro. In some embodiments, one $R^{89}$ is chloro and the remaining $R^{89}$ substituents are hydrogen.

In some embodiments of the compounds of formula (XX-I-2b), $A^{13}$ is selected from the group consisting of $C_6$-$C_{14}$ aryl optionally substituted with one or more $R^{95}$ substituents; and 5-14 membered heteroaryl optionally substituted with one or more $R^{95}$ substituents. In some embodiments, $A^{13}$ is $C_6$-$C_{14}$ aryl optionally substituted with one or more $R^{95}$ substituents. In some embodiments, $A^{13}$ is $C_6$-$C_{10}$ aryl optionally substituted with one or more $R^{95}$ substituents. In some embodiments, $A^{13}$ is selected from the group consisting of

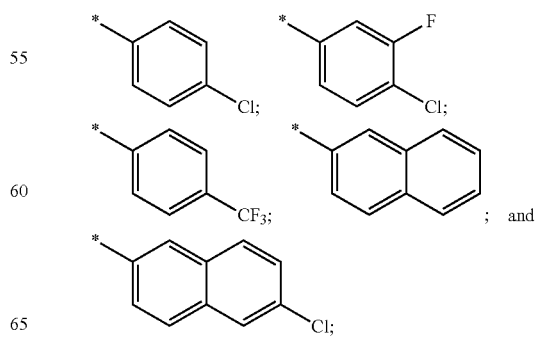

wherein the * represents the attachment point to the remainder of the molecule. In some embodiments, $A^{13}$ is phenyl optionally substituted with one or more $R^{95}$ substituents. In some embodiments, $A^{13}$ is selected from the group consisting of

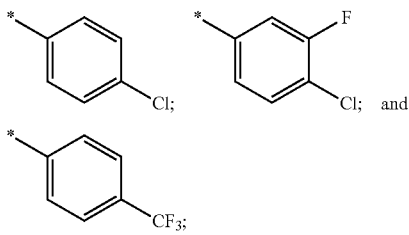

wherein the * represents the attachment point to the remainder of the molecule. In some embodiments, $A^{13}$ is

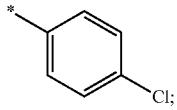

wherein the * represents the attachment point to the remainder of the molecule. In some embodiments, $A^{13}$ is

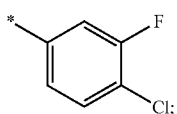

wherein the * represents the attachment point to the remainder of the molecule. In some embodiments, A is

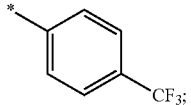 [SMILES: *c1ccc(C(F)(F)F)cc1]

wherein the * represents the attachment point to the remainder of the molecule. In some embodiments, $A^{13}$ is naphthyl optionally substituted with one or more $R^{95}$ substituents. In some embodiments, $A^{13}$ is selected from the group consisting of

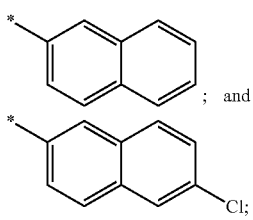

wherein the * represents the attachment point to the remainder of the molecule. In some embodiments, $A^{13}$ is

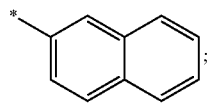

wherein the * represents the attachment point to the remainder of the molecule. In some embodiments, $A^{13}$ is

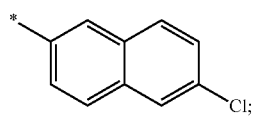

wherein the * represents the attachment point to the remainder of the molecule.

In some embodiments of the compounds of formula (XX-I-2b), $A^{13}$ is 5-14 membered heteroaryl optionally substituted with one or more $R^{95}$ substituents. In some embodiments, $A^{13}$ is 5-10 membered heteroaryl optionally substituted with one or more $R^{95}$ substituents. In some embodiments, $A^{13}$ is selected from the group consisting of

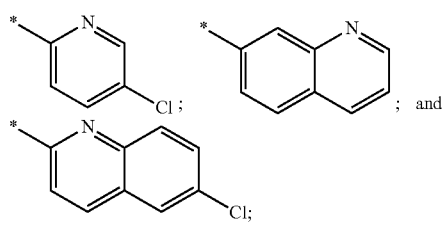

wherein the * represents the attachment point to the remainder of the molecule. In some embodiments, $A^{13}$ is pyridyl optionally substituted with one or more $R^{95}$ substituents. In some embodiments, $A^{13}$ is

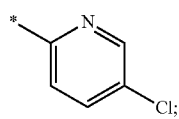

wherein the * represents the attachment point to the remainder of the molecule. In some embodiments, $A^{13}$ is quinolinyl optionally substituted with one or more $A^{13}$ substituents. In some embodiments, $A^{13}$ is selected from the group consisting of

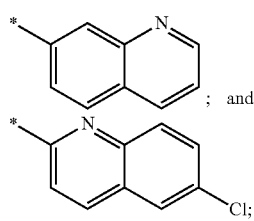

wherein the * represents the attachment point to the remainder of the molecule. In some embodiments, $A^{13}$ is

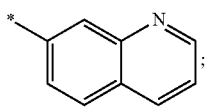 [SMILES: *c1ccc2cccnc2c1]

wherein the * represents the attachment point to the remainder of the molecule. In some embodiments, $A^{13}$ is and

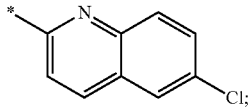 [SMILES: *c1ccc2cc(Cl)ccc2n1]

wherein the * represents the attachment point to the remainder of the molecule.

In some embodiments of the compounds of formula (XX-I-2b), the moiety

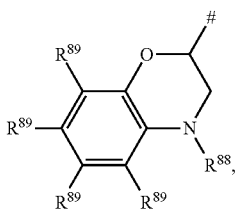

wherein # represents the attachment point to the remainder of the molecule, is

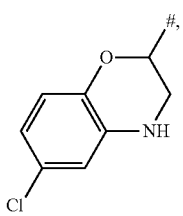

wherein # represents the attachment point to the remainder of the molecule.

In some embodiments, the compound of formula (XX) or the compound of formula (XX-I) is a compound of formula (XX-I-3):

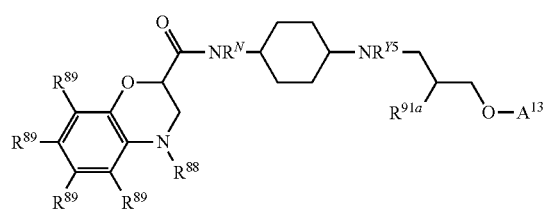

(XX-I-3)

or a pharmaceutically acceptable salt thereof;
wherein $R^N$, $R^{Y5}$, $A^{13}$, $R^{88}$, and $R^{89}$ are as defined in the compounds of formula (XX);
$R^{91a}$ is selected from the group consisting of hydrogen, $-OR^{91a-a}$, and $-NR^{91a-b}R^{91a-c}$;

$R^{91a-a}$ is selected from the group consisting of hydrogen, $C_1$-$C_6$ alkyl, and $C_1$-$C_6$ haloalkyl;
or $R^{91a-a}$ and $R^{Y5}$ may be taken together to form a carbonyl (C=O) moiety; and
$R^{91a-b}$ and $R^{91a-c}$, independently of each other, are selected from the group consisting of hydrogen, $C_1$-$C_6$ alkyl, and $C_1$-$C_6$ haloalkyl.

In some embodiments of the compounds of formula (XX-I-3), $R^N$ is hydrogen or $C_1$-$C_6$ alkyl. In some embodiments of the compounds of formula (XX-I-3), $R^N$ is hydrogen.

In some embodiments of the compounds of formula (XX-I-3), $R^{Y5}$ is hydrogen or $C_1$-$C_6$ alkyl. In some embodiments of the compounds of formula (XX-I-3), $R^{Y5}$ is hydrogen.

In some embodiments of the compounds of formula (XX-I-3), $R^{88}$ is hydrogen, $C_1$-$C_6$ alkyl, or $C_1$-$C_6$ haloalkyl. In some embodiments, $R^{88}$ is hydrogen.

In some embodiments of the compounds of formula (XX-I-3), $R^{89}$ is selected, independently at each occurrence, from the group consisting of hydrogen, halogen, $C_1$-$C_6$ alkyl, and $C_1$-$C_6$ haloalkyl. In some embodiments of the compounds of formula (XX-I-3), $R^{89}$ is, independently at each occurrence, hydrogen or halogen. In some embodiments, $R^{89}$ is, independently at each occurrence, hydrogen, fluoro or chloro. In some embodiments, one $R^{89}$ is chloro and the remaining $R^{89}$ substituents are hydrogen.

In some embodiments of the compounds of formula (XX-I-3), $R^{91a}$ is hydrogen or $-OR^{91a-a}$. In some embodiments, $R^{91a}$ is hydrogen. In some embodiments, $R^{91a}$ is $-OR^{91a-a}$, wherein $R^{91a-a}$ is selected from the group consisting of hydrogen, $C_1$-$C_6$ alkyl, and $C_1$-$C_6$ haloalkyl; or $R^{91a-a}$ and $R^{Y5}$ may be taken together to form a carbonyl (C=O) moiety. In some embodiments, $R^{91a}$ is $-OR^{91a-a}$, wherein $R^{91a-a}$ is hydrogen.

In some embodiments of the compounds of formula (XX-I-3), $A^{13}$ is selected from the group consisting of $C_6$-$C_{14}$ aryl optionally substituted with one or more $R^{95}$ substituents; and 5-14 membered heteroaryl optionally substituted with one or more $R^{95}$ substituents. In some embodiments, $A^{13}$ is $C_6$-$C_{14}$ aryl optionally substituted with one or more $R^{95}$ substituents. In some embodiments, $A^{13}$ is $C_6$-$C_{10}$ aryl optionally substituted with one or more $R^{95}$ substituents. In some embodiments, $A^{13}$ is selected from the group consisting of

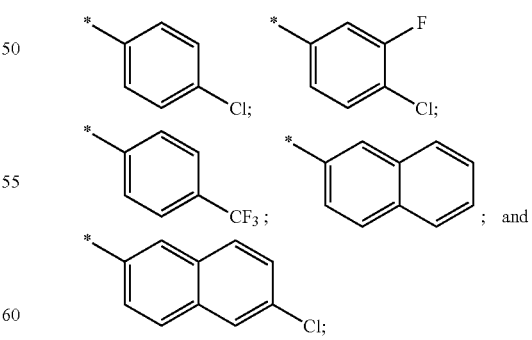

wherein the * represents the attachment point to the remainder of the molecule. In some embodiments, $A^{13}$ is phenyl optionally substituted with one or more $R^{95}$ substituents. In some embodiments, $A^{13}$ is selected from the group consisting of

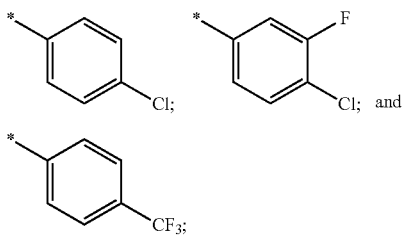

wherein the * represents the attachment point to the remainder of the molecule. In some embodiments, $A^{13}$ is

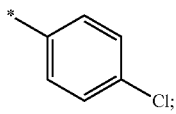

wherein the * represents the attachment point to the remainder of the molecule. In some embodiments, $A^{13}$ is

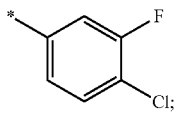 [SMILES: *c1ccc(Cl)c(F)c1]

wherein the * represents the attachment point to the remainder of the molecule. In some embodiments, $A^{13}$ is

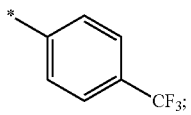

wherein the * represents the attachment point to the remainder of the molecule. In some embodiments, $A^{13}$ is naphthyl optionally substituted with one or more $R^{95}$ substituents. In some embodiments, $A^{13}$ is selected from the group consisting of

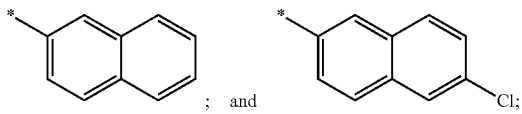 [SMILES: *c1ccc2ccccc2c1 ; *c1ccc2cc(Cl)ccc2c1]

wherein the * represents the attachment point to the remainder of the molecule. In some embodiments, $A^{13}$ is

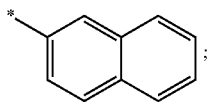 [SMILES: *c1ccc2ccccc2c1]

wherein the * represents the attachment point to the remainder of the molecule.

In some embodiments of the compounds of formula (XX-I-3), $A^{13}$ is 5-14 membered heteroaryl optionally substituted with one or more $R^{95}$ substituents. In some embodiments, $A^{13}$ is 5-10 membered heteroaryl optionally substituted with one or more $R^{95}$ substituents. In some embodiments, $A^{13}$ is selected from the group consisting of

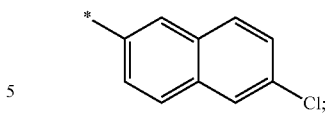

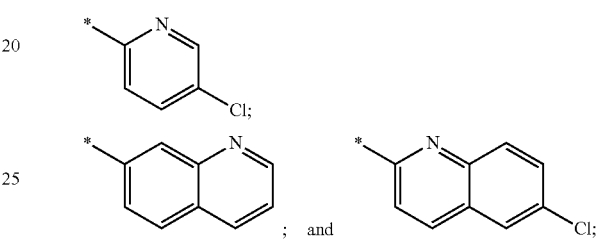

wherein the * represents the attachment point to the remainder of the molecule. In some embodiments, $A^{13}$ is pyridyl optionally substituted with one or more $R^{95}$ substituents. In some embodiments, $A^{13}$ is

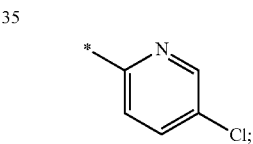

wherein the * represents the attachment point to the remainder of the molecule. In some embodiments, $A^{13}$ is quinolinyl optionally substituted with one or more $A^{13}$ substituents. In some embodiments, $A^{13}$ is selected from the group consisting of

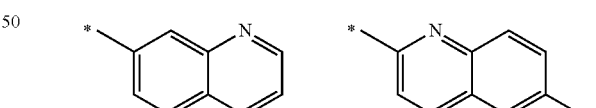

wherein the * represents the attachment point to the remainder of the molecule. In some embodiments, $A^{13}$ is

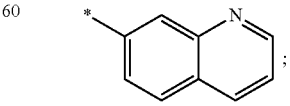

wherein the * represents the attachment point to the remainder of the molecule. In some embodiments, $A^{13}$ is and

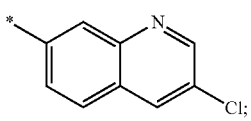 [SMILES: *c1ccc2cc(Cl)cnc2c1]

wherein the * represents the attachment point to the remainder of the molecule.

In some embodiments of the compounds of formula (XX-I-3), the moiety

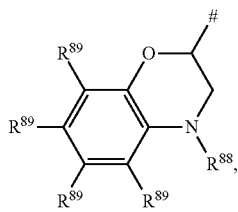

wherein # represents the attachment point to the remainder of the molecule, is

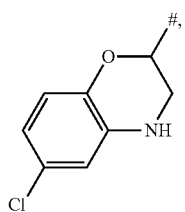

wherein # represents the attachment point to the remainder of the molecule.

In some embodiments, the compound of formula (XX) or the compound of formula (XX-I) is a compound of formula (XX-II-3):

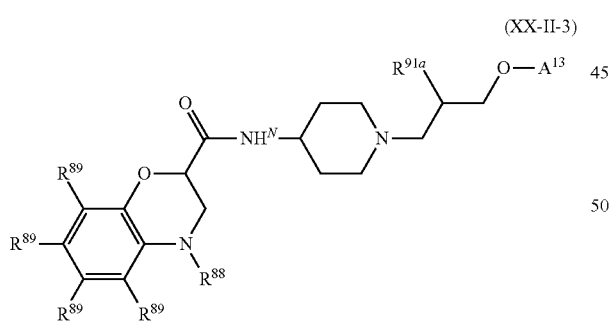

(XX-II-3)

or a pharmaceutically acceptable salt thereof;
wherein $R^N$, $R^{Y5}$, $A^{13}$, $R^{88}$, and $R^{89}$ are as defined in the compounds of formula (XX); $R^{91a}$ is selected from the group consisting of hydrogen, —$OR^{91a\text{-}a}$, and —$NR^{91a\text{-}b}R^{91a\text{-}c}$; $R^{91a\text{-}a}$ is selected from the group consisting of hydrogen, $C_1$-$C_6$ alkyl, and $C_1$-$C_6$ haloalkyl; or $R^{91a\text{-}a}$ and $R^{Y5}$ may be taken together to form a carbonyl (C=O) moiety; and $R^{91a\text{-}b}$ and $R^{91a\text{-}c}$, independently of each other, are selected from the group consisting of hydrogen, $C_1$-$C_6$ alkyl, and $C_1$-$C_6$ haloalkyl.

In some embodiments of the compounds of formula (XX-II-3), $R^N$ is hydrogen or $C_1$-$C_6$ alkyl. In some embodiments of the compounds of formula (XX-II-3), $R^N$ is hydrogen.

In some embodiments of the compounds of formula (XX-II-3), $R^{88}$ is hydrogen, $C_1$-$C_6$ alkyl, or $C_1$-$C_6$ haloalkyl. In some embodiments, $R^{88}$ is hydrogen.

In some embodiments of the compounds of formula (XX-II-3), $R^{89}$ is selected, independently at each occurrence, from the group consisting of hydrogen, halogen, $C_1$-$C_6$ alkyl, and $C_1$-$C_6$ haloalkyl. In some embodiments of the compounds of formula (XX-II-3), $R^{89}$ is, independently at each occurrence, hydrogen or halogen. In some embodiments, $R^{89}$ is, independently at each occurrence, hydrogen, fluoro or chloro. In some embodiments, one $R^{89}$ is chloro and the remaining $R^{89}$ substituents are hydrogen.

In some embodiments of the compounds of formula (XX-II-3), $R^{91a}$ is hydrogen or —$OR^{91a\text{-}a}$. In some embodiments, $R^{91a}$ is hydrogen. In some embodiments, $R^{91a}$ is —$OR^{91a\text{-}a}$, wherein $R^{91a\text{-}a}$ is selected from the group consisting of hydrogen, $C_1$-$C_6$ alkyl, and $C_1$-$C_6$ haloalkyl; or $R^{91a\text{-}a}$ and $R^{Y5}$ may be taken together to form a carbonyl (C=O) moiety. In some embodiments, $R^{91a}$ is —$OR^{91a\text{-}a}$, wherein $R^{91a\text{-}a}$ is hydrogen.

In some embodiments of the compounds of formula (XX-II-3), $A^{13}$ is selected from the group consisting of $C_6$-$C_{14}$ aryl optionally substituted with one or more $R^{95}$ substituents; and 5-14 membered heteroaryl optionally substituted with one or more $R^{95}$ substituents. In some embodiments, $A^{13}$ is $C_6$-$C_{14}$ aryl optionally substituted with one or more $R^{95}$ substituents. In some embodiments, $A^{13}$ is $C_6$-$C_{10}$ aryl optionally substituted with one or more $R^{95}$ substituents. In some embodiments, $A^{13}$ is selected from the group consisting of

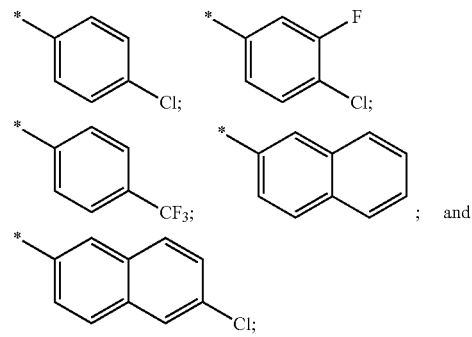

wherein the * represents the attachment point to the remainder of the molecule. In some embodiments, $A^{13}$ is phenyl optionally substituted with one or more $R^{95}$ substituents. In some embodiments, $A^{13}$ is selected from the group consisting of

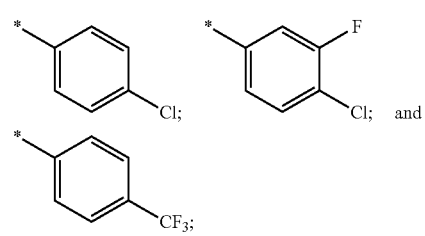

wherein the * represents the attachment point to the remainder of the molecule. In some embodiments, $A^{13}$ is

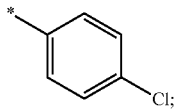

wherein the * represents the attachment point to the remainder of the molecule. In some embodiments, $A^{13}$ is

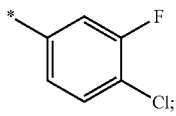

wherein the * represents the attachment point to the remainder of the molecule. In some embodiments, $A^{13}$ is

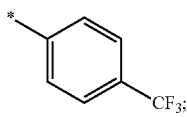 [SMILES: *c1ccc(C(F)(F)F)cc1]

wherein the * represents the attachment point to the remainder of the molecule. In some embodiments, $A^{13}$ is naphthyl optionally substituted with one or more $R^{95}$ substituents. In some embodiments, $A^{13}$ is selected from the group consisting of

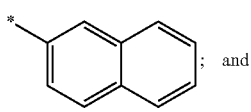 ; and 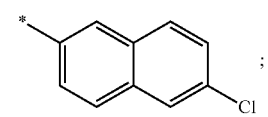 ;

wherein the * represents the attachment point to the remainder of the molecule. In some embodiments, $A^{13}$ is

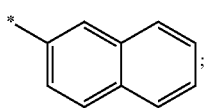 ;

wherein the * represents the attachment point to the remainder of the molecule. In some embodiments, $A^{13}$ is

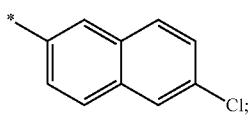 ;

wherein the * represents the attachment point to the remainder of the molecule.

In some embodiments of the compounds of formula (XX-II-3), $A^{13}$ is 5-14 membered heteroaryl optionally substituted with one or more $R^{95}$ substituents. In some embodiments, $A^{13}$ is 5-10 membered heteroaryl optionally substituted with one or more $R^{95}$ substituents. In some embodiments. $A^{13}$ is selected from the group consisting of

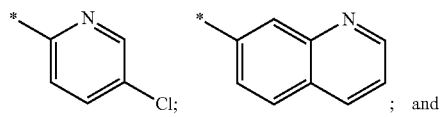 ; and

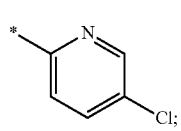 [SMILES: *c1ccc(Cl)cn1] ;

wherein the * represents the attachment point to the remainder of the molecule. In some embodiments, $A^{13}$ is pyridyl optionally substituted with one or more $R^{95}$ substituents. In some embodiments, $A^{13}$ is

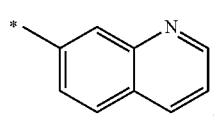 ;

wherein the * represents the attachment point to the remainder of the molecule. In some embodiments, $A^{13}$ is quinolinyl optionally substituted with one or more $A^{13}$ substituents. In some embodiments, $A^{13}$ is selected from the group consisting of

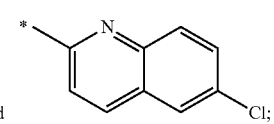 ; and 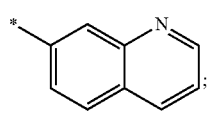 [SMILES: *c1ccc2cccnc2c1] ;

wherein the * represents the attachment point to the remainder of the molecule. In some embodiments, $A^{13}$ is

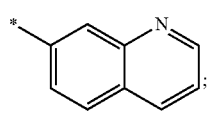 [SMILES: *c1ccc2cccnc2c1] ;

wherein the * represents the attachment point to the remainder of the molecule. In some embodiments, $A^{13}$ is and

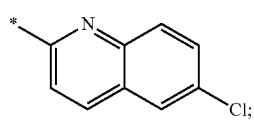 ;

wherein the * represents the attachment point to the remainder of the molecule.

In some embodiments of the compounds of formula (XX-II-3), the moiety

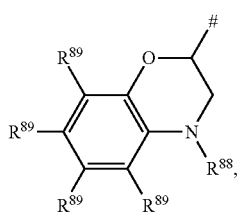

wherein # represents the attachment point to the remainder of the molecule, is

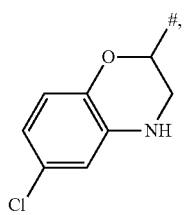

wherein # represents the attachment point to the remainder of the molecule.

In the descriptions herein, it is understood that every description, variation, embodiment or aspect of a moiety may be combined with every description, variation, embodiment or aspect of other moieties the same as if each and every combination of descriptions is specifically and individually listed. For example, every description, variation, embodiment or aspect provided herein with respect to $X^1$ of formula (I) may be combined with every description, variation, embodiment or aspect of $m^1$, $m^2$, $n^1$, $n^2$, $p^1$, $p^2$, $q^1$, $q^2$, r, s, $X^2$, $Y^1$, $Y^2$, $A^1$, $A^2$, $R^{1a}$, $R^{1b}$, $R^{2a}$, $R^{2b}$, $R^{3a}$, $R^{3b}$, $R^{4a}$, $R^{4b}$, $R^{5a}$, $R^{5b}$, $R^{6a}$, $R^{6b}$, $R^{7a}$, $R^{7b}$, $R^{8a}$, $R^{8b}$, $R^{9a}$, $R^{9b}$, $R^{10a}$, $R^{10b}$, $R^{11a}$, $R^{11b}$, $R^{12a}$, and $R^{12b}$ the same as if each and every combination were specifically and individually listed. It is also understood that all descriptions, variations, embodiments or aspects of formula (I), where applicable, apply equally to other formulae detailed herein, and are equally described, the same as if each and every description, variation, embodiment or aspect were separately and individually listed for all formulae. For example, all descriptions, variations, embodiments or aspects of formula (I), where applicable, apply equally to any of formulae (1-1), (1-2), (1-3), (1-4), (2-2), (2-3), (2-4), (3-3), (3-4), and (4-4) detailed herein, and are equally described, the same as if each and every description, variation, embodiment or aspect were separately and individually listed for all formulae. Similarly, every description, variation, embodiment or aspect provided herein with respect to $X^3$ of formula (II) may be combined with every description, variation, embodiment or aspect of $m^3$, $n^3$, $r^2$, $s^2$, $X^4$, $Y^3$, $Y^4$, $A^3$, $A^4$, $R^{17a}$, $R^{17b}$, $R^{18a}$, $R^{18b}$, $R^{19a}$, $R^{19b}$, $R^{20a}$, $R^{20b}$, $R^{21a}$, $R^{21b}$, $R^{22a}$, $R^{22b}$, $R^{23a}$, $R^{23b}$, $R^{24a}$, $R^{24b}$, $R^{25a}$, $R^{25b}$, same as if each and every combination were specifically and individually listed. It is also understood that all descriptions, variations, embodiments or aspects of formula (II), where applicable, apply equally to other formulae detailed herein, and are equally described, the same as if each and every description, variation, embodiment or aspect were separately and individually listed for all formulae. For example, all descriptions, variations, embodiments or aspects of formula (II) where applicable, apply equally to any of formulae (III), (IV), and (V) detailed herein, and are equally described, the same as if each and every description, variation, embodiment or aspect were separately and individually listed for all formulae. Similarly, every description, variation, embodiment or aspect provided herein with respect to $X^5$ of formula (XX) may be combined with every description, variation, embodiment or aspect of $R^N$, $Y^5$, $R^{Y5}$, $m^4$, $n^5$, $p^3$, $q^4$, r3, $A^{13}$, $R^{84a}$, $R^{84b}$, $R^{85a}$, $R^{85b}$, $R^{86a}$, $R^{86b}$, $R^{87a}$, $R^{87b}$, $R^{88}$, $R^{89}$, $R^{90a}$, $R^{90b}$, $R^{91a}$, $R^{91b}$, $R^{92a}$, $R^{92b}$, $R^{93a}$, and $R^{93b}$ the same as if each and every combination were specifically and individually listed. It is also understood that all descriptions, variations, embodiments or aspects of formula (XX), where applicable, apply equally to other formulae detailed herein, and are equally described, the same as if each and every description, variation, embodiment or aspect were separately and individually listed for all formulae. For example, all descriptions, variations, embodiments or aspects of formula (XX) where applicable, apply equally to any of formulae (XX-I), (XX-II), (XX-I-1), (XX-I-2), (XX-I-2b), (XX-I-3), and (XX-II-3) detailed herein, and are equally described, the same as if each and every description, variation, embodiment or aspect were separately and individually listed for all formulae.

Also provided are salts of compounds referred to herein, such as pharmaceutically acceptable salts. The present disclosure also includes any or all of the stereochemical forms, including any enantiomeric or diastereomeric forms, and any tautomers or other forms of the compounds described. Thus, if a particular stereochemical form, such as a specific enantiomeric form or diastereomeric form, is depicted for a given compound, then it is understood that any or all stereochemical forms, including any enantiomeric or diastereomeric forms, and any tautomers or other forms of any of that same compound are herein described and embraced by the invention.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form. Unless otherwise stated, "substantially pure" intends a composition that contains no more than 35% impurity, wherein the impurity denotes a compound other than the compound comprising the majority of the composition or a salt thereof. In some embodiments, a composition of substantially pure compound or a salt thereof is provided wherein the composition contains no more than 25%, 20%, 15%, 10%, or 5% impurity. In some embodiments, a composition of substantially pure compound or a salt thereof is provided wherein the composition contains or no more than 3%, 2%, 1% or 0.5% impurity.

In some embodiments, provided is compound selected from compounds in Table 1, or a stereoisomer, tautomer, solvate, prodrug or salt thereof. Although certain compounds described in Table 1 are presented as specific stereoisomers and/or in a non-stereochemical form, it is understood that any or all stereochemical forms, including any enantiomeric or diastereomeric forms, and any tautomers or other forms of any of the compounds of Table 1 are herein described.

TABLE 1

| Compound No. | Structure |
|---|---|
| 1 | 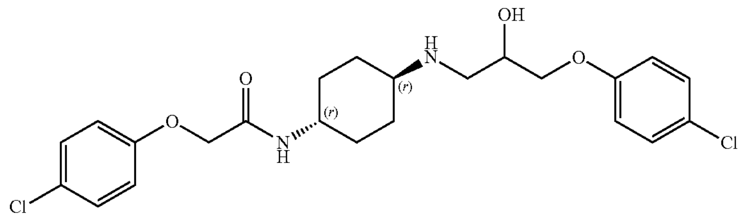 [SMILES: O=C(COc1ccc(Cl)cc1)N[C@H]1CC[C@H](NCC(O)COc2ccc(Cl)cc2)CC1] |
| 2 | 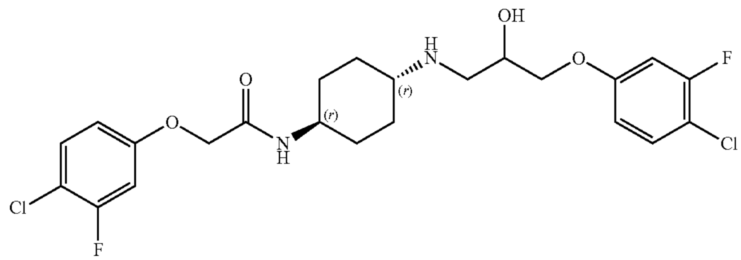 [SMILES: O=C(COc1ccc(Cl)c(F)c1)N[C@H]1CC[C@H](NCC(O)COc2ccc(Cl)c(F)c2)CC1] |
| 3 | 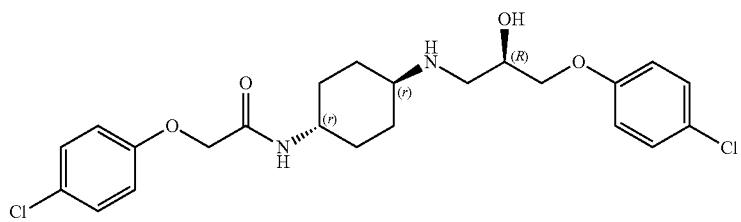 |
| 4 | 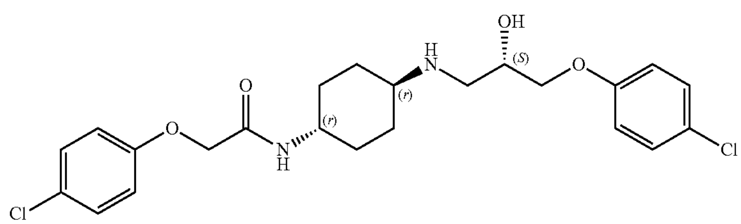 |
| 5 | 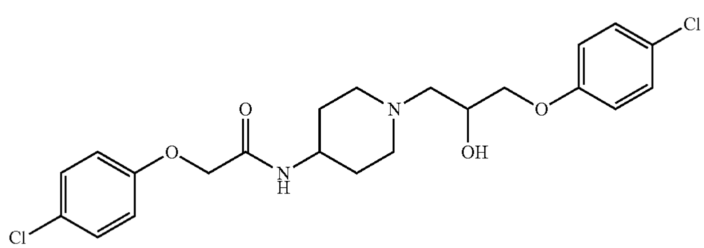 [SMILES: O=C(COc1ccc(Cl)cc1)NC1CCN(CC(O)COc2ccc(Cl)cc2)CC1] |
| 6 | 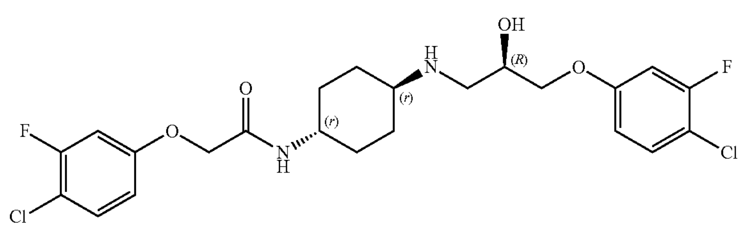 |

TABLE 1-continued

| Compound No. | Structure |
|---|---|
| 7 | (structure with 4-chloro-3-fluorophenoxyacetamide-cyclohexyl-NH-CH2-CH(S)(OH)-CH2-O-3-fluoro-4-chlorophenyl) |
| 8 | (structure with 4-chlorophenoxyacetamide-cyclohexyl-NH-C(O)-CH(OH)-CH2-O-4-chlorophenyl) |
| 9 | (structure with 4-chloro-3-fluorophenoxyacetamide-cyclohexyl-NH-C(O)-CH(OH)-CH2-O-3-fluoro-4-chlorophenyl) |
| 10 | (structure with 4-chloro-3-fluorophenoxyacetamide-cyclohexyl-NH-CH2-CH(OH)-CH2-O-4-chlorophenyl) |
| 11 | (structure with 3-fluoro-4-chlorophenoxyacetamide-(S)-piperidin-3-yl-N-CH2-CH(OH)-CH2-O-3-fluoro-4-chlorophenyl) |
| 12 | (structure with 3-fluoro-4-chlorophenoxyacetamide-(R)-piperidin-3-yl-N-CH2-CH(OH)-CH2-O-3-fluoro-4-chlorophenyl) |
| 13 | (structure with 3-fluoro-4-chlorophenoxyacetamide-piperidin-4-yl-N-CH2-CH(OH)-CH2-O-4-chloro-3-fluorophenyl) |

TABLE 1-continued

| Compound No. | Structure |
|---|---|
| 14 | 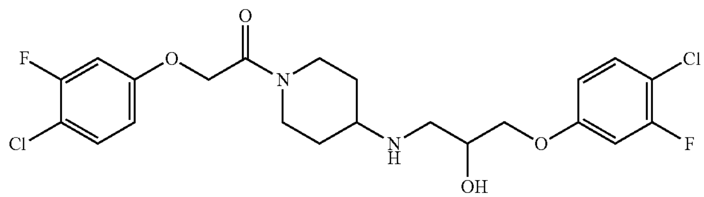 [SMILES: O=C(COc1ccc(Cl)c(F)c1)N1CCC(NCC(O)COc2ccc(Cl)c(F)c2)CC1] |
| 15 | 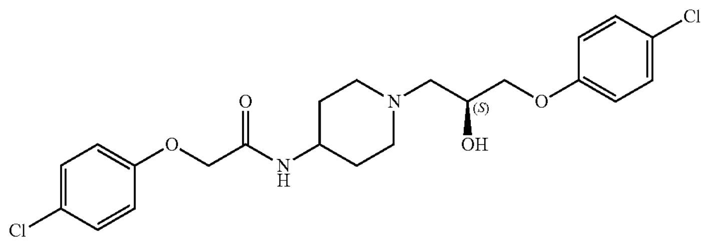 |
| 16 | 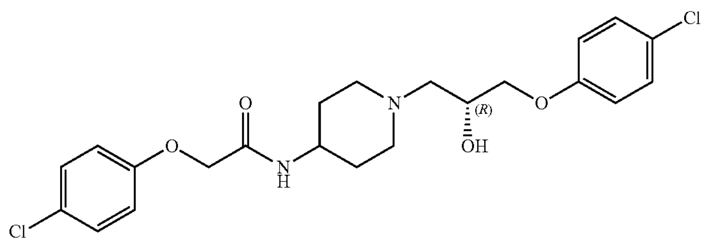 |
| 17 | 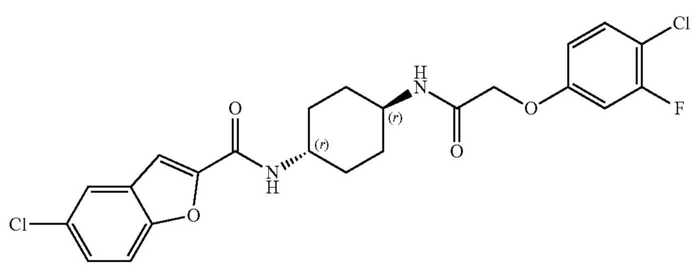 [SMILES: O=C(COc1ccc(Cl)c(F)c1)N[C@H]1CC[C@H](NC(=O)c2cc3cc(Cl)ccc3o2)CC1] |
| 18 | 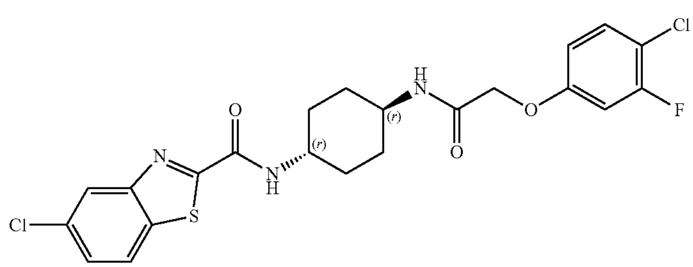 [SMILES: O=C(COc1ccc(Cl)c(F)c1)N[C@H]1CC[C@H](NC(=O)c2nc3cc(Cl)ccc3s2)CC1] |
| 19 | 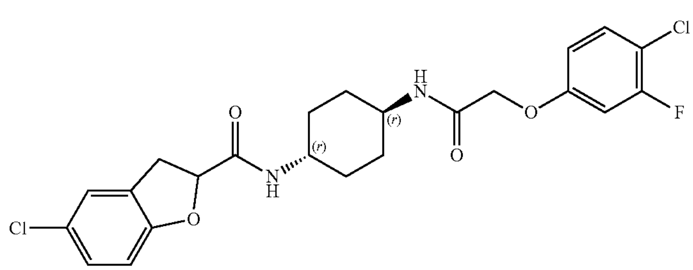 [SMILES: O=C(COc1ccc(Cl)c(F)c1)N[C@H]1CC[C@H](NC(=O)C2Cc3cc(Cl)ccc3O2)CC1] |

TABLE 1-continued

| Compound No. | Structure |
|---|---|
| 20 | 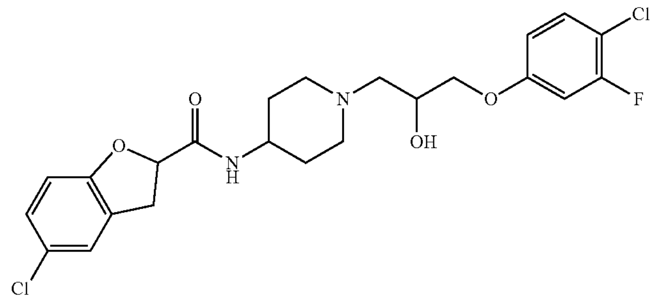 [SMILES: O=C(NC1CCN(CC(O)COc2ccc(Cl)c(F)c2)CC1)C1Cc2cc(Cl)ccc2O1] |
| 21 | 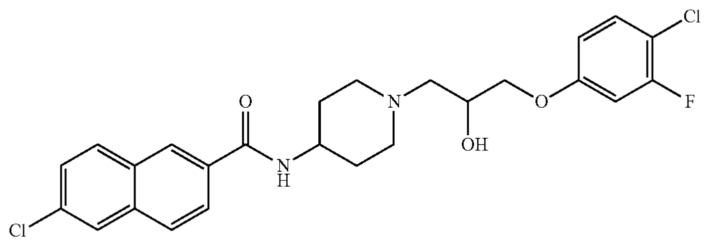 [SMILES: O=C(NC1CCN(CC(O)COc2ccc(Cl)c(F)c2)CC1)c1ccc2cc(Cl)ccc2c1] |
| 22 | 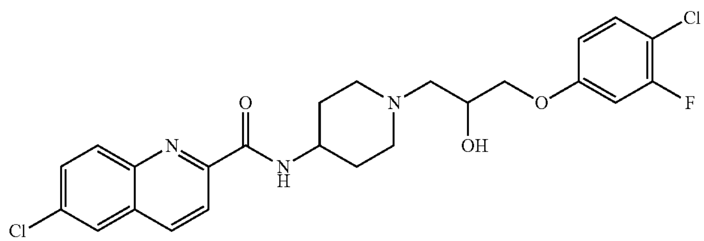 [SMILES: O=C(NC1CCN(CC(O)COc2ccc(Cl)c(F)c2)CC1)c1ccc2cc(Cl)ccc2n1] |
| 23 | 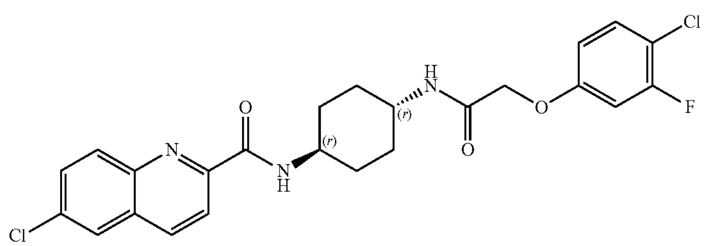 [SMILES: O=C(COc1ccc(Cl)c(F)c1)N[C@H]1CC[C@H](NC(=O)c2ccc3cc(Cl)ccc3n2)CC1] |
| 24 | 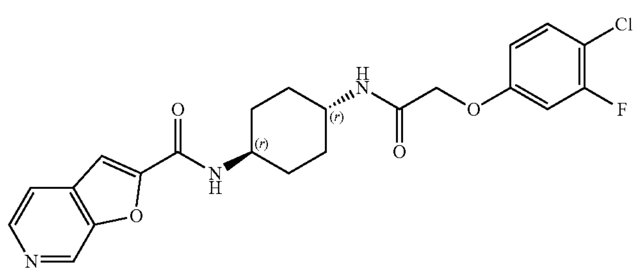 [SMILES: O=C(COc1ccc(Cl)c(F)c1)N[C@H]1CC[C@H](NC(=O)c2cc3ccncc3o2)CC1] |
| 25 | 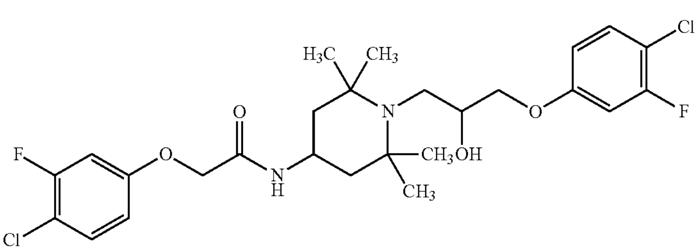 [SMILES: CC1(C)CC(NC(=O)COc2ccc(Cl)c(F)c2)CC(C)(C)N1CC(O)COc1ccc(Cl)c(F)c1] |

TABLE 1-continued

| Compound No. | Structure |
|---|---|
| 26 | 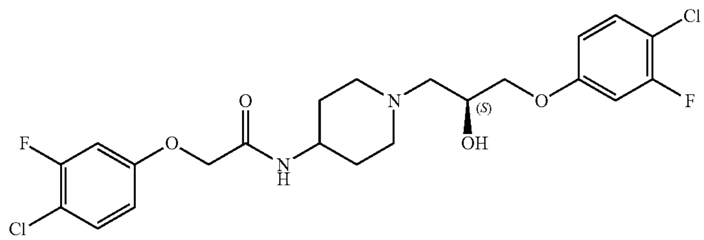 |
| 27 | 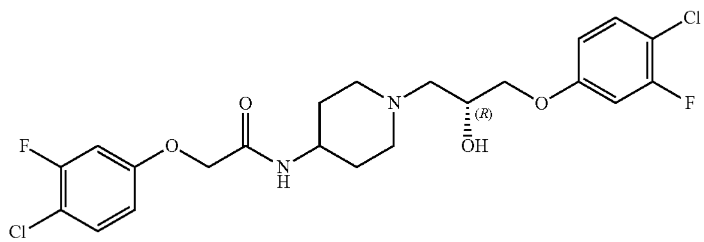 |
| 28 | 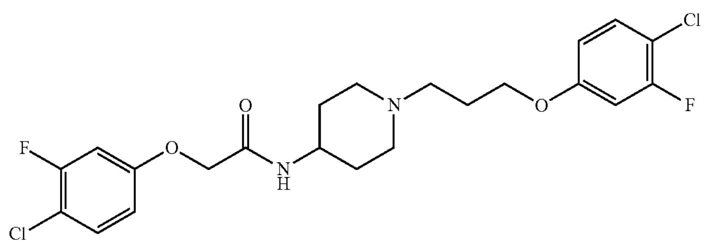 [SMILES: O=C(COc1ccc(Cl)c(F)c1)NC1CCN(CCCOc2ccc(Cl)c(F)c2)CC1] |
| 29 | 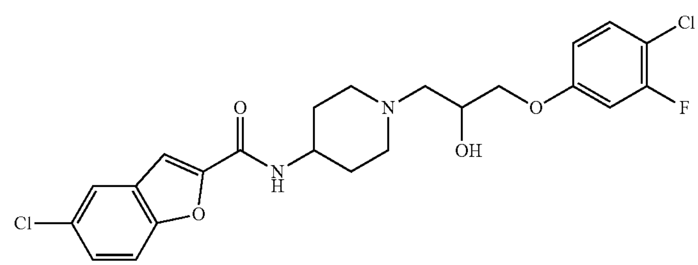 [SMILES: O=C(NC1CCN(CC(O)COc2ccc(Cl)c(F)c2)CC1)c1cc2cc(Cl)ccc2o1] |
| 30 | 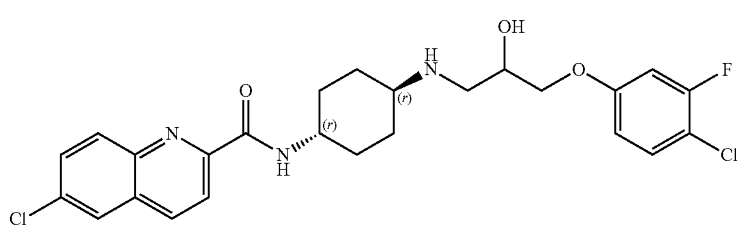 [SMILES: O=C(N[C@H]1CC[C@H](NCC(O)COc2ccc(Cl)c(F)c2)CC1)c1ccc2cc(Cl)ccc2n1] |
| 31 | 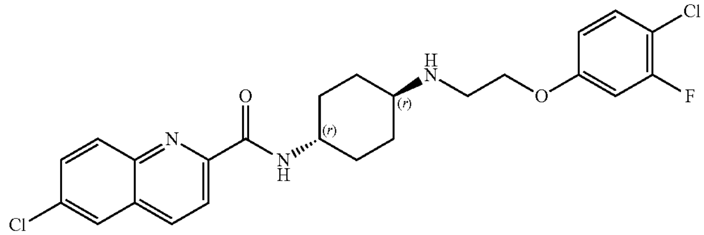 [SMILES: O=C(N[C@H]1CC[C@H](NCCOc2ccc(Cl)c(F)c2)CC1)c1ccc2cc(Cl)ccc2n1] |

TABLE 1-continued

| Compound No. | Structure |
|---|---|
| 32 | 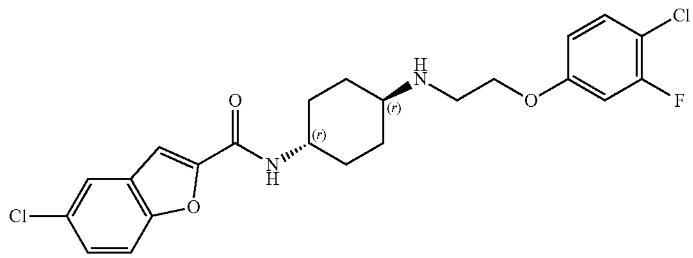 [SMILES: O=C(N[C@H]1CC[C@H](NCCOc2ccc(Cl)c(F)c2)CC1)c1cc2cc(Cl)ccc2o1] |
| 33 | 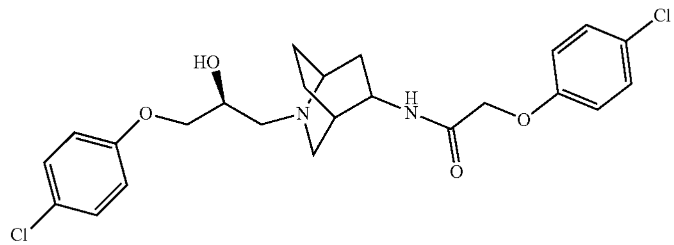 [SMILES: O=C(COc1ccc(Cl)cc1)NC1CC2CCC1CN2C[C@H](O)COc1ccc(Cl)cc1] |
| 34 | 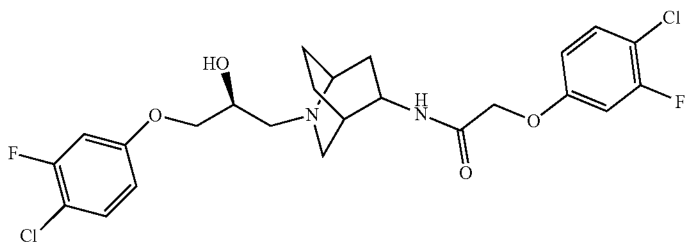 [SMILES: O=C(COc1ccc(Cl)c(F)c1)NC1CC2CCC1CN2C[C@H](O)COc1ccc(Cl)c(F)c1] |
| 35 | 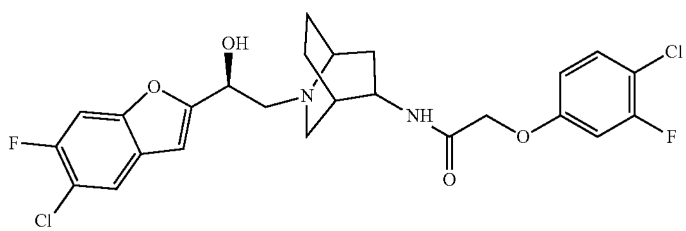 [SMILES: O=C(COc1ccc(Cl)c(F)c1)NC1CC2CCC1CN2C[C@H](O)c1cc2cc(Cl)c(F)cc2o1] |
| 36 | 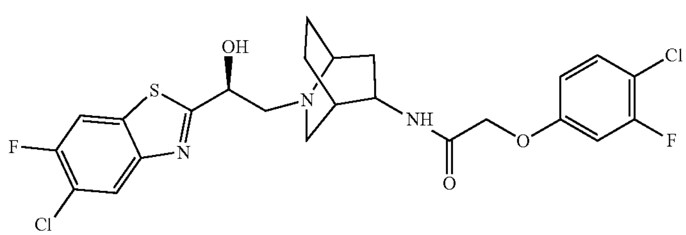 [SMILES: O=C(COc1ccc(Cl)c(F)c1)NC1CC2CCC1CN2C[C@H](O)c1nc2cc(Cl)c(F)cc2s1] |
| 37 | 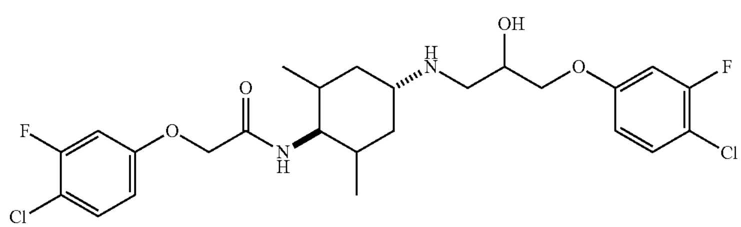 |

TABLE 1-continued
| Compound No. | Structure |
|---|---|
| 38 | 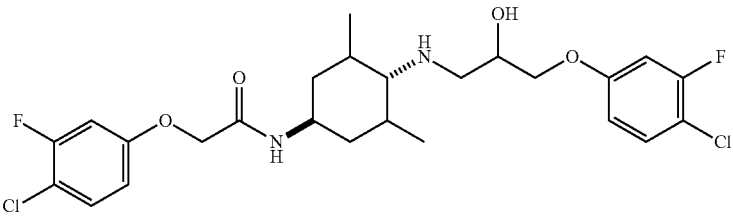 |
| 39 | 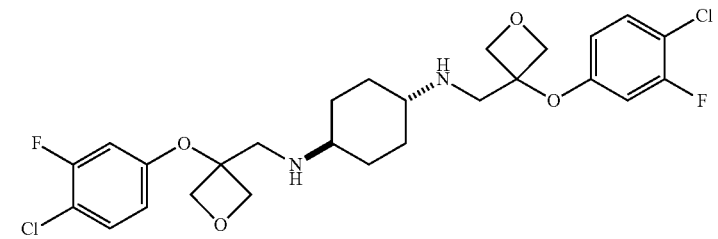 |
| 40 | 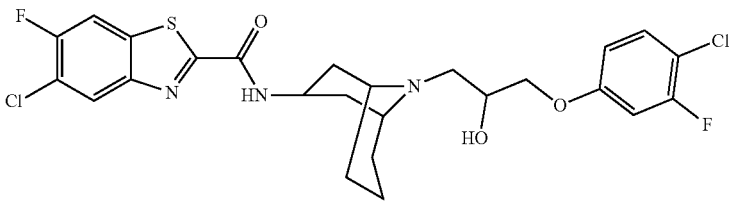 [SMILES: O=C(NC1CC2CCCC(C1)N2CC(O)COc1ccc(Cl)c(F)c1)c1nc2cc(Cl)c(F)cc2s1] |
| 41 | 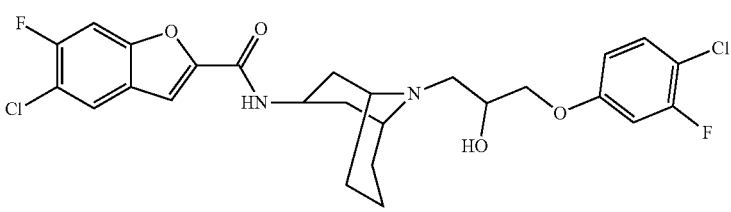 [SMILES: O=C(NC1CC2CCCC(C1)N2CC(O)COc1ccc(Cl)c(F)c1)c1cc2cc(Cl)c(F)cc2o1] |
| 42 | 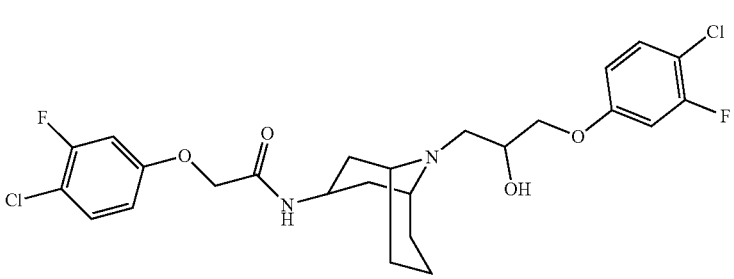 [SMILES: O=C(COc1ccc(Cl)c(F)c1)NC1CC2CCCC(C1)N2CC(O)COc1ccc(Cl)c(F)c1] |
| 43 | 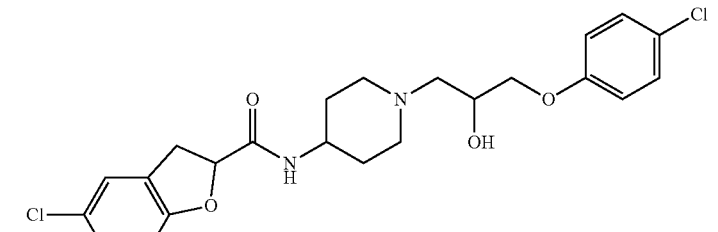 |

TABLE 1-continued

| Compound No. | Structure |
|---|---|
| 44 | 5-chloro-benzothiazole-2-carboxamide-N-(1-(3-(4-chlorophenoxy)-2-hydroxypropyl)piperidin-4-yl) |
| 45 | 5-chloro-1H-benzimidazole-2-carboxamide-N-(1-(3-(4-chlorophenoxy)-2-hydroxypropyl)piperidin-4-yl) |
| 46 | 6-chloro-1H-benzimidazole-2-carboxamide-N-(1-(3-(4-chlorophenoxy)-2-hydroxypropyl)piperidin-4-yl) |
| 47 | furo[2,3-c]pyridine-2-carboxamide-N-(1-(3-(4-chlorophenoxy)-2-hydroxypropyl)piperidin-4-yl) |
| 48 | 2,3-dihydrofuro[2,3-c]pyridine-2-carboxamide-N-(1-(3-(4-chlorophenoxy)-2-hydroxypropyl)piperidin-4-yl) |
| 49 | N-((3-(4-chlorophenoxy)oxetan-3-yl)methyl)-1-(3-(4-chlorophenoxy)-2-hydroxypropyl)piperidin-4-amine |

TABLE 1-continued
| Compound No. | Structure |
|---|---|
| 50 | 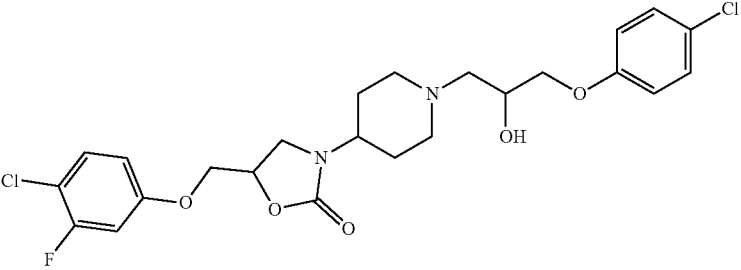 [SMILES: O=C1OC(COc2ccc(Cl)c(F)c2)CN1C1CCN(CC(O)COc2ccc(Cl)cc2)CC1] |
| 51 | 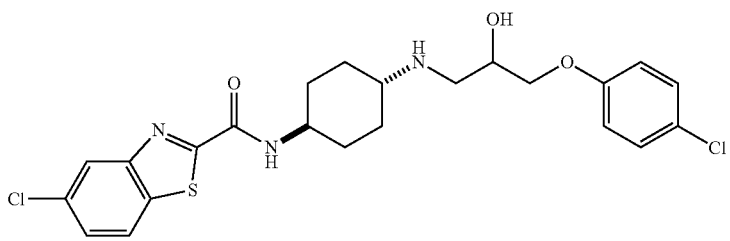 |
| 52 | 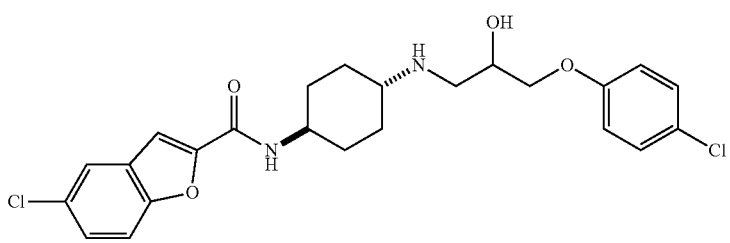 |
| 53 | 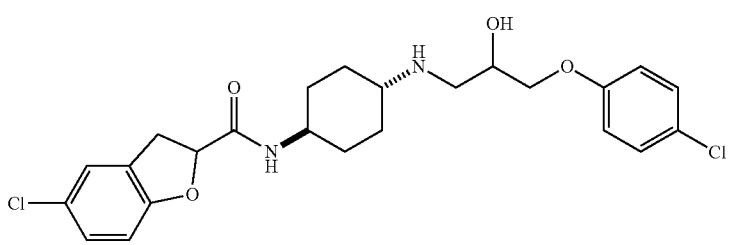 |
| 54 | 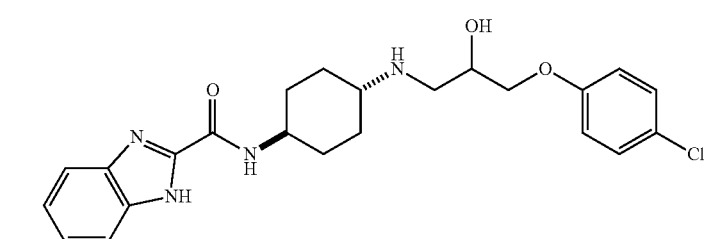 |
| 55 | 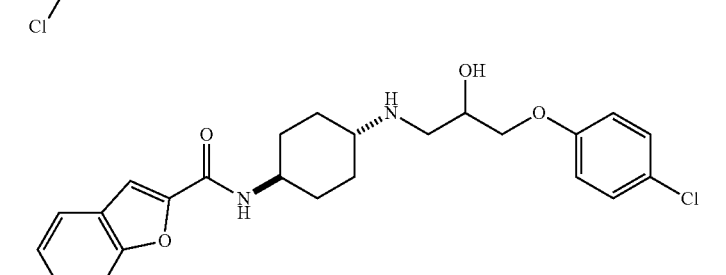 |

TABLE 1-continued

| Compound No. | Structure |
|---|---|
| 56 | 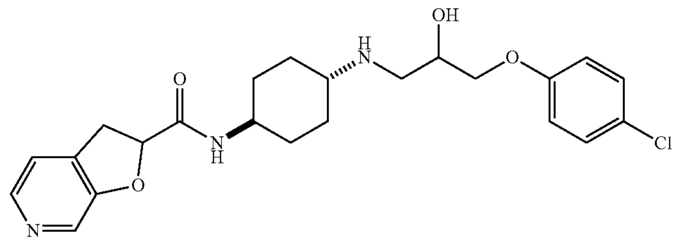 |
| 57 | 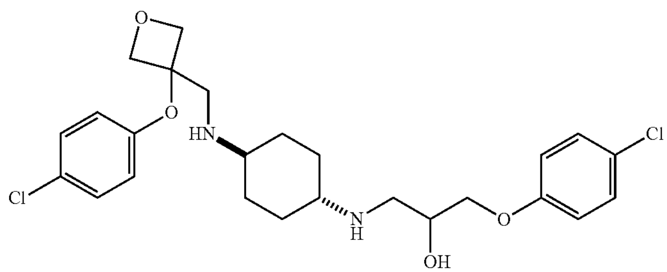 |
| 58 | 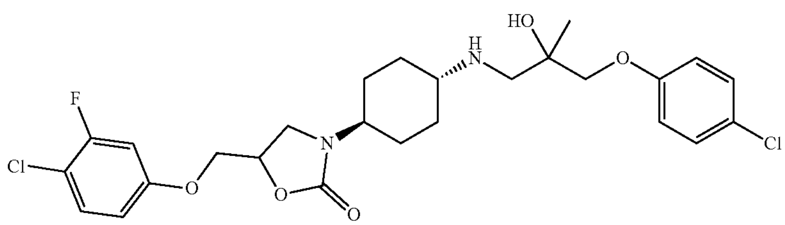 [SMILES: CC(O)(CN[C@H]1CC[C@H](N2CC(COc3ccc(Cl)c(F)c3)OC2=O)CC1)COc1ccc(Cl)cc1] |
| 59 | 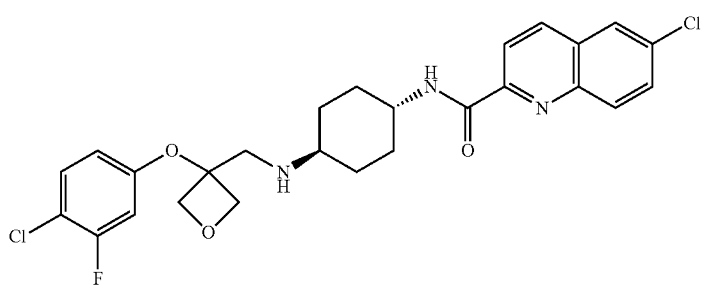 [SMILES: O=C(N[C@H]1CC[C@H](NCC2(Oc3ccc(Cl)c(F)c3)COC2)CC1)c1ccc2cc(Cl)ccc2n1] |
| 60 | 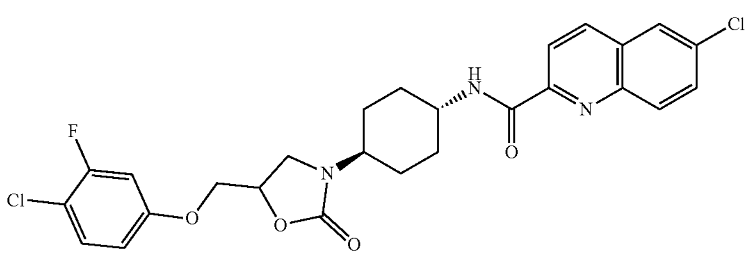 [SMILES: O=C(N[C@H]1CC[C@H](N2CC(COc3ccc(Cl)c(F)c3)OC2=O)CC1)c1ccc2cc(Cl)ccc2n1] |
| 61 | 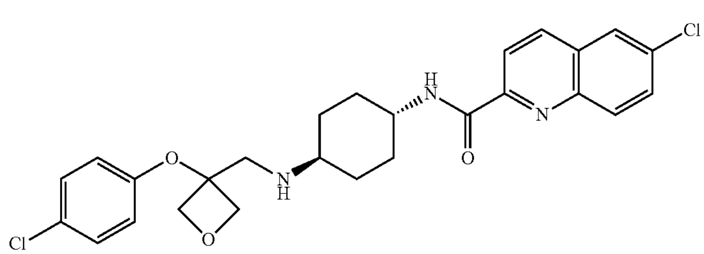 [SMILES: O=C(N[C@H]1CC[C@H](NCC2(Oc3ccc(Cl)cc3)COC2)CC1)c1ccc2cc(Cl)ccc2n1] |

TABLE 1-continued

| Compound No. | Structure |
|---|---|
| 62 | 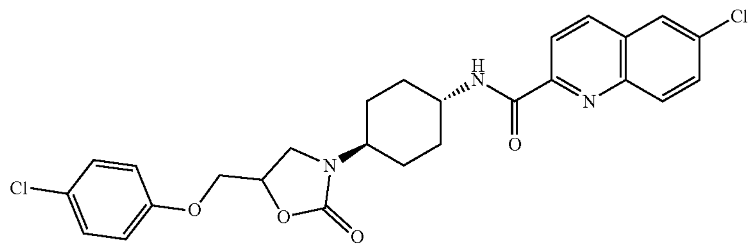 [SMILES: O=C(N[C@H]1CC[C@H](N2CC(COc3ccc(Cl)cc3)OC2=O)CC1)c1ccc2cc(Cl)ccc2n1] |
| 63 | 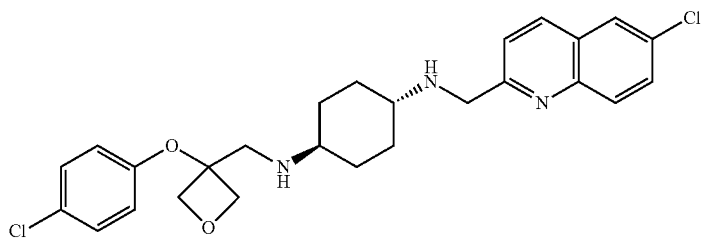 [SMILES: Clc1ccc(OC2(CN[C@H]3CC[C@H](NCc4ccc5cc(Cl)ccc5n4)CC3)COC2)cc1] |
| 64 | 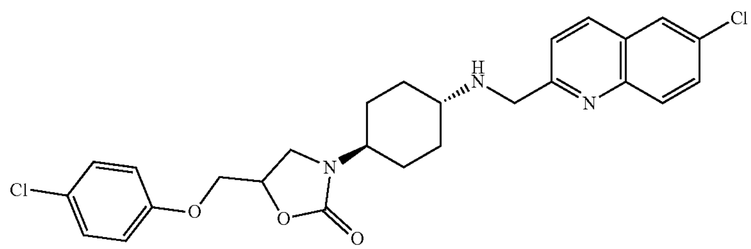 [SMILES: O=C1OC(COc2ccc(Cl)cc2)CN1[C@H]1CC[C@H](NCc2ccc3cc(Cl)ccc3n2)CC1] |
| 65 | 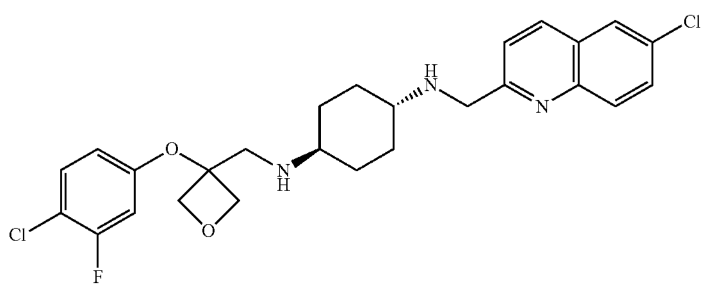 [SMILES: Fc1cc(OC2(CN[C@H]3CC[C@H](NCc4ccc5cc(Cl)ccc5n4)CC3)COC2)ccc1Cl] |
| 66 | 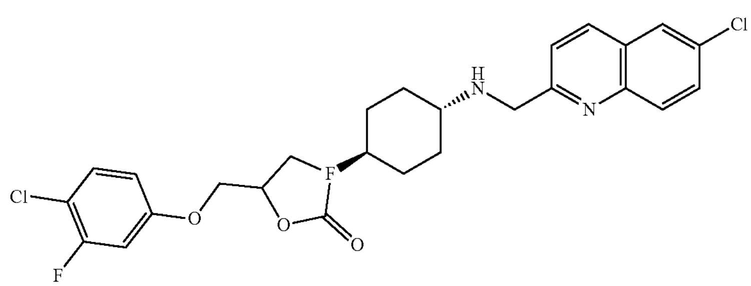 |
| 67 | 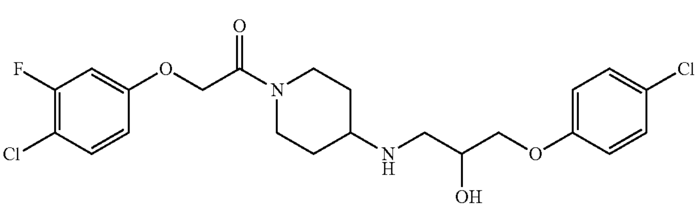 [SMILES: O=C(COc1ccc(Cl)c(F)c1)N1CCC(NCC(O)COc2ccc(Cl)cc2)CC1] |

TABLE 1-continued
| Compound No. | Structure |
|---|---|
| 68 | 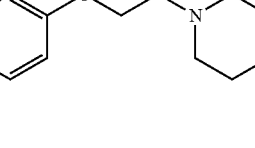 |
| 69 | 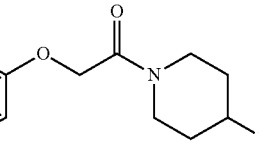 |
| 70 | 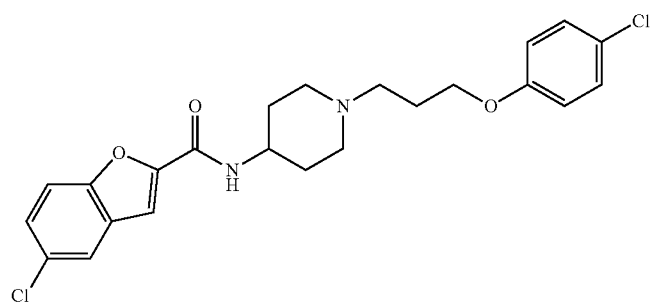 [SMILES: O=C(NC1CCN(CCCOc2ccc(Cl)cc2)CC1)c1cc2cc(Cl)ccc2o1] |
| 71 | 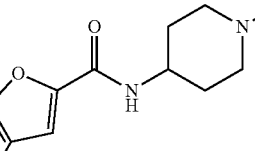 |
| 72 | 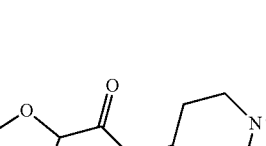 |
| 73 | 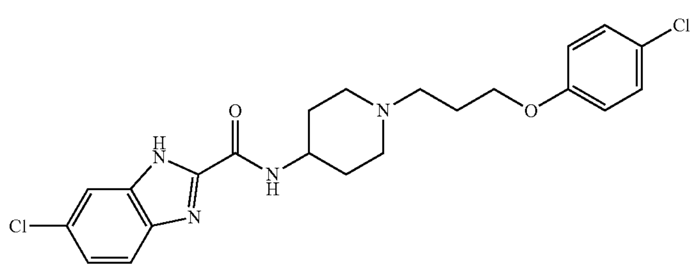 [SMILES: O=C(NC1CCN(CCCOc2ccc(Cl)cc2)CC1)c1nc2ccc(Cl)cc2[nH]1] |

TABLE 1-continued

| Compound No. | Structure |
|---|---|
| 74 | 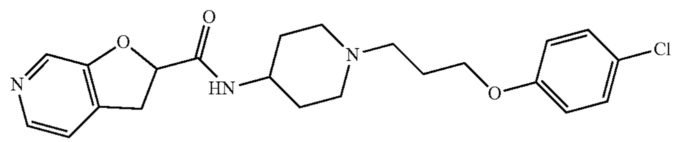 [SMILES: O=C(NC1CCN(CCCOc2ccc(Cl)cc2)CC1)C1Cc2ccncc2O1] |
| 75 | 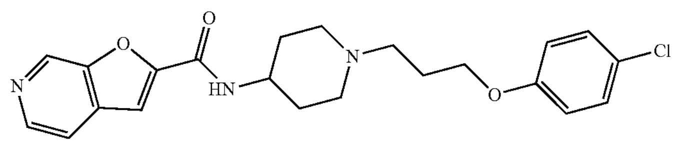 [SMILES: O=C(NC1CCN(CCCOc2ccc(Cl)cc2)CC1)c1cc2ccncc2o1] |
| 76 | 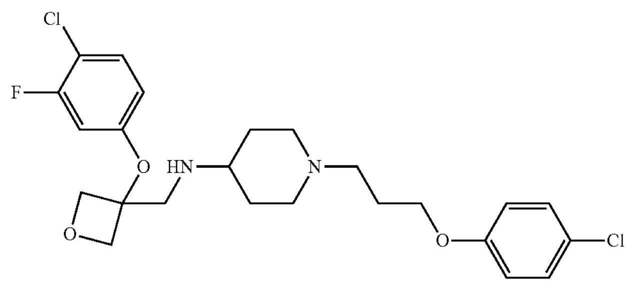 [SMILES: Fc1cc(OC2(CNC3CCN(CCCOc4ccc(Cl)cc4)CC3)COC2)ccc1Cl] |
| 77 | 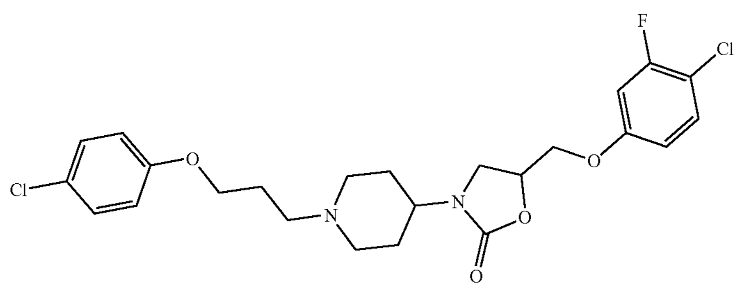 [SMILES: O=C1OC(COc2ccc(Cl)c(F)c2)CN1C1CCN(CCCOc2ccc(Cl)cc2)CC1] |
| 78 | 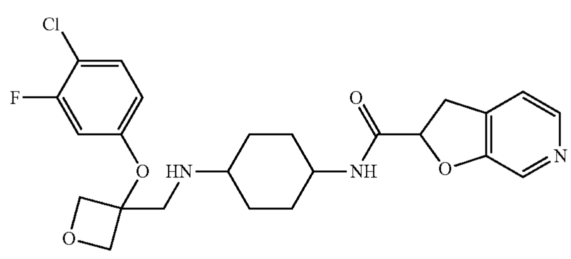 [SMILES: O=C(NC1CCC(NCC2(Oc3ccc(Cl)c(F)c3)COC2)CC1)C1Cc2ccncc2O1] |
| 79 | 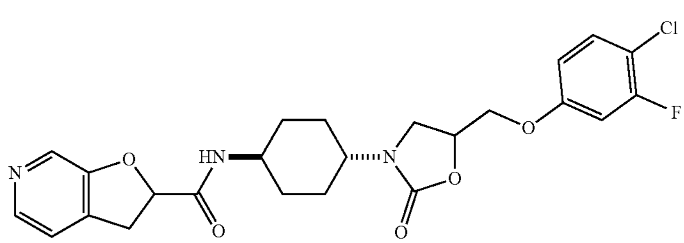 |

TABLE 1-continued

| Compound No. | Structure |
|---|---|
| 80 | 4-chlorophenoxy-CH2-CH(OH)-CH2-NH-(piperidin-4-yl), piperidine N-CH2-CH(OH)-(6-chlorobenzofuran-2-yl) |
| 81 | 5-chlorobenzofuran-2-carboxamide-N-(piperidin-4-yl), piperidine N-CH2-CH(OH)-(6-chlorobenzofuran-2-yl) |
| 82 | 5-chloro-2,3-dihydrobenzofuran-2-carboxamide-N-(piperidin-4-yl), piperidine N-CH2-CH(OH)-(6-chlorobenzofuran-2-yl) |
| 83 | 5-chlorobenzothiazole-2-carboxamide-N-(piperidin-4-yl), piperidine N-CH2-CH(OH)-(6-chlorobenzofuran-2-yl) |
| 84 | 5-chloro-1H-benzimidazole-2-carboxamide-N-(piperidin-4-yl), piperidine N-CH2-CH(OH)-(6-chlorobenzofuran-2-yl) |

TABLE 1-continued

| Compound No. | Structure |
|---|---|
| 85 | 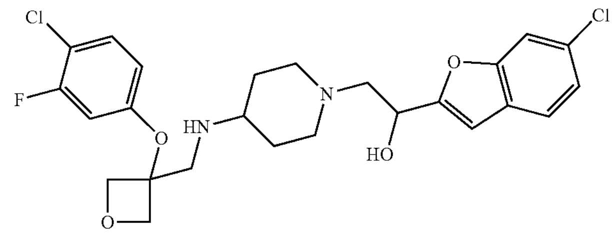 [SMILES: OC(CN1CCC(NCC2(Oc3ccc(Cl)c(F)c3)COC2)CC1)c1cc2ccc(Cl)cc2o1] |
| 86 | 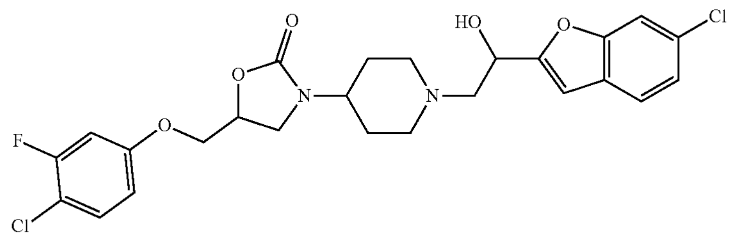 [SMILES: O=C1OC(COc2ccc(Cl)c(F)c2)CN1C1CCN(CC(O)c2cc3ccc(Cl)cc3o2)CC1] |
| 87 | 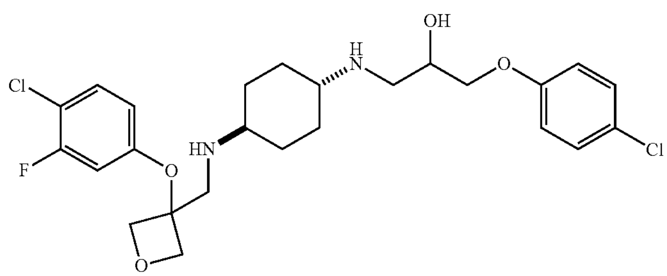 |
| 88 | 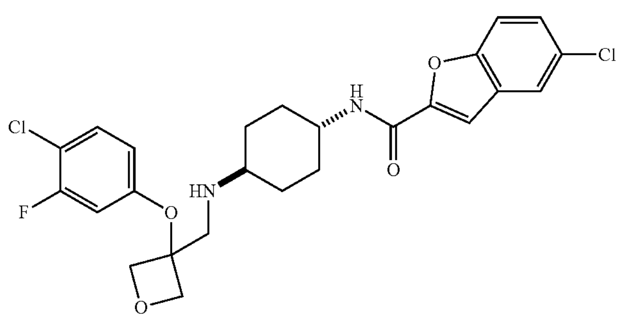 |
| 89 | 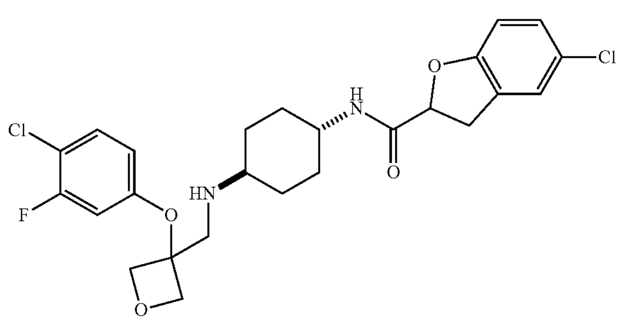 |

TABLE 1-continued

| Compound No. | Structure |
| --- | --- |
| 90 | 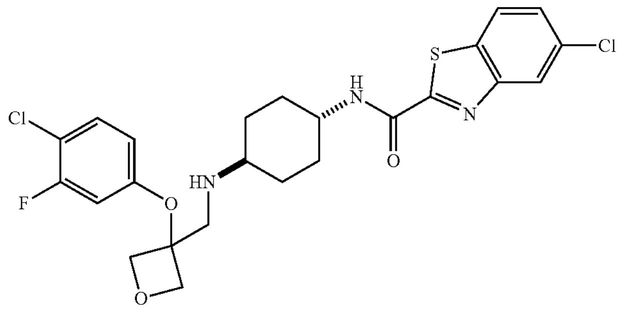 |
| 91 | 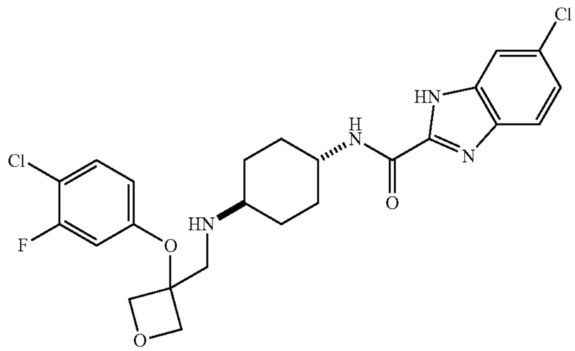 |
| 92 | 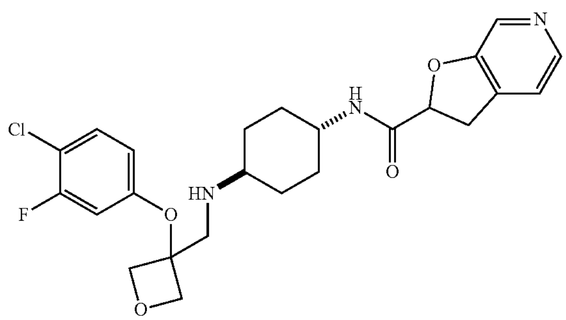 |
| 93 | 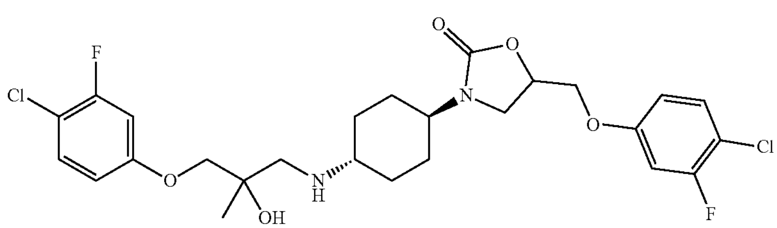 [SMILES: CC(O)(CN[C@H]1CC[C@H](N2CC(COc3ccc(Cl)c(F)c3)OC2=O)CC1)COc1ccc(Cl)c(F)c1] |
| 94 | 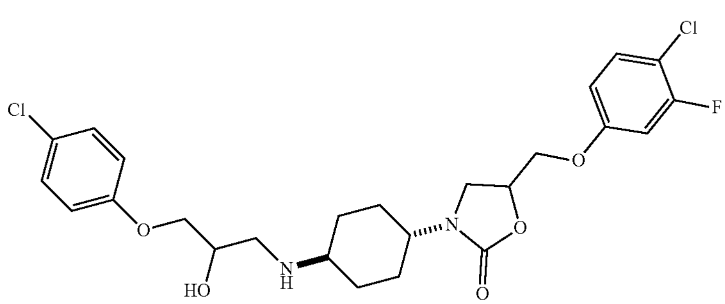 |

| Compound No. | Structure |
|---|---|
| 95 | 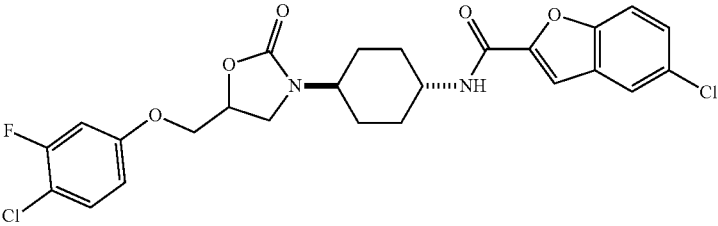 [SMILES: O=C(N[C@H]1CC[C@H](N2CC(COc3ccc(Cl)c(F)c3)OC2=O)CC1)c1cc2cc(Cl)ccc2o1] |
| 96 | 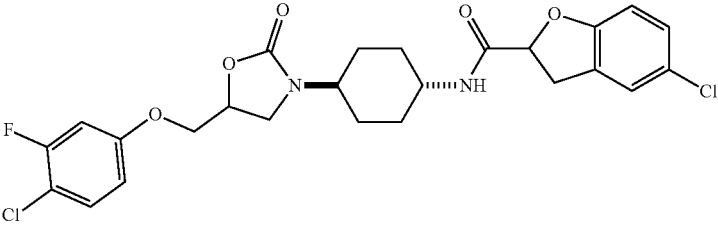 [SMILES: O=C(N[C@H]1CC[C@H](N2CC(COc3ccc(Cl)c(F)c3)OC2=O)CC1)C1Cc2cc(Cl)ccc2O1] |
| 97 | 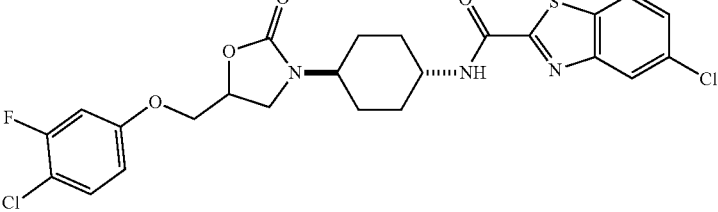 |
| 98 | 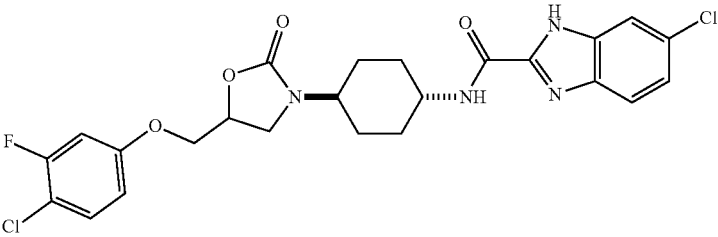 [SMILES: O=C(N[C@H]1CC[C@H](N2CC(COc3ccc(Cl)c(F)c3)OC2=O)CC1)c1nc2ccc(Cl)cc2[nH]1] |
| 99 | 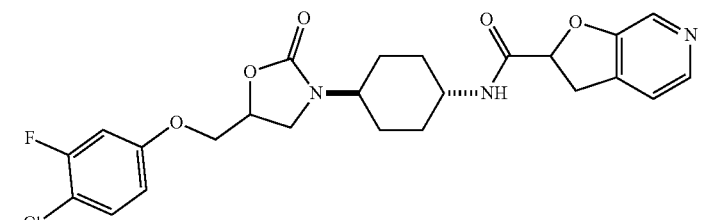 |
| 100 | 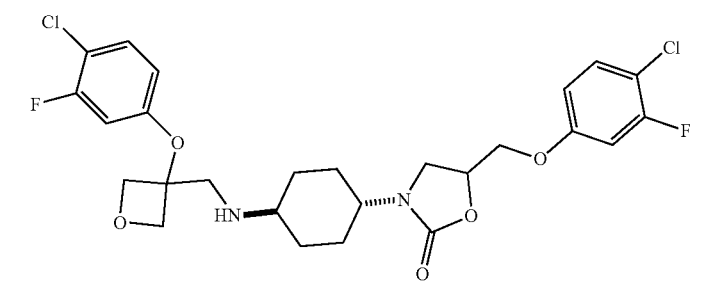 [SMILES: O=C1OC(COc2ccc(Cl)c(F)c2)CN1[C@H]1CC[C@H](NCC2(Oc3ccc(Cl)c(F)c3)COC2)CC1] |

TABLE 1-continued
| Compound No. | Structure |
|---|---|
| 101 | 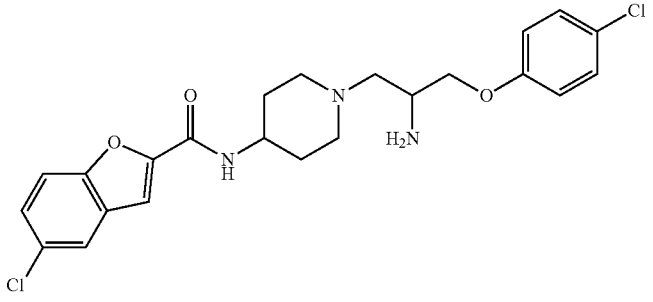 [SMILES: NC(COc1ccc(Cl)cc1)CN1CCC(NC(=O)c2nc3cc(Cl)ccc3s2)CC1] |
| 102 | 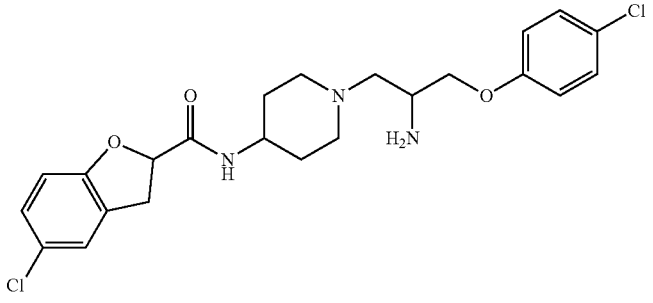 |
| 103 | 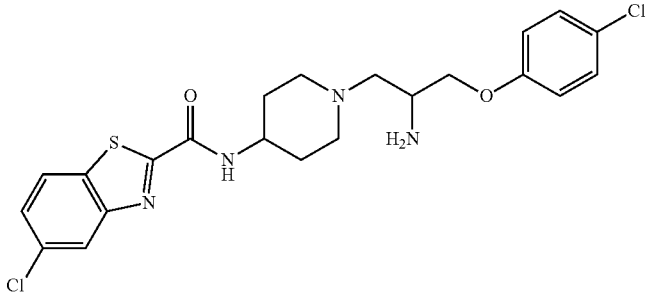 |
| 104 | 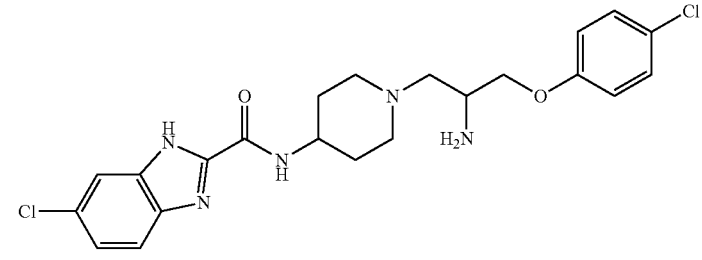 [SMILES: NC(COc1ccc(Cl)cc1)CN1CCC(NC(=O)c2nc3ccc(Cl)cc3[nH]2)CC1] |
| 105 | 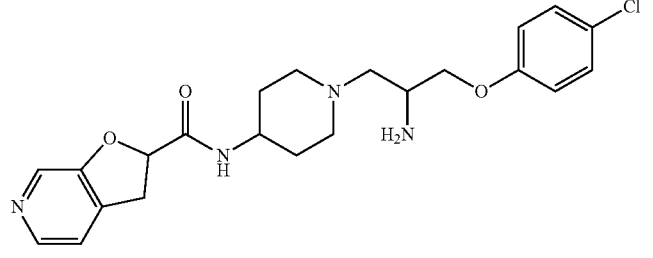 [SMILES: NC(COc1ccc(Cl)cc1)CN1CCC(NC(=O)C2Cc3ccncc3O2)CC1] |

TABLE 1-continued

| Compound No. | Structure |
|---|---|
| 106 | 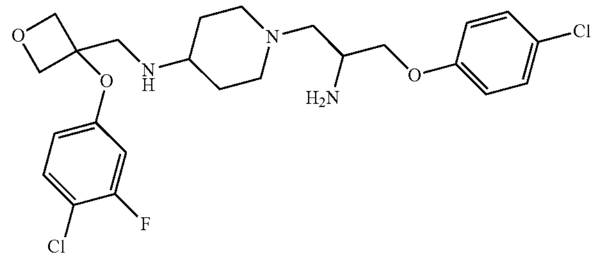 [SMILES: NC(COc1ccc(Cl)cc1)CN1CCC(NCC2(Oc3ccc(Cl)c(F)c3)COC2)CC1] |
| 107 | 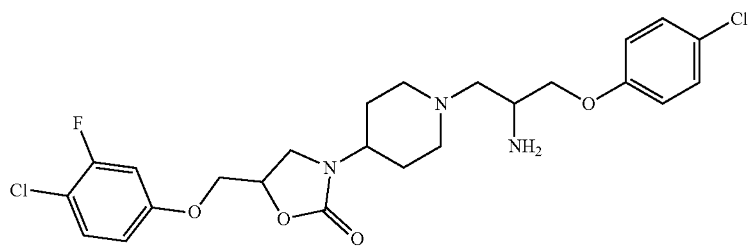 [SMILES: NC(COc1ccc(Cl)cc1)CN1CCC(N2CC(COc3ccc(Cl)c(F)c3)OC2=O)CC1] |
| 108 | 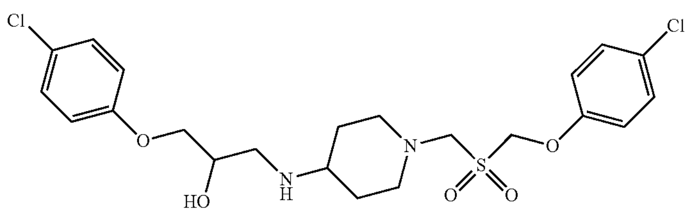 [SMILES: O=S(=O)(COc1ccc(Cl)cc1)CN1CCC(NCC(O)COc2ccc(Cl)cc2)CC1] |
| 109 | 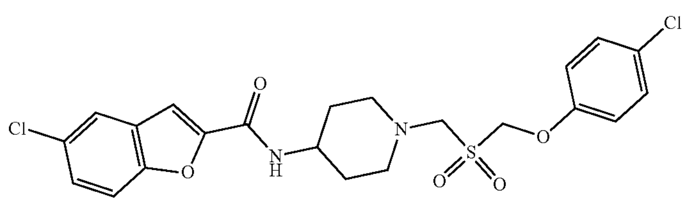 [SMILES: O=C(NC1CCN(CS(=O)(=O)COc2ccc(Cl)cc2)CC1)c1cc2cc(Cl)ccc2o1] |
| 110 | 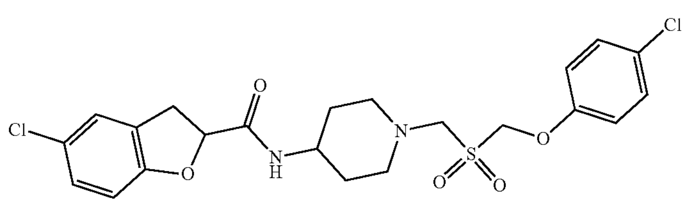 [SMILES: O=C(NC1CCN(CS(=O)(=O)COc2ccc(Cl)cc2)CC1)C1Cc2cc(Cl)ccc2O1] |
| 111 | 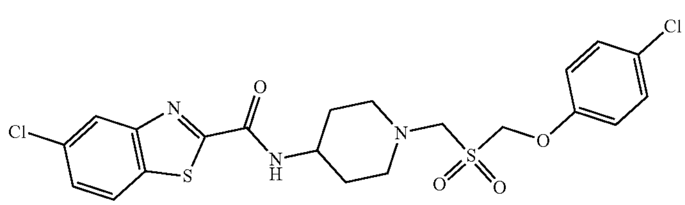 [SMILES: O=C(NC1CCN(CS(=O)(=O)COc2ccc(Cl)cc2)CC1)c1nc2cc(Cl)ccc2s1] |
| 112 | 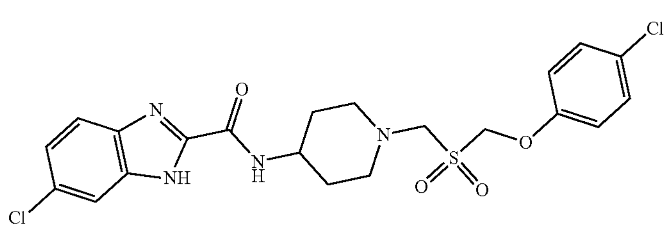 [SMILES: O=C(NC1CCN(CS(=O)(=O)COc2ccc(Cl)cc2)CC1)c1nc2ccc(Cl)cc2[nH]1] |

TABLE 1-continued

| Compound No. | Structure |
|---|---|
| 113 | 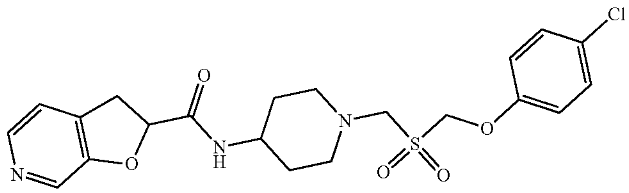 [SMILES: O=C(NC1CCN(CS(=O)(=O)COc2ccc(Cl)cc2)CC1)C1Cc2ccncc2O1] |
| 114 | 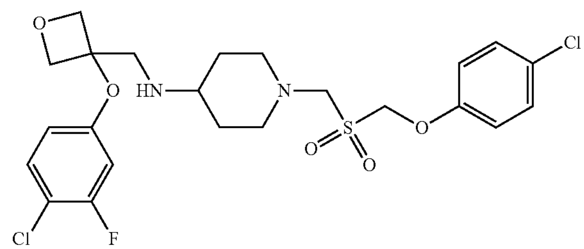 [SMILES: O=S(=O)(COc1ccc(Cl)cc1)CN1CCC(NCC2(Oc3ccc(Cl)c(F)c3)COC2)CC1] |
| 115 | 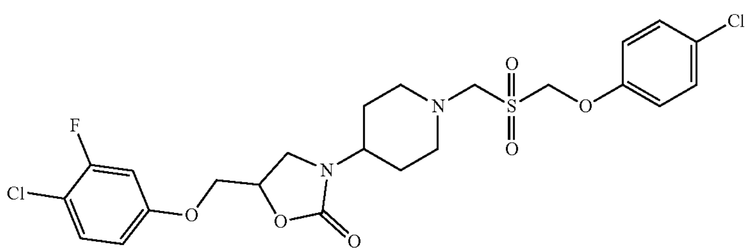 [SMILES: O=C1OC(COc2ccc(Cl)c(F)c2)CN1C1CCN(CS(=O)(=O)COc2ccc(Cl)cc2)CC1] |
| 116 | 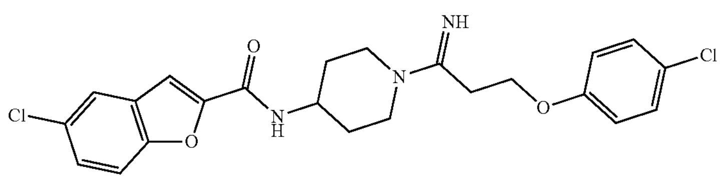 [SMILES: N=C(CCOc1ccc(Cl)cc1)N1CCC(NC(=O)c2cc3cc(Cl)ccc3o2)CC1] |
| 117 | 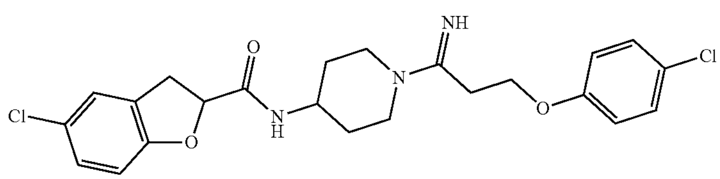 [SMILES: N=C(CCOc1ccc(Cl)cc1)N1CCC(NC(=O)C2Cc3cc(Cl)ccc3O2)CC1] |
| 118 | 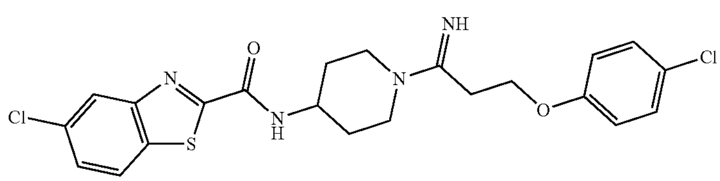 [SMILES: N=C(CCOc1ccc(Cl)cc1)N1CCC(NC(=O)c2nc3cc(Cl)ccc3s2)CC1] |
| 119 | 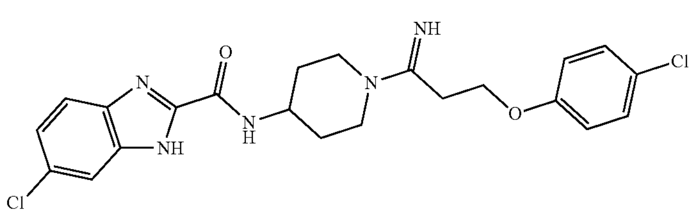 [SMILES: N=C(CCOc1ccc(Cl)cc1)N1CCC(NC(=O)c2nc3ccc(Cl)cc3[nH]2)CC1] |

TABLE 1-continued
| Compound No. | Structure |
|---|---|
| 120 | 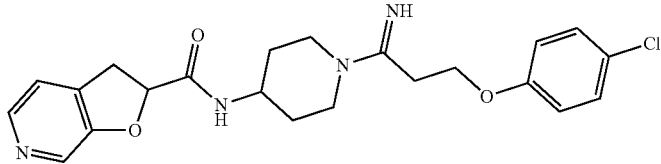 [SMILES: N=C(CCOc1ccc(Cl)cc1)N1CCC(NC(=O)C2Cc3ccncc3O2)CC1] |
| 121 | 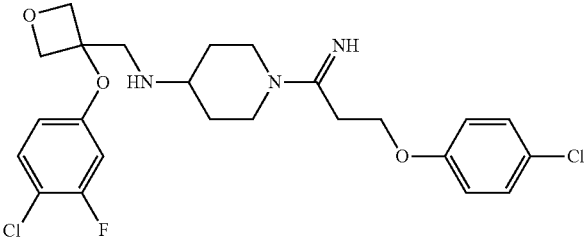 [SMILES: N=C(CCOc1ccc(Cl)cc1)N1CCC(NCC2(Oc3ccc(Cl)c(F)c3)COC2)CC1] |
| 122 | 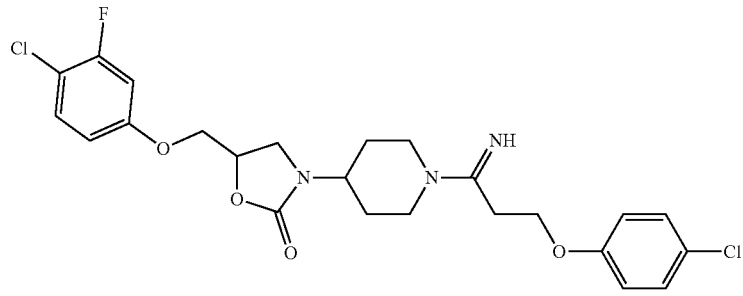 [SMILES: N=C(CCOc1ccc(Cl)cc1)N1CCC(N2CC(COc3ccc(Cl)c(F)c3)OC2=O)CC1] |
| 123 | 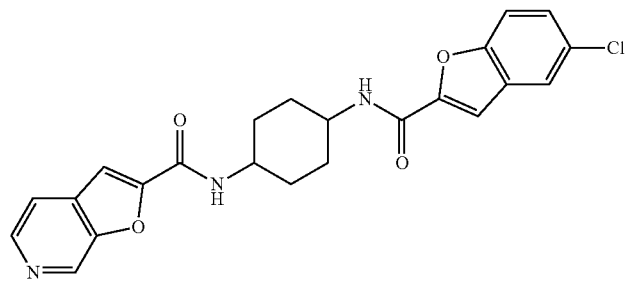 [SMILES: O=C(NC1CCC(NC(=O)c2cc3ccncc3o2)CC1)c1cc2cc(Cl)ccc2o1] |
| 124 | 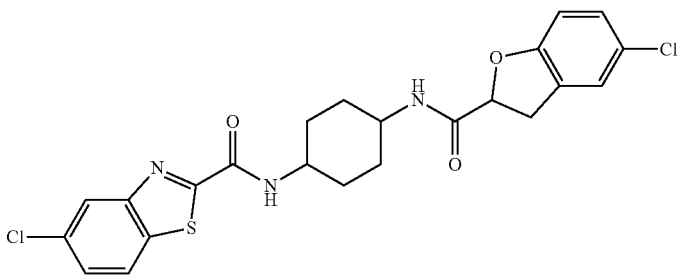 [SMILES: O=C(NC1CCC(NC(=O)C2Cc3cc(Cl)ccc3O2)CC1)c1nc2cc(Cl)ccc2s1] |

TABLE 1-continued

| Compound No. | Structure |
|---|---|
| 125 | 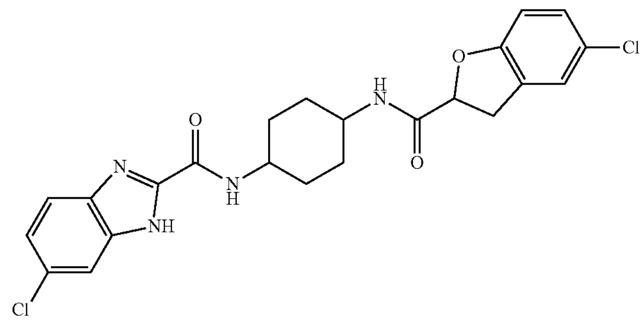 [SMILES: O=C(NC1CCC(NC(=O)C2Cc3cc(Cl)ccc3O2)CC1)c1nc2ccc(Cl)cc2[nH]1] |
| 126 | 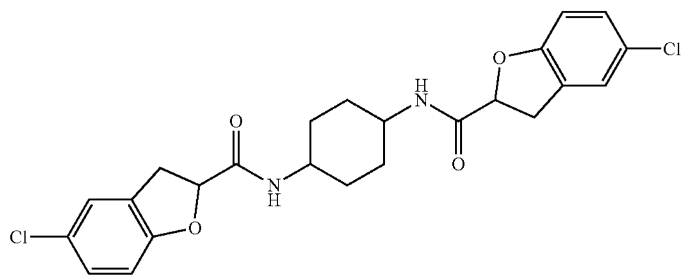 [SMILES: O=C(NC1CCC(NC(=O)C2Cc3cc(Cl)ccc3O2)CC1)C1Cc2cc(Cl)ccc2O1] |
| 127 | 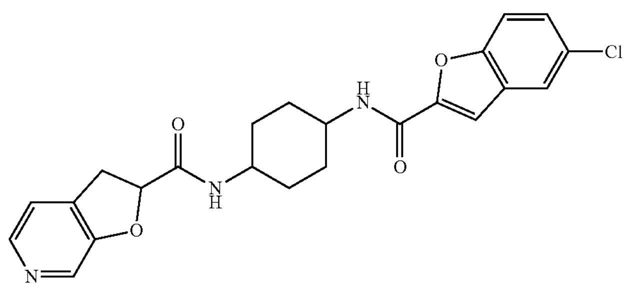 [SMILES: O=C(NC1CCC(NC(=O)C2Cc3ccncc3O2)CC1)c1cc2cc(Cl)ccc2o1] |
| 128 | 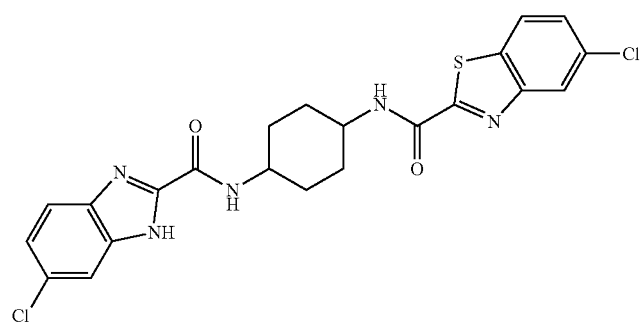 [SMILES: O=C(NC1CCC(NC(=O)c2nc3cc(Cl)ccc3s2)CC1)c1nc2ccc(Cl)cc2[nH]1] |
| 129 | 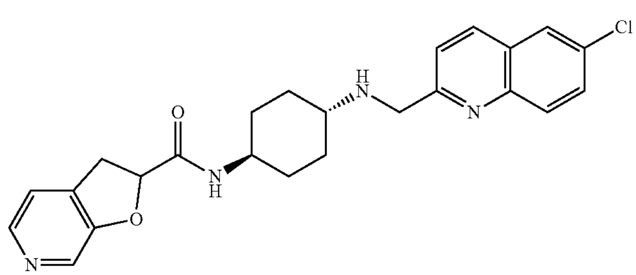 [SMILES: O=C(N[C@H]1CC[C@H](NCc2ccc3cc(Cl)ccc3n2)CC1)C1Cc2ccncc2O1] |

TABLE 1-continued

| Compound No. | Structure |
|---|---|
| 130 | 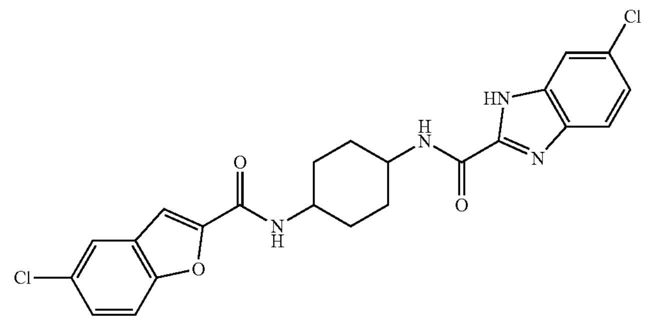 [SMILES: O=C(NC1CCC(NC(=O)c2cc3cc(Cl)ccc3o2)CC1)c1nc2ccc(Cl)cc2[nH]1] |
| 131 | 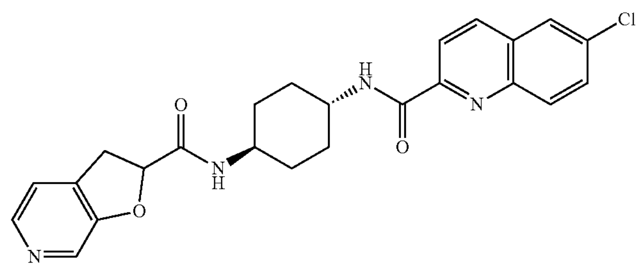 [SMILES: O=C(N[C@H]1CC[C@H](NC(=O)C2Cc3ccncc3O2)CC1)c1ccc2cc(Cl)ccc2n1] |
| 132 | 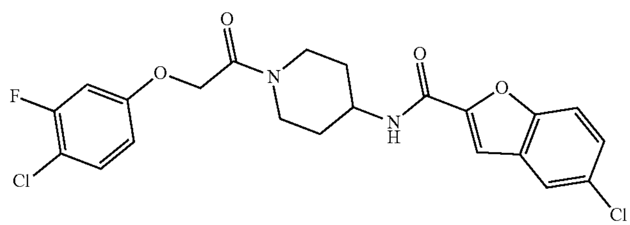 [SMILES: O=C(NC1CCN(C(=O)COc2ccc(Cl)c(F)c2)CC1)c1cc2cc(Cl)ccc2o1] |
| 133 | 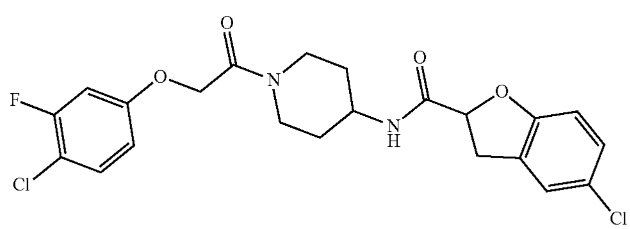 [SMILES: O=C(NC1CCN(C(=O)COc2ccc(Cl)c(F)c2)CC1)C1Cc2cc(Cl)ccc2O1] |
| 134 | 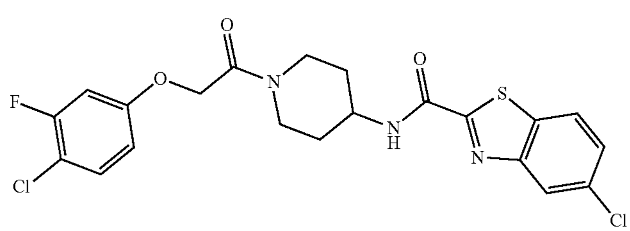 [SMILES: O=C(NC1CCN(C(=O)COc2ccc(Cl)c(F)c2)CC1)c1nc2cc(Cl)ccc2s1] |
| 135 | 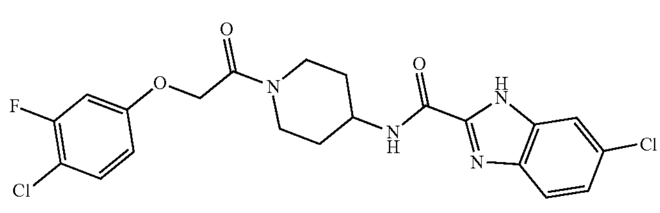 [SMILES: O=C(NC1CCN(C(=O)COc2ccc(Cl)c(F)c2)CC1)c1nc2ccc(Cl)cc2[nH]1] |

TABLE 1-continued

| Compound No. | Structure |
|---|---|
| 136 | 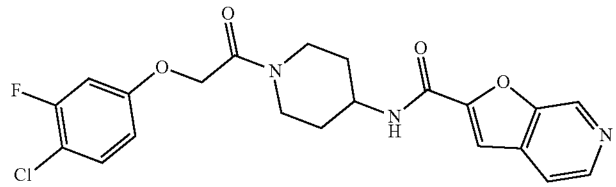 [SMILES: O=C(NC1CCN(C(=O)COc2ccc(Cl)c(F)c2)CC1)c1cc2ccncc2o1] |
| 137 | 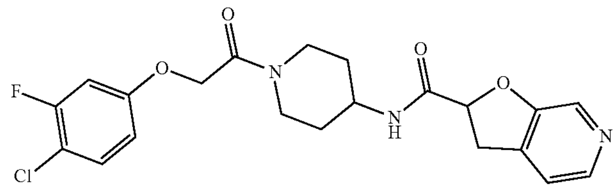 [SMILES: O=C(NC1CCN(C(=O)COc2ccc(Cl)c(F)c2)CC1)C1Cc2ccncc2O1] |
| 138 | 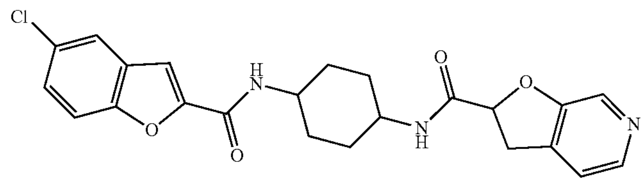 [SMILES: O=C(NC1CCC(NC(=O)C2Cc3ccncc3O2)CC1)c1cc2cc(Cl)ccc2o1] |
| 139 | 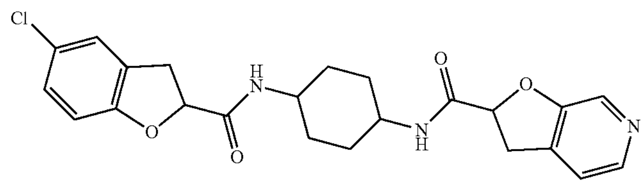 [SMILES: O=C(NC1CCC(NC(=O)C2Cc3ccncc3O2)CC1)C1Cc2cc(Cl)ccc2O1] |
| 140 | 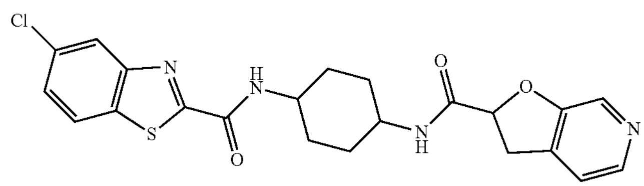 [SMILES: O=C(NC1CCC(NC(=O)C2Cc3ccncc3O2)CC1)c1nc2cc(Cl)ccc2s1] |
| 141 | 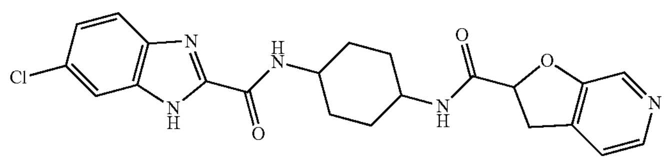 [SMILES: O=C(NC1CCC(NC(=O)C2Cc3ccncc3O2)CC1)c1nc2ccc(Cl)cc2[nH]1] |
| 142 | 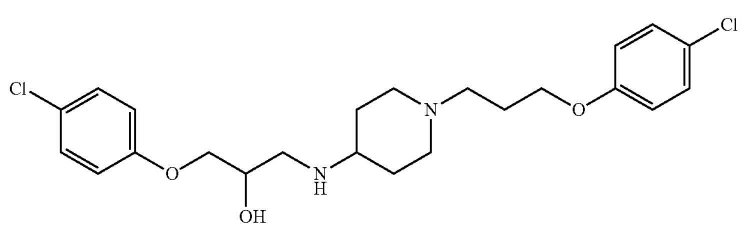 [SMILES: OC(CNC1CCN(CCCOc2ccc(Cl)cc2)CC1)COc1ccc(Cl)cc1] |
| 143 | 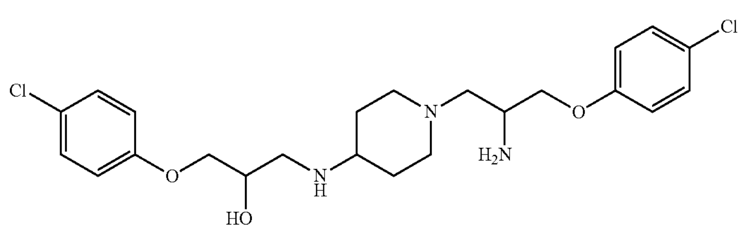 [SMILES: NC(COc1ccc(Cl)cc1)CN1CCC(NCC(O)COc2ccc(Cl)cc2)CC1] |

TABLE 1-continued

| Compound No. | Structure |
|---|---|
| 144 | 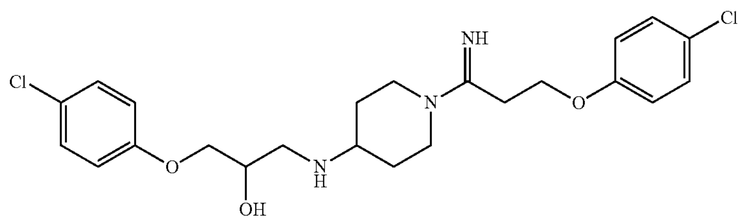 [SMILES: N=C(CCOc1ccc(Cl)cc1)N1CCC(NCC(O)COc2ccc(Cl)cc2)CC1] |
| 145 | 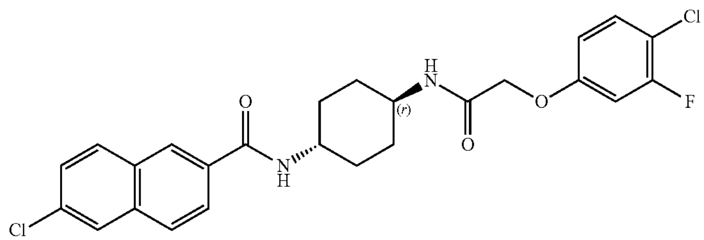 [SMILES: O=C(COc1ccc(Cl)c(F)c1)N[C@H]1CC[C@H](NC(=O)c2ccc3cc(Cl)ccc3c2)CC1] |
| 146 | 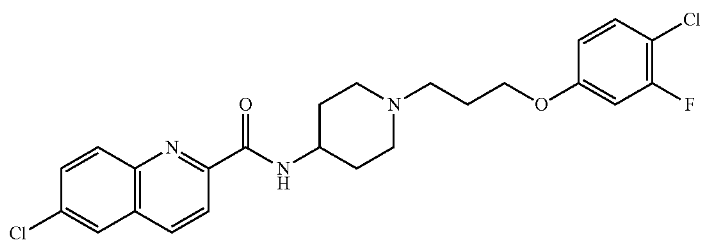 [SMILES: O=C(NC1CCN(CCCOc2ccc(Cl)c(F)c2)CC1)c1ccc2cc(Cl)ccc2n1] |
| 147 | 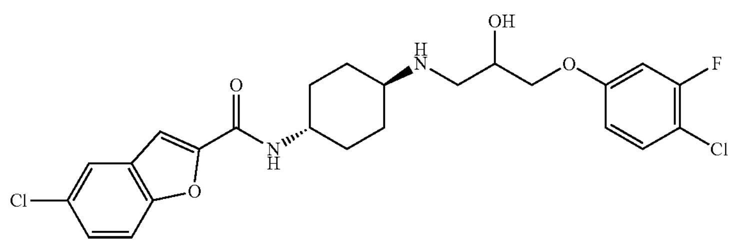 [SMILES: O=C(N[C@H]1CC[C@H](NCC(O)COc2ccc(Cl)c(F)c2)CC1)c1cc2cc(Cl)ccc2o1] |
| 148 | 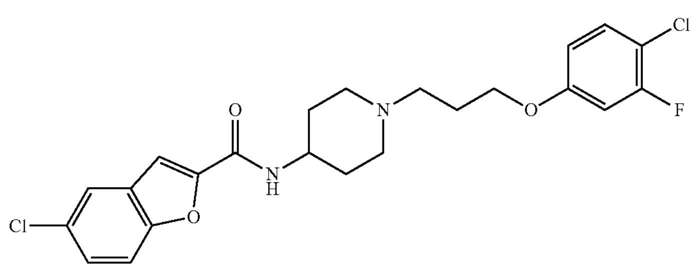 [SMILES: O=C(NC1CCN(CCCOc2ccc(Cl)c(F)c2)CC1)c1cc2cc(Cl)ccc2o1] |
| 149 | 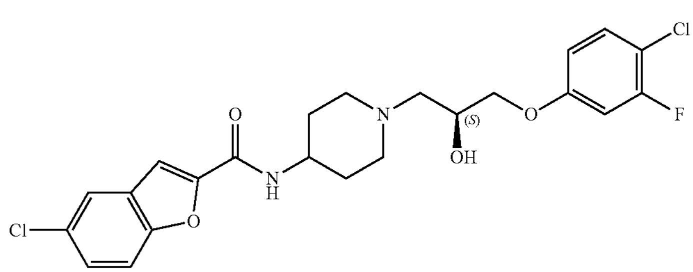 |

TABLE 1-continued

| Compound No. | Structure |
|---|---|
| 150 | (5-chlorobenzofuran-2-yl)-C(=O)-NH-(piperidin-4-yl), N-CH2-CH(R)(OH)-CH2-O-(4-chloro-3-fluorophenyl) |
| 151 | (6-chloroquinolin-2-yl)-CH2-NH-(cyclohexyl-(r))-NH-C(=O)-CH2-O-(4-chloro-3-fluorophenyl) |
| 152 | (6-chloroquinolin-2-yl)-C(=O)-NH-(piperidin-4-yl), N-CH2-CH(S)(OH)-CH2-O-(4-chloro-3-fluorophenyl) |
| 153 | (6-chloroquinolin-2-yl)-C(=O)-NH-(piperidin-4-yl), N-CH2-CH(R)(OH)-CH2-O-(4-chloro-3-fluorophenyl) |
| 154 | (5-chlorobenzofuran-2-yl)-C(=O)-NH-(cyclohexyl-(r))-NH-CH2-CH(R)(OH)-CH2-O-(3-fluoro-4-chlorophenyl) |
| 155 | (5-chlorobenzofuran-2-yl)-C(=O)-NH-(cyclohexyl-(r))-NH-CH2-CH(S)(OH)-CH2-O-(3-fluoro-4-chlorophenyl) |

TABLE 1-continued

| Compound No. | Structure |
|---|---|
| 156 | 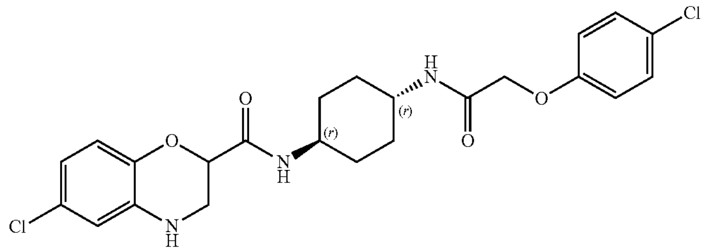 [SMILES: O=C(COc1ccc(Cl)cc1)N[C@H]1CC[C@H](NC(=O)C2CNc3cc(Cl)ccc3O2)CC1] |
| 157 | 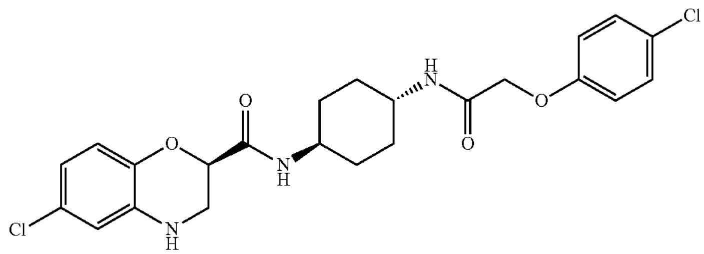 [SMILES: O=C(COc1ccc(Cl)cc1)N[C@H]1CC[C@H](NC(=O)[C@H]2CNc3cc(Cl)ccc3O2)CC1] |
| 158 | 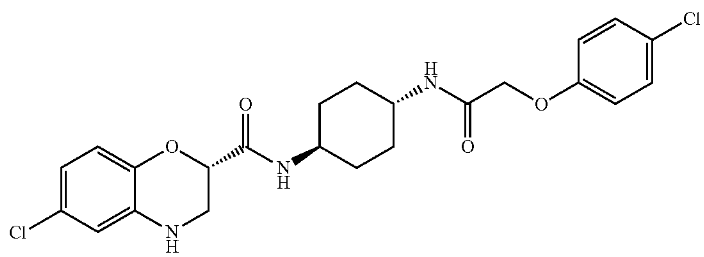 [SMILES: O=C(COc1ccc(Cl)cc1)N[C@H]1CC[C@H](NC(=O)[C@@H]2CNc3cc(Cl)ccc3O2)CC1] |
| 159 | 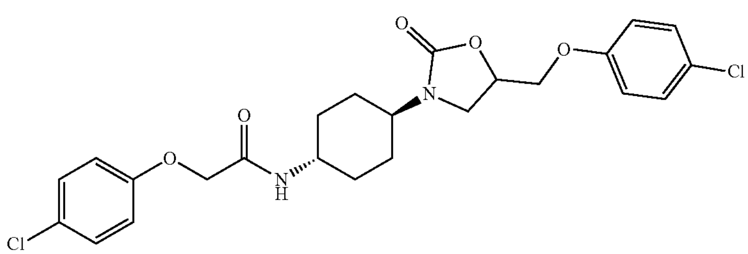 [SMILES: O=C(COc1ccc(Cl)cc1)N[C@H]1CC[C@H](N2CC(COc3ccc(Cl)cc3)OC2=O)CC1] |
| 160 | 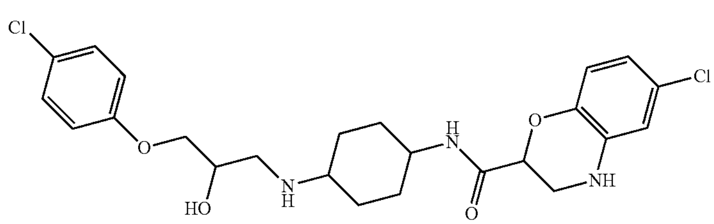 [SMILES: O=C(NC1CCC(NCC(O)COc2ccc(Cl)cc2)CC1)C1CNc2cc(Cl)ccc2O1] |
| 161 | 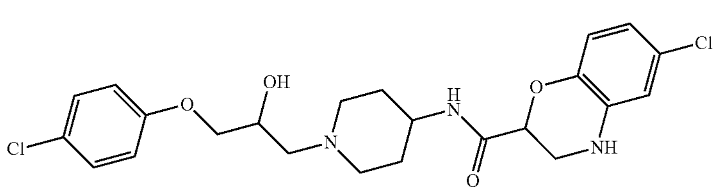 [SMILES: O=C(NC1CCN(CC(O)COc2ccc(Cl)cc2)CC1)C1CNc2cc(Cl)ccc2O1] |

TABLE 1-continued

| Compound No. | Structure |
|---|---|
| 162 | 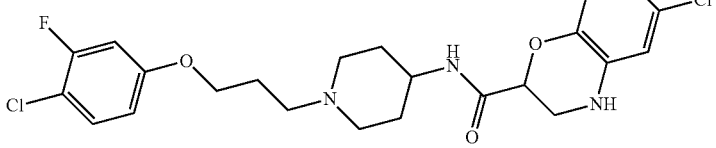 |
| 163 | 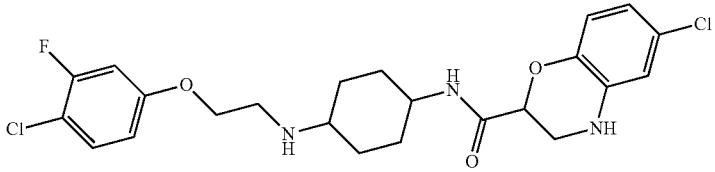 [SMILES: O=C(NC1CCC(NCCOc2ccc(Cl)c(F)c2)CC1)C1CNc2cc(Cl)ccc2O1] |
| 164 | 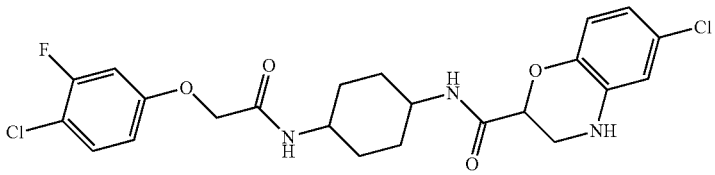 [SMILES: O=C(COc1ccc(Cl)c(F)c1)NC1CCC(NC(=O)C2CNc3cc(Cl)ccc3O2)CC1] |
| 165 | 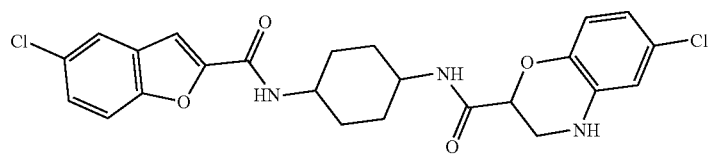 [SMILES: O=C(NC1CCC(NC(=O)C2CNc3cc(Cl)ccc3O2)CC1)c1cc2cc(Cl)ccc2o1] |
| 166 | 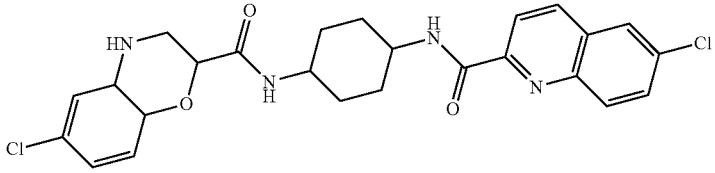 [SMILES: O=C(NC1CCC(NC(=O)C2CNC3C=C(Cl)C=CC3O2)CC1)c1ccc2cc(Cl)ccc2n1] |

Pharmaceutical Compositions and Formulations

Pharmaceutical compositions of any of the compounds detailed herein are embraced by this disclosure. Thus, the present disclosure includes pharmaceutical compositions comprising a compound as detailed herein or a salt thereof and a pharmaceutically acceptable carrier or excipient. In one aspect, the pharmaceutically acceptable salt is an acid addition salt, such as a salt formed with an inorganic or organic acid. Pharmaceutical compositions may take a form suitable for oral, buccal, parenteral, nasal, topical or rectal administration or a form suitable for administration by inhalation.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form.

In one variation, the compounds herein are synthetic compounds prepared for administration to an individual. In another variation, compositions are provided containing a compound in substantially pure form. In another variation, the present disclosure embraces pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

A compound detailed herein or salt thereof may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound or salt thereof may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

One or several compounds described herein or a salt thereof can be used in the preparation of a formulation, such as a pharmaceutical formulation, by combining the compound or compounds, or a salt thereof, as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in *Remington's Pharmaceutical Sciences*, Mack Publishing Company, Philadelphia, Pa., 20$^{th}$ ed. (2000), which is incorporated herein by reference.

Compounds as described herein may be administered to individuals in a form of generally accepted oral compositions, such as tablets, coated tablets, and gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants.

Any of the compounds described herein can be formulated in a tablet in any dosage form described, for example, a compound as described herein or a salt thereof can be formulated as a 10 mg tablet.

Compositions comprising a compound provided herein are also described. In one variation, the composition comprises a compound or salt thereof and a pharmaceutically acceptable carrier or excipient. In another variation, a composition of substantially pure compound is provided. In some embodiments, the composition is for use as a human or veterinary medicament. In some embodiments, the composition is for use in a method described herein. In some embodiments, the composition is for use in the treatment of a disease or disorder described herein.

Methods of Use and Uses

Compounds and compositions detailed herein, such as a pharmaceutical composition containing a compound of any formula provided herein or a salt thereof and a pharmaceutically acceptable carrier or excipient, may be used in methods of administration and treatment as provided herein. The compounds and compositions may also be used in in vitro methods, such as in vitro methods of administering a compound or composition to cells for screening purposes and/or for conducting quality control assays.

Provided herein is a method of treating a disease or disorder in an individual in need thereof comprising administering a compound describes herein or any embodiment, variation, or aspect thereof, or a pharmaceutically acceptable salt thereof. In some embodiments, the compound, pharmaceutically acceptable salt thereof, or composition is administered to the individual according to a dosage and/or method of administration described herein.

The compounds or salts thereof described herein and compositions described herein are believed to be effective for treating a variety of diseases and disorders. In some embodiments, a compound or salt thereof described herein or a composition described herein may be used in a method of treating a disease or disorder mediated by an integrated stress response (ISR) pathway. In some embodiments, the disease or disorder is mediated by eukaryotic translation initiation factor 2a (eIF2a) or eukaryotic translation initiation factor 2B (eIF2B). In some embodiments, the disease or disorder is mediated by phosphorylation of eIF2a and/or the guanine nucleotide exchange factor (GEF) activity of eIF2B.

In some embodiments, a compound or salt thereof described herein or a composition described herein may be used in a method of treating a disease or disorder, wherein the disease or disorder is a neurodegenerative disease, an inflammatory disease, an autoimmune disease, a metabolic syndrome, a cancer, a vascular disease, a musculoskeletal disease (such as a myopathy), an ocular disease, or a genetic disorder.

In some embodiments, the disease or disorder is a neurodegenerative disease. In some embodiments, the neurodegenerative disease is vanishing white matter disease, childhood ataxia with CNS hypomyelination, intellectual disability syndrome, Alzheimer's disease, prion disease, Creutzfeldt-Jakob disease, Parkinson's disease, amyotrophic lateral sclerosis (ALS) disease, Pelizaeus-Merzbacher disease, a cognitive impairment, a traumatic brain injury, a postoperative cognitive dysfunction (PCD), a neuro-otological syndrome, hearing loss, Huntington's disease, stroke, chronic traumatic encephalopathy, spinal cord injury, dementia, frontotemporal dementia (FTD), depression, or a social behavior impairment. In some embodiments, the cognitive impairment is triggered by ageing, radiation, sepsis, seizure, heart attack, heart surgery, liver failure, hepatic encephalopathy, anesthesia, brain injury, brain surgery, ischemia, chemotherapy, cancer treatment, critical illness, concussion, fibromyalgia, or depression. In some embodiments, the neurodegenerative disease is Alzheimer's disease. In some embodiments, the neurodegenerative disease is ageing-related cognitive impairment. In some embodiments, the neurodegenerative disease is a traumatic brain injury.

In some embodiments, a compound or salt thereof described herein or a composition described herein may be used in a method of treating Alzheimer's disease. In some embodiments, neurodegeneration, cognitive impairment, and/or amyloidogenesis is decreased.

In some embodiments, the disease or disorder is an inflammatory disease. In some embodiments, the inflammatory disease is arthritis, psoriatic arthritis, psoriasis, juvenile idiopathic arthritis, asthma, allergic asthma, bronchial asthma, tuberculosis, chronic airway disorder, cystic fibrosis, glomerulonephritis, membranous nephropathy, sarcoidosis, vasculitis, ichthyosis, transplant rejection, interstitial cystitis, atopic dermatitis, or inflammatory bowel disease. In some embodiments, the inflammatory bowel disease is Crohn' disease, ulcerative colitis, or celiac disease.

In some embodiments, the disease or disorder is an autoimmune disease. In some embodiments, the autoimmune disease is systemic lupus erythematosus, type 1 diabetes, multiple sclerosis, or rheumatoid arthritis.

In some embodiments, the disease or disorder is a metabolic syndrome. In some embodiments, the metabolic syndrome is alcoholic liver steatosis, obesity, glucose intolerance, insulin resistance, hyperglycemia, fatty liver, dyslipidemia, hyperlipidemia, hyperhomocysteinemia, or type 2 diabetes.

In some embodiments, the disease or disorder is a cancer. In some embodiments, the cancer is pancreatic cancer, breast cancer, kidney cancer, bladder cancer, prostate cancer, testicular cancer, urothelial cancer, endometrial cancer, ovarian cancer, cervical cancer, renal cancer, esophageal cancer, gastrointestinal stromal tumor (GIST), multiple myeloma, cancer of secretory cells, thyroid cancer, gastrointestinal carcinoma, chronic myeloid leukemia, hepatocellular carcinoma, colon cancer, melanoma, malignant glioma, glioblastoma, glioblastoma multiforme, astrocytoma, dysplastic gangliocytoma of the cerebellum, Ewing's sarcoma, rhabdomyosarcoma, ependymoma, medulloblastoma, ductal adenocarcinoma, adenosquamous carcinoma, nephroblastoma, acinar cell carcinoma, neuroblastoma, or lung cancer. In some embodiments, the cancer of secretory cells is non-Hodgkin's lymphoma, Burkitt's lymphoma, chronic lymphocytic leukemia, monoclonal gammopathy of undetermined significance (MGUS), plasmacytoma, lymphoplasmacytic lymphoma or acute lymphoblastic leukemia.

In some embodiments, the disease or disorder is a musculoskeletal disease (such as a myopathy). In some embodiments, the musculoskeletal disease is a myopathy, a muscular dystrophy, a muscular atrophy, a muscular wasting, or sarcopenia. In some embodiments, the muscular dystrophy is Duchenne muscular dystrophy (DMD), Becker's disease, myotonic dystrophy, X-linked dilated cardiomyopathy, spinal muscular atrophy (SMA), or metaphyseal chondrodysplasia, Schmid type (MCDS). In some embodiments, the myopathy is a skeletal muscle atrophy. In some embodiments, the musculoskeletal disease (such as the skeletal muscle atrophy) is triggered by ageing, chronic diseases, stroke, malnutrition, bedrest, orthopedic injury, bone fracture, cachexia, starvation, heart failure, obstructive lung disease, renal failure, Acquired Immunodeficiency Syndrome (AIDS), sepsis, an immune disorder, a cancer, ALS, a burn injury, denervation, diabetes, muscle disuse, limb immobilization, mechanical unload, myositis, or a dystrophy.

In some embodiments, the disease or disorder is a genetic disorder, such as Down syndrome or MEHMO syndrome (Mental retardation, Epileptic seizures, Hypogenitalism, Microcephaly, and Obesity).

In some embodiments, a compound or salt thereof described herein or a composition described herein may be used in a method of treating musculoskeletal disease. In some embodiments, skeletal muscle mass, quality and/or strength are increased. In some embodiments, synthesis of muscle proteins is increased. In some embodiments, skeletal muscle fiber atrophy is inhibited.

In some embodiments, the disease or disorder is a vascular disease. In some embodiments, the vascular disease is atherosclerosis, abdominal aortic aneurism, carotid artery disease, deep vein thrombosis, Buerger's disease, chronic venous hypertension, vascular calcification, telangiectasia or lymphoedema.

In some embodiments, the disease or disorder is an ocular disease. In some embodiments, the ocular disease is glaucoma, age-related macular degeneration, inflammatory retinal disease, retinal vascular disease, diabetic retinopathy, uveitis, rosacea, Sjogren's syndrome, or neovascularization in proliferative retinopathy.

In some embodiments, provided herein is a method of inhibiting an ISR pathway. The compounds or salts thereof described herein and compositions described herein are believed to be effective for inhibiting an ISR pathway. In some embodiments, the method of inhibiting an ISR pathway comprises inhibiting the ISR pathway in a cell by administering or delivering to the cell a compound described herein, or a pharmaceutically acceptable salt thereof, or a pharmaceutical composition described herein. In some embodiments, the method of inhibiting an ISR pathway comprises inhibiting the ISR pathway in an individual by administering to the individual a compound described herein, or a pharmaceutically acceptable salt thereof, or a pharmaceutical composition described herein. Inhibition of the ISR pathway can be determined by methods known in the art, such as western blot, immunohistochemistry, or reporter cell line assays.

In some embodiments, the inhibition of the ISR pathway comprises binding eIF2B. In some embodiments, the inhibition of the ISR pathway comprises increasing protein translation, increasing guanine nucleotide exchange factor (GEF) activity of eIF2B, delaying or preventing apoptosis in a cell, and/or inhibiting translation of one or more mRNAs comprising a 5' untranslated region (5'UTR) comprising at least one upstream open reading frame (uORF).

In some embodiments, provided herein are methods of increasing protein production using a compound or salt described herein. The protein production is increased relative to the same condition without the compound or salt. Protein production can be increased either in vivo or in vitro. For example, protein production can be increased in vivo by administering the compound or salt to an individual. In some embodiments, protein production is increased in vitro using the compound or salt with a cell-free protein synthesis system (CFPS) or a cell-based protein expression system. The protein produced can be a heterologous protein (e.g., a recombinant protein) or a native protein. Heterologous protein production can be achieved using a recombinant nucleic acid encoding the protein. In some embodiments, the protein produced is an antibody or a fragment thereof. Other exemplary proteins can include, but are not limited to, enzymes, allergenic peptides or proteins (for example, for use as a vaccine), recombinant protein, cytokines, peptides, hormones, erythropoietin (EPO), interferons, granulocyte-colony stimulating factor (G-CSF), anticoagulants, and clotting factors. The increase in protein production can be determined by methods known in the art, such as western blot or immunohistochemistry.

Cell-free protein synthesis (CFPS) systems are generally known, and include cellular machinery for protein expression in an in vitro environment. In some embodiments, the CFPS system includes a cellular extract (such as a eukaryotic cellular extract), which includes protein expression machinery. In some embodiment, the cellular machinery in the CFPS system comprises eukaryotic cellular machinery, such as eukaryotic initiation factor 2 (eIF2) and/or eukaryotic initiation factor 2B (eIF2B), or one or more subunits thereof.

In some embodiments, there is a cell-free protein synthesis (CFPS) system comprising eukaryotic initiation factor 2 (eIF2) and a nucleic acid encoding a protein with a compound or salt as described herein. In some embodiments, the protein is an antibody or a fragment thereof. Other exemplary proteins can include, but are not limited to, enzymes, allergenic peptides or proteins (for example, for use as a vaccine), recombinant protein, cytokines, peptides, hormones, erythropoietin (EPO), interferons, granulocyte-colony stimulating factor (G-CSF), anticoagulants, and clotting factors. In some embodiments, the CFPS system comprises a cell extract comprising the eIF2. In some embodiments, the CFPS system further comprises eIF2B.

In some embodiments, there is a method of producing a protein, comprising contacting a cell-free protein synthesis (CFPS) system comprising eukaryotic initiation factor 2 (eIF2) and a nucleic acid encoding a protein with a compound or salt thereof as described herein. In some embodiments, the protein is an antibody or a fragment thereof. Other exemplary proteins can include, but are not limited to, enzymes, allergenic peptides or proteins (for example, for use as a vaccine), recombinant protein, cytokines, peptides, hormones, erythropoietin (EPO), interferons, granulocyte-colony stimulating factor (G-CSF), anticoagulants, and clotting factors. In some embodiments, the CFPS system comprises a cell extract comprising the eIF2. In some embodiments, the CFPS system further comprises eIF2B. In some embodiments, the method comprises purifying the protein.

In some embodiments, there is a method of producing a protein, comprising contacting a eukaryotic cell comprising a nucleic acid encoding the protein with a compound or salt as described herein. In some embodiments, the method comprises culturing the cell in an in vitro culture medium comprising the compound or salt. In some embodiments, the nucleic acid encoding the protein is a recombinant nucleic acid. In some embodiments, the eukaryotic cell is a human embryonic kidney (HEK) cell or a Chinese hamster ovary (CHO) cell. In other embodiments, the eukaryotic cell is a yeast cell (such as Saccharomyces cerevisiae or Pichia pastoris), a wheat germ cell, an insect cell, a rabbit reticulocyte, a cervical cancer cell (such as a HeLa cell), a baby hamster kidney cell (such as BHK21 cells), a murine myeloma cell (such as NSO or Sp2/0 cells), an HT-1080 cell, a PER.C$_6$ cell, a plant cell, a hybridoma cell, or a human blood derived leukocyte. In some embodiments, the protein is an antibody or a fragment thereof. Other exemplary proteins can include, but are not limited to, enzymes, allergenic peptides or proteins (for example, for use as a vaccine), recombinant protein, cytokines, peptides, hormones, erythropoietin (EPO), interferons, granulocyte-colony stimulating factor (G-CSF), anticoagulants, and clotting factors. In some embodiments, the method comprises purifying the protein.

In some embodiments, there is a method of culturing a eukaryotic cell comprising a nucleic acid encoding a protein, comprising contacting the eukaryotic cell with an in vitro culture medium comprising a compound or salt as described herein. In some embodiments, the nucleic acid encoding the protein is a recombinant nucleic acid. In some embodiments, the eukaryotic cell is a human embryonic kidney (HEK) cell or a Chinese hamster ovary (CHO) cell. In other embodiments, the eukaryotic cell is a yeast cell (such as Saccharomyces cerevisiae or Pichia pastoris), a wheat germ cell, an insect cell, a rabbit reticulocyte, a cervical cancer cell (such as a HeLa cell), a baby hamster kidney cell (such as BHK21 cells), a murine myeloma cell (such as NSO or Sp2/0 cells), an HT-1080 cell, a PER.C$_6$ cell, a plant cell, a hybridoma cell, or a human blood derived leukocyte. In some embodiments, the protein is an antibody or a fragment thereof. Other exemplary proteins can include, but are not limited to, enzymes, allergenic peptides or proteins (for example, for use as a vaccine), recombinant protein, cytokines, peptides, hormones, erythropoietin (EPO), interferons, granulocyte-colony stimulating factor (G-CSF), anticoagulants, and clotting factors. In some embodiments, the method comprises purifying the protein.

In some embodiments, there is an in vitro cell culture medium, comprising the compound or salt described herein, and nutrients for cellular growth. In some embodiments, the culture medium comprises a eukaryotic cell comprising a nucleic acid encoding a protein. In some embodiments, the culture medium further comprises a compound for inducing protein expression. In some embodiments, the nucleic acid encoding the protein is a recombinant nucleic acid. In some embodiments, the protein is an antibody or a fragment thereof. Other exemplary proteins can include, but are not limited to, enzymes, allergenic peptides or proteins (for example, for use as a vaccine), recombinant protein, cytokines, peptides, hormones, erythropoietin (EPO), interferons, granulocyte-colony stimulating factor (G-CSF), anticoagulants, and clotting factors. In some embodiments, the eukaryotic cell is a human embryonic kidney (HEK) cell or a Chinese hamster ovary (CHO) cell. In other embodiments, the eukaryotic cell is a yeast cell (such as Saccharomyces cerevisiae or Pichia pastoris), a wheat germ cell, an insect cell, a rabbit reticulocyte, a cervical cancer cell (such as a HeLa cell), a baby hamster kidney cell (such as BHK21 cells), a murine myeloma cell (such as NSO or Sp2/0 cells), an HT-1080 cell, a PER.C$_6$ cell, a plant cell, a hybridoma cell, or a human blood derived leukocyte.

In some embodiments, provided herein is a method of increasing protein translation in a cell or cell free expression system. In some embodiments, the cell was stressed prior to administration of the compound, salt thereof, or composition. In some embodiments, protein translation is increased by at least about 10%, 20%, 30%, 40%, 50%, 60%, 70%, 80%, 90%, 95%, 98%, 100%, 125%, 150%, 175%, 200%, 250%, or 300% or more. In some embodiments, protein translation is increased by about 10% to about 300% (such as about 10% to about 20%, about 20% to about 30%, about 30% to about 40%, about 40% to about 50%, about 50% to about 60%, about 60% to about 70%, about 70% to about 80%, about 80% to about 90%, about 90% to about 100%, about 100% to about 125%, about 125% to about 150%, about 150% to about 175%, about 175% to about 200%, about 200% to about 250%, or about 250% to about 300%) In some embodiments, protein translation is increased as compared to prior to the administration of the compounds, salt thereof, or composition. In some embodiments, protein translation is increased as compared to an unstressed cell, a basal condition where cells are not subjected to a specific stress that activates the ISR. In some embodiments, protein translation is increased as compared to a stressed cell where ISR is active.

Some of the compounds described herein increase protein synthesis in a cell without full inhibition of ATF4 translation, under ISR-stressed or non-ISR stressed conditions. Exemplary compounds include compound 150, compound 153, and compound 30, or a salt thereof. Despite ATF4 participation in various pathologies, the ATF4 protein is an important factor for restoring cellular homeostasis in stressed cells, for example during oxidative stress response, cholesterol metabolism, protein folding amino acid synthesis, and autophagy. Thus, for certain treatments, it may be preferable to limit ATF4 inhibition. In some embodiments, the compound is used to increase protein synthesis by about 10% or more, about 20% or more, about 30% or more, about 40% or more, about 50% or more, about 60% or more, about 70% or more, about 80% or more, about 90% or more, about 100% or more, about 125% or more, about 150% or more, about 175% or more, about 200% or more, about 250% or more, or about 300% or more wherein ATF4 protein expression is inhibited by about 75% or less, about 50% or less, about 40% or less, about 30% or less, about 20% or less, about 10% or less, or about 5% or less. In some embodiments the compound is used to increase protein synthesis by about 10% to about 300% (such as about 10% to about 20%, about 20% to about 30%, about 30% to about 40%, about 40% to about 50%, about 50% to about 60%, about 60% to about 70%, about 70% to about 80%, about 80% to about 90%, about 90% to about 100%, about 100% to about 125%, about 125% to about 150%, about 150% to about 175%, about 175% to about 200%, about 200% to about 250%, or about 250% to about 300%), wherein ATF4 protein expression is inhibited by about 75% or less (such as about 50% or less, about 40% or less, about 30% or less, about 20% or less, about 10% or less, or about 5% or less).

In some embodiments, provided herein is a method of increasing protein translation in a cell. In some embodiments, the cell was stressed prior to administration of the compound, salt thereof, or composition. In some embodiments, protein translation is increased by at least about 10%, 20%, 30%, 40%, 50%, 60%, 70%, 80%, 90%, 95%, 98%, 100%, 125%, 150%, 175%, 200%, 250%, or 300% or more. In some embodiments, protein translation is increased as compared to prior to the administration of the compounds, salt thereof, or composition. In some embodiments, protein translation is increased as compared to an unstressed cell, a basal condition where cells are not subjected to a specific stress that activates the ISR. In some embodiments, protein translation is increased as compared to a stressed cell where ISR is active.

In some embodiments, provided herein is a method of increasing guanine nucleotide exchange factor (GEF) activity of eIF2B in cells. In some embodiments, provided herein is a method of delaying or preventing apoptosis in a cell. In some embodiments, provided herein is a method of inhibiting translation of one or more mRNAs comprising a 5' untranslated region (5'UTR) that contains at least one upstream open reading frame (uORF), encoding proteins with translational preferences, including but not limited to ATF4, ATF2, ATF5, CHOP, GADD34, BACE-1, C/EBPα, or MAP1LC3B. In some embodiments, the mRNA encodes ATF4, BACE-1, GADD34, or CHOP. In some embodiments, the mRNA encodes ATF4.

In some embodiments, expression of ATF4, BACE-1, GADD34 or CHOP is inhibited. In some embodiments, expression of ATF4 is inhibited. In some embodiments, expression of Aβ is inhibited. ATF4 increases expression of, among others, GADD45A, CDKN1A, and EIF4EBP1, which encode DDIT-1, p21, and 4E-BP1, respectively. These proteins induce musculoskeletal disease (such as skeletal muscle atrophy), and can be modulated by inhibiting expression of ATF4. Accordingly, in some embodiments, expression of one or more of CDKN1A, GADD45A, or EIF4EBP1 is inhibited.

In some embodiments, the compound, salt thereof, or composition inhibits translation of one or more mRNAs comprising a 5' untranslated region (5'UTR) comprising at least one upstream open reading frame (uORF) with an $IC_{50}$ of less than about 1 µM, such as less than about 750 nM, 600 nM, 500 nM, 300 nM, 200 nM, 100 nM, 80 nM, 60 nM, 40 nM, 25 nM, or less. In some embodiments, the compound, salt thereof, or composition inhibits translation of one or more mRNAs comprising a 5' untranslated region (5'UTR) comprising at least one upstream open reading frame (uORF) with an $IC_{50}$ between about 1 nM and 1 µM, such as between about 10 nM and 600 nM, 15 nM and 200 nM, or 20 nM and 180 nM.

In some embodiments, the compound, salt thereof, or composition inhibits expression of ATF4 with an $IC_{50}$ of less than about 1 µM, such as less than about 750 nM, 600 nM, 500 nM, 300 nM, 200 nM, 100 nM, 80 nM, 60 nM, 40 nM, 25 nM, or less. In some embodiments, the compound, salt thereof, or composition inhibits expression of ATF4 with an $IC_{50}$ between about 1 nM and 1 µM, such as between about 2 nM and 800 nM, 10 nM and 600 nM, 15 nM and 200 nM, or 20 nM and 180 nM.

In some aspects, the half maximal inhibitory concentration ($IC_{50}$) is a measure of the effectiveness of a substance in inhibiting a specific biological or biochemical function. In some aspects, the $IC_{50}$ is a quantitative measure that indicates how much of an inhibitor is needed to inhibit a given biological process or component of a process such as an enzyme, cell, cell receptor or microorganism by half. Methods of determining $IC_{50}$ in vitro and in vivo are known in the art.

In some embodiments, the individual is a mammal. In some embodiments, the individual is a primate, bovine, ovine, porcine, equine, canine, feline, rabbit, or rodent. In some embodiments, the individual is a human. In some embodiments, the individual has any of the diseases or disorders disclosed herein. In some embodiments, the individual is a risk for developing any of the diseases or disorders disclosed herein.

In some embodiments, the individual is human. In some embodiments, the human is at least about or is about any of 21, 25, 30, 35, 40, 45, 50, 55, 60, 65, 70, 75, 80, or 85 years old. In some embodiments, the human is a child. In some embodiments, the human is less than about or about any of 21, 18, 15, 12, 10, 8, 6, 5, 4, 3, 2, or 1 years old.

Also provided herein are uses of a compound described herein or a pharmaceutically acceptable salt thereof, or a pharmaceutical composition described herein, in the manufacture of a medicament. In some embodiments, the manufacture of a medicament is for the treatment of a disorder or disease described herein. In some embodiments, the manufacture of a medicament is for the prevention and/or treatment of a disorder or disease mediated by an ISR pathway. In some embodiments, the manufacture of a medicament is for the prevention and/or treatment of a disorder or disease mediated by eIF2a or eIF2B. In some embodiments, the manufacture of a medicament is for the prevention and/or treatment of a disorder or disease mediated by phosphorylation of eIF2a and/or the GEF activity of eIF2B.

Combinations

In certain aspects, a compound described herein is administered to an individual for treatment of a disease in combination with one or more additional pharmaceutical agents that can treat the disease. For example, in some embodiments, an effective amount of the compound is administered to an individual for the treatment of cancer in combination with one or more additional anticancer agents.

In some embodiments, activity of the additional pharmaceutical agent (such as additional anticancer agent) is inhibited by an activated ISR pathway. An ISR inhibitor, such as one of the compounds described herein, can inhibit the ISR pathway to enhance functionality of the additional pharmaceutical agent. By way of example, certain BRAF inhibitors (e.g., vemurafenib or dabrafenib) activate the ISR pathway in BRAF-mutated melanoma cells (e.g., BRAF with a V600F mutation) through the expression of ATF4. In some embodiments, there is a method of treating cancer comprising administering to an individual with cancer an effective amount of a compound described herein in combination with an effective amount of a BRAF inhibitor. In some embodiments, there is a method of treating a BRAF-mutated melanoma comprising administering to an individual with a BRAF-mutated melanoma an effective amount of a compound described herein in combination with an effective amount of a BRAF inhibitor. In some embodiments, there is a method of treating a BRAF-mutated melanoma comprising administering to an individual with a BRAF-mutated melanoma an effective amount of a compound described herein in combination with an effective amount of vemurafenib or dabrafenib.

As another example, certain anticancer agents (such as ubiquitin-proteasome pathway inhibitors (such as bortezomib), Cox-2 inhibitors (e.g., celecoxib), platinum-based antineoplastic drugs (e.g., cisplatin), anthracyclines (e.g. doxorubicin), or topoisomerase inhibitors (e.g., etoposide)) are used to treat cancer, but may have limited functionality against solid tumors. Resistance in certain solid tumors (e.g., breast cancers) has been associated with ATF4 stabilization and induction of autophagy. In some embodiments, an effective amount of an ISR inhibitor compound as described herein is administered to an individual with cancer to increase sensitivity to one or more anticancer agents.

In some embodiments, there is a method of treating a refractory cancer (such as a solid tumor) in an individual, comprising administering to the individual an effective amount of a compound described herein in combination with an effective amount of an anticancer agent. In some embodiments, there is a method of treating a refractory cancer (such as a solid tumor) in an individual, comprising administering to the individual an effective amount of a compound described herein in combination with an effective amount of an ubiquitin-proteasome pathway inhibitor (e.g., bortezomib), a Cox-2 inhibitor (e.g., celecoxib), a platinum-based antineoplastic drug (e.g., cisplatin), an anthracycline (e.g. doxorubicin), or a topoisomerase inhibitor (e.g., etoposide). In some embodiments, the refractory cancer is breast cancer. In some embodiments, the refractory cancer is melanoma.

In some embodiments, a compound described herein is used to treat cancer in combination with one or more anti-cancer agents, such as an anti-neoplastic agent, an immune checkpoint inhibitor, or any other suitable anticancer agent. Exemplary immune checkpoint inhibitors include anti-PD-1, anti-PD-L1, anti GITR, anti-OX-40, anti-LAG3, anti-TIM-3, anti-41BB, anti-CTLA-4 antibodies. Exemplary anti-neoplastic agents can include, for example, anti-microtubule agents, platinum coordination complexes, alkylating agents, topoisomerase II inhibitors, topoisomerase I inhibitors, antimetabolites, antibiotic agents, hormones and hormonal analogs, signal transduction pathway inhibitors, non-receptor tyrosine kinase angiogenesis inhibitors, proteasome inhibitors, and inhibitors of cancer metabolism. Other anti-cancer agents can include one or more of an immuno-stimulant, an antibody or fragment thereof (e.g., an anti-CD20, anti-HER2, anti-CD52, or anti-VEGF antibody or fragment thereof), or an immunotoxin (e.g., an anti-CD33 antibody or fragment thereof, an anti-CD22 antibody or fragment thereof, a calicheamicin conjugate, or a *pseudomonas* exotoxin conjugate).

ATF4-mediated expression of CHOP has also been shown to regulate the function and accumulation of myeloid-derived suppressor cells (MDSCs) in tumors. MDSCs in tumors reduce the ability to prime T cell function and reduce antitumoral or anticancer responses. Certain immunotherapeutic agents (such as anti-PD-1, anti PD-L1, anti-GITR, anti-OX-40, anti-LAG3, anti-TIM-3, anti-41BB, or anti-CTLA-4 antibodies) have been used to boost the immune response against cancer. ATF4-mediated expression of AXL has been associated with poor response to anti-PD1 therapy in melanoma. In some embodiments, an effective amount of an ISR inhibitor compound as described herein is administered to an individual with cancer to increase sensitivity to one or more immunotherapeutic agents. In some embodiments, there is a method of treating a refractory cancer (such as a melanoma) in an individual, comprising administering to the individual an effective amount of a compound described herein in combination with an effective amount of an immunotherapeutic agent (e.g. anti-PD-1, anti PD-L1, anti-GITR, anti-OX-40, anti-LAG3, anti-TIM-3, anti-41BB, or anti-CTLA-4 antibodies). In some embodiments, the refractory cancer is melanoma.

Dosing and Method of Administration

The dose of a compound administered to an individual (such as a human) may vary with the particular compound or salt thereof, the method of administration, and the particular disease, such as type and stage of cancer, being treated. In some embodiments, the amount of the compound or salt thereof is a therapeutically effective amount.

The effective amount of the compound may in one aspect be a dose of between about 0.01 and about 100 mg/kg. Effective amounts or doses of the compounds of the present disclosure may be ascertained by routine methods, such as modeling, dose escalation, or clinical trials, taking into account routine factors, e.g., the mode or route of administration or drug delivery, the pharmacokinetics of the agent, the severity and course of the disease to be treated, the subject's health status, condition, and weight. An exemplary dose is in the range of about from about 0.7 mg to 7 g daily, or about 7 mg to 350 mg daily, or about 350 mg to 1.75 g daily, or about 1.75 to 7 g daily.

Any of the methods provided herein may in one aspect comprise administering to an individual a pharmaceutical composition that contains an effective amount of a compound provided herein or a salt thereof and a pharmaceutically acceptable excipient.

A compound or composition provided herein may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life. In one variation, the compound is administered on a daily or intermittent schedule. The compound can be administered to an individual continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent, including a 'drug holiday' (e.g., once daily dosing for 7 days followed by no doses for 7 days, repeated for any 14 day time period, such as about 2 months, about 4 months, about 6 months or more). Any of the dosing frequencies can employ any of the compounds described herein together with any of the dosages described herein.

Articles of Manufacture and Kits

The present disclosure further provides articles of manufacture comprising a compound described herein or a salt thereof, a composition described herein, or one or more unit dosages described herein in suitable packaging. In certain embodiments, the article of manufacture is for use in any of the methods described herein. Suitable packaging is known in the art and includes, for example, vials, vessels, ampules, bottles, jars, flexible packaging and the like. An article of manufacture may further be sterilized and/or sealed.

The present disclosure further provides kits for carrying out the methods of the present disclosure, which comprises one or more compounds described herein or a composition comprising a compound described herein. The kits may employ any of the compounds disclosed herein. In one variation, the kit employs a compound described herein or a salt thereof. The kits may be used for any one or more of the uses described herein, and, accordingly, may contain instructions for the treatment of any disease or described herein, for example for the treatment of cancer.

Kits generally comprise suitable packaging. The kits may comprise one or more containers comprising any compound described herein. Each component (if there is more than one component) can be packaged in separate containers or some components can be combined in one container where cross-reactivity and shelf life permit.

The kits may be in unit dosage forms, bulk packages (e.g., multi-dose packages) or sub-unit doses. For example, kits may be provided that contain sufficient dosages of a compound as disclosed herein and/or an additional pharmaceutically active compound useful for a disease detailed herein to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present disclosure. The instructions included with the kit generally include information as to the components and their administration to an individual.

General Synthetic Methods

The compounds of the present disclosure may be prepared by a number of processes as generally described below and more specifically in the Examples hereinafter (such as the schemes provided in the Examples below). In the following process descriptions, the symbols when used in the formulae depicted are to be understood to represent those groups described above in relation to the formulae herein.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization and the desired enantiomer recovered. In another resolution process, a racemate may be separated using chiral High-Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

Solvates and/or polymorphs of a compound provided herein or a salt thereof are also contemplated. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and/or solubility. Various factors such as the recrystallization solvent, rate of crystallization, and storage temperature may cause a single crystal form to dominate.

Chromatography, recrystallization and other conventional separation procedures may also be used with intermediates or final products where it is desired to obtain a particular isomer of a compound or to otherwise purify a product of a reaction.

General methods of preparing compounds according to the present disclosure are depicted in the schemes below.

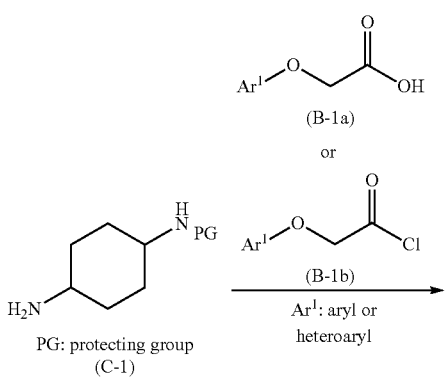

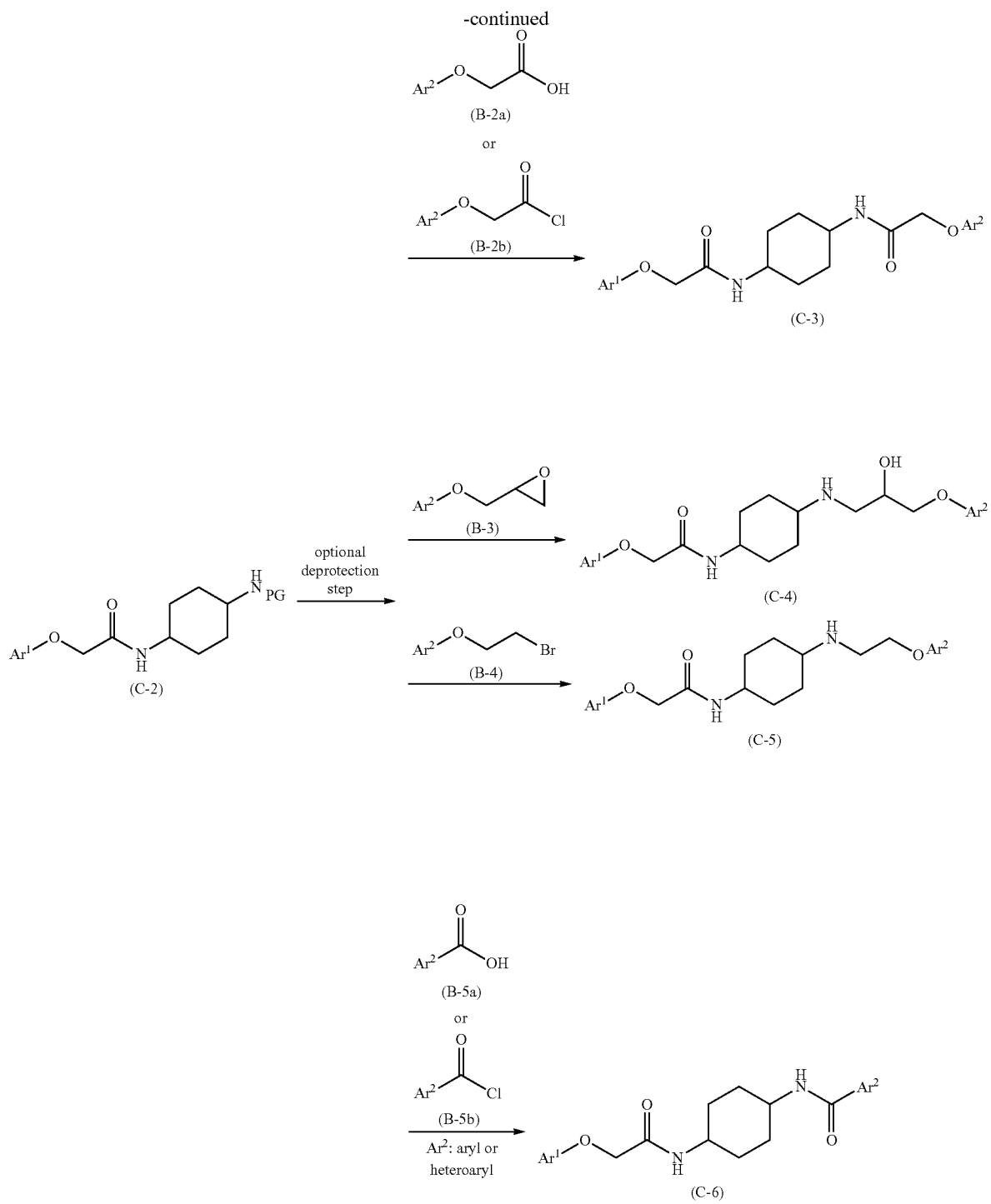

Compounds disclosed herein, such as compounds of formula (C-3), (C-4), (C-5), and (C-6), for example, can be synthesized according to the general method described in the scheme above. A compound of formula (C-1) is reacted with a carboxylic acid (B-1a), or a carboxylic acid derivative (e.g. an acyl chloride of formula (B-1b), under suitable conditions to give a compound of formula (C-2). The compound of formula (C-2), which may first be optionally deprotected, is reacted with a carboxylic acid (B-2a), or a carboxylic acid derivative (e.g. an acyl chloride of formula (B-2b), to give a compound of formula (C-3). The compound of formula (C-2), which may first be optionally deprotected, is reacted with an oxirane derivative of formula (B-3) to give a compound of formula (C-4). The compound of formula (C-2), which may first be optionally deprotected, is reacted with a haloalkyl derivative, such as a bromoalkyl compound of formula (B-4), to give a compound of formula (C-5). The compound of formula (C-2), which may first be optionally deprotected, is reacted with a carboxylic acid (B-5a), or a carboxylic acid derivative (e.g. an acyl chloride of formula (B-5b), to give a compound of formula (C-6).

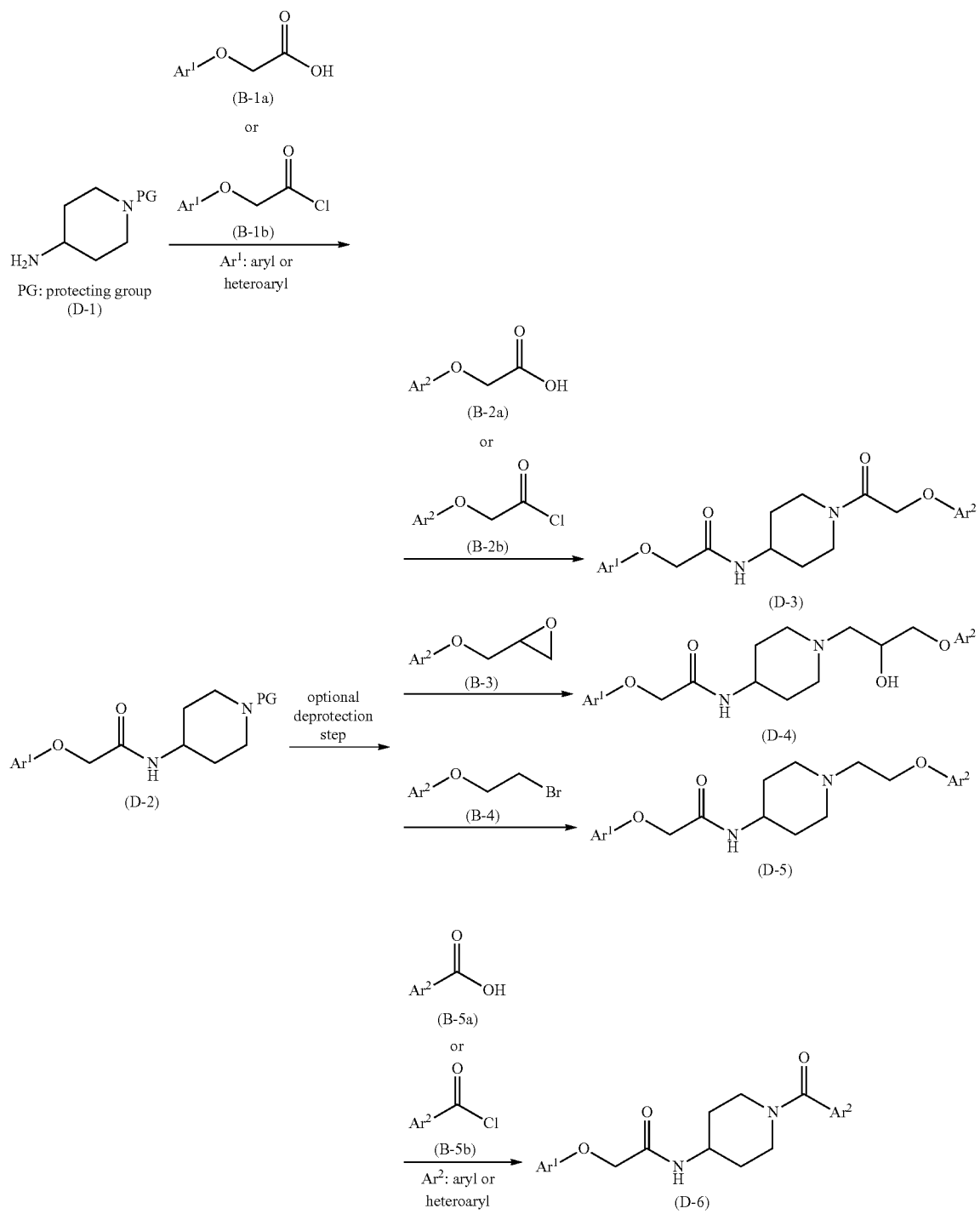

Compounds disclosed herein, such as compounds of formula (D-3), (D-4), (D-5), and (D-6), for example, can be synthesized according to the general method described in the scheme above. A compound of formula (D-1) is reacted with a carboxylic acid (B-1a), or a carboxylic acid derivative (e.g. an acyl chloride of formula (B-1b), under suitable conditions to give a compound of formula (D-2). The compound of formula (D-2), which may first be optionally deprotected, is reacted with a carboxylic acid (B-2a), or a carboxylic acid derivative (e.g. an acyl chloride of formula (B-2b), to give a compound of formula (D-3). The compound of formula (D-2), which may first be optionally deprotected, is reacted with an oxirane derivative of formula (B-3) to give a compound of formula (D-4). The compound of formula (D-2), which may first be optionally deprotected, is reacted with a haloalkyl derivative, such as a bromoalkyl compound of formula (B-4), to give a compound of formula (D-5). The compound of formula (D-2), which may first be optionally deprotected, is reacted with a carboxylic acid (B-5a), or a carboxylic acid derivative (e.g. an acyl chloride of formula (B-5b), to give a compound of formula (D-6).

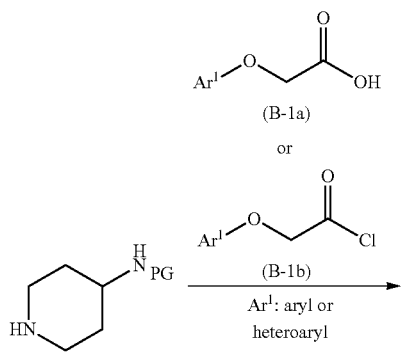
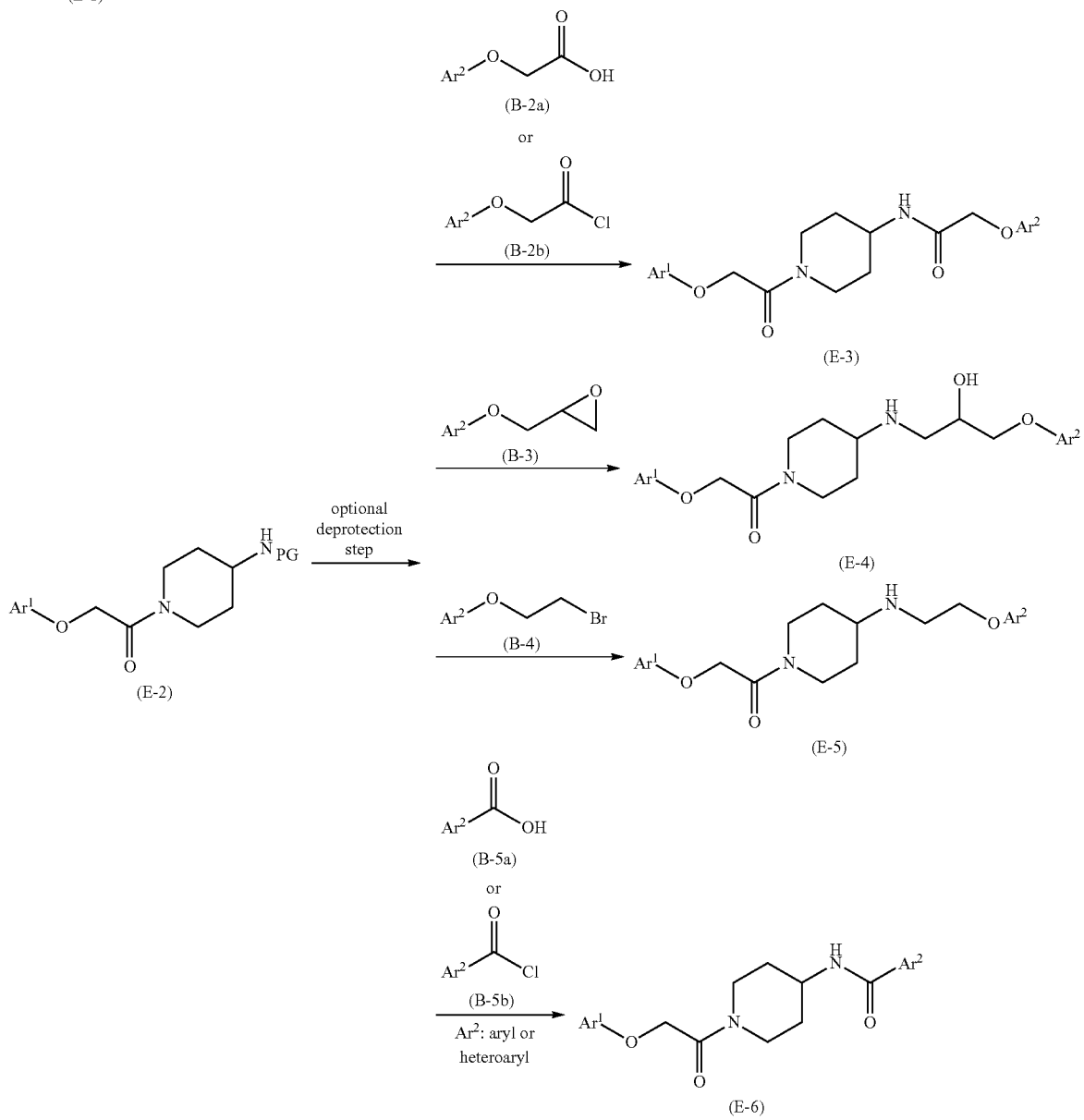
Compounds disclosed herein, such as compounds of formula (E-3), (E-4), (E-5), and (E-6), for example, can be synthesized according to the general method described in the scheme above. A compound of formula (E-1) is reacted with a carboxylic acid (B-1a), or a carboxylic acid derivative (e.g. an acyl chloride of formula (B-1b), under suitable conditions to give a compound of formula (E-2). The compound of formula (E-2), which may first be optionally deprotected, is reacted with a carboxylic acid (B-2a), or a carboxylic acid derivative (e.g. an acyl chloride of formula (B-2b), to give a compound of formula (E-3). The compound of formula (E-2), which may first be optionally deprotected, is reacted with an oxirane derivative of formula (B-3) to give a compound of formula (E-4). The compound of formula (E-2), which may first be optionally deprotected, is reacted with a haloalkyl derivative, such as a bromoalkyl compound of formula (B-4), to give a compound of formula (E-5). The compound of formula (E-2), which may first be optionally deprotected, is reacted with a carboxylic acid (B-5a), or a carboxylic acid derivative (e.g. an acyl chloride of formula (B-5b), to give a compound of formula (E-6).

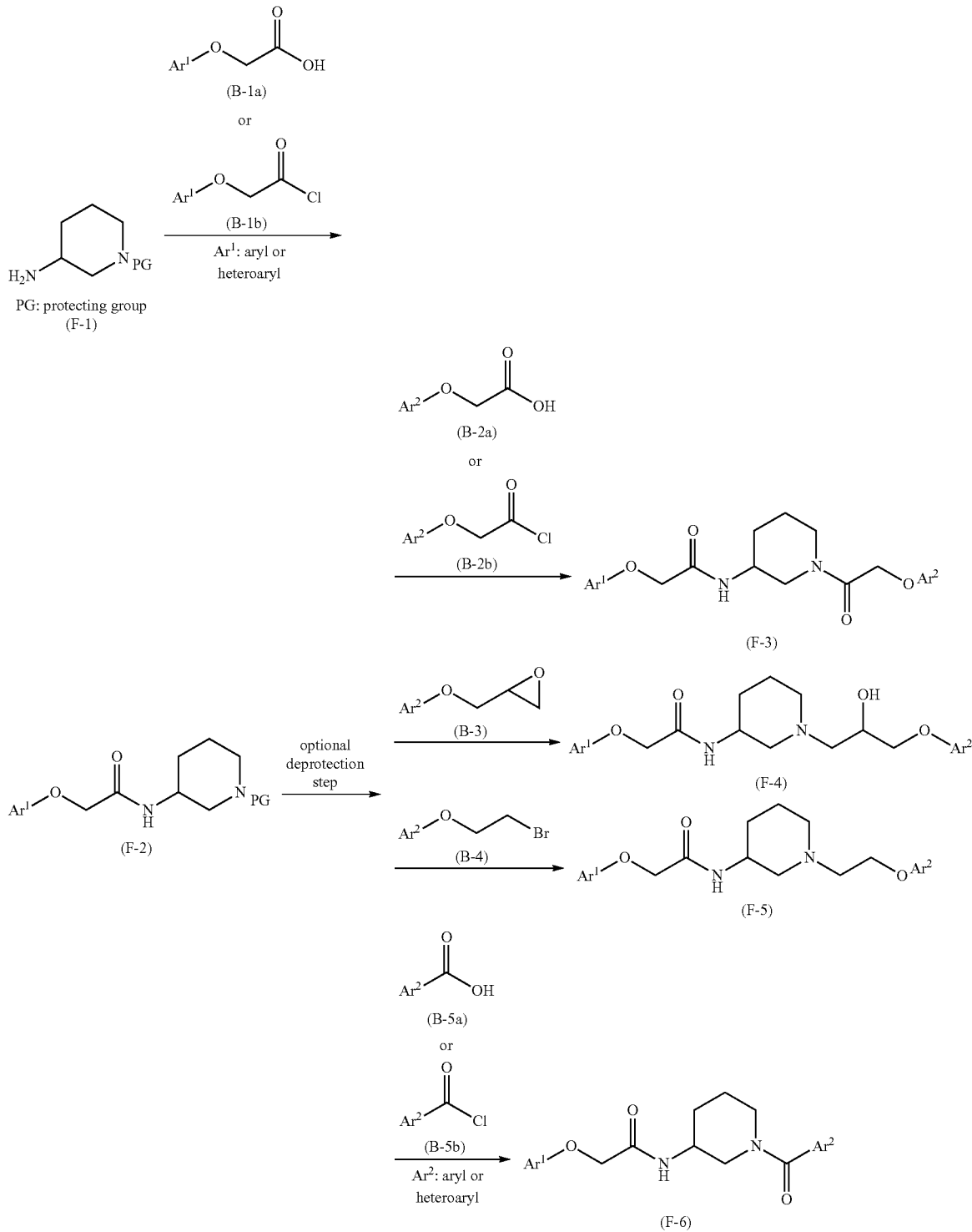

Compounds disclosed herein, such as compounds of formula (F-3), (F-4), (F-5), and (F-6), for example, can be synthesized according to the general method described in the scheme above. A compound of formula (F-1) is reacted with a carboxylic acid (B-1a), or a carboxylic acid derivative (e.g. an acyl chloride of formula (B-1b), under suitable conditions to give a compound of formula (F-2). The compound of formula (F-2), which may first be optionally deprotected, is reacted with a carboxylic acid (B-2a), or a carboxylic acid derivative (e.g. an acyl chloride of formula (B-2b), to give a compound of formula (F-3). The compound of formula (F-2), which may first be optionally deprotected, is reacted with an oxirane derivative of formula (B-3) to give a compound of formula (F-4). The compound of formula (F-2), which may first be optionally deprotected, is reacted with a haloalkyl derivative, such as a bromoalkyl compound of formula (B-4), to give a compound of formula (F-5). The compound of formula (F-2), which may first be optionally deprotected, is reacted with a carboxylic acid (B-5a), or a carboxylic acid derivative (e.g. an acyl chloride of formula (B-5b), to give a compound of formula (F-6).

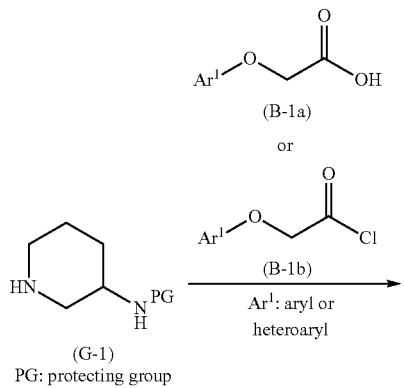

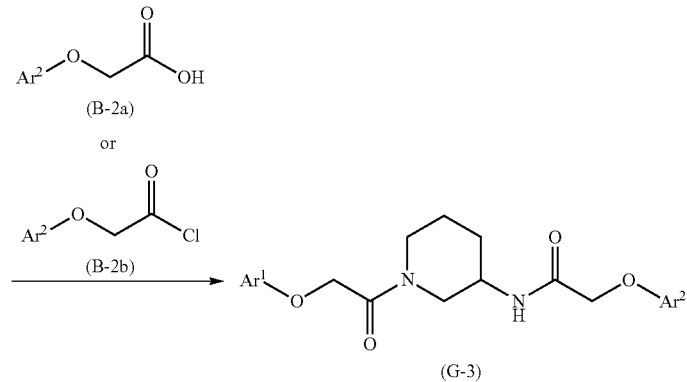

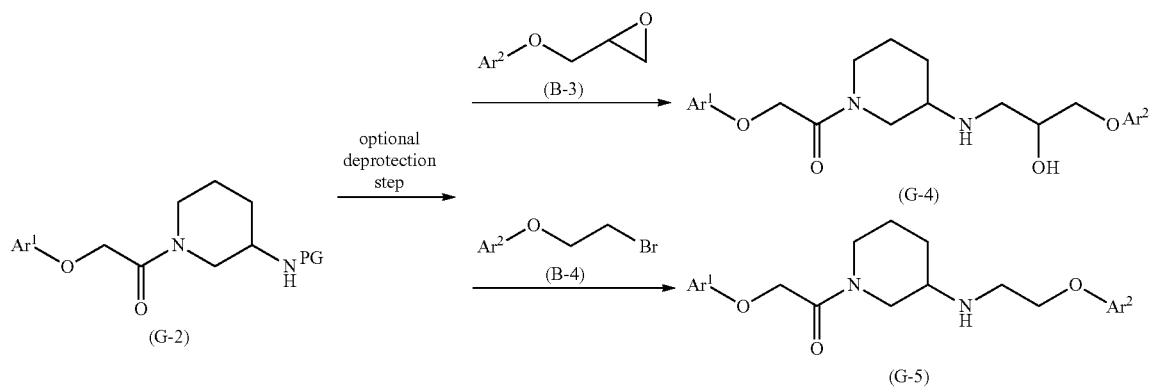

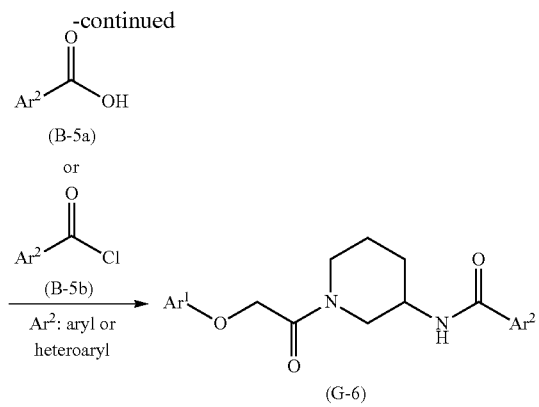

Compounds disclosed herein, such as compounds of formula (G-3), (G-4), (G-5), and (G-6), for example, can be synthesized according to the general method described in the scheme above. A compound of formula (G-1) is reacted with a carboxylic acid (B-1a), or a carboxylic acid derivative (e.g. an acyl chloride of formula (B-1b), under suitable conditions to give a compound of formula (G-2). The compound of formula (G-2), which may first be optionally deprotected, is reacted with a carboxylic acid (B-2a), or a carboxylic acid derivative (e.g. an acyl chloride of formula (B-2b), to give a compound of formula (G-3). The compound of formula (G-2), which may first be optionally deprotected, is reacted with an oxirane derivative of formula (B-3) to give a compound of formula (G-4). The compound of formula (G-2), which may first be optionally deprotected, is reacted with a haloalkyl derivative, such as a bromoalkyl compound of formula (B-4), to give a compound of formula (G-5). The compound of formula (G-2), which may first be optionally deprotected, is reacted with a carboxylic acid (B-5a), or a carboxylic acid derivative (e.g. an acyl chloride of formula (B-5b), to give a compound of formula (G-6).

ENUMERATED EMBODIMENTS

The following enumerated embodiments are representative of some aspects of the invention.

Embodiment 1

A compound of formula (I):

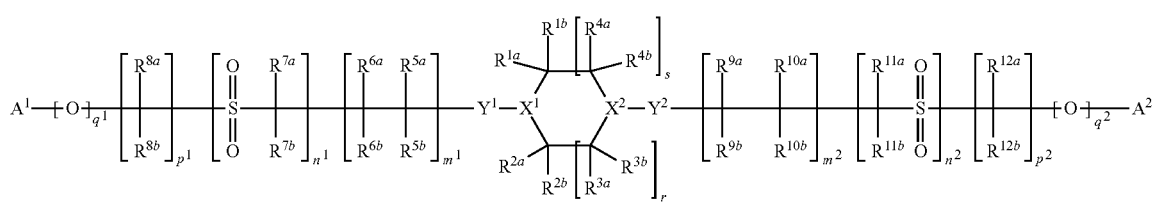

or a pharmaceutically acceptable salt thereof;
wherein:
$X^1$ and $X^2$, independently of each other, are CH or N;
$Y^1$ is selected from the group consisting of a bond, $NR^{Y1}$, and O; provided that when $X^1$ is N, then $Y^1$ is a bond;
$R^{Y1}$ is hydrogen or $C_1$-$C_6$ alkyl;
$Y^2$ is selected from the group consisting of a bond, $NR^{Y2}$, and O; provided that when $X^2$ is N, then $Y^2$ is a bond;
$R^{Y2}$ is hydrogen or $C_1$-$C_6$ alkyl;
$m^1$, $m^2$, $n^1$, $n^2$, $p^1$, $p^2$, $q^1$, and $q^2$, independently of each other, are 0 or 1;
r and s, independently of each other, are 0, 1, or 2;
$A^1$ is selected from the group consisting of:
a substituent of formula ($A^1$-a)

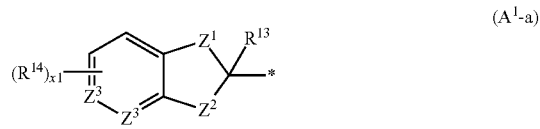

wherein
  represents the attachment point to the remainder of the molecule; $Z^1$ is selected from the group consisting of $CR^{Z1-1}R^{Z1-2}$, $NR^{Z1-2}$, O, S, and —$CR^{Z1-1}$=$CR^{Z1-1}$—;
  wherein $R^{Z1-1}$ is H or $R^{14}$; and $R^{Z1-2}$ is H or $R^{14}$;
$Z^2$ is selected from the group consisting of $CR^{Z2-1}R^{Z2-2}$, $NR^{Z2-2}$; O, S, and —$CR^{Z2-1}$=$CR^{Z2-1}$—;
  wherein $R^{Z2-1}$ is H or $R^{14}$; and $R^{Z2-2}$ is H or $R^{14}$;
$Z^3$, independently at each occurrence, is C or N, provided that at least one $Z^3$ is C;
$R^{13}$ is hydrogen or $R^{14}$, or $R^{13}$ and $R^{Z1-2}$ are taken together to form a double bond between the carbon atom bearing $R^{13}$ and $Z^1$, or $R^{13}$ and $R^{Z2-2}$ are taken together to form a double bond between the carbon atom bearing $R^{13}$ and $Z^2$; and x1 is 0, 1, 2, 3, or 4, provided than when one $Z^3$ is N, then x1 is not 4;

C$_6$-C$_{10}$ aryl optionally substituted with one or more $R^{14}$ substituents; and 5-10 membered heteroaryl optionally substituted with one or more $R^{14}$ substituents;

$R^{14}$ is selected, independently at each occurrence, from the group consisting of halogen, C$_1$-C$_6$ alkyl, C$_1$-C$_6$ haloalkyl, —OH, —O(C$_1$-C$_6$ alkyl), —O(C$_1$-C$_6$ haloalkyl), —SH, —S(C$_1$-C$_6$ alkyl), —S(C$_1$-C$_6$ haloalkyl), —NH$_2$, —NH(C$_1$-C$_6$ alkyl), —NH(C$_1$-C$_6$ haloalkyl), —N(C$_1$-C$_6$ alkyl)$_2$, —N(C$_1$-C$_6$ haloalkyl)$_2$, —NR$^{14-a}$R$^{14-b}$, —CN, —C(O)OH, —C(O)O(C$_1$-C$_6$ alkyl), —C(O)O(C$_1$-C$_6$ haloalkyl), —C(O)NH$_2$, —C(O)NH(C$_1$-C$_6$ alkyl), —C(O)NH(C$_1$-C$_6$ haloalkyl), —C(O)N(C$_1$-C$_6$ alkyl)$_2$, —C(O)N(C$_1$-C$_6$ haloalkyl)$_2$, —C(O)NR$^{14-a}$R$^{14-b}$, —S(O)$_2$OH, —S(O)$_2$O(C$_1$-C$_6$ alkyl), —S(O)$_2$O(C$_1$-C$_6$ haloalkyl), —S(O)$_2$NH$_2$, —S(O)$_2$NH(C$_1$-C$_6$ alkyl), —S(O)$_2$NH(C$_1$-C$_6$ haloalkyl), —S(O)$_2$N(C$_1$-C$_6$ alkyl)$_2$, —S(O)$_2$N(C$_1$-C$_6$ haloalkyl)$_2$, —S(O)$_2$NR$^{14-a}$R$^{14-b}$, —OC(O)H, —OC(O)(C$_1$-C$_6$ alkyl), —OC(O)(C$_1$-C$_6$ haloalkyl), —N(H)C(O)H, —N(H)C(O)(C$_1$-C$_6$ alkyl), —N(H)C(O)(C$_1$-C$_6$ haloalkyl), —N(C$_1$-C$_6$ alkyl)C(O)H, —N(C$_1$-C$_6$ alkyl)C(O)(C$_1$-C$_6$ alkyl), —N(C$_1$-C$_6$ alkyl)C(O)(C$_1$-C$_6$ haloalkyl), —N(C$_1$-C$_6$ haloalkyl)C(O)H, —N(C$_1$-C$_6$ haloalkyl)C(O)(C$_1$-C$_6$ alkyl), —N(C$_1$-C$_6$ haloalkyl)C(O)(C$_1$-C$_6$ haloalkyl), —OS(O)$_2$(C$_1$-C$_6$ alkyl), —OS(O)$_2$(C$_1$-C$_6$ haloalkyl), —N(H)S(O)$_2$(C$_1$-C$_6$ alkyl), —N(H)S(O)$_2$(C$_1$-C$_6$ haloalkyl), —N(C$_1$-C$_6$ alkyl)S(O)$_2$(C$_1$-C$_6$ alkyl), —N(C$_1$-C$_6$ alkyl)S(O)$_2$(C$_1$-C$_6$ haloalkyl), —N(C$_1$-C$_6$ haloalkyl)S(O)$_2$(C$_1$-C$_6$ alkyl), and —N(C$_1$-C$_6$ haloalkyl)S(O)$_2$(C$_1$-C$_6$ haloalkyl);

wherein $R^{14-a}$ and $R^{14-b}$ are taken together with the nitrogen atom which bears them to form a 3-10 membered heterocycle;

$A^2$ is selected from the group consisting of:

a substituent of formula (A$^2$-a)

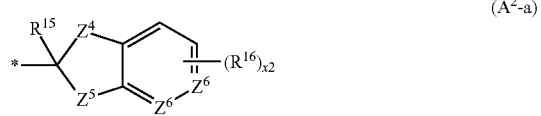

(A$^2$-a)

wherein

* represents the attachment point to the remainder of the molecule;

$Z^4$ is selected from the group consisting of CR$^{Z4-1}$R$^{Z4-2}$, NR$^{Z4-2}$, O, S, and —CR$^{Z4-1}$=CR$^{Z4-1}$—; wherein R$^{Z4-1}$ is H or R$^{16}$; and R$^{Z4-2}$ is H or R$^{16}$;

$Z^5$ is selected from the group consisting of CR$^{Z5-1}$R$^{Z5-2}$, NR$^{Z5-2}$; O, S, and —CR$^{Z5-1}$=CR$^{Z5-1}$—; wherein R$^{Z5-1}$ is H or R$^{16}$; and R$^{Z5-2}$ is H or R$^{16}$;

$Z^6$, independently at each occurrence, is C or N, provided that at least one $Z^6$ is C;

$R^{15}$ is hydrogen or R$^{16}$, or R$^{15}$ and R$^{Z4-2}$ are taken together to form a double bond between the carbon atom bearing R$^{15}$ and Z$^4$, or R$^{15}$ and R$^{Z5-2}$ are taken together to form a double bond between the carbon atom bearing R$^{15}$ and Z$^5$; and x2 is 0, 1, 2, 3, or 4, provided than when one $Z^6$ is N, then x2 is not 4;

C$_6$-C$_{10}$ aryl optionally substituted with one or more $R^{16}$ substituents; and 5-10 membered heteroaryl optionally substituted with one or more $R^{16}$ substituents;

$R^{16}$ is selected, independently at each occurrence, from the group consisting of halogen, C$_1$-C$_6$ alkyl, C$_1$-C$_6$ haloalkyl, —OH, —O(C$_1$-C$_6$ alkyl), —O(C$_1$-C$_6$ haloalkyl), —SH, —S(C$_1$-C$_6$ alkyl), —S(C$_1$-C$_6$ haloalkyl), —NH$_2$, —NH(C$_1$-C$_6$ alkyl), —NH(C$_1$-C$_6$ haloalkyl), —N(C$_1$-C$_6$ alkyl)$_2$, —N(C$_1$-C$_6$ haloalkyl)$_2$, —NR$^{16-a}$R$^{16-b}$, —CN, —C(O)OH, —C(O)O(C$_1$-C$_6$ alkyl), —C(O)O(C$_1$-C$_6$ haloalkyl), —C(O)NH$_2$, —C(O)NH(C$_1$-C$_6$ alkyl), —C(O)NH(C$_1$-C$_6$ haloalkyl), —C(O)N(C$_1$-C$_6$ alkyl)$_2$, —C(O)N(C$_1$-C$_6$ haloalkyl)$_2$, —C(O)NR$^{16-a}$R$^{16-b}$, —S(O)$_2$OH, —S(O)$_2$O(C$_1$-C$_6$ alkyl), —S(O)$_2$O(C$_1$-C$_6$ haloalkyl), —S(O)$_2$NH$_2$, —S(O)$_2$NH(C$_1$-C$_6$ alkyl), —S(O)$_2$NH(C$_1$-C$_6$ haloalkyl), —S(O)$_2$N(C$_1$-C$_6$ alkyl)$_2$, —S(O)$_2$N(C$_1$-C$_6$ haloalkyl)$_2$, —S(O)$_2$NR$^{16-a}$R$^{16-b}$, —OC(O)H, —OC(O)(C$_1$-C$_6$ alkyl), —OC(O)(C$_1$-C$_6$ haloalkyl), —N(H)C(O)H, —N(H)C(O)(C$_1$-C$_6$ alkyl), —N(H)C(O)(C$_1$-C$_6$ haloalkyl), —N(C$_1$-C$_6$ alkyl)C(O)H, —N(C$_1$-C$_6$ alkyl)C(O)(C$_1$-C$_6$ alkyl), —N(C$_1$-C$_6$ alkyl)C(O)(C$_1$-C$_6$ haloalkyl), —N(C$_1$-C$_6$ haloalkyl)C(O)H, —N(C$_1$-C$_6$ haloalkyl)C(O)(C$_1$-C$_6$ alkyl), —N(C$_1$-C$_6$ haloalkyl)C(O)(C$_1$-C$_6$ haloalkyl), —OS(O)$_2$(C$_1$-C$_6$ alkyl), —OS(O)$_2$(C$_1$-C$_6$ haloalkyl), —N(H)S(O)$_2$(C$_1$-C$_6$ alkyl), —N(H)S(O)$_2$(C$_1$-C$_6$ haloalkyl), —N(C$_1$-C$_6$ alkyl)S(O)$_2$(C$_1$-C$_6$ alkyl), —N(C$_1$-C$_6$ alkyl)S(O)$_2$(C$_1$-C$_6$ haloalkyl), —N(C$_1$-C$_6$ haloalkyl)S(O)$_2$(C$_1$-C$_6$ alkyl), and —N(C$_1$-C$_6$ haloalkyl)S(O)$_2$(C$_1$-C$_6$ haloalkyl);

wherein $R^{16-a}$ and $R^{16-b}$ are taken together with the nitrogen atom which bears them to form a 3-10 membered heterocycle;

$R^{1a}$ and $R^{1b}$ are independently selected from the group consisting of hydrogen, C$_1$-C$_6$ alkyl, and halogen;

$R^{2a}$ and $R^{2b}$ are independently selected from the group consisting of hydrogen, C$_1$-C$_6$ alkyl, and halogen;

when present, $R^{3a}$ and $R^{3b}$ are independently at each occurrence selected from the group consisting of hydrogen, C$_1$-C$_6$ alkyl, and halogen;

when present, $R^{4a}$ and $R^{4b}$ are independently at each occurrence selected from the group consisting of hydrogen, C$_1$-C$_6$ alkyl, and halogen;

or alternatively, $R^{1a}$ and $R^{2a}$ are taken together to form a C$_1$-C$_6$ alkylene moiety;

or alternatively, $R^{1a}$ and an $R^{3a}$ moiety, when present, are taken together to form a C$_1$-C$_6$ alkylene moiety, and $R^{1b}$ and the $R^{3b}$ in the geminal position to the $R^{3a}$ taken together with $R^{1a}$, are both hydrogen;

or alternatively, an $R^{3a}$ moiety, when present, and an $R^{4a}$ moiety, when present, are taken together to form a C$_1$-C$_6$ alkylene moiety, and the $R^{3b}$ in the geminal position to the $R^{3a}$ taken together with the $R^{4a}$ moiety and the $R^{4b}$ in the geminal position to the $R^{4a}$ taken together with the $R^{3a}$ moiety, are both hydrogen;

when present, $R^{5a}$ and $R^{5b}$ are taken together to form an oxo (=O) substituent or an imido (=NH) substituent, or alternatively, $R^{5a}$ and $R^{5b}$ are both hydrogen;

when present, $R^{6a}$ is selected from the group consisting of hydrogen, —OR$^{6a-a}$, and —NR$^{6a-b}$R$^{6a-c}$;

when present, $R^{6b}$ is hydrogen;

or alternatively, $R^{6a}$ and $R^{6b}$ are taken together to form a moiety selected from the group consisting of —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—

—$CH_2$—$CH_2$—O—, —O—$CH_2$—$CH_2$—$CH_2$—$CH_2$—, —$CH_2$—O—$CH_2$—$CH_2$—$CH_2$—, —$CH_2$—$CH_2$—O—$CH_2$—$CH_2$—, —$CH_2$—$CH_2$—$CH_2$—O—$CH_2$—, and —$CH_2$—$CH_2$—$CH_2$—$CH_2$—O—;

when present, $R^{7a}$ and $R^{7b}$ are both hydrogen;

when present, $R^{8a}$ and $R^{8b}$ are taken together to form an oxo (=O) substituent, or alternatively, $R^{8a}$ and $R^{8b}$ are both hydrogen;

when present, $R^{9a}$ and $R^{9b}$ are taken together to form an oxo (=O) substituent or an imido (=NH) substituent, or alternatively, $R^{9a}$ and $R^{9b}$ are both hydrogen;

when present, $R^{10a}$ is selected from the group consisting of hydrogen, —$OR^{10a-a}$, and —$NR^{10a-b}R^{10a-c}$;

when present, $R^{10b}$ is hydrogen;

or alternatively, $R^{10a}$ and $R^{10b}$ are taken together to form a moiety selected from the group consisting of —O—$CH_2$—$CH_2$—, —$CH_2$—O—$CH_2$—, —$CH_2$—$CH_2$—O—, —O—$CH_2$—$CH_2$—$CH_2$—, —$CH_2$—O—$CH_2$—$CH_2$—, —$CH_2$—$CH_2$—O—$CH_2$—, —$CH_2$—$CH_2$—$CH_2$—O—, —O—$CH_2$—$CH_2$—$CH_2$—$CH_2$—, —$CH_2$—O—$CH_2$—$CH_2$—$CH_2$—, —$CH_2$—$CH_2$—O—$CH_2$—$CH_2$—, —$CH_2$—$CH_2$—$CH_2$—O—$CH_2$—, and —$CH_2$—$CH_2$—$CH_2$—$CH_2$—O—;

when present, $R^{11a}$ and $R^{11b}$ are both hydrogen;

when present, $R^{12a}$ and $R^{12b}$ are taken together to form an oxo (=O) substituent, or alternatively, $R^{12a}$ and $R^{12b}$ are both hydrogen;

$R^{6a-a}$ is selected from the group consisting of hydrogen, $C_1$-$C_6$ alkyl, and $C_1$-$C_6$ haloalkyl;

$R^{10a-a}$ is selected from the group consisting of hydrogen, $C_1$-$C_6$ alkyl, and $C_1$-$C_6$ haloalkyl;

or $R^{6a-a}$ and $R^{Y1}$ may be taken together to form a carbonyl (C=O) moiety;

or $R^{10a-a}$ and $R^{Y2}$ may be taken together to form a carbonyl (C=O) moiety;

$R^{6a-b}$ and $R^{6a-c}$, independently of each other, are selected from the group consisting of hydrogen, $C_1$-$C_6$ alkyl, and $C_1$-$C_6$ haloalkyl; and $R^{10a-b}$ and $R^{10a-c}$, independently of each other, are selected from the group consisting of hydrogen, $C_1$-$C_6$ alkyl, and $C_1$-$C_6$ haloalkyl.

Embodiment 2

The compound of embodiment 1, wherein the compound of formula (I) is a compound of formula (1-1):

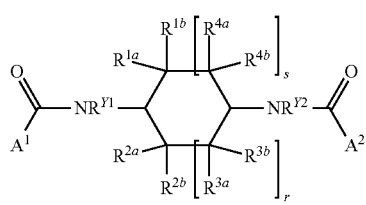

(1-1)

or a pharmaceutically acceptable salt thereof;
wherein:
$A^1$ is a substituent of formula ($A^1$-a)

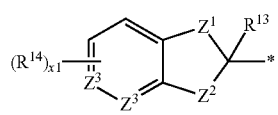

($A^1$-a)

and
$A^2$ is a substituent of formula ($A^2$-a)

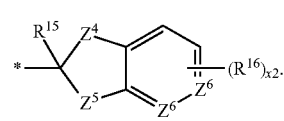

($A^2$-a)

Embodiment 3

The compound of embodiment 1, wherein the compound of formula (I) is a compound of formula (1-2):

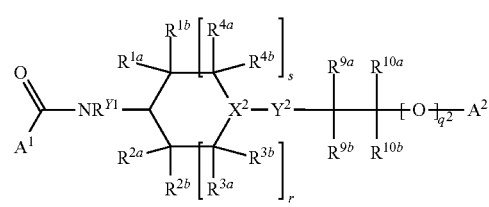

(1-2)

or a pharmaceutically acceptable salt thereof;
wherein:
$A^1$ is a substituent of formula ($A^1$-a)

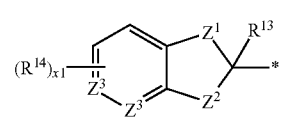

($A^1$-a)

and
$A^2$ is selected from the group consisting of:
a substituent of formula ($A^2$-a)

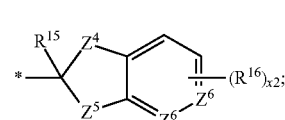

($A^2$-a)

$C_6$-$C_{10}$ aryl optionally substituted with one or more $R^{16}$ substituents; and 5-10 membered heteroaryl optionally substituted with one or more $R^{16}$ substituents.

Embodiment 4

The compound of embodiment 1, wherein the compound of formula (I) is a compound of formula (1-3):

(1-3)

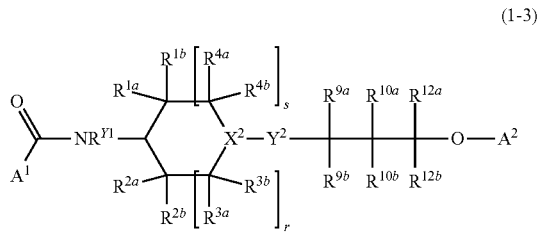

or a pharmaceutically acceptable salt thereof;
wherein:
A is a substituent of formula (A$^1$-a)

(A$^1$-a)

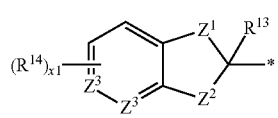

and
A$^2$ is C$_6$-C$_{10}$ aryl optionally substituted with one or more R$^{16}$ substituents; or 5-10 membered heteroaryl optionally substituted with one or more R$^{16}$ substituents.

Embodiment 5

The compound of embodiment 1, wherein the compound of formula (I) is a compound of formula (1-4):

(1-4)

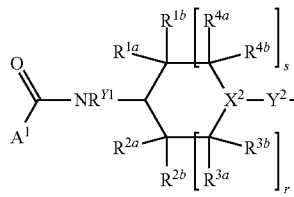

or a pharmaceutically acceptable salt thereof;
wherein:
A$^1$ is a substituent of formula (A$^1$-a)

(A$^1$-a)

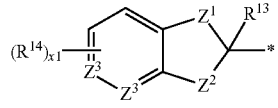

A$^2$ is C$_6$-C$_{10}$ aryl optionally substituted with one or more R$^{16}$ substituents; or 5-10 membered heteroaryl optionally substituted with one or more R$^{16}$ substituents;
R$^{11a}$ and R$^{11b}$ are both hydrogen; and
R$^{12a}$ and R$^{12b}$ are both hydrogen.

Embodiment 6

The compound of embodiment 1, wherein the compound of formula (I) is a compound of formula (2-2):

(2-2)

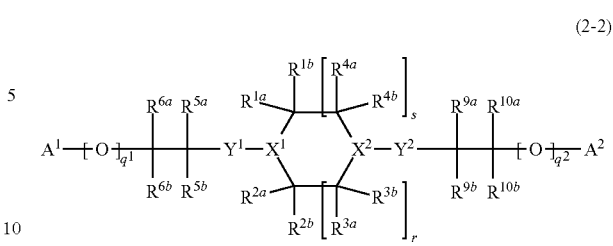

or a pharmaceutically acceptable salt thereof;
wherein:
A$^1$ is selected from the group consisting of:
a substituent of formula (A$^1$-a)

(A$^1$-a)

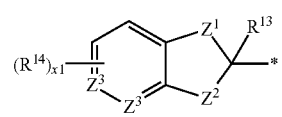

C$_6$-C$_{10}$ aryl optionally substituted with one or more R$^{14}$ substituents; and
5-10 membered heteroaryl optionally substituted with one or more R$^{14}$ substituents;
and
A$^2$ is selected from the group consisting of:
a substituent of formula (A$^2$-a)

(A$^2$-a)

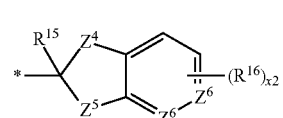

C$_6$-C$_{10}$ aryl optionally substituted with one or more R$^{16}$ substituents; and
5-10 membered heteroaryl optionally substituted with one or more R$^{16}$ substituents.

Embodiment 7

The compound of embodiment 1, wherein the compound of formula (I) is a compound of formula (2-3):

(2-3)

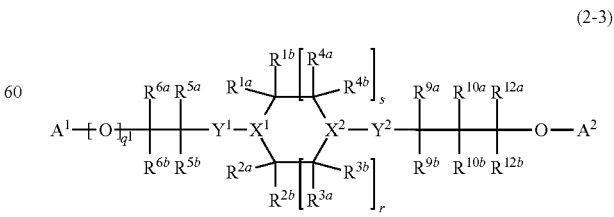

or a pharmaceutically acceptable salt thereof;

wherein:
A$^1$ is selected from the group consisting of:
a substituent of formula (A$^1$-a)

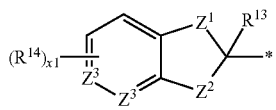
(A$^1$-a)

C$_6$-C$_{10}$ aryl optionally substituted with one or more R$^{14}$ substituents; and
5-10 membered heteroaryl optionally substituted with one or more R$^{14}$ substituents;
and
A$^2$ is C$_6$-C$_{10}$ aryl optionally substituted with one or more R$^{16}$ substituents; or 5-10 membered heteroaryl optionally substituted with one or more R$^{16}$ substituents.

Embodiment 8

The compound of embodiment 1, wherein the compound of formula (I) is a compound of formula (2-4):

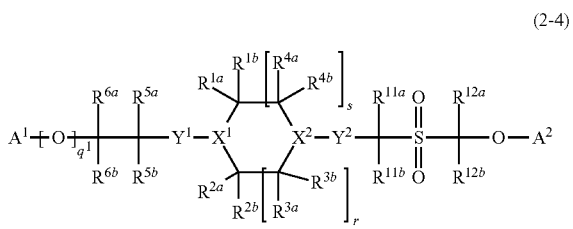
(2-4)

or a pharmaceutically acceptable salt thereof;
wherein:
A$^1$ is selected from the group consisting of:
a substituent of formula (A$^1$-a)

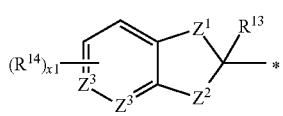
(A$^1$-a)

C$_6$-C$_{10}$ aryl optionally substituted with one or more R$^{14}$ substituents; and
5-10 membered heteroaryl optionally substituted with one or more R$^{14}$ substituents;
A$^2$ is C$_6$-C$_{10}$ aryl optionally substituted with one or more R$^{16}$ substituents; or 5-10 membered heteroaryl optionally substituted with one or more R$^{16}$ substituents;
R$^{11a}$ and R$^{11b}$ are both hydrogen; and
R$^{12a}$ and R$^{12b}$ are both hydrogen.

Embodiment 9

The compound of embodiment 1, wherein the compound of formula (I) is a compound of formula (3-3):

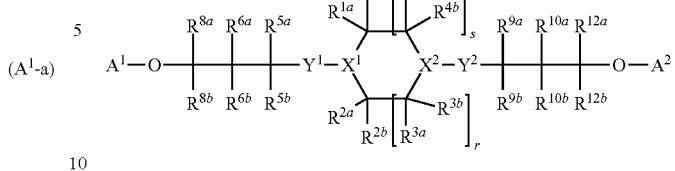
(3-3)

or a pharmaceutically acceptable salt thereof;
wherein:
A$^1$ is C$_6$-C$_{10}$ aryl optionally substituted with one or more R$^{14}$ substituents; or 5-10 membered heteroaryl optionally substituted with one or more R$^{14}$ substituents;
and
A$^2$ is C$_6$-C$_{10}$ aryl optionally substituted with one or more R$^{16}$ substituents; or 5-10 membered heteroaryl optionally substituted with one or more R$^{16}$ substituents.

Embodiment 10

The compound of embodiment 1, wherein the compound of formula (I) is a compound of formula (3-4):

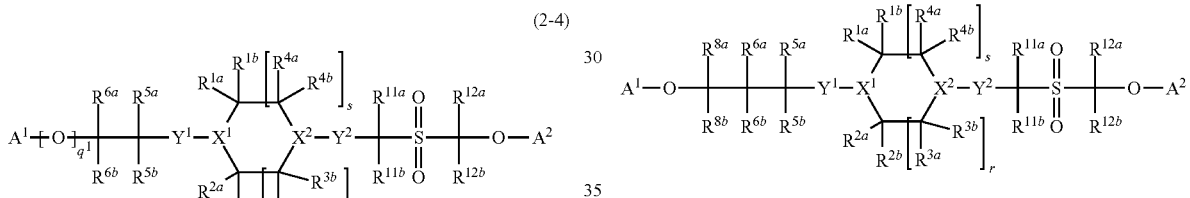
(3-4)

or a pharmaceutically acceptable salt thereof;
wherein:
A$^1$ is C$_6$-C$_{10}$ aryl optionally substituted with one or more R$^{14}$ substituents; or 5-10 membered heteroaryl optionally substituted with one or more R$^{14}$ substituents;
A$^2$ is C$_6$-C$_{10}$ aryl optionally substituted with one or more R$^{16}$ substituents; or 5-10 membered heteroaryl optionally substituted with one or more R$^{16}$ substituents;
R$^{11a}$ and R$^{11b}$ are both hydrogen; and
R$^{12a}$ and R$^{12b}$ are both hydrogen.

Embodiment 11

The compound of embodiment 1, wherein the compound of formula (I) is a compound of formula (4-4):

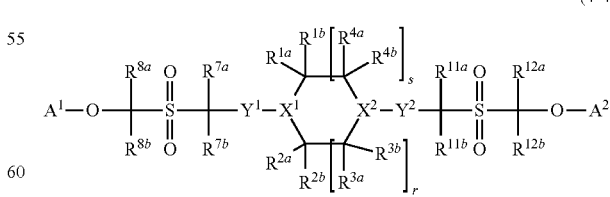
(4-4)

or a pharmaceutically acceptable salt thereof;
wherein:
A$^1$ is C$_6$-C$_{10}$ aryl optionally substituted with one or more R$^{14}$ substituents; or 5-10 membered heteroaryl optionally substituted with one or more R$^{14}$ substituents;

$A^2$ is $C_6$-$C_{10}$ aryl optionally substituted with one or more $R^{16}$ substituents; or 5-10 membered heteroaryl optionally substituted with one or more $R^{16}$ substituents;
$R^{7a}$ and $R^{7b}$ are both hydrogen;
$R^{8a}$ and $R^{8b}$ are both hydrogen;
$R^{11a}$ and $R^{11b}$ are both hydrogen; and
$R^{12a}$ and $R^{12b}$ are both hydrogen.

Embodiment 12

A compound of formula (II):

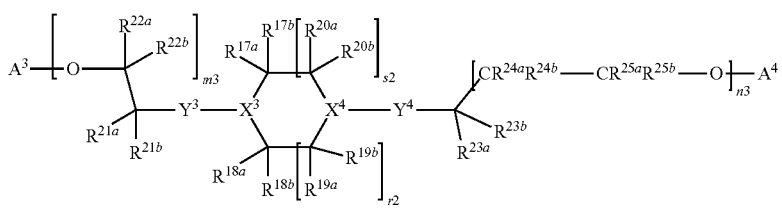

(II)

or a pharmaceutically acceptable salt thereof;
wherein:
m3 is 0 or 1;
n3 is 0 or 1;
r2 is 0, 1, or 2;
s2 is 0, 1, or 2;
$X^3$ is CH or N;
$X^4$ is CH or N;
provided that at least one of $X^3$ and $X^4$ is CH;
$Y^3$ is selected from the group consisting of a bond, $NR^{Y3}$, and O;
wherein $R^{Y3}$ is hydrogen or $C_1$-$C_6$ alkyl;
$Y^4$ is selected from the group consisting of a bond, $NR^{Y4}$, and O;
wherein $R^{Y4}$ is hydrogen or $C_1$-$C_6$ alkyl;
provided that:
when $X^3$ is N, then $Y^3$ is a bond and m3 is 1;
when $X^4$ is N, then $Y^4$ is a bond and n3 is 1;
$A^3$ is selected from the group consisting of:
a substituent of the formula ($A^3$-a)

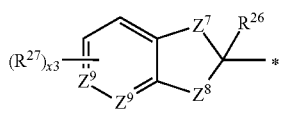

($A^3$-a)

wherein
represents the attachment point to the remainder of the molecule; $Z^7$ is selected from the group consisting of $CR^{Z7-1}R^{Z7-2}$, $NR^{Z7-2}$, O, S, and $—CR^{Z7-1}=CR^{Z7-1}—$;
wherein
$R^{Z7-1}$ is H or $R^{27}$; and
$R^{Z7-2}$ is H or $R^{27}$;
$Z^8$ is selected from the group consisting of $CR^{Z8-1}R^{Z8-2}$, $NR^{Z8-2}$; O, S, and $—CR^{Z8-1}=CR^{Z8-1}—$;
wherein
$R^{Z8-1}$ is H or $R^{27}$; and
$R^{Z8-2}$ is H or $R^{27}$;
$Z^9$, independently at each occurrence, is C or N, provided that at least one $Z^9$ is C;

$R^{26}$ is hydrogen or $R^{27}$, or $R^{26}$ and $R^{Z7-2}$ are taken together to form a double bond between the carbon atom bearing $R^{26}$ and $Z^7$; and
x3 is 0, 1, 2, 3, or 4, provided than when one $Z^9$ is N, then x3 is not 4;
$C_6$-$C_{10}$ aryl optionally with one or more $R^{27}$ substituent; and
5-10 membered heteroaryl optionally substituted with one or more $R^{27}$ substituent;
$R^{27}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —$NH_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —$NR^{27-a}R^{27-b}$, —CN, —C(O)OH, —C(O)O($C_1$-$C_6$ alkyl), —C(O)O($C_1$-$C_6$ haloalkyl), —C(O)$NH_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)$NR^{27-a}R^{27-b}$, —S(O)$_2$OH, —S(O)$_2$O($C_1$-$C_6$ alkyl), —S(O)$_2$O($C_1$-$C_6$ haloalkyl), —S(O)$_2NH_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2NR^{27-a}R^{27-b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);
wherein $R^{27-a}$ and $R^{27-b}$ are taken together with the nitrogen atom which bears them to form a 3-10 membered heterocycle;
$A^4$ is selected from the group consisting of:
a substituent of the formula ($A^4$-a)

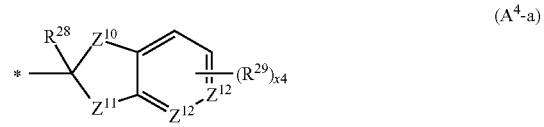

($A^4$-a)

wherein
represents the attachment point to the remainder of the molecule;

$Z^{10}$ is selected from the group consisting of $CR^{Z10-1}R^{Z10-2}$, $NR^{Z10-2}$, O, S, and $-CR^{Z10-1}=CR^{Z10-1}-$;
wherein
$R^{Z10-1}$ is H or $R^{29}$; and
$R^{Z10-2}$ is H or $R^{29}$;
$Z^{11}$ is selected from the group consisting of $CR^{Z11-1}R^{Z11-2}$, $NR^{Z11-2}$, O, S, and $-CR^{Z11-1}=CR^{Z11-1}-$;
wherein
$R^{Z11-1}$ is H or $R^{29}$; and
$R^{Z11-2}$ is H or $R^{29}$;
$Z^{12}$, independently at each occurrence, is C or N, provided that at least one $Z^{12}$ is C;
$R^{28}$ is hydrogen or $R^{29}$, or $R^{28}$ and $R^{Z10-2}$ are taken together to form a double bond between the carbon atom bearing $R^{28}$ and $Z^{10}$; and
x4 is 0, 1, 2, 3, or 4, provided than when one $Z^{12}$ is N, then x4 is not 4;
$C_6$-$C_{10}$ aryl optionally substituted with one or more $R^{29}$ substituent; and
5-10 membered heteroaryl optionally substituted with one or more $R^{29}$ substituent;
$R^{29}$ is selected, independently at each occurrence, from the group consisting of halogen, $C_1$-$C_6$ alkyl, $C_1$-$C_6$ haloalkyl, $-OH$, $-O(C_1$-$C_6$ alkyl), $-O(C_1$-$C_6$ haloalkyl), $-SH$, $-S(C_1$-$C_6$ alkyl), $-S(C_1$-$C_6$ haloalkyl), $-NH_2$, $-NH(C_1$-$C_6$ alkyl), $-NH(C_1$-$C_6$ haloalkyl), $-N(C_1$-$C_6$ alkyl)$_2$, $-N(C_1$-$C_6$ haloalkyl)$_2$, $-NR^{29-a}R^{29-b}$, $-CN$, $-C(O)OH$, $-C(O)O(C_1$-$C_6$ alkyl), $-C(O)O(C_1$-$C_6$ haloalkyl), $-C(O)NH_2$, $-C(O)NH(C_1$-$C_6$ alkyl), $-C(O)NH(C_1$-$C_6$ haloalkyl), $-C(O)N(C_1$-$C_6$ alkyl)$_2$, $-C(O)N(C_1$-$C_6$ haloalkyl)$_2$, $-C(O)NR^{29-a}R^{29-b}$, $-S(O)_2OH$, $-S(O)_2O(C_1$-$C_6$ alkyl), $-S(O)_2O(C_1$-$C_6$ haloalkyl), $-S(O)_2NH_2$, $-S(O)_2NH(C_1$-$C_6$ alkyl), $-S(O)_2NH(C_1$-$C_6$ haloalkyl), $-S(O)_2N(C_1$-$C_6$ alkyl)$_2$, $-S(O)_2N(C_1$-$C_6$ haloalkyl)$_2$, $-S(O)_2NR^{29-a}R^{29-b}$, $-OC(O)H$, $-OC(O)(C_1$-$C_6$ alkyl), $-OC(O)(C_1$-$C_6$ haloalkyl), $-N(H)C(O)H$, $-N(H)C(O)(C_1$-$C_6$ alkyl), $-N(H)C(O)(C_1$-$C_6$ haloalkyl), $-N(C_1$-$C_6$ alkyl)C(O)H, $-N(C_1$-$C_6$ alkyl)C(O)(C_1$-$C_6$ alkyl), $-N(C_1$-$C_6$ alkyl)C(O)(C_1$-$C_6$ haloalkyl), $-N(C_1$-$C_6$ haloalkyl)C(O)H, $-N(C_1$-$C_6$ haloalkyl)C(O)(C_1$-$C_6$ alkyl), $-N(C_1$-$C_6$ haloalkyl)C(O)(C_1$-$C_6$ haloalkyl), $-OS(O)_2(C_1$-$C_6$ alkyl), $-OS(O)_2(C_1$-$C_6$ haloalkyl), $-N(H)S(O)_2(C_1$-$C_6$ alkyl), $-N(H)S(O)_2(C_1$-$C_6$ haloalkyl), $-N(C_1$-$C_6$ alkyl)S(O)_2(C_1$-$C_6$ alkyl), $-N(C_1$-$C_6$ alkyl)S(O)_2(C_1$-$C_6$ haloalkyl), $-N(C_1$-$C_6$ haloalkyl)S(O)_2(C_1$-$C_6$ alkyl), and $-N(C_1$-$C_6$ haloalkyl)S(O)_2(C_1$-$C_6$ haloalkyl);
wherein $R^{29-a}$ and $R^{29-b}$ are taken together with the nitrogen atom which bears them to form a 3-10 membered heterocycle;
$R^{17a}$ and $R^{17b}$ are independently selected from the group consisting of hydrogen, $C_1$-$C_6$ alkyl, and halogen;
$R^{18a}$ and $R^{18b}$ are independently selected from the group consisting of hydrogen, $C_1$-$C_6$ alkyl, and halogen;
when present, $R^{19a}$ and $R^{19b}$ are independently at each occurrence selected from the group consisting of hydrogen, $C_1$-$C_6$ alkyl, and halogen;
when present, $R^{20a}$ and $R^{20b}$ are independently at each occurrence selected from the group consisting of hydrogen, $C_1$-$C_6$ alkyl, and halogen;
or alternatively, $R^{17a}$ and $R^{18a}$ are taken together to form a $C_1$-$C_6$ alkylene moiety;
or alternatively, $R^{17a}$ and an $R^{19a}$ moiety, when present, are taken together to form a $C_1$-$C_6$ alkylene moiety, and $R^{17b}$ and the $R^{19b}$ in the geminal position to the $R^{19a}$ taken together with $R^{17a}$, are both hydrogen;
or alternatively, an $R^{19a}$ moiety, when present, and an $R^{20a}$ moiety, when present, are taken together to form a $C_1$-$C_6$ alkylene moiety, and the $R^{19b}$ in the geminal position to the $R^{19a}$ taken together with the $R^{20a}$ moiety and the $R^{20b}$ in the geminal position to the $R^{20a}$ taken together with the $R^{19a}$ moiety, are both hydrogen;
$R^{21a}$ and $R^{21b}$ are taken together to form an oxo (=O) substituent or an imido (=NH) substituent, or alternatively, $R^{21a}$ and $R^{21b}$ are both hydrogen;
when present, $R^{22a}$ and $R^{22b}$ are both hydrogen;
$R^{23a}$ and $R^{23b}$ are taken together to form an oxo (=O) substituent or an imido (=NH) substituent, or alternatively, $R^{23a}$ and $R^{23b}$ are both hydrogen;
when present, $R^{24a}$ is selected from the group consisting of hydrogen, $-OH$, and $-NH_2$;
or alternatively, $R^{24a}$ and $R^{Y4}$ are taken together to form a #—C(=O)—O— group, wherein # represent the attachment point to the nitrogen atom bearing $R^{Y4}$;
when present, $R^{24b}$ is hydrogen; and
when present, $R^{25a}$ and $R^{25b}$ are both hydrogen;
or alternatively, $R^{25a}$, when present, and one $R^{29}$ of $A^4$ are taken together with the atoms connecting them to form a 5-6 membered heterocycloalkenyl optionally substituted with one or more $R^{29}$ substituent, and $R^{25b}$ is H;
or alternatively, $R^{25a}$, when present, $R^{25b}$, when present, and one $R^{29}$ of $A^4$ are taken together with the atoms connecting them to form a 5-6 membered heteroaryl optionally substituted with one or more $R^{29}$ substituent;
and further provided that one of (i), (ii), (iii) and (iv) applies:
(i) when m3 is 0 and n3 is 0, then:
$X^3$ is CH and $Y^3$ is $NR^{Y3}$;
$X^4$ is CH and $Y^4$ is $NR^{Y4}$;
$R^{21a}$ and $R^{21b}$ are taken together to form an oxo (=O) substituent;
$R^{23a}$ and $R^{23b}$ are taken together to form an oxo (=O) substituent;
$A^3$ is a substituent of the formula ($A^3$-a)

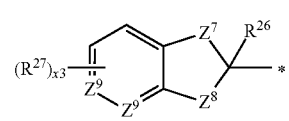

(A³-a)

wherein
represents the attachment point to the remainder of the molecule;
$Z^7$ is selected from the group consisting of $CR^{Z7-1}R^{Z7-2}$, $NR^{Z7-2}$, O, S, and $-CR^{Z7-1}=CR^{Z7-1}-$;
wherein
$R^{Z7-1}$ is H or $R^{27}$; and
$R^{Z7-2}$ is H or $R^{27}$;
$Z^8$ is selected from the group consisting of $CR^{Z8-1}R^{Z8-2}$, $NR^{Z8-2}$, O, S, and $-CR^{Z8-1}=CR^{Z8-1}-$;
wherein
$R^{Z8}-1$ is H or $R^{27}$; and
$R^{Z8-2}$ is H or $R^{27}$;

$Z^9$, independently at each occurrence, is C or N, provided that at least one $Z^9$ is C;

$R^{26}$ is hydrogen or $R^{27}$, or $R^{26}$ and $R^{27-2}$ are taken together to form a double bond between the carbon atom bearing $R^{26}$ and $Z^7$;

$R^{27}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —$NH_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —$NR^{27-a}R^{27-b}$, —CN, —C(O)OH, —C(O)O($C_1$-$C_6$ alkyl), —C(O)O($C_1$-$C_6$ haloalkyl), —C(O)$NH_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)$NR^{27-a}R^{27-b}$, —S(O)$_2$OH, —S(O)$_2$O($C_1$-$C_6$ alkyl), —S(O)$_2$O($C_1$-$C_6$ haloalkyl), —S(O)$_2$$NH_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$$NR^{27-a}R^{27-b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);

wherein $R^{27-a}$ and $R^{27-b}$ are taken together with the nitrogen atom which bears them to form a 3-10 membered heterocycle;

x3 is 0, 1, 2, 3, or 4, provided than when one $Z^9$ is N, then x3 is not 4;

$A^4$ is a substituent of the formula ($A^4$-a)

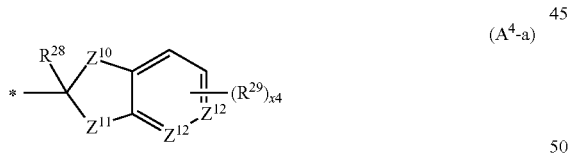

wherein
represents the attachment point to the remainder of the molecule; $Z^{10}$ is selected from the group consisting of $CR^{Z10-1}R^{Z10-2}$, $NR^{Z10-2}$, O, S, and —$CR^{Z10-1}$=$CR^{Z10-1}$—;
wherein
$R^{Z10-1}$ is H or $R^{29}$; and
$R^{Z10-2}$ is H or $R^{29}$;
$Z^{11}$ is selected from the group consisting of $CR^{Z11-1}R^{Z11-2}$, $NR^{Z11-2}$; O, S, and —$CR^{Z11-1}$=$CR^{Z11-1}$—;
wherein
$R^{Z11-1}$ is H or $R^{29}$; and
$R^{Z11-2}$ is H or $R^{29}$;
$Z^{12}$, independently at each occurrence, is C or N, provided that at least one $Z^{12}$ is C;

$R^{28}$ is hydrogen or $R^{29}$, or $R^{28}$ and $R^{Z10-2}$ are taken together to form a double bond between the carbon atom bearing $R^{28}$ and $Z^{10}$;

$R^{29}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —$NH_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —$NR^{29-a}R^{29-b}$, —CN, —C(O)OH, —C(O)O($C_1$-$C_6$ alkyl), —C(O)O($C_1$-$C_6$ haloalkyl), —C(O)$NH_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)$NR^{29-a}R^{29-b}$, —S(O)$_2$OH, —S(O)$_2$O($C_1$-$C_6$ alkyl), —S(O)$_2$O($C_1$-$C_6$ haloalkyl), —S(O)$_2$$NH_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$$NR^{29-a}R^{29-b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);

wherein $R^{29-a}$ and $R^{29-b}$ are taken together with the nitrogen atom which bears them to form a 3-10 membered heterocycle;

x4 is 0, 1, 2, 3, or 4, provided than when one $Z^{12}$ is N, then x4 is not 4; and provided that $A^3$ and $A^4$ are not both simultaneously a moiety selected from group consisting of:

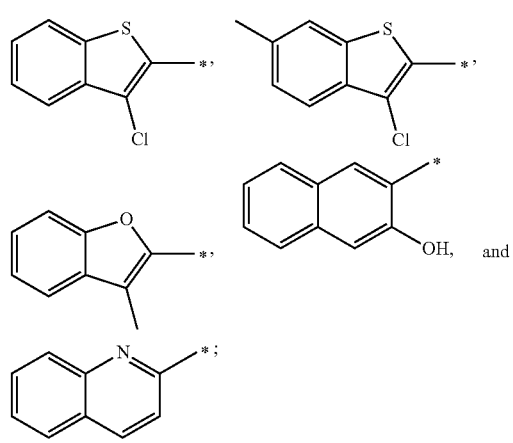

wherein the * represents the attachment point to the remainder of the molecule;

(ii) when m3 is 0 and n3 is 1, then:
r2 is 1 or 2;
s2 is 1 or 2;
$X^3$ is CH and $Y^3$ is $NR^{Y3}$;

$R^{21a}$ and $R^{21b}$ are taken together to form an oxo (=O) substituent;

$R^{24a}$ is selected from the group consisting of hydrogen, —OH, and —NH$_2$;

$A^3$ is a substituent of the formula ($A^3$-a)

$$(A^3\text{-a})$$

[Structure: $(R^{27})_{x3}$ attached to a ring containing $Z^9$, $Z^9$, $Z^8$, $Z^7$, with $R^{26}$ and attachment point *]

wherein

* represents the attachment point to the remainder of the molecule;

$Z^7$ is selected from the group consisting of $CR^{Z7-1}R^{Z7-2}$, $NR^{Z7-2}$, O, S, and —$CR^{Z7-1}$=$CR^{Z7-1}$—;
  wherein
  $R^{Z7-1}$ is H or $R^{27}$; and
  $R^{Z7-2}$ is H or $R^{27}$;

$Z^8$ is selected from the group consisting of $CR^{Z8-1}R^{Z8-2}$, $NR^{Z8-2}$; O, S, and —$CR^{Z8-1}$=$CR^{Z8-1}$—;
  wherein
  $R^{Z8-1}$ is H or $R^{27}$; and
  $R^{Z8-2}$ is H or $R^{27}$;

$Z^9$, independently at each occurrence, is C or N, provided that at least one $Z^9$ is C;

$R^{26}$ is hydrogen or $R^{27}$, or $R^{26}$ and $R^{Z7-2}$ are taken together to form a double bond between the carbon atom bearing $R^{26}$ and $Z^7$;

$R^{27}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —NH$_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —NR$^{27\text{-}a}$R$^{27\text{-}b}$, —CN, —C(O)OH, —C(O)O($C_1$-$C_6$ alkyl), —C(O)O($C_1$-$C_6$ haloalkyl), —C(O)NH$_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)NR$^{27\text{-}a}$R$^{27\text{-}b}$, —S(O)$_2$OH, —S(O)$_2$O($C_1$-$C_6$ alkyl), —S(O)$_2$O($C_1$-$C_6$ haloalkyl), —S(O)$_2$NH$_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$NR$^{27\text{-}a}$R$^{27\text{-}b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);
  wherein $R^{27\text{-}a}$ and $R^{27\text{-}b}$ are taken together with the nitrogen atom which bears them to form a 3-10 membered heterocycle;

x3 is 0, 1, 2, 3, or 4, provided than when one $Z^9$ is N, then x3 is not 4;

$A^4$ is $C_6$-$C_{10}$ aryl optionally substituted with one or more $R^{29}$ substituent, or 5-10 membered heteroaryl optionally substituted with one or more $R^{29}$ substituent;

$R^{29}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —NH$_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —NR$^{29\text{-}a}$R$^{29\text{-}b}$, —CN, —C(O)OH, —C(O)O($C_1$-$C_6$ alkyl), —C(O)O($C_1$-$C_6$ haloalkyl), —C(O)NH$_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)NR$^{29\text{-}a}$R$^{29\text{-}b}$, —S(O)$_2$OH, —S(O)$_2$O($C_1$-$C_6$ alkyl), —S(O)$_2$O($C_1$-$C_6$ haloalkyl), —S(O)$_2$NH$_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$NR$^{29\text{-}a}$R$^{29\text{-}b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);
  wherein $R^{29\text{-}a}$ and $R^{29\text{-}b}$ are taken together with the nitrogen atom which bears them to form a 3-10 membered heterocycle;

provided that when $R^{23a}$ and $R^{23b}$ are taken together to form an oxo (=O) substituent, then $R^{24a}$ is —OH or —NH$_2$;

(iii) when m3 is 1 and n3 is 0, then:

$X^4$ is CH and $Y^4$ is NR$^{Y4}$;

$R^{21a}$ and $R^{21b}$ are taken together to form an oxo (=O) substituent or an imido (=NH) substituent;

$R^{23a}$ and $R^{23b}$ are taken together to form an oxo (=O) substituent;

$A^3$ is $C_6$-$C_{10}$ aryl optionally substituted with one or more $R^{27}$ substituent, or 5-10 membered heteroaryl optionally substituted with one or more $R^{27}$ substituent;

$R^{27}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —NH$_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —NR$^{27\text{-}a}$R$^{27\text{-}b}$, —CN, —C(O)OH, —C(O)O($C_1$-$C_6$ alkyl), —C(O)O($C_1$-$C_6$ haloalkyl), —C(O)NH$_2$, —C(O) NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)NR$^{27\text{-}a}$R$^{27\text{-}b}$, —S(O)$_2$OH, —S(O)$_2$O($C_1$-$C_6$ alkyl), —S(O)$_2$O($C_1$-$C_6$ haloalkyl), —S(O)$_2$NH$_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)₂N(C₁-C₆ haloalkyl)₂, —S(O)₂NR²⁷⁻ᵃR²⁷⁻ᵇ, —OC(O)H, —OC(O)(C₁-C₆ alkyl), —OC(O)(C₁-C₆ haloalkyl), —N(H)C(O)H, —N(H)C(O)(C₁-C₆ alkyl), —N(H)C(O)(C₁-C₆ haloalkyl), —N(C₁-C₆ alkyl)C(O)H, —N(C₁-C₆ alkyl)C(O)(C₁-C₆ alkyl), —N(C₁-C₆ alkyl)C(O)(C₁-C₆ haloalkyl), —N(C₁-C₆ haloalkyl)C(O)H, —N(C₁-C₆ haloalkyl)C(O)(C₁-C₆ alkyl), —N(C₁-C₆ haloalkyl)C(O)(C₁-C₆ haloalkyl), —OS(O)₂(C₁-C₆ alkyl), —OS(O)₂(C₁-C₆ haloalkyl), —N(H)S(O)₂(C₁-C₆ alkyl), —N(H)S(O)₂(C₁-C₆ haloalkyl), —N(C₁-C₆ alkyl)S(O)₂(C₁-C₆ alkyl), —N(C₁-C₆ alkyl)S(O)₂(C₁-C₆ haloalkyl), —N(C₁-C₆ haloalkyl)S(O)₂(C₁-C₆ alkyl), and —N(C₁-C₆ haloalkyl)S(O)₂(C₁-C₆ haloalkyl);

wherein $R^{27-a}$ and $R^{27-b}$ are taken together with the nitrogen atom which bears them to form a 3-10 membered heterocycle;

$A^4$ is a substituent of the formula ($A^4$-a)

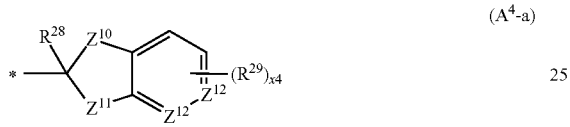

(A⁴-a)

wherein represents the attachment point to the remainder of the molecule; $Z^{10}$ is selected from the group consisting of $CR^{Z10-1}R^{Z10-2}$, $NR^{Z10-2}$, O, S, and —$CR^{Z10-1}$=$CR^{Z10-1}$—;

wherein $R^{Z10-1}$ is H or $R^{29}$; and $R^{Z10-2}$ is H or $R^{29}$;

$Z^{11}$ is selected from the group consisting of $CR^{Z11-1}R^{Z11-2}$, $NR^{Z11-2}$; O, S, and —$CR^{Z11-1}$=$CR^{Z11-1}$—;

wherein $R^{Z11-1}$ is H or $R^{29}$; and $R^{Z11-2}$ is H or $R^{29}$;

$Z^{12}$, independently at each occurrence, is C or N, provided that at least one $Z^{12}$ is C;

$R^{28}$ is hydrogen or $R^{29}$, or $R^{28}$ and $R^{Z10-2}$ are taken together to form a double bond between the carbon atom bearing $R^{28}$ and $Z^{10}$; $R^{29}$ is selected, independently at each occurrence, from the group consisting of halogen, C₁-C₆ alkyl, C₁-C₆ haloalkyl, —OH, —O(C₁-C₆ alkyl), —O(C₁-C₆ haloalkyl), —SH, —S(C₁-C₆ alkyl), —S(C₁-C₆ haloalkyl), —NH₂, —NH(C₁-C₆ alkyl), —NH(C₁-C₆ haloalkyl), —N(C₁-C₆ alkyl)₂, —N(C₁-C₆ haloalkyl)₂, —NR²⁹⁻ᵃR²⁹⁻ᵇ, —CN, —C(O)OH, —C(O)O(C₁-C₆ alkyl), —C(O)O(C₁-C₆ haloalkyl), —C(O)NH₂, —C(O)NH(C₁-C₆ alkyl), —C(O)NH(C₁-C₆ haloalkyl), —C(O)N(C₁-C₆ alkyl)₂, —C(O)N(C₁-C₆ haloalkyl)₂, —C(O)NR²⁹⁻ᵃR²⁹⁻ᵇ, —S(O)₂OH, —S(O)₂O(C₁-C₆ alkyl), —S(O)₂O(C₁-C₆ haloalkyl), —S(O)₂NH₂, —S(O)₂NH(C₁-C₆ alkyl), —S(O)₂NH(C₁-C₆ haloalkyl), —S(O)₂N(C₁-C₆ alkyl)₂, —S(O)₂N(C₁-C₆ haloalkyl)₂, —S(O)₂NR²⁹⁻ᵃR²⁹⁻ᵇ, —OC(O)H, —OC(O)(C₁-C₆ alkyl), —OC(O)(C₁-C₆ haloalkyl), —N(H)C(O)H, —N(H)C(O)(C₁-C₆ alkyl), —N(H)C(O)(C₁-C₆ haloalkyl), —N(C₁-C₆ alkyl)C(O)H, —N(C₁-C₆ alkyl)C(O)(C₁-C₆ alkyl), —N(C₁-C₆ alkyl)C(O)(C₁-C₆ haloalkyl), —N(C₁-C₆ haloalkyl)C(O)H, —N(C₁-C₆ haloalkyl)C(O)(C₁-C₆ alkyl), —N(C₁-C₆ haloalkyl)C(O)(C₁-C₆ haloalkyl), —OS(O)₂(C₁-C₆ alkyl), —OS(O)₂(C₁-C₆ haloalkyl), —N(H)S(O)₂(C₁-C₆ alkyl), —N(H)S(O)₂(C₁-C₆ haloalkyl), —N(C₁-C₆ alkyl)S(O)₂(C₁-C₆ alkyl), —N(C₁-C₆ alkyl)S(O)₂(C₁-C₆ haloalkyl), —N(C₁-C₆ haloalkyl)S(O)₂(C₁-C₆ alkyl), and —N(C₁-C₆ haloalkyl)S(O)₂(C₁-C₆ haloalkyl);

wherein $R^{29-a}$ and $R^{29-b}$ are taken together with the nitrogen atom which bears them to form a 3-10 membered heterocycle;

x4 is 0, 1, 2, 3, or 4, provided than when one $Z^{12}$ is N, then x4 is not 4;

(iv) when m3 is 1 and n3 is 1, then:

$R^{21a}$ and $R^{21b}$ are taken together to form an oxo (=O) substituent or an imido (=NH) substituent;

$A^3$ is C₆-C₁₀ aryl optionally substituted with one or more $R^{27}$ substituent, or 5-10 membered heteroaryl optionally substituted with one or more $R^{27}$ substituent;

$R^{27}$ is selected, independently at each occurrence, from the group consisting of halogen, C₁-C₆ alkyl, C₁-C₆ haloalkyl, —OH, —O(C₁-C₆ alkyl), —O(C₁-C₆ haloalkyl), —SH, —S(C₁-C₆ alkyl), —S(C₁-C₆ haloalkyl), —NH₂, —NH(C₁-C₆ alkyl), —NH(C₁-C₆ haloalkyl), —N(C₁-C₆ alkyl)₂, —N(C₁-C₆ haloalkyl)₂, —NR²⁷⁻ᵃR²⁷⁻ᵇ, —CN, —C(O)OH, —C(O)O(C₁-C₆ alkyl), —C(O)O(C₁-C₆ haloalkyl), —C(O)NH₂, —C(O)NH(C₁-C₆ alkyl), —C(O)NH(C₁-C₆ haloalkyl), —C(O)N(C₁-C₆ alkyl)₂, —C(O)N(C₁-C₆ haloalkyl)₂, —C(O)NR²⁷⁻ᵃR²⁷⁻ᵇ, —S(O)₂OH, —S(O)₂O(C₁-C₆ alkyl), —S(O)₂O(C₁-C₆ haloalkyl), —S(O)₂NH₂, —S(O)₂NH(C₁-C₆ alkyl), —S(O)₂NH(C₁-C₆ haloalkyl), —S(O)₂N(C₁-C₆ alkyl)₂, —S(O)₂N(C₁-C₆ haloalkyl)₂, —S(O)₂NR²⁷⁻ᵃR²⁷⁻ᵇ, —OC(O)H, —OC(O)(C₁-C₆ alkyl), —OC(O)(C₁-C₆ haloalkyl), —N(H)C(O)H, —N(H)C(O)(C₁-C₆ alkyl), —N(H)C(O)(C₁-C₆ haloalkyl), —N(C₁-C₆ alkyl)C(O)H, —N(C₁-C₆ alkyl)C(O)(C₁-C₆ alkyl), —N(C₁-C₆ alkyl)C(O)(C₁-C₆ haloalkyl), —N(C₁-C₆ haloalkyl)C(O)H, —N(C₁-C₆ haloalkyl)C(O)(C₁-C₆ alkyl), —N(C₁-C₆ haloalkyl)C(O)(C₁-C₆ haloalkyl), —OS(O)₂(C₁-C₆ alkyl), —OS(O)₂(C₁-C₆ haloalkyl), —N(H)S(O)₂(C₁-C₆ alkyl), —N(H)S(O)₂(C₁-C₆ haloalkyl), —N(C₁-C₆ alkyl)S(O)₂(C₁-C₆ alkyl), —N(C₁-C₆ alkyl)S(O)₂(C₁-C₆ haloalkyl), —N(C₁-C₆ haloalkyl)S(O)₂(C₁-C₆ alkyl), and —N(C₁-C₆ haloalkyl)S(O)₂(C₁-C₆ haloalkyl);

wherein $R^{27-a}$ and $R^{27-b}$ are taken together with the nitrogen atom which bears them to form a 3-10 membered heterocycle;

$A^4$ is C₆-C₁₀ aryl optionally substituted with one or more $R^{29}$ substituent, or 5-10 membered heteroaryl optionally substituted with one or more $R^{29}$ substituent;

$R^{29}$ is selected, independently at each occurrence, from the group consisting of halogen, C₁-C₆ alkyl, C₁-C₆ haloalkyl, —OH, —O(C₁-C₆ alkyl), —O(C₁-C₆ haloalkyl), —SH, —S(C₁-C₆ alkyl), —S(C₁-C₆ haloalkyl), —NH₂, —NH(C₁-C₆ alkyl), —NH(C₁-C₆ haloalkyl), —N(C₁-C₆ alkyl)₂, —N(C₁-C₆ haloalkyl)₂, —NR²⁹⁻ᵃR²⁹⁻ᵇ, —CN, —C(O)OH, —C(O)O(C₁-C₆ alkyl), —C(O)O(C₁-C₆ haloalkyl), —C(O)NH₂, —C(O)NH(C₁-C₆ alkyl), —C(O)NH(C₁-C₆ haloalkyl), —C(O)N(C₁-C₆ alkyl)₂, —C(O)N(C₁-C₆ haloalkyl)₂, —C(O)NR$^{29-a}$R$^{29-b}$, —S(O)₂OH, —S(O)₂O(C₁-C₆ alkyl), —S(O)₂O(C₁-C₆ haloalkyl), —S(O)₂NH₂, —S(O)₂NH(C₁-C₆ alkyl), —S(O)₂NH(C₁-C₆ haloalkyl), —S(O)₂N(C₁-C₆ alkyl)₂, —S(O)₂N(C₁-C₆ haloalkyl)₂, —S(O)₂NR$^{29-a}$R$^{29-b}$, —OC(O)H, —OC(O)(C₁-C₆ alkyl), —OC(O)(C₁-C₆ haloalkyl), —N(H)C(O)H, —N(H)C(O)(C₁-C₆ alkyl), —N(H)C(O)(C₁-C₆ haloalkyl), —N(C₁-C₆ alkyl)C(O)H, —N(C₁-C₆ alkyl)C(O)(C₁-C₆ alkyl), —N(C₁-C₆ alkyl)C(O)(C₁-C₆ haloalkyl), —N(C₁-C₆ haloalkyl)C(O)H, —N(C₁-C₆ haloalkyl)C(O)(C₁-C₆ alkyl), —N(C₁-C₆ haloalkyl)C(O)(C₁-C₆ haloalkyl), —OS(O)₂(C₁-C₆ alkyl), —OS(O)₂(C₁-C₆ haloalkyl), —N(H)S(O)₂(C₁-C₆ alkyl), —N(H)S(O)₂(C₁-C₆ haloalkyl), —N(C₁-C₆ alkyl)S(O)₂(C₁-C₆ alkyl), —N(C₁-C₆ alkyl)S(O)₂(C₁-C₆ haloalkyl), —N(C₁-C₆ haloalkyl)S(O)₂(C₁-C₆ alkyl), and —N(C₁-C₆ haloalkyl)S(O)₂(C₁-C₆ haloalkyl);

wherein R$^{29-a}$ and R$^{29-b}$ are taken together with the nitrogen atom which bears them to form a 3-10 membered heterocycle;

provided that:
when one of $X^3$ or $X^4$ is N, then r2 is 1 or 2 and s2 is 1 or 2; and
when R$^{23a}$ and R$^{23b}$ are taken together to form an oxo (=O) substituent, then R$^{24a}$ is —OH or —NH₂.

Embodiment 12

A compound of formula (XX):

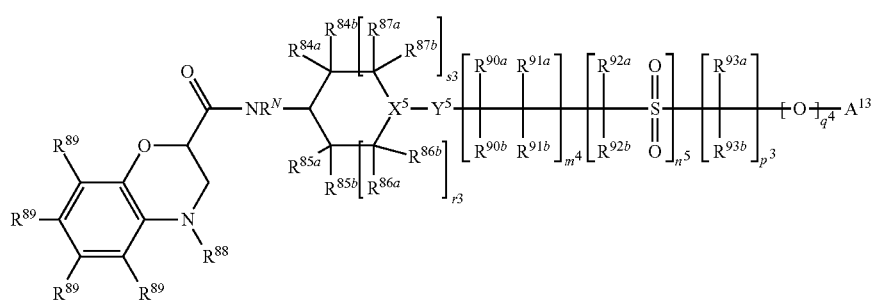

(XX)

or a pharmaceutically acceptable salt thereof;
wherein:
$X^5$ is CH or N;
$Y^5$ is selected from the group consisting of a bond, NR$^{Y5}$, and O; provided that when $X^5$ is N, then $Y^5$ is a bond;
R$^{Y5}$ is hydrogen or C₁-C₆ alkyl;
R$^N$ is hydrogen or C₁-C₆ alkyl;
$m^4$, $n^5$, $p^3$, and $q^4$, independently of each other, are 0 or 1;
r3 and s3, independently of each other, are 0, 1, or 2;
$A^{13}$ is selected from the group consisting of:
C₆-C₁₀ aryl optionally substituted with one or more R$^{95}$ substituents; and
5-10 membered heteroaryl optionally substituted with one or more R$^{95}$ substituents;
R$^{95}$ is selected, independently at each occurrence, from the group consisting of halogen, C₁-C₆ alkyl, C₁-C₆ haloalkyl, —OH, —O(C₁-C₆ alkyl), —O(C₁-C₆ haloalkyl), —SH, —S(C₁-C₆ alkyl), —S(C₁-C₆ haloalkyl), —NH₂, —NH(C₁-C₆ alkyl), —NH(C₁-C₆ haloalkyl), —N(C₁-C₆ alkyl)₂, —N(C₁-C₆ haloalkyl)₂, —NR$^{95-a}$R$^{95-b}$, —CN, —C(O)OH, —C(O)O(C₁-C₆ alkyl), —C(O)O(C₁-C₆ haloalkyl), —C(O)NH₂, —C(O)NH(C₁-C₆ alkyl), —C(O)NH(C₁-C₆ haloalkyl), —C(O)N(C₁-C₆ alkyl)₂, —C(O)N(C₁-C₆ haloalkyl)₂, —C(O)NR$^{95a}$R$^{95b}$, —S(O)₂OH, —S(O)₂O(C₁-C₆ alkyl), —S(O)₂O(C₁-C₆ haloalkyl), —S(O)₂NH₂, —S(O)₂NH(C₁-C₆ alkyl), —S(O)₂NH(C₁-C₆ haloalkyl), —S(O)₂N(C₁-C₆ alkyl)₂, —S(O)₂N(C₁-C₆ haloalkyl)₂, —S(O)₂NR$^{95a}$R$^{95b}$, —OC(O)H, —OC(O)(C₁-C₆ alkyl), —OC(O)(C₁-C₆ haloalkyl), —N(H)C(O)H, —N(H)C(O)(C₁-C₆ alkyl), —N(H)C(O)(C₁-C₆ haloalkyl), —N(C₁-C₆ alkyl)C(O)H, —N(C₁-C₆ alkyl)C(O)(C₁-C₆ alkyl), —N(C₁-C₆ alkyl)C(O)(C₁-C₆ haloalkyl), —N(C₁-C₆ haloalkyl)C(O)H, —N(C₁-C₆ haloalkyl)C(O)(C₁-C₆ alkyl), —N(C₁-C₆ haloalkyl)C(O)(C₁-C₆ haloalkyl), —OS(O)₂(C₁-C₆ alkyl), —OS(O)₂(C₁-C₆ haloalkyl), —N(H)S(O)₂(C₁-C₆ alkyl), —N(H)S(O)₂(C₁-C₆ haloalkyl), —N(C₁-C₆ alkyl)S(O)₂(C₁-C₆ alkyl), —N(C₁-C₆ alkyl)S(O)₂(C₁-C₆ haloalkyl), —N(C₁-C₆ haloalkyl)S(O)₂(C₁-C₆ alkyl), and —N(C₁-C₆ haloalkyl)S(O)₂(C₁-C₆ haloalkyl);

wherein R$^{95-a}$ and R$^{95-b}$ are taken together with the nitrogen atom which bears them to form a 3-10 membered heterocycle;

R$^{84a}$ and R$^{84b}$ are independently selected from the group consisting of hydrogen, C₁-C₆ alkyl, and halogen;

R$^{85a}$ and R$^{85b}$ are independently selected from the group consisting of hydrogen, C₁-C₆ alkyl, and halogen;

when present, R$^{86a}$ and R$^{86b}$ are independently at each occurrence selected from the group consisting of hydrogen, C₁-C₆ alkyl, and halogen;

when present, R$^{87a}$ and R$^{87b}$ are independently at each occurrence selected from the group consisting of hydrogen, C₁-C₆ alkyl, and halogen;

or, R$^{84a}$ and R$^{85a}$ are taken together to form a C₁-C₆ alkylene moiety;

or, R$^{84a}$ and an R$^{86a}$ moiety, when present, are taken together to form a C₁-C₆ alkylene moiety;

or, an R$^{86a}$ moiety, when present, and an R$^{87a}$ moiety, when present, are taken together to form a C₁-C₆ alkylene moiety;

R$^{88}$ is selected from the group consisting of hydrogen, C₁-C₆ alkyl, C₁-C₆ haloalkyl, —C(O)(C₁-C₆ alkyl), —C(O)(C₁-C₆ haloalkyl), —C(O)OH, —C(O)O(C₁-C₆ alkyl), —C(O)O(C₁-C₆ haloalkyl), —C(O)NH₂, —C(O)NH(C₁-C₆ alkyl), —C(O)NH(C₁-C₆ haloalkyl), —C(O)N(C₁-C₆ alkyl)₂, —C(O)N(C₁-C₆ haloalkyl)₂, —C(O)NR$^{88\text{-}a}$R$^{88\text{-}b}$, —S(O)$_2$OH, —S(O)$_2$O(C$_1$-C$_6$ alkyl), —S(O)$_2$O(C$_1$-C$_6$ haloalkyl), —S(O)$_2$NH$_2$, —S(O)$_2$NH(C$_1$-C$_6$ alkyl), —S(O)$_2$NH(C$_1$-C$_6$ haloalkyl), —S(O)$_2$N(C$_1$-C$_6$ alkyl)$_2$, —S(O)$_2$N(C$_1$-C$_6$ haloalkyl)$_2$, and —S(O)$_2$NR$^{88\text{-}a}$R$^{88\text{-}b}$; wherein R$^{88\text{-}a}$ and R$^{88\text{-}b}$ are taken together with the nitrogen atom which bears them to form a 3-10 membered heterocycle;

R$^{89}$ is selected, independently at each occurrence, from the group consisting of hydrogen, halogen, C$_1$-C$_6$ alkyl, C$_1$-C$_6$ haloalkyl, —OH, —O(C$_1$-C$_6$ alkyl), —O(C$_1$-C$_6$ haloalkyl), —SH, —S(C$_1$-C$_6$ alkyl), —S(C$_1$-C$_6$ haloalkyl), —NH$_2$, —NH(C$_1$-C$_6$ alkyl), —NH(C$_1$-C$_6$ haloalkyl), —N(C$_1$-C$_6$ alkyl)$_2$, —N(C$_1$-C$_6$ haloalkyl)$_2$, —NR$^{89\text{-}a}$R$^{89\text{-}b}$, —CN, —C(O)OH, —C(O)O(C$_1$-C$_6$ alkyl), —C(O)O(C$_1$-C$_6$ haloalkyl), —C(O)NH$_2$, —C(O)NH(C$_1$-C$_6$ alkyl), —C(O)NH(C$_1$-C$_6$ haloalkyl), —C(O)N(C$_1$-C$_6$ alkyl)$_2$, —C(O)N(C$_1$-C$_6$ haloalkyl)$_2$, —C(O)NR$^{89\text{-}a}$R$^{89\text{-}b}$, —S(O)$_2$OH, —S(O)$_2$O(C$_1$-C$_6$ alkyl), —S(O)$_2$O(C$_1$-C$_6$ haloalkyl), —S(O)$_2$NH$_2$, —S(O)$_2$NH(C$_1$-C$_6$ alkyl), —S(O)$_2$NH(C$_1$-C$_6$ haloalkyl), —S(O)$_2$N(C$_1$-C$_6$ alkyl)$_2$, —S(O)$_2$N(C$_1$-C$_6$ haloalkyl)$_2$, —S(O)$_2$NR$^{89\text{-}a}$R$^{89\text{-}b}$, —OC(O)H, —OC(O)(C$_1$-C$_6$ alkyl), —OC(O)(C$_1$-C$_6$ haloalkyl), —N(H)C(O)H, —N(H)C(O)(C$_1$-C$_6$ alkyl), —N(H)C(O)(C$_1$-C$_6$ haloalkyl), —N(C$_1$-C$_6$ alkyl)C(O)H, —N(C$_1$-C$_6$ alkyl)C(O)(C$_1$-C$_6$ alkyl), —N(C$_1$-C$_6$ alkyl)C(O)(C$_1$-C$_6$ haloalkyl), —N(C$_1$-C$_6$ haloalkyl)C(O)H, —N(C$_1$-C$_6$ haloalkyl)C(O)(C$_1$-C$_6$ alkyl), —N(C$_1$-C$_6$ haloalkyl)C(O)(C$_1$-C$_6$ haloalkyl), —OS(O)$_2$(C$_1$-C$_6$ alkyl), —OS(O)$_2$(C$_1$-C$_6$ haloalkyl), —N(H)S(O)$_2$(C$_1$-C$_6$ alkyl), —N(H)S(O)$_2$(C$_1$-C$_6$ haloalkyl), —N(C$_1$-C$_6$ alkyl)S(O)$_2$(C$_1$-C$_6$ alkyl), —N(C$_1$-C$_6$ alkyl)S(O)$_2$(C$_1$-C$_6$ haloalkyl), —N(C$_1$-C$_6$ haloalkyl)S(O)$_2$(C$_1$-C$_6$ alkyl), and —N(C$_1$-C$_6$ haloalkyl)S(O)$_2$(C$_1$-C$_6$ haloalkyl);

wherein R$^{89\text{-}a}$ and R$^{89\text{-}b}$ are taken together with the nitrogen atom which bears them to form a 3-10 membered heterocycle;

when present, R$^{90a}$ and R$^{90b}$ are taken together to form an oxo (=O) substituent or an imido (=NH) substituent, or alternatively, R$^{90a}$ and R$^{90b}$ are both hydrogen; when present, R$^{91a}$ is selected from the group consisting of hydrogen, —OR$^{91a\text{-}a}$, and —NR$^{91a\text{-}b}$R$^{91a\text{-}c}$;

when present, R$^{91b}$ is hydrogen;

or alternatively, R$^{91a}$ and R$^{91b}$ are taken together to form a moiety selected from the group consisting of —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, and —CH$_2$—CH$_2$—CH$_2$—CH$_2$—O—;

when present, R$^{92a}$ and R$^{92b}$ are both hydrogen;

when present, R$^{93a}$ and R$^{93b}$ are taken together to form an oxo (=O) substituent, or alternatively, R$^{93a}$ and R$^{93b}$ are both hydrogen;

R$^{91a\text{-}a}$ is selected from the group consisting of hydrogen, C$_1$-C$_6$ alkyl, and C$_1$-C$_6$ haloalkyl;

or R$^{91a\text{-}a}$ and R$^{y5}$ may be taken together to form a carbonyl (C=O) moiety; and R$^{91a\text{-}b}$ and R$^{91a\text{-}c}$, independently of each other, are selected from the group consisting of hydrogen, C$_1$-C$_6$ alkyl, and C$_1$-C$_6$ haloalkyl;

provided that when m$^4$ is 0, n$^5$ is 0, and q$^4$ is 0, then p$^3$ is 1 and A$^{13}$ is a substituent of formula (A$^{13}$-a)

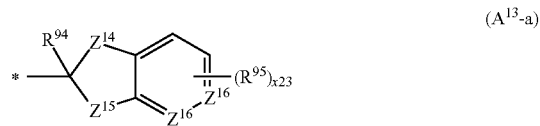

(A$^{13}$-a)

wherein
represents the attachment point to the remainder of the molecule; Z$^{14}$ is selected from the group consisting of CR$^{Z14\text{-}1}$R$^{Z14\text{-}2}$, NR$^{Z14\text{-}2}$, C(R$^{Z14\text{-}1}$R$^{Z14\text{-}2}$)N(R$^{Z14\text{-}2}$), O, C(R$^{Z14\text{-}1}$R$^{Z14\text{-}2}$)O, S, C(R$^{Z14\text{-}1}$R$^{Z14\text{-}2}$)S, and —CR$^{Z14\text{-}1}$=CR$^{Z14\text{-}1}$—;
wherein R$^{Z14\text{-}1}$ is hydrogen or R$^{16}$; and R$^{Z14\text{-}2}$ is hydrogen or R$^{95}$;

Z$^{15}$ is selected from the group consisting of CR$^{Z15\text{-}1}$R$^{Z15\text{-}2}$, NR$^{Z15\text{-}2}$, C(R$^{Z15\text{-}1}$R$^{Z15\text{-}2}$)N(R$^{Z15\text{-}2}$), O, C(R$^{Z15\text{-}1}$R$^{Z15\text{-}2}$)O, S, C(R$^{Z15\text{-}1}$R$^{Z15\text{-}2}$)S, and —CR$^{Z15\text{-}1}$=CR$^{Z15\text{-}1}$—;
wherein R$^{Z15\text{-}1}$ is hydrogen or R$^{95}$; and R$^{Z15\text{-}2}$ is hydrogen or R$^{95}$;

Z$^{16}$, independently at each occurrence, is CH, CR$^{95}$, or N;

R$^{94}$ is hydrogen or R$^{95}$, or R$^{94}$ and R$^{Z14\text{-}2}$ are taken together to form a double bond between the carbon atom bearing R$^{94}$ and Z$^{14}$, or R$^{94}$ and R$^{Z15\text{-}2}$ are taken together to form a double bond between the carbon atom bearing R$^{94}$ and Z$^{15}$; and x23 is 0, 1, 2, 3, or 4.

Embodiment 13

A compound selected from the group consisting of a compound of Table 1, or a pharmaceutically acceptable salt thereof.

Embodiment 14

A pharmaceutical composition comprising a compound of any of the preceding embodiments, or a pharmaceutically acceptable salt thereof, and a pharmaceutically acceptable carrier.

Embodiment 15

A method of treating a disease or disorder mediated by an integrated stress response (ISR) pathway in an individual in need thereof comprising administering to the individual a therapeutically effective amount of a compound of any one of embodiments 1 to 13, or a pharmaceutically acceptable salt thereof, or a therapeutically effective amount of a pharmaceutical composition of embodiment 14.

Embodiment 16

The method of embodiment 14, wherein the compound, the pharmaceutically acceptable salt, or the pharmaceutical composition is administered in combination with a therapeutically effective amount of one or more additional anti-cancer agents.

Embodiment 17

The method of embodiment 15, wherein the disease or disorder is mediated by phosphorylation of eIF2a and/or the guanine nucleotide exchange factor (GEE) activity of eIF2B.

Embodiment 18

The method of any one of embodiments 15-17, wherein the disease or disorder is mediated by a decrease in protein synthesis.

Embodiment 19

The method of any one of embodiments 15-18, wherein the disease or disorder is mediated by the expression of ATF4, CHOP or BACE-1.

Embodiment 20

The method of any of embodiments 15-19, wherein the disease or disorder is a neurodegenerative disease, an inflammatory disease, an autoimmune disease, a metabolic syndrome, a cancer, a vascular disease, an ocular disease, a musculoskeletal disease, or a genetic disorder.

Embodiment 21

The method of embodiment 20, wherein the disease is vanishing white matter disease, childhood ataxia with CNS hypomyelination, intellectual disability syndrome, Alzheimer's disease, prion disease, Creutzfeldt-Jakob disease, Parkinson's disease, amyotrophic lateral sclerosis (ALS) disease, cognitive impairment, frontotemporal dementia (FTD), traumatic brain injury, postoperative cognitive dysfunction (PCD), neuro-otological syndromes, hearing loss, Huntington's disease, stroke, chronic traumatic encephalopathy, spinal cord injury, dementias or cognitive impairment, arthritis, psoriatic arthritis, psoriasis, juvenile idiopathic arthritis, asthma, allergic asthma, bronchial asthma, tuberculosis, chronic airway disorder, cystic fibrosis, glomerulonephritis, membranous nephropathy, sarcoidosis, vasculitis, ichthyosis, transplant rejection, interstitial cystitis, atopic dermatitis or inflammatory bowel disease, Crohn's disease, ulcerative colitis, celiac disease, systemic lupus erythematosus, type 1 diabetes, multiple sclerosis, rheumatoid arthritis, alcoholic liver steatosis, obesity, glucose intolerance, insulin resistance, hyperglycemia, fatty liver, dyslipidemia, hyperlipidemia, type 2 diabetes, pancreatic cancer, breast cancer, kidney cancer, bladder cancer, prostate cancer, testicular cancer, urothelial cancer, endometrial cancer, ovarian cancer, cervical cancer, renal cancer, esophageal cancer, gastrointestinal stromal tumor (GIST), multiple myeloma, cancer of secretory cells, thyroid cancer, gastrointestinal carcinoma, chronic myeloid leukemia, hepatocellular carcinoma, colon cancer, melanoma, malignant glioma, glioblastoma, glioblastoma multiforme, astrocytoma, dysplastic gangliocytoma of the cerebellum, Ewing's sarcoma, rhabdomyosarcoma, ependymoma, medulloblastoma, ductal adenocarcinoma, adenosquamous carcinoma, nephroblastoma, acinar cell carcinoma, lung cancer, non-Hodgkin's lymphoma, Burkitt's lymphoma, chronic lymphocytic leukemia, monoclonal gammopathy of undetermined significance (MGUS), plasmocytoma, lymphoplasmacytic lymphoma, acute lymphoblastic leukemia, Pelizaeus-Merzbacher disease, atherosclerosis, abdominal aortic aneurism, carotid artery disease, deep vein thrombosis, Buerger's disease, chronic venous hypertension, vascular calcification, telangiectasia or lymphoedema, glaucoma, age-related macular degeneration, inflammatory retinal disease, retinal vascular disease, diabetic retinopathy, uveitis, rosacea, Sjogren's syndrome or neovascularization in proliferative retinopathy, hyperhomocysteinemia, skeletal muscle atrophy, myopathy, muscular dystrophy, muscular wasting, sarcopenia, Duchenne muscular dystrophy (DMD), Becker's disease, myotonic dystrophy, X-linked dilated cardiomyopathy, spinal muscular atrophy (SMA), Down syndrome, MEHMO syndrome, metaphyseal chondrodysplasia, Schmid type (MCDS), depression, or social behavior impairment.

Embodiment 22

A method of producing a protein, comprising contacting a eukaryotic cell comprising a nucleic acid encoding the protein with the compound or salt of any one of embodiments 1-13.

Embodiment 23

The method of embodiment 22, comprising culturing the cell in an in vitro culture medium comprising the compound or salt.

Embodiment 24

A method of culturing a eukaryotic cell comprising a nucleic acid encoding a protein, comprising contacting the eukaryotic cell with an in vitro culture medium comprising a compound or salt of any one of embodiments 1-13.

Embodiment 25

The method of any one of embodiments 22-24, wherein the nucleic acid encoding the protein is a recombinant nucleic acid.

Embodiment 26

The method of any one of embodiments 22-25, wherein the cell is a human embryonic kidney (HEK) cell or a Chinese hamster ovary (CHO) cell.

Embodiment 27

The method of any one of embodiments 22-25, wherein the cell is a yeast cell, a wheat germ cell, an insect cell, a rabbit reticulocyte, a cervical cancer cell, a baby hamster kidney cell, a murine myeloma cell, an HT-1080 cell, a PER.$C_6$ cell, a plant cell, a hybridoma cell, or a human blood derived leukocyte

Embodiment 28

A method of producing a protein, comprising contacting a cell-free protein synthesis (CEPS) system comprising eukaryotic initiation factor 2 (eIF2) and a nucleic acid encoding a protein with the compound or salt of any one of embodiments 1-13.

Embodiment 29

The method of any one of embodiments 22-28, wherein the protein is an antibody or a fragment thereof.

Embodiment 30

The method of any one of embodiments 22-28, wherein the protein is a recombinant protein, an enzyme, an allergenic peptide, a cytokine, a peptide, a hormone, erythropoietin (EPO), an interferon, a granulocyte-colony stimulating factor (G-CSF), an anticoagulant, or a clotting factor.

Embodiment 31

The method of any one of embodiments 22-30, comprising purifying the protein.

Embodiment 32

An in vitro cell culture medium, comprising the compound or salt of any one of embodiments 1-13 and nutrients for cellular growth.

Embodiment 33

The cell culture medium of embodiment 32, comprising a eukaryotic cell comprising a nucleic acid encoding a protein.

Embodiment 34

The cell culture medium of embodiment 32 or 33, further comprising a compound for inducing protein expression.

Embodiment 35

The cell culture medium of any one of embodiments 32-34, wherein the nucleic acid encoding the protein is a recombinant nucleic acid.

Embodiment 36

The cell culture medium of any one of embodiments 32-35, wherein the protein is an antibody or a fragment thereof.

Embodiment 37

The cell culture medium of any one of embodiments 32-35, wherein the protein is a recombinant protein, an enzyme, an allergenic peptide, a cytokine, a peptide, a hormone, erythropoietin (EPO), an interferon, a granulocyte-colony stimulating factor (G-CSF), an anticoagulant, or a clotting factor.

Embodiment 38

The cell culture medium of any one of embodiments 32-37, wherein the eukaryotic cell is a human embryonic kidney (HEK) cell or a Chinese hamster ovary (CHO) cell.

Embodiment 39

The cell culture medium of any one of embodiments 32-37, wherein the cell is a yeast cell, a wheat germ cell, an insect cell, a rabbit reticulocyte, a cervical cancer cell, a baby hamster kidney cell, a murine myeloma cell, an HT-1080 cell, a PER.$C_6$ cell, a plant cell, a hybridoma cell, or a human blood derived leukocyte Embodiment 40

A cell-free protein synthesis (CEPS) system comprising eukaryotic initiation factor 2 (eIF2) and a nucleic acid encoding a protein with the compound or salt of any one of embodiments 1-13.

Embodiment 41

The CEPS system of embodiment 40, comprising a eukaryotic cell extract comprising eIF2.

Embodiment 42

The CEPS system of embodiment 40 or 41, further comprising eIF2B.

Embodiment 43

The CEPS system of any one of embodiments 40-42, wherein the protein is an antibody or a fragment thereof.

Embodiment 44

The CEPS system of any one of embodiments 40-43, wherein the protein is a recombinant protein, an enzyme, an allergenic peptide, a cytokine, a peptide, a hormone, erythropoietin (EPO), an interferon, a granulocyte-colony stimulating factor (G-CSF), an anticoagulant, or a clotting factor.

Embodiment 1A

A compound of formula (1-2):

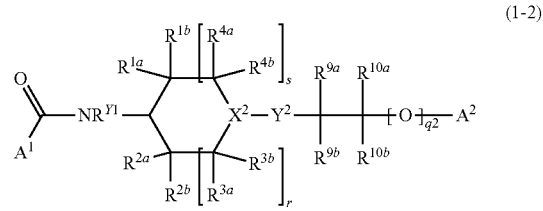

(1-2)

or a pharmaceutically acceptable salt thereof;
wherein:
  $X^2$ is CH;
  $R^{Y1}$ is hydrogen or $C_1$-$C_6$ alkyl;
  $Y^2$ is selected from the group consisting of $NR^{Y2}$ and O;
  $R^{Y2}$ is hydrogen or $C_1$-$C_6$ alkyl;
  q is 1;
  r and s, independently of each other, are 0, 1, or 2;
  $A^1$ is a substituent of formula ($A^1$-a)

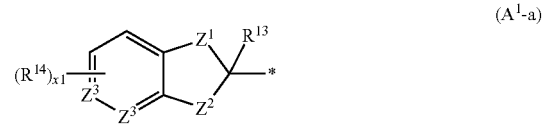

($A^1$-a)

wherein
  represents the attachment point to the remainder of the molecule; $Z^1$ is selected from the group consisting of $CR^{Z1-1}R^{Z1-2}$, $NR^{Z1-2}$, O, S, and —$CR^{Z1-1}$=$CR^{Z1-1}$—;
  wherein $R^{Z1-1}$ is H or $R^{14}$; and $R^{Z1-2}$ is H or $R^{14}$;
  $Z^2$ is selected from the group consisting of $CR^{Z2-1}R^{Z2-2}$, $NR^{Z2-2}$; O, S, and —$CR^{Z2-1}$=$CR^{Z2-1}$—;
  wherein $R^{Z2-1}$ is H or $R^{14}$; and $R^{Z2-2}$ is H or $R^{14}$;
  $Z^3$, independently at each occurrence, is C or N, provided that at least one $Z^3$ is C;

$R^{13}$ is hydrogen or $R^{14}$, or $R^{13}$ and $R^{Z1-2}$ are taken together to form a double bond between the carbon atom bearing R and Z, or R and R are taken together to form a double bond between the carbon atom bearing $R^{13}$ and $Z^2$; and x1 is 1, 2, 3, or 4, and at least one $R^{14}$ is halogen;

$R^{14}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —NH$_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —NR$^{14-a}$R$^{14-b}$, —CN, —C(O)OH, —C(O)O($C_1$-$C_6$ alkyl), —C(O)O($C_1$-$C_6$ haloalkyl), —C(O)NH$_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)NR$^{14-a}$R$^{14-b}$, —S(O)$_2$OH, —S(O)$_2$O($C_1$-$C_6$ alkyl), —S(O)$_2$O($C_1$-$C_6$ haloalkyl), —S(O)$_2$NH$_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$NR$^{14-a}$R$^{14-b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);

wherein $R^{14-a}$ and $R^{14-b}$ are taken together with the nitrogen atom which bears them to form a 3-10 membered heterocycle;

$A^2$ is $C_6$-$C_{10}$ aryl substituted by at least one halogen substituent and optionally further substituted with one or more $R^{16}$ substituents, or 5-10 membered heteroaryl substituted by at least one halogen substituent and optionally further substituted with one or more $R^{16}$ substituents;

$R^{16}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —NH$_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —NR$^{16-a}$R$^{16-b}$, —CN, —C(O)OH, —C(O)O($C_1$-$C_6$ alkyl), —C(O)O($C_1$-$C_6$ haloalkyl), —C(O)NH$_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)NR$^{16-a}$R$^{16-b}$, —S(O)$_2$OH, —S(O)$_2$O($C_1$-$C_6$ alkyl), —S(O)$_2$O($C_1$-$C_6$ haloalkyl), —S(O)$_2$NH$_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$NR$^{16a}$R$^{16b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);

wherein $R^{16-a}$ and $R^{16-b}$ are taken together with the nitrogen atom which bears them to form a 3-10 membered heterocycle;

$R^{1a}$ and $R^{1b}$ are independently selected from the group consisting of hydrogen, $C_1$-$C_6$ alkyl, and halogen;

$R^{2a}$ and $R^{2b}$ are independently selected from the group consisting of hydrogen, $C_1$-$C_6$ alkyl, and halogen;

when present, $R^{3a}$ and $R^{3b}$ are independently at each occurrence selected from the group consisting of hydrogen, $C_1$-$C_6$ alkyl, and halogen;

when present, $R^{4a}$ and $R^{4b}$ are independently at each occurrence selected from the group consisting of hydrogen, $C_1$-$C_6$ alkyl, and halogen;

or alternatively, $R^{1a}$ and $R^{2a}$ are taken together to form a $C_1$-$C_6$ alkylene moiety;

or alternatively, $R^{1a}$ and an $R^{3a}$ moiety, when present, are taken together to form a $C_1$-$C_6$ alkylene moiety, and $R^{1b}$ and the $R^{3b}$ in the geminal position to the $R^{3a}$ taken together with $R^{1a}$, are both hydrogen;

or alternatively, an $R^{3a}$ moiety, when present, and an $R^{4a}$ moiety, when present, are taken together to form a $C_1$-$C_6$ alkylene moiety, and the $R^{3b}$ in the geminal position to the $R^{3a}$ taken together with the $R^{4a}$ moiety and the $R^{4b}$ in the geminal position to the $R^{4a}$ taken together with the $R^{3a}$ moiety, are both hydrogen;

$R^{9a}$ and $R^{9b}$ are taken together to form an oxo (=O) substituent or an imido (=NH) substituent;

$R^{10a}$ is hydrogen; and $R^{10b}$ is hydrogen.

Embodiment 2A

The compound of embodiment 1A, or a pharmaceutically acceptable salt thereof, wherein x1 is 1 and $R^{14}$ is halogen.

Embodiment 3A

A compound of formula (1-3):

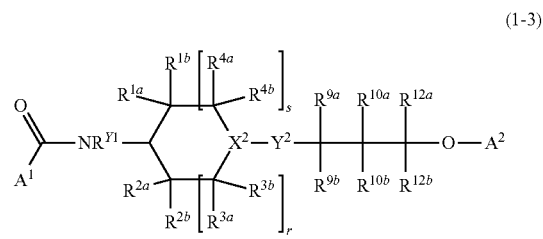

(1-3)

or a pharmaceutically acceptable salt thereof;

wherein:

$X^2$ is CH or N;

$R^{Y1}$ is hydrogen or $C_1$-$C_6$ alkyl;

$Y^2$ is selected from the group consisting of a bond, $NR^{Y2}$, and O; provided that when $X^2$ is N, then $Y^2$ is a bond;

$R^{Y2}$ is hydrogen or $C_1$-$C_6$ alkyl;

r and s, independently of each other, are 0, 1, or 2;

$A^1$ is selected from the group consisting of:
a substituent of formula ($A^1$-a)

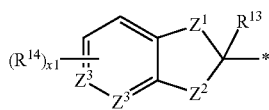
(A$^1$-a)

wherein
* represents the attachment point to the remainder of the molecule;

$Z^1$ is selected from the group consisting of $CR^{Z1-1}R^{Z1-2}$, $NR^{Z1-2}$, O, S, and —$CR^{Z1-1}$=$CR^{Z1-1}$—; wherein $R^{Z1-1}$ is H or $R^{14}$; and $R^{Z1-2}$ is H or $R^{14}$;

$Z^2$ is selected from the group consisting of $CR^{Z2-1}R^{Z2-2}$, $NR^{Z2-2}$; O, S, and —$CR^{Z2-1}$=$CR^{Z2-1}$—; wherein $R^{Z2-1}$ is H or $R^{14}$; and $R^{Z2-2}$ is H or $R^{14}$;

$Z^3$, independently at each occurrence, is C or N, provided that at least one $Z^3$ is C;

$R^{13}$ is hydrogen or $R^{14}$, or $R^{13}$ and $R^{Z1-2}$ are taken together to form a double bond between the carbon atom bearing R and Z, or R and R are taken together to form a double bond between the carbon atom bearing $R^{13}$ and $Z^2$; and x1 is 1, 2, 3, or 4, and at least one $R^{14}$ is halogen;

$R^{14}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —NH$_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —NR$^{14-a}$R$^{14-b}$, —CN, —C(O)OH, —C(O)O($C_1$-$C_6$ alkyl), —C(O)O($C_1$-$C_6$ haloalkyl), —C(O)NH$_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)NR$^{14-a}$R$^{14-b}$, —S(O)$_2$OH, —S(O)$_2$O($C_1$-$C_6$ alkyl), —S(O)$_2$O($C_1$-$C_6$ haloalkyl), —S(O)$_2$NH$_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$NR$^{14-a}$R$^{14-b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);

wherein $R^{14-a}$ and $R^{14-b}$ are taken together with the nitrogen atom which bears them to form a 3-10 membered heterocycle;

$A^2$ is $C_6$-$C_{10}$ aryl substituted by at least one halogen substituent and optionally further substituted with one or more $R^{16}$ substituents, or 5-10 membered heteroaryl substituted by at least one halogen substituent and optionally further substituted with one or more $R^{16}$ substituents;

$R^{16}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —NH$_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —NR$^{16-a}$R$^{16-b}$, —CN, —C(O)OH, —C(O)O($C_1$-$C_6$ alkyl), —C(O)O($C_1$-$C_6$ haloalkyl), —C(O)NH$_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)NR$^{16-a}$R$^{16-b}$, —S(O)$_2$OH, —S(O)$_2$O($C_1$-$C_6$ alkyl), —S(O)$_2$O($C_1$-$C_6$ haloalkyl), —S(O)$_2$NH$_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$NR$^{16-a}$R$^{16-b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);

wherein $R^{16-a}$ and $R^{16-b}$ are taken together with the nitrogen atom which bears them to form a 3-10 membered heterocycle;

$R^{1a}$ and $R^{1b}$ are independently selected from the group consisting of hydrogen, $C_1$-$C_6$ alkyl, and halogen;

$R^{2a}$ and $R^{2b}$ are independently selected from the group consisting of hydrogen, $C_1$-$C_6$ alkyl, and halogen;

when present, $R^{3a}$ and $R^{3b}$ are independently at each occurrence selected from the group consisting of hydrogen, $C_1$-$C_6$ alkyl, and halogen;

when present, $R^{4a}$ and $R^{4b}$ are independently at each occurrence selected from the group consisting of hydrogen, $C_1$-$C_6$ alkyl, and halogen;

or alternatively, $R^{1a}$ and $R^{2a}$ are taken together to form a $C_1$-$C_6$ alkylene moiety;

or alternatively, $R^{1a}$ and an $R^{3a}$ moiety, when present, are taken together to form a $C_1$-$C_6$ alkylene moiety, and $R^{1b}$ and the $R^{3b}$ in the geminal position to the $R^{3a}$ taken together with $R^{1a}$, are both hydrogen;

or alternatively, an $R^{3a}$ moiety, when present, and an $R^{4a}$ moiety, when present, are taken together to form a $C_1$-$C_6$ alkylene moiety, and the $R^{3b}$ in the geminal position to the $R^{3a}$ taken together with the $R^{4a}$ moiety and the $R^{4b}$ in the geminal position to the $R^{4a}$ taken together with the $R^{3a}$ moiety, are both hydrogen;

$R^{9a}$ and $R^{9b}$ are taken together to form an oxo (=O) substituent or an imido (=NH) substituent, or alternatively, $R^{9a}$ and $R^{9b}$ are both hydrogen;

$R^{10a}$ is selected from the group consisting of hydrogen, —OR$^{10a-a}$, and —NR$^{10a-b}$R$^{10a-c}$;

$R^{10b}$ is hydrogen;

$R^{12a}$ and $R^{12b}$ are taken together to form an oxo (=O) substituent, or alternatively, $R^{12a}$ and $R^{12b}$ are both hydrogen;

$R^{10a-a}$ is selected from the group consisting of hydrogen, $C_1$-$C_6$ alkyl, and $C_1$-$C_6$ haloalkyl;

or $R^{10a-a}$ and $R^{Y2}$ may be taken together to form a carbonyl (C=O) moiety; and $R^{10a-b}$ and $R^{10a-c}$, independently of each other, are selected from the group consisting of hydrogen, $C_1$-$C_6$ alkyl, and $C_1$-$C_6$ haloalkyl.

Embodiment 4A

The compound of embodiment 3A, or a pharmaceutically acceptable salt thereof, wherein x1 is 1 and $R^{14}$ is halogen.

Embodiment 5A

A compound of formula (2-3):

$$A^1\text{---}(O)_{q1}\overset{R^{6a}}{\underset{R^{6b}}{|}}\overset{R^{5a}}{\underset{R^{5b}}{|}}\text{---}Y^1\text{---}X^1\overset{\left[\overset{R^{1b}}{\underset{R^{2b}}{|}}\overset{\left[\overset{R^{4a}}{\underset{R^{3a}}{|}}\right]_s}{\underset{\left[\overset{}{R^{3b}}\right]_r}{|}}\right]}{\underset{R^{2a}}{\overset{R^{1a}}{|}}}\text{---}X^2\text{---}Y^2\overset{R^{9a}}{\underset{R^{9b}}{|}}\overset{R^{10a}}{\underset{R^{10b}}{|}}\overset{R^{12a}}{\underset{R^{12b}}{|}}\text{---}O\text{---}A^2 \quad (2\text{-}3)$$

or a pharmaceutically acceptable salt thereof;
wherein:
$X^1$ and $X^2$, independently of each other, are CH or N; provided that at least one of $X^1$ and $X^2$ is CH;
$Y^1$ is selected from the group consisting of a bond, $NR^{Y1}$, and O; provided that when $X^1$ is N, then $Y^1$ is a bond;
$R^{Y1}$ is hydrogen or $C_1$-$C_6$ alkyl;
$Y^2$ is selected from the group consisting of a bond, $NR^{Y2}$, and O; provided that when $X^2$ is N, then $Y^2$ is a bond;
$R^{Y2}$ is hydrogen or $C_1$-$C_6$ alkyl;
q1 is 1;
r and s, independently of each other, are 0, 1, or 2;
$A^1$ is $C_6$-$C_{10}$ aryl substituted by at least one halogen substituent and optionally further substituted with one or more $R^{14}$ substituents, or 5-10 membered heteroaryl substituted by at least one halogen substituent and optionally further substituted with one or more $R^{14}$ substituents;
$R^{14}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —NH$_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —NR$^{14\text{-}a}$R$^{14\text{-}b}$, —CN, —C(O)OH, —C(O)O($C_1$-$C_6$ alkyl), —C(O)O($C_1$-$C_6$ haloalkyl), —C(O)NH$_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)NR$^{14\text{-}a}$R$^{14\text{-}b}$, —S(O)$_2$OH, —S(O)$_2$O($C_1$-$C_6$ alkyl), —S(O)$_2$O($C_1$-$C_6$ haloalkyl), —S(O)$_2$NH$_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$NR$^{14\text{-}a}$R$^{14\text{-}b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);
wherein $R^{14\text{-}a}$ and $R^{14\text{-}b}$ are taken together with the nitrogen atom which bears them to form a 3-10 membered heterocycle;
$A^2$ is $C_6$-$C_{10}$ aryl substituted by at least one halogen substituent and optionally further substituted with one or more $R^{16}$ substituents, or 5-10 membered heteroaryl substituted by at least one halogen substituent and optionally further substituted with one or more $R^{16}$ substituents;
$R^{16}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —NH$_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —NR$^{16\text{-}a}$R$^{16\text{-}b}$, —CN, —C(O)OH, —C(O)O($C_1$-$C_6$ alkyl), —C(O)O($C_1$-$C_6$ haloalkyl), —C(O)NH$_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)NR$^{16\text{-}a}$R$^{16\text{-}b}$, —S(O)$_2$OH, —S(O)$_2$O($C_1$-$C_6$ alkyl), —S(O)$_2$O($C_1$-$C_6$ haloalkyl), —S(O)$_2$NH$_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$NR$^{16\text{-}a}$R$^{16\text{-}b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);
wherein $R^{16\text{-}a}$ and $R^{16\text{-}b}$ are taken together with the nitrogen atom which bears them to form a 3-10 membered heterocycle;
$R^{1a}$ and $R^{1b}$ are independently selected from the group consisting of hydrogen, $C_1$-$C_6$ alkyl, and halogen;
$R^{2a}$ and $R^{2b}$ are independently selected from the group consisting of hydrogen, $C_1$-$C_6$ alkyl, and halogen;
when present, $R^{3a}$ and $R^{3b}$ are independently at each occurrence selected from the group consisting of hydrogen, $C_1$-$C_6$ alkyl, and halogen;
when present, $R^{4a}$ and $R^{4b}$ are independently at each occurrence selected from the group consisting of hydrogen, $C_1$-$C_6$ alkyl, and halogen;
or alternatively, $R^{1a}$ and $R^{2a}$ are taken together to form a $C_1$-$C_6$ alkylene moiety;
or alternatively, $R^{1a}$ and an $R^{3a}$ moiety, when present, are taken together to form a $C_1$-$C_6$ alkylene moiety, and $R^{1b}$ and the $R^{3b}$ in the geminal position to the $R^{3a}$ taken together with $R^{1a}$, are both hydrogen;
or alternatively, an $R^{3a}$ moiety, when present, and an $R^{4a}$ moiety, when present, are taken together to form a $C_1$-$C_6$ alkylene moiety, and the $R^{3b}$ in the geminal position to the $R^{3a}$ taken together with the $R^{4a}$ moiety and the $R^{4b}$ in the geminal position to the $R^{4a}$ taken together with the $R^{3a}$ moiety, are both hydrogen;
$R^{5a}$ and $R^{5b}$ are taken together to form an oxo (=O) substituent or an imido (=NH) substituent;
$R^{6a}$ is hydrogen;
$R^{6b}$ is hydrogen;

$R^{9a}$ and $R^{9b}$ are taken together to form an oxo (=O) substituent or an imido (=NH) substituent, or alternatively, $R^{9a}$ and $R^{9b}$ are both hydrogen;

$R^{10a}$ is selected from the group consisting of hydrogen, —$OR^{10a-a}$, and —$NR^{10a-b}R^{10a-c}$;

$R^{10b}$ is hydrogen;

$R^{12a}$ and $R^{12b}$ are taken together to form an oxo (=O) substituent, or alternatively, $R^{12a}$ and $R^{12b}$ are both hydrogen;

$R^{10a-a}$ is selected from the group consisting of hydrogen, $C_1$-$C_6$ alkyl, and $C_1$-$C_6$ haloalkyl;

or $R^{10a-a}$ and $R^{12}$ may be taken together to form a carbonyl (C=O) moiety;

$R^{10a-b}$ and $R^{10a-c}$, independently of each other, are selected from the group consisting of hydrogen, $C_1$-$C_6$ alkyl, and $C_1$-$C_6$ haloalkyl; and provided that when $X^2$ is N, then:

$A^1$ is $C_6$-$C_{10}$ aryl substituted by at least two halogen substituents and optionally further substituted with one or more $R^{14}$ substituents, or 5-10 membered heteroaryl substituted by at least two halogen substituents and optionally further substituted with one or more $R^{14}$ substituents; and $A^2$ is $C_6$-$C_{10}$ aryl substituted by at least two halogen substituents and optionally further substituted with one or more $R^{16}$ substituents, or 5-10 membered heteroaryl substituted by at least two halogen substituents and optionally further substituted with one or more $R^{16}$ substituents.

Embodiment 6A

The compound of embodiment 5A, or a pharmaceutically acceptable salt thereof, wherein $X^1$ is CH and $X^2$ is CH.

Embodiment 7A

The compound of embodiment 5A, or a pharmaceutically acceptable salt thereof, wherein $X^1$ is N and $X^2$ is CH.

Embodiment 8A

The compound of embodiment 5A, or a pharmaceutically acceptable salt thereof, wherein:

$X^1$ is CH;

$X^2$ is N;

$A^1$ is $C_6$-$C_{10}$ aryl substituted by at least two halogen substituents and optionally further substituted with one or more $R^{14}$ substituents, or 5-10 membered heteroaryl substituted by at least two halogen substituents and optionally further substituted with one or more $R^{14}$ substituents; and $A^2$ is $C_6$-$C_{10}$ aryl substituted by at least two halogen substituents and optionally further substituted with one or more $R^{16}$ substituents, or 5-10 membered heteroaryl substituted by at least two halogen substituents and optionally further substituted with one or more $R^{16}$ substituents.

Embodiment 9A

A compound of formula (XX):

(XX)

or a pharmaceutically acceptable salt thereof;

wherein:

$X^5$ is CH or N;

$Y^5$ is selected from the group consisting of a bond, $NR^{Y5}$, and O; provided that when $X^5$ is N, then $Y^5$ is a bond;

$R^{Y5}$ is hydrogen or $C_1$-$C_6$ alkyl;

$R^N$ is hydrogen or $C_1$-$C_6$ alkyl;

$m^4$, $n^5$, $p^3$, and $q^4$, independently of each other, are 0 or 1;

r3 and s3, independently of each other, are 0, 1, or 2;

$A^{13}$ is selected from the group consisting of:

$C_6$-$C_{10}$ aryl optionally substituted with one or more $R^{95}$ substituents; and 5-10 membered heteroaryl optionally substituted with one or more $R^{95}$ substituents;

$R^{95}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —$NH_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —$NR^{95-a}R^{95-b}$, —CN, —C(O)OH, —C(O)O($C_1$-$C_6$ alkyl), —C(O)O($C_1$-$C_6$ haloalkyl), —C(O)$NH_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)$NR^{95a}R^{95b}$, —S(O)$_2$OH, —S(O)$_2$O($C_1$-$C_6$ alkyl), —S(O)$_2$O($C_1$-$C_6$ haloalkyl), —S(O)$_2NH_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2NR^{95a}R^{95b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);

wherein $R^{95-a}$ and $R^{95-b}$ are taken together with the nitrogen atom which bears them to form a 3-10 membered heterocycle;

$R^{84a}$ and $R^{84b}$ are independently selected from the group consisting of hydrogen, $C_1$-$C_6$ alkyl, and halogen;

$R^{85a}$ and $R^{85b}$ are independently selected from the group consisting of hydrogen, $C_1$-$C_6$ alkyl, and halogen;

when present, $R^{86a}$ and $R^{86b}$ are independently at each occurrence selected from the group consisting of hydrogen, $C_1$-$C_6$ alkyl, and halogen;

when present, $R^{87a}$ and $R^{87b}$ are independently at each occurrence selected from the group consisting of hydrogen, $C_1$-$C_6$ alkyl, and halogen;

or, $R^{84a}$ and $R^{85a}$ are taken together to form a $C_1$-$C_6$ alkylene moiety;

or, $R^{84a}$ and an $R^{86a}$ moiety, when present, are taken together to form a $C_1$-$C_6$ alkylene moiety;

or, an $R^{86a}$ moiety, when present, and an $R^{87a}$ moiety, when present, are taken together to form a $C_1$-$C_6$ alkylene moiety;

$R^{88}$ is selected from the group consisting of hydrogen, $C_1$-$C_6$ alkyl, $C_1$-$C_6$ haloalkyl, —C(O)($C_1$-$C_6$ alkyl), —C(O)($C_1$-$C_6$ haloalkyl), —C(O)OH, —C(O)O($C_1$-$C_6$ alkyl), —C(O)O($C_1$-$C_6$ haloalkyl), —C(O)NH$_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)NR$^{88-a}$R$^{88-b}$, —S(O)$_2$OH, —S(O)$_2$O($C_1$-$C_6$ alkyl), —S(O)$_2$O($C_1$-$C_6$ haloalkyl), —S(O)$_2$NH$_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, and —S(O)$_2$NR$^{88-a}$R$^{88-b}$; wherein R$^{88-a}$ and R$^{88-b}$ are taken together with the nitrogen atom which bears them to form a 3-10 membered heterocycle;

$R^{89}$ is selected, independently at each occurrence, from the group consisting of hydrogen, halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —NH$_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —NR$^{89-a}$R$^{89-b}$, —CN, —C(O)OH, —C(O)O($C_1$-$C_6$ alkyl), —C(O)O($C_1$-$C_6$ haloalkyl), —C(O)NH$_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)NR$^{89-a}$R$^{89-b}$, —S(O)$_2$OH, —S(O)$_2$O($C_1$-$C_6$ alkyl), —S(O)$_2$O($C_1$-$C_6$ haloalkyl), —S(O)$_2$NH$_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$NR$^{89-a}$R$^{89-b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);

wherein $R^{89-a}$ and $R^{89-b}$ are taken together with the nitrogen atom which bears them to form a 3-10 membered heterocycle;

when present, $R^{90a}$ and $R^{90b}$ are taken together to form an oxo (=O) substituent or an imido (=NH) substituent, or alternatively, $R^{90a}$ and $R^{90b}$ are both hydrogen;

when present, $R^{91a}$ is selected from the group consisting of hydrogen, —OR$^{91a-a}$, and —NR$^{91a-b}$R$^{91a-c}$;

when present, $R^{91b}$ is hydrogen;

or alternatively, $R^{91a}$ and $R^{91b}$ are taken together to form a moiety selected from the group consisting of —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, and —CH$_2$—CH$_2$—CH$_2$—CH$_2$—O—;

when present, $R^{92a}$ and $R^{92b}$ are both hydrogen;

when present, $R^{93a}$ and $R^{93b}$ are taken together to form an oxo (=O) substituent, or alternatively, $R^{93a}$ and $R^{93b}$ are both hydrogen;

$R^{91a-a}$ is selected from the group consisting of hydrogen, $C_1$-$C_6$ alkyl, and $C_1$-$C_6$ haloalkyl;

or $R^{91a-a}$ and $R^{y5}$ may be taken together to form a carbonyl (C=O) moiety; and $R^{91a-b}$ and $R^{91a-c}$, independently of each other, are selected from the group consisting of hydrogen, $C_1$-$C_6$ alkyl, and $C_1$-$C_6$ haloalkyl;

provided that when m$^4$ is 0, n$^5$ is 0, and q$^4$ is 0, then p$^3$ is 1 and $A^{13}$ is a substituent of formula ($A^{13}$-a)

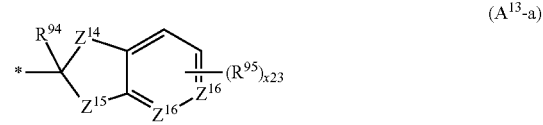

($A^{13}$-a)

wherein represents the attachment point to the remainder of the molecule;

$Z^{14}$ is selected from the group consisting of CR$^{Z14-1}$R$^{Z14-2}$, NR$^{Z14-2}$, C(R$^{Z14-1}$R$^{Z14-2}$)N(R$^{Z14-2}$), O, C(R$^{Z14-1}$R$^{Z14-2}$)O, S, C(R$^{Z14-1}$R$^{Z14-2}$)S, and —CR$^{Z14-1}$=CR$^{z141}$—;

wherein R$^{Z14-1}$ is hydrogen or R$^{16}$; and R$^{Z14-2}$ is hydrogen or R$^{95}$;

$Z^{15}$ is selected from the group consisting of CR$^{Z15-1}$R$^{Z15-2}$, NR$^{Z15-2}$, C(R$^{Z15-1}$R$^{Z15-2}$)N(R$^{Z15-2}$), O, C(R$^{Z15-1}$R$^{Z15-2}$)O, S, C(R$^{Z15-1}$R$^{Z15-2}$)S, and —CR$^{Z15-1}$=CR$^{Z15-1}$—;

wherein R$^{Z15-1}$ is hydrogen or R$^{95}$; and R$^{Z15-2}$ is hydrogen or R$^{95}$;

$Z^{16}$, independently at each occurrence, is CH, CR$^{95}$, or N; R$^{94}$ is hydrogen or R$^{95}$, or R$^{94}$ and R$^{Z14-2}$ are taken together to form a double bond between the carbon atom bearing R$^{94}$ and $Z^{14}$, or R$^{94}$ and R$^{Z15-2}$ are taken together to form a double bond between the carbon atom bearing R$^{94}$ and $Z^{15}$; and x23 is 0, 1, 2, 3, or 4.

Embodiment 10A

The compound of embodiment 9A, wherein the compound of formula (XX) is a compound of formula (XX-I):

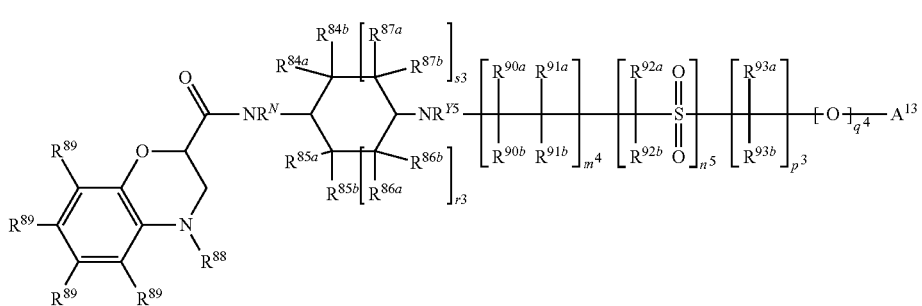

(XX-I)

or a pharmaceutically acceptable salt thereof.

Embodiment 11A

The compound of embodiment 10A, wherein the compound of formula (XX-I) is a compound of formula (XX-I-1):

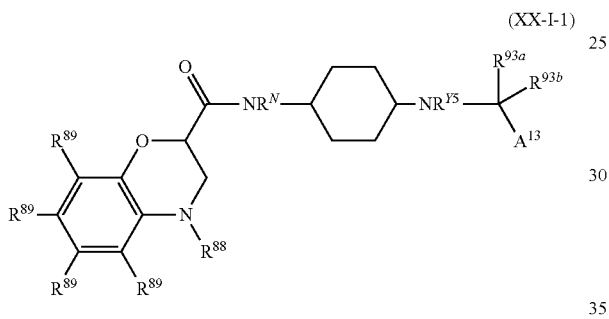

(XX-I-1)

or a pharmaceutically acceptable salt thereof;
wherein $R^N$, $R^{Y5}$, $R^{88}$, $R^{89}$, $R^{93a}$, and $R^{93b}$ are as defined in the compounds of formula (XX), and wherein $A^{13}$ is a substituent of formula ($A^{13}$-a)

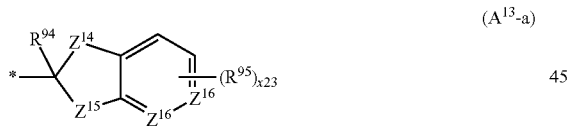

($A^{13}$-a)

wherein
* represents the attachment point to the remainder of the molecule;
$Z^{14}$ is selected from the group consisting of $CR^{Z14-1}R^{Z14-2}$, $NR^{Z14-2}$, $C(R^{Z14-1}R^{Z14-2})N(R^{Z14-2})$, O, $C(R^{Z14-1}R^{Z14-2})O$, S, $C(R^{Z14-1}R^{Z14-2})S$, and —$CR^{Z14-1}$=$CR^{Z14-1}$—;
wherein $R^{Z14-1}$ is hydrogen or $R^{16}$; and $R^{Z14-2}$ is hydrogen or $R^{95}$;
$Z^{15}$ is selected from the group consisting of $CR^{Z15-1}R^{Z15-2}$, $NR^{Z15-2}$, $C(R^{Z15-1}R^{Z15-2})N(R^{Z15-2})$, O, $C(R^{Z15-1}R^{Z15-2})O$, S, $C(R^{Z15-1}R^{Z15-2})S$, and —$CR^{Z15-1}$=$CR^{Z151}$—;
wherein $R^{Z15-1}$ is hydrogen or $R^{95}$; and $R^{Z15-2}$ is hydrogen or $R^{95}$;
$Z^{16}$, independently at each occurrence, is CH, $CR^{95}$, or N; $R^{94}$ is hydrogen or $R^{95}$, or $R^{94}$ and $R^{Z14-2}$ are taken together to form a double bond between the carbon atom bearing $R^{94}$ and $Z^{14}$, or $R^{94}$ and $R^{Z15-2}$ are taken together to form a double bond between the carbon atom bearing $R^{94}$ and $Z^{15}$;
x23 is 0, 1, 2, 3, or 4; and
$R^{95}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —$NH_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —$NR^{95-a}R^{95-b}$, —CN, —C(O)OH, —C(O)O($C_1$-$C_6$ alkyl), —C(O)O($C_1$-$C_6$ haloalkyl), —C(O)$NH_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)$NR^{95-a}R^{95-b}$, —S(O)$_2$OH, —S(O)$_2$O($C_1$-$C_6$ alkyl), —S(O)$_2$O($C_1$-$C_6$ haloalkyl), —S(O)$_2NH_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2NR^{95-a}R^{95-b}$, —OC(O)H, —OC(O)($C_1$-$C_6$ alkyl), —OC(O)($C_1$-$C_6$ haloalkyl), —N(H)C(O)H, —N(H)C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl)C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S(O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl).

Embodiment 12A

The compound of embodiment 10A, wherein the compound of formula (XX-I) is a compound of formula (XX-I-2):

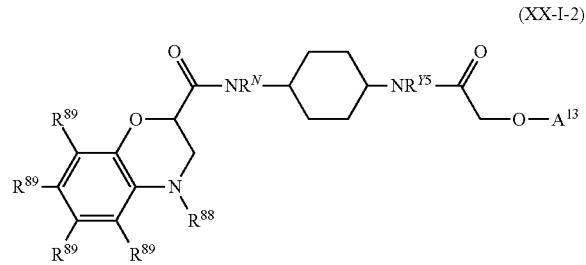

(XX-I-2)

or a pharmaceutically acceptable salt thereof.

Embodiment 13A

The compound of embodiment 10A, wherein the compound of formula (XX-I) is a compound of formula (XX-I-2b):

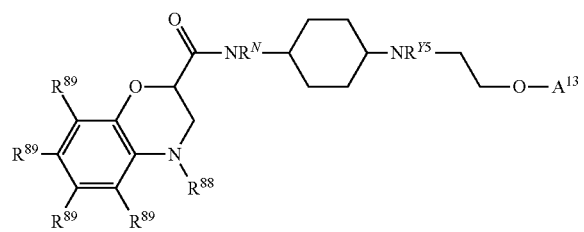

(XX-I-2b)

or a pharmaceutically acceptable salt thereof.

Embodiment 14A

The compound of embodiment 10A, wherein the compound of formula (XX-I) is a compound of formula (XX-I-3):

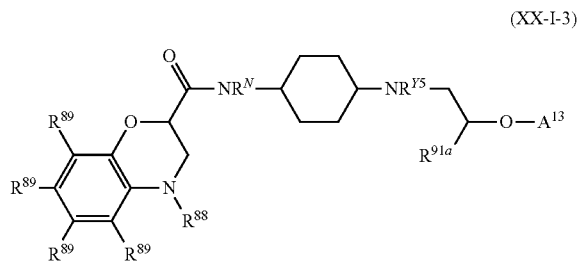

(XX-I-3)

or a pharmaceutically acceptable salt thereof.

Embodiment 15A

The compound of embodiment 9A, wherein the compound of formula (XX) is a compound of formula (XX-II):

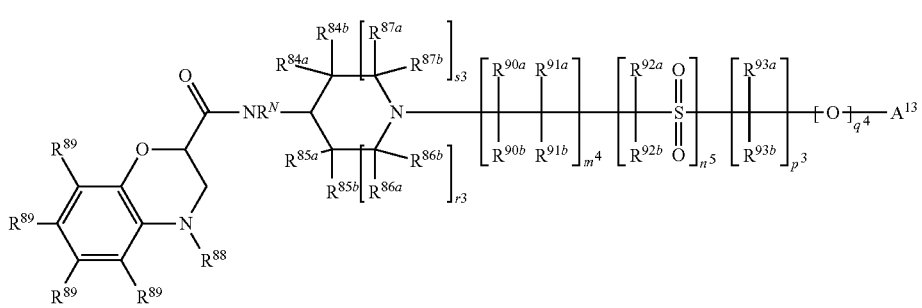

(XX-II)

or a pharmaceutically acceptable salt thereof.

Embodiment 16A

The compound of embodiment 15A, wherein the compound of formula (XX-II) is a compound of formula (XX-II-3):

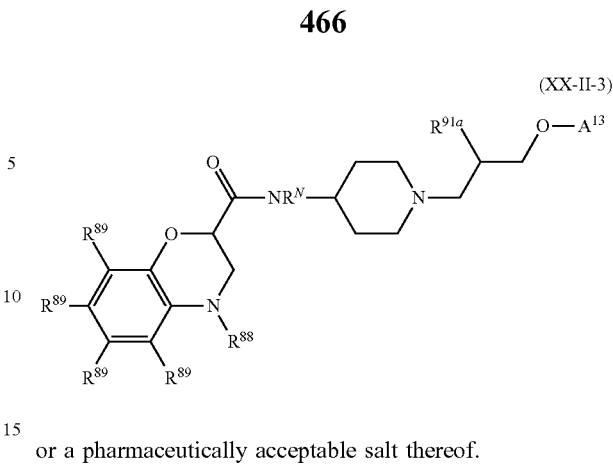

(XX-II-3)

or a pharmaceutically acceptable salt thereof.

Embodiment 17A

A compound selected from the group consisting of a compound of Table 1, or a pharmaceutically acceptable salt thereof.

Embodiment 18A

A pharmaceutical composition comprising a compound of any of the preceding embodiments, or a pharmaceutic ally acceptable salt thereof, and a pharmaceutically acceptable carrier.

Embodiment 19A

A method of treating a disease or disorder mediated by an integrated stress response (ISR) pathway in an individual in need thereof comprising administering to the individual a therapeutically effective amount of a compound of any one of embodiments 1A to 17A, or a pharmaceutically acceptable salt thereof, or a therapeutically effective amount of a pharmaceutical composition of embodiment 18A.

Embodiment 20A

The method of embodiment 19A, wherein the compound, the pharmaceutically acceptable salt, or the pharmaceutical composition is administered in combination with a therapeutically effective amount of one or more additional anti-cancer agents.

Embodiment 21A

The method of embodiment 19A, wherein the disease or disorder is mediated by phosphorylation of eIF2a and/or the guanine nucleotide exchange factor (GEE) activity of eIF2B.

Embodiment 22A

The method of any one of embodiments 19A-21A, wherein the disease or disorder is mediated by a decrease in protein synthesis.

Embodiment 23A

The method of any one of embodiments 19A-22A, wherein the disease or disorder is mediated by the expression of ATF4, CHOP or BACE-1.

Embodiment 24A

The method of any of embodiments 19A-23A, wherein the disease or disorder is a neurodegenerative disease, an inflammatory disease, an autoimmune disease, a metabolic syndrome, a cancer, a vascular disease, an ocular disease, a musculoskeletal disease, or a genetic disorder.

Embodiment 25A

The method of embodiment 24A, wherein the disease is vanishing white matter disease, childhood ataxia with CNS hypomyelination, intellectual disability syndrome, Alzheimer's disease, prion disease, Creutzfeldt-Jakob disease, Parkinson's disease, amyotrophic lateral sclerosis (ALS) disease, cognitive impairment, frontotemporal dementia (FTD), traumatic brain injury, postoperative cognitive dysfunction (PCD), neuro-otological syndromes, hearing loss, Huntington's disease, stroke, chronic traumatic encephalopathy, spinal cord injury, dementias or cognitive impairment, arthritis, psoriatic arthritis, psoriasis, juvenile idiopathic arthritis, asthma, allergic asthma, bronchial asthma, tuberculosis, chronic airway disorder, cystic fibrosis, glomerulonephritis, membranous nephropathy, sarcoidosis, vasculitis, ichthyosis, transplant rejection, interstitial cystitis, atopic dermatitis or inflammatory bowel disease, Crohn's disease, ulcerative colitis, celiac disease, systemic lupus erythematosus, type 1 diabetes, multiple sclerosis, rheumatoid arthritis, alcoholic liver steatosis, obesity, glucose intolerance, insulin resistance, hyperglycemia, fatty liver, dyslipidemia, hyperlipidemia, type 2 diabetes, pancreatic cancer, breast cancer, kidney cancer, bladder cancer, prostate cancer, testicular cancer, urothelial cancer, endometrial cancer, ovarian cancer, cervical cancer, renal cancer, esophageal cancer, gastrointestinal stromal tumor (GIST), multiple myeloma, cancer of secretory cells, thyroid cancer, gastrointestinal carcinoma, chronic myeloid leukemia, hepatocellular carcinoma, colon cancer, melanoma, malignant glioma, glioblastoma, glioblastoma multiforme, astrocytoma, dysplastic gangliocytoma of the cerebellum, Ewing's sarcoma, rhabdomyosarcoma, ependymoma, medulloblastoma, ductal adenocarcinoma, adenosquamous carcinoma, nephroblastoma, acinar cell carcinoma, lung cancer, non-Hodgkin's lymphoma, Burkitt's lymphoma, chronic lymphocytic leukemia, monoclonal gammopathy of undetermined significance (MGUS), plasmocytoma, lymphoplasmacytic lymphoma, acute lymphoblastic leukemia, Pelizaeus-Merzbacher disease, atherosclerosis, abdominal aortic aneurism, carotid artery disease, deep vein thrombosis, Buerger's disease, chronic venous hypertension, vascular calcification, telangiectasia or lymphoedema, glaucoma, age-related macular degeneration, inflammatory retinal disease, retinal vascular disease, diabetic retinopathy, uveitis, rosacea, Sjogren's syndrome or neovascularization in proliferative retinopathy, hyperhomocysteinemia, skeletal muscle atrophy, myopathy, muscular dystrophy, muscular wasting, sarcopenia, Duchenne muscular dystrophy (DMD), Becker's disease, myotonic dystrophy, X-linked dilated cardiomyopathy, spinal muscular atrophy (SMA), Down syndrome, MEHMO syndrome, metaphyseal chondrodysplasia, Schmid type (MCDS), depression, or social behavior impairment.

Embodiment 26A

A method of producing a protein, comprising contacting a eukaryotic cell comprising a nucleic acid encoding the protein with the compound or salt of any one of embodiments 1A-17A.

Embodiment 27A

The method of embodiment 26A, comprising culturing the cell in an in vitro culture medium comprising the compound or salt.

Embodiment 28A

A method of culturing a eukaryotic cell comprising a nucleic acid encoding a protein, comprising contacting the eukaryotic cell with an in vitro culture medium comprising a compound or salt of any one of embodiments 1-17A.

Embodiment 29A

The method of any one of embodiments 26A-28A, wherein the nucleic acid encoding the protein is a recombinant nucleic acid.

Embodiment 30A

The method of any one of embodiments 26A-29A, wherein the cell is a human embryonic kidney (HEK) cell or a Chinese hamster ovary (CHO) cell.

Embodiment 31A

The method of any one of embodiments 26A-29A, wherein the cell is a yeast cell, a wheat germ cell, an insect cell, a rabbit reticulocyte, a cervical cancer cell, a baby hamster kidney cell, a murine myeloma cell, an HT-1080 cell, a PER.C$_6$ cell, a plant cell, a hybridoma cell, or a human blood derived leukocyte

Embodiment 32A

A method of producing a protein, comprising contacting a cell-free protein synthesis (CEPS) system comprising eukaryotic initiation factor 2 (eIF2) and a nucleic acid encoding a protein with the compound or salt of any one of embodiments 1A-17A.

Embodiment 33A

The method of any one of embodiments 26A-32A, wherein the protein is an antibody or a fragment thereof.

Embodiment 34A

The method of any one of embodiments 26A-32A, wherein the protein is a recombinant protein, an enzyme, an allergenic peptide, a cytokine, a peptide, a hormone, erythropoietin (EPO), an interferon, a granulocyte-colony stimulating factor (G-CSF), an anticoagulant, or a clotting factor.

Embodiment 35A

The method of any one of embodiments 26A-34A, comprising purifying the protein.

Embodiment 36A

An in vitro cell culture medium, comprising the compound or salt of any one of embodiments 1A-17A and nutrients for cellular growth.

Embodiment 37A

The cell culture medium of embodiment 36A, comprising a eukaryotic cell comprising a nucleic acid encoding a protein.

Embodiment 38

The cell culture medium of embodiment 36A or 37A, further comprising a compound for inducing protein expression.

Embodiment 39A

The cell culture medium of any one of embodiments 36A-38A, wherein the nucleic acid encoding the protein is a recombinant nucleic acid.

Embodiment 40A

The cell culture medium of any one of embodiments 36A-39A, wherein the protein is an antibody or a fragment thereof.

Embodiment 41A

The cell culture medium of any one of embodiments 36A-39A, wherein the protein is a recombinant protein, an enzyme, an allergenic peptide, a cytokine, a peptide, a hormone, erythropoietin (EPO), an interferon, a granulocyte-colony stimulating factor (G-CSF), an anticoagulant, or a clotting factor.

Embodiment 42A

The cell culture medium of any one of embodiments 36A-41A, wherein the eukaryotic cell is a human embryonic kidney (HEK) cell or a Chinese hamster ovary (CHO) cell.

Embodiment 43A

The cell culture medium of any one of embodiments 36A-41A, wherein the cell is a yeast cell, a wheat germ cell, an insect cell, a rabbit reticulocyte, a cervical cancer cell, a baby hamster kidney cell, a murine myeloma cell, an HT-1080 cell, a PER.C$_6$ cell, a plant cell, a hybridoma cell, or a human blood derived leukocyte

Embodiment 44A

A cell-free protein synthesis (CEPS) system comprising eukaryotic initiation factor 2 (eIF2) and a nucleic acid encoding a protein with the compound or salt of any one of embodiments 1A-17A.

Embodiment 45A

The CEPS system of embodiment 40A, comprising a eukaryotic cell extract comprising eIF2.

Embodiment 46A

The CEPS system of embodiment 44A or 45A, further comprising eIF2B.

Embodiment 47A

The CEPS system of any one of embodiments 44A-46A, wherein the protein is an antibody or a fragment thereof.

Embodiment 48A

The CEPS system of any one of embodiments 44A-47A, wherein the protein is a recombinant protein, an enzyme, an allergenic peptide, a cytokine, a peptide, a hormone, erythropoietin (EPO), an interferon, a granulocyte-colony stimulating factor (G-CSF), an anticoagulant, or a clotting factor.

EXAMPLES

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as defined by the claims.

The chemical reactions in the Examples described can be readily adapted to prepare a number of other compounds disclosed herein, and alternative methods for preparing the compounds of this disclosure are deemed to be within the scope of this disclosure. For example, the synthesis of non-exemplified compounds according to the present disclosure can be successfully performed by modifications apparent to those skilled in the art, e.g., by appropriately protecting interfering groups, by utilizing other suitable reagents known in the art other than those described, or by making routine modifications of reaction conditions, reagents, and starting materials. Alternatively, other reactions disclosed herein or known in the art will be recognized as having applicability for preparing other compounds of the present disclosure.

In some cases, stereoisomers are separated to give single enantiomers or diastereomers as single, unknown stereoisomers, and are arbitrarily drawn as single isomers. Where appropriate, information is given on separation method and elution time and order. In the biological examples, compounds tested were prepared in accordance to the synthetic procedures described therein. For any given compound of unknown absolute stereochemistry for which specific rotation is available, biological data for that compound was obtained using the enantiomer or diastereoisomer associated with said specific rotation.

In some cases, optical rotation was determined on Jasco DIP-360 digital polarimeter at a wavelength of 589 nm (sodium D line) and are reported as $[\alpha]_D^T$ for a given temperature T (expressed in ° C.). Where appropriate, information is given on solvent and concentration (expressed as g/100 mL).

Abbreviations br. s. Broad singlet
chloroform-d Deuterated chloroform
methanol-d$_4$ Deuterated methanol
DIAD Diisopropyl azodicarboxylate
DCM Dichloromethane
DBA Diethylamine
DIPEA Diisopropylethylamine
DMF N,N-Dimethylformamide
DMSO-d$_6$ Deuterated dimethylsulfoxide
d Doublet
EDC.HCl 1-Ethyl-3-(3-dimethylaminopropyl)carbodiimide hydrochloric acid
EtOAc Ethyl acetate
EtOH Ethanol
g Gram
HATU (0-(7-azabenzotriazol-1-yl)-N,N,N',N'-tetramethyluronium hexafluorophosphate)
HOBT Hydroxybenzotriazole
HPLC High Performance Liquid Chromatography
L Litre
LCMS Liquid Chromatography Mass Spectrometry
MeCN Acetonitrile
MeOH Methanol
mg Milligram
mL Millilitre
mmol Millimoles
m multiplet
NMR Nuclear Magnetic Resonance
iPrOH Isopropanol
q quartet
RT Room temperature
s singlet
SFC Supercritical Fluid Chromatography
TFA trifluoroacetic acid
THF Tetrahydrofuran
TLC Thin layer chromatography
t triplet

EXAMPLES

Example 1

Synthesis of trans-2-(4-chlorophenoxy)-N-(4-((3-(4-chlorophenoxy)-2-hydroxypropyl)amino)cyclohexyl) acetamide

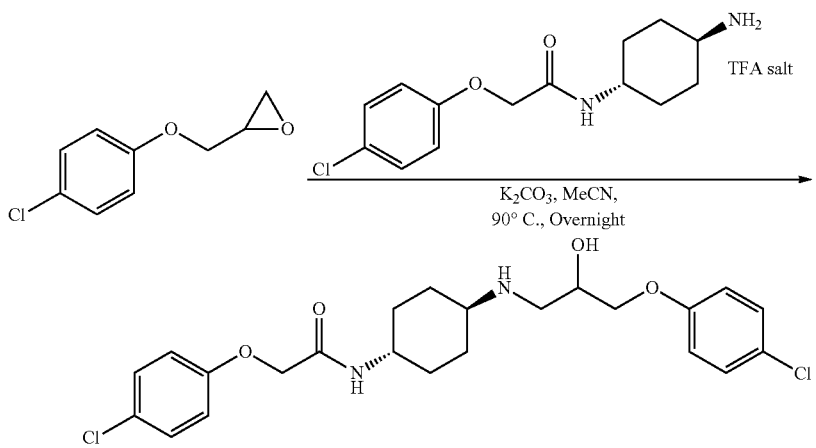

To a stirred solution of trans-A-(4-aminocyclohexyl)-2-(4-chlorophenoxy)acetamido trifluoroacetate salt (100 mg, 0.252 mmol, 1 equiv) in MeCN (10 mL), was added 2-((4-chlorophenoxy)methyl)oxirane (84 mg, 0.454 mmol, 1.8 equiv) and K$_2$CO$_3$ (70 mg, 0.504 mmol, 2 equiv) at RT. The reaction mixture was stirred overnight at 90° C. Progress of the reaction was monitored by TLC and LCMS. After completion of the reaction, the reaction mixture was diluted with water (30 mL) and extracted with EtOAc (100 mL×2). The organic layer was washed with water (50 mL) and brine solution (50 mL). Organic layer was dried over anhydrous sodium sulfate and concentrated under reduced pressure to obtain crude compound, which was purified by reverse phase HPLC to obtain trans-2-(4-chlorophenoxy)-N-(4-((3-(4-chlorophenoxy)2-hydroxypropyl)amino)cyclohexyl)acetamide (Compound 1-6 mg, 5%) as an off white solid compound. LCMS: 467 [M+H]$^+$; $^1$HNMR (400 MHz, DMSO-d$_6$) δ 8.26 (s, 1H), 7.92 (d, J=8.1 Hz, 1H), 7.33 (t, J=8.2 Hz, 4H), 6.96 (d, J=8.5 Hz, 4H), 4.44 (s, 2H), 3.91 (dq, 7=29.5, 6.4, 5.7 Hz, 3H), 3.57 (d, J=11.4 Hz, 2H), 2.81-2.72 (m, 2H), 1.95-1.85 (m, 2H), 1.75 (dd, J=11.9, 4.6 Hz, 2H), 1.35-1.21 (m, 3H), 1.13 (t, J=12.6 Hz, 2H).

Example 2

Synthesis of trans-2-(4-chloro-3-fluorophenoxy)-N-(4-((3-(4-chloro-3-fluorophenoxy)-2-hydroxypropyl)amino)cyclohexyl)acetamide

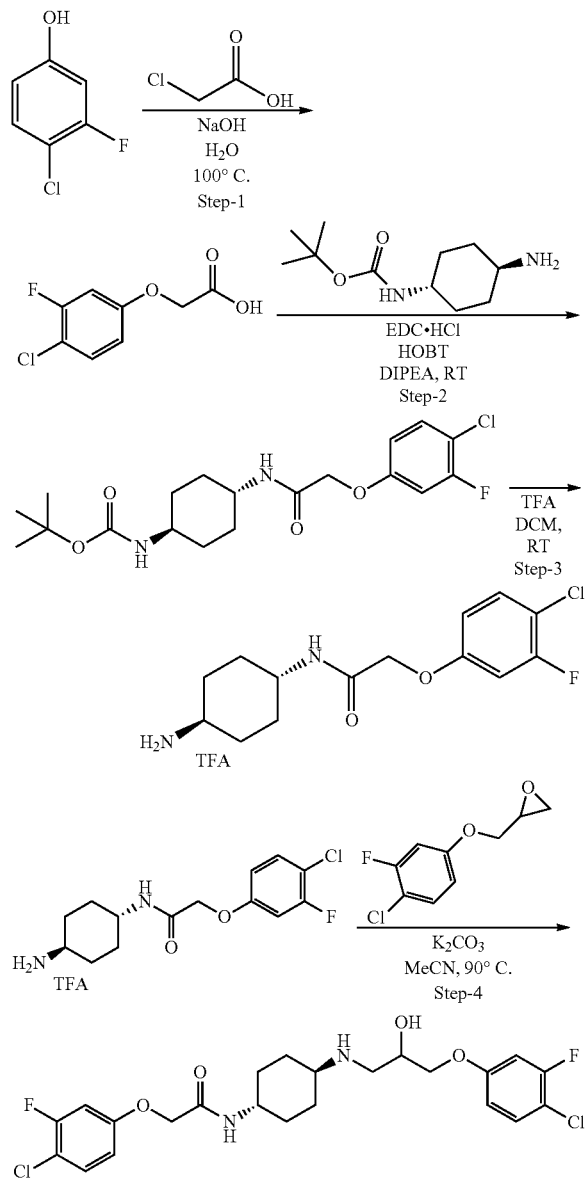

Step 1—Synthesis of 2-(4-chloro-3-fluorophenoxy)acetic acid

To a stirred mixture of 4-chloro-3-fluorophenol (1 g, 0.068 mol, 1 equiv) and 2-chloroacetic acid (2.5 g, 0.273 mol, 4 equiv) in water (20 mL), was added NaOH (1.08 g, 0.273 mol, 4 equiv) and the reaction mixture was heated at 100° C. overnight. The reaction was monitored by TLC and LCMS. After completion of the reaction, the reaction mixture was neutralized by using 3N HCl (20 mL). The resultant solid was filtered off and residue was washed with water and dried under vacuum to obtain 2-(4-chloro-3-fluorophenoxy) acetic acid (700 mg, 51%) as white solid. LCMS: 204 [M+H]$^+$.

Step 2—Synthesis of trans-tert-butyl (4-(2-(4-chloro-3-fluorophenoxy)acetamido)cyclohexyl)carbamate To a stirred mixture of 2-(4-Chloro-3-fluorophenoxy) acetic acid (500 mg, 2.43 mmol, 1 equiv) in DMF (5 mL), was added DIPEA (1.6 mL, 9.76 mmol, 4 equiv), HOBT (540 mg, 3.18 mmol, 1.5 equiv) and EDC.HCl (702 mg, 3.66 mmol, 1.5 equiv). The reaction mixture was stirred at RT for 30 min and then trans-tert-butyl 4-aminocyclohexyl)carbamate (838 mg, 9.76 mmol, 4 equiv) was added. The resultant reaction mixture was stirred at RT overnight. The reaction was monitored by LCMS. After completion of the reaction, the reaction mixture was filtered off and the residue was washed with water and dried under vacuum to obtain trans-tert-butyl (4-(2-(4-chloro-3-fluorophenoxy)acetamido)cyclohexyl)carbamate (170 mg, 18%) as white solid. LCMS: 399 [M+H]$^+$.

Step 3—Synthesis of trans-N-(4-aminocyclohexyl)-2-(4-chloro-3-fluorophenoxy)acetamide trifluoroacetate salt To a stirred solution of trans-tert-butyl (4-(2-(4-chloro-3-fluorophenoxy)acetamido) cyclohexyl)carbamate (150 mg, 0.395 mmol, 1 equiv) in DCM (5 mL) was added trifluoroacetic acid (3 mL) and the resultant reaction mixture was stirred at RT for 1 hr under nitrogen atmosphere. The reaction was monitored by TLC and LCMS. After completion of reaction, the reaction mixture was concentrated under reduced pressure to obtain a sticky crude compound which was triturated with hexane (10 mL) and diethyl ether and dried under vacuum to obtain trans-N-(4-aminocyclohexyl)-2-(4-chloro-3-fluorophenoxy)acetamide trifluoroacetate salt (100 mg, 89%) as brown solid. LCMS: 300 [M+H]$^+$.

Step 4—Synthesis of trans-2-(4-chloro-3-fluorophenoxy)-N-(4-((3-(4-chloro-3-fluorophenoxy)-2-hydroxypropyl)amino)cyclohexyl)acetamide To a stirred solution of trans-N-(4-aminocyclohexyl)-2-(4-chloro-3-fluorophenoxy)acetamide trifluoroacetate salt (100 mg, 0.24 mmol, 1 equiv), and 2-((4-chloro-3-fluorophenoxy)methyl)oxirane (67 mg, 0.338 mmol, 1.4 equiv) in MeCN (5 mL), was added K$_2$CO$_3$ (99 mg, 0.72 mmol, 3 equiv). The resultant reaction mixture was heated at 90° C. overnight. The reaction was monitored by TLC and LCMS. After completion of the reaction, the reaction mixture was diluted with water (30 mL) and extracted with EtOAc (2×50 mL) and washed with water (2×20 mL), brine solution (2×20 mL), dried over anhydrous sodium sulfate and concentrated under reduced pressure to obtain a crude mixture which was purified by reversed-phase HPLC to obtain trans-2-(4-chloro-3-fluorophenoxy)-N-(4-((3-(4-chloro-3-fluorophenoxy)-2-hydroxypropyl)amino)cyclohexyl)acetamide (Compound 2-7 mg, 4%) as light greenish solid. LCMS: 503 [M+H]$^+$; $^1$H NMR (400 MHz, DMSO-d$_6$) δ 7.92 (d, J=6.36 Hz, 2H), 7.37-7.57 (m, 2H), 7.06 (d, J=11.74 Hz, 2H), 6.83 (m, 2H), 4.48 (s, 4H), 3.97 (m., 1H), 3.89 (d, J=6.85 Hz, 1H), 3.80 (m, 1H), 3.55 (m, 3H), 1.85 (m, 1H), 1.77 (d, J=14.18 Hz, 3H), 1.35 (hr. s., 1H), 1.23 (hr. s., 2H).

Example 3

Synthesis of 2-(4-chlorophenoxy)-N-(1-(3-(4-chlorophenoxy)-2-hydroxypropyl)piperidin-4-yl)acetamide

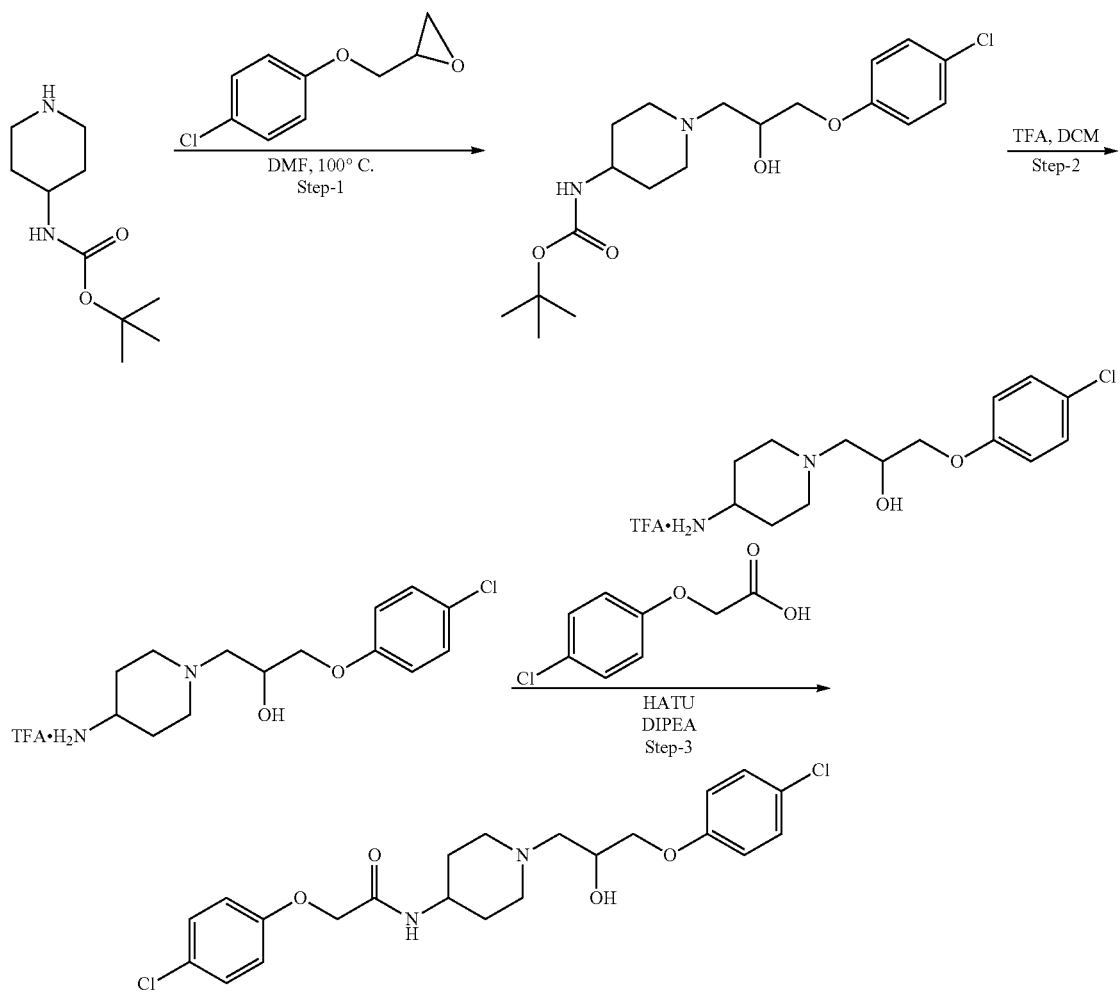

Step 1—Synthesis of tert-butyl (1-(3-(4-chlorophenoxy)-2-hydroxypropyl)piperidin-4-yl)carbamate To a stirred solution of tert-butyl piperidin-4-yl)carbamate (0.500 g, 2.500 mmol, 1.0 equiv) in DMF (5 mL) was added 2-((4-chlorophenoxy)methyl)oxirane (0.460 g, 2.500 mmol, 2.0 equiv) at RT. The resulting reaction mixture was heated at 100° C. for 12 hr. Progress of the reaction was monitored by $^1$H NMR. Reaction was quenched by adding water and the resulting precipitate was filtered off. The obtained solid was washed with water (25 mL×2) and dried under vacuum to obtain tert-butyl (1-(3-(4-chlorophenoxy)-2-hydroxypropyl)piperidin-4-yl)carbamate (0.700 g, 73% Yield) as a white solid. LCMS 386.3 [M+H]$^+$; $^1$H NMR (400 MHz, DMSO-d$_6$) δ 7.26-7.38 (m, J=8.77 Hz, 2H), 6.89-7.01 (m, J=8.77 Hz, 2H), 6.74 (d, J=7.45 Hz, 1H), 4.84 (d, J=4.38 Hz, 1H), 3.82-3.99 (m, 3H), 3.17 (d, J=5.26 Hz, 1H), 2.75-2.92 (m, 2H), 2.25-2.41 (m, 2H), 1.91-2.07 (m, 2H), 1.65 (d, J=10.52 Hz, 2H), 1.37 (s, 9H).

Step 2—Synthesis of 1-(4-aminopiperidin-1-yl)-3-(4-chlorophenoxy)propan-2-ol trifluoroacetate salt To a stirred solution of tert-butyl (1-(3-(4-chlorophenoxy)-2-hydroxypropyl)piperidin-4-yl)carbamate (0.700 g, 21.822 mmol, 1.0 equiv) in DCM (30 mL) was added trifluoroacetic acid (5 mL) at RT. The reaction mixture was allowed to stir at RT overnight. DCM and excess of trifluoroacetic acid were removed under reduced pressure to obtain 1-(4-aminopiperidin-1-yl)-3-(4-chlorophenoxy)propan-2-ol trifluoroacetate salt (0.800 g, 100% Yield) as an oil. $^1$HNMR (400 MHz, DMSO-d$_6$) δ 9.61 (br. s., 1H), 8.18 (br. s., 2H), 7.27-7.45 (m, J=9.21 Hz, 2H), 6.92-7.04 (m, J=8.77 Hz, 2H), 4.24-4.33 (m, 1H), 3.62 (d, 7=10.96 Hz, 2H), 3.04-3.33 (m, 5H), 2.01-2.20 (m, 2H), 1.86-1.96 (m, 1H), 1.78 (d, J=13.15 Hz, 1H).

Step 3—Synthesis of 2-(4-chlorophenoxy)-N-(1-(3-(4-chlorophenoxy)-2-hydroxypropyl)piperidin-4-yl)acetamide To a solution of 1-(4-aminopiperidin-1-yl)-3-(4-chlorophenoxy)propan-2-ol trifluoroacetate salt (0.700 g, 1.758 mmol, 1.0 equiv) in DMF (10 mL) was added 2-(4-chlorophenoxy)acetic acid (0.396 g, 1.934 mmol, 1.1 equiv) and HATU (1.340 g, 3.517 mmol, 2.0 equiv) at RT. The reaction mixture was stirred for 10 minutes and then DIPEA (1.6 mL, 8.793 mmol, 5.0 equiv) was added. The resultant reaction mixture was allowed to stir at RT overnight. Progress of the reaction was monitored by LCMS. The reaction mixture was diluted with water (50 mL) and extracted with EtOAc (100 mL×2). The combined organic layer was washed with water (50 mL×4), dried over anhydrous sodium sulfate and concentrated under reduced pressure to obtain the crude compound which was purified by reverse phase HPLC to obtain 2-(4-chlorophenoxy)-N-(1-(3-(4-chlorophenoxy)-2-hydroxypropyl)piperidin-4-yl)acetamide (Compound 5-0.550 g, 70% Yield) as an off-white solid. LCMS: 453.1 [M+H]$^+$; $^1$HNMR (400 MHz, DMSO-d$_6$) δ 8.09-8.16 (m, 1H), 7.34 (d, J=8.77 Hz, 2H), 6.90-7.01 (m, 2H), 5.59 (br. s., 1H), 4.48 (s, 2H), 4.14 (br. s., 1H), 3.94 (dq, J=4.60, 10.01 Hz, 1H), 3.78 (br. s. 1H), 2.90 (br. s., 2H), 1.82 (d, J=10.09 Hz, 1H), 1.58-1.75 (m, 1H).

Example 4

Synthesis of trans-3-(4-chlorophenoxy)-N-(4-(2-(4-chlorophenoxy)acetamido)cyclohexyl)-2-hydroxypropanamide

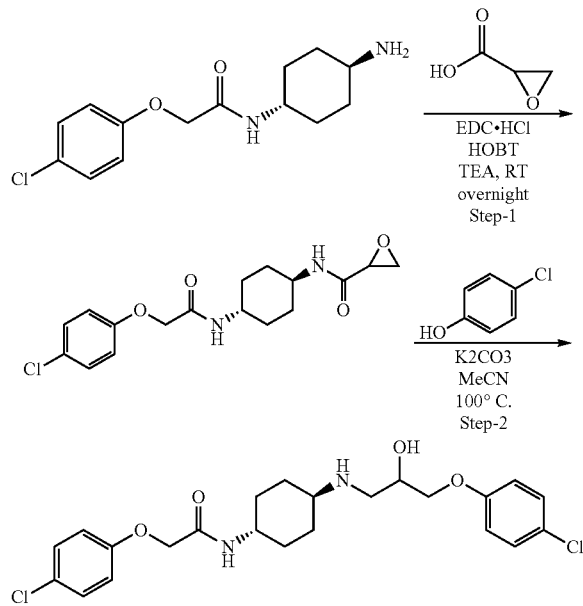

Step 1—Synthesis of trans-N-(4-(2-(4-chlorophenoxy)acetamido)cyclohexyl)oxirane-2-carboxamide To a stirred mixture of trans-N-(4-aminocyclohexyl)-2-(4-chlorophenoxy)acetamide (300 mg, 1.063 mmol, 1 equiv) in DMF (15 mL), was added triethylamine (0.5 mL, 4.252 mmol, 4 equiv), HOBT (144 mg, 1.595 mmol, 1.5 equiv) and EDC.HCl (305 mg, 1.595 mmol, 1.5 equiv). The reaction mixture was stirred at RT for 30 min. Oxirane-2-carboxylic acid (140 mg, 1.595 mmol, 1.5 equiv) was then added. The resultant reaction mixture was stirred at RT overnight. Progress of the reaction was monitored by LCMS. After completion of the reaction, water (50 mL) was added and extracted with EtOAc (50 mL×2). The combined organic layer was washed with water (30 mL), brine solution (2×30 mL), dried over anhydrous sodium sulfate and concentrated under reduced pressure to obtain trans-N-(4-(2-(4-chlorophenoxy)acetamido)cyclohexyl)oxirane-2-carboxamide (300 mg) as a white solid which was taken for the next step without any further purification. LCMS: 353 [M+H]$^+$.

Step 2—Synthesis of trans-3-(4-chlorophenoxy)-N-(4-(2-(4-chlorophenoxy)acetamido)cyclohexyl)-2-hydroxypropanamide To a stirred solution of trans-N-(4-(2-(4-chlorophenoxy)acetamido)cyclohexyl)oxirane-2-carboxamide (300 mg, 0.849 mmol, 1 equiv) and 4-chlorophenol (108 mg, 0.849 mmol, 1 equiv) in DMF (10 mL), was added K$_2$CO$_3$ (234 mg, 1.698 mmol, 2 equiv) and the resultant reaction mixture was heated at 100° C. overnight. Progress of the reaction was monitored by TLC and LCMS. After completion of reaction, the reaction mixture was diluted with water (50 mL) and extracted with EtOAc (50 mL×2). The combined organic layer was washed with water (30 mL), brine solution (30 mL×2), dried over anhydrous sodium sulfate and concentrated under reduced pressure to obtain a crude mixture which was purified by reversed-phase HPLC to obtain trans-3-(4-chlorophenoxy)-N-(4-(2-(4-chlorophenoxy)acetamido)cyclohexyl)-2-hydroxypropanamide (Compound 8-50 mg) as white solid. LCMS 481[M+H]$^+$; $^1$HNMR (400 MHz, DMSO-d$_6$) δ 7.94 (d, J=8.77 Hz, 1H), 7.69 (d, 7=8.77 Hz, 1H), 7.34 (d, J=9.21 Hz, 4H), 6.97 (d, J=9.21 Hz, 4H), 5.94 (d, J=5.70 Hz, 1H), 4.45 (s, 2H), 4.19 (hr. s., 1H), 4.01-4.12 (m, 2H), 3.58 (hr. s., 2H), 1.74 (hr. s., 4H), 1.23 (hr. s. 4H).

Example 5

Synthesis of trans-3-(4-chloro-3-fluorophenoxy)-N-(4-(2-(4-chloro-3-fluorophenoxy)acetamido)cyclohexyl)-2-hydroxypropanamide

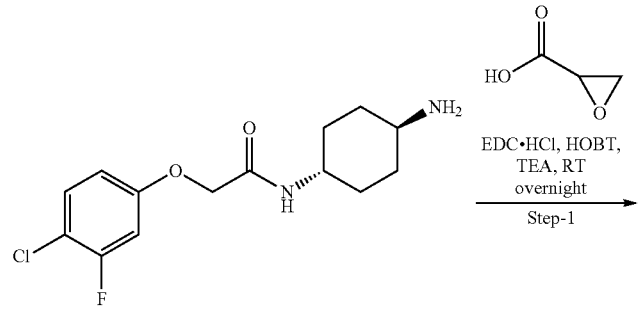

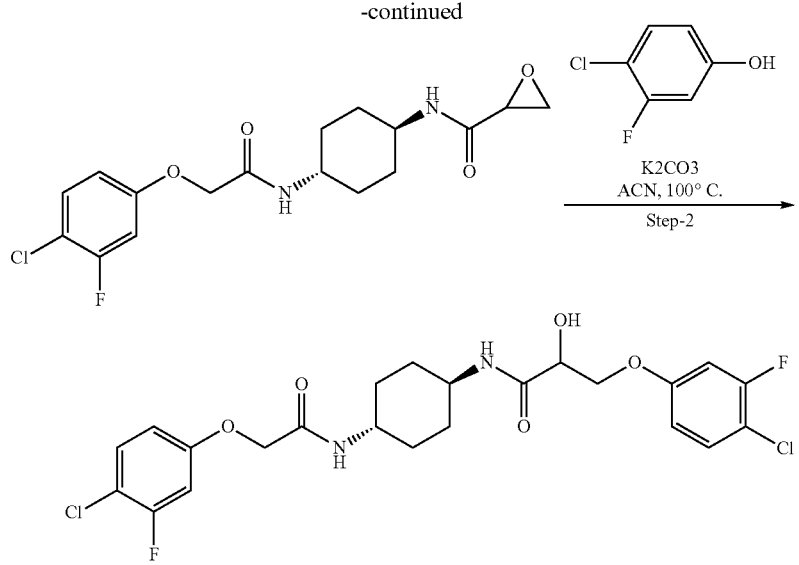

Step 1—Synthesis of trans-N-(4-(2-(4-chloro-3-fluorophenoxy)acetamido)cyclohexyl)oxirane-2-carboxamide To a stirred mixture of trans-N-(4-aminocyclohexyl)-2-(4-chloro-3-fluorophenoxy)acetamide (1000 mg, 3.18 mmol, 1 equiv) in DMF (30 mL), was added triethylamine (1.8 mL, 12.72 mmol, 3 equiv), HOBT (643 mg, 4.77 mmol, 1.5 equiv) and EDC.HCl (643 mg, 4.77 mmol, 1.5 equiv). The reaction mixture was stirred at RT for 30 min. Oxirane-2-carboxylic acid (420 mg, 4.77 mmol, 1.5 equiv) was added and the resultant reaction mixture was stirred at RT overnight. Reaction was monitored by LCMS. After completion of the reaction, the reaction mixture was diluted with water (100 mL) and extracted with EtOAc (2×100 mL) and washed with water and brine solution (2×50 mL), dried over anhydrous sodium sulfate and concentrated under reduced pressure to obtain trans-N-(4-(2-(4-chloro-3-fluorophenoxy)acetamido)cyclohexyl)oxirane-2-carboxamide (220 mg, 20% Yield) as a white solid. LCMS: 370 [M+H]$^+$.

Step 2—Synthesis of trans-3-(4-chloro-3-fluorophenoxy)-N-(4-(2-(4-chloro-3-fluorophenoxy)acetamido)cyclohexyl)-2-hydroxypropanamide To a stirred solution of trans-N-(4-(2-(4-chloro-3-fluorophenoxy)acetamido)cyclohexyl)oxirane-2-carboxamide (100 mg, 0.27 mmol, 1 equiv) in DMF (10 mL) was added K$_2$CO$_3$ (75 mg, 0.54 mmol, 2 equiv) followed by the addition of 4-chloro-3-fluorophenol (40 mg, 0.27 mmol, 1 equiv). The resultant reaction mixture was heated at 100° C. overnight. The reaction was monitored by TLC and LCMS. After completion of reaction, the reaction mixture was diluted with water (50 mL) and extracted with EtOAc (2×50 mL) and washed with water and brine solution (2×30 mL) and dried over anhydrous sodium sulfate and concentrated under reduced pressure to obtain a crude mixture which was purified by reversed-phase HPLC to obtain trans-3-(4-chloro-3-fluorophenoxy)-N-(4-(2-(4-chloro-3-fluorophenoxy)acetamido)cyclohexyl)-2-hydroxypropanamide (Compound 9—60 mg, 48% Yield) as a white solid. LCMS: 517 [M+H]$^+$; $^1$HNMR (400 MHz, DMSO-d$_6$) δ 7.97 (d, J=7.89 Hz, 1H), 7.70 (d, J=8.33 Hz, 1H), 7.41-7.57 (m, 2H), 7.00-7.13 (m, 2H), 6.84 (d, J=8.33 Hz, 2H), 5.98 (br. s, 1H), 4.49 (s, 2H), 4.04-4.25 (m, 2H), 3.58 (br. s, 2H), 1.74 (s, 4H), 1.23-1.45 (m, 4H).

Example 6

Synthesis of trans-2-(4-chloro-3-fluorophenoxy)-N-(4-((3-(4-chlorophenoxy)-2-hydroxypropyl)amino)cyclohexyl)acetamide

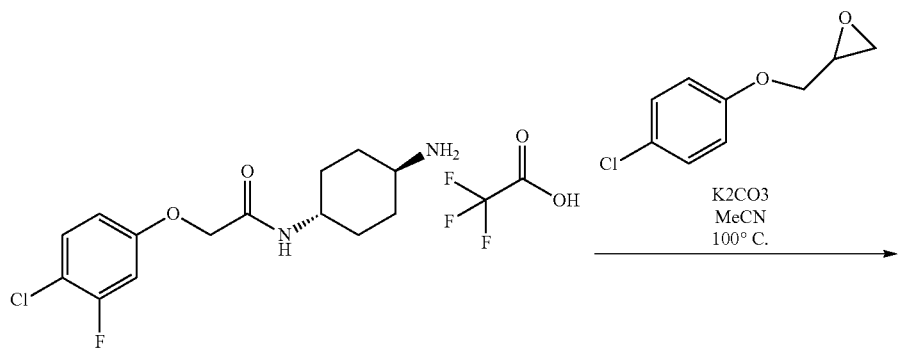

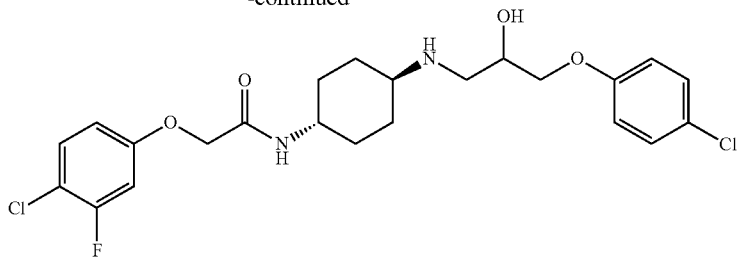

To a stirred solution of trans-N-(4-aminocyclohexyl)-2-(4-chloro-3-fluorophenoxy)acetamide trifluoroacetate salt (200 mg, 0.63 mmol, 1 equiv) in DMF (10 mL) was added K$_2$CO$_3$ (264 mg, 1.9 mmol, 3 equiv) followed by the addition of 2-((4-chlorophenoxy)methyl)oxirane (175 mg, 0.95 mmol, 1 equiv). The resultant reaction mixture was heated at 100° C. overnight. The reaction was monitored by TLC and LCMS. After completion of reaction, the reaction mixture was diluted with water (70 mL) and extracted with EtOAc (2×50 mL) and washed with water and brine solution (2×30 mL) and dried over anhydrous sodium sulfate and concentrated under reduced pressure to obtain a crude mixture which was purified by reversed-phase HPLC to obtain trans-2-(4-chloro-3-fluorophenoxy)-N-(4-((3-(4-chlorophenoxy)-2-hydroxypropyl)amino)cyclohexyl)acetamide (Compound 10-20 mg, 15% Yield) as a white solid. LCMS: 485 [M+H]$^+$; $^1$HNMR (400 MHz, DMSO-d$_6$) δ 7.92 (d, J=8.33 Hz, 2H), 7.49 (t, J=8.55 Hz, 1H), 7.31 (d, J=8.77 Hz, 2H), 7.06 (d, J=8.77 Hz, 1H), 6.96 (d, J=8.33 Hz, 2H), 6.84 (d, J=8.77 Hz, 1H), 4.48 (s, 2H), 3.94 (d, J=5.26 Hz, 1H), 3.85 (s, 2H), 3.56 (br. s., 2H), 1.90 (s, 4H), 1.75 (s, 4H).

Example 7

Synthesis of 2-(4-chloro-3-fluorophenoxy)-N-((3S)-1-(3-(4-chloro-3-fluorophenoxy)-2-hydroxypropyl)piperidin-3-yl)acetamide

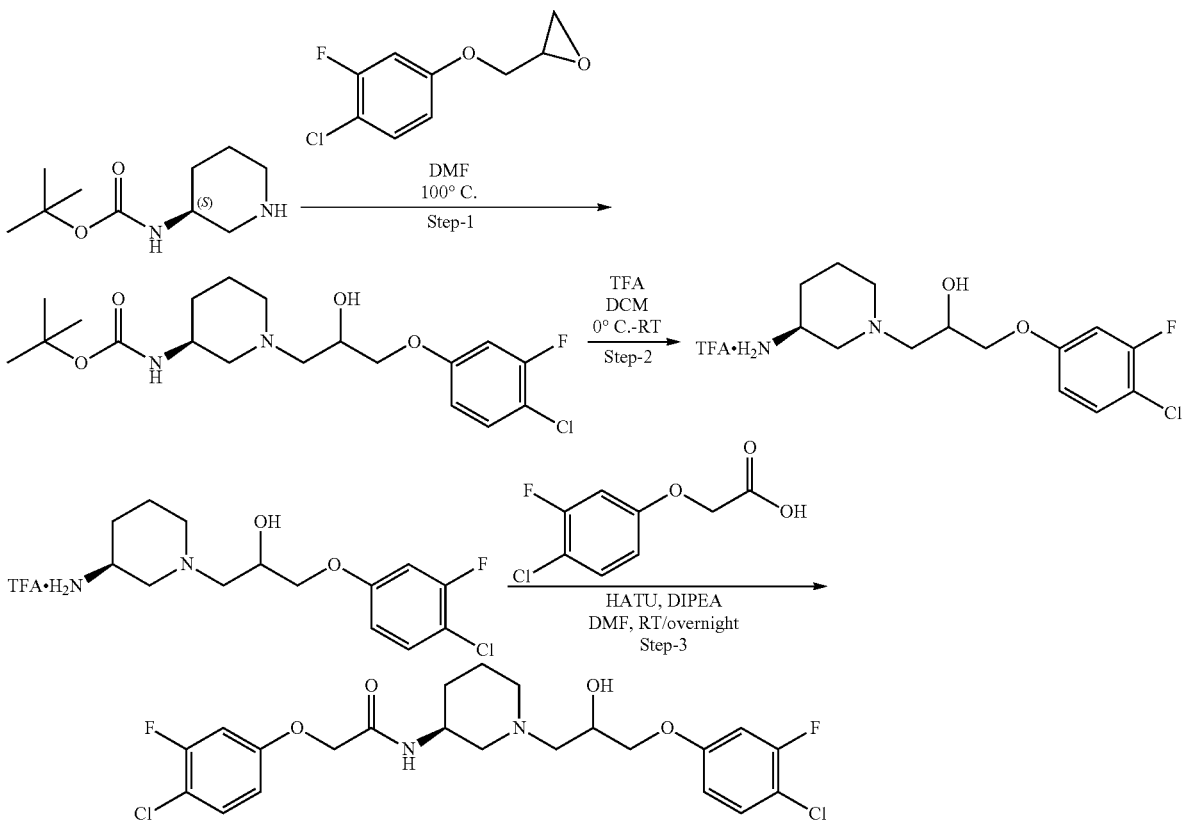

Step 1—Synthesis of tert-butyl ((3S)-1-(3-(4-chloro-3-fluorophenoxy)-2-hydroxypropyl)piperidin-3-yl)carbamate To a stirred solution of tert-butyl (S)-piperidin-3-yl)carbamate (0.500 g, 2.47 mmol, 1.0 equiv) in DMF (5 mL) was added 2-((4-chloro-3-fluorophenoxy)methyl)oxirane (0.602 g, 2.98 mmol, 2.0 equiv) at RT. The resulting reaction mixture was heated at 100° C. for 12 hr. Product formation was confirmed by $^1$H NMR spectroscopy. The reaction was stopped by adding water and the resulting precipitate was filtered off. The obtained solid was washed with water (25 mL×2) and dried under vacuum to obtain tert-butyl ((3S)-1-(3-(4-chloro-3-fluorophenoxy)-2-hydroxypropyl)piperidin-3-yl)carbamate. (1.0 g 95% Yield, as a white solid). LMCS 403 [M+H]$^+$.

Step 2—Synthesis of 1-(((3S)-1-(3-(4-chloro-3-fluorophenoxy)-2-hydroxypropyl)piperidin-3-yl)-$\lambda^4$-azanyl)-2,2,2-trifluoroethan-1-one trifluoroacetate salt To a stirred solution of tert-butyl ((3S)-1-(3-(4-chloro-3-fluorophenoxy)-2-hydroxypropyl)piperidin-3-yl)carbamate (1.0 g, 2.48 mmol, 1.0 equiv) in DCM (30 mL) was added trifluoroacetic acid (5 mL) at RT. The reaction mixture was allowed to stir at RT overnight. DCM and excess trifluoroacetic acid was removed under reduced pressure to obtain 1-(((3S)-1-(3-(4-chloro-3-fluorophenoxy)-2-hydroxypropyl)piperidin-3-yl)-$\lambda^4$-azanyl)-2,2,2-trifluoroethan-1-one trifluoroacetate salt (1.3 g, 100% Yield as an yellow oil). LCMS 303 [M+H]$^+$.

Step 3—Synthesis of 2-(4-chloro-3-fluorophenoxy)-N-((3S)-1-(3-(4-chloro-3-fluorophenoxy)-2-hydroxypropyl)piperidin-3-yl)acetamide To a solution of 1-(((3S)-1-(3-(4-chloro-3-fluorophenoxy)-2-hydroxypropyl)piperidin-3-yl)-$\lambda^4$-azanyl)-2,2,2-trifluoroethan-1-one trifluoroacetate salt (1.0 g, 2.48 mmol, 1.0 equiv) in DMF (15 mL) was added 2-(4-chloro-3-fluorophenoxy)acetic acid (0.607 g, 2.97 mmol, 1.2 equiv) and HATU (1.89 g, 4.96 mmol) at RT. The resulting reaction mixture was stirred for 10 minutes, and DIPEA (2.1 mL, 12.4 mmol) was added. The reaction mixture was allowed to stir at RT overnight. Product formation was confirmed by LCMS. The reaction mixture was diluted with water (50 mL) and extracted with EtOAc (100 mL×2). The combined organic extracts were washed with water (50 mL×4), dried over anhydrous sodium sulfate and concentrated. The crude product obtained was purified by reverse phase HPLC to obtain 2-(4-chloro-3-fluorophenoxy)-N-((3S)-1-(3-(4-chloro-3-fluorophenoxy)-2-hydroxypropyl)piperidin-3-yl)acetamide (Compound 11-30 mg, as an off-white solid). LCMS 489 [M+H]$^+$; $^1$HNMR (400 MHz, DMSO-$d_6$) δ 7.90 (d, J=7.02 Hz, 1H), 7.30-7.54 (m, 2H), 7.03 (m, 2H), 6.69-6.92 (m, 2H), 4.93 (hr. s., 1H), 4.51 (s, 1H), 4.00 (d, J=7.02 Hz, 1H), 3.84-3.94 (m, 2H), 3.81 (hr. s., 1H), 2.69 (d, J=12.72 Hz, 1H), 2.27-2.42 (m, 2H), 2.16 (m, 2H), 1.75 (hr. s., 1H), 1.62 (d, J=9.21 Hz, 2H), 1.46 (d, J=7.02 Hz, 1H), 1.32 (hr. s., 1H), 1.23 (hr. s. 1H).

Example 8

Synthesis of 2-(4-chloro-3-fluorophenoxy)-N-((3R)-1-(3-(4-chloro-3-fluorophenoxy)-2-hydroxypropyl)piperidin-3-yl)acetamide

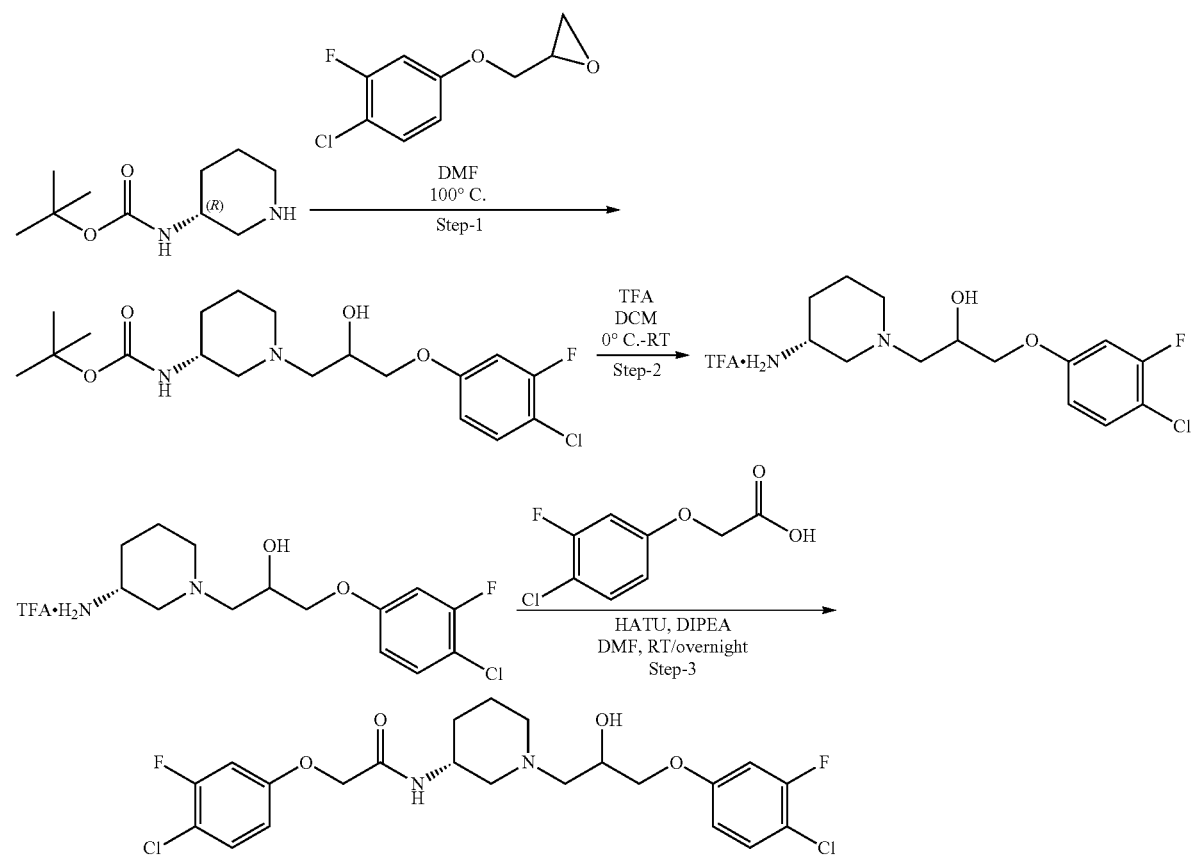

Step 1—Synthesis of tert-butyl ((3R)-1-(3-(4-chloro-3-fluorophenoxy)-2-hydroxypropyl)piperidin-3-yl)carbamate To a stirred solution of tert-butyl (R)-piperidin-3-yl)carbamate (0.500 g, 2.47 mmol, 1.0 equiv) in DMF (5 mL) was added 2-((4-chloro-3-fluorophenoxy)methyl)oxirane (0.602 g, 2.98 mmol, 2.0 equiv) at RT. The resulting reaction mixture was heated at 100° C. for 12 h. Product formation was confirmed by $^1$H NMR spectroscopy. Reaction was stopped by adding water and the resulting precipitate was filtered off. Obtained solid was washed with water (25 mL×2) and dried under vacuum to obtain tert-butyl ((3R)-1-(3-(4-chloro-3-fluorophenoxy)-2-hydroxypropyl)piperidin-3-yl)carbamate. (1.1 g as an white solid). LCMS: 403 [M+H]$^+$.

Step 2—Synthesis of 1-(((3R)-1-(3-(4-chloro-3-fluorophenoxy)-2-hydroxypropyl)piperidin-3-yl)-λ$^4$-azanyl)-2,2,2-trifluoroethan-1-one trifluoroacetate salt To a stirred solution of tert-butyl ((3R)-1-(3-(4-chloro-3-fluorophenoxy)-2-hydroxypropyl)piperidin-3-yl)carbamate (1.0 g, 2.48 mmol, 1.0 equiv) in DCM (30 mL) was added trifluoroacetic acid (5 mL) at RT. the reaction mixture was allowed to stir at RT overnight. DCM and excess trifluoroacetic acid was removed under reduced pressure to obtain 1-(((3R)-1-(3-(4-chloro-3-fluorophenoxy)-2-hydroxypropyl)piperidin-3-yl)-λ$^4$-azanyl)-2,2,2-trifluoroethan-1-one trifluoroacetate salt (1.4 g, as an oil). LCMS: 303 [M+H]$^+$.

Step 3—Synthesis of 2-(4-chloro-3-fluorophenoxy)-N-((3R)-1-(3-(4-chloro-3-fluorophenoxy)-2-hydroxypropyl)piperidin-3-yl)acetamide To a solution of 1-(((3R)-1-(3-(4-chloro-3-fluorophenoxy)-2-hydroxypropyl)piperidin-3-yl)-λ$^4$-azanyl)-2,2,2-trifluoroethan-1-one trifluoroacetate salt (1.0 g, 2.48 mmol, 1.0 equiv) in DMF (15 mL) was added 2-(4-chloro-3-fluorophenoxy)acetic acid (0.607 g, 2.97 mmol, 1.2 equiv) and HATU (1.89 g, 4.96 mmol) at RT. The resulting reaction mixture was stirred for 10 minutes and then DIPEA (2.1 mL, 12.4 mmol) was added. The reaction mixture was allowed to stir at RT overnight. Product formation was confirmed by LCMS. The reaction mixture was diluted with water (50 mL) and extracted with EtOAc (100 mL×2). The combined organic extracts were washed with water (50 mL×4), dried over anhydrous sodium sulfate and concentrated. The crude product obtained was purified by reverse phase HPLC to obtain 2-(4-chloro-3-fluorophenoxy)-N-((3R)-1-(3-(4-chloro-3-fluorophenoxy)-2-hydroxypropyl)piperidin-3-yl)acetamide (Compound 12-10 mg, as an off-white solid). LCMS: 489 [M+H]$^+$; $^1$HNMR (400 MHz, DMSO-d$_6$) δ 7.90 (d, J=7.02 Hz, 1H), 7.30-7.54 (m, 2H), 7.03 (m, 2H), 6.69-6.92 (m, 2H), 4.93 (br. s., 1H), 4.51 (s, 1H), 4.00 (d, J=7.02 Hz, 1H), 3.84-3.94 (m, 2H), 3.81 (br. s., 1H), 2.69 (d, J=12.72 Hz, 1H), 2.27-2.42 (m, 2H), 2.16 (m., 2H), 1.75 (br. s., 1H), 1.62 (d, J=9.21 Hz, 2H), 1.46 (d, J=7.02 Hz, 1H), 1.32 (br. s., 1H), 1.23 (br. s., 1H).

Example 9

Synthesis of 2-(4-chloro-3-fluorophenoxy)-N-(1-(3-(4-chloro-3-fluorophenoxy)-2-hydroxypropyl)piperidin-4-yl)acetamide

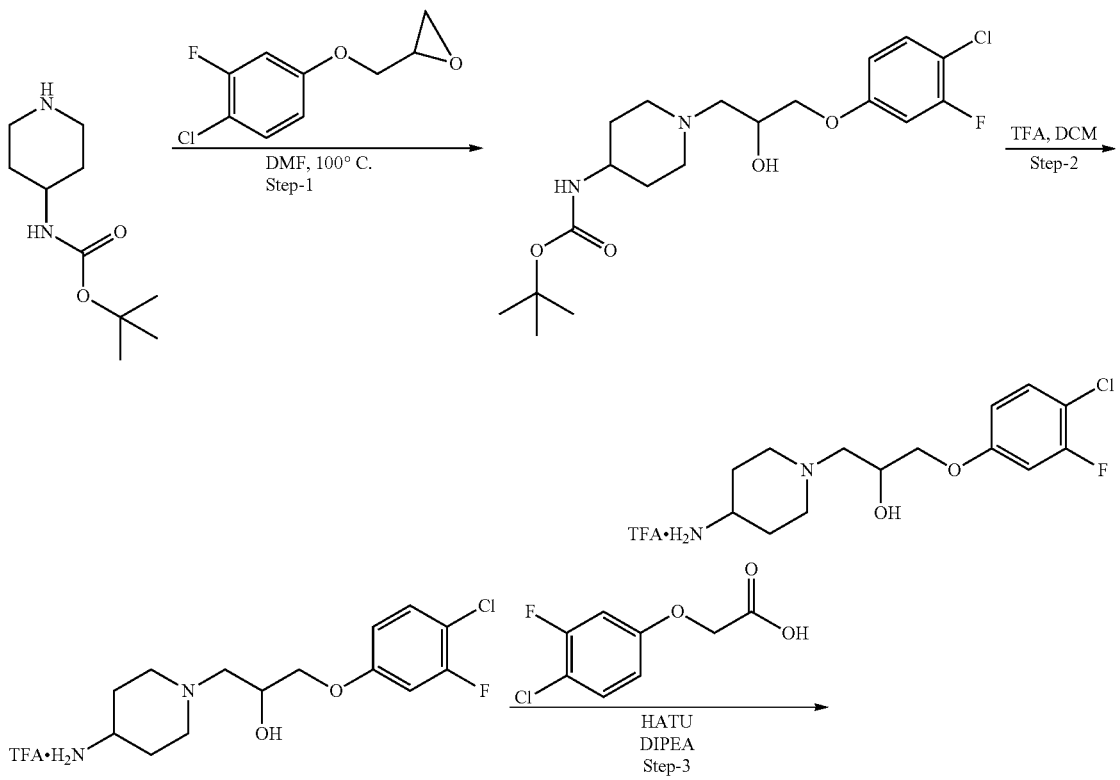

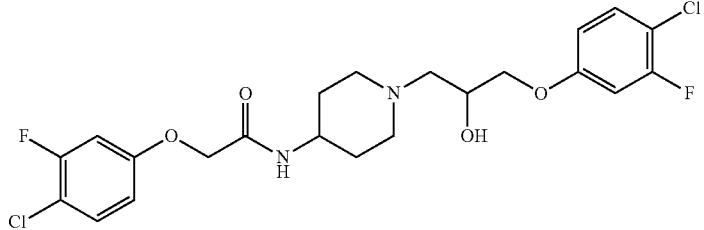

Step 1—Synthesis of tert-butyl (1-(3-(4-chloro-3-fluorophenoxy)-2-hydroxypropyl)piperidin-4-yl) carbamate To a stirred solution of tert-butyl piperidin-4-yl)carbamate (0.500 g, 2.500 mmol, 1.0 equiv) in DMF (5 mL) was added 2-((4-chloro-3-fluorophenoxy)methyl)oxirane (0.507 g, 2.500 mmol, 1.0 equiv) at RT. The resulting reaction mixture was heated at 100° C. for 12 hr. Progress of the reaction was monitored by $^1$H NMR. The reaction was stopped by adding water and the resulting precipitate was filtered off. The obtained solid was washed with water (25 mL×2) and dried under vacuum to obtain tert-butyl (1-(3-(4-chloro-3-fluorophenoxy)-2-hydroxypropyl)piperidin-4-yl)carbamate (1.000 g, 99% Yield) as a white solid. LCMS: 403.3 [M+H]$^+$; $^1$HNMR (400 MHz, DMSO-d$_6$) δ 7.45 (t, J=8.77 Hz, 1H), 7.05 (dd, J=2.63, 11.40 Hz, 1H), 6.84 (dd, J=1.75, 8.77 Hz, 1H), 6.74 (d, J=7.45 Hz, 1H), 4.86 (d, J=3.95 Hz, 1H), 3.98 (d, J=6.58 Hz, 1H), 3.82-3.93 (m, 2H), 3.17 (br. s., 1H), 2.74-2.90 (m, 2H), 2.26-2.42 (m, 2H), 1.90-2.09 (m, 2H), 1.60-1.70 (m, 2H), 1.37 (s, 9H).

Step 2—Synthesis of 1-(4-aminopiperidin-1-yl)-3-(4-chloro-3-fluorophenoxy)propan-2-al trifluoroacetate salt To a stirred solution of tert-butyl (1-(3-(4-chloro-3-fluorophenoxy)-2-hydroxypropyl)piperidin-4-yl)carbamate (1.00 g, 2.48 mmol, 1.0 equiv) in DCM (30 mL) was added trifluoroacetic acid (5 mL) at RT. The reaction mixture was allowed to stir at RT overnight. DCM and excess trifluoroacetic acid was removed under reduced pressure to obtain 1-(4-aminopiperidin-1-yl)-3-(4-chloro-3-fluorophenoxy)propan-2-ol trifluoroacetate salt (1.00 g, 96% Yield) as an yellow oil. $^1$HNMR (400 MHz, DMSO-d$_6$) δ 9.60 (br. s., 1H), 8.15 (br. s., 2H), 7.50 (t, J=9.21 Hz, 1H), 7.09 (d, J=11.40 Hz, 1H), 6.85 (d, J=7.89 Hz, 1H), 5.75 (br. s., 1H), 4.29 (br. s., 1H), 4.00 (br. s., 2H), 3.62 (d, J=10.96 Hz, 2H), 3.28 (br. s., 2H), 3.18 (d, 7=10.52 Hz, 3H), 2.07 (d, J=11.84 Hz, 2H), 1.83-2.01 (m, 2H).

Step 3—Synthesis of 2-(4-chloro-3-fluorophenoxy)-N-(1-(3-(4-chloro-3-fluorophenoxy)-2-hydroxypropyl)piperidin-4-yl)acetamide To a solution of 1-(4-aminopiperidin-1-yl)-3-(4-chloro-3-fluorophenoxy)propan-2-ol trifluoroacetate salt (1.00 g, 2.40 mmol, 1.0 equiv) in DMF (10 mL) was added 2-(4-chloro-3-fluorophenoxy)acetic acid (0.540 g, 2.64 mmol, 1.1 equiv) and HATU (1.830 g, 4.80 mmol, 2.0 equiv) at RT. The reaction mixture was stirred for 10 minutes and then DIPEA (1.7 mL, 9.41 mmol, 5.0 equiv) was added. The resultant reaction mixture was allowed to stir at RT overnight. Progress of the reaction was monitored by LCMS. The reaction mixture was diluted with water (50 mL) and extracted with EtOAc (100 mL×2). The combined organic layer was washed with water (50 mL×4), dried over anhydrous sodium sulfate and concentrated under reduced pressure to obtain a crude compound which was purified by reverse phase HPLC to obtain 2-(4-chloro-3-fluorophenoxy)-N-(1-(3-(4-chloro-3-fluorophenoxy)-2-hydroxypropyl)piperidin-4-yl)acetamide (Compound 13-0.500 g, 43% Yield) as an off-white solid. LCMS: 489.2 [M+H]$^+$; $^1$HNMR (400 MHz, DMSO-d$_6$) δ 7.97 (d, J=7.89 Hz, 1H), 7.45 (t, J=8.77 Hz, 1H), 7.49 (t, J=8.99 Hz, 1H), 7.05 (d, J=2.63 Hz, 1H), 7.07 (d, J=2.63 Hz, 1H), 6.84 (d, J=8.77 Hz, 2H), 4.87 (br. s., 1H), 4.50 (s, 2H), 4.00 (d, J=6.58 Hz, 1H), 3.83-3.95 (m, 2H), 3.60 (d, 7=7.45 Hz, 1H), 2.74-2.98 (m, 2H), 2.27-2.46 (m, 2H), 1.99-2.15 (m, 2H), 1.65 (br. s., 1H), 1.38-1.57 (m, 2H).

Example 10

Synthesis of 2-(4-chloro-3-fluorophenoxy)-1-(4-((3-(4-chloro-3-fluorophenoxy)-2-hydroxypropylamino) piperidin-1-yl)ethan-1-one

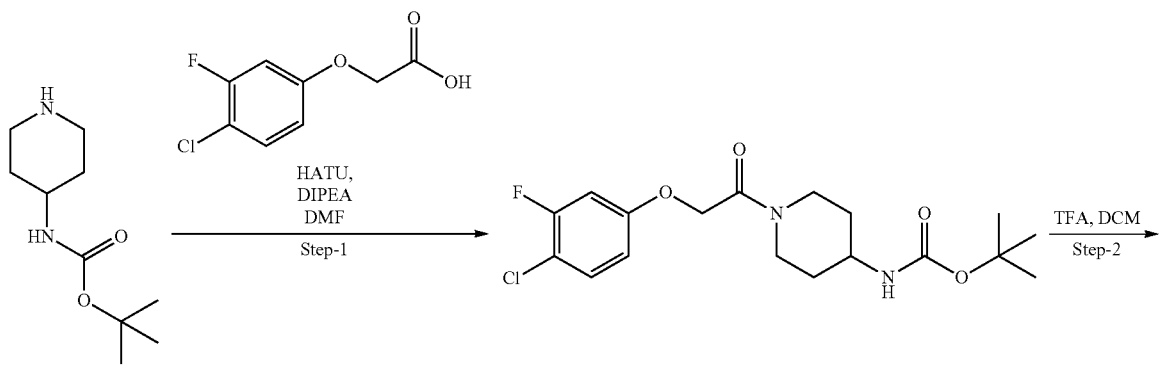

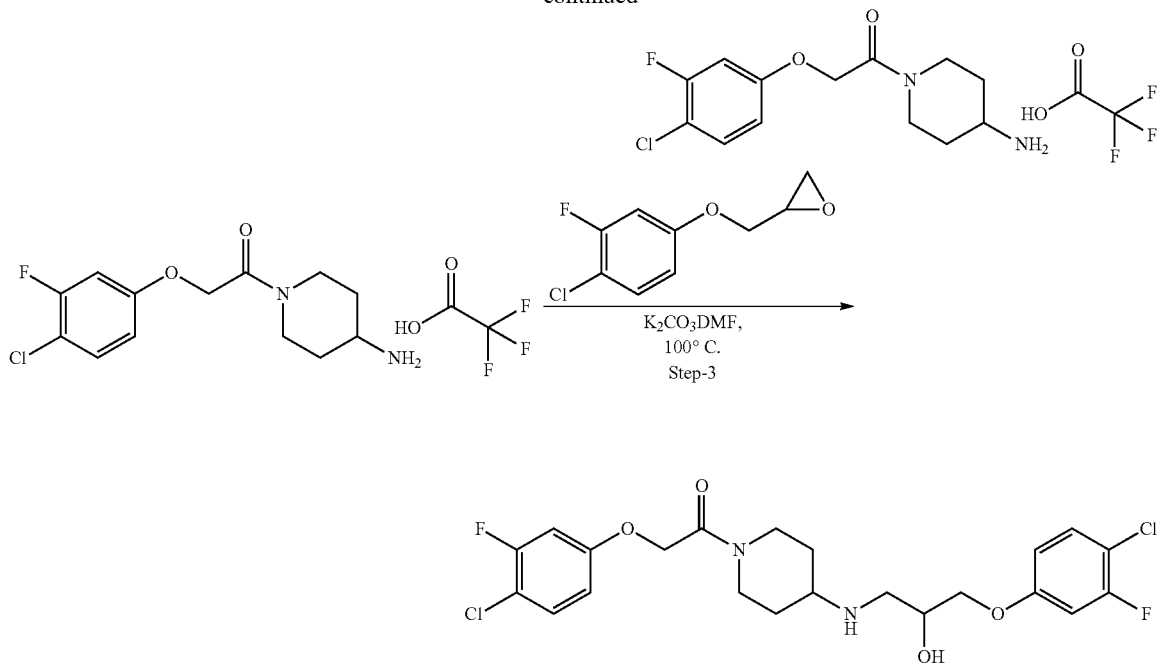

Step 1—Synthesis of tert-butyl (1-(2-(4-chloro-3-fluorophenoxy)acetyl)piperidin-4-yl)carbamate To a solution of tert-butyl piperidin-4-yl)carbamate (0.250 g, 1.25 mmol, 1.0 equiv) in DMF (10 mL) was added 2-(4-chloro-3-fluorophenoxy)acetic acid (0.281 g, 1.37 mmol, 1.1 equiv) and HATU (0.950 g, 2.50 mmol, 2.0 equiv) at RT. The reaction mixture was stirred for 10 minutes and then DIPEA (0.7 mL, 3.75 mmol, 5.0 equiv) was added. The resultant reaction mixture was allowed to stir at RT overnight. Progress of the reaction was monitored by LCMS. The reaction mixture was diluted with water (50 mL) and extracted with ethyl acetate (50 mL×2). Combined organic layer was washed with water (25 mL×4), dried over anhydrous $Na_2SO_4$ and concentrated under reduced pressure to obtain the crude compound which was crystallized in hexane to obtain tert-butyl (1-(2-(4-chloro-3-fluorophenoxy)acetyl) piperidin-4-yl)carbamate (0.480 g, 100% Yield) as an off-white solid. LCMS: 387.3 [M+H]$^+$; $^1$HNMR (400 MHz, DMSO-d$_6$) 57.46 (t, J=8.99 Hz, 1H), 7.05 (dd, J=2.85, 11.62 Hz, 1H), 6.91 (d, J=7.02 Hz, 1H), 6.80 (dd, J=2.41, 8.99 Hz, 1H), 4.87 (q, J=14.62 Hz, 2H), 4.15 (d, J=13.59 Hz, 1H), 3.72 (d, J=14.03 Hz, 1H), 3.48 (br. s., 1H), 3.07 (t, J=11.62 Hz, 1H), 2.68-2.78 (m, 1H), 1.74 (br. s., 2H), 1.38 (s, 9H), 1.16-1.26 (m, 2H).

Step 2—Synthesis of 1-(4-aminopiperidin-1-yl)-2-(4-chloro-3-fluorophenoxy)ethan-1-one trifluoroacetate salt To a stirred solution of tert-butyl (1-(2-(4-chloro-3-fluorophenoxy)acetyl)piperidin-4-yl)carbamate (0.480 g, 1.24 mmol, 1.0 equiv) in DCM (30 mL) was added trifluoroacetic acid (3 mL) at RT. the reaction mixture was allowed to stir at RT overnight. DCM and excess trifluoroacetic acid was removed under reduced pressure to obtain 1-(4-aminopiperidin-1-yl)-2-(4-chloro-3-fluorophenoxy)ethan-1-one trifluoroacetate salt (1.00 g, 100% Yield) as an yellow oil. $^1$HNMR (400 MHz, DMSO-d$_6$) δ 7.93 (br. s., 3H), 7.47 (t, J=8.77 Hz, 1H), 7.05 (dd, J=2.85, 11.62 Hz, 1H), 6.81 (dd, J=1.97, 8.99 Hz, 1H), 4.96 (d, J=14.47 Hz, 1H), 4.87 (d, J=14.91 Hz, 1H), 4.32 (d, J=13.59 Hz, 1H), 3.82 (d, J=14.03 Hz, 1H), 3.27 (br. s., 1H), 3.08 (t, J=12.72 Hz, 1H), 2.63-2.79 (m, 2H), 1.91 (br. s., 2H), 1.39-1.57 (m, 1H), 1.25-1.38 (m, 2H).

Step 3—Synthesis of 2-(4-chloro-3-fluorophenoxy)-1-(4-((3-(4-chloro-3-fluorophenoxy)-2-hydroxypropyl)amino)piperidin-1-yl)ethan-1-one To a stirred solution of 1-(4-aminopiperidin-1-yl)-2-(4-chloro-3-fluorophenoxy)ethan-1-one trifluoroacetate salt (0.500 g, 1.25 mmol, 1.0 equiv) in DMF (10 mL) was added $K_2CO_3$ (0.518, 3.75 mmol, 3.0 equiv) followed by the addition of 2-((4-chloro-3-fluorophenoxy)methyl)oxirane (0.355 g, 1.75 mmol, 2.0 equiv) at RT. The resulting reaction mixture was heated at 100° C. for 12 hr. Product formation was confirmed by LCMS. The reaction was stopped by adding water (70 mL) and extracted with EtOAc (2×50 mL). The combined organic layer was washed with water (5×30 mL), dried over anhydrous sodium sulfate and concentrated under reduced pressure to obtain a crude mixture which was purified by reverse phase HPLC to obtain 2-(4-chloro-3-fluorophenoxy)-1-(4-((3-(4-chloro-3-fluorophenoxy)-2-hydroxypropyl)amino)piperidin-1-yl)ethan-1-one (Compound 14-120 mg, 20% Yield) as an off-white solid. LCMS: 489.3 [M+H]$^+$; $^1$HNMR (400 MHz, DMSO-d$_6$) δ 7.48 (q, J=9.21 Hz, 2H), 6.98-7.11 (m, 2H), 6.81 (d, J=8.77 Hz, 1H), 6.85 (d, J=8.77 Hz, 1H), 5.61 (br. s., 1H), 4.81-5.01 (m, 3H), 4.29 (d, J=13.16 Hz, 1H), 3.95-4.08 (m, 3H), 3.82 (d, 7=13.15 Hz, 1H), 2.97-3.16 (m, 3H), 2.81-2.97 (m, 2H), 2.63-2.78 (m, 2H), 1.97 (br. s., 2H), 1.45 (br. s., 2H), 1.26 (d, J=19.29 Hz, 2H).

Example 11

Synthesis of trans-5-chloro-N-(4-(2-(4-chloro-3-fluorophenoxy)acetamido)cyclohexyl)benzofuran-2-carboxamide

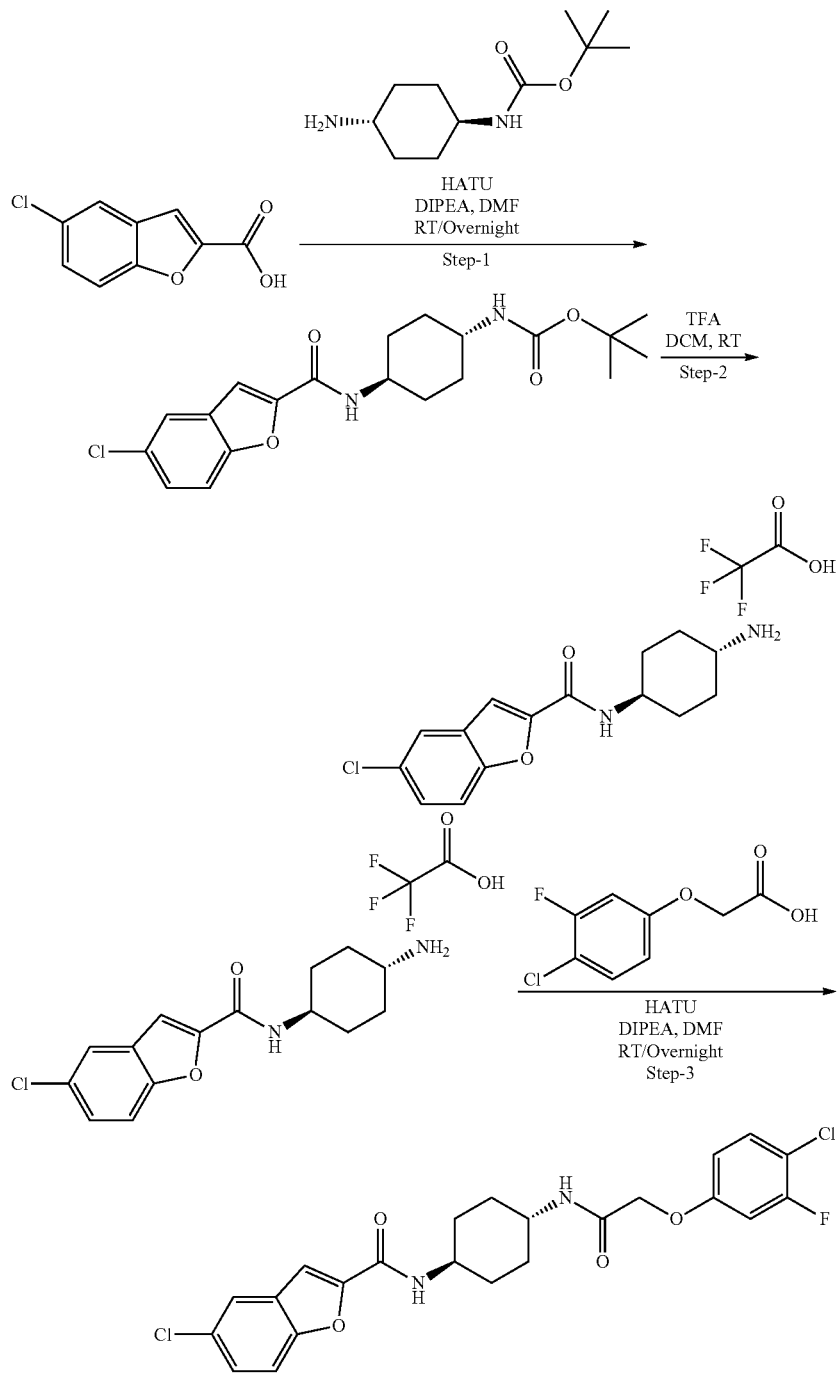

Step 1—Synthesis of trans-tert-butyl (4-(5-chlorobenzofuran-2-carboxamido)cyclohexyl)carbamate To a solution of 5-chlorobenzofuran-2-carboxylic acid (0.274 g, 1.4 mmol, 1.5 equiv) in DMF (10 mL) was added DIPEA (0.5 mL, 2.7 mmol, 3.0 equiv) followed by the addition of HATU (0.706 g, 1.8 mmol, 2.0 equiv) and the resultant reaction mixture was stirred for 30 min. Trans-tert-butyl (4-aminocyclohexyl)carbamate (0.200 g, 0.90 mmol, 1.0 equiv) was added and the reaction mixture was allowed to stir overnight at RT and the resulting precipitate was filtered off and washed with excess methanol to obtain trans-tert-butyl (4-(5-chlorobenzofuran-2-carboxamido)cyclohexyl)carbamate (350 mg, 64% Yield) as an off-white solid. LCMS: 393 [M+H]$^+$.

Step 2—Synthesis of trans-N-(4-aminocyclohexyl)-5-chlorobenzofuran-2-carboxamide trifluoroacetate salt To a stirred solution of trans-tert-butyl (4-(5-chlorobenzofuran-2-carboxamido)cyclohexyl)carbamate (350 mg, 0.89 mmol, 1 equiv) in DCM (10 mL) was added trifluoroacetic acid (5 mL) and the resultant reaction mixture was stirred at RT for 1 h under nitrogen atmosphere. Reaction was monitored by LCMS. After completion of reaction, the reaction mixture was concentrated under reduced pressure to obtain sticky crude compound which was triturated with hexane (10 mL) and diethyl ether and dried under vacuum to obtain trans-N-(4-aminocyclohexyl)-5-chlorobenzofuran-2-carboxamide trifluoroacetate salt (500 mg, quantitative yield) as an off-white solid. LCMS: 293 [M+H]$^+$.

Step 3—Synthesis of trans-5-chloro-N-(4-(2-(4-chloro-3-fluorophenoxy)acetamido)cyclohexyl)benzofuran-2-carboxamide To a solution of trans-N-(4-aminocyclohexyl)-5-chlorobenzofuran-2-carboxamide trifluoroacetate salt (0.200 g, 0.51 mmol, 1.0 equiv) in DCM (10 mL) was added DIPEA (0.3 mL, 1.5 mmol, 3.0 equiv) followed by the addition of HATU (0.388 g, 1.02 mmol, 2.0 equiv), The resulting mixture was stirred for 30 min. 2-(4-chloro-3-fluorophenoxy)acetic acid (0.164 g, 0.76 mmol, 1.5 equiv) was added and the reaction mixture was allowed to stir overnight at RT and the resulting precipitate was filtered off and washed with excess methanol to obtain trans-5-chloro-N-(4-(2-(4-chloro-3-fluorophenoxy)acetamido)cyclohexyl)benzofuran-2-carboxamide (Compound 17-100 mg, 42% Yield) as an off-white solid. LCMS: 479 [M+H]$^+$; $^1$HNMR (400 MHz, DMSO-$d_6$) δ 8.61 (d, J=7.89 Hz, 1H), 8.01 (d, J=8.33 Hz, 1H), 7.87 (d, J=2.19 Hz, 1H), 7.69 (d, J=8.77 Hz, 1H), 7.32-7.60 (m, 3H), 7.07 (dd, J=2.63, 11.40 Hz, 1H), 6.85 (d, J=10.96 Hz, 1H), 4.51 (s, 2H), 3.76 (d, J=9.21 Hz, 1H), 3.60 (hr. s., 1H), 1.73-1.98 (m, 4H), 1.28-1.54 (m, 4H).

Example 12

Synthesis of trans-6-chloro-N-(4-(2-(4-chloro-3-fluorophenoxy)acetamido)cyclohexyl)benzo[d]thiazole-2-carboxamide

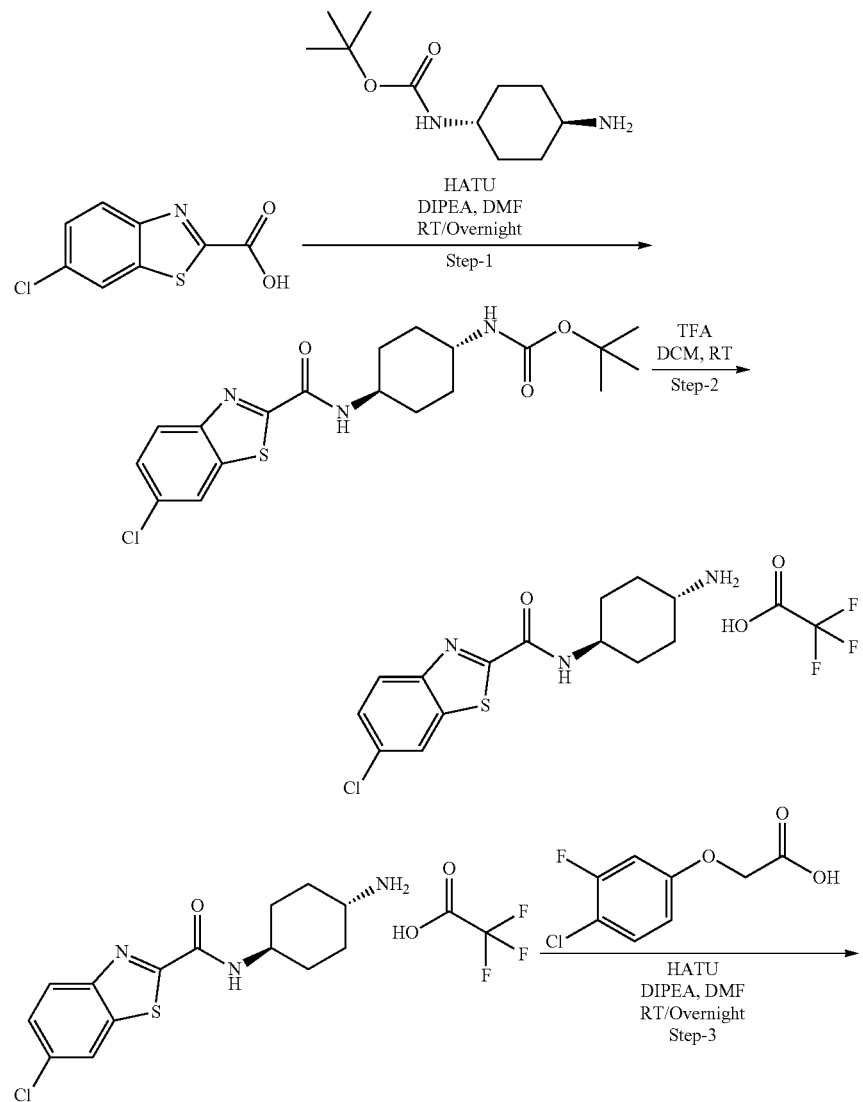

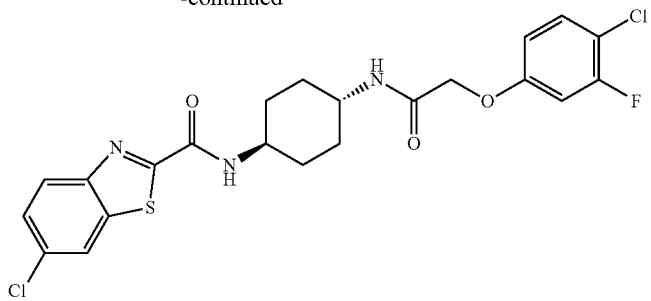

Step 1—Synthesis of trans-tert-butyl (4-(6-chlorobenzo[d]thiazole-2-carboxamido)cyclohexyl)carbamate To a solution of 6-chlorobenzo[d]thiazole-2-carboxylic acid (0.025 g, 0.11 mmol, 1.0 equiv) in DMF (10 mL) was added DIPEA (0.2 mL, 0.33 mmol, 3.0 equiv) followed by the addition of HATU (0.089 g, 0.23 mmol, 2.0 equiv) and the resulting mixture was stirred for 30 min. Trans-tert-butyl (4-aminocyclohexyl)carbamate (0.025 g, 0.11 mmol, 1.0 equiv) was added and the reaction mixture was allowed to stir overnight at RT and the resulting precipitate was filtered off and washed with excess methanol to obtain trans-tert-butyl (4-(6-chlorobenzo[d]thiazole-2-carboxamido)cyclohexyl)carbamate (60 mg, quantitative yield) as an off-white solid. LCMS: 410 [M+H]$^+$; $^1$HNMR (400 MHz, DMSO-d$_6$) δ 9.04 (d, J=8.3 Hz, 1H), 8.39 (s, 1H), 8.11 (d, J=8.8 Hz, 1H), 7.66 (d, J=9.2 Hz, 1H), 6.75 (d, J=7.0 Hz, 1H), 3.71 (br. s., 2H), 3.18 (br. s., 2H), 1.80 (d, J=12.7 Hz, 3H), 1.54 (d, J=9.6 Hz, 2H), 1.38 (s, 9H), 1.25 (d, J=11.4 Hz, 2H).

Step 2—Synthesis of trans-N-(4-aminocyclohexyl)-6-chlorobenzo[d]thiazole-2-carboxamide trifluoroacetate salt To a stirred solution of trans-tert-butyl (4-(6-chlorobenzo[d]thiazole-2-carboxamido)cyclohexyl)carbamate (60 mg, 0.16 mmol, 1 equiv) in DCM (2 mL) was added trifluoroacetic acid (3 mL) and the resultant reaction mixture was stirred at RT for 1 h under nitrogen atmosphere. Reaction was monitored by LCMS. After completion of reaction, the reaction mixture was concentrated under reduced pressure to obtain sticky crude compound which was triturated with hexane (10 mL), diethyl ether (10 mL) and dried under vacuum to obtain trans-N-(4-aminocyclohexyl)-6-chlorobenzo[d]thiazole-2-carboxamide trifluoroacetate salt (70 mg, quantitative yield) as an off-white solid. LCMS: 310 [M+H]$^+$; $^1$HNMR (400 MHz, DMSO-d$_6$) δ 9.12 (d, J=8.3 Hz, 1H), 8.40 (s, 1H), 8.12 (d, J=8.8 Hz, 1H), 7.76 (br. s., 2H), 7.67 (dd, J=2.2, 8.8 Hz, 1H), 3.75 (br. s., 2H), 2.98 (br. s., 2H), 1.97 (d, J=11.0 Hz, 2H), 1.89 (d, J=10.5 Hz, 2H), 1.68-1.47 (m, 2H), 1.47-1.34 (m, 2H).

Step 3—Synthesis of trans-6-chloro-N-(4-(2-(4-chloro-3-fluorophenoxy)acetamido)cyclohexyl)benzo[d]thiazole-2-carboxamide To a solution of trans-N-(4-aminocyclohexyl)-6-chlorobenzo[d]thiazole-2-carboxamide trifluoroacetate salt (0.070 g, 0.15 mmol, 1.0 equiv) in DMF (10 mL) was added DIPEA (0.1 mL, 0.45 mmol, 3.0 equiv) followed by the addition of HATU (0.114 g, 0.30 mmol, 2.0 equiv) and the resulting mixture was stirred for 30 min. 2-(4-chloro-3-fluorophenoxy)acetic acid (0.40 g, 0.18 mmol, 1.5 equiv) was added and the reaction mixture was allowed to stir overnight at RT and the resulting precipitate was filtered off and washed with excess methanol to obtain trans-6-chloro-N-(4-(2-(4-chloro-3-fluorophenoxy)acetamido)cyclohexyl)benzo[d]thiazole-2-carboxamide (Compound 18-15 mg, 18% Yield) as a white solid. LCMS: 497 [M+H]$^+$; $^1$HNMR (400 MHz, DMSO-d6) δ 9.05 (d, J=9.21 Hz, 1H), 8.39 (br. s., 1H), 8.12 (d, J=8.33 Hz, 1H), 7.99 (d, J=8.33 Hz, 1H), 7.66 (d, J=8.77 Hz, 1H), 7.50 (t, J=8.77 Hz, 1H), 7.07 (d, J=13.59 Hz, 1H), 6.86 (d, J=11.40 Hz, 1H), 4.51 (s, 2H), 3.77 (br. s., 1H), 3.60 (br. s., 1H), 1.81 (d, J=13.59 Hz, 4H), 1.59 (d, J=11.40 Hz, 2H), 1.39 (d, J=11.84 Hz, 2H).

Example 13

Synthesis of trans-5-chloro-N-(4-(2-(4-chloro-3-fluorophenoxy)acetamido)cyclohexyl)-2,3-dihydrobenzofuran-2-carboxamide

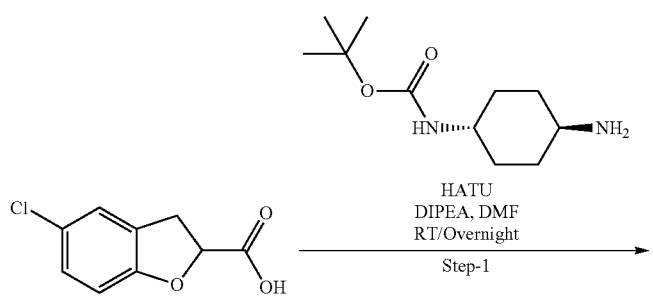

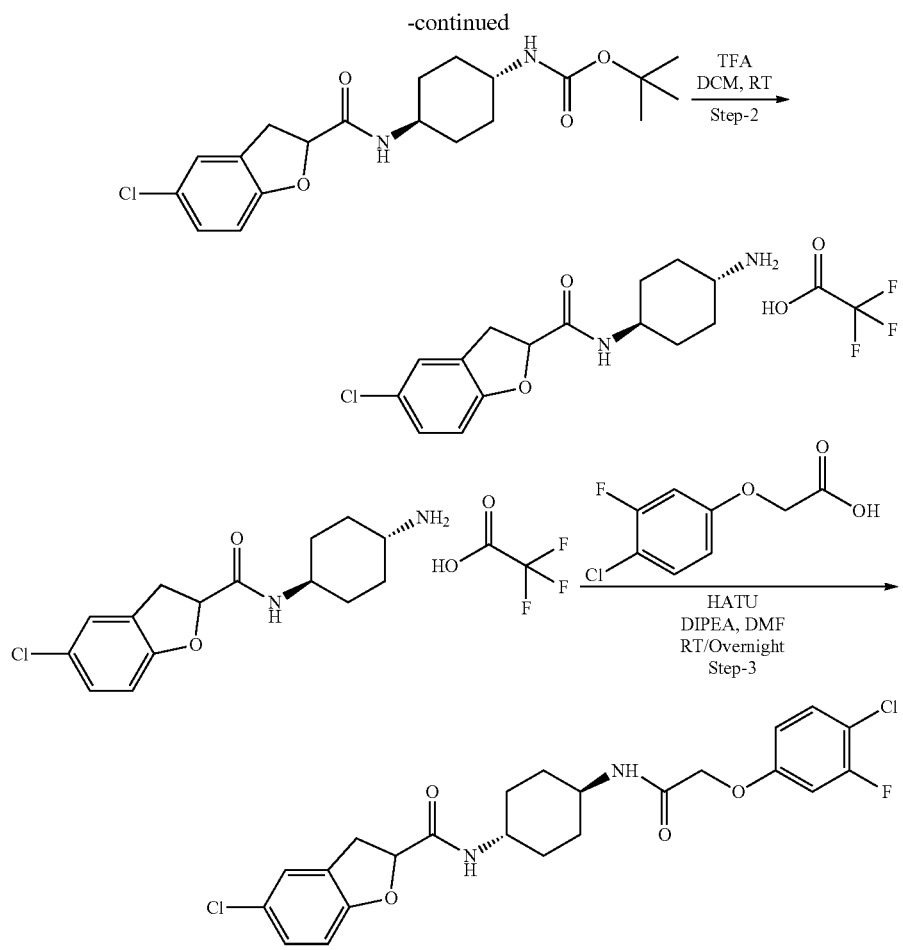

Step 1—Synthesis of trans-tert-butyl (4-(5-chloro-2,3-dihydrobenzofuran-2-carboxamido)cyclohexyl) carbamate To a solution of 5-chloro-2,3-dihydrobenzofuran-2-carboxylic acid (0.050 g, 0.25 mmol, 1.0 equiv) in DMF (05 mL) was added DIPEA (0.2 mL, 0.75 mmol, 3.0 equiv) followed by the addition of HATU (0.190 g, 0.50 mmol, 2.0 equiv) and the resulting mixture was stirred for 30 min. Trans-tert-butyl (4-aminocyclohexyl)carbamate (0.200 g, 0.90 mmol, 1.0 equiv) was added and the reaction mixture was allowed to stir overnight at RT and the resulting precipitate was filtered off and washed with excess methanol to obtain trans-tert-butyl (4-(5-chloro-2,3-dihydrobenzofuran-2-carboxamido)cyclohexyl)carbamate (100 mg, quantitative yield) as an off-white solid. LCMS: 394 [M+H]$^+$.

Step 2—Synthesis of trans-N-(4-aminocyclohexyl)-5-chloro-2,3-dihydrobenzofuran-2-carboxamide trifluoroacetate salt To a stirred solution of trans-tert-butyl (4-(5-chloro-2,3-dihydrobenzofuran-2-carboxamido)cyclohexyl)carbamate (100 mg, 0.25 mmol, 1 equiv) in DCM (10 mL) was added trifluoroacetic acid (5 mL) and the resultant reaction mixture was stirred at RT for 1 h under nitrogen atmosphere. Reaction was monitored by LCMS. After completion of reaction, the reaction mixture was concentrated under reduced pressure to obtain sticky crude compound which was triturated with hexane (10 mL) and diethyl ether and dried under vacuum to obtain trans-N-(4-aminocyclohexyl)-5-chloro-2,3-dihydrobenzofuran-2-carboxamide trifluoroacetate salt (100 mg, quantitative yield) as an off-white solid. LCMS: 294 [M+H]$^+$.

Step 3—Synthesis of trans-5-chloro-N-(4-(2-(4-chloro-3-fluorophenoxy)acetamido)cyclohexyl)-2,3-dihydrobenzofuran-2-carboxamide To a solution of trans-N-(4-aminocyclohexyl)-5-chloro-2,3-dihydrobenzofuran-2-carboxamide trifluoroacetate salt (0.100 g, 0.25 mmol, 1.0 equiv) in DMF (10 mL) was added DIPEA (0.13 mL, 0.75 mmol, 3.0 equiv) followed by the addition of HATU (0.190 g, 0.50 mmol, 2.0 equiv), The resulting mixture was stirred for 30 min. 2-(4-chloro-3-fluorophenoxy)acetic acid (0.083 g, 0.38 mmol, 1.5 equiv) was added and the reaction mixture was allowed to stir overnight at RT and the resulting precipitate was filtered off and washed with excess methanol to obtain trans-5-chloro-N-(4-(2-(4-chloro-3-fluorophenoxy)acetamido)cyclohexyl)-2,3-dihydrobenzofuran-2-carboxamide (Compound 19—70 mg, 60% Yield) as an off-white solid. LCMS: 481 [M+H]$^+$; $^1$HNMR (400 MHz, DMSO-d$_6$) δ 8.03 (d, J=7.45 Hz, 1H), 7.96 (d, J=8.33 Hz, 1H), 7.49 (t, J=8.99 Hz, 1H), 7.26 (hr. s., 1H), 7.15 (d, J=8.77 Hz, 1H), 7.04 (d, J=4.38 Hz, 1H), 6.84 (d, J=8.33 Hz, 2H), 5.06-5.17 (m, 1H), 4.49 (s, 2H), 3.56 (hr. s., 2H), 3.43 (d, J=10.09 Hz, 1H), 3.18 (hr. s., 1H), 1.77 (hr. s., 4H), 1.32 (hr. s., 4H).

Example 14

Synthesis of 5-chloro-N-(1-(3-(4-chloro-3-fluorophenoxy)-2-hydroxypropyl)piperidin-4-yl)-2,3-dihydrobenzofuran-2-carboxamide

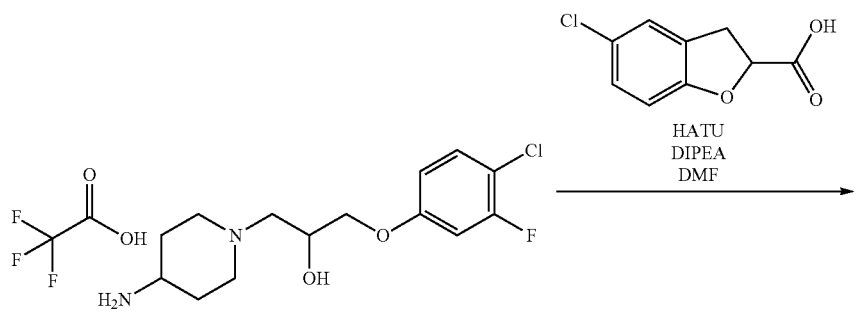

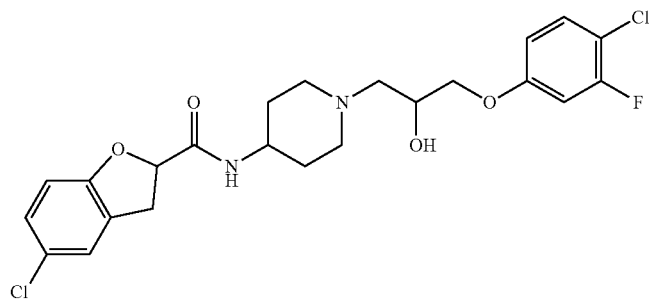

To a solution of 1-(4-aminopiperidin-1-yl)-3-(4-chloro-3-fluorophenoxy)propan-2-ol trifluoroacetate salt (0.105 g, 0.25 mmol, 1.0 equiv) in DMF (10 mL) was added 5-chloro-2,3-dihydrobenzofuran-2-carboxylic acid (0.050 g, 0.25 mmol, 1.0 equiv) and HATU (0.190 g, 9.0 mmol, 2.0 equiv) at RT. The resulting reaction mixture was stirred for 10 min and then DIPEA (0.2 mL, 0.75 mmol, 3.0 equiv) was added. The reaction mixture was allowed to stir at RT overnight. Product formation was confirmed by LCMS. The reaction mixture was diluted with water (50 mL) and extracted with ethyl acetate (100 mL×2). Combined organic extracts were washed with water (50 mL×4), dried over anhydrous $Na_2SO_4$ and concentrated under reduced pressure to obtain crude which was purified by reversed phase HPLC to obtain 5-chloro-N-(1-(3-(4-chloro-3-fluorophenoxy)-2-hydroxypropyl)piperidin-4-yl)-2,3-dihydrobenzofuran-2-carboxamide (Compound 20-10 mg) as an off-white solid. LCMS: 483 [M+H]$^+$; $^1$HNMR (400 MHz, DMSO-d$_6$) δ 8.05 (d, J=8.3 Hz, 1H), 7.46 (t, J=8.8 Hz, 1H), 7.26 (hr. s., 1H), 7.15 (d, J=7.9 Hz, 1H), 7.06 (d, J=11.0 Hz, 1H), 6.83 (d, J=8.3 Hz, 2H), 5.08-5.17 (m, 1H), 4.87 (hr. s., 1H), 4.00 (d, J=6.6 Hz, 1H), 3.89 (hr. s., 1H), 3.57 (hr. s., 1H), 3.45 (dd, J=16.2, 11.0 Hz, 2H), 3.14-3.23 (m, 1H), 2.80 (hr. s., 2H), 2.33 (hr. s., 2H), 2.06 (d, J=17.1 Hz, 2H), 1.65 (hr. s., 2H), 1.48 ppm (d, J=12.3 Hz, 2H).

Example 15

Synthesis of 6-chloro-N-(1-(3-(4-chloro-3-fluorophenoxy)-2-hydroxypropyl)piperidin-4-yl)-2-napthaminde

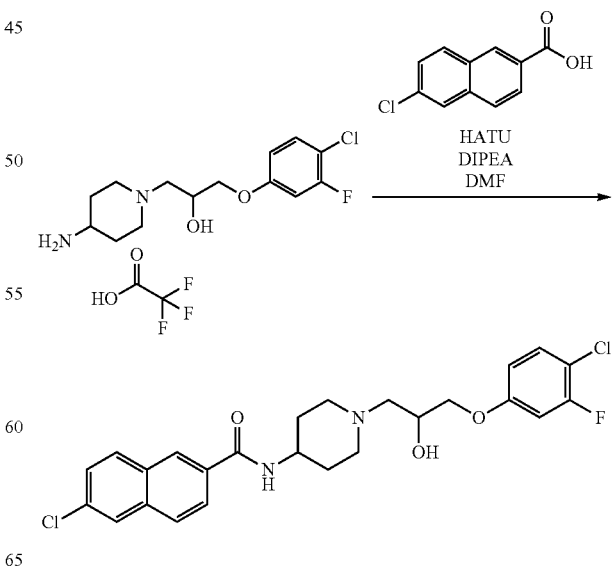

To a solution of 1-(4-aminopiperidin-1-yl)-3-(4-chloro-3-fluorophenoxy)propan-2-ol trifluoroacetate salt (0.202 g, 0.485 mmol, 1.0 equiv) in DMF (10 mL) was added 6-chloro-2-naphthoic acid (0.100 g, 0.485 mmol, 1.0 equiv) and HATU (0.369 g, 0.970 mmol, 2.0 equiv) at RT. The resulting reaction mixture was allowed to stir for 10 min. DIPEA (187 mg, 1.48 mmol, 3.0 equiv) was added and the resultant reaction mixture was allowed to stir at RT overnight. Product formation was confirmed by LCMS. The reaction mixture was diluted with water (50 mL) and extracted with ethyl acetate (100 mL×2). Combined organic extracts were washed with water (50 mL×4), dried over anhydrous Na₂SO₄ and concentrated to obtain crude which was purified by reversed phase HPLC to obtain 6-chloro-N-(1-(3-(4-chloro-3-fluorophenoxy)-2-hydroxypropyl)piperidin-4-yl)-2-naphthamide (Compound 21—60 mg, 26% Yield) as an off-white solid. LCMS: 491 [M+H]⁺; ¹HNMR (400 MHz, DMSO-d₆) δ 8.40-8.53 (m, 2H), 8.05-8.18 (m, 2H), 7.98 (s, 2H), 7.60 (dd, J=8.8, 1.8 Hz, 1H), 7.47 (t, J=8.8 Hz, 1H), 7.08 (dd, 7=11.8, 2.6 Hz, 1H), 6.86 (d, J=8.8 Hz, 1H), 4.91-5.07 (m, 1H), 3.98-4.11 (m, 2H), 3.79-3.98 (m, 2H), 2.93-3.10 (m, 3H), 2.31 (d, J=13.6 Hz, 3H), 1.85 (d, J=11.0 Hz, 2H), 1.66 (d, 7=11.8 Hz, 2H).

Example 16

Synthesis of 6-chloro-N-(1-(3-(4-chloro-3-fluorophenoxy)-2-hydroxypropyl)piperidin-4-yl)quinoline-2-carboxamide

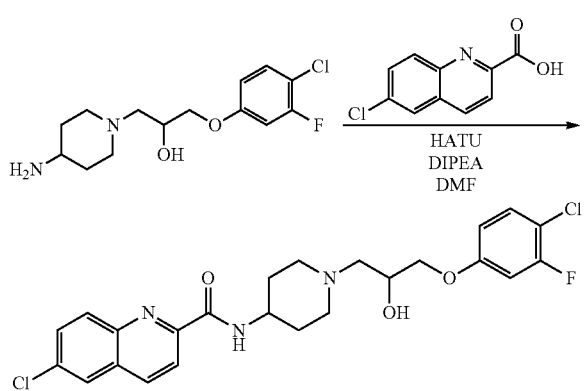

To a solution of 1-(4-aminopiperidin-1-yl)-3-(4-chloro-3-fluorophenoxy)propan-2-ol (0.138 g, 0.48 mmol, 1.0 equiv) in DMF (10 mL) was added 6-chloroquinoline-2-carboxylic acid (0.100 g, 0.48 mmol, 1.0 equiv) and HATU (0.365 g, 0.96 mmol, 2.0 equiv) at RT. The resulting reaction mixture was stir for 10 min. DIPEA (0.24 mL, 1.44 mmol, 3.0 equiv) was added and the resultant reaction mixture was allowed to stir at RT overnight. Product formation was confirmed by LCMS. The reaction mixture was diluted with water (50 mL) and extracted with ethyl acetate (100 mL×2). Combined organic extracts were washed with water (50 mL×4), dried over anhydrous Na₂SO₄ and concentrated under reduced pressure to obtain crude which was purified by reversed phase HPLC to obtain 6-chloro-N-(1-(3-(4-chloro-3-fluorophenoxy)-2-hydroxypropyl)piperidin-4-yl)quinoline-2-carboxamide (Compound 22-15 mg, 6.5% Yield) white solid. LCMS: 492 [M+H]⁺; ¹HNMR (400 MHz, DMSO-d₆) δ 8.68 (d, J=8.3 Hz, 1H), 8.53 (s, 1H), 8.24 (d, J=2.2 Hz, 1H), 8.17 (dd, J=4.8, 8.8 Hz, 2H), 7.88 (dd, J=2.4, 9.0 Hz, 1H), 7.47 (t, J=9.0 Hz, 1H), 7.06 (d, J=3.1 Hz, 1H), 6.86 (d, J=8.8 Hz, 1H), 4.90 (hr. s., 1H), 4.04 (d, J=7.0 Hz, 1H), 3.95-3.86 (m, 2H), 3.85 (hr. s., 1H), 3.00-2.82 (m, 2H), 2.40-2.27 (m, 2H), 2.20-2.05 (m, 2H), 1.79 (hr. s., 2H), 1.71 (d, J=11.0 Hz, 2H).

Example 17

Synthesis of trans-6-chloro-N-(4-(2-(4-chloro-3-fluorophenoxy)acetamido)cyclohexyl)quinoline-2-carboxamide

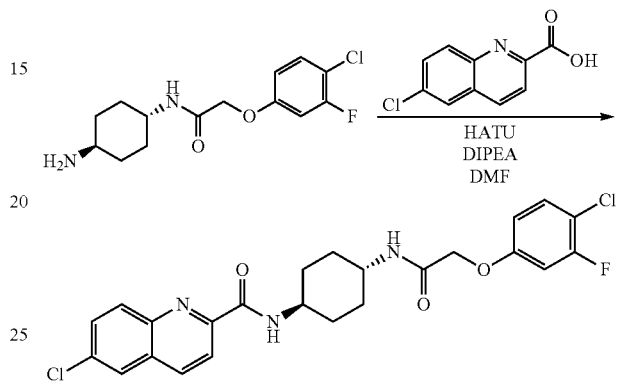

To a solution of trans-N-(4-aminocyclohexyl)-2-(4-chloro-3-fluorophenoxy)acetamide (0.200 g, 0.6 mmol, 1.0 equiv) in DMF (10 mL) was added 6-chloroquinoline-2-carboxylic acid (0.138 g, 0.6 mmol, 1.0 equiv) and HATU (0.456 g, 1.2 mmol, 2.0 equiv) at RT. The reaction mixture was stir for 10 min. DIPEA (0.31 mL, 1.8 mmol, 3.0 equiv) was added and the resultant reaction mixture was allowed to stir at RT overnight. Product formation was confirmed by LCMS. The reaction mixture was diluted with water (50 mL) and extracted with ethyl acetate (100 mL×2). Combined organic extracts were washed with water (50 mL×4), dried over anhydrous Na₂SO₄ and concentrated under reduced pressure to obtain crude which was purified by reversed phase HPLC to obtain trans-6-chloro-N-(4-(2-(4-chloro-3-fluorophenoxy)acetamido)cyclohexyl)quinoline-2-carboxamide (Compound 23-110 mg, 34% Yield) as an off-white solid. LCMS: 490 [M+H]⁺; ¹HNMR (400 MHZ, DMSO-d₆) δ 8.66 (d, J=8.3 Hz, 1H), 8.54 (d, J=8.3 Hz, 1H), 8.33-8.14 (m, 3H), 8.01 (d, J=7.9 Hz, 1H), 7.88 (d, J=9.2 Hz, 1H), 7.50 (t, J=8.8 Hz, 1H), 7.11-7.01 (m, 1H), 6.86 (d, J=8.3 Hz, 1H), 4.52 (s, 2H), 3.83 (d, J=7.5 Hz, 1H), 3.65 (hr. s., 1H), 2.01-1.71 (m, 4H), 1.69-1.53 (m, 2H), 1.47-1.32 (m, 2H).

Example 18

Synthesis of trans-N-(4-(2-(4-chloro-3-fluorophenoxy)acetamido)cyclohexyl)furo[2,3-c]pyridine-2-carboxamide

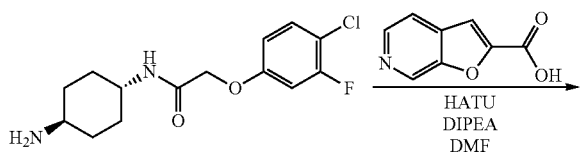

503
-continued

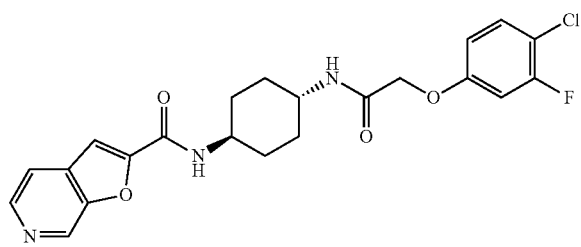

To a solution of trans-N-(4-aminocyclohexyl)-2-(4-chloro-3-fluorophenoxy)acetamide (0.200 g, 0.6 mmol, 1.0 equiv) in DMF (10 mL) was added furo[2,3-c]pyridine-2-carboxylic acid (0.108 g, 0.6 mmol, 1.0 equiv) and HATU (0.456 g, 1.2 mmol, 2.0 equiv) at RT. The reaction mixture was stir for 10 min. DIPEA (0.31 mL, 1.8 mmol, 3.0 equiv) was added and the resultant reaction mixture continued stirring at RT for overnight. Product formation was confirmed by LCMS. The reaction mixture was diluted with water (50 mL) and extracted with ethyl acetate (100 mL×2). Combined organic extracts were washed with water (50 mL×4), dried over anhydrous $Na_2SO_4$ and concentrated under reduced pressure to obtain crude which was purified by reversed phase HPLC to obtain trans-N-(4-(2-(4-chloro-3-fluorophenoxy)acetamido)cyclohexyl)furo[2,3-c]pyridine-2-carboxamide (Compound 24-90 mg, 30% Yield) as an off white solid. LCMS: 446 $[M+H]^+$; $^1$HNMR (400 MHZ, DMSO-$d_6$) δ 9.04 (s, 1H), 8.79 (d, J=7.9 Hz, 1H), 8.47 (d, J=5.3 Hz, 1H), 8.01 (d, J=8.3 Hz, 1H), 7.81 (d, J=5.3 Hz, 1H), 7.60 (s, 1H), 7.50 (t, J=9.0 Hz, 1H), 7.13-7.00 (m, 1H), 6.86 (d, J=8.3 Hz, 1H), 4.51 (s, 2H), 3.78 (br. s., 1H), 3.63 (br. s., 1H), 1.82 (d, J=16.2 Hz, 4H), 1.57-1.30 (m, 4H).

Example 19

Synthesis of 2-(4-chloro-3-fluorophenoxy)-N-(1-(3-(4-chloro-3-fluorophenoxy)-2-hydroxypropyl)-2,2,6,6-tetramethylpiperidin-4-yl)acetamide

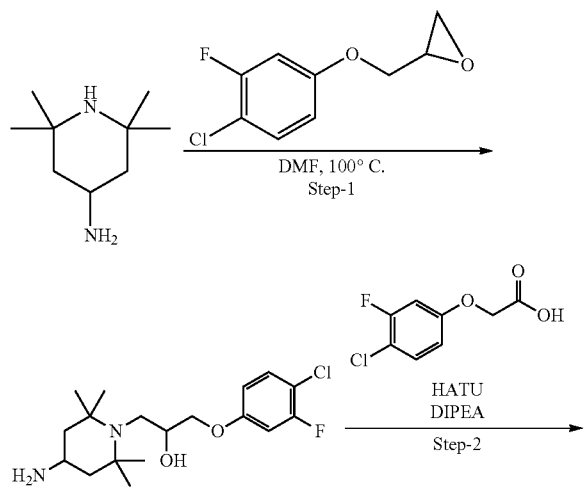

504
-continued

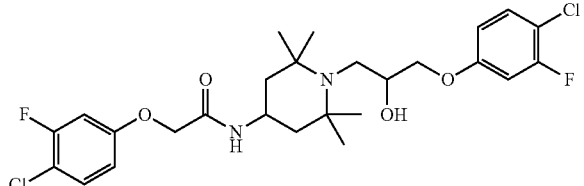

Step 1—Synthesis of 1-(4-amino-2,2,6,6-tetramethylpiperidin-1-yl)-3-(4-chloro-3-fluorophenoxy)propan-2-ol To a stirred solution of 2,2,6,6-tetramethylpiperidin-4-amine (1.00 g, 6.39 mmol, 1.0 equiv) in DMF (10 mL) was added 2-((4-chloro-3-fluorophenoxy)methyl)oxirane (1.19 g, 6.39 mmol, 1.0 equiv) at RT. The resulting reaction mixture was heated at 100° C. for 12 h. Progress of the reaction was monitored by $^1$H NMR. Reaction was quenched by adding water and extracted with ethyl acetate (100 mL×2). Combined organic layer was washed with water (50 mL×4), dried over anhydrous $Na_2SO_4$ and concentrated under reduced pressure. The resulting crude material was triturated with hexane and diethyl ether to obtain 1-(4-amino-2,2,6,6-tetramethylpiperidin-1-yl)-3-(4-chloro-3-fluorophenoxy)propan-2-ol (0.330 g, 15% Yield) as an off-white solid. LCMS: 359.3 $[M+H]^+$; $^1$HNMR (400 MHZ, DMSO-$d_6$) δ 7.51-7.39 (m, 1H), 7.06 (dd, J=2.9, 11.6 Hz, 1H), 6.83 (dd, J=1.8, 8.8 Hz, 1H), 4.97 (hr. s., 1H), 4.05-3.95 (m, 1H), 3.89 (dd, J=5.9, 9.9 Hz, 1H), 3.85-3.74 (m, 1H), 2.81-2.57 (m, 3H), 1.69 (d, J=11.4 Hz, 2H), 1.13-1.06 (m, 6H), 1.01-0.88 (m, 6H).

Step-2: Synthesis of 2-(4-chloro-3-fluorophenoxy)-N-(1-(3-(4-chloro-3-fluorophenoxy)-2-hydroxypropyl)-2,2,6,6-tetramethylpiperidin-4-yl)acetamide To a solution of 1-(4-amino-2,2,6,6-tetramethylpiperidin-1-yl)-3-(4-chloro-3-fluorophenoxy)propan-2-ol (0.169 g, 0.472 mmol, 1.0 equiv) in DMF (2 mL) was added 2-(4-chloro-3-fluorophenoxy)acetic acid (0.096 g, 0.472 mmol, 1.0 equiv) and HATU (0.358 g, 0.944 mmol, 2.0 equiv) at RT. The reaction mixture was stirred for 10 min and then DIPEA (0.4 mL, 2.36 mmol, 5.0 equiv) was added. The resultant reaction mixture was allowed to stir at RT for overnight. Progress of the reaction was monitored by LCMS. The reaction mixture was diluted with water (50 mL) and extracted with ethyl acetate (100 mL×2). Combined organic layer was washed with water (50 mL×4), dried over anhydrous $Na_2SO_4$ and concentrated under reduced pressure to obtain the crude compound which was purified by reversed phase HPLC to obtain 2-(4-chloro-3-fluorophenoxy)-N-(1-(3-(4-chloro-3-fluorophenoxy)-2-hydroxypropyl)-2,2,6,6-tetramethylpiperidin-4-yl)acetamide (Compound 25-0.015 g, 6% Yield) as an off-white solid. LCMS: 545.3 $[M+H]^+$; $^1$HNMR (400 MHz, DMSO-$d_6$) δ 7.54-7.38 (m, 2H), 7.09 (d, J=9.6 Hz, 1H), 6.98 (d, J=13.6 Hz, 1H), 6.88-6.73 (m, 2H), 5.76 (hr. s., 1H), 5.08 (d, J=15.3 Hz, 1H), 5.01-4.85 (m, 2H), 4.00 (hr. s., 2H), 1.69 (hr. s., 2H), 1.23 (hr. s., 12H).

Example 20

Synthesis of 2-(4-chloro-3-fluorophenoxy)-N-(1-(3-(4-chloro-3-fluorophenoxy)propyl)piperidin-4-yl)acetamide

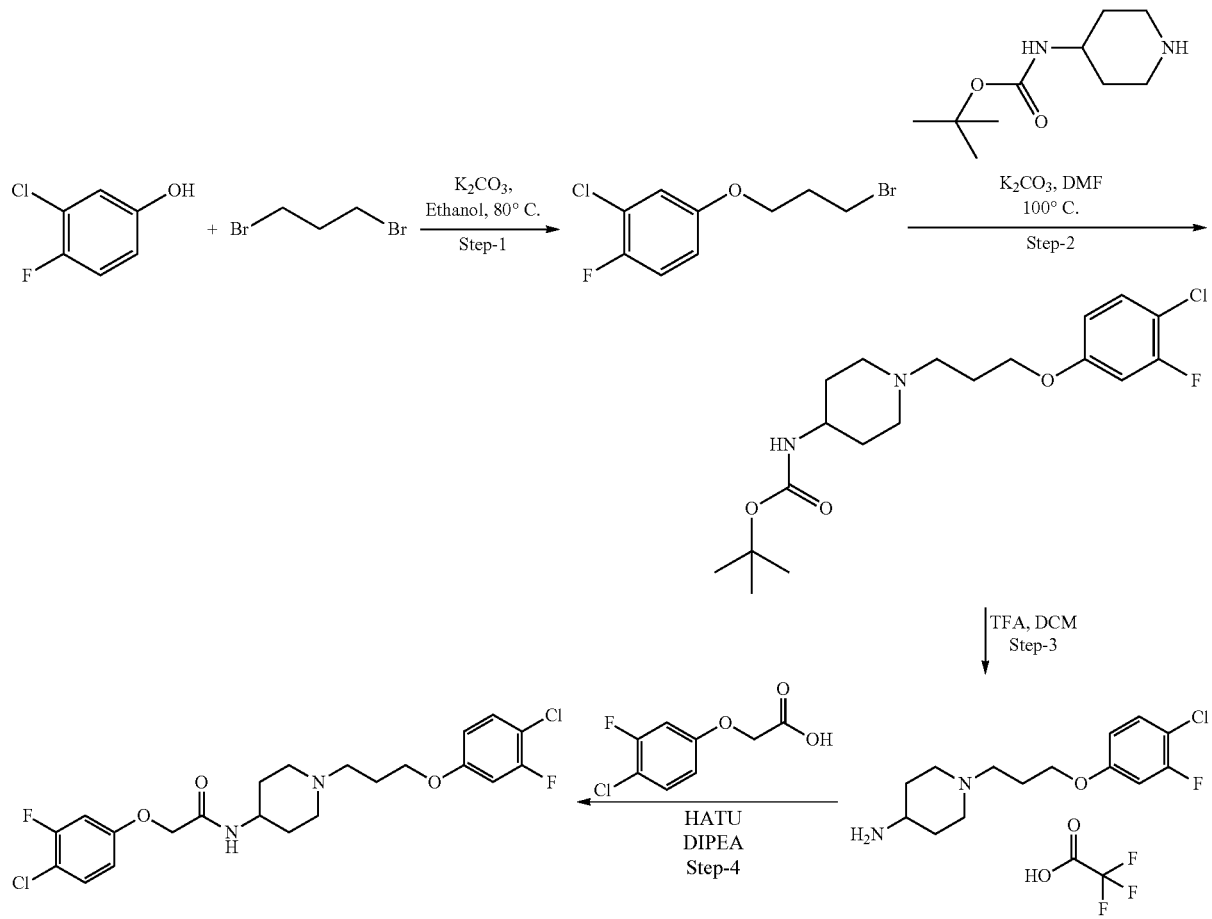

Step 1—Synthesis of 4-(3-bromopropoxy)-2-chloro-1-fluorobenzene

To solution of 3-chloro-4-fluorophenol (0.100 g, 0.68 mmol, 1.0 equiv) in ethanol (5 mL) was added K$_2$CO$_3$ (0.187 g, 1.36 mmol, 2.0 equiv) followed by the addition of 3-chloro-4-fluorophenol (0.151 g, 0.75 mmol, 1.1 equiv). The resulting reaction mixture was heated at 80° C. for overnight. Product formation was confirmed by NMR spectroscopy. After completion of reaction the reaction mixture was diluted with water (20 mL) and extracted with ethyl acetate (50 mL×2). Combined organic layer was washed with water (20 mL), dried over anhydrous Na$_2$SO$_4$ and concentrated under reduced pressure to obtain the crude compound which was purified by flash chromatography (0-30% ethyl acetate in hexane as an eluent) to obtain 4-(3-bromopropoxy)-2-chloro-1-fluorobenzene (0.090 g, 50% Yield) as a yellow semi-solid. $^1$HNMR (400 MHz, DMSO-d$_6$) δ7.57-7.33 (m, 1H), 7.14-7.03 (m, 1H), 6.90-6.76 (m, 1H), 4.22-3.96 (m, 3H), 3.71-3.55 (m, 1H), 2.30-2.09 (m, 1H), 1.10 (t, J=7.0 Hz, 2H).

Step 2—Synthesis of tert-butyl (1-(3-(4-chloro-3-fluorophenoxy)propyl)piperidin-4-yl)carbamate To solution of tert-butyl piperidin-4-yl)carbamate (0.067 g, 0.36 mmol, 1.0 equiv) in DMF (1 mL) was added K$_2$CO$_3$ (0.059 g, 0.430 mmol, 1.2 equiv) followed by the addition of 4-(3-bromopropoxy)-2-chloro-1-fluorobenzene (0.090 g, 0.36 mmol, 1.0 equiv). The resulting reaction mixture was heated at 100° C. for overnight. Product formation was confirmed by NMR spectroscopy. After completion of reaction the reaction mixture was diluted with water (20 mL) and extracted with ethyl acetate (50 mL×2). Combined organic layer was washed with water (20 mL×4), dried over anhydrous Na$_2$SO$_4$ and concentrated under reduced pressure to obtain tert-butyl (1-(3-(4-chloro-3-fluorophenoxy)propyl)piperidin-4-yl)carbamate (0.056 g, 50% Yield) as a crude which was used for next step without any further purification. LCMS: 387.3 [M+H]$^+$; $^1$HNMR (400 MHz, DMSO-d$_6$) δ 7.55-7.36 (m, 1H), 7.11-7.03 (m, 1H), 6.83 (t, J=8.8 Hz, 1H), 6.71 (d, J=7.5 Hz, 1H), 4.14 (t, J=6.4 Hz, 1H), 4.08-3.93 (m, 1H), 3.17 (br. s. 2H), 2.76 (br. s., 1H), 2.27-2.05 (m, 2H), 1.89-1.77 (m, 2H), 1.64 (br. s., 3H), 1.57-1.44 (m, 1H), 1.37 (s, 9H).

Step 3—Synthesis of 1-(3-(4-chloro-3-fluorophenoxy)propyl)piperidin-4-amine trifluoroacetate salt:

To a stirred solution of tert-butyl (1-(3-(4-chloro-3-fluorophenoxy)propyl)piperidin-4-yl)carbamate (0.056 g, 0.145 mmol, 1.0 equiv) in DCM (30 mL) was added trifluoroacetic acid (1 mL) at RT. The reaction mixture was allowed to stir at RT overnight. DCM and excess of trifluoroacetic acid was removed under reduced pressure to obtain 1-(3-(4-chloro-3-fluorophenoxy)propyl)piperidin-4-amine trifluoroacetate salt (0.100 g, quantitative yield) as an oil. LCMS: 287.3 [M+H]+; $^1$HNMR (400 MHz, DMSO-$d_6$) δ 8.24 (br. s., 2H), 7.52-7.41 (m, 1H), 7.16-6.98 (m, 1H), 6.84 (d, J=6.6 Hz, 1H), 4.21-3.95 (m, 1H), 3.55 (d, J=11.0 Hz, 1H), 3.32 (br. s., 2H), 3.09 (br. s., 2H), 3.02 (br. s., 1H), 2.95 (br. s., 1H), 2.23-1.96 (m, 4H), 1.78 (d, J=11.0 Hz, 2H), 1.67 (d, J=11.8 Hz, 1H).

Step 4—Synthesis of 2-(4-chloro-3-fluorophenoxy)-N-(1-(3-(4-chloro-3-fluorophenoxy)propyl)piperidin-4-yl)acetamide To a solution of 1-(3-(4-chloro-3-fluorophenoxy)propyl)piperidin-4-amine trifluoroacetate salt (0.627 g, 1.93 mmol, 1.0 equiv) in DMF (5 mL) was added 2-(4-chloro-3-fluorophenoxy)acetic acid (0.394 g, 1.93 mmol, 1.0 equiv) and HATU (1.46 g, 3.86 mmol, 2.0 equiv) at RT. The reaction mixture was stirred for 10 minutes and then DIPEA (1 mL, 5.79 mmol, 5.0 equiv) was added. The resultant reaction mixture was allowed to stir at RT for overnight. Progress of the reaction was monitored by LCMS. The reaction mixture was diluted with water (50 mL) and extracted with ethyl acetate (100 mL×2). Combined organic layer was washed with water (50 mL×4), dried over anhydrous $Na_2SO_4$ and concentrated under reduced pressure to obtain the crude compound which was purified by reversed phase HPLC to obtain 2-(4-chloro-3-fluorophenoxy)-N-(1-(3-(4-chloro-3-fluorophenoxy)propyl)piperidin-4-yl)acetamide (Compound 28-0.020 g, 3% Yield) as an off-white solid. LCMS: 473.2 [M+H]+; $^1$HNMR (400 MHz, DMSO-$d_6$) δ 7.98 (d, J=7.9 Hz, 1H), 7.57-7.41 (m, 2H), 7.04 (s, 1H), 7.07 (s, 1H), 6.83 (t, J=9.6 Hz, 2H), 4.50 (s, 2H), 4.01 (t, J=6.1 Hz, 2H), 3.60 (hr. s., 1H), 2.80 (d, 7=11.4 Hz, 2H), 2.38 (t, J=6.8 Hz, 2H), 1.95 (t, J=10.7 Hz, 2H), 1.92-1.82 (m, 2H), 1.68 (d, J=9.6 Hz, 2H), 1.54-1.42 (m, 2H).

Example 21

Synthesis of 5-chloro-N-(1-(3-(4-chloro-3-fluorophenoxy)-2-hydroxypropyl)piperidin-4-yl)benzofuran-2-carboxamide

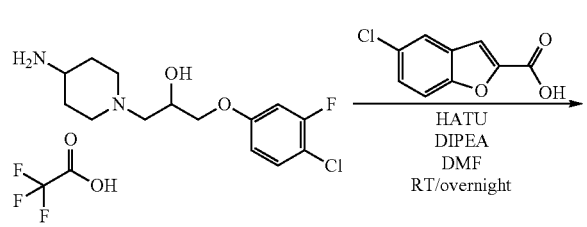

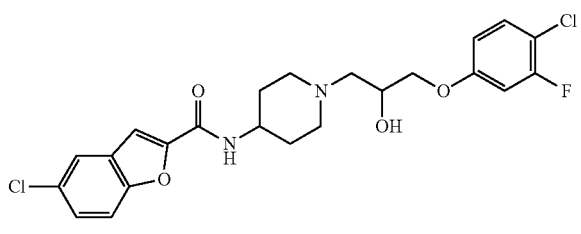

To a solution of 1-(4-aminopiperidin-1-yl)-3-(4-chloro-3-fluorophenoxy)propan-2-ol trifluoroacetate salt (0.200 g, 0.48 mmol, 1.0 equiv) in DMF (10 mL) was added 5-chlorobenzofuran-2-carboxylic acid (0.095 g, 0.48 mmol, 1.0 equiv) and HATU (0.364 g, 0.96 mmol, 2.0 equiv) at RT. The resulting reaction mixture was stir at RT for 10 min and DIPEA (0.3 mL, 1.44 mmol, 3.0 equiv) was added. The reaction mixture was allowed to stir at RT overnight. Product formation was confirmed by LCMS. After completion of reaction the reaction mixture was diluted with water (50 mL) and extracted with ethyl acetate (100 mL×2). Combined organic extracts were washed with water (50 mL×4), dried over anhydrous $Na_2SO_4$ and concentrated. The crude product was purified by reverse phase HPLC to obtain 5-chloro-N-(1-(3-(4-chloro-3-fluorophenoxy)-2-hydroxypropyl)piperidin-4-yl)benzofuran-2-carboxamide (Compound 29-50 mg, 21% yield) as a white solid. LCMS: 481.2 [M+H]+; $^1$HNMR (500 MHz, DMSO-d6) δ 8.65 (d, J=7.9 Hz, 1H), 7.87 (d, J=2.3 Hz, 1H), 7.70 (d, J=8.8 Hz, 1H), 7.55-7.43 (m, 3H), 7.08 (dd, J=11.5, 2.9 Hz, 1H), 6.89-6.82 (m, 1H), 4.92 (s, 1H), 4.02 (dd, 7=9.6, 3.0 Hz, 1H), 3.95-3.86 (m, 3H), 3.76 (s, 1H), 3.34 (s, 9H), 2.94 (d, J=11.6 Hz, 1H), 2.88 (s, 1H), 2.10 (t, J=12.7 Hz, 2H), 1.74 (s, 2H), 1.63 (t, J=12.3 Hz, 2H).

Example 22

Synthesis of trans-6-chloro-N-(4-((3-(4-chloro-3-fluorophenoxy)-2-hydroxypropyl)amino)cyclohexyl)quinoline-2-carboxamide

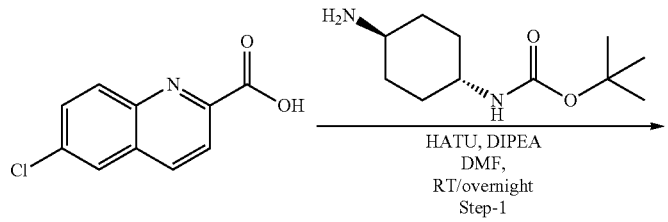

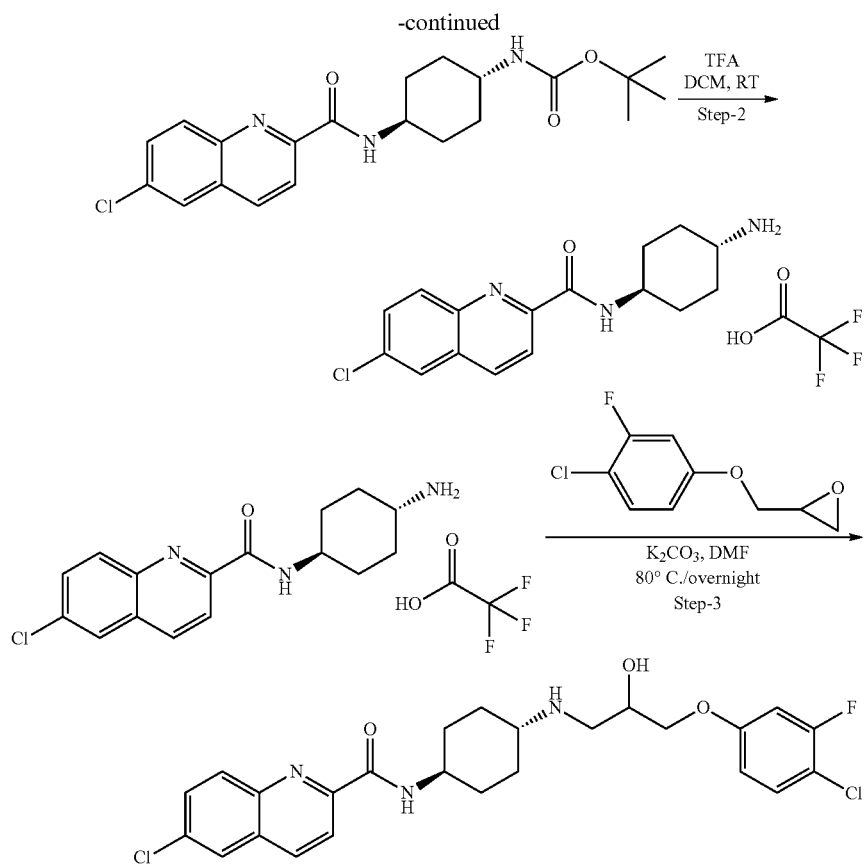

Step 1—Synthesis of trans-tert-butyl (4-(6-chloro-quinoline-2-carboxamido)cyclohexyl)carbamate To a stirred mixture of 6-chloroquinoline-2-carboxylic acid (100 mg, 0.48 mmol, 1 equiv) and trans-tert-butyl (4-aminocyclohexyl)carbamate (103 mg, 0.48 mmol, 1 equiv) in DMF (5 mL) was added HATU (365 mg, 0.96 mmol, 2 equiv) and continued stir at RT for 30 min. DIPEA (0.3 ml, 1.44 mmol, 3 equiv) was added and again stirred at RT for overnight. Reaction progress was monitored by LCMS. After completion of reaction, the reaction mixture was poured into water (50 mL), the resulting yellow precipitate was filtered off and again washed with water (20 mL×2). Thus obtained solid was dried under vacuum to obtain trans-tert-butyl (4-(6-chloroquinoline-2-carboxamido)cyclohexyl)carbamate (120 mg, 71.85%) as a yellow solid. LCMS: 404.6 [M+H]$^+$

Step 2—Synthesis of trans-N-(4-aminocyclohexyl)-6-chloroquinoline-2-carboxamide trifluoroacetate salt To a stirred solution of trans-tert-butyl (4-(6-chloroquinoline-2-carboxamido)cyclohexyl)carbamate (120 mg, 0.297 mmol, 1 equiv) in DCM (5 mL) was added TFA (0.5 mL) and the resultant reaction mixture was stirred at RT for overnight under nitrogen atmosphere. Reaction was monitored by LCMS. After completion of reaction, the reaction mixture was concentrated under reduced pressure to obtain trans-N-(4-aminocyclohexyl)-6-chloroquinoline-2-carboxamide trifluoroacetate salt (130 mg, quant, yield) as a light pink solid. LCMS: 304.4 [M+H]$^+$

Step 3—Synthesis of trans-6-chloro-N-(4-((3-(4-chloro-3-fluorophenoxy)-2-hydroxypropyl)amino)cyclohexyl)quinoline-2-carboxamide To a stirred mixture of trans-(4-aminocyclohexyl)-6-chloroquinoline-2-carboxamide trifluoroacetate salt (130 mg, 0.311 mmol, 1 equiv) and K$_2$CO$_3$ (130 mg, 0.935 mmol, 3 equiv) in DMF (10 mL) was stirred at RT for 30 minute. 2-((4-chloro-3-fluorophenoxy)methyl)oxirane (63 mg, 0.311 mmol, 1 equiv) was added and heated at 70° C. for overnight. Reaction was monitored by LCMS. After completion of reaction, the reaction mixture was poured into ice cold water (50 ml) and extracted with EtOAc (2×30 mL). Combined organic layer was washed with water (4×20 mL), brine solution (20 mL), dried over anhydrous sodium sulfate and concentrated under reduced pressure to obtain crude product which was purified by reversed-phase HPLC to obtain trans-6-chloro-N-(4-((3-(4-chloro-3-fluorophenoxy)-2-hydroxypropyl)amino)cyclohexyl)quinoline-2-carboxamide (Compound 30—35 mg, 30%) as an off white solid. LCMS: 506.4 [M+H]$^+$; $^1$HNMR (500 MHz, DMSO-de) δ 8.65 (d, J=8.5 Hz, 1H), 8.54 (d, J=8.6 Hz, 1H), 8.32 (s, 1H), 8.25 (d, J=2.5 Hz, 1H), 8.17 (t, J=8.7 Hz, 2H), 7.88 (dd, J=9.0, 2.5 Hz, 1H), 7.47 (t, J=8.8 Hz, 1H), 7.09 (dd, J=11.5, 2.9 Hz, 1H), 6.85 (dd, J=8.9, 2.8 Hz, 1H), 4.00 (d, J=7.1 Hz, 1H), 3.92 (d, J=8.8 Hz, 2H), 3.81 (d, J=10.9 Hz, 1H), 2.79 (d, J=11.8 Hz, 1H), 2.69 (d, J=8.6 Hz, 1H), 1.98 (d, J=11.9 Hz, 2H), 1.92-1.85 (m, 2H), 1.58-1.47 (m, 2H), 1.21 (q, J=12.9, 11.8 Hz, 3H).

Example 23

Synthesis of trans-6-chloro-N-(4-((2-(4-chloro-3-fluorophenoxy)ethyl)amino)cyclohexyl)quinoline-2-carboxamide

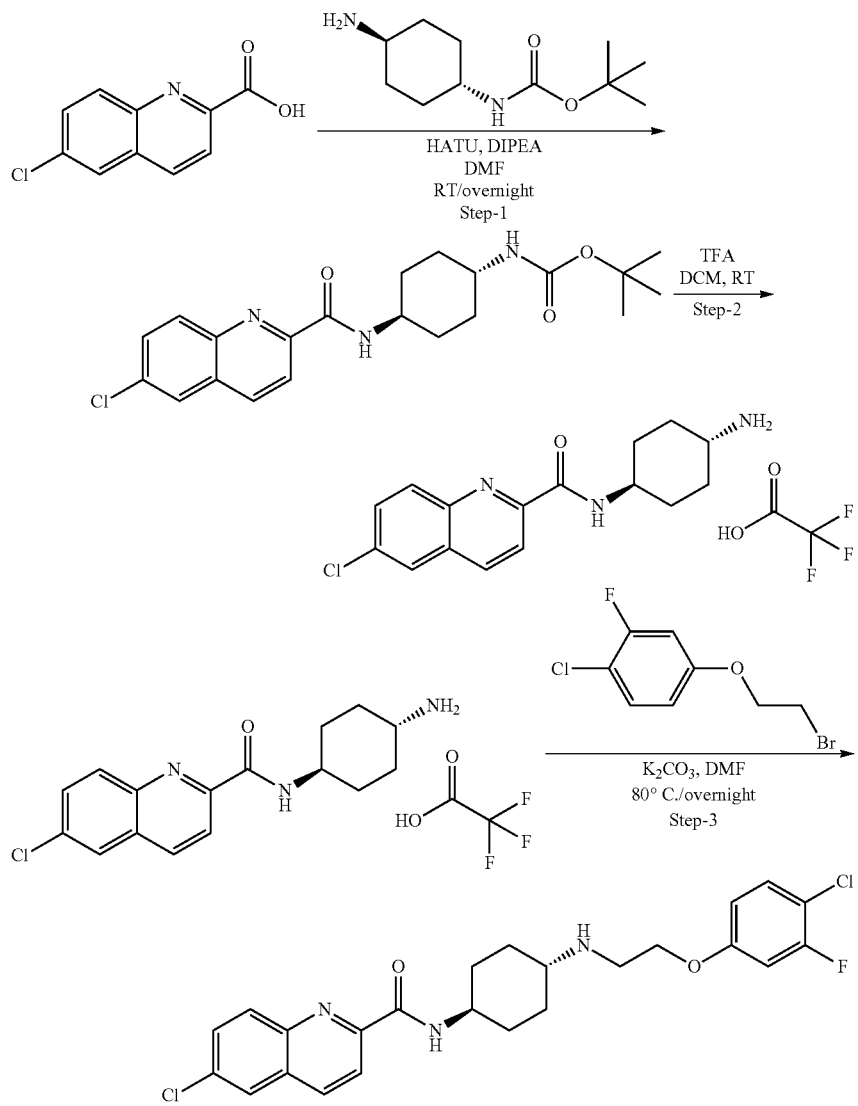

Step 1—Synthesis of trans-tert-butyl (4-(6-chloro-quinoline-2-carboxamido)cyclohexyl)carbamate To a stirred mixture of 6-chloroquinoline-2-carboxylic acid (100 mg, 0.48 mmol, 1 equiv) and trans-tert-butyl (4-aminocyclohexyl)carbamate (103 mg, 0.48 mmol, 1 equiv) in DMF (5 mL) was added HATU (365 mg, 0.96 mmol, 2 equiv) and continued stir at RT for 30 min. DIPEA (0.3 ml, 1.44 mmol, 3 equiv) was added and again stirred at RT for overnight. Reaction progress was monitored by LCMS. After completion of reaction, the reaction mixture was poured into water (50 ml), the resulting yellow precipitate was filtered off and again washed with water (20 mL×2). The obtained solid was dried under vacuum to obtain trans-tert-butyl (4-(6-chloroquinoline-2-carboxamido)cyclohexyl)carbamate (120 mg, 71.85%) as a yellow solid. LCMS: 404.6 [M+H]$^+$

Step 2—Synthesis of trans-N-(4-aminocyclohexyl)-6-chloroquinoline-2-carboxamide trifluoroacetate salt To a stirred solution of trans-tert-butyl (4-(6-chloroquinoline-2-carboxamido)cyclohexyl)carbamate (120 mg, 0.297 mmol, 1 equiv) in DCM (5 mL), was added TFA (0.5 mL) and the resultant reaction mixture was stirred at RT for overnight under nitrogen atmosphere. Reaction was monitored by LCMS. After completion of reaction, the reaction mixture was concentrated under reduced pressure to obtain trans-N-(4-aminocyclohexyl)-6-chloroquinoline-2-carboxamide trifluoroacetate salt (130 mg, quant, yield) as a light pink solid. LCMS: 304.4 [M+H]$^+$ Step 3—Synthesis of trans-6-chloro-N-(4-((2-(4-chloro-3-fluorophenoxy)ethyl)amino)cyclohexyl)quinoline-2-carboxamide To a stirred solution of trans-N-(4-aminocyclohexyl)-6-chloroquinoline-2-carboxamide trifluoroacetate salt (130 mg, 0.311 mmol, 1 equiv) in DMF (10 mL) was added $K_2CO_3$ (130 mg, 0.935 mmol, 3 equiv) and allowed to stir at RT for 30 min. 4-(2-bromoethoxy)-1-chloro-2-fluorobenzene (80 mg, 0.311 mmol, 1 equiv) was added and heated at 80° C. for overnight. Reaction progress was monitored by LCMS. After completion of reaction, the reaction mixture was poured into ice cold water (50 ml) and extracted with EtOAc (2×30 mL). Combined organic layer washed with water (4×20 mL), brine solution (1×20 mL), dried over anhydrous sodium sulfate and concentrated under reduced pressure to obtain crude which was purified by reversed-phase HPLC to obtain trans-6-chloro-N-(4-((2-(4-chloro-3-fluorophenoxy)ethyl)amino)cyclohexyl)quinoline-2-carboxamide (Compound 31-5 mg, 3.3%) as an off white solid. LCMS: 476.4 [M+H]$^+$; $^1$HNMR (500 MHz, DMSO-d$_6$) δ 8.64 (d, J=8.5 Hz, 1H), 8.54 (d, J=8.6 Hz, 1H), 8.39-8.33 (m, 2H), 8.25 (d, j=2.4 Hz, 1H), 8.17 (t, j=8.6 Hz, 2H), 7.88 (dd, J=9.0, 2.4 Hz, 1H), 7.47 (t, J=8.9 Hz, 1H), 7.09 (dd, J=11.5, 2.9 Hz, 1H), 6.85 (dd, J=8.8, 2.8 Hz, 1H), 4.04 (t, J=5.6 Hz, 2H), 3.81 (dq, J=11.0, 7.1, 6.1 Hz, 1H), 2.92 (t, J=5.6 Hz, 2H), 1.99-1.92 (m, 2H), 1.87 (d, J=12.4 Hz, 2H), 1.56-1.47 (m, 2H), 1.23 (s, 1H), 1.18-1.09 (m, 2H).

Example 24

Synthesis of trans-5-chloro-N-(4-((2-(4-chloro-3-fluorophenoxy)ethyl)amino)cyclohexyl)benzofuran-2-carboxamide

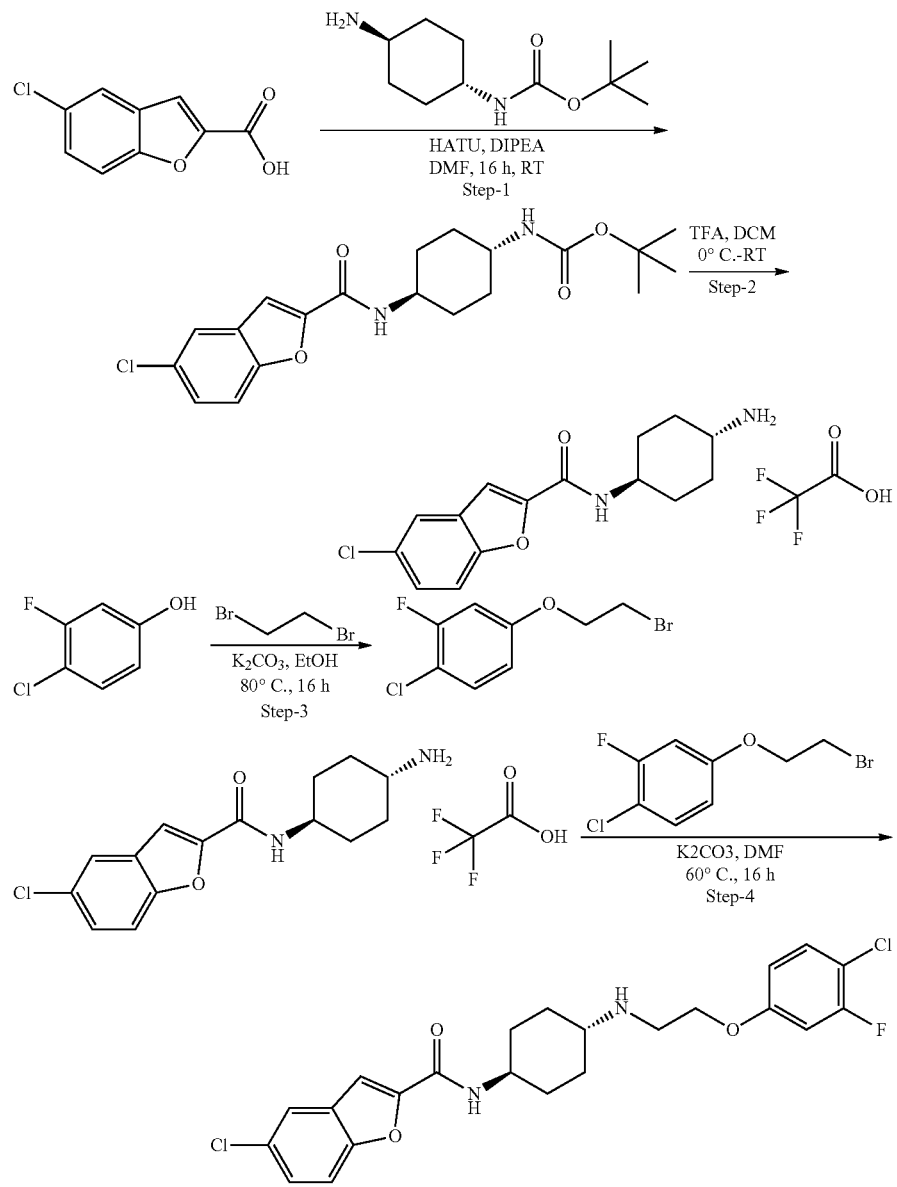

Step 1—Synthesis of trans-tert-butyl N-[4-[(5-chlorobenzofuran-2-carbonyl)amino]cyclohexyl]carbamate To a solution of 5-chlorobenzofuran-2-carboxylic acid (0.300 g, 1.53 mmol, 1.0 equiv) in DMF (5 mL) was added HATU (0.872 g, 2.3 mmol, 1.5 equiv) and trans-tert-butyl N-(4-aminocyclohexyl)carbamate (0.327 g, 1.53 mmol, 1 equiv) followed by the addition of DIPEA (0.395 g, 3.06 mmol, 2.0 equiv). The reaction mixture was allowed to stir at RT for overnight. Product formation was confirmed by LCMS. After completion of reaction the reaction mixture was diluted with water and the resulting precipitate was filtered off and the obtained crude product was crystallized in MeOH to obtain trans-tert-butyl N-[4-[(5-chlorobenzofuran-2-carbonyl)amino]cyclohexyl]carbamate (0.450 g, 75% Yield) as an off-white solid. LCMS: 393.3 [M+H]$^+$

Step 2—Synthesis of trans-N-(4-aminocyclohexyl)-5-chlorobenzofuran-2-carboxamide trifluoroacetate salt To a stirred solution of trans-tert-butyl N-[4-[(5-chlorobenzofuran-2-carbonyl)amino]cyclohexyl]carbamate (0.450 g, 1.15 mmol, 1.0 equiv) in DCM (10 mL), was added Trifluoroacetic acid (4 mL). The reaction mixture was allowed to stir at RT for 1 h. Product formation was confirmed by LCMS. After completion of reaction, the reaction mixture was concentrated under reduced pressure to obtain trans-N-(4-aminocyclohexyl)-5-chlorobenzofuran-2-carboxamide trifluoroacetate salt (0.450 g, Quant. Yield). LCMS: 292.3 [M+H]$^+$

Step 3—Synthesis of 4-(2-bromoethoxy)-1-chloro-2-fluoro-benzene

To a stirred solution 4-chloro-3-fluoro-phenol (1.00 g, 6.83 mmol, 1.0 equiv) in EtOH (30 mL), was added K$_2$CO$_3$ (1.414 g, 10.25 mmol, 1.5 equiv), followed by the addition of 1,2-dibromoethane (1.284 g, 6.83 mmol, 1.0 equiv) and the mixture was allowed to stir at 80° C. for overnight. Product formation was confirmed by LCMS and TLC. After completion of reaction, reaction mixture was concentrated under reduced pressure. The residue was diluted with water and extracted with ethyl acetate (50 mL×3). Combined organic layer was washed with brine (15 mL), dried over anhydrous Na$_2$SO$_4$ and concentrated. The crude product obtained was purified by flash chromatography (0-40% Ethyl acetate in hexane as an eluent) to obtain 4-(2-bromoethoxy)-1-chloro-2-fluoro-benzene (0.60 g, 35% Yield). LCMS: 252.3 [M+H]$^+$

Step 4—Synthesis of trans-5-chloro-N-(4-((2-(4-chloro-3-fluorophenoxy)ethyl)amino)cyclohexyl)benzofuran-2-carboxamide To a stirred solution of trans-N-(4-aminocyclohexyl)-5-chlorobenzofuran-2-carboxamide trifluoroacetate salt (0.100 g, 0.25 mmol, 1.0 equiv) in DMF (3 mL), was added K$_2$CO$_3$ (0.053 g, 0.38 mmol, 1.5 equiv), followed by the addition of 4-(2-bromoethoxy)-1-chloro-2-fluoro-benzene (0.063 g, 0.25 mmol, 1.0 equiv) and the mixture was allowed to stir at 60° C. for overnight. Product formation was confirmed by LCMS and TLC. After completion of reaction the mixture was concentrated under reduced pressure. The residue was diluted with water and extracted with ethyl acetate (30 mL×3). Combined organic layer was washed with water (15 mL×6), dried over anhydrous Na$_2$SO$_4$ and concentrated. The crude product obtained was purified by reverse phase HPLC to obtain trans-5-chloro-N-(4-((2-(4-chloro-3-fluorophenoxy)ethyl)amino)cyclohexyl)benzofuran-2-carboxamide (Compound 32-8.6 mg, 7.5% Yield) as an off-white solid. LCMS: 465.3 [M+H]$^+$; $^1$HNMR (400 MHz, DMSO-d$_6$) δ 8.57 (d, J=8.1 Hz, 1H), 7.86 (d, J=2.3 Hz, 1H), 7.69 (d, J=8.8 Hz, 1H), 7.52 (s, 1H), 7.46 (t, 7=8.8 Hz, 2H), 7.07 (dd, J=11.6, 2.8 Hz, 1H), 6.88-6.80 (m, 1H), 4.02 (t, J=5.4 Hz, 2H), 3.81-3.67 (m, 1H), 2.90 (s, 2H), 1.98-1.90 (m, 2H), 1.87-1.79 (m, 2H), 1.42 (q, J=12.8, 12.3 Hz, 2H), 1.23 (s, 1H), 1.10 (q, J=12.4 Hz, 2H).

Example 25

Chiral Resolution of trans-2-(4-chlorophenoxy)-N-((1r, 4r)-4-((3-(4-chlorophenoxy)-2-hydroxypropyl)amino)cyclohexyl)acetamide

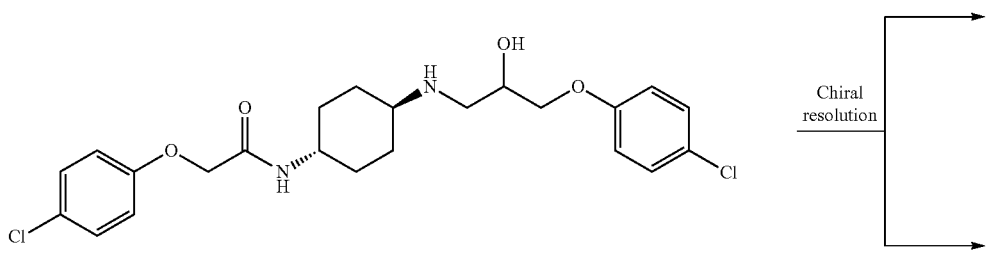

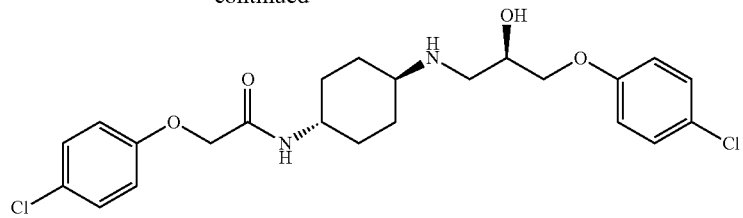

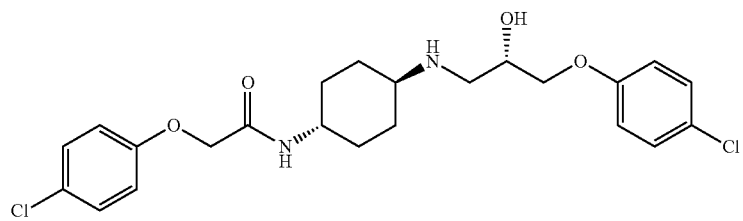

The enantiomers, (+)-2-(4-chlorophenoxy)-N-(4-((3-(4-chlorophenoxy)-2-hydroxypropyl)amino)cyclohexyl)acetamide (Compound 3—$[\alpha]_D^{20}$=12.47° (c=0.109, MeOH); elution time: 6.89 min) and (−)-2-(4-chlorophenoxy)-N-(4-((3-(4-chlorophenoxy)-2-hydroxypropyl)amino)cyclohexyl)acetamide (Compound 4—$[\alpha]_D^{20}$=−13.5° (c=0.0976, MeOH); elution time: 12.75 min), were separated by chiral SFC (Daicel Chiralcel® OD-H, 250×4.6 mm, 5 μm). Isocratic program with analytical grade liquid carbon dioxide and HPLC grade MeOH (0.2% DBA).

Example 26

Chiral Resolution of trans-2-(4-chloro-3-fluorophenoxy)-N-(4-((3-(4-chloro-3-fluorophenoxy)-2-hydroxypropyl)amino)cyclohexyl)acetamide The enantiomers, (+)-2-(4-chloro-3-fluorophenoxy)-N-(4-((3-(4-chloro-3-fluorophenoxy)-2-hydroxypropyl)amino)cyclohexyl)acetamide (Compound 6—$[\alpha]_D^{20}$=15.55° (c=0.1075, MeOH); elution time: 12.16 min) and (−)-2-(4-chloro-3-fluorophenoxy)-N-(4-((3-(4-chloro-3-fluorophenoxy)-2-hydroxypropyl)amino)cyclohexyl)acetamide (Compound 7—$[\alpha]_D^{20}$=−8.41° (c=0.1067, MeOH); elution time: 16.97 min), were separated by chiral SFC (Daicel Chiralcel® OD-H, 250×4.6 mm, 5 μm). Isocratic program with analytical grade liquid carbon dioxide and HPLC grade MeOH (0.2% DBA). LCMS: 503 [M+H]$^+$; $^1$HNMR (400 MHz, DMSO-$d_6$) 57.92 (d, J=6.36 Hz, 2H), 7.37-7.57 (m, 2H), 7.06 (d, J=11.74 Hz, 2H), 6.83 (m, 2H), 4.48 (s, 4H), 3.97 (m, 1H), 3.89 (d, J=6.85 Hz, 1H), 3.80 (m, 1H), 3.55 (m, 3H), 1.85 (m, 1H), 1.77 (d, J=14.18 Hz, 3H), 1.35 (hr. s., 1H), 1.23 (hr. s., 2H).

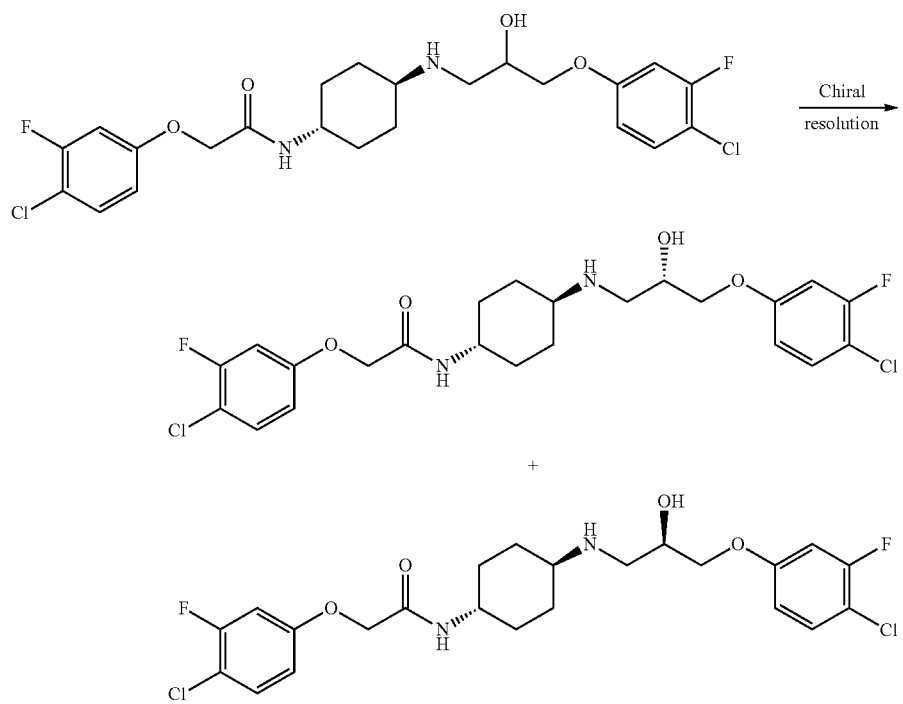

Example 27

Chiral Resolution of 2-(4-chlorophenoxy)-N-(1-(3-(4-chlorophenoxy)-2-hydroxypropyl)piperidin-4-yl)acetamide

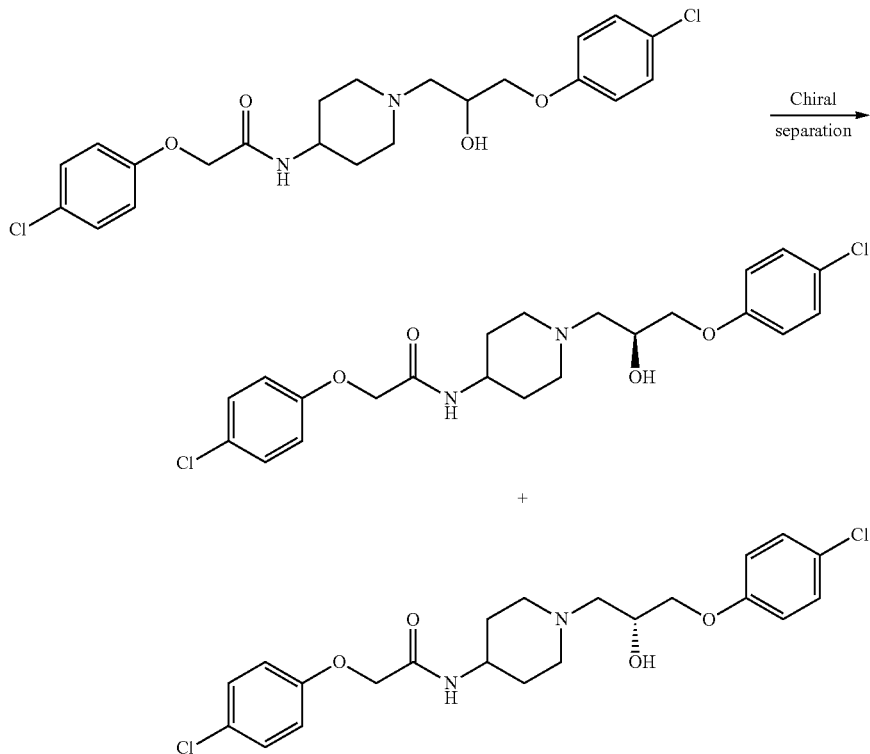

The enantiomers, (−)-2-(4-chlorophenoxy)-N-(1-(3-(4-chlorophenoxy)-2-hydroxypropyl)piperidin-4-yl)acetamide (Compound 15-elution time: 16.39) and (+)-2-(4-chlorophenoxy)-N-(1-(3-(4-chlorophenoxy)-2-hydroxypropyl)piperidin-4-yl)acetamide (Compound 16—$[\alpha]_D^{20}$=7.91° (c=0.1045, MeOH); elution time: 24.53 min), were separated by chiral SFC (Daicel Chiralcel® AD-H, 250×4.6 mm, 5 μm). Isocratic program with analytical grade liquid carbon dioxide and HPLC grade EtOH (0.2% DBA).

Example 28

Chiral Resolution of 2-(4-chloro-3-fluorophenoxy)-N-(1-(3-(4-chloro-3-fluorophenoxy)-2-hydroxypropyl)piperidin-4-yl)acetamide

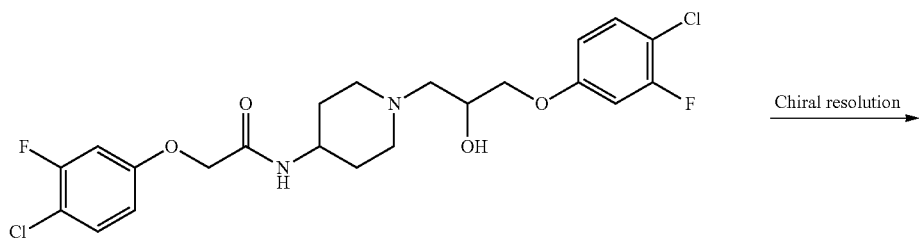

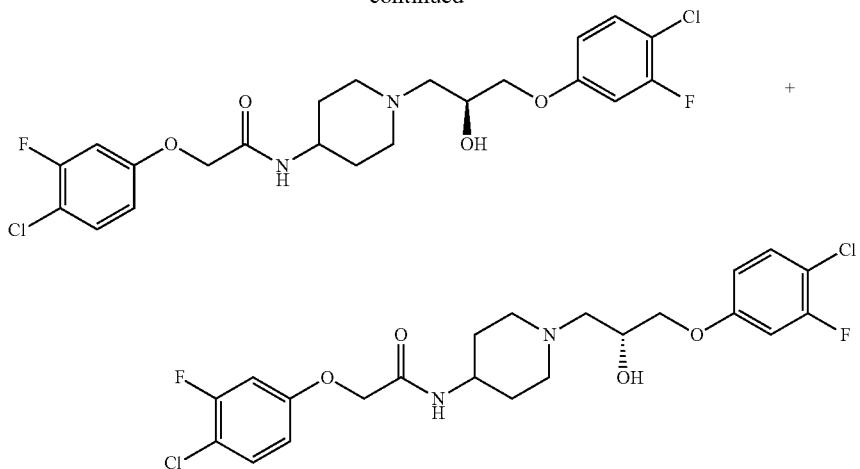

The enantiomers (−)-2-(4-chloro-3-fluorophenoxy)-N-(1-(3-(4-chloro-3-fluorophenoxy)-2-hydroxypropyl)piperidin-4-yl)acetamide (Compound 26—[α]$_D^{20}$ −7.23° (c=0.1098, MeOH); elution time: 9.15 min) and (+)-2-(4-chloro-3-fluorophenoxy)-N-(1-(3-(4-chloro-3-fluorophenoxy)-2-hydroxypropyl)piperidin-4-yl)acetamide (Compound 27—[α]$_D^{20}$ 7.84° (c=0.1012, MeOH); elution time: 12.52 min) were separated by chiral SFC (CHIRALPAK-AD-H, 250×20 mm, 5 μm). Isocratic Program with analytical grade liquid carbon dioxide and HPLC grade EtOH (0.1% trifluoroacetic acid).

Example 29

Synthesis of trans-6-chloro-N-(4-(2-(4-chloro-3-fluorophenoxy)acetamido)cyclohexyl)-2-naphthamide To a solution of trans-N-(4-aminocyclohexyl)-2-(4-chloro-3-fluorophenoxy)acetamide 2,2,2-trifluoroacetate (0.100 g, 0.241 mmol, 1.0 equiv) in DMF (5 mL) was added 6-chloro-2-naphthoic acid (0.050 g, 0.241 mmol, 1.0 equiv) and HATU (0.137 g, 0.36 mmol, 1.50 equiv) at RT. The reaction mixture was stir for 10 min. DIPEA (0.5 mL) was added and the resultant reaction mixture was allowed to stir at RT overnight. Product formation was confirmed by LCMS. The reaction mixture was diluted with water (50 mL) and extracted with ethyl acetate (100 mL×2). Combined organic extracts were washed with water (50 mL×4), dried over anhydrous Na$_2$SO$_4$ and concentrated under reduced pressure to obtain crude which was crystallized in MeOH to obtain trans-6-chloro-N-(4-(2-(4-chloro-3-fluorophenoxy) acetamido)cyclohexyl)-2-naphthamide (Compound 145— 60 mg, 51.28% Yield) as an off-white solid. LCMS: 489.3 [M+H]$^+$; $^1$H NMR (400 MHz, DMSO-d$_6$) δ 8.57-8.37 (m,

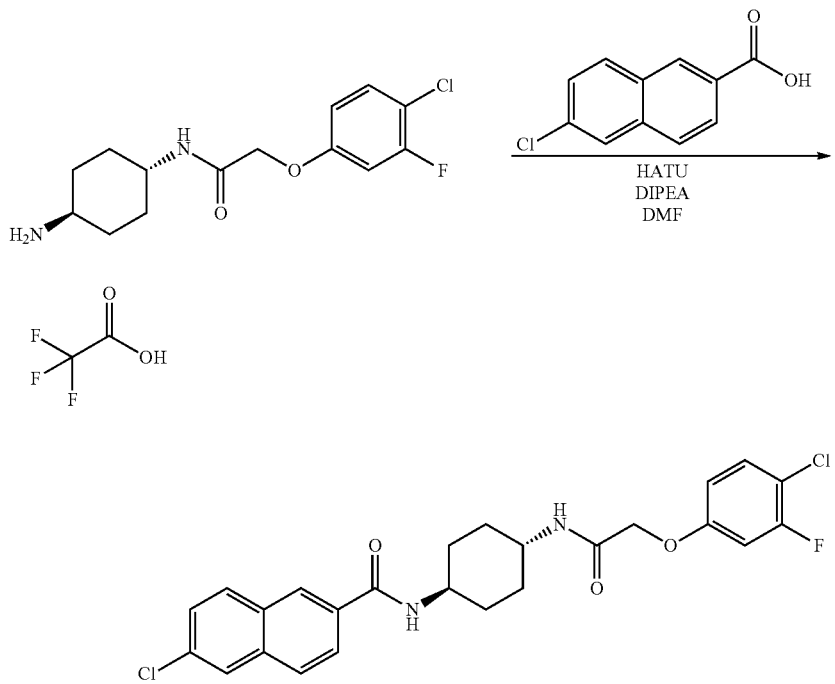

2H), 8.11 (s, 1H), 8.09-7.95 (m, 3H), 7.59 (d, J=8.8 Hz, 1H), 7.50 (t, J=9.0 Hz, 1H), 7.08 (dd, J=2.6, 11.4 Hz, 1H), 6.86 (d, J=7.5 Hz, 1H), 4.52 (s, 2H), 3.81 (hr. s., 1H), 3.63 (hr. s., 1H), 1.91 (hr. s., 2H), 1.85 (hr. s., 2H), 1.53-1.29 (m, 4H).

Example 30

Synthesis of 6-chloro-N-(1-(3-(4-chloro-3-fluorophenoxy)propyl)piperidin-4-yl)quinoline-2-carboxamide

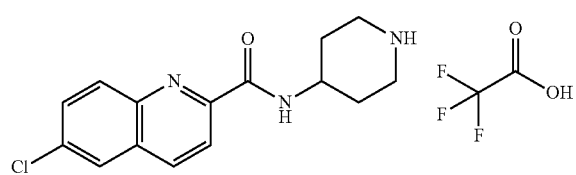

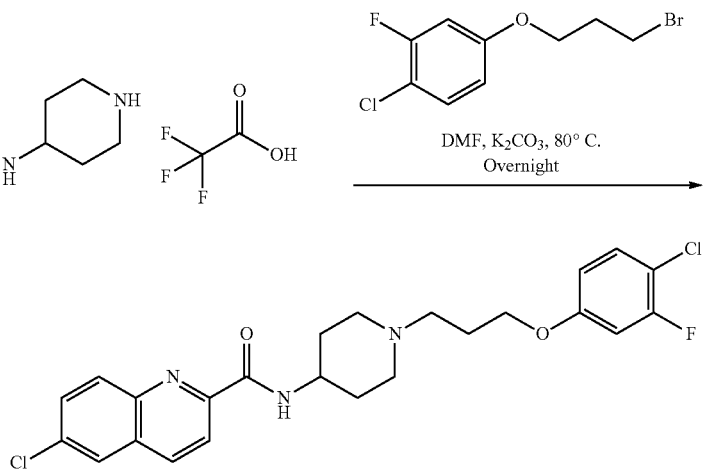

To a stirred solution 6-chloro-N-(piperidin-4-yl)quinoline-2-carboxamide 2,2,2-trifluoroacetate (0.100 g, 0.247 mmol, 1.0 equiv) in DMF (5 mL), was added K$_2$CO$_3$ (0.102 g, 0.742 mmol, 3.0 equiv), followed by the addition of 4-(3-bromopropoxy)-1-chloro-2-fluorobenzene (0.072 g, 0.272 mmol, 1.0 equiv) and the mixture was allowed to stir at 80° C. for overnight. Product formation was confirmed by LCMS. The reaction mixture was diluted with water and extracted with ethyl acetate (30 mL×3). Combined organic extracts were washed with water (15 mL×4), dried over anhydrous Na$_2$SO$_4$ and concentrated. The crude product obtained was purified by reverse phase HPLC to obtain 6-chloro-N-(1-(3-(4-chloro-3-fluorophenoxy)propyl)piperidin-4-yl)quinoline-2-carboxamide (Compound 146—25 mg, 21% Yield) as an off-white solid. LCMS: 476.3 [M+H]$^+$; $^1$H NMR (400 MHz, DMSO-d$_6$) δ 9.55 (hr. s., 1H), 9.01 (d, J=7.5 Hz, 1H), 8.55 (d, J=8.8 Hz, 1H), 8.27 (hr. s., 1H), 8.19 (d, 7=6.6 Hz, 1H), 7.95-7.85 (m, 1H), 7.51 (t, J=9.0 Hz, 1H), 7.10 (d, J=11.4 Hz, 1H), 6.86 (d, 7=9.2 Hz, 1H), 4.11 (hr. s., 2H), 3.60 (d, J=11.4 Hz, 2H), 3.27-3.07 (m, 3H), 2.17 (hr. s., 2H), 2.12-1.88 (m, 3H).

Example 31

Synthesis of trans-5-chloro-N-(4-((3-(4-chloro-3-fluorophenoxy)-2-hydroxypropyl)amino)cyclohexyl)benzofuran-2-carboxamide

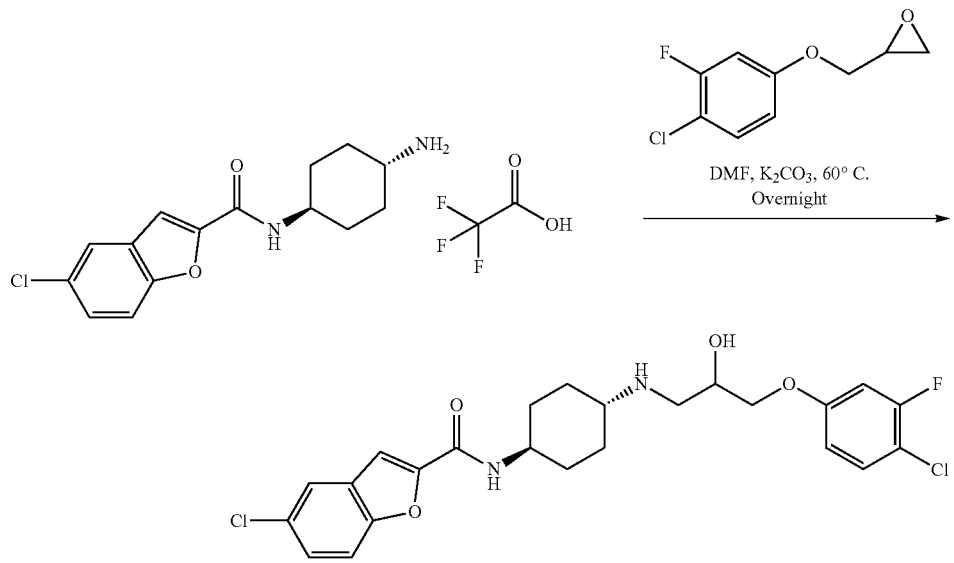

To a stirred solution trans-N-(4-aminocyclohexyl)-5-chlorobenzofuran-2-carboxamide 2,2,2-trifluoroacetate (0.250 g, 0.62 mmol, 1.0 equiv) in DMF (3 mL), was added K₂CO₃ (0.128 g, 0.93 mmol, 1.5 equiv), followed by the addition of 2-[(4-chloro-3-fluoro-phenoxy)methyl]oxirane (0.125 g, 0.62 mmol, 1.0 equiv) and the mixture was allowed to stir at 80° C. for overnight. Product formation was confirmed by LCMS. The reaction mixture was diluted with water and extracted with ethyl acetate (30 mL×3). Combined organic extracts were washed with water (15 mL×4), dried over anhydrous Na₂SO₄ and concentrated. The crude product obtained was purified by reverse phase HPLC to obtain trans-chloro-N-(4-((3-(4-chloro-3-fluorophenoxy)-2-hydroxypropyl)amino)cyclohexyl)benzofuran-2-carboxamide (Compound 147—35 mg, 11.5% Yield) as an off-white solid. LCMS 495.2 [M+H]⁺; ¹H NMR (400 MHz, DMSO-d6) δ 8.57 (d, J=8.1 Hz, 1H), 7.86 (d, J=2.2 Hz, 1H), 7.69 (d, J=8.8 Hz, 1H), 7.54-7.41 (m, 3H), 7.08 (dd, J=11.3, 2.9 Hz, 1H), 6.84 (dd, J=8.7, 3.0 Hz, 1H), 4.01 (ddd, J=9.0, 6.0, 3.7 Hz, 1H), 3.95-3.82 (m, 2H), 3.76 (dd, J=13.7, 7.7 Hz, 1H), 2.74 (s, 1H), 1.94 (d, J=11.6 Hz, 2H), 1.84 (d, J=12.2 Hz, 2H), 1.41 (q, J=12.6 Hz, 2H), 1.23 (s, 1H), 1.14 (d, J=12.2 Hz, 2H).

Example 32

Synthesis of 5-chloro-N-(1-(3-(4-chloro-3-fluorophenoxy)propyl)piperidin-4-yl)benzofuran-2-carboxamide

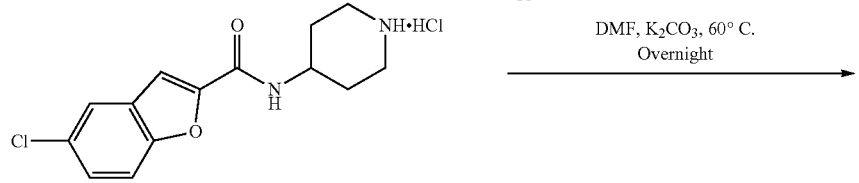

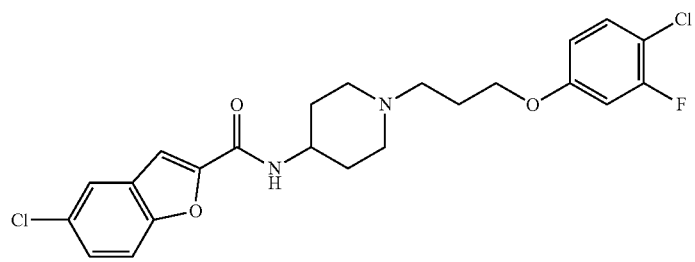

To a stirred solution 5-chloro-N-(piperidin-4-yl)benzofuran-2-carboxamide hydrochloride (0.200 g, 0.63 mmol, 1.0 equiv) in DMF (3 mL), was added K₂CO₃ (0.131 g, 0.95 mmol, 1.5 equiv), followed by the addition of 4-(3-bromopropoxy)-1-chloro-2-fluoro-benzene (0.168 g, 0.63 mmol, 1.0 equiv) and the mixture was allowed to stir at 60° C. for overnight. Product formation was confirmed by LCMS. The reaction mixture was diluted with water and stirred at RT for 10 min and resulting solid was filtered off, washed with excess water. Obtained solid material was dried under vacuum and washed with hexane to obtain 5-chloro-N-(1-(3-(4-chloro-3-fluorophenoxy)propyl)piperidin-4-yl)benzofuran-2-carboxamide (Compound 148—180 mg, 61% Yield). LCMS 465.3 [M+H]⁺; ¹H NMR (400 MHz, DMSO-d6) δ 8.62 (d, J=7.9 Hz, 1H), 7.86 (d, J=2.3 Hz, 1H), 7.69 (d, J=8.8 Hz, 1H), 7.52 (s, 1H), 7.46 (dd, J=11.3, 7.7 Hz, 2H), 7.06 (dd, J=11.6, 2.9 Hz, 1H), 6.83 (dd, J=8.9, 2.8 Hz, 1H), 4.03 (t, J=6.3 Hz, 2H), 3.76 (dtd, J=13.8, 10.1, 9.6, 4.4 Hz, 1H), 2.88 (d, J=11.2 Hz, 2H), 2.41 (t, J=7.1 Hz, 2H), 1.98 (t, J=11.5 Hz, 2H), 1.86 (p, J=6.6 Hz, 2H), 1.81-1.72 (m, 2H), 1.61 (qd, J=12.1, 3.6 Hz, 2H), 1.24 (d, J=5.1 Hz, 2H).

Example 33

Synthesis of trans-2-(3-chloro-4-fluorophenoxy)-N-(4-(((6-chloroquinolin-2-yl)methyl)amino)cyclohexyl)acetamide

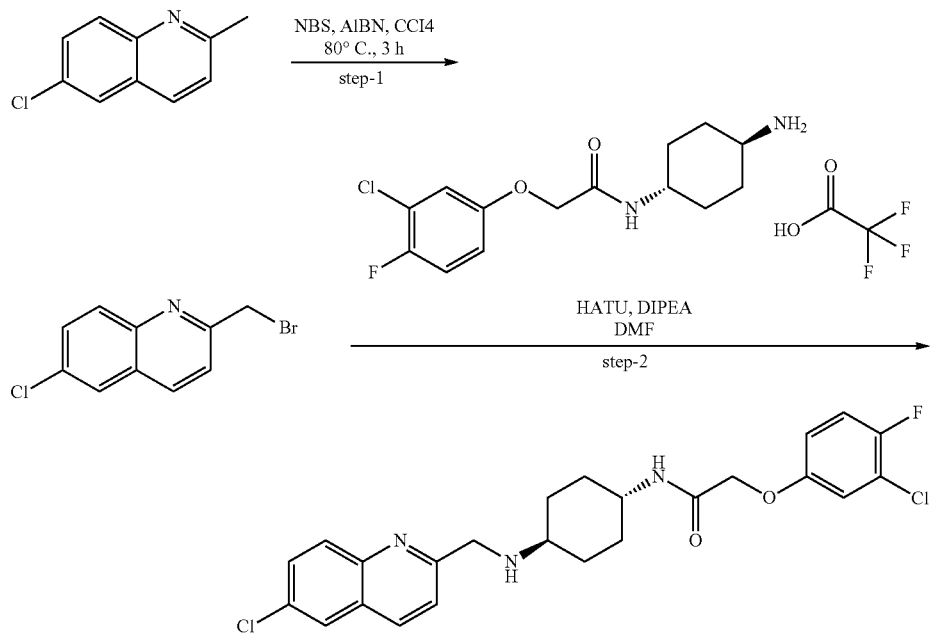

Step 1—Synthesis of 2-(bromomethyl)-6-chloroquinoline

To a stirred solution of 6-chloro-2-methylquinoline (1.0 g, 5.6 mmol, 1 equiv) in CCl$_4$ (10 mL) was added NBS (1.1 g, 6.18 mmol, 1.1 equiv) and AIBN (0.10 g, 0.56 mmol, 0.1 equiv). The reaction mixture was heated at 80° C. for 3 h. Progress of the reaction was monitored by TLC and LCMS. After completion of the reaction, the reaction mixture was diluted with aqueous solution of sodium bicarbonate (15 mL) and extracted with DCM (25 mL×3). Combined organic layer was washed with brine (40 mL), dried over anhydrous sodium sulfate and concentrated under reduced pressure. Crude product was purified by flash chromatography (0 to 50% ethyl acetate in hexane as an eluent) to obtain 2-(bromomethyl)-6-chloroquinoline (0.400 g). LCMS 255.9 [M+H]$^+$

Step 2—Synthesis of trans-2-(3-chloro-4-fluorophenoxy)-N-(4-(((6-chloroquinolin-2-yl)methyl)amino)cyclohexyl)acetamide To a stirred solution of trans-N-(4-aminocyclohexyl)-2-(3-chloro-4-fluorophenoxy)acetamide 2,2,2-trifluoroacetate (0.566 g, 1.37 mmol, 0.1 equiv), in DCM (10 mL) was TEA (0.212 g, 2.1 mmol, 1.5 equiv) followed by the addition of added 2-(bromomethyl)-6-chloroquinoline (0.35 g, 1.37 mmol, 1 equiv). The reaction mixture was allowed to stir at RT for 3 h. Progress of the reaction was monitored by LCMS. After completion of the reaction, the reaction mixture was diluted with water (20 mL) and extracted with DCM (25 mL×3). Combined organic layer was washed with water (15 mL×4), dried over anhydrous sodium sulfate and concentrated under reduced pressure. Crude compound was purified by reversed phase HPLC to obtain trans-2-(3-chloro-4-fluorophenoxy)-N-(4-(((6-chloroquinolin-2-yl)methyl)amino)cyclohexyl)acetamide (Compound 151-0.040 g, 6% Yield) as an off-white solid. LCMS 476.2 [M+H]$^+$; $^1$H NMR (400 MHz, DMSO-d$_6$) δ 8.30 (d, J=6.5 Hz, 1H), 8.09 (s, 1H), 7.97 (s, 1H), 7.89 (d, J=7.9 Hz, 1H), 7.71 (t, J=12.6 Hz, 2H), 7.48 (t, J=8.8 Hz, 1H), 7.05 (d, J=12.0 Hz, 1H), 6.83 (d, J=8.9 Hz, 1H), 4.48 (s, 2H), 4.01 (s, 2H), 3.58 (d, J=10.4 Hz, 1H), 3.17 (s, 1H), 2.39 (s, 2H), 1.93 (dd, J=16.3, 10.2 Hz, 2H), 1.76 (d, J=12.3 Hz, 2H), 1.28-1.09 (m, 5H).

Example 34

Synthesis of trans-6-chloro-N-(4-(2-(4-chlorophenoxy)acetamido)cyclohexyl)-3,4-dihydro-2H-benzo[b][1,4]oxazine-2-carboxamide

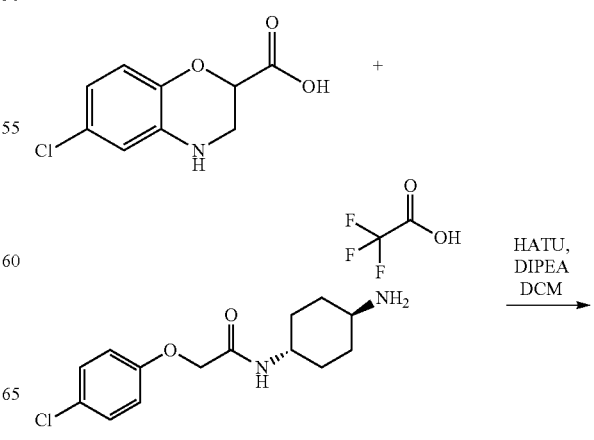

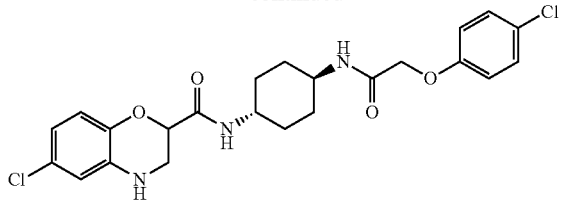

To a solution of 2-((5-chloropyridin-2-yl)oxy)acetic acid (1.0 g, 4.67 mmol, 1.0 equiv) in DMF (10 mL) was added DIPEA (2.5 mL, 14.01 mmol, 3.0 equiv) followed by the addition of HATU (3.5 g, 9.34 mmol, 3.0 equiv). The resulting mixture was stirred for 30 min. trans-N-(4-aminocyclohexyl)-2-(4-chlorophenoxy)acetamide 2,2,2-trifluoroacetate (1.7 g, 4.67 mmol, 2.0 equiv) was added and the reaction mixture was allowed to stir overnight at RT. The resulting precipitate was filtered off and washed with excess methanol to obtain trans-6-chloro-N-(4-(2-(4-chlorophenoxy)acetamido)cyclohexyl)-3,4-dihydro-2H-benzo[b][1,4]oxazine-2-carboxamide (Compound 156—700 mg, 31% Yield) as an off-white solid. LCMS 478 [M+H]$^+$; NMR (400 MHz, DMSO-$d_6$) δ 7.94 (d, J=7.9 Hz, 1H), 7.82 (d, J=7.9 Hz, 1H), 7.39-7.25 (m, J=8.8 Hz, 2H), 7.03-6.88 (m, j=8.8 Hz, 2H), 6.78 (d, j=8.3 Hz, 1H), 6.59 (s, 1H), 6.50 (d, J=8.3 Hz, 1H), 6.18 (br. s., 1H), 4.50-4.37 (m, 3H), 3.57 (br. s., 2H), 3.44 (d, J=11.8 Hz, 1H), 3.22-3.10 (m, 1H), 1.76 (br. s., 4H), 1.34 (d, J=9.2 Hz, 4H).

Example 35

Chiral Resolution of 5-chloro-N-(1-(3-(4-chloro-3-fluorophenoxy)-2-hydroxypropyl)piperidin-4-yl)benzofuran-2-carboxamide

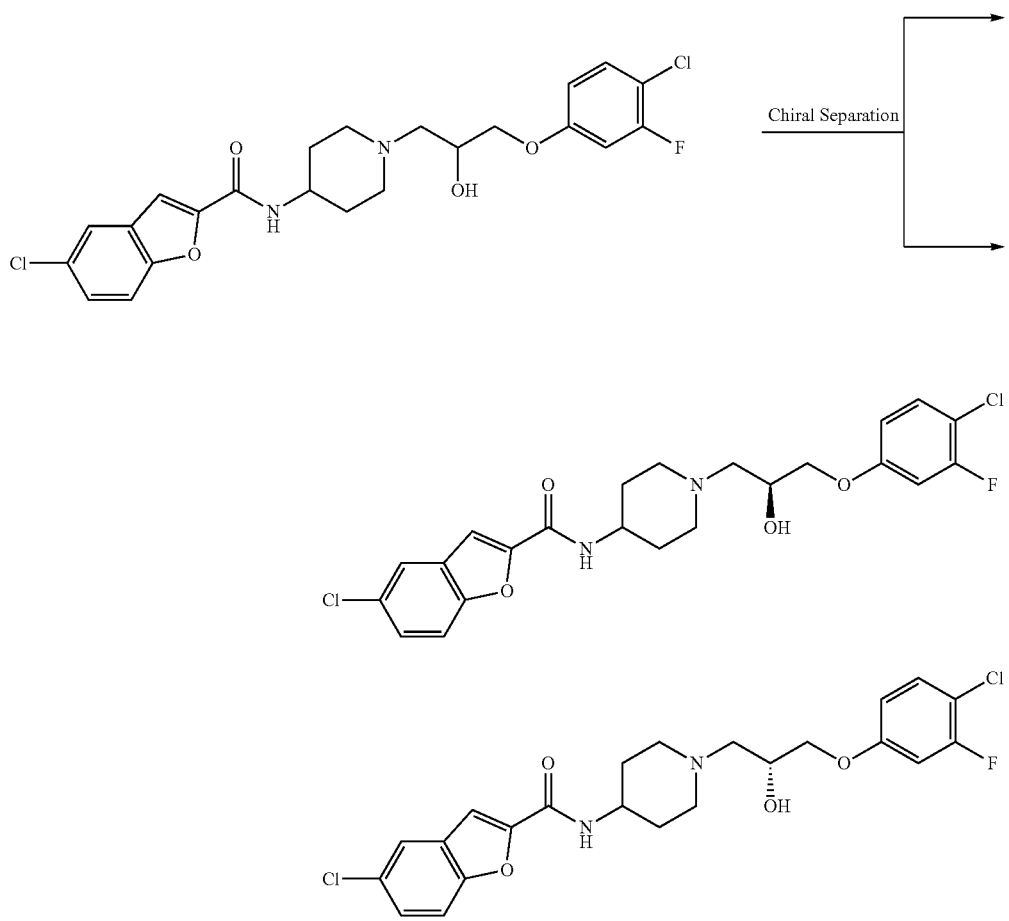

The enantiomers, (+)-5-chloro-N-(1-(3-(4-chloro-3-fluorophenoxy)-2-hydroxypropyl)piperidin-4-yl)benzofuran-2-carboxamide (Compound 149—[α]$^{TM}$=−13.09 (c=0.1016 w/v %, MeOH); elution time: 15.61 min) and (−)-5-chloro-N-(1-(3-(4-chloro-3-fluorophenoxy)-2-hydroxypropyl)piperidin-4-yl)benzofuran-2-carboxamide (Compound 150—[α]$_D^{20}$=+13.16 (c=0.1006 w/v %, MeOH); elution time: 17.32 min), were separated by chiral SFC (Daicel Chiralcel® OD-H, 250×4.6 mm, 5 μm). Isocratic program with analytical grade liquid carbon dioxide and HPLC grade MeOH (0.2% DBA).

Example 36

Chiral Resolution of 6-chloro-N-(1-(3-(4-chloro-3-fluorophenoxy)-2-hydroxypropy)piperidin-4-yl)quinoline-2-carboxamide

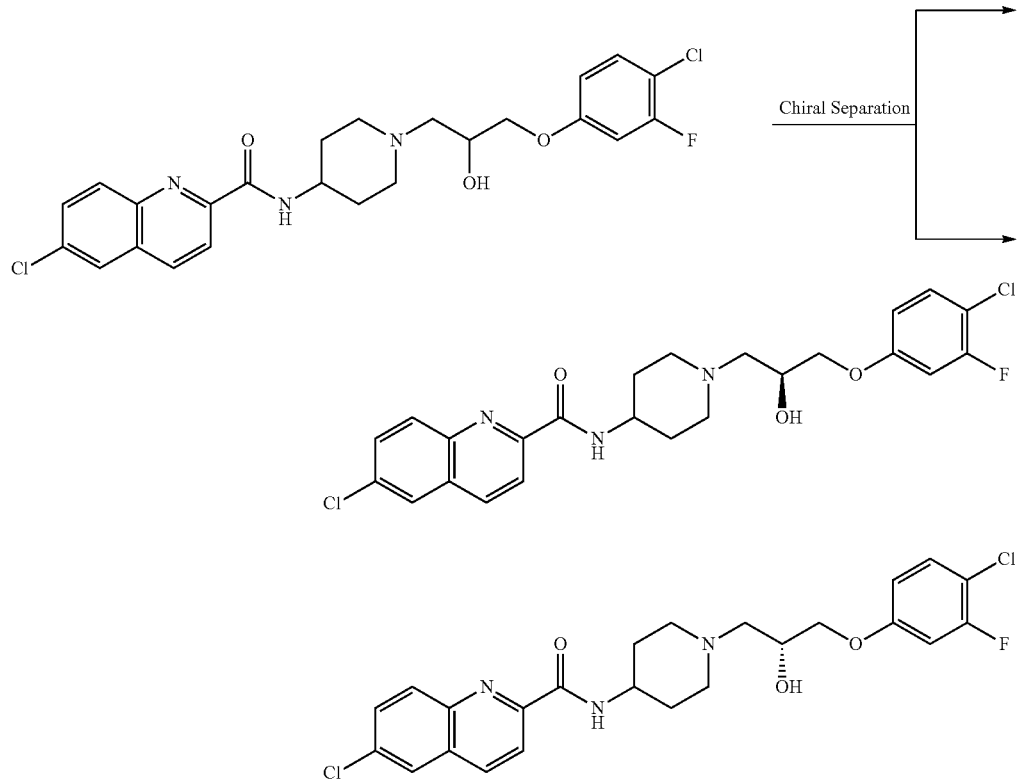

The enantiomers, (+)-6-chloro-N-(1-(3-(4-chloro-3-fluorophenoxy)-2-hydroxypropyl)piperidin-4-yl)quinoline-2-carboxamide (Compound 152—$[\alpha]_D^{20}$=−95.75 (c=0.1036, w/v %, MeOH); elution time: 22.17 min) and (−)-6-chloro-N-(1-(3-(4-chloro-3-fluorophenoxy)-2-hydroxypropyl)piperidin-4-yl)quinoline-2-carboxamide (Compound 153—$[\alpha]_D^{20}$=+113.73 (c=0.1016, w/v %, MeOH); elution time: 27.55 min), were separated by chiral SFC (Chiralpak AD-H, 250×4.6 mm, 5 µm). Isocratic Program with analytical grade liquid carbon dioxide and HPLC grade EtOH (0.2% DBA).

Example 37

Chiral Resolution of trans-5-chloro-N-(4-((3-(4-chloro-3-fluorophenoxy)-2-hydroxypropyl)amino)cyclohexyl)benzofuran-2-carboxamide

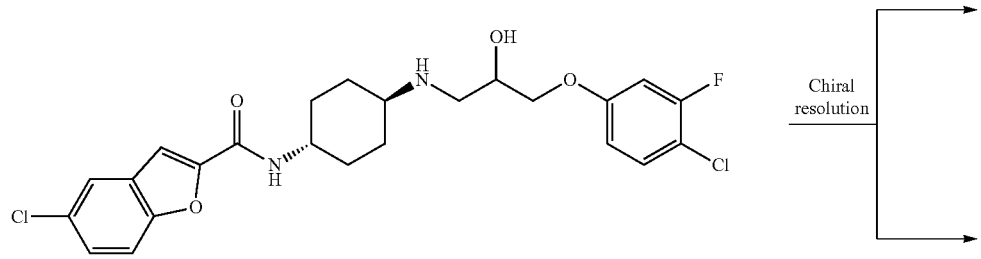

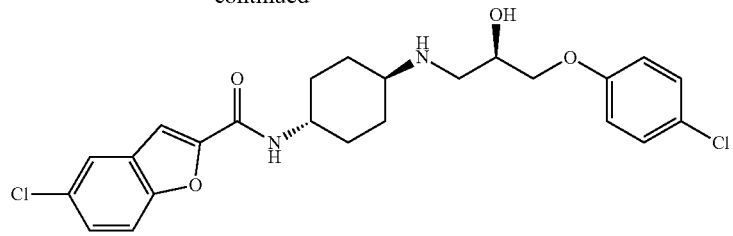

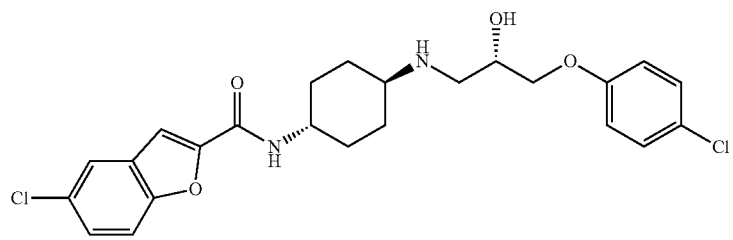

The enantiomers, (+)-trans-5-chloro-N-(4-((3-(4-chloro-3-fluorophenoxy)-2-hydroxypropyl)amino)cyclohexyl)benzofuran-2-carboxamide (Compound 154—$[\alpha]_D^{20}$=+13.91 (c=0.1049, w/v %, MeOH); elution time: 11.77 min) and (−)-trans-5-chloro-N-(4-((3-(4-chloro-3-fluorophenoxy)-2-hydroxypropyl)amino)cyclohexyl)benzofuran-2-carboxamide (Compound 155—$[\alpha]_D^{20}$=−12.46 (c=0.1011 w/v %, MeOH); elution time: 18.08 min), were separated by chiral SFC (Daicel Chiralcel® OD-H, 250×4.6 mm, 5 μm). Isocratic Program with analytical grade liquid carbon dioxide and HPLC grade MeOH (0.2% DBA).

Example 38

Chiral Resolution of trans-6-chloro-N-(4-(2-(4-chlorophenoxy)acetamido)cyclohexyl)-3,4-dihydro-2H-benzo[b][1,4]oxazine-2-carboxamide

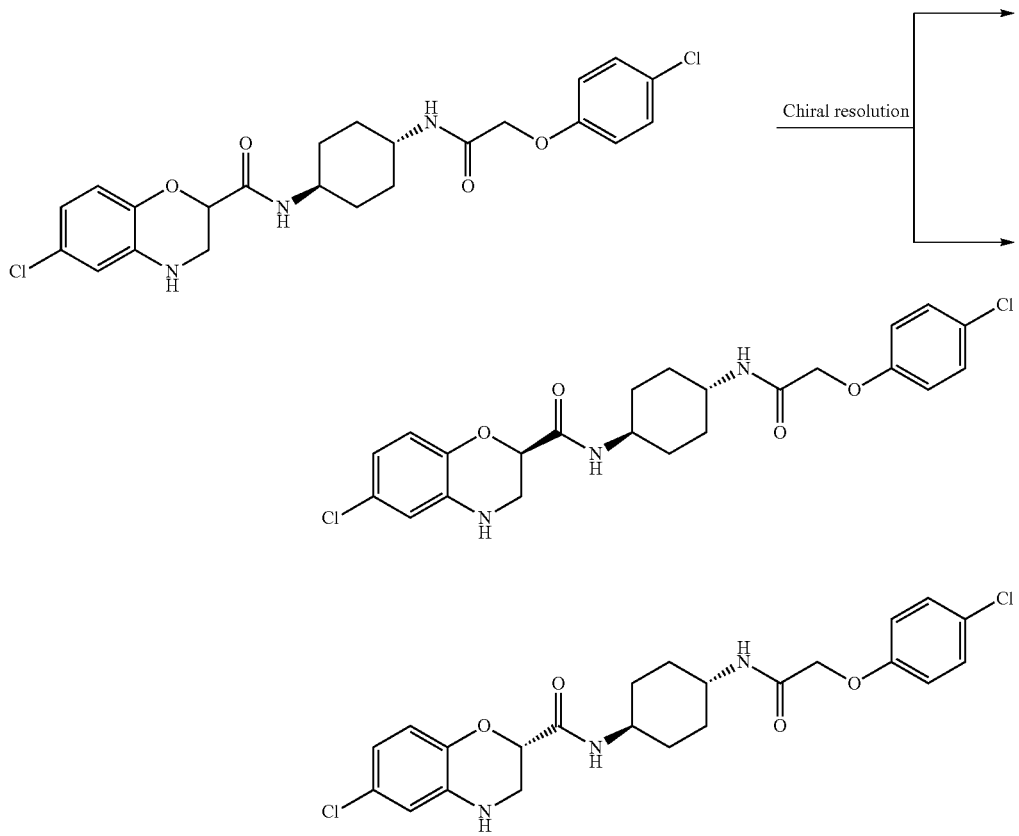

The enantiomers, (+)-trans-6-chloro-N-(4-(2-(4-chlorophenoxy)acetamido)cyclohexyl)-3,4-dihydro-2H-benzo[b][1,4]oxazine-2-carboxamide (Compound 158—$[\alpha]^{TM}$=+26.68 (c=0.053, w/v %, MeOH); elution time: 11.45 min) and (−)-trans-6-chloro-N-(4-(2-(4-chlorophenoxy)acetamido)cyclohexyl)-3,4-dihydro-2H-benzo[b][1,4]oxazine-2-carboxamide (Compound 157—$[\alpha]_D^{20}$=−15.97 (c=0.063 w/v %, MeOH); elution time: 10.09 min), were separated by chiral SFC (Daicel Chiralcel® OD-H, 250×20 mm, 5 μm). Isocratic Program with analytical grade liquid carbon dioxide and HPLC grade iPrOH (0.2% DBA).

Example 39

Synthesis of trans-2-(4-chlorophenoxy)-N-(4-(5-((4-chlorophenoxy)methyl)-2-oxooxazolidin-3-yl)cyclohexyl)acetamide

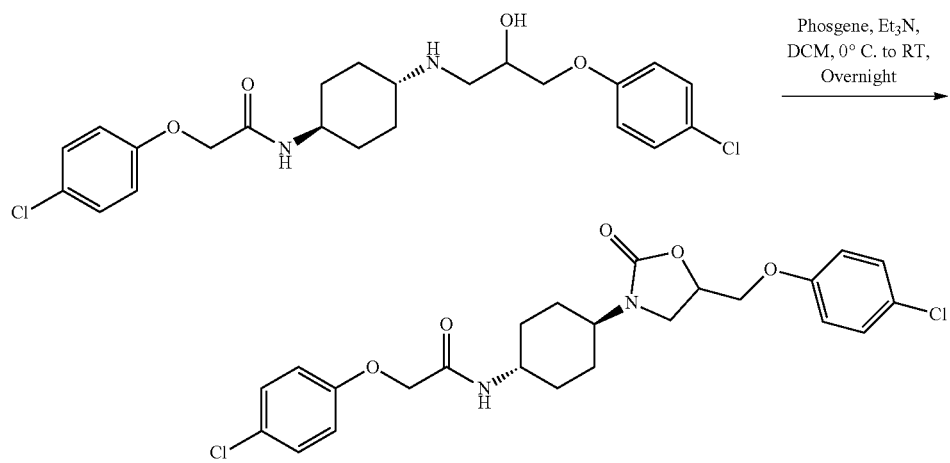

To a stirred solution of trans-2-(4-chlorophenoxy)-N-(4-((3-(4-chlorophenoxy)-2-hydroxypropyl)amino)cyclohexyl)acetamide (100 mg, 0.21 mmol, 1 equiv) in DCM (5 mL), was added Et$_3$N (0.2 mL, 1.1 mmol, 5 equiv). The mixture was allowed to stir for 15 min. under nitrogen atmosphere. Isoindoline (26 mg, 1.05 mmol, 5 equiv) was added to the mixture and the reaction mixture was cooled to 0° C. Phosgene (20% in toluene, 1 mL) was added to the mixture dropwise. The temperature was allowed to rise to RT and the reaction mixture stirred overnight at RT. Progress of the reaction was monitored by LCMS. After completion of the reaction, the reaction mixture was diluted with water (30 mL) and extracted with DCM (50 mL×2). The organic layer was washed with water (50 mL), brine solution (50 mL). The organic layer was dried over anhydrous sodium sulfate and concentrated under reduced pressure to obtain a crude compound, which was purified by reversed phase HPLC to obtain trans-2-(4-chlorophenoxy)-N-(4-(5-((4-chlorophenoxy)methyl)-2-oxooxazolidin-3-yl)cyclohexyl)acetamide (Compound 159—25 mg, 24% Yield) as a white solid. LCMS 493.2 [M+H]$^+$; $^1$H NMR (400 MHz, DMSO-d6) δ 7.97 (d, J=8.0 Hz, 1H), 7.34 (d, J=8.4 Hz, 4H), 7.01-6.93 (m, 4H), 4.84 (h, J=4.5 Hz, 1H), 4.45 (s, 2H), 4.18 (dd, J=10.9, 3.2 Hz, 1H), 4.08 (dd, J=10.9, 5.2 Hz, 1H), 3.64 (t, J=8.9 Hz, 2H), 3.54-3.42 (m, 1H), 3.37 (dd, J=8.7, 5.9 Hz, 1H), 1.86-1.77 (m, 2H), 1.74-1.66 (m, 2H), 1.57 (q, J=12.7, 12.3 Hz, 2H), 1.38 (tt, J=13.1, 6.5 Hz, 2H).

BIOLOGICAL EXAMPLES

Example B1—ATF4 Expression Inhibition Assay

HEK293T cells were maintained at 37° C. and 5% CO$_2$ in Dulbecco's Modified Eagle's Media (DMEM) supplemented with 10% fetal bovine serum (FBS), 2 mM L-glutamine, 100 U/ml penicillin, and 100 μg/ml streptomycin. After reaching 80% of confluence, cells were detached and seeded on 6 well plates in complete media, allowed to recover overnight and treated for 3 hours with 100 nM thapsigargin (Tg) in the presence of 100 nM or 1 μM concentration of a test compound (percent inhibition assays) or various concentrations ranging from 1 nM to 1 μM (IC$_{50}$ assay). Cells without treatment or cells treated with Tg alone were used as controls.

After 3 hours of treatment with Tg and the test compound, cells were lysed with SDS-PAGE lysis buffer. Lysates were transferred to 1.5 ml tubes and sonicated for 3 min, and total protein amounts were quantified using BCA Protein Assay Kit (Pierce). Equal amount of proteins were loaded on SDS-PAGE gels. Proteins were transferred onto 0.2 μm PVDF membranes (BioRad) and probed with primary antibodies diluted in Tris-buffered saline supplemented with 0.1% Tween 20 and 3% bovine serum albumin.

ATF4 (11815) antibody was used as primary antibody (Cell Signaling Technologies). A horseradish peroxidase (HRP)-conjugated secondary antibody (Rockland) was employed to detect immune-reactive bands using enhanced chemiluminescence (ECL Western Blotting Substrate, Pierce). Quantification of protein bands was done by densitometry using ImageJ.

Percentages of ATF4 inhibition after induction with Tg in the presence of 100 nM or 1 μM of certain test compounds are shown in Table 2 and FIG. 1. Percentage of ATF4 inhibition was calculated as the percent reduction normalized to Tg treatment (0% inhibition) and untreated cells (100% inhibition). Also shown in Table 2 is the calculated IC$_{50}$ for the test compounds. Under ISR stressed conditions (resulting from treatment with Tg), ATF4 expression is generally upregulated. Accordingly, inhibition of ATF4 expression as a result of the test compound indicates suppression of the ISR pathway.

TABLE 2

| Compound No. | % ATF4 inhibition at 100 nM | % ATF4 inhibition at 1 μM | ATF4 inhibition IC$_{50}$ (nM) |
|---|---|---|---|
| 1 | 0 | 71 | 353.1 |
| 2 | 40 | 56 | 162.9 |
| 3 | 35 | 77 | 145 |
| 4 | 31 | 54 | n.d. |
| 5 | 42 | 94 | 169.7 |
| 6 | 52 | 83 | 82.82 |
| 7 | 0 | 0 | n.d. |
| 8 | 0 | 0 | n.d. |
| 9 | 12 | 20 | n.d. |
| 10 | 0 | 11 | n.d. |
| 11 | 0 | 0 | n.d. |
| 12 | 0 | 0 | n.d. |
| 13 | 57 | 93 | 57.22 |
| 14 | 0 | 0 | n.d. |
| 15 | 77 | 99 | 52.14 |
| 16 | 0 | 38 | n.d. |
| 17 | 95 | 98 | 9.52 |
| 18 | 96 | 98 | 34.14 |
| 19 | 94 | 100 | n.d. |
| 20 | 14 | 64 | n.d. |
| 21 | 54 | 78 | n.d. |
| 22 | 21 | 81 | 102.7 |
| 23 | 97 | 99 | 2.1 |
| 24 | 18 | 54 | n.d. |
| 25 | 0 | 0 | n.d. |
| 26 | 91 | 97 | 26.96 |
| 27 | 54 | 73 | n.d. |
| 28 | 88 | 97 | 25.83 |
| 29 | 87 | 95 | 51.81 |
| 30 | 35 | 35 | >3,000 |
| 31 | 41 | 93 | n.d. |
| 32 | 38 | 78 | n.d. |
| 145 | 97 | 97 | 17.05 |
| 146 | 88 | 100 | 49.93 |
| 147 | 95 | 100 | 33.09 |
| 148 | 30 | 90 | n.d. |
| 149 | 62 | 96 | 29.85 |
| 150 | 0 | 43 | n.d. |
| 151 | 10 | 67 | 90.72 |
| 152 | 86 | 91 | 49.02 |
| 153 | 0 | 0 | n.d. |
| 154 | 92 | 96 | 13.68 |
| 155 | 60 | 75 | n.d. |
| 156 | 94 | 97 | 15.98 |
| 157 | 96 | 100 | 23.8 |
| 158 | 96 | 96 | 9.1 |
| 159 | 52 | 84 | <100 |

Example B2—Protein Translation Assay

CHO cells were maintained at 37° C. and 5% CO$_2$ in DMEM supplemented with 10% fetal bovine serum (FBS), 2 mM L-glutamine, 100 U/ml penicillin, and 100 μg/ml streptomycin. After reaching 80% of confluence, cells were detached and seeded on 6 well plates in complete media, allowed to recover overnight and treated for 2 hours with 1 μM of the test compound (to assess protein synthesis levels in unstressed condition), or for 1 hour with 100 nM and 1 μM of the test compound and then co-treated with 300 nM Tg and 100 nM and 1 μM of the test compound (to assess the recovery of protein synthesis in a stressed condition). Cells treated with Tg alone were used as controls.

After the 2 hours treatments, media were replaced by adding 10 μg/ml puromycin (Sigma Aldrich) in complete media for 30 min. Media were removed and cells were lysed with SDS-PAGE lysis buffer. Lysates were transferred to 1.5 ml tubes and sonicated for 3 minutes and total protein amount were quantified using BCA Protein Assay Kit (Pierce). Equal amount of protein (30 μg) was loaded on SDS-PAGE gels. Proteins were transferred onto 0.2 μm PVDF membranes (BioRad) and probed with primary antibodies diluted in Tris-buffered saline supplemented with 0.1% Tween 20 and 3% bovine serum albumin.

Puromycin (12D10) antibody was used as primary antibody (Merck Millipore). A HRP-conjugated secondary antibody (Rockland) was employed to detect immune-reactive bands using enhanced chemiluminescence (ECL Western Blotting Substrate, Pierce). Quantification of protein bands was done by densitometry using ImageJ.

Figure 2:
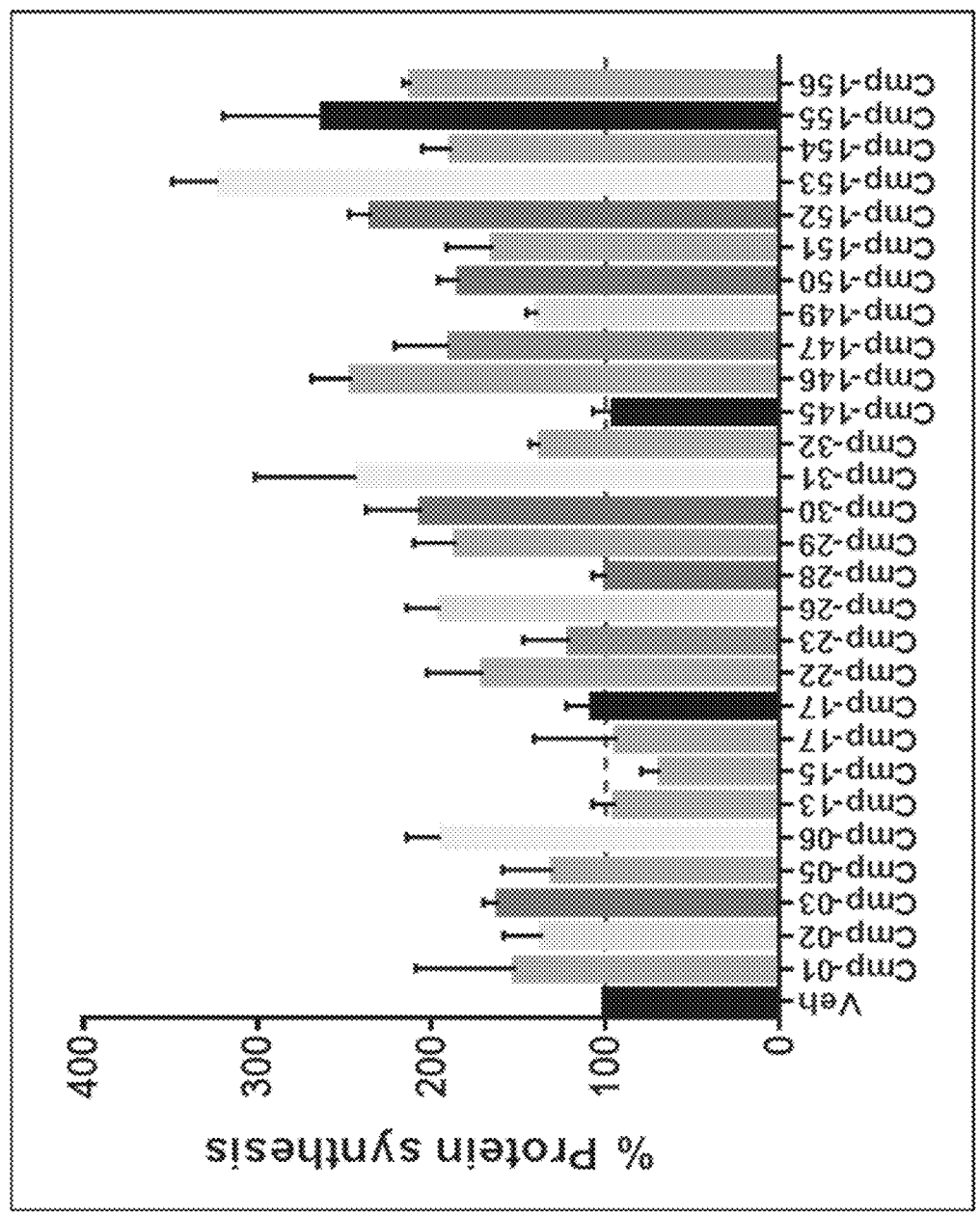
FIG. 2 shows protein synthesis levels in the presence of media alone or certain test compounds in unstressed cells. The levels were normalized to the media alone condition, which correspond to 100% protein synthesis.

Percent increase of protein synthesis in unstressed cells (without Tg treatment) in the presence of media alone or certain test compounds is shown in Table 3 and FIG. 2. The percentage levels were normalized to the media alone condition, which correspond to 100% protein synthesis. All compounds stimulated protein synthesis above baseline, indicating that the test compounds result in increased protein synthesis in unstressed cells.

Figure 3A:
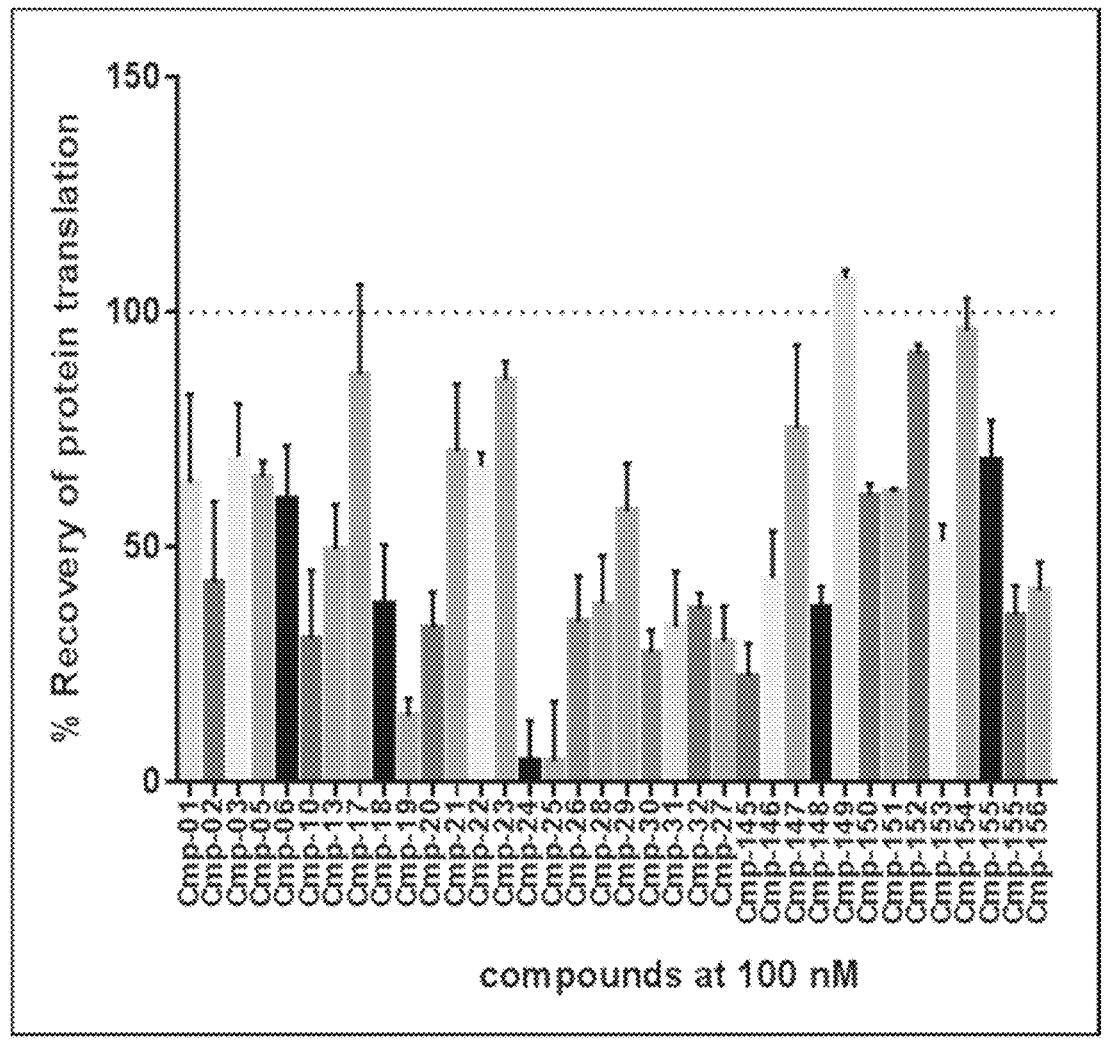
FIG. 3A and FIG. 3B show percent recovery of protein synthesis in a stressed cell in the presence of one of several test compounds at a concentration of 100 nM (FIG. 3A) or 1 µM (FIG. 3B). The levels were normalized to the media alone and to Tg alone conditions, which correspond to 100% and 0% respectively.
Figure 3B:
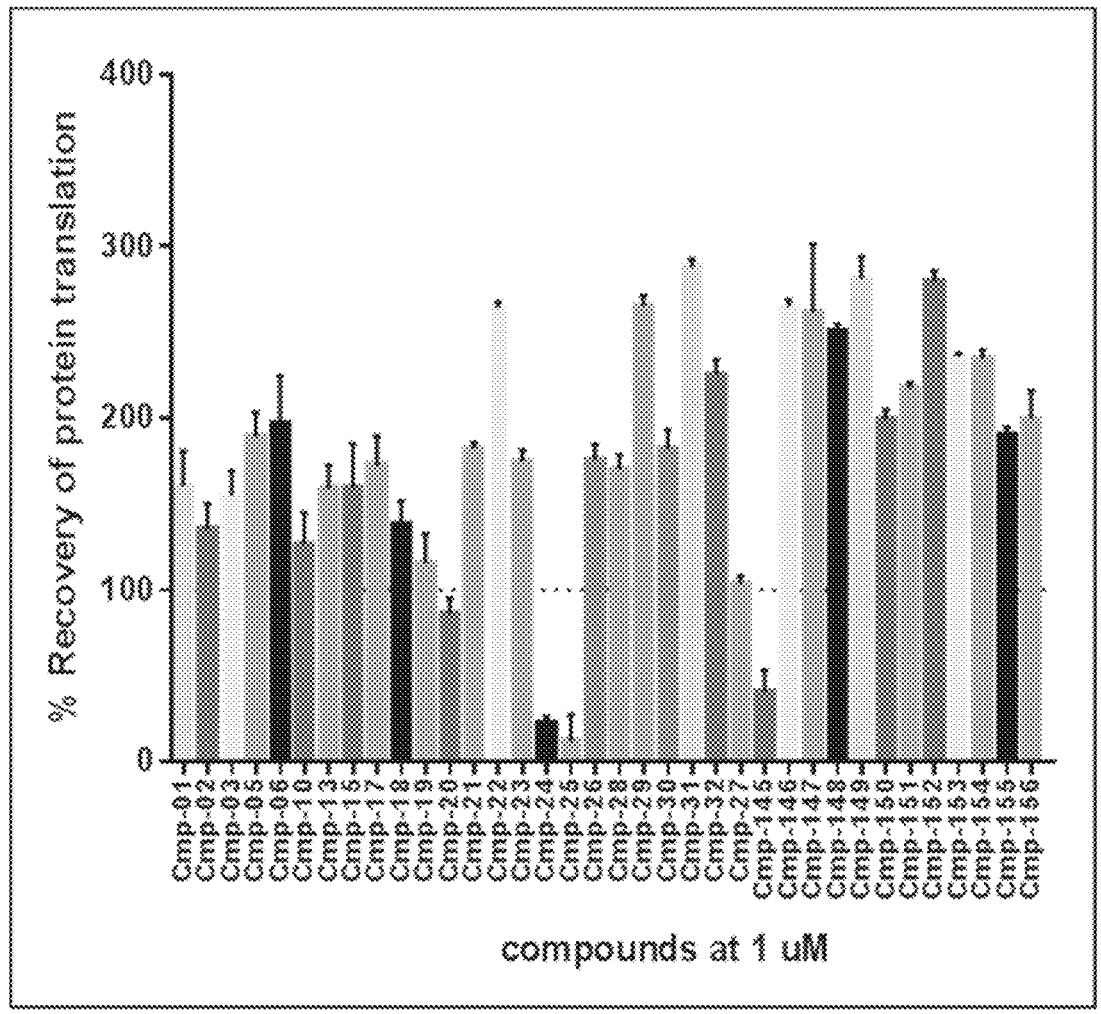

Percent recovery of protein synthesis in stressed cells (with Tg treatment) due to the test compounds at 100 nM or 1 μM is shown in FIGS. 3A and 3B, respectively, and in Table 3. The levels were normalized to the media alone and to Tg alone conditions, which correspond to 100% and 0% respectively.

TABLE 3

| Compound No. | % Recovery of protein expression (100 nM test compound) | % Recovery of protein expression (1 μM test compound) | % Protein expression relative to untreated (1 μM test compound) |
|---|---|---|---|
| 1 | 63.8 | 160.3 | 151.7 |
| 2 | 42.5 | 135.2 | 136.2 |
| 3 | 69.4 | 154.7 | 161.5 |
| 5 | 64.9 | 189.1 | 130.2 |
| 6 | 60.2 | 196.8 | 194.9 |
| 10 | 30.6 | 126.7 | n.d. |
| 13 | 49.6 | 159.2 | 94.0 |
| 15 | 35.6 | 159.2 | 68.3 |
| 17 | 87.0 | 172.5 | 93.2 |
| 18 | 38.0 | 138.0 | 107.0 |
| 19 | 14.1 | 115.5 | n.d. |
| 20 | 38.6 | 93.9 | n.d. |
| 21 | 70.5 | 182.0 | n.d. |
| 22 | 67.3 | 264.2 | 170.1 |
| 23 | 79.2 | 175.7 | 119.6 |
| 24 | 11.8 | 24.34 | n.d. |
| 25 | 11.4 | 22.9 | n.d. |
| 26 | 34.2 | 175.7 | 111.8 |
| 28 | 38.0 | 170.3 | 99.3 |
| 29 | 48.4 | 266.7 | 185.7 |
| 30 | 23.1 | 181.5 | 205.9 |
| 31 | 25.0 | 287.7 | 243.4 |
| 32 | 37.7 | 233.8 | 137.2 |
| 145 | 22.6 | 40.6 | 95.4 |
| 146 | 43.4 | 264.8 | 245.6 |
| 147 | 75.2 | 261.5 | 189.5 |
| 148 | 37.2 | 250.2 | 123.2 |
| 149 | 107.3 | 281.2 | 138.4 |
| 150 | 61.0 | 199.5 | 183.9 |
| 151 | 61.8 | 217.4 | 164.3 |
| 152 | 99.1 | 279.5 | 239.1 |
| 153 | 51.5 | 235.6 | 322.8 |
| 154 | 96.3 | 234.5 | 188.3 |
| 155 | 68.5 | 190.3 | 262.6 |
| 156 | 25.1 | 199.8 | 197.1 |
| 157 | 39.7 | 97.3 | 117.9 |
| 158 | 86.8 | 198.7 | 167.9 |
| 159 | 23.9 | 79.4 | n.d. |

Figure 3C:
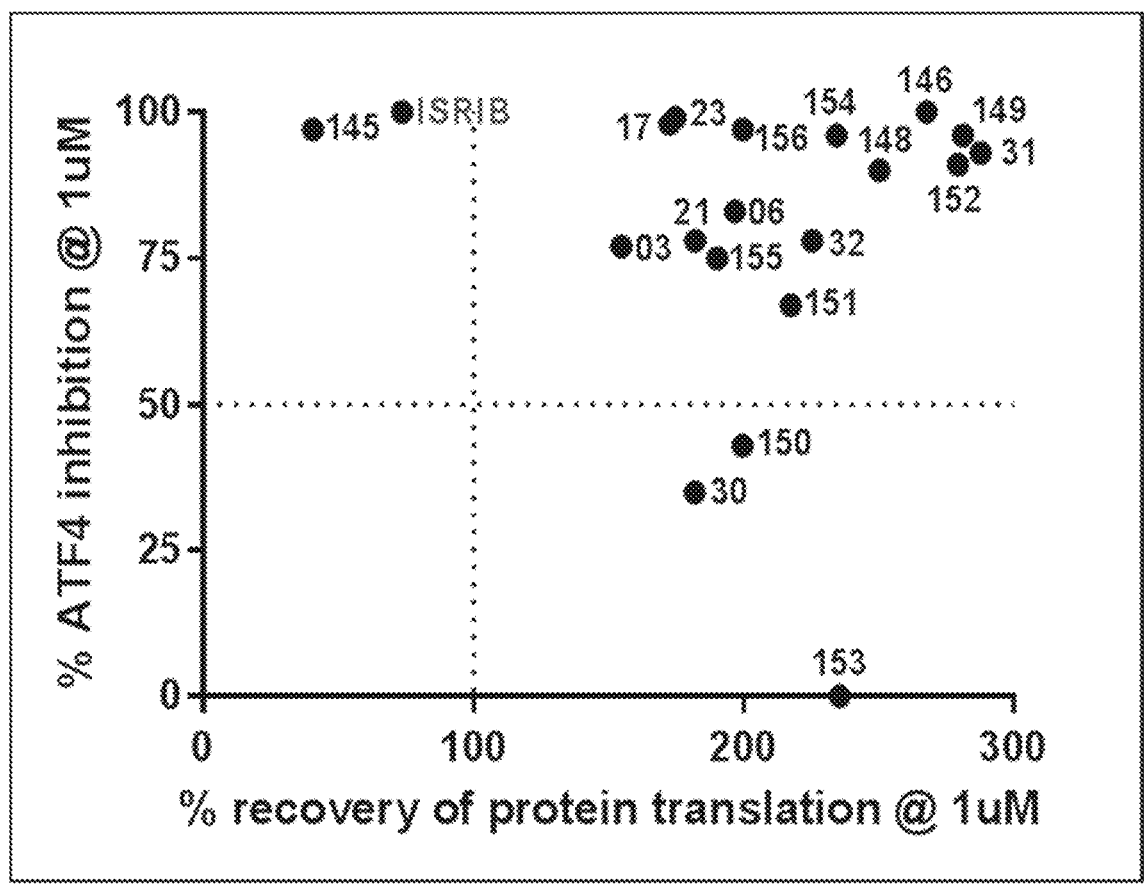
FIG. 3C shows percent ATF4 inhibition for select compounds against percent recovery of protein synthesis.

Data summarized in Tables 2 and 3 show that some compounds have differential activity in ATF4 inhibition and protein synthesis under ISR-inducing conditions. That is, some compounds are able to effectively inhibit ATF4 expression but do not restore protein synthesis. Other compounds effectively restore protein synthesis but do not inhibit ATF4 expression under ISR-inducing conditions. Still other compounds inhibit ATF4 expression and restore protein synthesis. Certain compounds (such as compounds 30, 150, 153) show increased protein translation with limited (less than 50%) ATF4 inhibition. FIG. 3C shows percent ATF4 inhibition (see Example B1) for select compounds against percent recovery of protein synthesis. This differential modulation of activities represents a unique characteristic that can be exploited when selecting specific compounds for a desired use.

Example B3—ATF4 Inhibition Assay Under Aβ Stimulation

Chinese hamster ovary (CHO) cells that stably express human APP751 incorporating the familial Alzheimer's disease mutation V717F were used as a source of Aβ monomer and low-n oligomers. These cells, referred to as 7PA2 CHO cells, were cultured in 100 mm dishes with Dulbecco's modified Eagle's medium (DMEM) containing 10% fetal bovine serum, 2 mM L-glutamine, 100 U/ml penicillin, and 100 µg/ml penicillin, streptomycin and 200 µg/ml G418. Upon reaching 90-100% confluency, cells were washed with 5 mL of glutamine- and serum-free DMEM and incubated for approximately 16 h in 5 mL of the same DMEM. Conditioned media (CM) was collected.

SH-SY5Y cells were maintained at 37° C. and 5% $CO_2$ in RPMI 1640 media supplemented with 10% fetal bovine serum (FBS), penicillin and streptomycin. After reaching 80% of confluence, cells were detached and seeded on 6 well plates in complete media, allowed to recover 48 h and treated for 16 hours with CM from WT CHO cells or 7PA2 CHO cells in the presences of 1 µM of test compounds 3, 6, 15, 17, 23, 149, 152, or 153.

After 16 hours treatment, culture media were removed and cells were lysed with SDS-PAGE lysis buffer. Lysates were transferred to 1.5 ml tubes and sonicated for 3 min. Total protein amount were quantified using BCA Protein Assay Kit (Pierce). Equal amount of proteins (30 µg) was loaded on SDS-PAGE gels. Proteins were transferred onto 0.2 µm PVDF membranes (BioRad) and probed with primary antibodies diluted in Tris-buffered saline supplemented with 0.1% Tween 20 and 3% bovine serum albumin.

ATF4 (11815) antibody was used as primary antibody (Cell Signaling Technologies). A β-actin antibody was used as a control primary antibody. An HRP-conjugated secondary antibody (Rockland) was employed to detect immune-reactive bands using enhanced chemiluminescence (ECL Western Blotting Substrate, Pierce). Quantification of protein bands was done by densitometry using ImageJ.

Figure 4A:
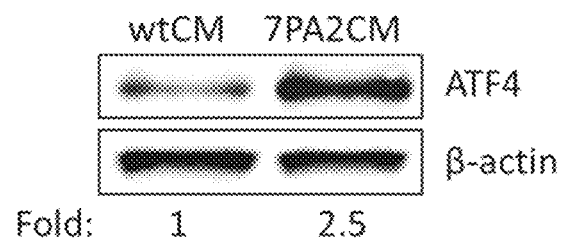
FIG. 4A shows representative levels of ATF4 expression and β-actin expression (control) in SH-SY5Y cells after being treated with cell culture media conditioned using wild-type CHO cells (wtCM) or 7PA2 CHO cells (7PA2CM).

Representative levels of ATF4 expression from the treatment with CM from WT CHO cells (wtCM) or 7PA2 CHO cells (7PA2CM) are shown in FIG. 4A. The levels were normalized to β-actin expression and fold change was calculated as the levels relative to the ATF4 expression level from wtCM-treated SH-SY5Y cells (normalized to 1).

Figure 4B:
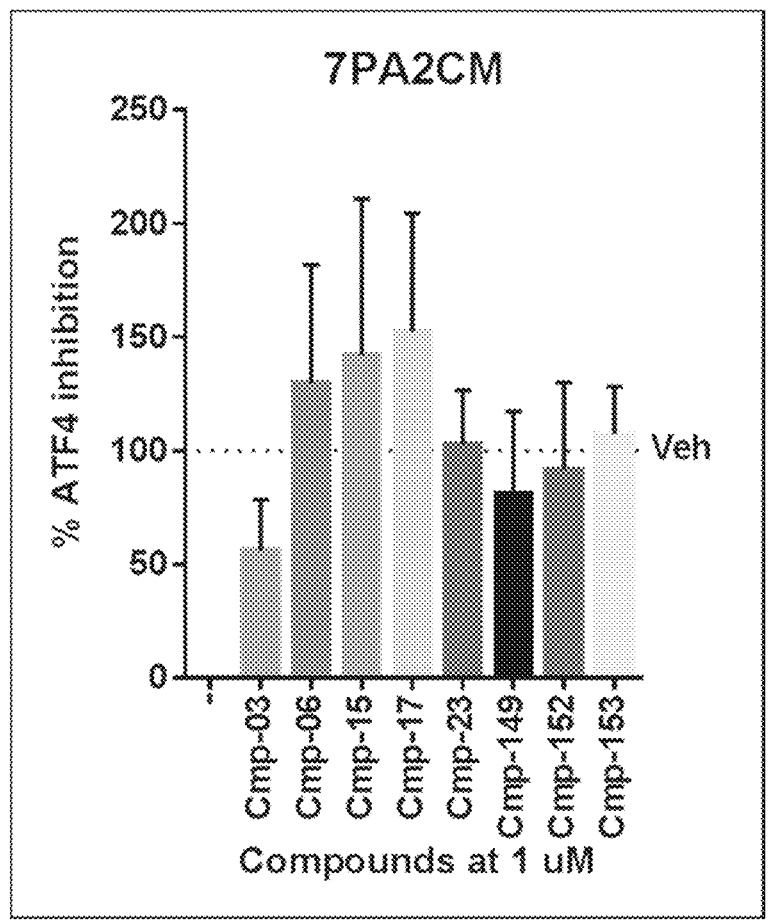
FIG. 4B shows percent inhibition of ATF4 expression in SH-5Y5Y cells after incubation with conditioned media from 7PA2 CHO cells and one of several test compounds. The levels were normalized to the media alone and to conditioned media from 7PA2 CHO cells alone, which correspond to 100% and 0% respectively.

Percent inhibition of ATF4 expression in SH-SY5Y cells after incubation with CM from the 7PA2 CHO cells as a result of the test compounds is shown in FIG. 4B. Percentage of ATF4 inhibition was calculated as the percent reduction normalized to CM from, 7PA2 CHO cells treatment (0% inhibition) and CM from WT CHO cells treatment (100% inhibition).

Example B4—Electrophysiology and Long-Term Potentiation

Hippocampal slices were prepared as described in Ardiles et al., *Pannexin 1 regulates bidirectional hippocampal synaptic plasticity in adult mice*. Front Cell Neurosci, vol. 8, art. 326 (2014). Six to eleven-month-old WT $C_{57}BL/6$ or transgenic APP/PS1 mice (Jackson Lab 34829-JAX) were deeply anesthetized with isoflurane and their brains were quickly removed. 5-10 slices (350 µm) from each animal were dissected in ice-cold dissection buffer using a vibratome (Leica VT1200S, Leica Microsystems, Nussloch, Germany). Slices were incubated with 5 µM ISRIB, 5 µM compound 3, 1 µM compound 152, or a vehicle (complete medium containing 0.1% DMSO) 20 min before conditioning stimulation. Synaptic responses were evoked by stimulating the Schaffer collaterals with 0.2 ms pulses delivered through concentric bipolar stimulating electrodes, and recorded extracellularly in the stratum radiatum of the CA1 subfield. Long-term potentiation (LTP) was induced by four-theta burst stimulation (TBS) (10 trains of four pulses at 100 Hz; 5 Hz inter-burst interval) delivered at 0.1 Hz. LTP magnitude based on field excitatory postsynaptic potential (fEPSP) was calculated as the average (normalized to baseline) of the responses recorded 60 min after conditioning stimulation. Similar experiments can be performed using a different test compound in place of ISRIB, compound 3, or compound 152.

Figure 5A:
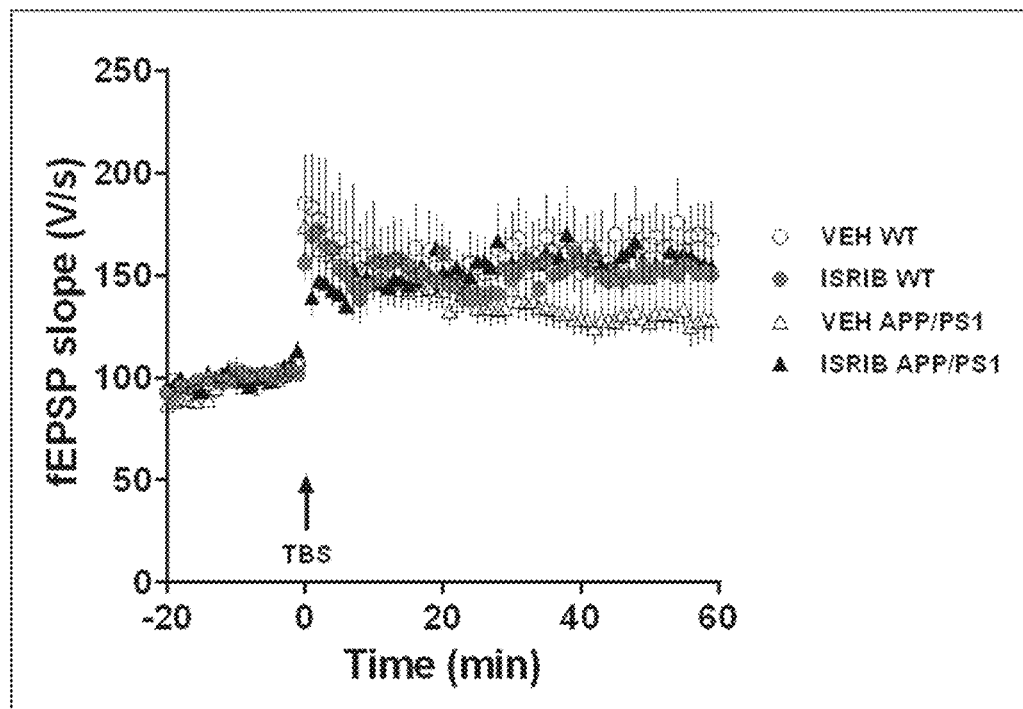
FIG. 5A shows long-term potentiation (LTP) of a stimulated hippocampal slice from a WT C57BL/6 mouse or a transgenic APP/PS1 mouse with or without incubation with ISRIB. LTP was based on field excitatory postsynaptic potential (fEPSP) slope, measured from 20 minutes prior to theta burst stimulation (TBS) to 60 minutes after TBS.
Figure 5B:
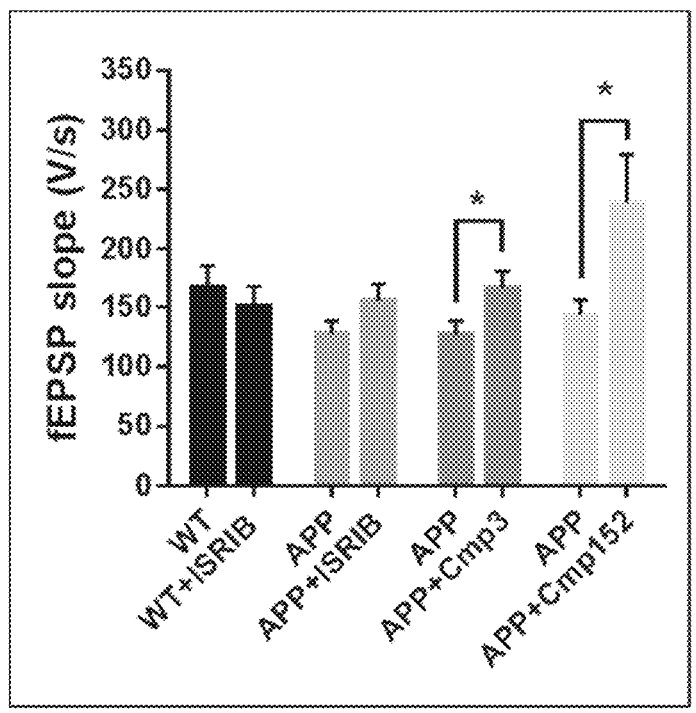
FIG. 5B shows the responses recorded in the last 10 minutes after conditioning stimulation of the slices from the WT C57BL/6 and APP/PS1 mice treated with ISRIB (APP+ISRIB), and from APP/PS1 mice treated with compound 3 (APP+Cmp3), or compound 152 (APP+Cmp152), or the vehicle (APP).

Results for ISRIB are shown in FIG. 5A. Treatment of the slices from both the WT C57BL/6 and APP/PS1 mice treated with the vehicle (empty circles and empty triangles, respectively) resulted in LTP 60 minutes after stimulation, with the APP/PS1 sample showing significantly reduced LTP. Treatment of the slices from the APP/PS1 mouse with ISRIB (black triangles), however, resulted in partial LTP recovery (FIG. 5A). FIG. 5B shows the responses recorded in the last 10 minutes after conditioning stimulation of the slices from the WT C57BL/6 and APP/PS1 mice treated with ISRIB (APP+ISRIB), and from APP/PS1 mice treated with compound 3 (APP+Cmp3), or compound 152 (APP+Cmp152), or the vehicle (APP).

Example B5—Learning Memory in Aged Mice

Wild type 19-month old male C57Bl/6J mice were used in an 8-arm radial water maze (RAWM) to measure the hippocampal-mediated learning memory. The maze involved a pool 118.5 cm in diameter and 25 cm high with 8 arms, each 41 cm in length, and an escape platform that could be moved. The pool was filled with water that was rendered opaque by adding white paint (Crayola, 54-2128-053). The escape platform remains hidden during the experiment. Visual cues were placed around the room such that they were visible to animals exploring the maze.

mice were intraperitoneally injected with 5 mg/kg of compound 3 formulated in 50% Polyethylene glycol (PEG-400) in distilled water and other 9 animals were intraperitoneally injected with the vehicle 50% PEG-400 in distilled water as a control group. Animals ran 6 trials a day for two days. Animals were allowed 1 minute to locate the escape platform. On successfully finding the platform, animals remained there for 10 seconds before being returned to their holding cage. On a failed trial, animals were guided to the escape platform and then returned to their holding cage 10 seconds later.

Behavioral tests were recorded and scored using a video tracking and analysis setup (Ethovision XT 8.5, Noldus Information Technology). The program automatically analyzed the number of incorrect arm entries (termed number of errors) made per trial. Last three trials were averaged to determine learning memory after training.

At the end of the behavioral test, animals were sacrificed and the hippocampi were extracted and immediately frozen in liquid nitrogen and then stored at −80° C. The frozen samples were then homogenized with a T 10 basic ULTRA-TURRAX (IKa) in ice-cold buffer lysis (Cell Signaling 9803) and protease and phosphatase inhibitors (Roche). Lysates were sonicated for 3 minutes and centrifuged at 13,000 rpm for 20 minutes at 4° C. Protein concentration in supernatants was determined using BCA Protein Assay Kit (Pierce). Equal amount of proteins was loaded on SDS-PAGE gels. Proteins were transferred onto 0.2 µm PVDF membranes (BioRad) and probed with primary antibodies diluted in Tris-buffered saline supplemented with 0.1% Tween 20 and 3% bovine serum albumin.

ATF4 (11815) antibody (Cell Signaling Technologies) and β-actin (Sigma-Aldrich) antibodies were used as primary antibodies. A HRP-conjugated secondary antibody (Rockland) was employed to detect immune-reactive bands using enhanced chemiluminescence (ECL Western Blotting Substrate, Pierce). Quantification of protein bands was done by densitometry using ImageJ software.

Figure 6B:
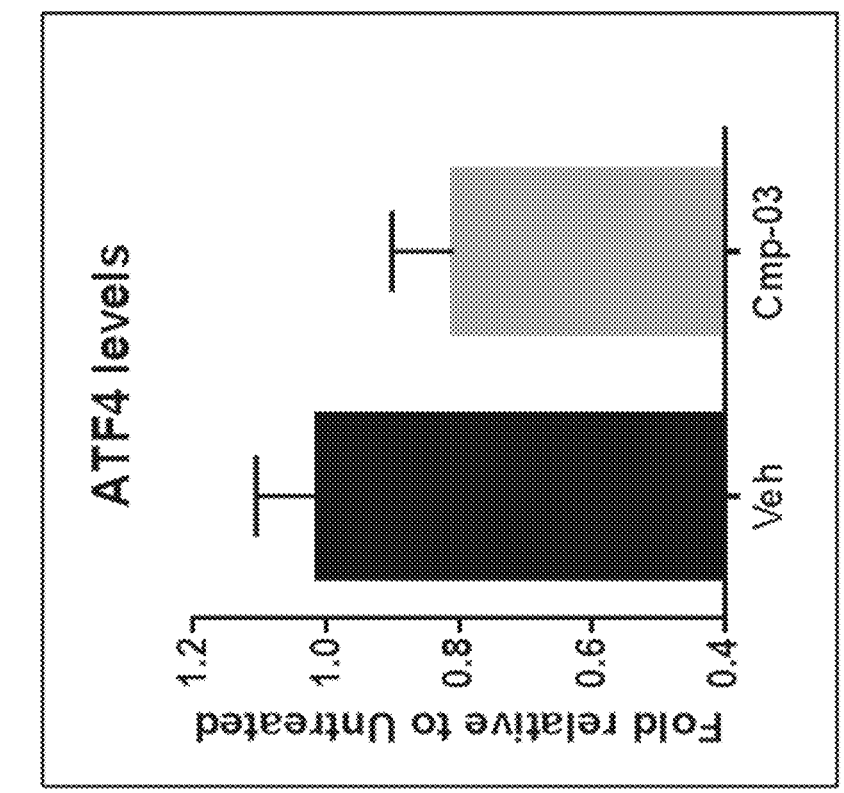
FIG. 6B shows levels of ATF4 expression normalized to β-actin expression in hippocampi extracted from mice treated with compound 3 versus a vehicle control ("Veh").
Figure 6A:
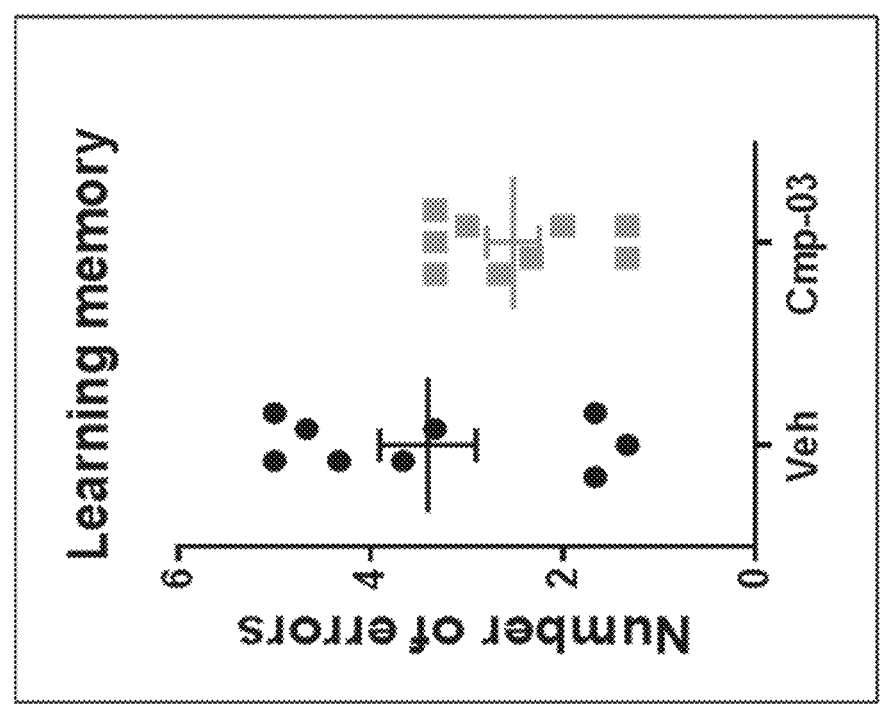
FIG. 6A shows results of an 8-arm radial water maze (RAWM) task used to measure learning in aged mice treated with compound 3 versus a vehicle control ("Veh").
Figure 6C:
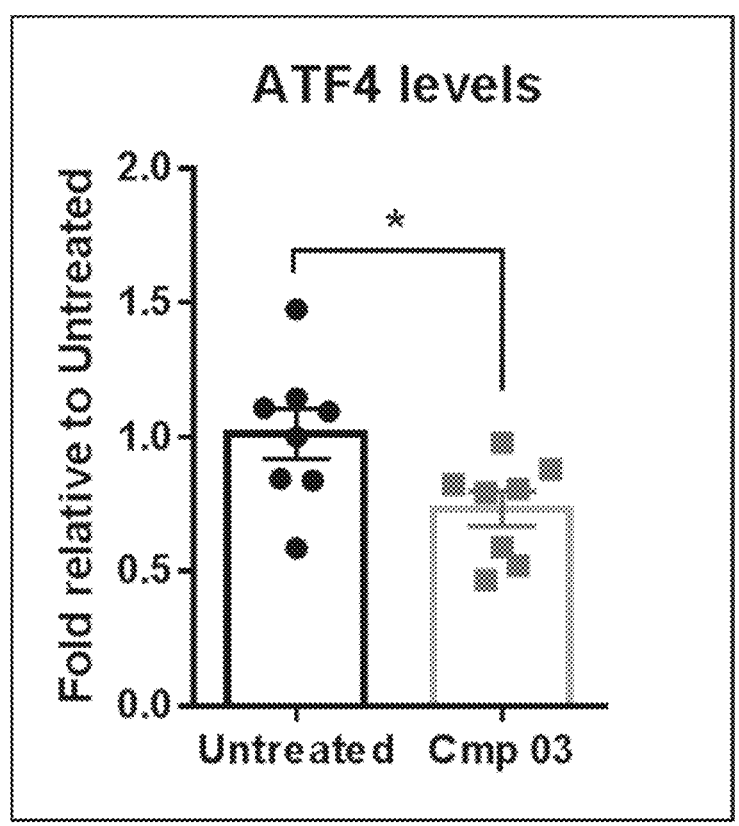
FIG. 6C shows individual data points for the levels of ATF4 expression normalized to β-actin expression in hippocampi extracted from mice treated with compound 3 versus a vehicle control ("Veh").

Results of RAWM task are shown in FIG. 6A. Aged animals with vehicle progressively learned the location of the escape platform during the trials. Interestingly, aged animals with compound 3 performed better than vehicle-treated animals suggesting an enhanced learning memory. Levels of ATF4 expression normalized to β-actin expression in hippocampi are shown in FIG. 6B, with individual data points being shown in FIG. 6C. Animals that received compound 3 showed lower levels of ATF4 expression compared with vehicle-treated animals. There is a clear trend indicating that the ISR pathway is being inhibited and a better performance in a learning memory task.

Example B6—Learning Memory, Long-Term Memory and Social Behavior after Traumatic Brain Injury (TBI)

Wild type three-month-old male C57Bl/6J mice were randomly assigned to TBI or sham surgeries. Animals were anesthetized and maintained at 2% isoflurane and secured to a stereotaxic frame with nontraumatic ear bars. The hair on their scalp was removed, and eye ointment and betadine were applied to their eyes and scalp, respectively. A midline incision was made to expose the skull. A unilateral TBI was induced in the right parietal lobe using the controlled cortical impact model (Nat Neurosci. 2014 August; 17(8): 1073-82). Mice received a 3.5-mm diameter craniectomy, a removal of part of the skull, using an electric microdrill. The coordinates of the craniectomy were: anteroposterior, −2.00 mm and mediolateral, +2.00 mm with respect to bregma. After the craniectomy, the contusion was induced using a 3-mm convex tip attached to an electromagnetic impactor (Leica). The contusion depth was set to 0.95 mm from dura with a velocity of 4.0 m/s sustained for 300 ms. These injury parameters were chosen to target, but not penetrate, the hippocampus. Sham animals received craniectomy surgeries but without the focal injury. After focal TBI surgery, the scalp was sutured and the animal was allowed to recover in an incubation chamber set to 37° C. Animals were returned to their home cage after showing normal walking and grooming behavior. All animals fully recovered from the surgical procedures as exhibited by normal behavior and weight maintenance monitored throughout the duration of the experiments.

After 28 days post injury (dpi), animals were tested on the RAWM assay (see above). Animals ran 12 trials during learning test and 4 trials during memory test. Last three trials from learning test and all four trials from memory test were averaged to determine learning memory (learning test) and long-term memory (memory test).

Animals were intraperitoneally injected with 5 mg/kg of compound 3 formulated in 50% PEG-400 in distilled water (n=10) or vehicle (50% PEG-400 in distilled water; n=10 for TBI group and n=8 for sham group) starting the day prior to behavior tests (27 dpi), after each of the final trials of the learning-test days (28 and 29 dpi) and before the social behavior test (42 dpi, see below) for a total of four injections. No injections were given when long-term memory was tested on day 35 dpi.

To quantitate social tendencies of the treated mice, the time spent with a novel conspecific mouse was measured in a Crawley's three-chamber box (J Vis Exp. 2011; (48): 2473). Treated animals were left to explore all three empty chambers freely for 10 minutes for habituation. Social pair mouse was placed in the housing cage at one side of the apparatus and treated animals in opposite chamber so that the mouse can freely explore the entire apparatus for 10 minutes. The time spent with the never-before-met animal was recorded. Direct contact between the treated mouse and the housing cage or stretching of the body of the subject mouse in an area 3-5 cm around the housing cage is counted as an active contact.

Figure 7B:
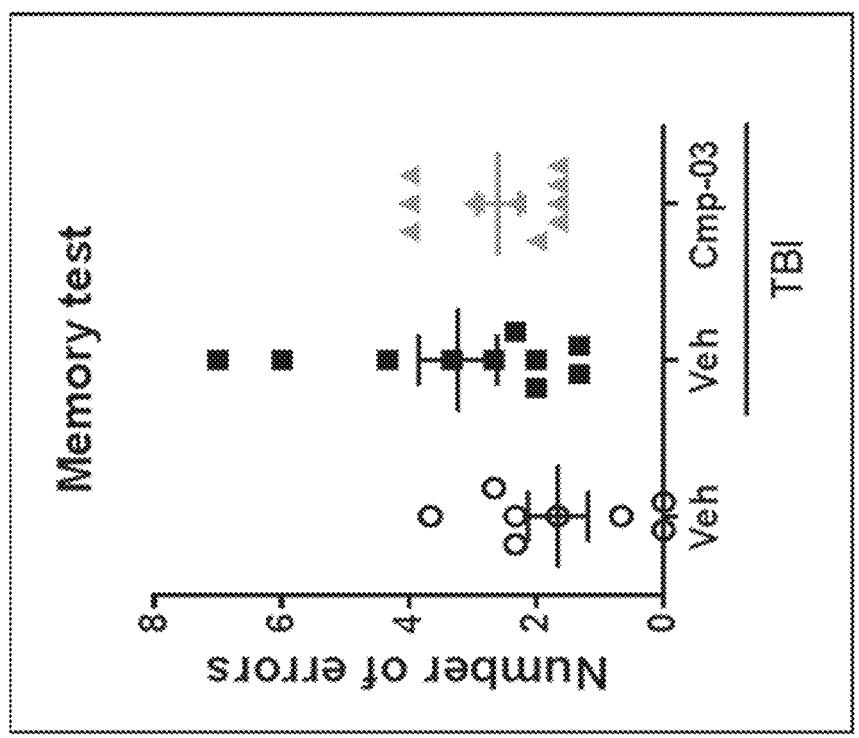
FIG. 7B shows long-term memory test results of mice without a traumatic brain injury (TBI), with TBI and untreated, and with TBI treated with compound 3.
Figure 7A:
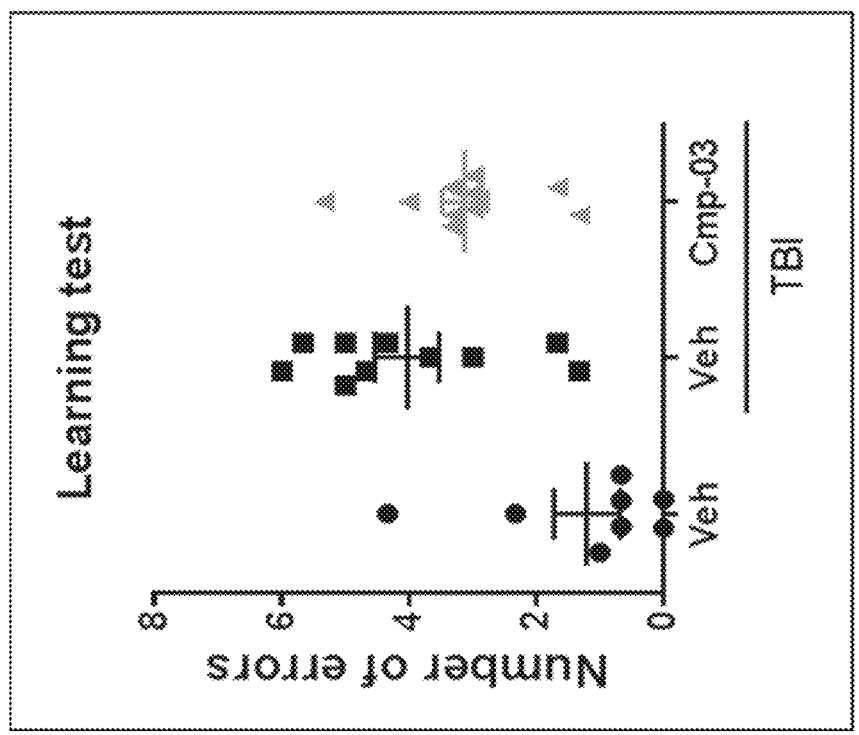
FIG. 7A shows learning memory test results of mice without a traumatic brain injury (TBI), with TBI and untreated, and with TBI treated with compound 3.
Figure 7C:
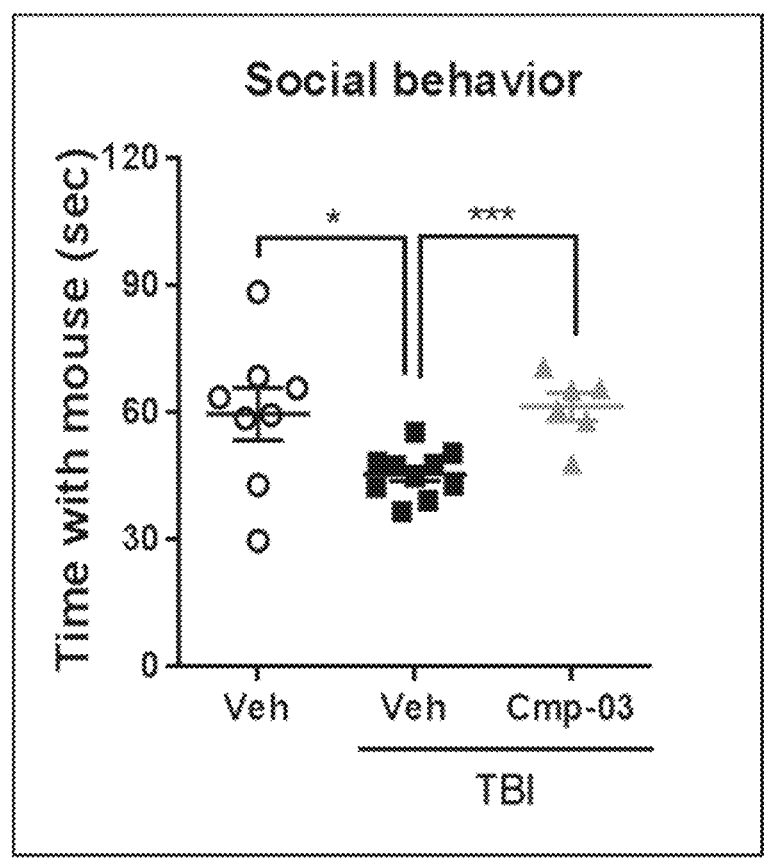
FIG. 7C shows social behavior (indicated by time spent with a companion mouse) of mice without a traumatic brain injury (TBI), with TBI and untreated, and with TBI treated with compound 3.

Learning memory and long-term memory after TBI in mice are shown in FIGS. 7A and 7B respectively. Compared with vehicle-treated animals (squares), compound 3-treated animals (triangles) made significantly less errors over the course of training (FIG. 7A) and a similar trend was seen when memory was tested 7 days (35 dpi) after training (FIG. 7B).

Social behavior results are shown in FIG. 1C. Vehicle-treated TBI-injured animals spent significantly less time in the compartment with the novel animal compared to vehicle-treated animals from sham group indicating impairment in sociability. Interestingly, compound 3-treated TBI-injured animals spent more time with the novel mouse at levels similar to those animals from sham group indicating normal sociability, social motivation and affiliation. Individual values and mean±SEM are shown in FIG. 1C. Statistical analyses were performed using GraphPad Prism software and significant difference was assessed by t test (*<0.05, <0.01, and *<0.001).

Example B7—Fasting-Induced Muscle Atrophy

Wild type eight-weeks-old male Balb/c mice obtained from the vivarium Fundacion Ciencia & Vida Chile (Santiago, Chile) were used. Mice were housed in independent plastic cages in a room maintained at 25° C. with a 12-h: 12-h light:dark cycle.

Twenty-four hours before and during the 2 days of fasted procedures, animals received oral administration via feeding tubes (15 gauge) of vehicle (50% Polyethylene glycol 400 (Sigma-Aldrich P3265) in distilled water or 10 mg/kg of compound 3 formulated in vehicle solution.

After 2 days of fasting the animals were sacrificed and muscles were removed from both hindlimbs. Mice with feed and water ad libitum were used as control.

For in vivo measurements of protein synthesis, puromycin (Sigma-Aldrich, P8833) was prepared at 0.04 µmol/g body weight in a volume of 200 µL of PBS, and subsequently administered into the animals via IP injection, 30 min prior to muscle collection.

Upon collection, muscles were immediately frozen in liquid nitrogen and then stored at −80° C. The frozen muscles were then homogenized with a T 10 basic ULTRA-TURRAX (IKa) in ice-cold buffer lysis (Cell Signaling 9803) and protease and phosphatase inhibitors (Roche). Lysates were sonicated for 3 min and centrifuged at 13,000 rpm for 20 minutes at 4° C. Protein concentration in supernatants was determined using BCA Protein Assay Kit (Pierce). Equal amount of proteins was loaded on SDS-PAGE gels. Proteins were transferred onto 0.2 um PVDF membranes (BioRad) and probed with primary antibodies diluted in Tris-buffered saline supplemented with 0.1% Tween 20 and 3% bovine serum albumin.

Puromycin (12D10) (Merck Millipore) and β-actin (Sigma-Aldrich) antibodies were used as primary antibodies. A HRP-conjugated secondary antibody (Rockland) was employed to detect immune-reactive bands using enhanced chemiluminescence (ECL Western Blotting Substrate, Pierce). Quantification of protein bands was done by densitometry using ImageJ software.

For immunohistochemical analysis of cross-sectional area (CSA), muscles from control (Fed) and fasted animals were submerged individually in optimal cutting temperature (OCT) compound (Tissue-Tek; Sakura) at resting length, and frozen in isopentane cooled with liquid nitrogen. Cross-sections (10-µm thick) from the mid-belly of the muscles were obtained with a cryostat (Leica) and immunostained with puromycin antibody (12D10) (Merck Millipore). A HRP-polymer conjugated secondary antibody (Biocare Medical, MM620L) followed by diaminobenzidine substrate incubation (ImmPACT DAB-Vector, SK-4105) were employed to detect puromycinylated structures in CSA.

Figure 8A:
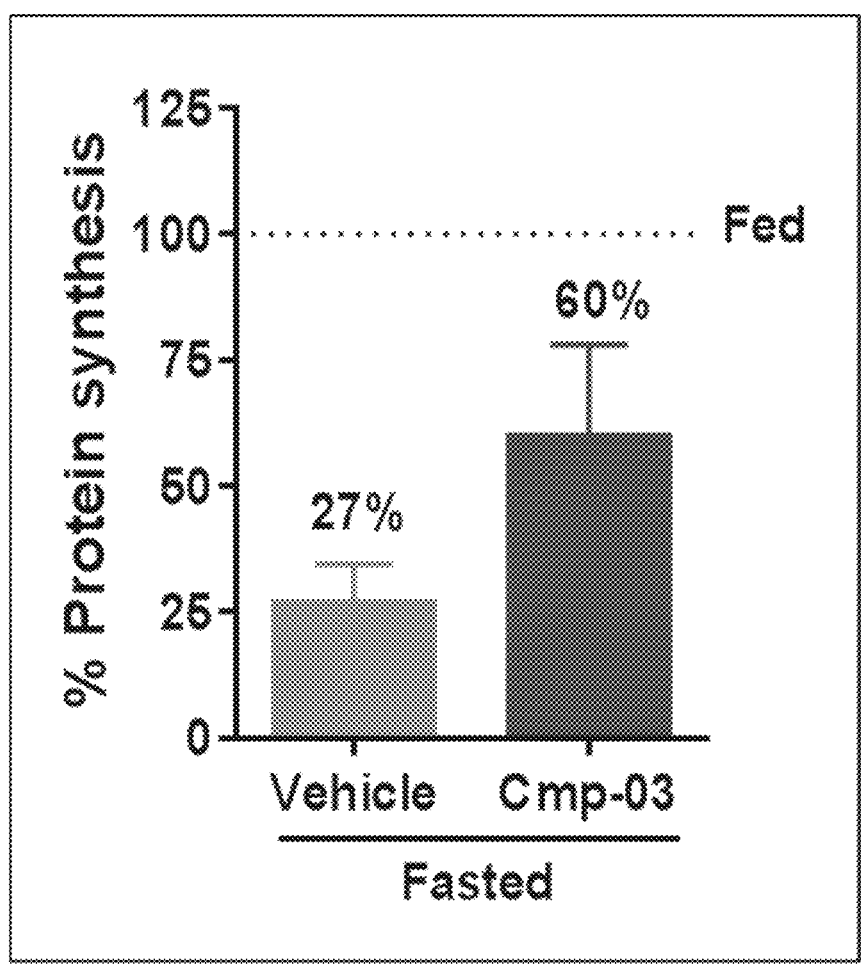
FIG. 8A shows protein synthesis in muscles from fasting mice or fasting mice treated with compound 3. Protein synthesis was normalized to β-actin expression and percentage was calculated as the percent relative to protein synthesis levels from control mice (Fed) which correspond to 100%.

Percent of protein synthesis in fasted muscles is shown in FIG. 8A for compound 3 and the vehicle control. The levels were normalized to β-actin expression and percentage was calculated as the percent relative to protein synthesis levels from control mice (Fed) which correspond to 100%.

Figure 8B:
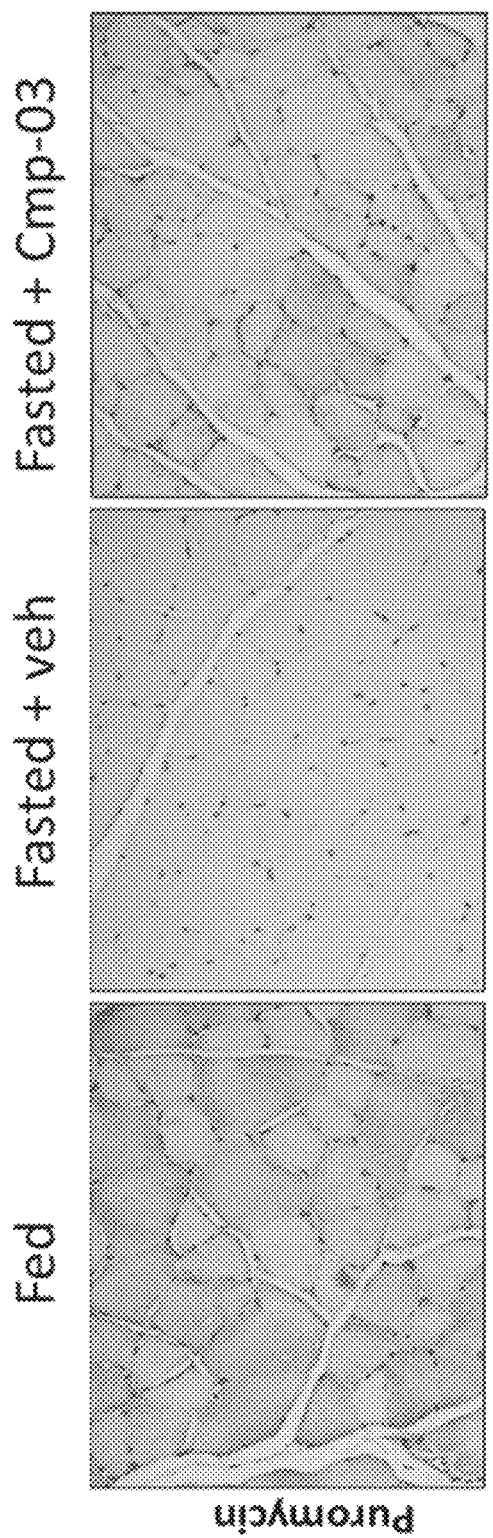
FIG. 8B shows visualization of a muscle fiber cross-sectional area (CSA) stained with puromycin from a fed mouse, a fasting mouse, and a fasting mouse treated with compound 3.

Muscle fiber CSA were visualized with a Zeiss Axio Lab.A1 microscope and an Axiocam (Zeiss) digital camera. Puromycin staining in CSA is shown in FIG. 8B for compound 3. Muscle sections from control mice (fed) shows fibers stained with puromycin indicating de novo protein synthesis. No staining was detected in vehicle-treated fasted mice indicating a significant reduction of protein synthesis. Fasted mice treated with compound 3, however, showed a partial staining in muscle fibers indicating a partial recovery of protein synthesis as seen in FIG. 8A.

Figure 9A:
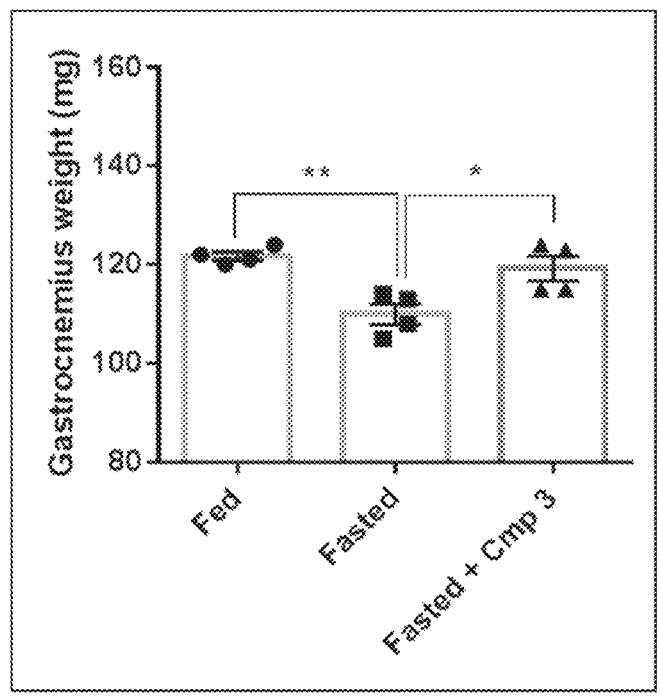
FIG. 9A and FIG. 9B show gastrocnemius weight from mice that were fed, fasted, or fasted with compound 3 (FIG.
Figure 9B:
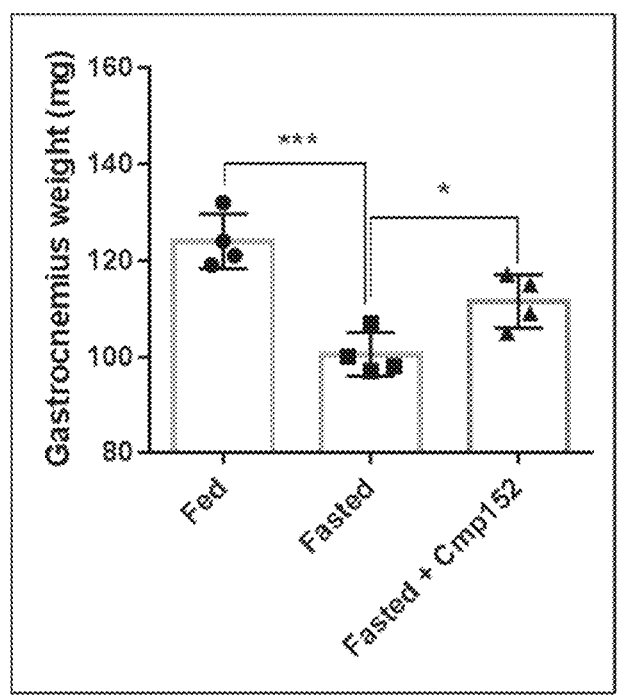
Figure 9C:
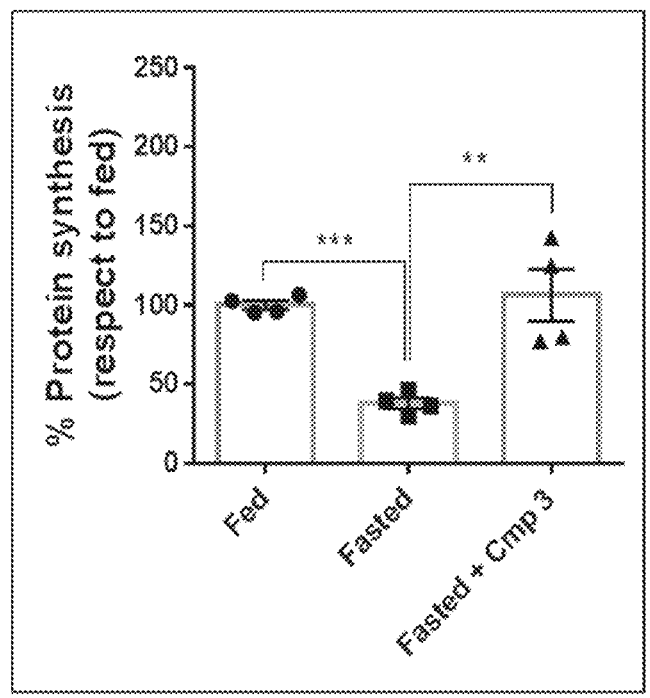
FIG. 9C and FIG. 9D show percent of protein synthesis from mice that were fed, fasted, or fasted with compound 3 (FIG. 9C) or compound 152 (FIG. 9D) administration, normalized to β-actin expression and percentage calculated as the percent relative to protein synthesis levels from fed mice.
Figure 9D:
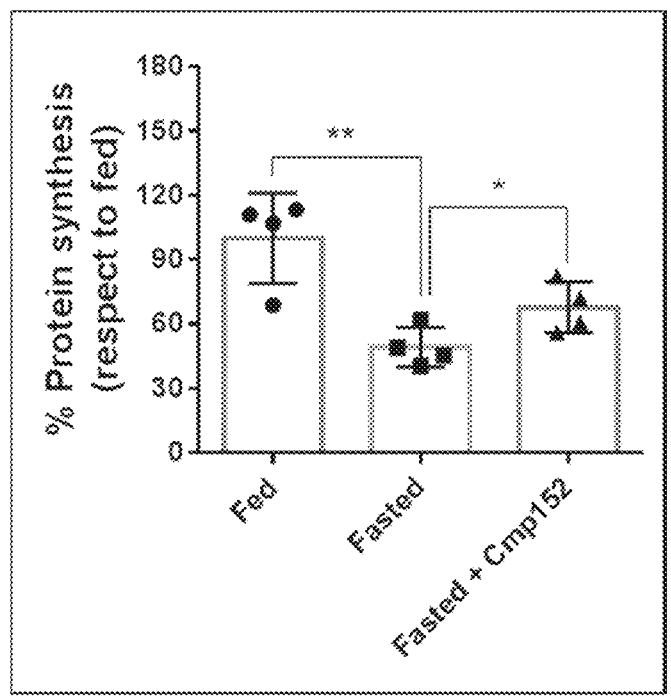
Figure 9E:
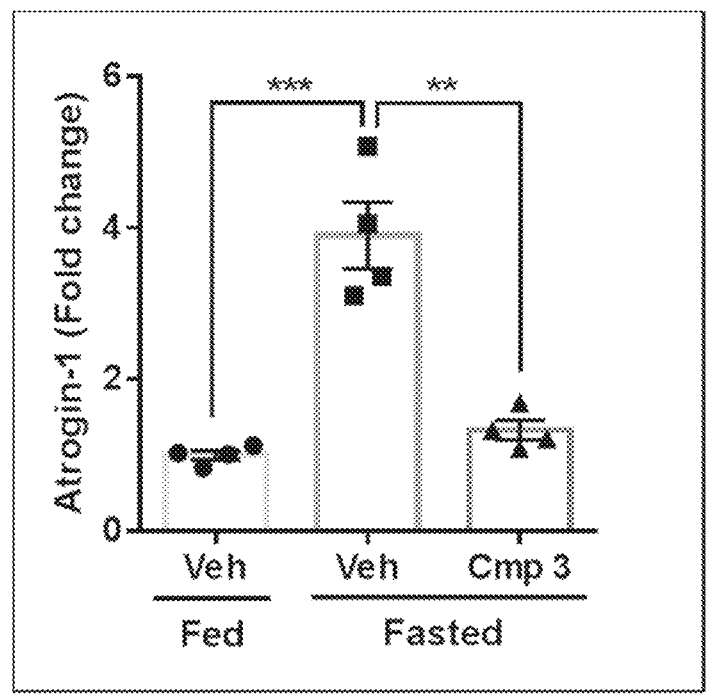
FIG. 9E and FIG. 9F shows Atrogin-1 expression in gastrocnemius from mice that were fed, fasted, or fasted and treated with compound 3 (FIG. 9E) or compound 152 (FIG. 9F), normalized to β-actin expression and fold change calculated as the levels relative to the expression levels from fed mice.
Figure 9F:
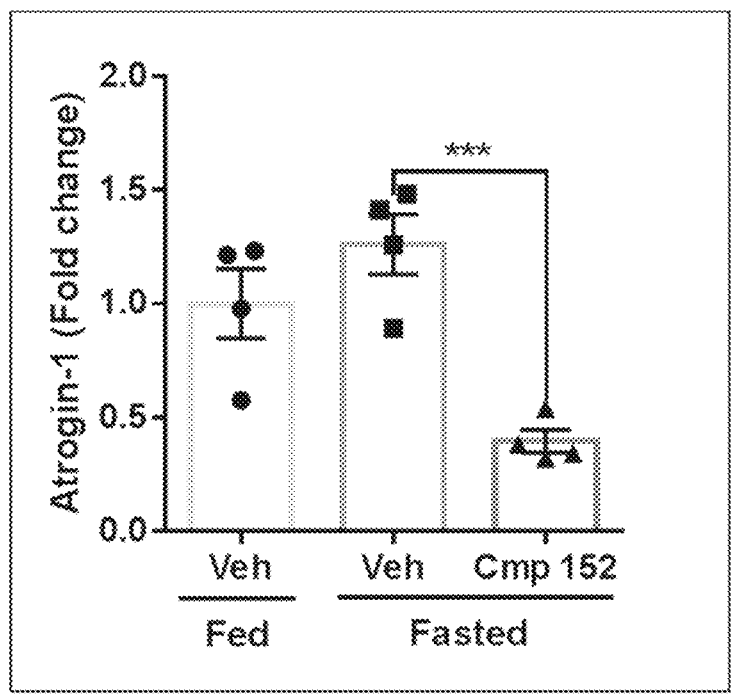

Gastrocnemius weight from control (fed) and fasted animals treated with compound 3 or compound 152 are shown in FIG. 9A and FIG. 9B respectively. Percent of protein synthesis from control (fed) or fasted animals treated with compound 3 or compound 152 are shown in FIG. 9C and FIG. 9D respectively. The levels were normalized to β-actin expression and percentage was calculated as the percent relative to protein synthesis levels from control mice (fed) which correspond to 100%. Atrogin-1 expression in gastrocnemius from control (fed) and fasted animals treated with compound 3 or compound 152 are shown in FIG. 9E and FIG. 9F respectively. The levels were normalized to β-actin expression and fold change was calculated as the levels relative to the expression levels from control mice (fed) which corresponds to 1. Data was shown as individual values and mean±standard error of mean (SEM). Statistical analyses were performed using GraphPad Prism software and significant difference was assessed by t test (*<0.05, <0.01, *<0.001).

Muscle fiber CSAs were visualized with a Zeiss Axio Lab.A1 microscope and an Axiocam (Zeiss) digital camera. ATF4 staining in CSA is shown in FIG. 9G. Histological muscle sections from fasted mice treated with vehicle show fibers containing positive ATF4 staining, indicating the activation of the ISR. No staining was detected in control (fed) or in fasted mice treated with compound 152, indicating a complete inhibition of the ISR pathways in the muscle of these animals.

Example B8—Immobilization-Induced Muscle Atrophy

Wild type eight-weeks-old male Balb/c mice obtained from the vivarium Fundacion Ciencia & Vida Chile (Santiago, Chile) were used. Mice were housed in independent plastic cages, fed ad libitum in a room maintained at 25° C. with a 12-h:12-h light:dark cycle.

Twenty-four hours before and during the 3 days of immobilization procedures, animals received oral administration via feeding tubes (15 gauge) of vehicle (50% Polyethylene glycol 400 (Sigma-Aldrich P3265) in distilled water or 10 mg/kg of compound 3 formulated in vehicle.

One hindlimb was immobilized with a plastic stick placed over and under the limb and fixed with a medical adhesive bandage. Animals were daily monitored. The immobilization procedure prevented movement of the immobilized leg alone. After 3 days, the animals were sacrificed and gastrocnemius, quadriceps and tibialis anterior muscles were removed from both hindlimbs, the contralateral, non-immobilized leg being used as an internal control.

For in vivo measurements of protein synthesis, puromycin (Sigma-Aldrich, P8833) was prepared at 0.04 µmol/g body weight in a volume of 200 µL of PBS, and subsequently administered into the animals via intraperitoneal injection, 30 min prior to muscle collection.

Upon collection, muscles were immediately frozen in liquid nitrogen and then stored at −80° C. The frozen muscles were then homogenized with a T 10 basic ULTRA-TURRAX (IKa) in ice-cold buffer lysis (Cell Signaling 9803) and protease and phosphatase inhibitors (Roche). Lysates were sonicated for 3 min and centrifuged at 13,000 rpm for 20 minutes at 4° C. Protein concentration in supernatants was determined using BCA Protein Assay Kit (Pierce). Equal amount of proteins was loaded on SDS-PAGE gels. Proteins were transferred onto 0.2 um PVDF membranes (BioRad) and probed with primary antibodies diluted in Tris-buffered saline supplemented with 0.1% Tween 20 and 3% bovine serum albumin.

Puromycin (12D10) (Merck Millipore) and β-actin (Sigma-Aldrich) antibodies were used as primary antibodies. A HRP-conjugated secondary antibody (Rockland) was employed to detect immune-reactive bands using enhanced chemiluminescence (ECL Western Blotting Substrate, Pierce). Quantification of protein bands was done by densitometry using ImageJ software.

Figure 10A:
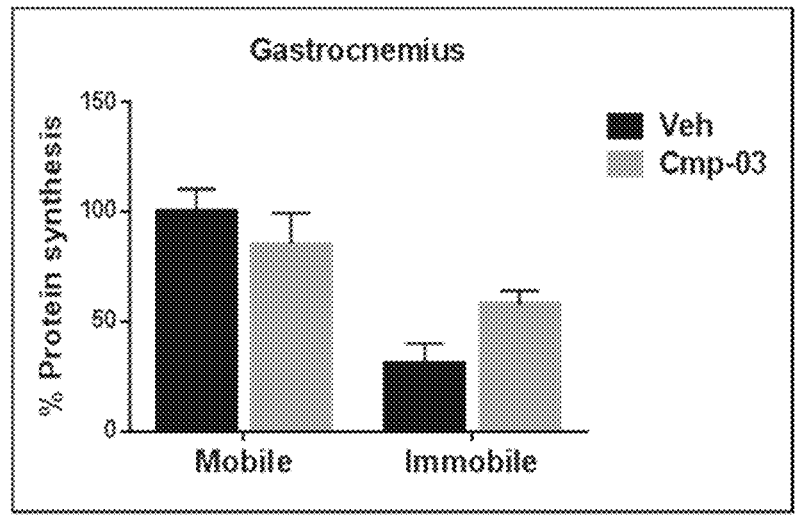
FIG. 10A-C shows protein synthesis in the gastrocnemius (FIG. 10A), tibialis anterior (FIG. 10B) and quadriceps (FIG. 10C) muscles for the mobile hindlimb and the immobilized hindlimb (triggering immobilization-induced muscle atrophy) in mice with unilateral hindlimb immobilization, treated either with a vehicle control or compound 3. The levels were normalized to β-actin expression and percentage was calculated as the percent relative to protein synthesis levels from mobile limb of control mice (vehicle-treated) which correspond to 100%.
Figure 10B:
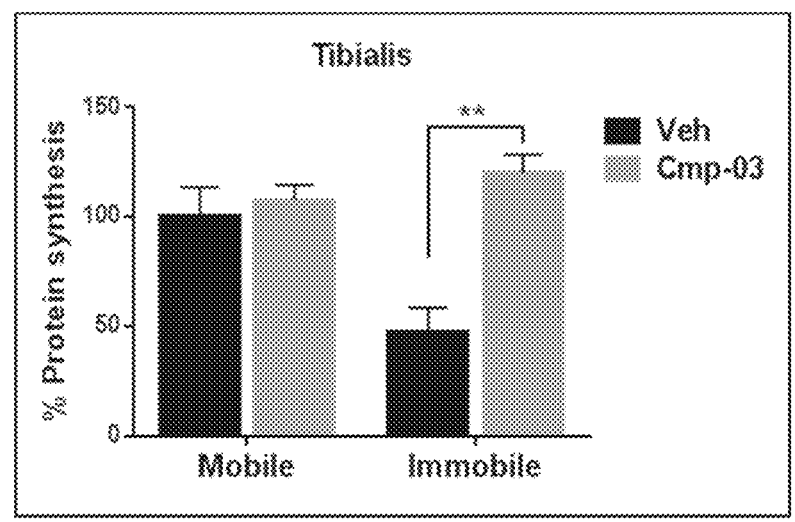
Figure 10C:
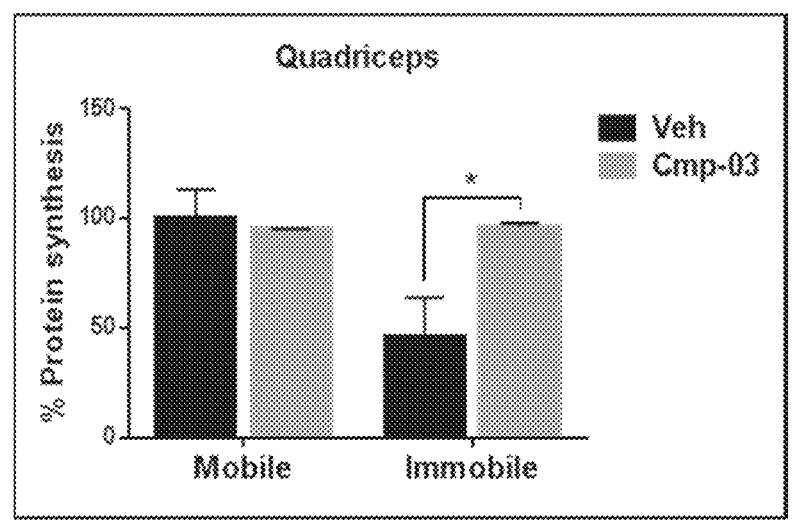

Percent of protein synthesis in mobile and immobile hind limbs sections from gastrocnemius, tibialis anterior, and quadriceps are shown in FIGS. 10A, 10B and 10C respectively as mean±SEM. Statistical analyses were performed using GraphPad Prism software and significant difference was assessed by t test (*<0.05 and **<0.01). The levels were normalized to β-actin expression and percentage was calculated as the percent relative to protein synthesis levels from mobile limb of control mice (vehicle-treated) which correspond to 100%. In all three immobilized muscles from vehicle-treated mice there is a significant reduction of protein synthesis. Interestingly, there is a complete recovery of protein synthesis in tibialis anterior and quadriceps and a partial recovery of protein synthesis in gastrocnemius from compound-3-treated immobilized hindlimbs, suggesting that compound 3 could inhibits the ISR-induced repression of protein synthesis.

For immunohistochemical analysis of cross-sectional area (CSA), gastrocnemius from mobile and immobile hind limbs were submerged individually in optimal cutting temperature (OCT) compound (Tissue-Tek; Sakura) at resting length, and frozen in isopentane cooled with liquid nitrogen. Cross-sections (10-μm thick) from the mid-belly of the muscle was obtained with a cryostat (Leica) and immunostained with ATF4 antibody (Abeam). A HRP-polymer conjugated secondary antibody (Biocare Medical, MM620L) followed by diaminobenzidine substrate incubation (ImmPACT DAB-Vector, SK-4105) were employed to detect puromycinylated structures in CSA.

Figure 10D:
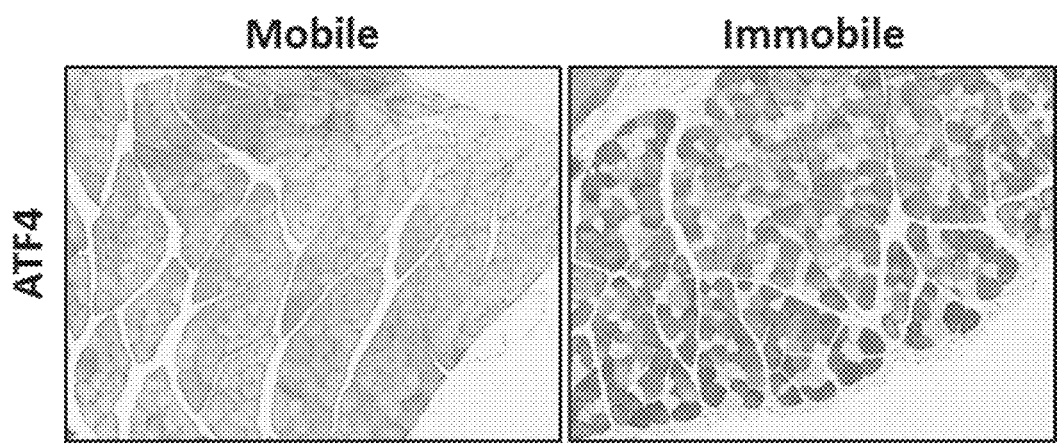
FIG. 10D shows visualization of a muscle fiber cross-sectional area (CSA) of gastrocnemius from mobile or immobile hind limbs stained for ATF4.

Muscle fiber CSAs were visualized with a Zeiss Axio Lab.A1 microscope and an Axiocam (Zeiss) digital camera. ATF4 staining in CSA is shown in FIG. 10D. Histological muscle sections from immobilized hind limb show fibers stained with ATF4, indicating the activation of the ISR. As expected, there is a strong correlation between the activation of the ISR pathway and the reduction of protein synthesis in immobilized muscles.

Example B9—Cachexia-Induced Muscle Atrophy

Wild type six-weeks-old male Balb/c mice obtained from the vivarium Fundacion Ciencia & Vida Chile (Santiago, Chile) were used. Mice were housed in independent plastic cages in a room maintained at 25° C. with a 12-h:12-h light:dark cycle.

$1 \times 10^6$ CT26 colon carcinoma cell line (ATCC #CRL-2638, ATCC Manassas, Va.) were injected subcutaneously in the right lower flank of each animal for induction of cachexia-induced muscle atrophy as described (Nat Commun. 2012 Jun. 12; 3:896). Non-injected animals were used as controls. At day 6 post tumor-cell injection, animals were randomized into two groups and treated with 10 mg/kg of compound 3 formulated in 50% Polyethylene glycol (PEG-400) in distilled water, or with vehicle (50% PEG-400 in distilled water) by daily oral gavage for 13 days.

For in vivo measurements of protein synthesis, 30 min before the study ends, animals were injected intraperitoneally with puromycin (Sigma-Aldrich, P8833) at 0.04 μmol/g body weight in a volume of 200 μL of PBS. After 13 days of daily dosage, the animals were sacrificed and gastrocnemius, quadriceps and tibialis anterior muscles were dissected and weighed from both hindlimbs to assess muscle atrophy.

Upon collection, muscles were immediately frozen in liquid nitrogen and then stored at −80° C. The frozen muscles were then homogenized with a T 10 basic ULTRA-TURRAX (IKa) in ice-cold buffer lysis (Cell Signaling 9803) and protease and phosphatase inhibitors (Roche). Lysates were sonicated for 3 min and centrifuged at 13,000 rpm for 20 minutes at 4° C. Protein concentration in supernatants was determined using BCA Protein Assay Kit (Pierce). Equal amount of proteins was loaded on SDS-PAGE gels. Proteins were transferred onto 0.2 um PVDF membranes (BioRad) and probed with primary antibodies diluted in Tris-buffered saline supplemented with 0.1% Tween 20 and 3% bovine serum albumin.

Puromycin (12D10) (Merck Millipore) and β-actin (Sigma-Aldrich) antibodies were used as primary antibodies. A HRP-conjugated secondary antibody (Rockland) was employed to detect immune-reactive bands using enhanced chemiluminescence (ECL Western Blotting Substrate, Pierce). Quantification of protein bands was done by densitometry using ImageJ software.

Figure 11C:
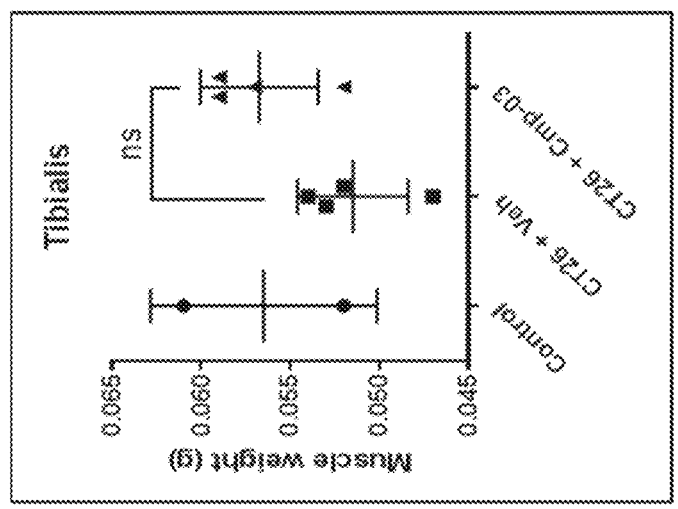
FIG. 11A-C shows muscle weight of gastrocnemius (FIG. 11A), quadriceps (FIG. 11B), and tibialis anterior (FIG. 11C) muscles of control, mice with cachexia induced muscle atrophy, and mice with cachexia induced muscle atrophy treated with compound 3.
Figure 11B:
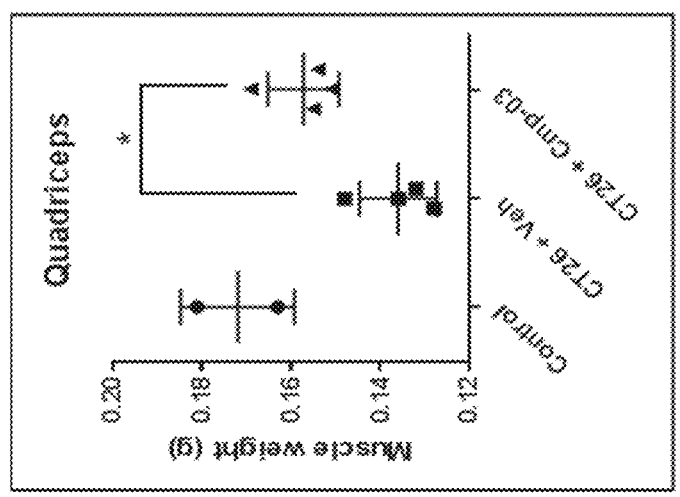
Figure 11A:
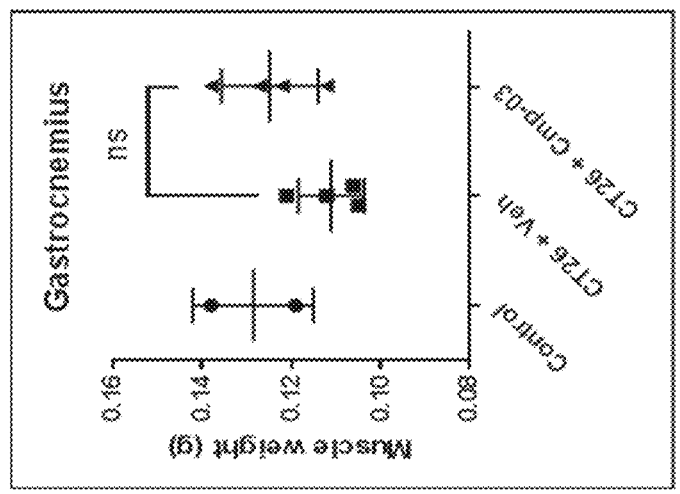

Gastrocnemius, quadriceps, and tibialis anterior muscle weight from animals injected with CT26 tumor cells and treated with either vehicle or compound 3 are shown in FIGS. 11A, 11B, and 11C respectively. Treatment with compound 3 prevented the CT26-induced muscle weight loss.

Figure 11F:
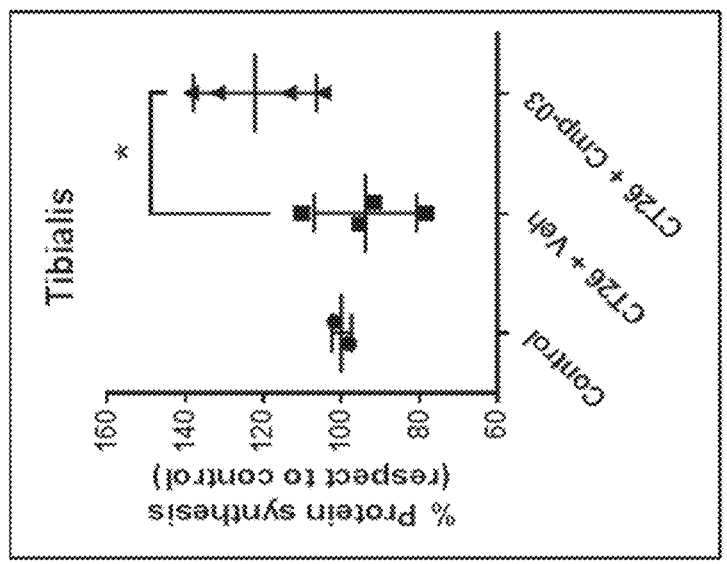
FIG. 11D-F shows percent protein synthesis (normalized to β-actin expression) in gastrocnemius (FIG. 11D), quadriceps (FIG. 11E), and tibialis anterior (FIG. 11F) muscles of control, mice with cachexia induced muscle atrophy, and mice with cachexia induced muscle atrophy treated with compound 3. Cachexia was induced by injecting mice with CT26 colon carcinoma cells in the flank of each animal.
Figure 11E:
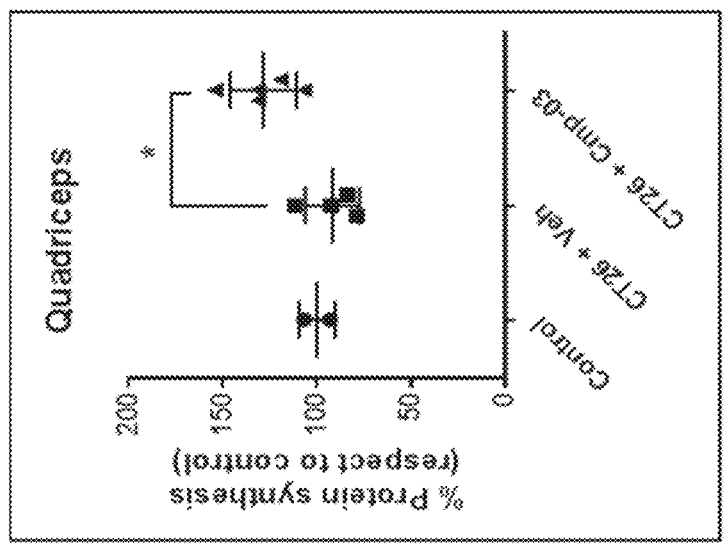
Figure 11D:
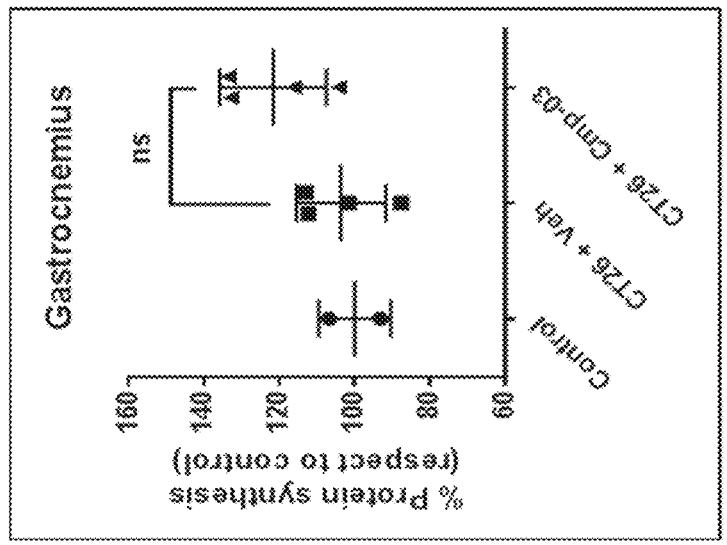

Percent of protein synthesis in gastrocnemius, quadriceps and tibialis anterior from animals injected with CT26 tumor cells and treated with either vehicle or compound 3 are shown in FIGS. 11D, 11E and 11F respectively. The levels were normalized to β-actin expression and percentage was calculated as the percent relative to protein synthesis levels from muscle section of control mice which correspond to 100%. Data is shown as individual values and mean±standard error of mean (SEM). Statistical analyses were performed using GraphPad Prism software and significant difference was assessed by t test (*<0.05). Treatments with compound 3 in tumor-induced muscle-wasting animals significantly increase protein synthesis in quadriceps and tibialis anterior compared to vehicle-treated tumor-injected animals. Example B10-Tumor growth and density model Wild type six-weeks-old male Balb/c mice obtained from the vivarium Fundacion Ciencia & Vida Chile (Santiago, Chile) were used. Mice were housed in independent plastic cages in a room maintained at 25° C. with a 12-h:12-h light:dark cycle.

$1 \times 10^6$ CT26 colon carcinoma cell line (ATCC #CRL-2638, ATCC Manassas, Va.) were injected subcutaneously in the right lower flank of each animal as described (Nat Commun. 2012 Jun. 12; 3:896). Non-injected animals were used as controls. At day 6 post tumor-cell injection, mean tumor volume was about 100 mm³, animals were weighed and randomized into two groups and treated with 10 mg/kg of compound 3 formulated in 50% Polyethylene glycol (PEG-400) in distilled water, or with vehicle (50% PEG-400 in distilled water) by daily oral gavage for 13 days.

Figure 12B:
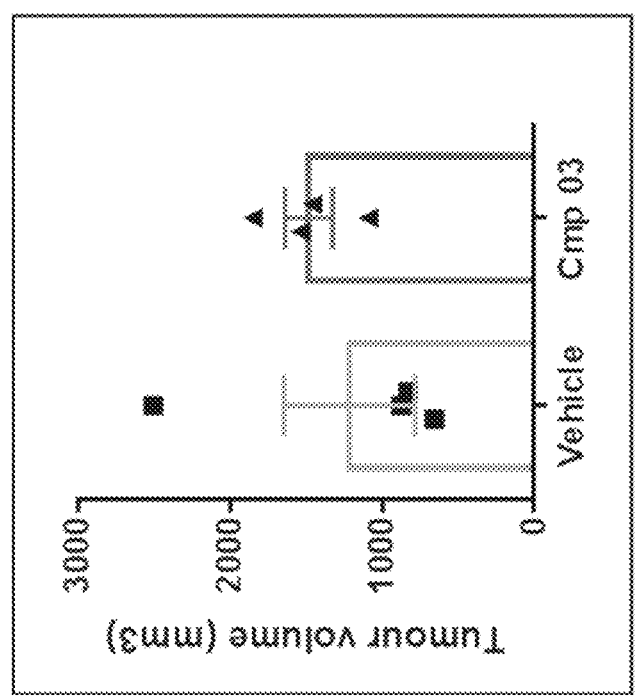
FIG. 12A-12C shows tumor volume (FIG. 12A), tumor weight (FIG. 12B), and tumor density (FIG. 12C) of a subcutaneously injected CT26 colon carcinoma cell line tumor from untreated (vehicle) mice or mice treated with compound 3 for 13 days, starting 6 days post tumor injection.
Figure 12A:
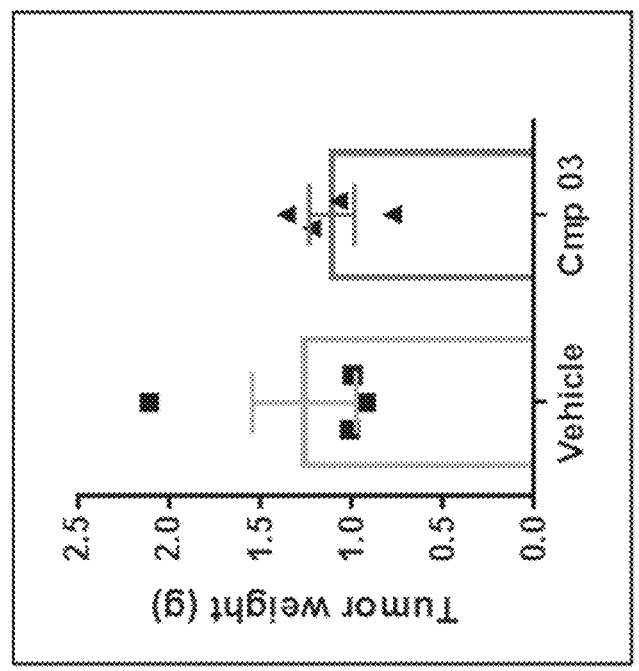
Figure 12C:
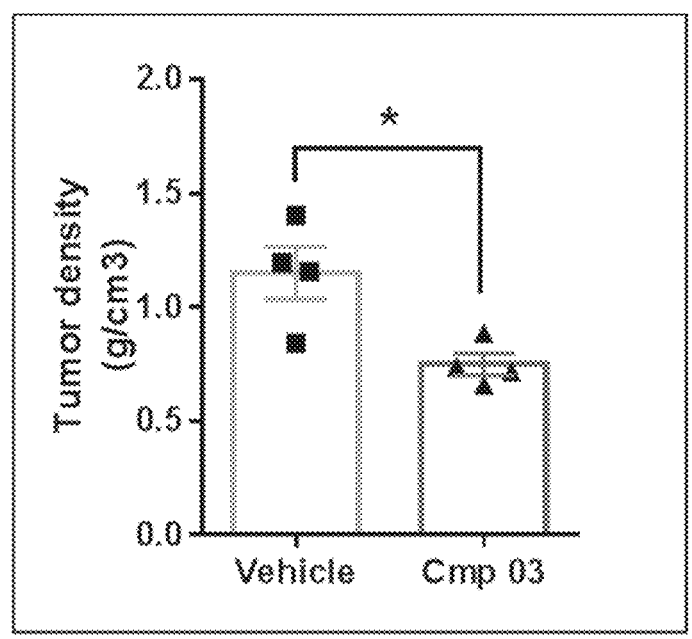

At the end of the study, tumors were measured with digital caliper and tumors volumes, expressed in mm³, were calculated with the following formula:

$$\text{Tumor volume (mm}^3\text{)} = (a \times b^2)/2$$

where "a" is the largest perpendicular diameter and "b" is the smallest diameter. Animals were then sacrificed and tumors were extracted and weighed. The volumes and weight of the tumors of each animal are shown in FIGS. 12A and 12B respectively. Tumor density was calculated as weight/volume ratio for each animal and is shown in FIG. 12C. Bars represent mean±SEM. Statistical analyses were performed using GraphPad Prism software and significant difference was assessed by t test (*<0.05).

As shown in FIGS. 12A-12C, compound 3 does not reduce tumor volume but significantly reduce the tumor density, suggesting that treatment with ISR-inhibitor compounds could make tumors less compact and hence more accessible to some tumor-directed therapies such as checkpoints inhibitors, adoptive cell transfer, monoclonal antibodies or cytokines that boost immune system.

Example B11—Protein Synthesis with a Cell-Free System

The expression of the green fluorescence protein (GFP) was evaluated using the 1-Step Human In vitro Protein Expression Kit based on HeLa cell lysates (ThermoFisher Scientific). HeLa lysate, accessory proteins, reaction mix and pCFE-GFP plasmid from the kit were thawed in ice. Reactions were prepared at room temperature in a 96-well optical plate by adding 12.5 µL of HeLa lysate, 2.5 µL accessory proteins, 5 µL reaction mix, 1 µg of pCFE-GFP plasmid and 1 µM of test compounds in 5 µL or 5 µL of distilled $H_2O$ as a basal expression of GFP (vehicle). A well with $dH_2O$ instead of pCFE-GFP plasmid was used as basal autofluorescence of the reaction. All reactions were made in duplicated. Fluorescence intensity was measured by a multi-mode microplate reader (Synergy-4; Biotek) during 6-hour treatments and capturing fluorescence at 15-minute intervals with 485/20 and 528/20 excitation and emission filters.

Figure 13A:
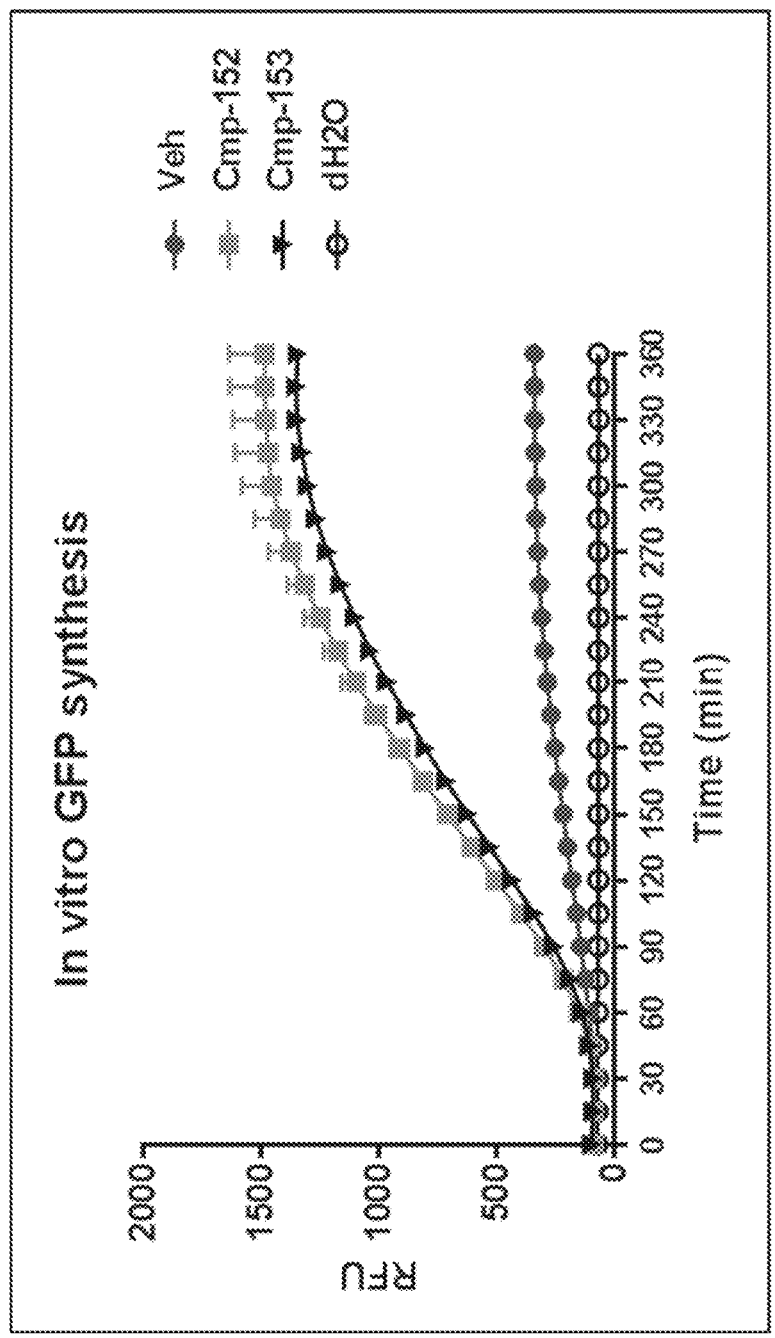
FIG. 13A shows relative fluorescence intensity (RFU) of GFP resulting from cell-free expression in a system treated with compound 152, compound 153, or a vehicle control.
Figure 13B:
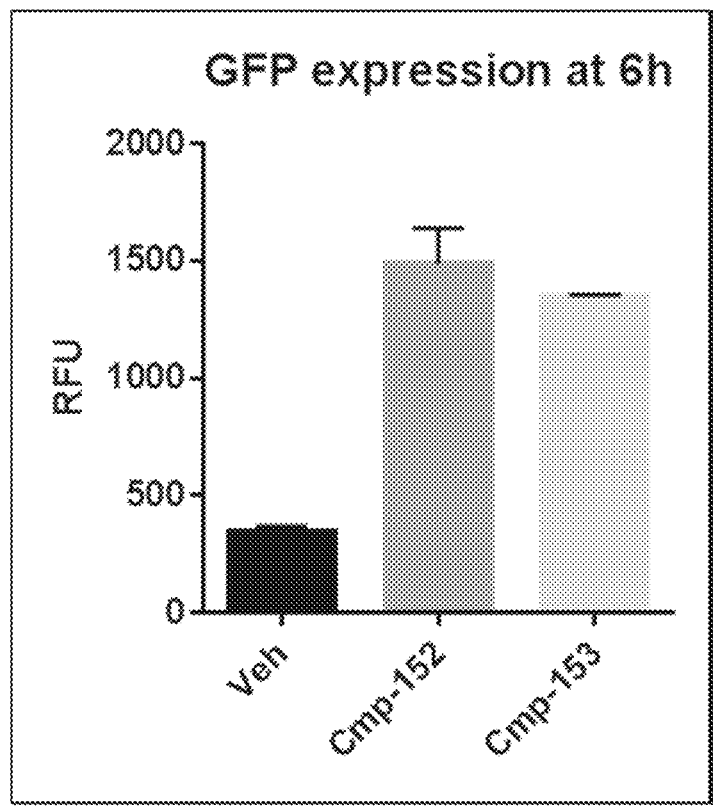
FIG. 13B compares the RFU from GFP cell-free expression systems treated with compound 152, compound 153, or vehicle control after 6 hours.

Relative fluorescence intensity (RFU) of GFP resulting from cell-free expression treated with compounds 152 or 153 or vehicle are shown in FIG. 13A. Comparison of RFU of GFP at 6 hours is shown in FIG. 13B. The addition of compounds 152 or 153 to the kit's reaction mix increase the expression of GFP and hence its fluorescence up to 4-fold compared to the expression obtained using the kit's reagents alone.

Example B12—Protein Synthesis with a Yeast Cell-Based Assay

Two GS115H *Pichia pastoris* yeast strains that stably express phospholipase C protein (PEG) under the control of a methanol-inducible promoter (pAOX-PLC) or a constitutive promoter (pGAP-PLC) were used to assess the secretion levels of PEG and its enzymatic activity. pAOX-PLC and pGAP-PLC yeast single colonies were inoculated in 2 ml of YPD (1% yeast extract, 2% peptone, 2% glucose) and grown at 30° C. in a deep 24-well microplate in a shaking incubator for 16-18 h at 250 rpm. These cultures were diluted to an OD600 of 1 in 2 ml of YPM (1% yeast extract, 2% peptone, 100 mM phosphate buffer pH 6 and 0.5% methanol) or 2 ml of YPM containing 10 µM of compound 152 to induce gene expression and incubated at 30° C. in a shaking incubator at 250 rpm. Methanol was added every 24 h in order to maintain 0.5% methanol concentration. Condition without compound 152 was used as a control for basal secretion and subsequent activity assessment of PLC. After 72 h of induction, cells were harvested by centrifugation and the supernatant analyzed for protein expression by SDS-PAGE and PLC activity.

Figure 14B:
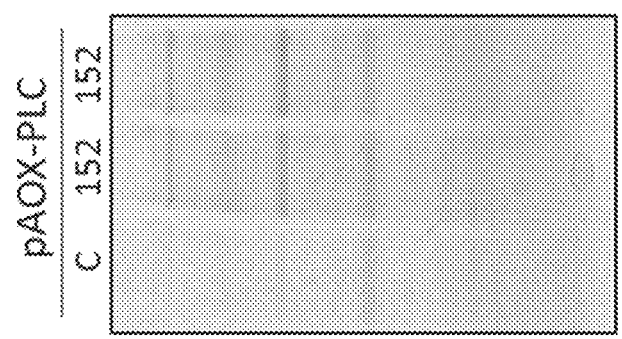
FIG. 14A and FIG. 14B show an SDS-PAGE gel of yeast cells engineered to express phospholipase C (PLC) under a methanol-inducible promoter (pAOX-PLC.
Figure 14A:
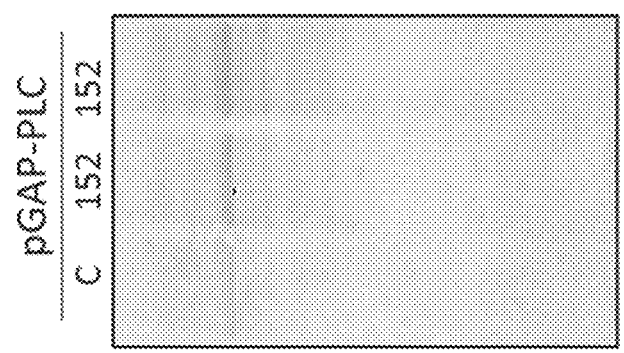

Gels were stained with 0.1% Coomassie Blue R250 in 10% acetic acid, 50% methanol, and 40% $H_2O$ for 20 minutes. Stained gel was then washed twice for 2 hours with 10% acetic acid, 50% methanol and 40% $dH_2O$ until the Coomassie Blue background was nearly clear. Photographs of the gels were taken in a gel imaging system. The secretion of PLC for pAOX-PLC or pGAP-PLC strains in the presence or absence of compound 152 are shown by the arrows in FIGS. 14A and 14B. Secretion of PLC under the compound 152-treatment is shown in duplicates.

Figure 14C:
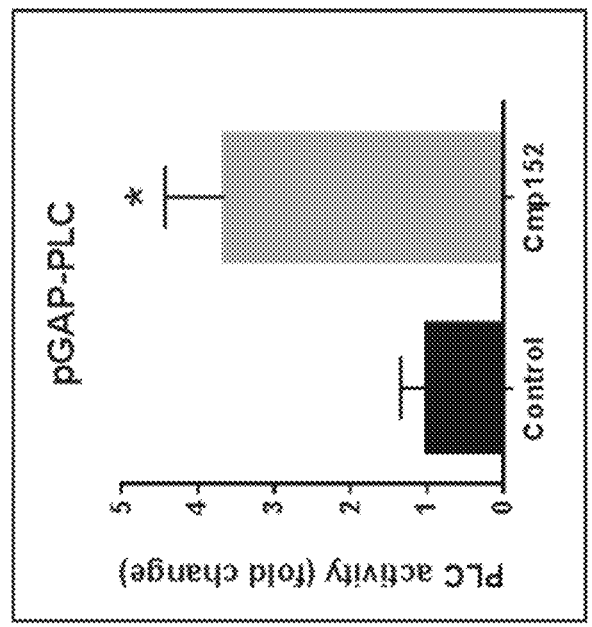
FIG. 14C and FIG. 14D shows activity of PLC secreted from yeast cells engineered to express phospholipase C (PLC) under a methanol-inducible promoter (pAOX-PLC.
Figure 14D:
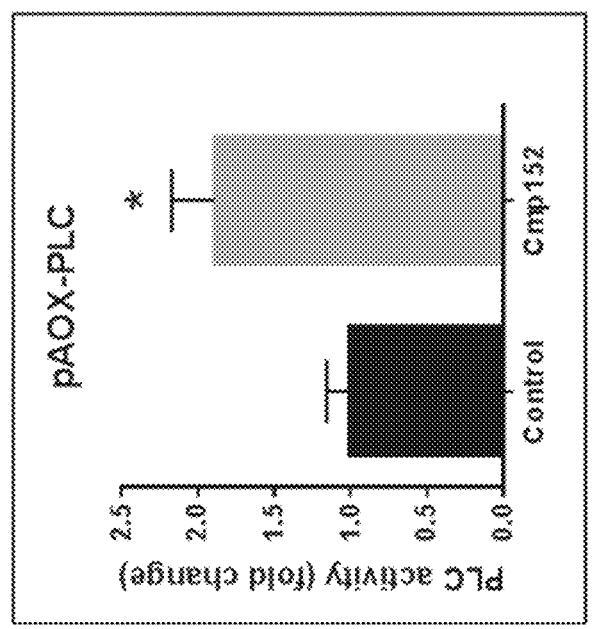

PLC activity was measured in 96 well microplates using 1 mM O-(4-Nitrophenylphosphoryl)choline as a substrate. The assay was carried out at 50° C. in a 96 microwell plate by incubating 10 µL of culture supernatant, 10 µL 100 mM NPPC and 80 µL of 250 mM HEPES pH 7, 60% sorbitol, 0.1 mM $ZnCl_2$. Absorbance at 405 nm was monitored every 30 s for 1 h at 50° C. in a Synergy HT microplate reader (Biotek). 1 PLC unit is defined as the amount of enzyme releasing 1 nmol of p-nitrophenol per minute. Activity of PLC secreted from pAOX-PLC or pGAP-PLC strains in the presence or absence of compound 152 is shown in FIGS. 14C and 14D respectively as mean±SEM. Fold change was calculated as the activity relative to the activity levels from untreated yeasts. Statistical analyses were performed using GraphPad Prism software and significant difference was assessed by t test (*<0.05).

Results show that treatment with an ISR-inhibitor compound increases the synthesis of a heterologous protein and also its secretion in a cell-based system. In addition, the activity of the over expressed protein also increases during these conditions as shown in FIGS. 14C and 14D.

Example B13—Protein Synthesis with a CHO Cell-Based Assay

CHO cells were maintained at 37° C. and 5% $CO_2$ in DMEM supplemented with 10% fetal bovine serum (FBS), 2 mM L-glutamine, 100 U/ml penicillin, and 100 µg/ml streptomycin. After reaching 80% of confluence, cells were detached and seeded on 6-well plates in complete media, allowed to recover for 48 h. Cells were then washed three times with PBS and treated with compound 152 and 153 at 1 µM, 5 µM or 10 µM in 1 mL of media without FBS for 24 h. Treatment with 0.1% DMSO was used as control (vehicle). After 24 h treatment, supernatant (SN) which contains secreted proteins was extracted and protease and phosphatase inhibitors (Roche) were added to each sample. SN were centrifuged at 2,000 g for 10 min to discard any cellular debris and 900 µL SN were transferred to empty microtubes with 400 µL methanol by mixing well. 200 µL of chloroform was added to the mix and then samples were centrifuged at 14,000 g for 2 minutes. Top aqueous layer was discarded by pipetting off and 400 µL methanol was added to each sample by mixing well. Samples were then centrifuged at 17,000 g for 8 minutes and methanol was discarded by pipetting off without disturbing the protein pellet. Samples were left dry at room temperature and pellets were resuspended with SDS-PAGE sample buffer. Secreted proteins were analyzed by SDS-PAGE and Coomassie staining. Gels were stained with 0.1% Coomassie Blue R250 in 10% acetic acid, 50% methanol, and 40% $H_2O$ for 20 minutes. Stained gel was then washed twice for 2 hours with 10% acetic acid, 50% methanol and 40% $dH_2O$ until the Coomassie Blue background was nearly clear. Photographs of the gels were taken in a gel imaging system.

Figure 15A:
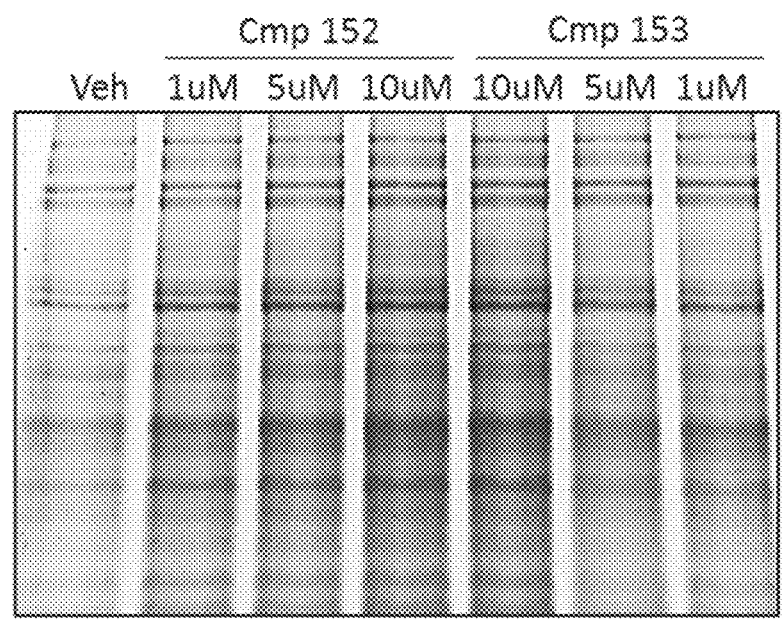
FIG. 15A shows an SDS-PAGE gel of secreted proteins from CHO cells cultured in the presence of 1 μm, 5 μm, or 10 μm of compound 152 or compound 153 for 24 hours. The secreted proteins were quantitated relative to a control, as shown in FIG. 15B.
Figure 15B:
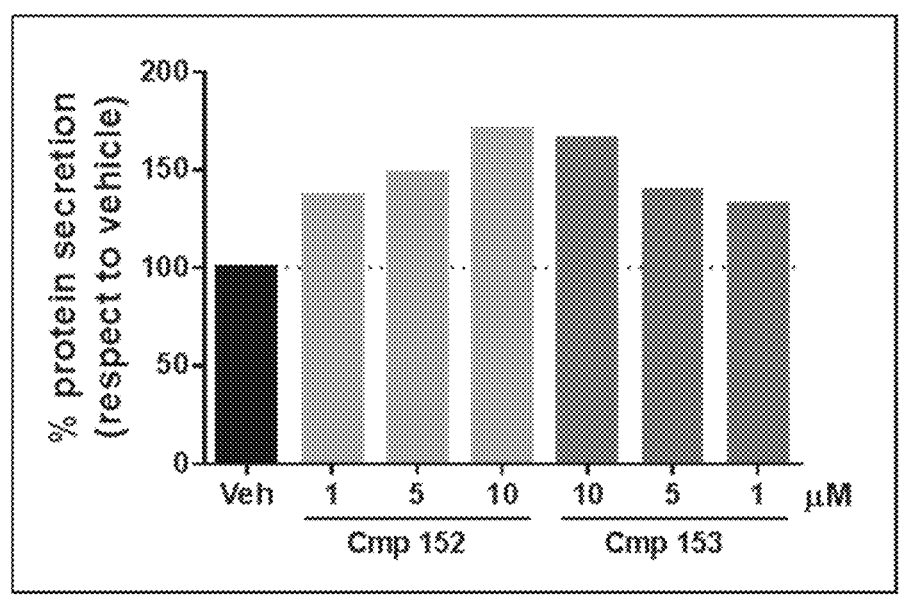

Total protein secretion from CHO cells treated with compound 152 or 153 at the indicated concentration or vehicle alone for 24 hours are shown in FIG. 15A. Quantification of protein bands from the gel was done by densitometry using ImageJ. Percent of secreted proteins in each treatment is shown in FIG. 15B. Percentage was calculated as the percent relative to protein secretion levels from vehicle-treated CHO cells which correspond to 100%. Treatment with ISR-inhibitor compounds can increase the secretion of proteins in a cell-based assay and could be used as enhancers of recombinant proteins in those systems.

All references throughout, such as publications, patents, patent applications and published patent applications, are incorporated herein by reference in their entireties.

The invention claimed is:
1. A compound of formula (1-2):

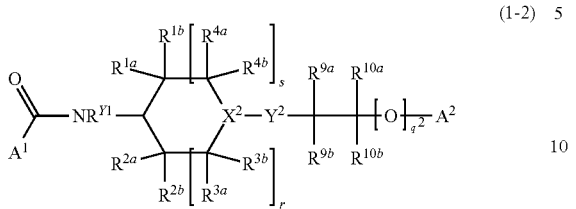

or a pharmaceutically acceptable salt thereof;
wherein:
$X^2$ is CH;
$R^{Y1}$ is hydrogen or $C_1$-$C_6$ alkyl;
$Y^2$ is selected from the group consisting of $NR^{Y2}$ and O;
$R^{Y2}$ is hydrogen or $C_1$-$C_6$ alkyl;
$q^2$ is 1;
r and s, independently of each other, are 0, 1, or 2;
$A^1$ is a substituent of formula ($A^1$-a)
wherein

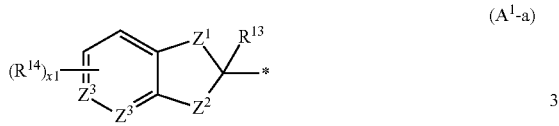

represents the attachment point to the remainder of the molecule;
$Z^1$ is selected from the group consisting of $CR^{Z1-1}$ $R^{Z1-2}$, $NR^{Z1-2}$, O, S, and —$CR^{Z1-1}$=$CR^{Z1-1}$;
wherein $R^{Z1-1}$ is H or $R^{14}$; and $R^{Z1-2}$ is H or $R^{14}$;
$Z^2$ is selected from the group consisting of $CR^{Z2-1}$ $R^{Z2-2}$, $NR^{Z2-2}$;
and —$CR^{Z2-1}$=$CR^{Z2-1}$;
wherein $R^{Z2-1}$ is H or $R^{14}$; and $R^{Z2-2}$ is H or $R^{14}$;
$Z^3$, independently at each occurrence, is C or N, provided that at least one $Z^3$ is C;
$R^{13}$ is hydrogen or $R^{14}$, or $R^{13}$ and $R^{Z1-2}$ are taken together to form a double bond between the carbon atom bearing $R^{13}$ and $Z^1$, or $R^{13}$ and $R^{Z2-2}$ are taken together to form a double bond between the carbon atom bearing $R^{13}$ and $Z^2$; and
x1 is 1, 2, 3, or 4, and at least one $R^{14}$ is halogen;
$R^{14}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —$NH_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —$NR^{14-a}R^{14-b}$, —CN, —C(O)OH, —C(O)O ($C_1$-$C_6$ alkyl), —C(O)O($C_1$-$C_6$ haloalkyl), —C(O)$NH_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)$NR^{14-a}R^{14-b}$, —S(O)$_2$OH, —S(O)$_2$O($C_1$-$C_6$ alkyl), —S(O)$_2$O($C_1$-$C_6$ haloalkyl), —S(O)$_2NH_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$ $NR^{14-a}$ $R^{14-b}$, —OC(O)H, —OC(O)($C_1$-$C_6$ alkyl), —OC(O)($C_1$-$C_6$ haloalkyl), —N(H)C(O)H, —N(H) C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl) C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$ ($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S (O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);
wherein $R^{14-a}$ and $R^{14-b}$ are taken together with the nitrogen atom which bears them to form a 3-10 membered heterocycle;
$A^2$ is $C_6$-$C_{10}$ aryl substituted by at least one halogen substituent and optionally further substituted with one or more $R^{16}$ substituents, or 5-10 membered heteroaryl substituted by at least one halogen substituent and optionally further substituted with one or more $R^{16}$ substituents;
$R^{16}$ is selected, independently at each occurrence, from the group consisting of halogen, $C_1$-$C_6$ alkyl, $C_1$-$C_6$ haloalkyl, —OH, —O($C_1$-$C_6$ alkyl), —O($C_1$-$C_6$ haloalkyl), —SH, —S($C_1$-$C_6$ alkyl), —S($C_1$-$C_6$ haloalkyl), —$NH_2$, —NH($C_1$-$C_6$ alkyl), —NH($C_1$-$C_6$ haloalkyl), —N($C_1$-$C_6$ alkyl)$_2$, —N($C_1$-$C_6$ haloalkyl)$_2$, —$NR^{16-a}R^{16-b}$, —CN, —C(O)OH, —C(O)O ($C_1$-$C_6$ alkyl), —C(O)O($C_1$-$C_6$ haloalkyl), —C(O) $NH_2$, —C(O)NH($C_1$-$C_6$ alkyl), —C(O)NH($C_1$-$C_6$ haloalkyl), —C(O)N($C_1$-$C_6$ alkyl)$_2$, —C(O)N($C_1$-$C_6$ haloalkyl)$_2$, —C(O)$NR^{16-a}R^{16-b}$, —S(O)$_2$OH, —S(O)$_2$O($C_1$-$C_6$ alkyl), —S(O)$_2$O($C_1$-$C_6$ haloalkyl), —S(O)$_2NH_2$, —S(O)$_2$NH($C_1$-$C_6$ alkyl), —S(O)$_2$NH($C_1$-$C_6$ haloalkyl), —S(O)$_2$N($C_1$-$C_6$ alkyl)$_2$, —S(O)$_2$N($C_1$-$C_6$ haloalkyl)$_2$, —S(O)$_2$ $NR^{16-a}$ $R^{16-b}$, —OC(O)H, —OC(O)($C_1$-$C_6$ alkyl), —OC(O)($C_1$-$C_6$ haloalkyl), —N(H)C(O)H, —N(H) C(O)($C_1$-$C_6$ alkyl), —N(H)C(O)($C_1$-$C_6$ haloalkyl), —N($C_1$-$C_6$ alkyl)C(O)H, —N($C_1$-$C_6$ alkyl)C(O)($C_1$-$C_6$ alkyl), —N($C_1$-$C_6$ alkyl)C(O)($C_1$-$C_6$ haloalkyl), —N($C_1$-$C_6$ haloalkyl)C(O)H, —N($C_1$-$C_6$ haloalkyl) C(O)($C_1$-$C_6$ alkyl), —N($C_1$-$C_6$ haloalkyl)C(O)($C_1$-$C_6$ haloalkyl), —OS(O)$_2$($C_1$-$C_6$ alkyl), —OS(O)$_2$ ($C_1$-$C_6$ haloalkyl), —N(H)S(O)$_2$($C_1$-$C_6$ alkyl), —N(H)S(O)$_2$($C_1$-$C_6$ haloalkyl), —N($C_1$-$C_6$ alkyl)S (O)$_2$($C_1$-$C_6$ alkyl), —N($C_1$-$C_6$ alkyl)S(O)$_2$($C_1$-$C_6$ haloalkyl), —N($C_1$-$C_6$ haloalkyl)S(O)$_2$($C_1$-$C_6$ alkyl), and —N($C_1$-$C_6$ haloalkyl)S(O)$_2$($C_1$-$C_6$ haloalkyl);
wherein $R^{16-a}$ and $R^{16-b}$ are taken together with the nitrogen atom which bears them to form a 3-10 membered heterocycle;
$R^{1a}$ and $R^{1b}$ are independently selected from the group consisting of hydrogen, $C_1$-$C_6$ alkyl, and halogen;
$R^{2a}$ and $R^{2b}$ are independently selected from the group consisting of hydrogen, $C_1$-$C_6$ alkyl, and halogen;
when present, $R^{3a}$ and $R^{3b}$ are independently at each occurrence selected from the group consisting of hydrogen, $C_1$-$C_6$ alkyl, and halogen;
when present, $R^{4a}$ and $R^{4b}$ are independently at each occurrence selected from the group consisting of hydrogen, $C_1$-$C_6$ alkyl, and halogen;
or alternatively, $R^{1a}$ and $R^{2a}$ are taken together to form a $C_1$-$C_6$ alkylene moiety;
or alternatively, $R^{1a}$ and an $R^{3a}$ moiety, when present, are taken together to form a $C_1$-$C_6$ alkylene moiety, and $R^{1b}$ and the $R^{3b}$ in the geminal position to the $R^{3a}$ taken together with Ria, are both hydrogen;

or alternatively, an $R^{3a}$ moiety, when present, and an $R^{4a}$ moiety, when present, are taken together to form a $C_1$-$C_6$ alkylene moiety, and the $R^{3b}$ in the geminal position to the $R^{3a}$ taken together with the $R^{4a}$ moiety and the $R^{4b}$ in the geminal position to the $R^{4a}$ taken together with the $R^{3a}$ moiety, are both hydrogen;

$R^{9a}$ and $R^{9b}$ are taken together to form an oxo (=O) substituent or an imido (=NH) substituent, or alternatively, $R^{9a}$ and $R^{9b}$ are both hydrogen;

$R^{10a}$ is hydrogen; and $R^{10b}$ is hydrogen.

2. The compound of claim 1, or a pharmaceutically acceptable salt thereof, wherein ($A^1$-a) is selected from the group consisting of

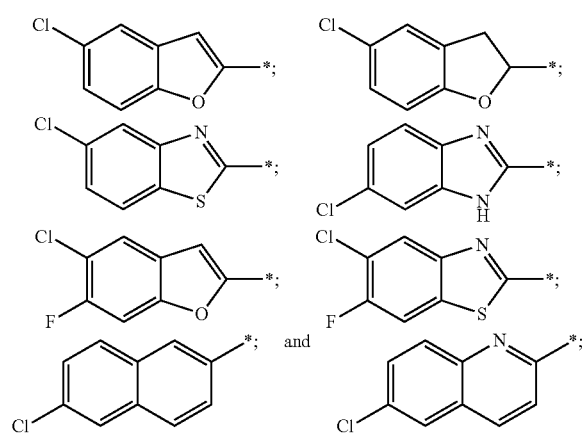

wherein the * represents the attachment point to the remainder of the molecule.

3. The compound of claim 1, or a pharmaceutically acceptable salt thereof, wherein $A^2$ is selected from the group consisting of:

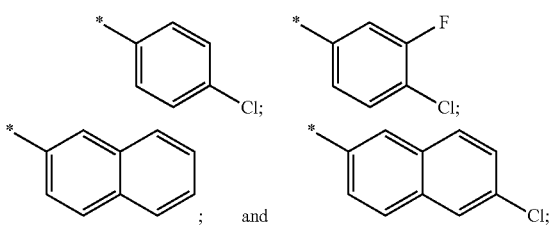

wherein the * represents the attachment point to the remainder of the molecule.

4. The compound of claim 2, or a pharmaceutically acceptable salt thereof, wherein $A^2$ is selected from the group consisting of:

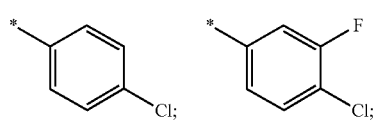

-continued

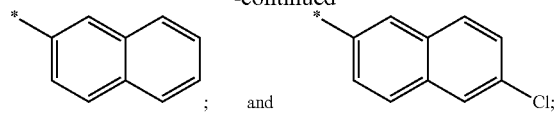

wherein the * represents the attachment point to the remainder of the molecule.

5. The compound of claim 1, or a pharmaceutically acceptable salt thereof, wherein $R^{9a}$ and $R^{9b}$ are taken together to form an oxo (=O) substituent.

6. The compound of claim 1, or a pharmaceutically acceptable salt thereof, wherein $R^{9a}$ and $R^{9b}$ are both hydrogen.

7. The compound of claim 1, or a pharmaceutically acceptable salt thereof, wherein the compound is

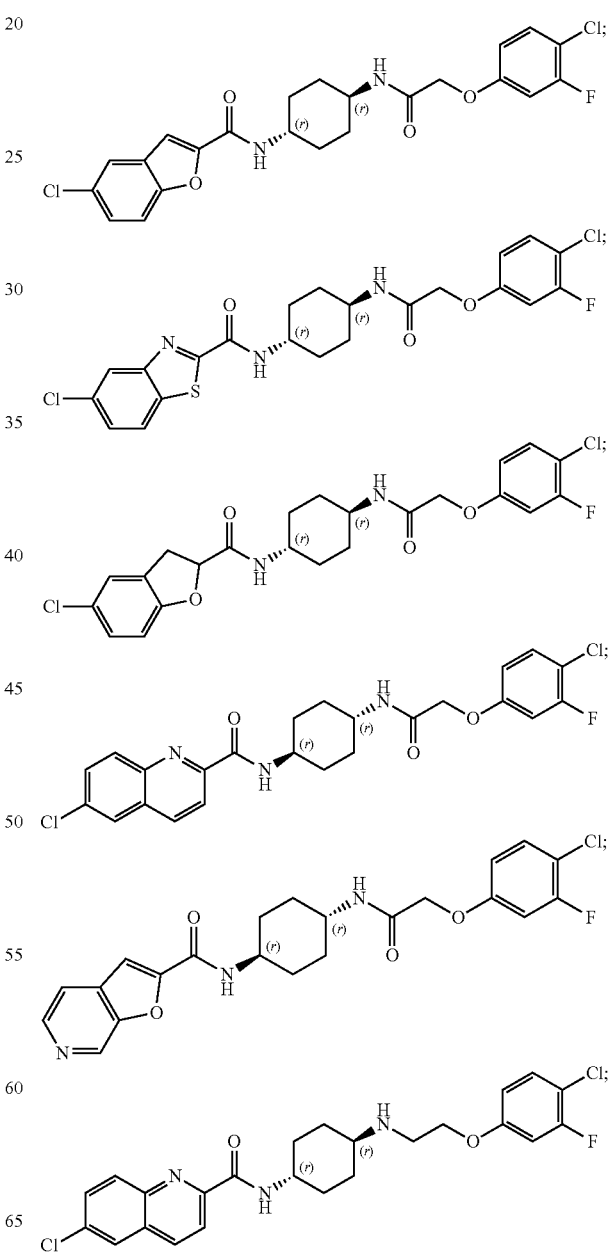

-continued

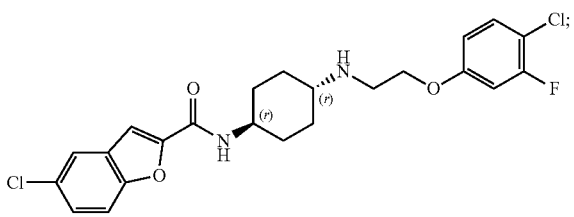

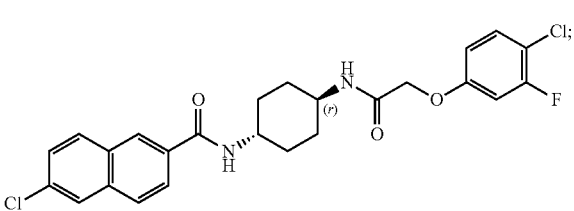

or a pharmaceutically acceptable salt of any of the foregoing.

8. The compound of claim 7, or a pharmaceutically acceptable salt thereof, wherein the compound, or the pharmaceutically acceptable salt thereof, is

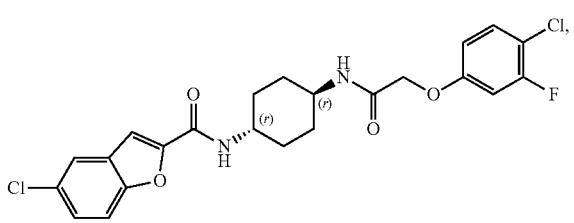 [SMILES: O=C(COc1ccc(Cl)c(F)c1)N[C@H]1CC[C@H](NC(=O)c2cc3cc(Cl)ccc3o2)CC1]

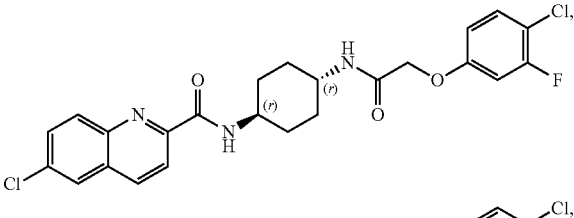

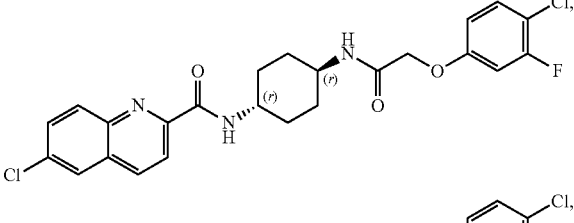

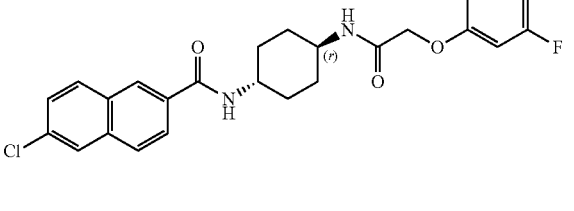

or a pharmaceutically acceptable salt of any of the foregoing.

9. The compound of claim 1, or a pharmaceutically acceptable salt thereof, wherein the compound, or the pharmaceutically acceptable salt thereof, is

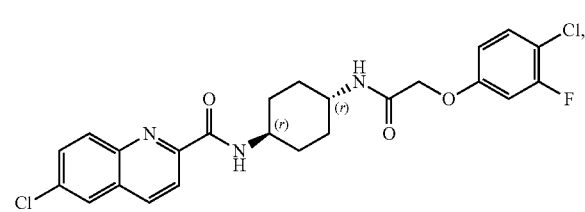 [SMILES: O=C(COc1ccc(Cl)c(F)c1)N[C@H]1CC[C@H](NC(=O)c2ccc3cc(Cl)ccc3n2)CC1]

or a pharmaceutically acceptable salt thereof.

10. The compound of claim 1, or a pharmaceutically acceptable salt thereof, wherein the compound, or the pharmaceutically acceptable salt thereof, is

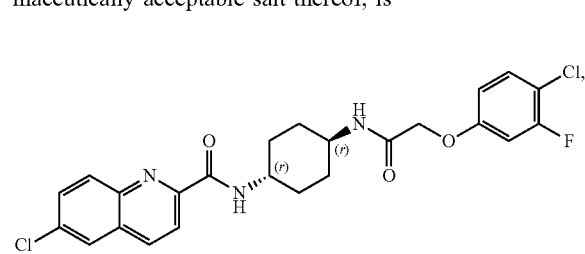

or a pharmaceutically acceptable salt thereof.

11. The compound of claim 1, or a pharmaceutically acceptable salt thereof, wherein the compound, or the pharmaceutically acceptable salt thereof, is or a pharmaceutically acceptable salt thereof.

12. The compound of claim 1, or a pharmaceutically acceptable salt thereof, wherein the compound, or the pharmaceutically acceptable salt thereof, is or a pharmaceutically acceptable salt thereof.

13. A pharmaceutical composition comprising a compound of claim 1, or a pharmaceutically acceptable salt thereof, and a pharmaceutically acceptable carrier.

14. A method of treating a disease or disorder mediated by an integrated stress response (ISR) pathway in an individual in need thereof comprising administering to the individual a therapeutically effective amount of a compound of claim 1, or a pharmaceutically acceptable salt thereof.

15. A method of producing a protein, comprising contacting a eukaryotic cell comprising a nucleic acid encoding the protein with the compound of claim 1, or a salt thereof.

16. A method of culturing a eukaryotic cell comprising a nucleic acid encoding a protein, comprising contacting the eukaryotic cell with an in vitro culture medium comprising the compound of claim 1, or a salt thereof.

17. A method of producing a protein, comprising contacting a cell-free protein synthesis (CFPS) system comprising eukaryotic initiation factor 2 (eIF2) and a nucleic acid encoding a protein with the compound of claim 1, or a salt thereof.

18. An in vitro cell culture medium, comprising the compound of claim 1, or a salt thereof and nutrients for cellular growth.

19. A cell-free protein synthesis (CFPS) system comprising eukaryotic initiation factor 2 (eIF2) and a nucleic acid encoding a protein with the compound of claim 1, or a salt thereof.

20. The method of claim 14, wherein the disease or disorder mediated by an integrated stress response (ISR) pathway is a neurodegenerative disease, an inflammatory disease, an autoimmune disease, a metabolic syndrome, a cancer, a vascular disease, a musculoskeletal disease, an ocular disease, or a genetic disorder.

21. The method of claim 20, wherein the disease or disorder mediated by an integrated stress response (ISR) pathway is a neurodegenerative disease.

22. The method of claim 21, wherein the neurodegenerative disease is vanishing white matter disease.

23. The method of claim 21, wherein the neurodegenerative disease is amyotrophic lateral sclerosis (ALS).

24. The method of claim 21, wherein the neurodegenerative disease is frontotemporal dementia (FTD).

25. The method of claim 20, wherein the disease or disorder mediated by an integrated stress response (ISR) pathway is an inflammatory disease.

26. The method of claim 20, wherein the disease or disorder mediated by an integrated stress response (ISR) pathway is an autoimmune disease.

27. The method of claim 20, wherein the disease or disorder mediated by an integrated stress response (ISR) pathway is a metabolic syndrome.

28. The method of claim 20, wherein the disease or disorder mediated by an integrated stress response (ISR) pathway is a cancer.

29. The method of claim 28, wherein the cancer is prostate cancer.

30. The method of claim 20, wherein the disease or disorder mediated by an integrated stress response (ISR) pathway is a musculoskeletal disease.

31. The method of claim 30, wherein the musculoskeletal disease is muscular atrophy.

32. The method of claim 20, wherein the disease or disorder mediated by an integrated stress response (ISR) pathway is a genetic disorder.

33. The method of claim 32, wherein the genetic disorder is Down syndrome.

34. The method of claim 20, wherein the disease or disorder mediated by an integrated stress response (ISR) pathway is a vascular disease.

35. The method of claim 20, wherein the disease or disorder mediated by an integrated stress response (ISR) pathway is an ocular disease.

36. A compound, where the compound is

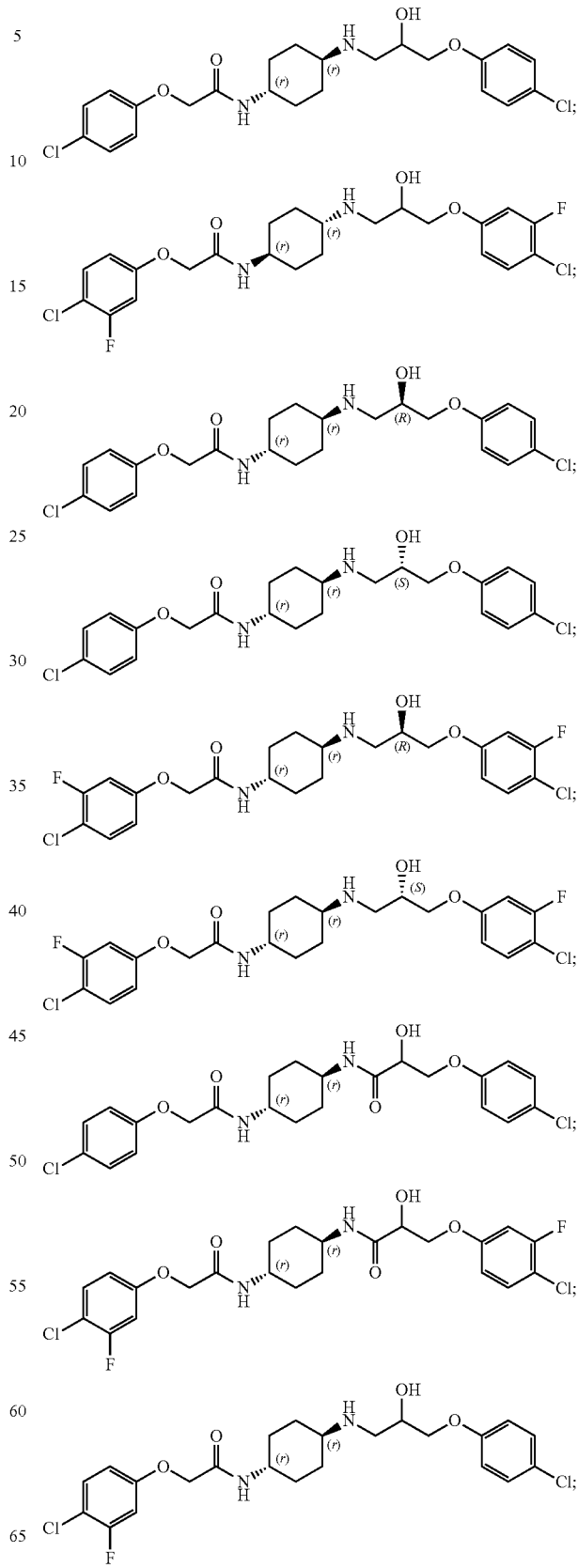

557
-continued
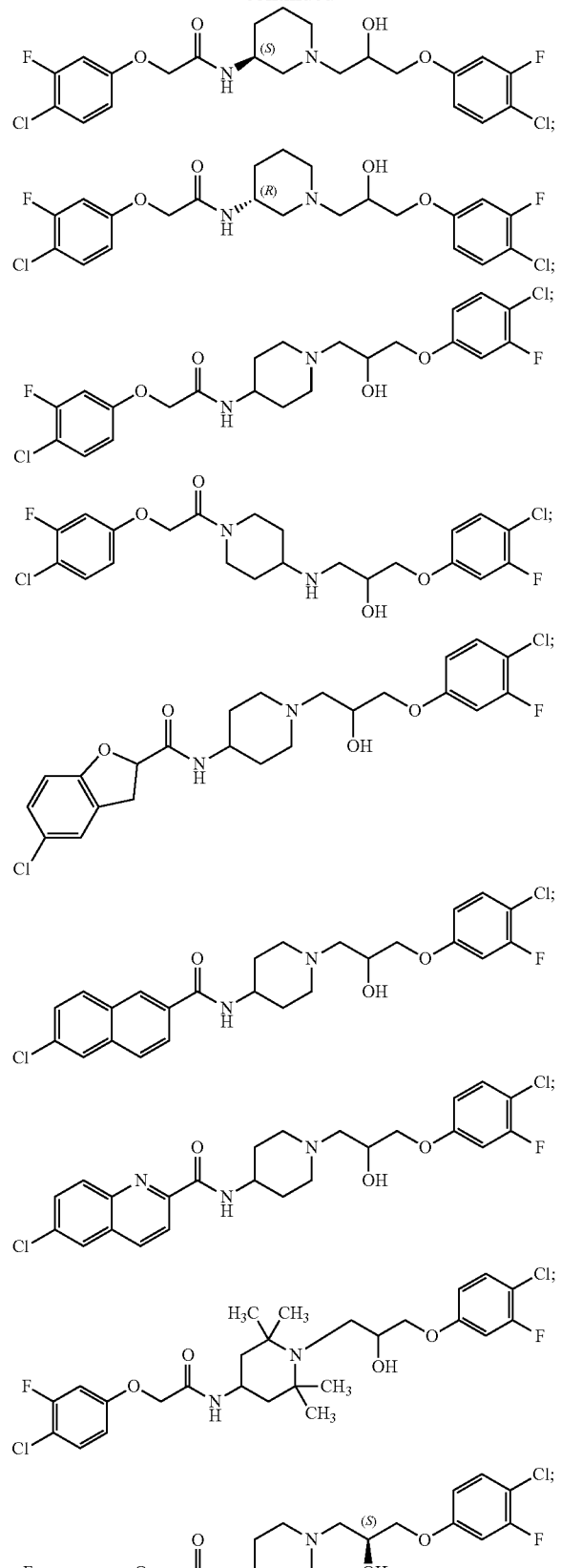
558
-continued
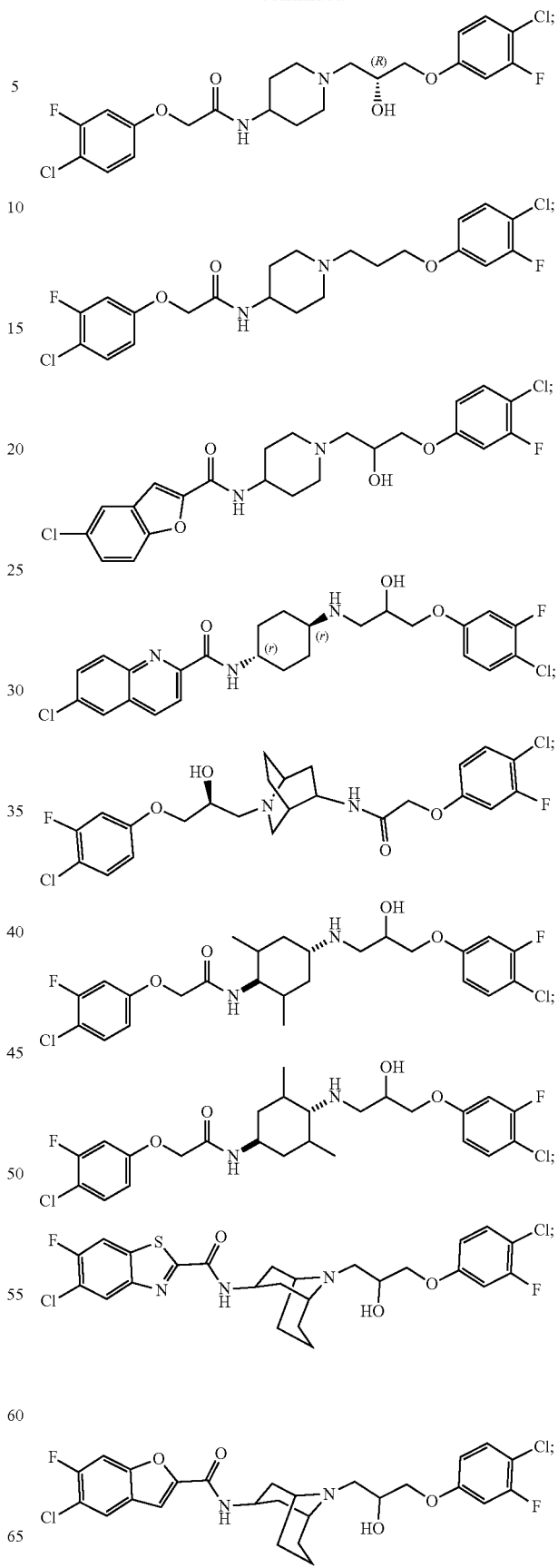

559
-continued
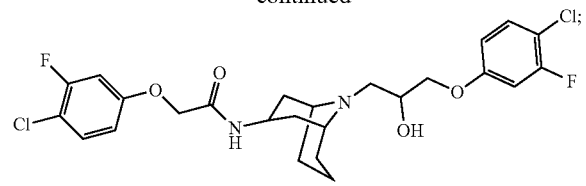
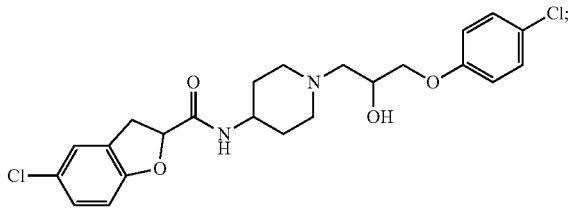
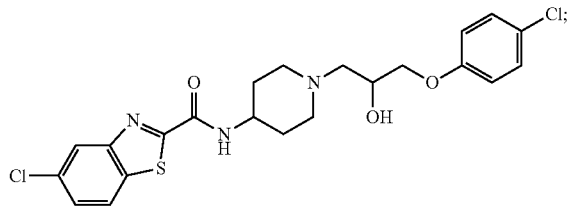
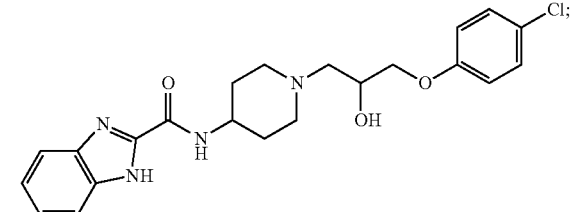
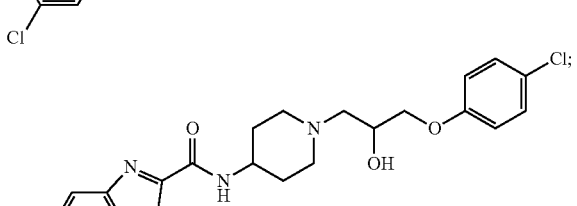
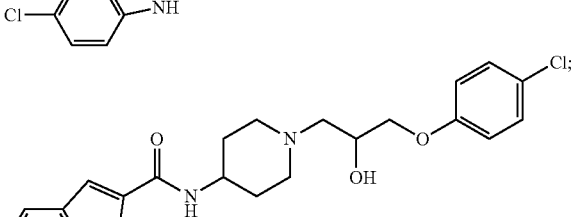
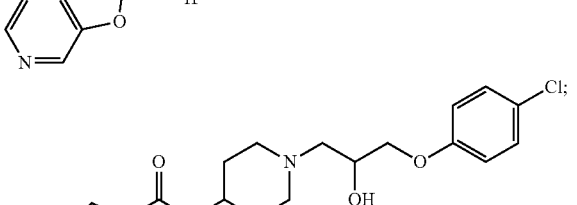
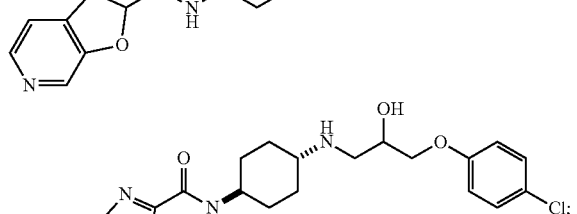
560
-continued
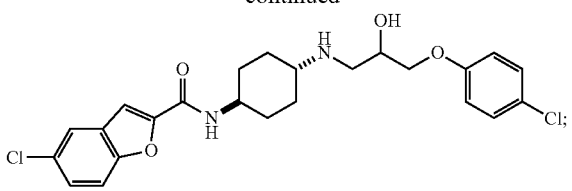
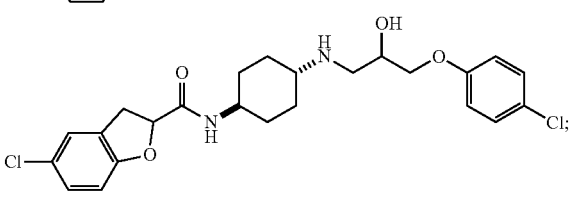
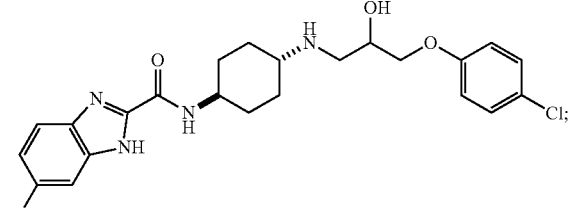
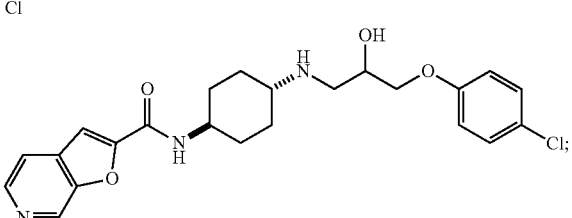
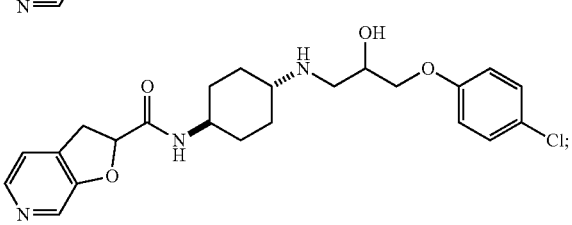
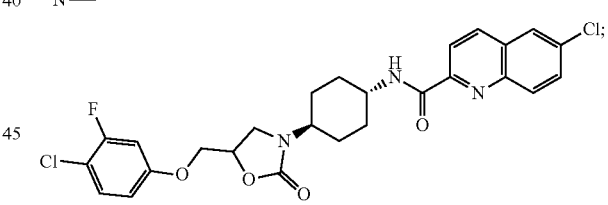
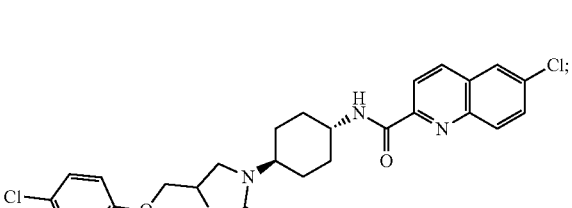
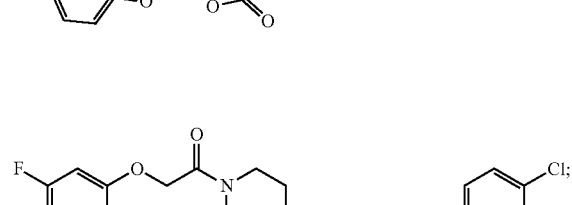
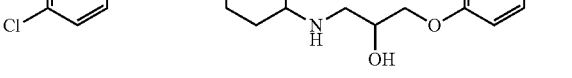

561
-continued
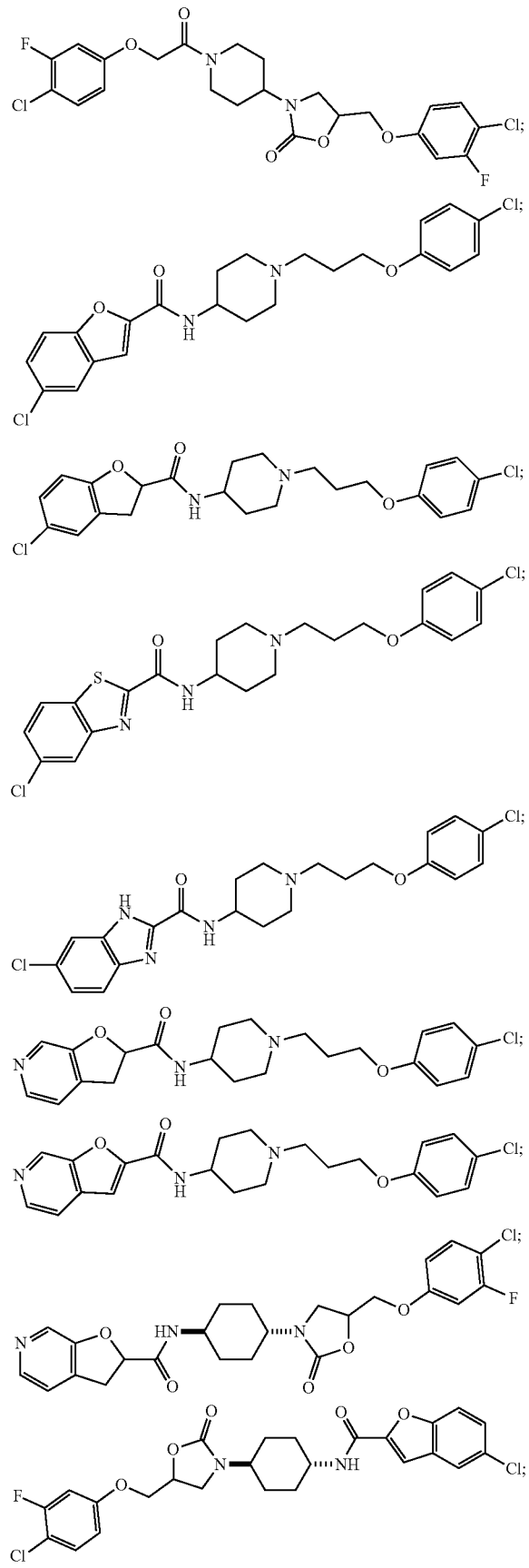
562
-continued
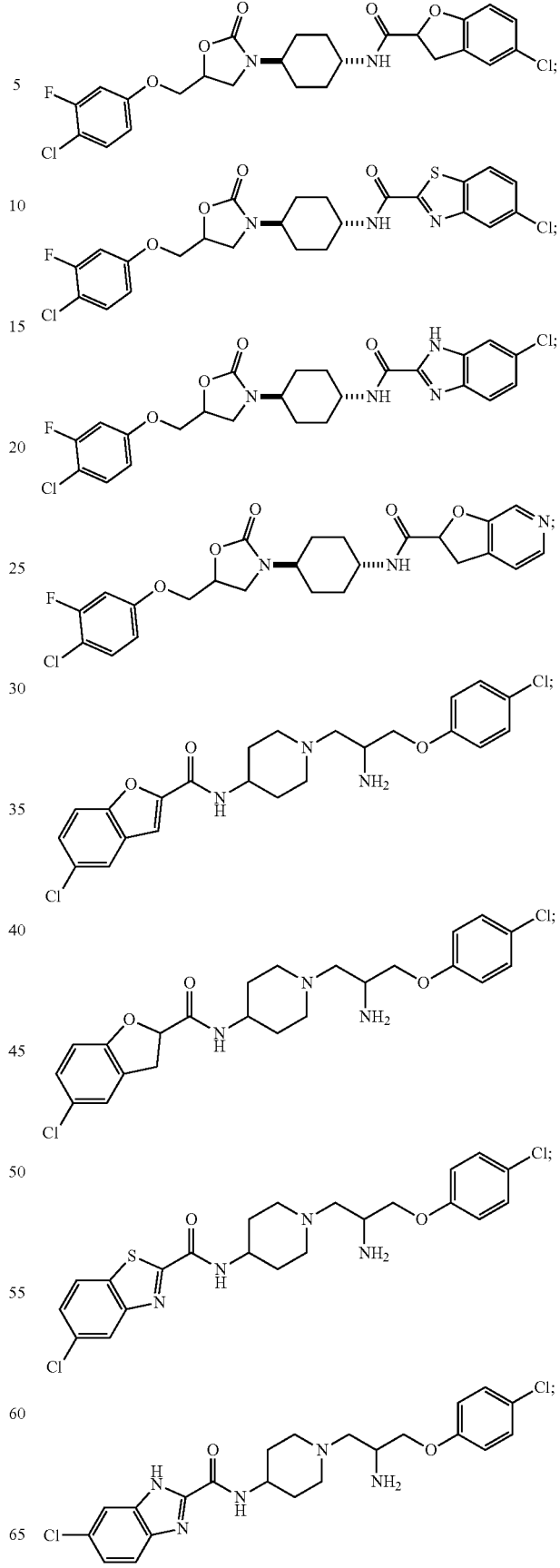

or a pharmaceutically acceptable salt of any of the foregoing.

37. The compound of claim 36, or a pharmaceutically acceptable salt thereof, wherein the compound, or the pharmaceutically acceptable salt thereof, is

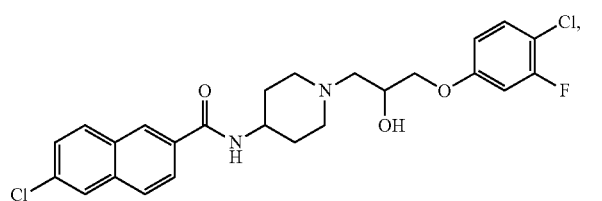

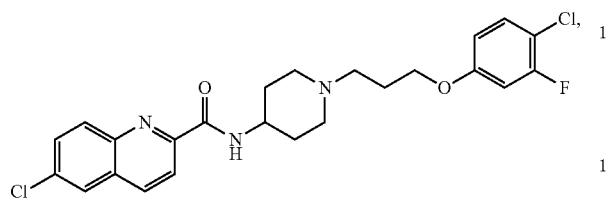

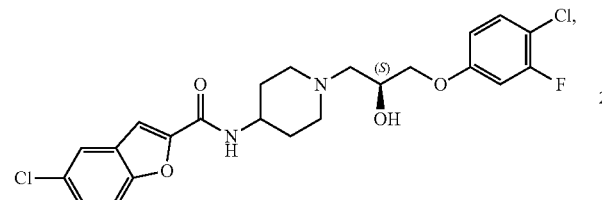

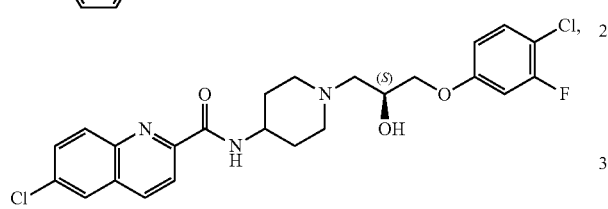

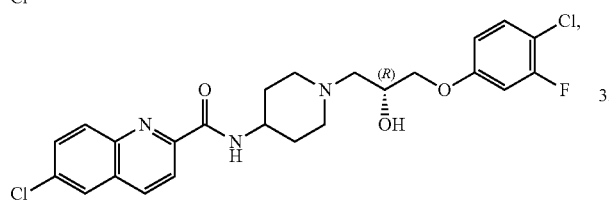

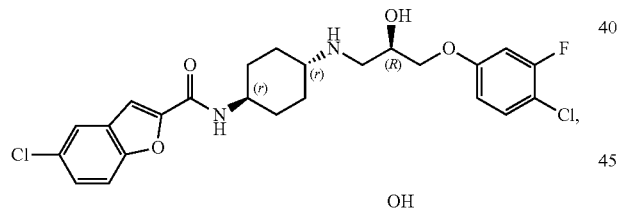

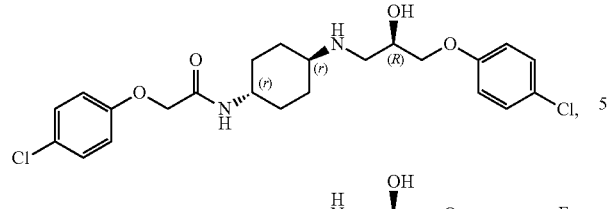

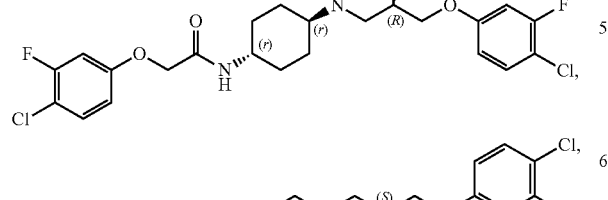

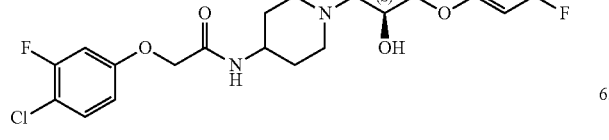

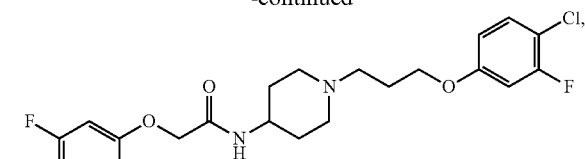

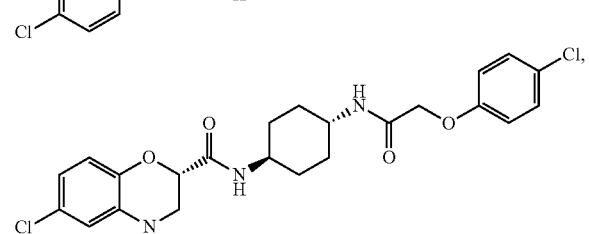

or a pharmaceutically acceptable salt of any of the foregoing.

38. The compound of claim 36, or a pharmaceutically acceptable salt thereof, wherein the compound, or the pharmaceutically acceptable salt thereof, is

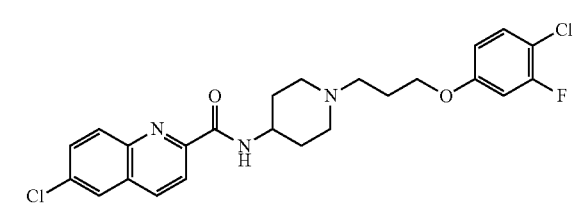 [SMILES: O=C(NC1CCN(CCCOc2ccc(Cl)c(F)c2)CC1)c1ccc2cc(Cl)ccc2n1]

or a pharmaceutically acceptable salt thereof.

39. The compound of claim 36, or a pharmaceutically acceptable salt thereof, wherein the compound, or the pharmaceutically acceptable salt thereof, is

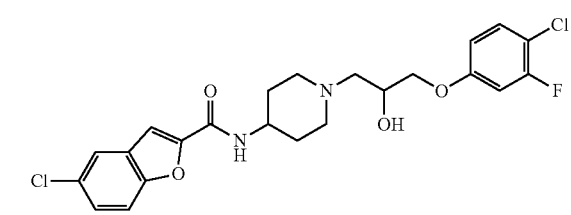 [SMILES: O=C(NC1CCN(CC(O)COc2ccc(Cl)c(F)c2)CC1)c1cc2cc(Cl)ccc2o1]

or a pharmaceutically acceptable salt thereof.

40. The compound of claim 36, or a pharmaceutically acceptable salt thereof, wherein the compound, or the pharmaceutically acceptable salt thereof, is

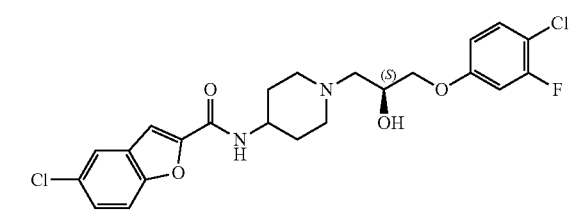

or a pharmaceutically acceptable salt thereof.

41. The compound of claim 36, or a pharmaceutically acceptable salt thereof, wherein the compound, or the pharmaceutically acceptable salt thereof, is

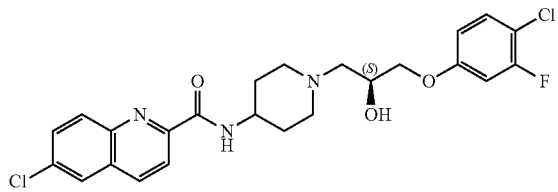

or a pharmaceutically acceptable salt thereof.

42. The compound of claim 36, or a pharmaceutically acceptable salt thereof, wherein the compound, or the pharmaceutically acceptable salt thereof, is

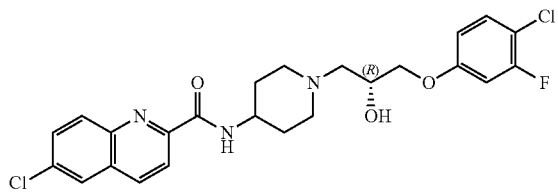

or a pharmaceutically acceptable salt thereof.

43. The compound of claim 36, or a pharmaceutically acceptable salt thereof, wherein the compound, or the pharmaceutically acceptable salt thereof, is

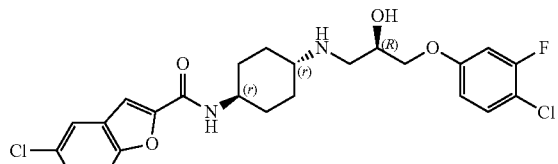

or a pharmaceutically acceptable salt thereof.

44. The compound of claim 36, or a pharmaceutically acceptable salt thereof, wherein the compound, or the pharmaceutically acceptable salt thereof, is

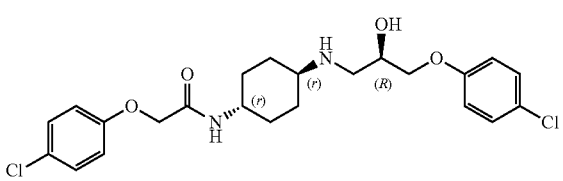

or a pharmaceutically acceptable salt thereof.

45. The compound of claim 36, or a pharmaceutically acceptable salt thereof, wherein the compound, or the pharmaceutically acceptable salt thereof, is

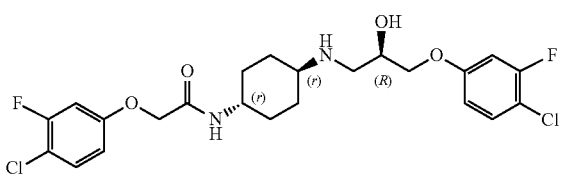

or a pharmaceutically acceptable salt thereof.

46. The compound of claim 36, or a pharmaceutically acceptable salt thereof, wherein the compound, or the pharmaceutically acceptable salt thereof, is

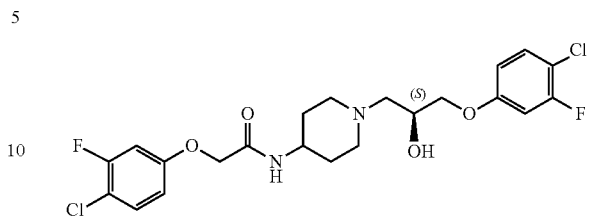

or a pharmaceutically acceptable salt thereof.

47. The compound of claim 36, or a pharmaceutically acceptable salt thereof, wherein the compound, or the pharmaceutically acceptable salt thereof, is

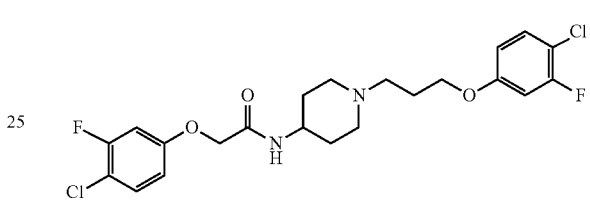

or a pharmaceutically acceptable salt thereof.

48. The compound of claim 36, or a pharmaceutically acceptable salt thereof, wherein the compound, or the pharmaceutically acceptable salt thereof, is

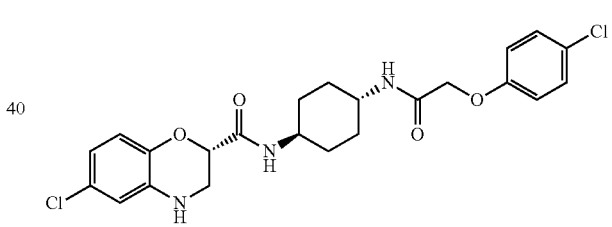

or a pharmaceutically acceptable salt thereof.

49. The compound of claim 36, or a pharmaceutically acceptable salt thereof, wherein the compound, or the pharmaceutically acceptable salt thereof, is

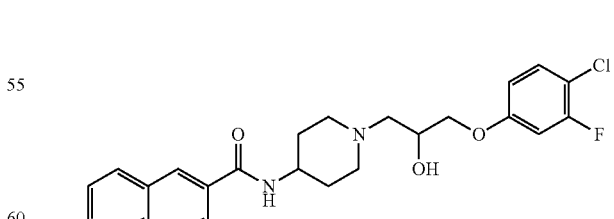

or a pharmaceutically acceptable salt thereof.

50. The compound of claim 36, or a pharmaceutically acceptable salt thereof, wherein the compound, or the pharmaceutically acceptable salt thereof, is

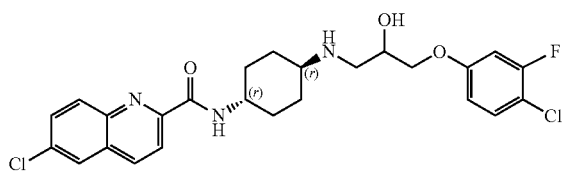 [SMILES: O=C(N[C@H]1CC[C@H](NCC(O)COc2ccc(Cl)c(F)c2)CC1)c1ccc2cc(Cl)ccc2n1]

or a pharmaceutically acceptable salt thereof.

51. The compound of claim 36, or a pharmaceutically acceptable salt thereof, wherein the compound, or the pharmaceutically acceptable salt thereof, is

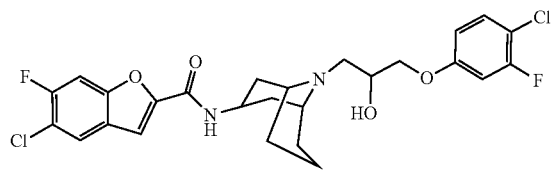 [SMILES: O=C(NC1CC2CCCC(C1)N2CC(O)COc1ccc(Cl)c(F)c1)c1cc2cc(Cl)c(F)cc2o1]

or a pharmaceutically acceptable salt thereof.

52. The compound of claim 36, or a pharmaceutically acceptable salt thereof, wherein the compound, or the pharmaceutically acceptable salt thereof, is

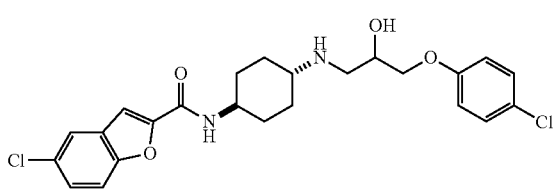

or a pharmaceutically acceptable salt thereof.

53. The compound of claim 36, or a pharmaceutically acceptable salt thereof, wherein the compound, or the pharmaceutically acceptable salt thereof, is

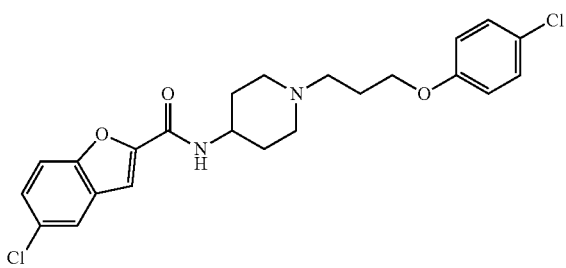 [SMILES: O=C(NC1CCN(CCCOc2ccc(Cl)cc2)CC1)c1cc2cc(Cl)ccc2o1]

or a pharmaceutically acceptable salt thereof.

54. The compound of claim 36, or a pharmaceutically acceptable salt thereof, wherein the compound, or the pharmaceutically acceptable salt thereof, is

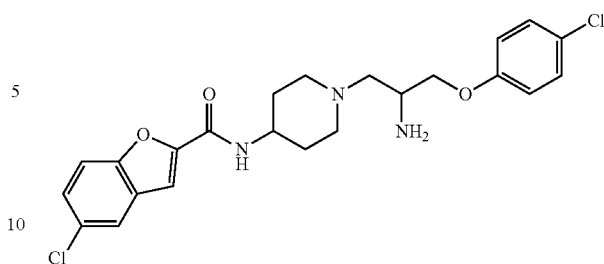

or a pharmaceutically acceptable salt thereof.

55. The compound of claim 36, or a pharmaceutically acceptable salt thereof, wherein the compound, or the pharmaceutically acceptable salt thereof, is

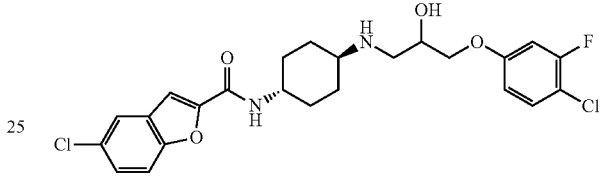

or a pharmaceutically acceptable salt thereof.

56. The compound of claim 36, or a pharmaceutically acceptable salt thereof, wherein the compound, or the pharmaceutically acceptable salt thereof, is

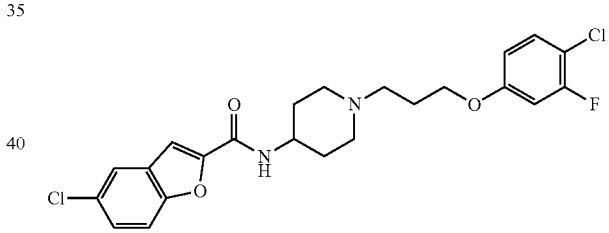

or a pharmaceutically acceptable salt thereof.

57. The compound of claim 36, or a pharmaceutically acceptable salt thereof, wherein the compound, or the pharmaceutically acceptable salt thereof, is

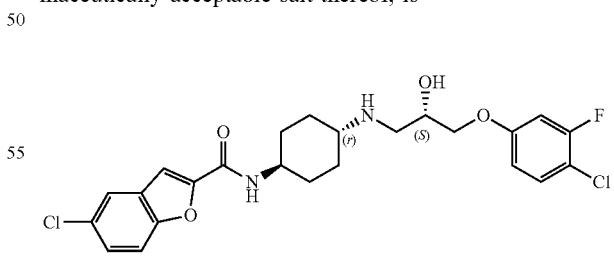

or a pharmaceutically acceptable salt thereof.

58. The compound of claim 36, or a pharmaceutically acceptable salt thereof, wherein the compound, or the pharmaceutically acceptable salt thereof, is

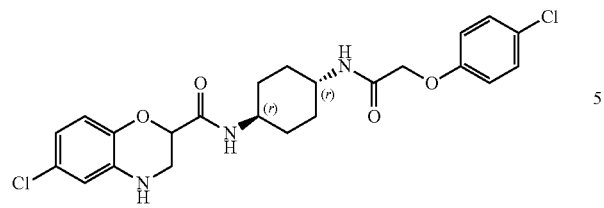
or a pharmaceutically acceptable salt thereof.
* * * * *